United States Patent
Zhong et al.

(10) Patent No.: US 12,091,438 B2
(45) Date of Patent: *Sep. 17, 2024

(54) ANTI-MESOTHELIN CONSTRUCTS AND USES THEREOF

(71) Applicant: Anwita Biosciences, Inc., San Carlos, CA (US)

(72) Inventors: Ziyang Zhong, Belmont, CA (US); Fan Ye, Mountain View, CA (US); Matthew Siegel, Menlo Park, CA (US); Jianing Huang, San Mateo, CA (US)

(73) Assignee: Anwita Biosciences, Inc., San Carlos, CA (US)

( * ) Notice: Subject to any disclaimer, the term of this patent is extended or adjusted under 35 U.S.C. 154(b) by 823 days.

This patent is subject to a terminal disclaimer.

(21) Appl. No.: 17/253,487

(22) PCT Filed: Jun. 17, 2019

(86) PCT No.: PCT/US2019/037557
§ 371 (c)(1),
(2) Date: Dec. 17, 2020

(87) PCT Pub. No.: WO2019/246003
PCT Pub. Date: Dec. 26, 2019

(65) Prior Publication Data
US 2021/0340272 A1 Nov. 4, 2021

Related U.S. Application Data

(60) Provisional application No. 62/809,496, filed on Feb. 22, 2019, provisional application No. 62/686,481, filed on Jun. 18, 2018.

(51) Int. Cl.
| | | |
|---|---|---|
| *C07K 16/44* | (2006.01) | |
| *A61K 45/06* | (2006.01) | |
| *A61P 35/00* | (2006.01) | |
| *C07K 14/54* | (2006.01) | |
| *C07K 14/765* | (2006.01) | |
| *C07K 16/30* | (2006.01) | |
| *A61K 38/00* | (2006.01) | |
| *A61K 39/00* | (2006.01) | |

(52) U.S. Cl.
CPC ............. *C07K 14/54* (2013.01); *A61K 45/06* (2013.01); *A61P 35/00* (2018.01); *C07K 14/5443* (2013.01); *C07K 14/765* (2013.01); *C07K 16/30* (2013.01); *C07K 16/44* (2013.01); *A61K 38/00* (2013.01); *A61K 2039/505* (2013.01); *C07K 2317/31* (2013.01); *C07K 2317/565* (2013.01); *C07K 2317/569* (2013.01); *C07K 2319/00* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 4,485,045 A | 11/1984 | Regen | |
| 4,544,545 A | 10/1985 | Ryan et al. | |
| 4,816,567 A | 3/1989 | Cabilly et al. | |
| 5,013,556 A | 5/1991 | Woodle et al. | |
| 5,571,894 A | 11/1996 | Wels et al. | |
| 5,587,458 A | 12/1996 | King et al. | |
| 5,869,046 A | 2/1999 | Presta et al. | |
| 6,054,297 A | 4/2000 | Carter et al. | |
| 6,407,213 B1 | 6/2002 | Carter et al. | |
| 6,639,055 B1 | 10/2003 | Carter et al. | |
| 6,719,971 B1 | 4/2004 | Carter et al. | |
| 6,800,738 B1 | 10/2004 | Carter et al. | |
| 7,189,690 B2 | 3/2007 | Rosen et al. | |
| 8,969,289 B2 | 3/2015 | Gosselin et al. | |
| 9,272,002 B2 * | 3/2016 | Powell, Jr. | C07K 16/28 |
| 9,676,849 B2 * | 6/2017 | Farrington | C07K 16/28 |
| 10,011,858 B2 | 7/2018 | Igawa et al. | |
| 11,028,166 B2 | 6/2021 | Cini et al. | |
| 11,426,468 B2 | 8/2022 | Janssen et al. | |

(Continued)

FOREIGN PATENT DOCUMENTS

| | | |
|---|---|---|
| CN | 105198999 A | 12/2015 |
| WO | 1991001743 A1 | 2/1991 |

(Continued)

OTHER PUBLICATIONS

Construct. 2023. Google Dictionary from Oxford Languages. Retrieved on Dec. 6, 2023 from https://www.google.com (Year: 2023).*
Moiety. 2023. Merriam-Webster.com. Retrieved Dec. 6, 2023, from https://www.merriam-webster.com/dictionary/moiety (Year: 2023).*
Rudikoff et al. Proc. Natl. Acad. Sci. 1982. 79: 1979-1983 (Year: 1982).*
Bedouelle et al. Fees J. Jan. 2006;273(1):34-46 (Year: 2006).*
Vajdos et al. J Mol Biol. Jul. 5, 2002;320(2):415-28 (Year: 2002).*
Dinethra. Health Writer Hub. 2015. Retrieved on Dec. 7, 2023 from <URL: https://www.healthwriterhub.com/disease-disorder-condition-syndrome-whats-the-difference/> (Year: 2015).*

(Continued)

*Primary Examiner* — Zachary S Skelding
*Assistant Examiner* — Brianna K Swartwout
(74) *Attorney, Agent, or Firm* — Lin Yu; Juniv LLP

(57) ABSTRACT

The present application relates to anti-mesothelin constructs (such as antimesothelin antibodies, cytokine fusion proteins that comprise the anti-mesothelin constructs), methods of preparing the anti-mesothelin constructs and methods of using the constructs (e.g., methods of treating a disease or condition). The present application also relates to a combination therapy for treating cancer that comprises administering anti-mesothelin agent and a cytokine (such as IL-21 or IL-15). Combination therapy may further comprises administration of an anti-Her2 agent.

17 Claims, 19 Drawing Sheets

Specification includes a Sequence Listing.

(56) References Cited

U.S. PATENT DOCUMENTS

| | | | |
|---|---|---|---|
| 2006/0204506 | A1* | 9/2006 | Ebel .......................... A61P 43/00 536/23.53 |
| 2007/0048282 | A1 | 3/2007 | Rosen et al. |
| 2007/0071675 | A1 | 3/2007 | Wu et al. |
| 2007/0079271 | A1 | 4/2007 | Ushiyama |
| 2007/0269422 | A1 | 11/2007 | Beimaert et al. |
| 2014/0256636 | A1 | 9/2014 | Acharya et al. |
| 2016/0152686 | A1 | 6/2016 | Camphausen et al. |
| 2017/0281792 | A1* | 10/2017 | Dennis .............. A61K 47/6817 |
| 2021/0230242 | A1* | 7/2021 | Zhong .................... C07K 16/32 |
| 2022/0195021 | A1 | 6/2022 | Zhong et al. |

FOREIGN PATENT DOCUMENTS

| | | | |
|---|---|---|---|
| WO | 1993016185 | A2 | 8/1993 |
| WO | 1994004678 | A1 | 3/1994 |
| WO | 1996027011 | A1 | 9/1996 |
| WO | 2001045746 | A2 | 6/2001 |
| WO | 2001079271 | A1 | 10/2001 |
| WO | 2002076489 | A1 | 10/2002 |
| WO | 2004041865 | A2 | 5/2004 |
| WO | 2006106905 | A1 | 10/2006 |
| WO | 2011124718 | A1 | 10/2011 |
| WO | 2011140086 | A2 | 11/2011 |
| WO | 2012059486 | A1 | 5/2012 |
| WO | 2014182532 | A1 | 11/2014 |
| WO | 2015188141 | A2 | 12/2015 |
| WO | 2016009041 | A1 | 1/2016 |
| WO | 2016044605 | A1 | 3/2016 |
| WO | 2016187594 | A1 | 11/2016 |
| WO | 2016196211 | A1 | 12/2016 |
| WO | 2017158436 | A1 | 9/2017 |
| WO | WO-2017190684 | A1 * | 11/2017 ............ A61K 35/76 |
| WO | 2018102795 | A2 | 6/2018 |
| WO | 2018151868 | A2 | 8/2018 |
| WO | 2020172528 | A1 | 8/2020 |

OTHER PUBLICATIONS

MedlinePlus. Benign Tumor. 2016. Retrieved on Dec. 7, 2023 from <URL: https://web.archive.org/web/20160727213745/https://medlineplus.gov/benigntumors.html> (Year: 2016).*

Tang et al. Anticancer Agents Med Chem. 2013. 13(2):276-280 (Year: 2013).*

Pastan et al. Cancer Res. 2014. 74(11): 2907-2912 (Year: 2014).*

Somers et al. Biomarker Insights. 2014. 9:29-37 (Year: 2014).*

WO 2017/190684 A1 English Translation (Year: 2017).*

Adams et al., "Extending the half-life of a fab fragment through generation of a humanized anti-human serum albumin Fv domain: An investigation into the correlation between affinity and serum half-life," MAbs 2016, 8, 1336-46.

Chang and Pastan, "Molecular cloning of mesothelin, a differentiation antigen present on mesothelium, mesotheliomas, and ovarian cancers," Proc. Natl. Acad. Sci. U.S.A. 1996, 93, 136-40.

Dennis et al., "Albumin binding as a general strategy for improving the pharmacokinetics of proteins," J. Biol. Chem. 2002, 277, 35035-43.

Gubbels et al., "Mesothelin-MUC16 binding is a high affinity, N-glycan dependent interaction that facilitates peritoneal metastasis of ovarian tumors," Mol. Cancer 2006, 5, 50.

Hassan et al., "Mesothelin: a new target for immunotherapy," Clin. Cancer. Res. 2004, 10, 3937-42.

Kojima et al., "Molecular cloning and expression of megakaryocyte potentiating factor cDNA," J. Biol. Chem. 1995, 270, 21984-90.

Prantner et al., "Anti-mesothelin nanobodies for both conventional and nanoparticle-based biomedical applications," J. Biomed. Nanotechnol. 2015, 11, 1201-12.

Rump et al., "Binding of ovarian cancer antigen CA125/MUC16 to mesothelin mediates cell adhesion," J. Biol. Chem. 2004, 279, 9190-8.

Tang et al., "A human single-domain antibody elicits potent antitumor activity by targeting an epitope in mesothelin close to the cancer cell surface," Mol. Cancer Ther. 2013, 12, 416-26.

Yamaguchi et al., "A novel cytokine exhibiting megakaryocyte potentiating activity from a human pancreatic tumor cell line HPC-Y5," J. Biol. Chem. 1994, 269, 805-8.

Liu et al., "An engineered IL-21 with half-life extension enhances anti-tumor immunity as a monotherapy or in combination with PD-1 or TIGIT blockade," Int. Immunopharmacol. 2021, 101, 108307.

Walker et al., "Anti-serum albumin domain antibodies in the development of highly potent, efficacious and long-acting interferon," Protein Eng. Des. Sel. 2010, 23, 271-8.

Atwell et al., "Stable heterodimers from remodeling the domain interface of a homodimer using a phage display library," J. Mol. Biol. 1997, 270, 26-35.

Carter et al., "High level Escherichia coli expression and production of a bivalent humanized antibody fragment," Biotechnology (NY) 1992, 10, 163-67.

Choe et al., "Fc-Binding ligands of immunoglobulin G: An overview of high affinity proteins and peptides," Materials (Basel) 2016, 9, 994.

Cohen et al., "Oxidation of the alarmin IL-33 regulates ST2-dependent inflammation," Nat. Commun. 2015, 6, 8327.

Dudakov et al., "Interleukin-22: immunobiology and pathology," Annu. Rev. Immunol. 2015, 33, 747-85.

Epstein et al., "Biological activity of liposome-encapsulated murine interferon gamma is mediated by a cell membrane receptor," Proc. Natl. Acad. Sci. U.S.A. 1985, 82, 3688-92.

Firan et al., "The MHC class I-related receptor, FcRn, plays an essential role in the maternofetal transfer of gamma-globulin in humans," Int. Immunol. 2001, 13, 993-1002.

Greenberg et al., "A new antigen receptor gene family that undergoes rearrangement and extensive somatic diversification in sharks," Nature 1995, 374, 168-73.

Gunasekaran et al., "Enhancing antibody Fc heterodimer formation through electrostatic steering effects: applications to bispecific molecules and monovalent IgG," J. Biol. Chem. 2010, 285, 19637-46.

Hamers-Casterman et al., "Naturally occurring antibodies devoid of light chains," Nature 1993, 363, 446-8.

Han et al., "IL-15:IL-15 receptor alpha superagonist complex: high-level co-expression in recombinant mammalian cells, purification and characterization," Cytokine 2011, 56, 804-10.

Hassanzadeh-Ghassabeh et al., "Nanobodies and their potential applications," Nanomedicine (Lond) 2013, 8, 1013-26.

Huang et al., "A novel strategy to produce high level and high purity of bioactive IL 15 fusion proteins from mammalian cells," Protein Expr. Purif. 2018, 148, 30-9.

Hudson et al., "Engineered antibodies," Nat. Med. 2003, 9, 129-34.

Hwang et al., "Hepatic uptake and degradation of unilamellar sphingomyelin/cholesterol liposomes: a kinetic study," Proc. Natl. Acad. Sci. U.S.A. 1980, 77, 4030-4.

Kam et al., "Carbon nanotubes as multifunctional biological transporters and near-infrared agents for selective cancer cell destruction," Proc. Natl. Acad. Sci. U.S.A. 2005, 102, 11600-5.

Klein et al., "Progress in overcoming the chain association issue in bispecific heterodimeric IgG antibodies," MAbs 2012, 4, 653-63.

Leonard and Wan, "IL-21 signaling in immunity," F1000Res. 2016, 5(F1000 Faculty Rev), 224.

Liew et al., "Interleukin-33 in health and disease," Nat. Rev. Immunol. 2016, 16, 676-89.

Lin et al., "The role of IL-7 in immunity and cancer," Anticancer Res. 2017, 37, 963-7.

MacKall et al., "Harnessing the biology of IL-7 for therapeutic application," Nat. Rev. Immunol. 2011, 11, 330-42.

Merchant et al., "An efficient route to human bispecific IgG," Nat. Biotechnol. 1998, 16, 677-81.

Moore et al., "A novel bispecific antibody format enables simultaneous bivalent and monovalent co-engagement of distinct target antigens," MAbs 2011, 3, 546-57.

Morrison et al., "Chimeric human antibody molecules: mouse antigen-binding domains with human constant region domains," Proc. Natl. Acad. Sic. U.S.A. 1984, 81, 6851-5.

(56) References Cited

OTHER PUBLICATIONS

Nilvebrant and Hober, "The albumin-binding domain as a scaffold for protein engineering," Comput. Struct. Biotechnol. 2013, 6, e201303009.

Nygren et al., "Analysis and use of the serum albumin binding domains of streptococcal protein G," J. Mol. Recogn. 1988, 1, 69-74.

Pluckthun, Antibodies from *Escherichia coli*. In The Pharmacology of Monoclonal Antibodies; Rosenburg and Moore Eds.; Springer-Verlag: New York, 1994; vol. 113, pp. 269-315.

Ridgway et al., "Knobs-into-holes' engineering of antibody CH3 domains for heavy chain heterodimerization," Protein Eng. 1996, 9, 617-21.

Robinson and Schluns, "The potential and promise of IL-15 in immuno-oncogenic therapies," Immunol. Lett. 2017, 159-68.

Schmidt et al., "Safety and clinical effect of subcutaneous human interleukin-21 in patients with metastatic melanoma or renal cell carcinoma: a phase I trial," Clin. Cancer Res. 2010, 16, 5312-9.

Sheriff and Constantine, "Redefining the minimal antigen-binding fragment," Nat. Struct. Biol. 1996, 3, 733-6.

Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem. 2001, 276, 6591-604.

Sola and Griebenow, "Effects of glycosylation on the stability of protein pharmaceuticals," J. Pharm. Sci. 2009, 98, 1223-45.

Sola et al., "Modulation of protein biophysical properties by chemical glycosylation: biochemical insights and biomedical implications," Cell. Mol. Life Sci. 2007, 64, 2133-52.

Steel et al., "Interleukin-15 biology and its therapeutic implications in cancer," Trends Pharmacol. Sci 2012, 33, 35-41.

Streltsov et al., "Structural evidence for evolution of shark Ig new antigen receptor variable domain antibodies from a cell-surface receptor," Proc. Natl. Acad. Sci. U.S.A. 2004, 101, 12444-9.

Woolven et al., "The structure of the llama heavy chain constant genes reveals a mechanism for heavy-chain antibody formation," Immunogenetics 1999, 50, 98-101.

Yeung et al., "Engineering human IgG1 affinity to human neonatal Fc receptor: impact of affinity improvement on pharmacokinetics in primates," J. Immunol. 2009, 182, 7663-71.

Chichili et al., "Linkers in the structural biology of protein-protein interactions," Protein Sci. 2013, 22, 153-67.

\* cited by examiner

SEQUENCE LISTING

```
<160> NUMBER OF SEQ ID NOS: 345

<210> SEQ ID NO 1
<211> LENGTH: 133
<212> TYPE: PRT
<213> ORGANISM: Homo sapiens

<400> SEQUENCE: 1

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 2
<211> LENGTH: 123
<212> TYPE: PRT
<213> ORGANISM: Homo sapiens

<400> SEQUENCE: 2

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60
```

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu
        115                 120

<210> SEQ ID NO 3
<211> LENGTH: 46
<212> TYPE: PRT
<213> ORGANISM: Artificial Sequence
<220> FEATURE:
<223> OTHER INFORMATION: Synthetic Construct

<400> SEQUENCE: 3

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45

<210> SEQ ID NO 4
<211> LENGTH: 46
<212> TYPE: PRT
<213> ORGANISM: Artificial Sequence
<220> FEATURE:
<223> OTHER INFORMATION: Synthetic Construct

<400> SEQUENCE: 4

Leu Ala Glu Ala Lys Val Leu Ala Asn Arg Glu Leu Asp Lys Tyr Gly
1               5                   10                  15

Val Ser Asp Phe Ala Lys Arg Leu Ile Asn Lys Ala Lys Thr Val Glu
            20                  25                  30

Gly Val Glu Ala Leu Lys Asp Glu Ile Leu Ala Ala Leu Pro
        35                  40                  45

<210> SEQ ID NO 5
<211> LENGTH: 46
<212> TYPE: PRT
<213> ORGANISM: Artificial Sequence
<220> FEATURE:
<223> OTHER INFORMATION: Synthetic Construct

<400> SEQUENCE: 5

Leu Ala Glu Ala Lys Val Leu Ala Asn Arg Glu Leu Asp Lys Tyr Gly
1               5                   10                  15

Val Ser Asp Phe Ala Lys Arg Ala Ile Asn Lys Ala Lys Thr Val Glu
            20                  25                  30

Gly Val Glu Ala Leu Lys Asp Glu Ile Leu Ala Ala Leu Pro
        35                  40                  45

<210> SEQ ID NO 6
<211> LENGTH: 46
<212> TYPE: PRT
<213> ORGANISM: Artificial Sequence
<220> FEATURE:
<223> OTHER INFORMATION: Synthetic Construct

<400> SEQUENCE: 6

```
Leu Ala Glu Ala Lys Val Leu Ala Asn Arg Glu Leu Asp Lys Tyr Gly
1               5                   10                  15

Val Ser Asp Phe Ala Lys Arg Ala Ile Asn Lys Ala Lys Thr Val Glu
            20                  25                  30

Gly Ala Glu Ala Leu Lys Asp Glu Ile Leu Ala Ala Leu Pro
        35                  40                  45
```

<210> SEQ ID NO 7
<211> LENGTH: 46
<212> TYPE: PRT
<213> ORGANISM: Artificial Sequence
<220> FEATURE:
<223> OTHER INFORMATION: Synthetic Construct

<400> SEQUENCE: 7

```
Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45
```

<210> SEQ ID NO 8
<211> LENGTH: 46
<212> TYPE: PRT
<213> ORGANISM: Artificial Sequence
<220> FEATURE:
<223> OTHER INFORMATION: Synthetic Construct

<400> SEQUENCE: 8

```
Leu Ala Glu Ala Lys Val Leu Ala Asn Arg Glu Leu Asp Lys Tyr Gly
1               5                   10                  15

Val Ser Asp Tyr Ala Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45
```

<210> SEQ ID NO 9
<211> LENGTH: 46
<212> TYPE: PRT
<213> ORGANISM: Artificial Sequence
<220> FEATURE:
<223> OTHER INFORMATION: Synthetic Construct

<400> SEQUENCE: 9

```
Leu Ala Glu Ala Lys Val Leu Ala Asn Arg Glu Leu Asp Lys Tyr Gly
1               5                   10                  15

Val Ala Asp Ala Tyr Ala Asn Leu Ile Asn Asn Ala Lys Thr Val Glu
            20                  25                  30

Gly Val Lys Ala Leu Ile Asp Glu Ile Leu Ala Ala Leu Pro
        35                  40                  45
```

<210> SEQ ID NO 10
<211> LENGTH: 45
<212> TYPE: PRT
<213> ORGANISM: Artificial Sequence
<220> FEATURE:
<223> OTHER INFORMATION: Synthetic Construct

<400> SEQUENCE: 10

```
Leu Lys Glu Ala Lys Glu Lys Ala Ile Glu Glu Leu Lys Lys Ala Gly
1               5                   10                  15
```

```
Ile Thr Ser Asp Tyr Tyr Phe Asp Leu Ile Asn Lys Ala Lys Thr Val
            20                  25                  30

Glu Gly Val Asn Ala Leu Lys Asp Glu Ile Leu Lys Ala
        35                  40                  45
```

<210> SEQ ID NO 11
<211> LENGTH: 51
<212> TYPE: PRT
<213> ORGANISM: Artificial Sequence
<220> FEATURE:
<223> OTHER INFORMATION: Synthetic Construct

<400> SEQUENCE: 11

```
Thr Ile Asp Glu Trp Leu Leu Lys Glu Ala Lys Glu Lys Ala Ile Glu
1               5                   10                  15

Glu Leu Lys Lys Ala Gly Ile Thr Ser Asp Tyr Tyr Phe Asp Leu Ile
            20                  25                  30

Asn Lys Ala Lys Thr Val Glu Gly Val Asn Ala Leu Lys Asp Glu Ile
        35                  40                  45

Leu Lys Ala
    50
```

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

```
Gly Gly Thr Ala Ser Ser Tyr Thr
1               5
```

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

```
Ile Leu Trp Ser Gly Asn Thr Thr
1               5
```

<210> SEQ ID NO 14
<211> LENGTH: 16
<212> TYPE: PRT
<213> ORGANISM: Artificial Sequence
<220> FEATURE:
<223> OTHER INFORMATION: Synthetic Construct

<400> SEQUENCE: 14

```
Ala Arg Gly Gly Trp Gly Thr Thr Ala Glu Val Ser Asn Tyr Ala Tyr
1               5                   10                  15
```

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Gly Arg Thr Phe Ser Gly Ser

```
<210> SEQ ID NO 16
<211> LENGTH: 7
<212> TYPE: PRT
<213> ORGANISM: Artificial Sequence
<220> FEATURE:
<223> OTHER INFORMATION: Synthetic Construct

<400> SEQUENCE: 16

Phe Asn Trp Asp Gly Ser Ser
1               5

<210> SEQ ID NO 17
<211> LENGTH: 18
<212> TYPE: PRT
<213> ORGANISM: Artificial Sequence
<220> FEATURE:
<223> OTHER INFORMATION: Synthetic Construct

<400> SEQUENCE: 17

Ala Gly Tyr Tyr His Thr Gly Gly Pro Leu Leu Arg Asp Asn Glu Tyr
1               5                   10                  15

Arg Tyr

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

Gly Ser Ile Ser Ser Ile Arg His
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Val Ser Asn Asp Gly Ser Ala
1               5

<210> SEQ ID NO 20
<211> LENGTH: 12
<212> TYPE: PRT
<213> ORGANISM: Artificial Sequence
<220> FEATURE:
<223> OTHER INFORMATION: Synthetic Construct

<400> SEQUENCE: 20

Asn Ala Asp Thr Trp Gly Trp Pro Gly Ala Asp Tyr
1               5                   10

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21
```

Gly Leu Thr Phe Ser Ser Arg Ala
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Ile Ile His Ser Gly Asp Tyr Thr
1               5

<210> SEQ ID NO 23
<211> LENGTH: 22
<212> TYPE: PRT
<213> ORGANISM: Artificial Sequence
<220> FEATURE:
<223> OTHER INFORMATION: Synthetic Construct

<400> SEQUENCE: 23

Ala Ala Asp Ser Val Asn Lys Arg Gly Ala Ser Ser Tyr Tyr Val Arg
1               5                   10                  15

Thr Thr Glu Tyr Asp Tyr
            20

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct

<400> SEQUENCE: 24

Gly Leu Thr Phe Thr Ser His Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

Ile Ser Trp Ser Gly Gly Asn Thr
1               5

<210> SEQ ID NO 26
<211> LENGTH: 24
<212> TYPE: PRT
<213> ORGANISM: Artificial Sequence
<220> FEATURE:
<223> OTHER INFORMATION: Synthetic Construct

<400> SEQUENCE: 26

Ala Ala Asp Arg Ser Ser Phe Arg Ser Tyr Gly Gly Ser Ser Arg Val
1               5                   10                  15

Lys Val Glu Gly Glu Tyr Asn Tyr
            20

<210> SEQ ID NO 27
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 27

Gly Arg Thr Leu Glu Ser Tyr Val
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Construct

<400> SEQUENCE: 28

Ile Asn Trp Ser Ser Gly Arg Leu
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Ala Ala Gly Arg Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

Gly Arg Ala Leu Ser Ser Tyr Ala
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Ile Thr Trp Asn Gly Gly Arg Thr
1               5

<210> SEQ ID NO 32
<211> LENGTH: 16
<212> TYPE: PRT
<213> ORGANISM: Artificial Sequence
<220> FEATURE:
<223> OTHER INFORMATION: Synthetic Construct

<400> SEQUENCE: 32

Ala Ala Asp Pro Arg Gly Asp Val Tyr His Arg Asp Lys Tyr Asn Ile
1               5                   10                  15

<210> SEQ ID NO 33
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 33

Gly Arg Ala Phe Ser Gly Tyr Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Met Thr Trp Ser Gly Asp Arg Thr
1               5

<210> SEQ ID NO 35
<211> LENGTH: 18
<212> TYPE: PRT
<213> ORGANISM: Artificial Sequence
<220> FEATURE:
<223> OTHER INFORMATION: Synthetic Construct

<400> SEQUENCE: 35

Ala Thr Lys Leu Gly Thr Tyr Tyr Asn Ser His Asp Leu Arg Arg Pro
1               5                   10                  15

Asp Tyr

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Gly Ile Thr Phe Pro Val Asn Ala
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Ile Ser Ala Gly Gly Thr Thr
1               5

<210> SEQ ID NO 38
<211> LENGTH: 12
<212> TYPE: PRT
<213> ORGANISM: Artificial Sequence
<220> FEATURE:
<223> OTHER INFORMATION: Synthetic Construct

<400> SEQUENCE: 38

Tyr Leu Gln Arg Arg Ile Gly Met Leu Arg Asp Tyr
1               5                   10

<210> SEQ ID NO 39
<211> LENGTH: 8
<212> TYPE: PRT
<213> ORGANISM: Artificial Sequence

```
<220> FEATURE:
<223> OTHER INFORMATION: Synthetic Construct

<400> SEQUENCE: 39

Gly Phe Thr Phe Asp Asn Lys Gln
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct

<400> SEQUENCE: 40

Ile Ser Ile Ser Asp Gly Ala Thr
1               5

<210> SEQ ID NO 41
<211> LENGTH: 19
<212> TYPE: PRT
<213> ORGANISM: Artificial Sequence
<220> FEATURE:
<223> OTHER INFORMATION: Synthetic Construct

<400> SEQUENCE: 41

Ala Thr Asn Pro Thr Gln Ile Met Ile Gly Thr Met Arg Cys Asp Leu
1               5                   10                  15

Glu Ser Lys

<210> SEQ ID NO 42
<211> LENGTH: 8
<212> TYPE: PRT
<213> ORGANISM: Artificial Sequence
<220> FEATURE:
<223> OTHER INFORMATION: Synthetic Construct

<400> SEQUENCE: 42

Gly Arg Thr Asn Ser Thr Val Ala
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Construct

<400> SEQUENCE: 43

Ile Val Trp Ser Asn Gly Tyr Ser
1               5

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44

Ala Leu Asp Ile Arg Asp Ser Glu Ile Thr Val Gln Gln Lys Tyr
1               5                   10                  15

<210> SEQ ID NO 45
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 45

Gly Pro Thr Tyr Thr Thr Glu Thr
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Construct

<400> SEQUENCE: 46

Ile Arg Trp Arg Gly Ala His Thr
1               5

<210> SEQ ID NO 47
<211> LENGTH: 17
<212> TYPE: PRT
<213> ORGANISM: Artificial Sequence
<220> FEATURE:
<223> OTHER INFORMATION: Synthetic Construct

<400> SEQUENCE: 47

Ala Ala Ser Arg Ser Phe Asp Tyr Pro Arg Arg Glu Asp Glu Tyr Arg
1               5                   10                  15

Tyr

<210> SEQ ID NO 48
<211> LENGTH: 8
<212> TYPE: PRT
<213> ORGANISM: Artificial Sequence
<220> FEATURE:
<223> OTHER INFORMATION: Synthetic Construct

<400> SEQUENCE: 48

Gly Arg Thr Phe Ser Pro Tyr Thr
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct

<400> SEQUENCE: 49

Ile Thr Trp Lys Ser Gly Ser Thr
1               5

<210> SEQ ID NO 50
<211> LENGTH: 17
<212> TYPE: PRT
<213> ORGANISM: Artificial Sequence
<220> FEATURE:
<223> OTHER INFORMATION: Synthetic Construct

<400> SEQUENCE: 50

Ala Ser Thr Ser Phe Ala Tyr Gly Leu Thr Asn Ser Asn Lys Tyr Asn
1               5                   10                  15

Tyr
```

```
<210> SEQ ID NO 51
<211> LENGTH: 8
<212> TYPE: PRT
<213> ORGANISM: Artificial Sequence
<220> FEATURE:
<223> OTHER INFORMATION: Synthetic Construct

<400> SEQUENCE: 51

Gly Arg Ser Phe Ser Thr Tyr Arg
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Construct

<400> SEQUENCE: 52

Ile Thr Ala Ser Gly Ser Trp Thr
1               5

<210> SEQ ID NO 53
<211> LENGTH: 17
<212> TYPE: PRT
<213> ORGANISM: Artificial Sequence
<220> FEATURE:
<223> OTHER INFORMATION: Synthetic Construct

<400> SEQUENCE: 53

Ala Ala Ala Glu Ile Leu Thr Ala Ile Thr Thr Ser Ser Asp Tyr Asp
1               5                   10                  15

Tyr

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct

<400> SEQUENCE: 54

Gly Arg Met Phe Ser Ser Tyr Ala
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic Construct

<400> SEQUENCE: 55

Ile Ser Tyr Asn Gly Gly Ala Thr
1               5

<210> SEQ ID NO 56
<211> LENGTH: 18
<212> TYPE: PRT
<213> ORGANISM: Artificial Sequence
<220> FEATURE:
<223> OTHER INFORMATION: Synthetic Construct

<400> SEQUENCE: 56

Ala Ala Arg Gly Gly His Trp Tyr Ser Ile His Asp Pro Ser Asn Phe
1               5                   10                  15
```

Arg Ala

<210> SEQ ID NO 57
<211> LENGTH: 8
<212> TYPE: PRT
<213> ORGANISM: Artificial Sequence
<220> FEATURE:
<223> OTHER INFORMATION: Synthetic Construct

<400> SEQUENCE: 57

Gly Arg Arg Val Arg Thr Ala Ala
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Construct

<400> SEQUENCE: 58

Ile Thr Trp Arg Gly Gly Glu Arg
1               5

<210> SEQ ID NO 59
<211> LENGTH: 17
<212> TYPE: PRT
<213> ORGANISM: Artificial Sequence
<220> FEATURE:
<223> OTHER INFORMATION: Synthetic Construct

<400> SEQUENCE: 59

Ala Ala Gly Pro Trp Tyr Thr Asn His Asp Thr Ser Gln Gly Tyr Asn
1               5                   10                  15

Tyr

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

Gly Arg Thr Ile Ser Asn Tyr Ala
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Construct

<400> SEQUENCE: 61

Ile Asn Trp Asn Gly Gly Gly Ile
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic Construct

<400> SEQUENCE: 62

```
Ala Ala Gln Arg Ala Gly Thr Trp Thr Tyr
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Synthetic Construct

<400> SEQUENCE: 63

Gly Ile Ser Asp Ile Ser Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic Construct

<400> SEQUENCE: 64

Ile Gly Ser Gly Gly Asn Thr
1               5

<210> SEQ ID NO 65
<211> LENGTH: 13
<212> TYPE: PRT
<213> ORGANISM: Artificial Sequence
<220> FEATURE:
<223> OTHER INFORMATION: Synthetic Construct

<400> SEQUENCE: 65

Asn Ala Ala Gln Arg Ile Gly Ala Gly Pro Ile Val Leu
1               5                   10

<210> SEQ ID NO 66
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 4

<400> SEQUENCE: 66

Gly Ser Gly Ser
1

<210> SEQ ID NO 67
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 4

<400> SEQUENCE: 67

Gly Gly Ser Gly
1

<210> SEQ ID NO 68
<211> LENGTH: 5
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of up to 3

<400> SEQUENCE: 68

Gly Gly Gly Gly Ser
1               5

<210> SEQ ID NO 69
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 3

<400> SEQUENCE: 69

Pro Ala Pro Ala
1

<210> SEQ ID NO 70
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 3

<400> SEQUENCE: 70

Pro Gln Pro Gln
1

<210> SEQ ID NO 71
<211> LENGTH: 8
<212> TYPE: PRT
<213> ORGANISM: Artificial Sequence
<220> FEATURE:
<223> OTHER INFORMATION: Synthetic Construct

<400> SEQUENCE: 71

Ile Lys Arg Ala Asp Ala Ala Pro
1               5

<210> SEQ ID NO 72
<211> LENGTH: 12
<212> TYPE: PRT
<213> ORGANISM: Artificial Sequence
<220> FEATURE:
<223> OTHER INFORMATION: Synthetic Construct

<400> SEQUENCE: 72

Ala Glu Ala Ala Ala Lys Glu Ala Ala Ala Lys Ala
1               5                   10

<210> SEQ ID NO 73
<211> LENGTH: 12
<212> TYPE: PRT
<213> ORGANISM: Artificial Sequence
```

```
<220> FEATURE:
<223> OTHER INFORMATION: Synthetic Construct

<400> SEQUENCE: 73

Gly Thr Asn Glu Val Cys Lys Cys Pro Lys Cys Pro
1               5                   10

<210> SEQ ID NO 74
<211> LENGTH: 35
<212> TYPE: PRT
<213> ORGANISM: Artificial Sequence
<220> FEATURE:
<223> OTHER INFORMATION: Synthetic Construct

<400> SEQUENCE: 74

Glu Pro Lys Ile Pro Gln Pro Gln Pro Lys Pro Gln Pro Gln Pro Gln
1               5                   10                  15

Pro Gln Pro Lys Pro Gln Pro Lys Pro Glu Pro Glu Cys Thr Cys Pro
            20                  25                  30

Lys Cys Pro
        35

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct

<400> SEQUENCE: 75

Gly His Thr Phe Ser Val Tyr Ala
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Construct

<400> SEQUENCE: 76

Ile Asn Trp Gly Asp Gly Leu Thr
1               5

<210> SEQ ID NO 77
<211> LENGTH: 11
<212> TYPE: PRT
<213> ORGANISM: Artificial Sequence
<220> FEATURE:
<223> OTHER INFORMATION: Synthetic Construct

<400> SEQUENCE: 77

Ala Ala Arg Gln Arg Arg Glu Gly Trp Asp Tyr
1               5                   10

<210> SEQ ID NO 78
<211> LENGTH: 8
<212> TYPE: PRT
<213> ORGANISM: Artificial Sequence
<220> FEATURE:
<223> OTHER INFORMATION: Synthetic Construct

<400> SEQUENCE: 78

Gly Arg Thr Ala Ser Ser Tyr Val
1               5
```

```
<210> SEQ ID NO 79
<211> LENGTH: 8
<212> TYPE: PRT
<213> ORGANISM: Artificial Sequence
<220> FEATURE:
<223> OTHER INFORMATION: Synthetic Construct

<400> SEQUENCE: 79

Val Ser Arg Ser Gly Val Ser Thr
1               5

<210> SEQ ID NO 80
<211> LENGTH: 19
<212> TYPE: PRT
<213> ORGANISM: Artificial Sequence
<220> FEATURE:
<223> OTHER INFORMATION: Synthetic Construct

<400> SEQUENCE: 80

Ala Ala Asp Gly Lys Asn Phe Ser Asn Arg Trp Trp Ser Arg Asp Glu
1               5                   10                  15

Tyr Lys Tyr

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct

<400> SEQUENCE: 81

Gly Arg Thr Glu Thr Thr Tyr Asn
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic Construct

<400> SEQUENCE: 82

Ile Ser Arg Gly Ala Thr Ile Thr
1               5

<210> SEQ ID NO 83
<211> LENGTH: 16
<212> TYPE: PRT
<213> ORGANISM: Artificial Sequence
<220> FEATURE:
<223> OTHER INFORMATION: Synthetic Construct

<400> SEQUENCE: 83

Ala Ala Ser Phe Thr Asn Leu Ala Val Val Ala Arg Asp Tyr Tyr Tyr
1               5                   10                  15

<210> SEQ ID NO 84
<211> LENGTH: 8
<212> TYPE: PRT
<213> ORGANISM: Artificial Sequence
<220> FEATURE:
<223> OTHER INFORMATION: Synthetic Construct

<400> SEQUENCE: 84

Gly Arg Thr Phe Ser His Tyr Ala
1               5
```

<210> SEQ ID NO 85
<211> LENGTH: 8
<212> TYPE: PRT
<213> ORGANISM: Artificial Sequence
<220> FEATURE:
<223> OTHER INFORMATION: Synthetic Construct

<400> SEQUENCE: 85

Ile Thr Glu Ser Pro Asp Ser Thr
1               5

<210> SEQ ID NO 86
<211> LENGTH: 21
<212> TYPE: PRT
<213> ORGANISM: Artificial Sequence
<220> FEATURE:
<223> OTHER INFORMATION: Synthetic Construct

<400> SEQUENCE: 86

Ala Ala Ala Arg Ser Thr Leu Arg Trp Pro Phe Arg Gly Gln Gly Gln
1               5                   10                  15

Tyr Asp Tyr Asp Tyr
            20

<210> SEQ ID NO 87
<211> LENGTH: 8
<212> TYPE: PRT
<213> ORGANISM: Artificial Sequence
<220> FEATURE:
<223> OTHER INFORMATION: Synthetic Construct

<400> SEQUENCE: 87

Gly Arg Thr Trp Ser Thr Tyr Pro
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct

<400> SEQUENCE: 88

Ile Arg Trp Thr Thr Gly Ser Thr
1               5

<210> SEQ ID NO 89
<211> LENGTH: 15
<212> TYPE: PRT
<213> ORGANISM: Artificial Sequence
<220> FEATURE:
<223> OTHER INFORMATION: Synthetic Construct

<400> SEQUENCE: 89

Asn Ala Glu Val Arg Ala Trp Tyr Asn Arg Arg Lys Ala Asp Tyr
1               5                   10                  15

<210> SEQ ID NO 90
<211> LENGTH: 8
<212> TYPE: PRT
<213> ORGANISM: Artificial Sequence
<220> FEATURE:
<223> OTHER INFORMATION: Synthetic Construct

<400> SEQUENCE: 90

Gly Arg Thr Asp Ser Thr Gly Ile
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic Construct

<400> SEQUENCE: 91

Ile Arg Trp Ser Asn Asn Tyr Ala
1               5

<210> SEQ ID NO 92
<211> LENGTH: 15
<212> TYPE: PRT
<213> ORGANISM: Artificial Sequence
<220> FEATURE:
<223> OTHER INFORMATION: Synthetic Construct

<400> SEQUENCE: 92

Ala Ala Gly Thr Gly Trp Gly Phe Ser Ile Ser Asp Tyr Asn Tyr
1               5                   10                  15

<210> SEQ ID NO 93
<211> LENGTH: 8
<212> TYPE: PRT
<213> ORGANISM: Artificial Sequence
<220> FEATURE:
<223> OTHER INFORMATION: Synthetic Construct

<400> SEQUENCE: 93

Gly Arg Ser Phe Asn Thr Tyr Ala
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct

<400> SEQUENCE: 94

Ile Thr Trp Ser Gly Ala Ser Thr
1               5

<210> SEQ ID NO 95
<211> LENGTH: 18
<212> TYPE: PRT
<213> ORGANISM: Artificial Sequence
<220> FEATURE:
<223> OTHER INFORMATION: Synthetic Construct

<400> SEQUENCE: 95

Ala Ala Ser Ser Gln Tyr Gly Gly Ala Ala Ser Ala Pro Thr Ala Tyr
1               5                   10                  15

Leu Tyr

<210> SEQ ID NO 96
<211> LENGTH: 8
<212> TYPE: PRT
<213> ORGANISM: Artificial Sequence
<220> FEATURE:
<223> OTHER INFORMATION: Synthetic Construct

<400> SEQUENCE: 96

```
Gly Arg Thr Ile Ser Asn Tyr Ala
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic Construct

<400> SEQUENCE: 97

Val Ser Trp Thr Gly His Gly Thr
1               5

<210> SEQ ID NO 98
<211> LENGTH: 19
<212> TYPE: PRT
<213> ORGANISM: Artificial Sequence
<220> FEATURE:
<223> OTHER INFORMATION: Synthetic Construct

<400> SEQUENCE: 98

Ala Ala Asp Gly Lys Asn Phe Ser Asn Arg Trp Trp Ser Arg Asp Glu
1               5                   10                  15

Tyr Lys Tyr

<210> SEQ ID NO 99
<211> LENGTH: 8
<212> TYPE: PRT
<213> ORGANISM: Artificial Sequence
<220> FEATURE:
<223> OTHER INFORMATION: Synthetic Construct

<400> SEQUENCE: 99

Gly Ser Leu Ser Ser Ile Asn Thr
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic Construct

<400> SEQUENCE: 100

Ile Ser Ser Ser Gly Ser Thr
1               5

<210> SEQ ID NO 101
<211> LENGTH: 14
<212> TYPE: PRT
<213> ORGANISM: Artificial Sequence
<220> FEATURE:
<223> OTHER INFORMATION: Synthetic Construct

<400> SEQUENCE: 101

Ala Ala Gly Lys Gly Ser Thr Trp Tyr Asn Gly Ala Tyr Lys
1               5                   10

<210> SEQ ID NO 102
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 102

Glu Arg Thr Tyr Ser Arg Tyr Ala
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic Construct

<400> SEQUENCE: 103

Ile Ser Trp Ser Gly Thr
1               5

<210> SEQ ID NO 104
<211> LENGTH: 21
<212> TYPE: PRT
<213> ORGANISM: Artificial Sequence
<220> FEATURE:
<223> OTHER INFORMATION: Synthetic Construct

<400> SEQUENCE: 104

Ala Tyr Gly Tyr Tyr Ser Gly Ala Ala Asn Tyr Arg Asp Leu Ala Ser
1               5                   10                  15

Ser Thr Tyr Arg Tyr
            20

<210> SEQ ID NO 105
<211> LENGTH: 8
<212> TYPE: PRT
<213> ORGANISM: Artificial Sequence
<220> FEATURE:
<223> OTHER INFORMATION: Synthetic Construct

<400> SEQUENCE: 105

Gly Arg Thr Phe Ser Ser Val Ser
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic Construct

<400> SEQUENCE: 106

Ala Asp Trp Ser Gly Thr Thr
1               5

<210> SEQ ID NO 107
<211> LENGTH: 12
<212> TYPE: PRT
<213> ORGANISM: Artificial Sequence
<220> FEATURE:
<223> OTHER INFORMATION: Synthetic Construct

<400> SEQUENCE: 107

Ala Ala Ser Asp Pro Arg Arg Ser Ala Tyr Lys Tyr
1               5                   10

<210> SEQ ID NO 108
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 108

Gly Arg Thr Phe Gly Ser Tyr Thr
1               5

<210> SEQ ID NO 109
<211> LENGTH: 8
<212> TYPE: PRT
<213> ORGANISM: Artificial Sequence
<220> FEATURE:
<223> OTHER INFORMATION: Synthetic Construct

<400> SEQUENCE: 109

Ile Ser Arg Ser Gly Gly Ser Thr
1               5

<210> SEQ ID NO 110
<211> LENGTH: 15
<212> TYPE: PRT
<213> ORGANISM: Artificial Sequence
<220> FEATURE:
<223> OTHER INFORMATION: Synthetic Construct

<400> SEQUENCE: 110

Ala Ala Ser Asn Thr Gly Gly Arg Ala Ser Ala Ser Tyr Lys Tyr
1               5                   10                  15

<210> SEQ ID NO 111
<211> LENGTH: 8
<212> TYPE: PRT
<213> ORGANISM: Artificial Sequence
<220> FEATURE:
<223> OTHER INFORMATION: Synthetic Construct

<400> SEQUENCE: 111

Gly Gly Thr Phe Ile Arg Tyr Ala
1               5

<210> SEQ ID NO 112
<211> LENGTH: 8
<212> TYPE: PRT
<213> ORGANISM: Artificial Sequence
<220> FEATURE:
<223> OTHER INFORMATION: Synthetic Construct

<400> SEQUENCE: 112

Ile Ser Gln Thr Gly Gly Ser Thr
1               5

<210> SEQ ID NO 113
<211> LENGTH: 15
<212> TYPE: PRT
<213> ORGANISM: Artificial Sequence
<220> FEATURE:
<223> OTHER INFORMATION: Synthetic Construct

<400> SEQUENCE: 113

Ala Val Ser Thr Val Gln Ser Lys Arg Met Leu Met Tyr Gly Tyr
1               5                   10                  15

<210> SEQ ID NO 114
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 114

Gly Arg Thr Ala Arg Ser Tyr Asn
1               5

<210> SEQ ID NO 115
<211> LENGTH: 8
<212> TYPE: PRT
<213> ORGANISM: Artificial Sequence
<220> FEATURE:
<223> OTHER INFORMATION: Synthetic Construct

<400> SEQUENCE: 115

Ile Ile Ser Ser Pro Arg Gly Thr
1               5

<210> SEQ ID NO 116
<211> LENGTH: 17
<212> TYPE: PRT
<213> ORGANISM: Artificial Sequence
<220> FEATURE:
<223> OTHER INFORMATION: Synthetic Construct

<400> SEQUENCE: 116

Ala Ala Thr Thr Ser Ser Thr Tyr Tyr Ser Asp Lys Thr Tyr Tyr Ala
1               5                   10                  15

Tyr

<210> SEQ ID NO 117
<211> LENGTH: 8
<212> TYPE: PRT
<213> ORGANISM: Artificial Sequence
<220> FEATURE:
<223> OTHER INFORMATION: Synthetic Construct

<400> SEQUENCE: 117

Gly Arg Ile Leu Ala Asp Thr Pro
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic Construct

<400> SEQUENCE: 118

Ile Thr Ser Gly Gly Thr Thr
1               5

<210> SEQ ID NO 119
<211> LENGTH: 11
<212> TYPE: PRT
<213> ORGANISM: Artificial Sequence
<220> FEATURE:
<223> OTHER INFORMATION: Synthetic Construct

<400> SEQUENCE: 119

Ala Ala Asn Ala Glu Gly Ser Gly Ser Arg Tyr
1               5                   10

<210> SEQ ID NO 120
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 120

Gly Arg Ile Leu Ala Asp Thr Pro
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic Construct

<400> SEQUENCE: 121

Ile Thr Ser Gly Gly Thr Thr
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic Construct

<400> SEQUENCE: 122

Lys Val Met Tyr His Ala Gly Ser
1               5

<210> SEQ ID NO 123
<211> LENGTH: 125
<212> TYPE: PRT
<213> ORGANISM: Artificial Sequence
<220> FEATURE:
<223> OTHER INFORMATION: Synthetic Construct

<400> SEQUENCE: 123

Gln Val Gln Leu Val Glu Ser Gly Gly Gly Leu Val Gln Ala Gly Gly
1               5                   10                  15

Ser Leu Arg Leu Ser Cys Val Ala Ser Gly Gly Thr Ala Ser Ser Tyr
            20                  25                  30

Thr Met Ala Trp Phe Arg Gln Ala Pro Gly Lys Glu Arg Asp Phe Val
        35                  40                  45

Ala Ser Ile Leu Trp Ser Gly Asn Thr Thr Ala Tyr Ala Asn Phe Val
    50                  55                  60

Lys Gly Arg Phe Thr Ile Ser Arg Asp Asn Ala Lys Asn Met Met Tyr
65                  70                  75                  80

Leu Gln Met Asn Ser Leu Lys Pro Glu Asp Thr Ala Val Tyr Tyr Cys
                85                  90                  95

Ala Arg Ala Arg Gly Gly Trp Gly Thr Thr Ala Glu Val Ser Asn Tyr
            100                 105                 110

Ala Tyr Trp Gly Gln Gly Thr Gln Val Thr Val Ser Ser
        115                 120                 125

<210> SEQ ID NO 124
<211> LENGTH: 125
<212> TYPE: PRT
<213> ORGANISM: Artificial Sequence
<220> FEATURE:
<223> OTHER INFORMATION: Synthetic Construct

<400> SEQUENCE: 124

Gln Val Gln Leu Val Glu Ser Gly Gly Gly Leu Val Gln Ala Gly Gly
1               5                   10                  15
```

```
Ser Leu Arg Leu Ser Cys Ala Ala Ser Gly Arg Thr Phe Ser Gly Ser
        20                  25                  30

Met Gly Trp Phe Arg Gln Ala Pro Gly Glu Glu Arg Lys Leu Val Ser
        35                  40                  45

Thr Phe Asn Trp Asp Gly Ser Ser Tyr Tyr Ala Asp Ser Val Lys Gly
50                  55                  60

Arg Phe Thr Ile Ser Lys Asp Asn Ala Lys Asn Thr Met Tyr Leu Gln
65                  70                  75                  80

Met Asn Ser Leu Lys Pro Glu Asp Thr Ala Val Tyr Tyr Cys Ala Ala
                85                  90                  95

Ala Gly Tyr Tyr His Thr Gly Gly Pro Leu Leu Arg Asp Asn Glu Tyr
            100                 105                 110

Arg Tyr Trp Gly Gln Gly Thr Gln Val Thr Val Ser Ser
        115                 120                 125

<210> SEQ ID NO 125
<211> LENGTH: 119
<212> TYPE: PRT
<213> ORGANISM: Artificial Sequence
<220> FEATURE:
<223> OTHER INFORMATION: Synthetic Construct

<400> SEQUENCE: 125

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ser Ile Arg
        20                  25                  30

His Met Arg Trp Tyr Arg Gln Ala Pro Gly Lys Gln Arg Glu Leu Val
        35                  40                  45

Ala Thr Val Ser Asn Asp Gly Ser Ala Tyr Tyr Leu Gly Ser Val Lys
50                  55                  60

Gly Arg Phe Thr Ile Ser Arg Thr Asn Ala Lys Asn Thr Leu Leu Tyr
65                  70                  75                  80

Leu Gln Met Asn Ser Leu Lys Pro Glu Asp Ser Ala Leu Tyr Ile Cys
                85                  90                  95

Asn Ala Asp Thr Trp Gly Trp Pro Gly Ala Asp Tyr Trp Gly Gln Gly
            100                 105                 110

Thr Gln Val Thr Val Ser Ser
        115

<210> SEQ ID NO 126
<211> LENGTH: 129
<212> TYPE: PRT
<213> ORGANISM: Artificial Sequence
<220> FEATURE:
<223> OTHER INFORMATION: Synthetic Construct

<400> SEQUENCE: 126

Gln Val Gln Leu Val Glu Ser Gly Gly Gly Leu Val Gln Ala Gly Gly
1               5                   10                  15

Ser Leu Thr Leu Ser Cys Ser Val Ser Gly Leu Thr Phe Ser Ser Arg
        20                  25                  30

Ala Met Gly Trp Phe Arg Gln Ala Ser Gly Lys Glu Arg Glu Phe Val
        35                  40                  45

Ala Ala Ile Ile His Ser Gly Asp Tyr Thr Tyr Tyr Ala Asp Ser Val
50                  55                  60

Lys Gly Arg Phe Thr Val Ser Arg Asp Asn Ala Lys Asn Thr Val Tyr
```

```
                65                  70                  75                  80
Leu Gln Met Asn Ser Leu Lys Leu Gly Asp Thr Ala Val Tyr Tyr Cys
                    85                  90                  95

Ala Ala Asp Ser Val Asn Lys Arg Gly Ala Ser Ser Tyr Tyr Val Arg
                    100                 105                 110

Thr Thr Glu Tyr Asp Tyr Trp Gly Gln Gly Thr Gln Val Thr Val Ser
                    115                 120                 125

Ser

<210> SEQ ID NO 127
<211> LENGTH: 131
<212> TYPE: PRT
<213> ORGANISM: Artificial Sequence
<220> FEATURE:
<223> OTHER INFORMATION: Synthetic Construct

<400> SEQUENCE: 127

Gln Val Gln Leu Val Glu Ser Gly Gly Gly Leu Val Gln Ala Gly Gly
1               5                   10                  15

Ser Leu Thr Leu Ser Cys Ala Ala Ser Gly Leu Thr Phe Thr Ser His
                20                  25                  30

Thr Met Gly Trp Phe Arg Gln Ala Pro Gly Lys Glu Arg Glu Phe Val
                35                  40                  45

Ala Thr Ile Ser Trp Ser Gly Gly Asn Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80

Pro Gln Met Asn Ser Leu Lys Pro Glu Asp Ala Ala Val Tyr Tyr Cys
                85                  90                  95

Ala Ala Asp Arg Ser Ser Phe Arg Ser Tyr Gly Gly Ser Ser Arg Val
                100                 105                 110

Lys Val Glu Gly Glu Tyr Asn Tyr Trp Gly Gln Gly Thr Arg Val Thr
                115                 120                 125

Val Ser Ser
        130

<210> SEQ ID NO 128
<211> LENGTH: 112
<212> TYPE: PRT
<213> ORGANISM: Artificial Sequence
<220> FEATURE:
<223> OTHER INFORMATION: Synthetic Construct

<400> SEQUENCE: 128

Gln Val Gln Leu Val Glu Ser Gly Gly Gly Leu Val Glu Ala Gly Asp
1               5                   10                  15

Ser Leu Arg Leu Ser Cys Val Val Ser Gly Arg Thr Leu Glu Ser Tyr
                20                  25                  30

Val Met Ala Trp Phe Arg Gln Ala Pro Gly Lys Glu Arg Glu Ala Val
                35                  40                  45

Ala Ser Ile Asn Trp Ser Ser Gly Arg Leu Ile Tyr Ala Asp Phe Val
            50                  55                  60

Lys Gly Arg Phe Thr Ile Ser Arg Asp Tyr Glu Lys Asn Thr Ile Tyr
65                  70                  75                  80

Leu Ser Met Asn Asn Leu Lys Pro Glu Asp Thr Ala Val Tyr Tyr Cys
                85                  90                  95

Ala Ala Gly Arg Tyr Trp Gly Gln Gly Thr Gln Val Thr Val Ser Ser
```

<210> SEQ ID NO 129
<211> LENGTH: 123
<212> TYPE: PRT
<213> ORGANISM: Artificial Sequence
<220> FEATURE:
<223> OTHER INFORMATION: Synthetic Construct

<400> SEQUENCE: 129

Gln Val Gln Leu Val Glu Ser Gly Gly Gly Leu Val Gln Ala Gly Gly
1               5                   10                  15

Ser Leu Arg Leu Ser Cys Thr Ala Ser Gly Arg Ala Leu Ser Ser Tyr
            20                  25                  30

Ala Val Gly Trp Phe Arg Gln Ala Pro Gly Lys Glu Arg Glu Phe Val
        35                  40                  45

Ala Ala Ile Thr Trp Asn Gly Arg Thr Tyr Tyr Ala Asp Ser Glu
    50                  55                  60

Lys Gly Arg Ser Ile Ile Ser Met Asp Val Ala Lys Ser Thr Val Tyr
65                  70                  75                  80

Leu Gln Met Asn Ser Leu Lys Leu Glu Asp Thr Ala Val Tyr Tyr Cys
                85                  90                  95

Ala Ala Asp Pro Arg Gly Asp Val Tyr His Arg Asp Lys Tyr Asn Ile
            100                 105                 110

Trp Gly Gln Gly Thr Gln Val Thr Val Ser Ser
        115                 120

<210> SEQ ID NO 130
<211> LENGTH: 125
<212> TYPE: PRT
<213> ORGANISM: Artificial Sequence
<220> FEATURE:
<223> OTHER INFORMATION: Synthetic Construct

<400> SEQUENCE: 130

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Phe Ser Gly Tyr
            20                  25                  30

Thr Met Ala Trp Phe Arg Gln Ala Pro Gly Lys Glu Arg Glu Phe Val
        35                  40                  45

Ala Gly Met Thr Trp Ser Gly Asp Arg Thr Tyr Tyr Ser Asp Ser Val
    50                  55                  60

Lys Asp Arg Phe Ala Ile Ser Arg Asp Asn Val Lys Asn Met Gly Tyr
65                  70                  75                  80

Leu Gln Met Asn Ser Leu Lys Pro Glu Asp Thr Ala Val Tyr Tyr Cys
                85                  90                  95

Ala Thr Lys Leu Gly Thr Tyr Tyr Asn Ser His Asp Leu Arg Arg Pro
            100                 105                 110

Asp Tyr Trp Gly Gln Gly Thr Gln Val Thr Val Ser Ser
        115                 120                 125

<210> SEQ ID NO 131
<211> LENGTH: 118
<212> TYPE: PRT
<213> ORGANISM: Artificial Sequence
<220> FEATURE:
<223> OTHER INFORMATION: Synthetic Construct

<400> SEQUENCE: 131

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Pro Val Asn
            20                  25                  30

Ala Tyr Gly Trp Tyr Arg Gln Ala Pro Gly Lys Gln Arg Asp Leu Val
        35                  40                  45

Ala Ile Ile Ser Ala Gly Gly Thr Thr Asn Tyr Ala Asp Ser Val Lys
50                      55                  60

Gly Arg Phe Ala Ile Ser Lys Asp Asn Val Asn Asn Thr Val Tyr Leu
65                  70                  75                  80

Gln Met Asn Ser Leu Thr Ser Glu Asp Thr Gly Val Tyr Tyr Cys Tyr
                85                  90                  95

Leu Gln Arg Arg Ile Gly Met Leu Arg Asp Tyr Trp Gly Gln Gly Thr
            100                 105                 110

Gln Val Thr Val Ser Ser
            115
```

<210> SEQ ID NO 132
<211> LENGTH: 130
<212> TYPE: PRT
<213> ORGANISM: Artificial Sequence
<220> FEATURE:
<223> OTHER INFORMATION: Synthetic Construct

<400> SEQUENCE: 132

```
Gln Arg Gln Val Ala Glu Ser Gly Gly Gly Ser Val Gln Pro Gly Gly
1               5                   10                  15

Ser Leu Arg Leu Ser Cys Ala Ala Ser Gly Phe Thr Phe Asp Asn Lys
            20                  25                  30

Gln Val Ala Trp Phe Arg Glu Val Pro Gly Lys Glu Arg Glu Gln Ile
        35                  40                  45

Ser Cys Ile Ser Ile Ser Asp Gly Ala Thr Arg Tyr Thr Asp Ser Val
50                      55                  60

Lys Gly Arg Phe Ala Val Ser Arg Asp Tyr Ala Thr Asn Thr Val Val
65                  70                  75                  80

Leu Gln Met Asn Asn Leu Arg Pro Glu Asp Thr Ala Ile Tyr Tyr Cys
                85                  90                  95

Ala Thr Asn Pro Thr Gln Ile Met Ile Gly Thr Met Arg Cys Asp Leu
            100                 105                 110

Glu Ser Lys Trp Tyr Gly Thr Trp Gly Pro Gly Thr Gln Val Thr Val
        115                 120                 125

Ser Gly
    130
```

<210> SEQ ID NO 133
<211> LENGTH: 122
<212> TYPE: PRT
<213> ORGANISM: Artificial Sequence
<220> FEATURE:
<223> OTHER INFORMATION: Synthetic Construct

<400> SEQUENCE: 133

```
Gln Val Gln Leu Val Glu Ser Gly Gly Gly Leu Val Arg Ala Gly Asp
1               5                   10                  15

Ser Leu Arg Leu Ser Cys Ala Ala Ser Gly Arg Thr Asn Ser Thr Val
            20                  25                  30

Ala Met Gly Trp Phe Arg Gln Thr Pro Gly Lys Glu Arg Glu Phe Val
```

```
                 35                  40                  45
Ala Val Ile Val Trp Ser Asn Gly Tyr Ser His Tyr Ala Asp Ser Val
        50                  55                  60
Lys Asp Arg Phe Ser Ile Ser Arg Asn Lys Ala Arg Asn Thr Val Tyr
 65                  70                  75                  80
Leu Gln Leu Asn Ser Leu Lys Pro Glu Asp Thr Ala Val Tyr Tyr Cys
                 85                  90                  95
Ala Leu Asp Ile Arg Asp Ser Glu Ile Thr Val Gln Lys Tyr Trp
                100                 105                 110
Gly Met Gly Thr Gln Val Thr Val Ser Ser
            115                 120

<210> SEQ ID NO 134
<211> LENGTH: 124
<212> TYPE: PRT
<213> ORGANISM: Artificial Sequence
<220> FEATURE:
<223> OTHER INFORMATION: Synthetic Construct

<400> SEQUENCE: 134

Gln Val Gln Leu Ile Glu Ser Gly Gly Gly Leu Val Gln Pro Gly Asp
 1               5                  10                  15
Ser Leu Arg Leu Ser Cys Ala Ala Ser Gly Pro Thr Tyr Thr Thr Glu
                20                  25                  30
Thr Met Gly Trp Phe Arg Gln Ala Pro Gly Lys Glu Arg Glu Phe Val
            35                  40                  45
Ser Ser Ile Arg Trp Arg Gly Ala His Thr Asn Tyr Gly Asp Phe Val
        50                  55                  60
Lys Gly Arg Phe Thr Ile Ser Lys Asp Ser Ala Lys Gln Thr Val Tyr
 65                  70                  75                  80
Leu Gln Met Asn Ser Leu Lys Pro Glu Asp Thr Ala Val Tyr Phe Cys
                 85                  90                  95
Ala Ala Ser Arg Ser Phe Asp Tyr Pro Arg Arg Glu Asp Glu Tyr Arg
                100                 105                 110
Tyr Trp Gly Gln Gly Thr Gln Val Thr Val Ser Ser
            115                 120

<210> SEQ ID NO 135
<211> LENGTH: 124
<212> TYPE: PRT
<213> ORGANISM: Artificial Sequence
<220> FEATURE:
<223> OTHER INFORMATION: Synthetic Construct

<400> SEQUENCE: 135

Gln Val Gln Leu Val Glu Ser Gly Gly Gly Leu Val Gln Ala Gly Gly
 1               5                  10                  15
Ser Leu Arg Leu Ser Cys Ala Ala Thr Gly Arg Thr Phe Ser Pro Tyr
                20                  25                  30
Thr Met Gly Trp Phe Arg Gln Ala Pro Gly Lys Glu Arg Glu Phe Val
            35                  40                  45
Thr Arg Ile Thr Trp Lys Ser Gly Ser Thr Tyr Tyr Ala Asp Ser Val
        50                  55                  60
Lys Gly Arg Phe Thr Ile Ser Arg Asp Asn Ala Lys Asn Thr Val Thr
 65                  70                  75                  80
Leu Gln Met Asp Ser Leu Lys Pro Glu Asp Thr Ala Val Tyr Phe Cys
                 85                  90                  95
```

```
Ala Ser Thr Ser Phe Ala Tyr Gly Leu Thr Asn Ser Asn Lys Tyr Asn
            100                 105                 110

Tyr Trp Gly Gln Gly Thr Gln Val Thr Val Ser Gly
        115                 120
```

<210> SEQ ID NO 136
<211> LENGTH: 124
<212> TYPE: PRT
<213> ORGANISM: Artificial Sequence
<220> FEATURE:
<223> OTHER INFORMATION: Synthetic Construct

<400> SEQUENCE: 136

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Thr Tyr
            20                  25                  30

Arg Met Gly Trp Phe Arg Gln Ala Pro Gly Lys Ala Arg Glu Phe Val
        35                  40                  45

Ala Thr Ile Thr Ala Ser Gly Ser Trp Thr Tyr Tyr Ser Asp Ser Val
    50                  55                  60

Lys Gly Arg Ser Thr Ile Ser Arg Asp Asn Ala Lys Asn Thr Val Tyr
65                  70                  75                  80

Leu Gln Met Asn Ser Leu Lys Pro Gly Asp Thr Ala Val Tyr Tyr Cys
                85                  90                  95

Ala Ala Ala Glu Ile Leu Thr Ala Ile Thr Thr Ser Ser Asp Tyr Asp
            100                 105                 110

Tyr Trp Gly Gln Gly Thr Gln Val Thr Val Ser Ser
        115                 120
```

<210> SEQ ID NO 137
<211> LENGTH: 125
<212> TYPE: PRT
<213> ORGANISM: Artificial Sequence
<220> FEATURE:
<223> OTHER INFORMATION: Synthetic Construct

<400> SEQUENCE: 137

```
Gln Val Gln Leu Ser Glu Arg Gly Gly Gly Leu Val Gln Ala Gly Asp
1               5                   10                  15

Ser Leu Arg Leu Ser Cys Ala Ala Ser Gly Arg Met Phe Ser Ser Tyr
            20                  25                  30

Ala Val Gly Trp Phe Arg Gln Ala Pro Gly Lys Glu Arg Glu Tyr Val
        35                  40                  45

Ala Ala Ile Ser Tyr Asn Gly Gly Ala Thr Tyr Tyr Leu Asn Ser Val
    50                  55                  60

Glu Gly Arg Phe Thr Ile Ser Arg Asp Asn Ala Lys Asn Met Val Tyr
65                  70                  75                  80

Leu Gln Met Asn Ser Leu Lys Pro Glu Asp Thr Ala Ile Tyr Thr Cys
                85                  90                  95

Ala Ala Arg Gly Gly His Trp Tyr Ser Ile His Asp Pro Ser Asn Phe
            100                 105                 110

Arg Ala Trp Gly Gln Gly Thr Gln Val Thr Val Ser Ser
        115                 120                 125
```

<210> SEQ ID NO 138
<211> LENGTH: 124
<212> TYPE: PRT
<213> ORGANISM: Artificial Sequence
<220> FEATURE:
<223> OTHER INFORMATION: Synthetic Construct

<400> SEQUENCE: 138

Gln Val Gln Leu Ile Glu Ser Gly Gly Gly Leu Val Gln Ala Gly Gly
1               5                   10                  15

Ser Leu Arg Leu Ser Cys Val Ala Ser Gly Arg Val Arg Thr Ala
            20                  25                  30

Ala Met Ala Trp Phe Arg Arg Val Pro Gly Lys Glu Arg Glu Phe Val
            35                  40                  45

Ser Ser Ile Thr Trp Arg Gly Gly Glu Arg Asn Tyr Ala Asp Ala Val
        50                  55                  60

Lys Asp Arg Phe Thr Ile Ser Lys Asp Asn Ala Lys Asn Thr Val Tyr
65                  70                  75                  80

Leu Gln Met Asn Ser Leu Lys Pro Glu Asp Thr Ala Ser Tyr Tyr Cys
                85                  90                  95

Ala Ala Gly Pro Trp Tyr Thr Asn His Asp Thr Ser Gln Gly Tyr Asn
            100                 105                 110

Tyr Trp Gly Gln Gly Thr Gln Val Thr Val Ser Ser
        115                 120

<210> SEQ ID NO 139
<211> LENGTH: 117
<212> TYPE: PRT
<213> ORGANISM: Artificial Sequence
<220> FEATURE:
<223> OTHER INFORMATION: Synthetic Construct

<400> SEQUENCE: 139

Gln Val Gln Leu Ala Glu Ser Gly Gly Gly Leu Val Gln Ala Gly Gly
1               5                   10                  15

Ser Leu Arg Leu Ser Cys Ser Ala Ser Gly Arg Thr Ile Ser Asn Tyr
            20                  25                  30

Ala Met Gly Trp Phe Arg Gln Ala Pro Gly Lys Glu Arg Glu Phe Val
            35                  40                  45

Ala Ser Ile Asn Trp Asn Gly Gly Ile Thr Tyr Thr Ser Ser Val
        50                  55                  60

Lys Gly Arg Phe Thr Ile Ser Arg Asp Asn Ala Lys Ser Thr Val Tyr
65                  70                  75                  80

Leu Gln Met Asn Ser Leu Lys Pro Glu Asp Ala Ala Val Tyr Tyr Cys
                85                  90                  95

Ala Ala Gln Arg Ala Gly Thr Thr Thr Tyr Trp Gly Gln Gly Thr Gln
            100                 105                 110

Val Thr Val Ser Ser
        115

<210> SEQ ID NO 140
<211> LENGTH: 119
<212> TYPE: PRT
<213> ORGANISM: Artificial Sequence
<220> FEATURE:
<223> OTHER INFORMATION: Synthetic Construct

<400> SEQUENCE: 140

Gln Val Gln Leu Val Glu Ser Gly Gly Gly Leu Val Gln Pro Gly Gly
1               5                   10                  15

Ser Leu Thr Leu Ser Cys Ala Ala Ser Gly Ile Ser Asp Ile Ser Ser
            20                  25                  30

Met Gly Trp Tyr Arg Gln Ala Pro Gly Glu Gln Arg Glu Leu Val Ala
            35                  40                  45

Ile Ile Gly Ser Gly Gly Asn Thr Lys Tyr Ser Asp Ser Leu Lys Gly
 50                  55                  60

Arg Phe Thr Ile Ser Ile Asp Asn Ala Lys Asn Thr Val Tyr Leu Arg
 65                  70                  75                  80

Met Asn Ser Leu Lys Pro Glu Asp Thr Ser Val Tyr Tyr Cys Asn Ala
                 85                  90                  95

Ala Gln Arg Ile Gly Ala Gly Pro Ile Val Leu Tyr Trp Gly Gln Gly
            100                 105                 110

Thr Gln Val Thr Val Ser Ser
        115

<210> SEQ ID NO 141
<211> LENGTH: 118
<212> TYPE: PRT
<213> ORGANISM: Artificial Sequence
<220> FEATURE:
<223> OTHER INFORMATION: Synthetic Construct

<400> SEQUENCE: 141

Gln Val Gln Leu Val Glu Ser Gly Gly Gly Leu Val Gln Ala Gly Gly
 1               5                  10                  15

Ser Leu Arg Leu Ser Cys Ala Ala Ser Gly His Thr Phe Ser Val Tyr
            20                  25                  30

Ala Ile Gly Trp Phe Arg Gln Ala Pro Gly Lys Glu Arg Glu Phe Val
            35                  40                  45

Ser Ser Ile Asn Trp Gly Asp Gly Leu Thr Tyr Tyr Thr Asp Ser Val
 50                  55                  60

Lys Gly Arg Phe Ile Ile Ser Lys Asp Asn Ala Lys Asn Thr Asp Tyr
 65                  70                  75                  80

Leu Gln Met Asn Ser Leu Lys Pro Glu Asp Thr Ala Val Tyr Tyr Cys
                 85                  90                  95

Ala Ala Arg Gln Arg Arg Glu Gly Trp Asp Tyr Trp Gly Gln Gly Thr
            100                 105                 110

Gln Val Thr Val Ser Ser
        115

<210> SEQ ID NO 142
<211> LENGTH: 126
<212> TYPE: PRT
<213> ORGANISM: Artificial Sequence
<220> FEATURE:
<223> OTHER INFORMATION: Synthetic Construct

<400> SEQUENCE: 142

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Ala Ser Ser Tyr
            20                  25                  30

Val Ile Ala Trp Phe Arg Gln Ala Pro Gly Lys Ala Arg Glu Tyr Val
            35                  40                  45

Ala Ser Val Ser Arg Ser Gly Val Ser Thr Tyr Tyr Ala Asp Ser Val
 50                  55                  60

Lys Gly Arg Phe Thr Ile Ser Arg Asp Lys Pro Lys Asn Thr Val Phe
 65                  70                  75                  80

Leu Gln Met Asn Ser Leu Lys Leu Glu Asp Thr Ala Val Tyr Tyr Cys
                 85                  90                  95

```
Ala Ala Asp Gly Lys Asn Phe Ser Asn Arg Trp Trp Ser Arg Asp Glu
            100                 105                 110

Tyr Lys Tyr Trp Gly Gln Gly Thr Gln Val Thr Val Ser Gly
        115                 120                 125
```

<210> SEQ ID NO 143
<211> LENGTH: 123
<212> TYPE: PRT
<213> ORGANISM: Artificial Sequence
<220> FEATURE:
<223> OTHER INFORMATION: Synthetic Construct

<400> SEQUENCE: 143

```
Gln Val Gln Leu Val Glu Ser Gly Gly Gly Leu Val Gln Thr Gly Gly
1               5                   10                  15

Ser Leu Arg Leu Ser Cys Val Val Ser Gly Arg Thr Glu Thr Thr Tyr
            20                  25                  30

Asn Ile Gly Trp Phe Arg Gln Ala Pro Gly Lys Glu Arg Glu Leu Val
        35                  40                  45

Thr Ala Ile Ser Arg Gly Ala Thr Ile Thr Tyr Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Glu Asp Thr Ala Val Tyr Tyr Cys
                85                  90                  95

Ala Ala Ser Phe Thr Asn Leu Ala Val Val Ala Arg Asp Tyr Tyr Tyr
            100                 105                 110

Trp Gly Gln Gly Thr Gln Val Thr Val Ser Ser
        115                 120
```

<210> SEQ ID NO 144
<211> LENGTH: 128
<212> TYPE: PRT
<213> ORGANISM: Artificial Sequence
<220> FEATURE:
<223> OTHER INFORMATION: Synthetic Construct

<400> SEQUENCE: 144

```
Gln Ala Gln Leu Val Glu Ser Gly Gly Gly Leu Val Gln Ala Gly Gly
1               5                   10                  15

Ser Leu Arg Leu Ser Cys Val Val Ser Gly Arg Thr Phe Ser His Tyr
            20                  25                  30

Ala Met Gly Trp Phe Arg Gln Pro Pro Gly Lys Glu Arg Glu Phe Val
        35                  40                  45

Ala Ala Ile Thr Glu Ser Pro Asp Ser Thr Ile Tyr Ala Asp Ser Val
    50                  55                  60

Lys Gly Arg Phe Thr Ile Ser Arg Asp Gly Ala Val Asn Thr Val Tyr
65                  70                  75                  80

Leu Lys Met Asn Asn Leu Lys Pro Glu Asp Thr Ala Val Tyr Tyr Cys
                85                  90                  95

Ala Ala Ala Arg Ser Thr Leu Arg Trp Pro Phe Arg Gly Gln Gly Gln
            100                 105                 110

Tyr Asp Tyr Asp Tyr Trp Gly Gln Gly Thr Gln Val Thr Val Ser Gly
        115                 120                 125
```

<210> SEQ ID NO 145
<211> LENGTH: 122
<212> TYPE: PRT

<213> ORGANISM: Artificial Sequence
<220> FEATURE:
<223> OTHER INFORMATION: Synthetic Construct

<400> SEQUENCE: 145

```
Gln Val His Leu Val Glu Ser Gly Gly Gly Leu Val Gln Ala Gly Gly
1               5                   10                  15
Ser Leu Met Leu Ser Cys Ala Ala Ser Gly Arg Thr Trp Ser Thr Tyr
            20                  25                  30
Pro Met Gly Trp Phe Arg Gln Ala Pro Gly Lys Glu Arg Glu Phe Val
        35                  40                  45
Ala Ala Ile Arg Trp Thr Thr Gly Ser Thr Tyr Tyr Gln Asp Ser Val
    50                  55                  60
Lys Gly Arg Phe Thr Ile Ser Arg Asp Asn Ala Lys Asn Thr Val Tyr
65                  70                  75                  80
Leu Gln Met Asn Ser Leu Lys Pro Glu Asp Thr Ala Val Tyr Tyr Cys
                85                  90                  95
Asn Ala Glu Val Arg Ala Trp Tyr Asn Arg Arg Lys Ala Asp Tyr Trp
            100                 105                 110
Gly Gln Gly Thr Gln Val Thr Val Ser Ser
        115                 120
```

<210> SEQ ID NO 146
<211> LENGTH: 122
<212> TYPE: PRT
<213> ORGANISM: Artificial Sequence
<220> FEATURE:
<223> OTHER INFORMATION: Synthetic Construct

<400> SEQUENCE: 146

```
Gln Val His Leu Val Glu Ala Gly Gly Gly Leu Val Gln Ala Gly Gly
1               5                   10                  15
Ser Leu Arg Val Ser Cys Ala Ile Ser Gly Arg Thr Asp Ser Thr Gly
            20                  25                  30
Ile Leu Gly Trp Phe Arg Arg Ala Pro Gly Lys Glu Arg Glu Phe Val
        35                  40                  45
Ala Leu Ile Arg Trp Ser Asn Asn Tyr Ala Trp Tyr Glu Asp Ser Ala
    50                  55                  60
Lys Gly Arg Phe Thr Ile Ser Arg Asp Asn Ala Lys Asn Thr Val Tyr
65                  70                  75                  80
Leu Gln Met Asn Ser Leu Lys Pro Glu Asp Thr Ala Val Tyr Tyr Cys
                85                  90                  95
Ala Ala Gly Thr Gly Trp Gly Phe Ser Ile Ser Asp Tyr Asn Tyr Trp
            100                 105                 110
Gly Gln Gly Thr Gln Val Thr Val Ser Gly
        115                 120
```

<210> SEQ ID NO 147
<211> LENGTH: 125
<212> TYPE: PRT
<213> ORGANISM: Artificial Sequence
<220> FEATURE:
<223> OTHER INFORMATION: Synthetic Construct

<400> SEQUENCE: 147

```
Gln Val Gln Leu Val Glu Ser Gly Gly Gly Leu Val Gln Ala Gly Asn
1               5                   10                  15
Ser Leu Arg Leu Ser Cys Ala Ala Thr Gly Arg Ser Phe Asn Thr Tyr
            20                  25                  30
```

Ala Met Ala Trp Phe Arg Gln Ala Pro Gly Lys Glu Arg Glu Phe Val
        35                  40                  45

Ala Ser Ile Thr Trp Ser Gly Ala Ser Thr Pro Tyr Ser Asp Ser Val
    50                  55                  60

Lys Gly Arg Phe Thr Ile Ser Arg Asp Asn Ala Lys Ser Thr Val Tyr
65                  70                  75                  80

Leu Gln Met Asn Ser Leu Lys Arg Glu Asp Thr Ala Val Tyr Tyr Cys
                85                  90                  95

Ala Ala Ser Ser Gln Tyr Gly Gly Ala Ser Ala Pro Thr Ala Tyr
            100                 105                 110

Leu Tyr Trp Gly Gln Gly Thr Gln Val Thr Val Ser Gly
        115                 120                 125

<210> SEQ ID NO 148
<211> LENGTH: 126
<212> TYPE: PRT
<213> ORGANISM: Artificial Sequence
<220> FEATURE:
<223> OTHER INFORMATION: Synthetic Construct

<400> SEQUENCE: 148

Gln Val Gln Leu Ala Glu Ser Gly Gly Gly Leu Val Gln Ala Gly Gly
1               5                   10                  15

Ser Leu Arg Leu Ser Cys Ser Ala Ser Gly Arg Thr Ile Ser Asn Tyr
            20                  25                  30

Ala Met Gly Trp Phe Arg Gln Ala Pro Gly Gln Glu Arg Glu Phe Val
        35                  40                  45

Ala Ala Val Ser Trp Thr Gly His Gly Thr Phe His Ala Thr Ala Val
    50                  55                  60

Lys Gly Arg Phe Thr Ile Ser Arg Asp Asn Ala Glu Asn Thr Val Phe
65                  70                  75                  80

Leu Gln Met Asn Ser Leu Lys Leu Glu Asp Thr Ala Val Tyr Tyr Cys
                85                  90                  95

Ala Ala Asp Gly Lys Asn Phe Ser Asn Arg Trp Trp Ser Arg Asp Glu
            100                 105                 110

Tyr Lys Tyr Trp Gly Gln Gly Thr Gln Val Thr Val Ser Ser
        115                 120                 125

<210> SEQ ID NO 149
<211> LENGTH: 121
<212> TYPE: PRT
<213> ORGANISM: Artificial Sequence
<220> FEATURE:
<223> OTHER INFORMATION: Synthetic Construct

<400> SEQUENCE: 149

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Leu Ser Ile Asn
            20                  25                  30

Thr Met Ala Trp Tyr Arg Gln Ala Pro Gly Lys Gln Arg Glu Leu Val
        35                  40                  45

Ala Val Ile Ser Ser Ser Gly Ser Thr Asn Tyr Ala Asp Ser Val Lys
    50                  55                  60

Gly Arg Phe Thr Ile Ser Arg Asp Asn Ala Lys Thr Thr Val Tyr Leu
65                  70                  75                  80

Gln Leu Asn Arg Leu Lys Pro Glu Asp Thr Ala Ala Tyr Tyr Cys Ala

```
                85                  90                  95
Ala Gly Lys Gly Ser Thr Trp Tyr Asn Gly Ala Tyr Lys Tyr Trp Gly
            100                 105                 110

Gln Gly Thr Gln Val Thr Val Ser Ser
        115                 120

<210> SEQ ID NO 150
<211> LENGTH: 126
<212> TYPE: PRT
<213> ORGANISM: Artificial Sequence
<220> FEATURE:
<223> OTHER INFORMATION: Synthetic Construct

<400> SEQUENCE: 150

Gln Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser Arg Tyr
            20                  25                  30

Ala Met Ala Trp Phe Arg Gln Ala Pro Gly Lys Glu Arg Glu Phe Val
        35                  40                  45

Ala Ala Ile Ser Trp Ser Gly Thr Ala Tyr Arg Asp Ser Val Lys Gly
    50                  55                  60

Arg Phe Thr Ile Ser Gly Asp Asn Ala Lys Asn Thr Val Tyr Leu Gln
65              70                  75                  80

Met Asn Ser Leu Asn Val Glu Asp Thr Ala Val Tyr Tyr Cys Ala Tyr
                85                  90                  95

Gly Tyr Tyr Ser Gly Ala Ala Asn Tyr Arg Asp Leu Ala Ser Ser Thr
            100                 105                 110

Tyr Arg Tyr Trp Gly Gln Gly Thr Gln Val Thr Val Ser Ser
        115                 120                 125

<210> SEQ ID NO 151
<211> LENGTH: 118
<212> TYPE: PRT
<213> ORGANISM: Artificial Sequence
<220> FEATURE:
<223> OTHER INFORMATION: Synthetic Construct

<400> SEQUENCE: 151

Gln Val Gln Leu Val Glu Ser Gly Gly Gly Leu Val Gln Pro Gly Gly
1               5                   10                  15

Ser Leu Arg Leu Ser Cys Glu Ala Ser Gly Arg Thr Phe Ser Ser Val
            20                  25                  30

Ser Met Gly Trp Phe Arg Gln Ala Pro Gly Lys Glu Arg Val Ile Val
        35                  40                  45

Ala Ala Ala Asp Trp Ser Gly Thr Thr Tyr Tyr Thr Gly Ser Leu Lys
    50                  55                  60

Gly Arg Phe Thr Ile Ser Arg Asp Asn Ala Lys Asn Met Val Tyr Leu
65              70                  75                  80

Gln Met Asn Ser Leu Lys Pro Glu Asp Thr Ala Val Tyr Tyr Cys Ala
                85                  90                  95

Ala Ser Asp Pro Arg Arg Ser Ala Tyr Lys Tyr Trp Gly Gln Gly Thr
            100                 105                 110

Gln Val Thr Val Ser Ser
        115

<210> SEQ ID NO 152
<211> LENGTH: 122
```

<212> TYPE: PRT
<213> ORGANISM: Artificial Sequence
<220> FEATURE:
<223> OTHER INFORMATION: Synthetic Construct

<400> SEQUENCE: 152

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly Ser Tyr
            20                  25                  30

Thr Met Gly Trp Phe Arg Gln Ala Pro Gly Gln Glu Arg Glu Phe Val
        35                  40                  45

Ala Ser Ile Ser Arg Ser Gly Ser Thr Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Asn Thr Gly Gly Arg Ala Ser Ala Ser Tyr Lys Tyr Trp
            100                 105                 110

Gly Gln Gly Thr Gln Val Thr Val Ser Ser
            115                 120
```

<210> SEQ ID NO 153
<211> LENGTH: 122
<212> TYPE: PRT
<213> ORGANISM: Artificial Sequence
<220> FEATURE:
<223> OTHER INFORMATION: Synthetic Construct

<400> SEQUENCE: 153

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ile Arg Tyr
            20                  25                  30

Ala Met Ala Trp Phe Arg Gln Ala Pro Gly Lys Glu Arg Val Phe Val
        35                  40                  45

Ala Ser Ile Ser Gln Thr Gly Gly Ser Thr Asp Tyr Ser Asp Ser Val
    50                  55                  60

Lys Glu Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Val Ser Thr Val Gln Ser Lys Arg Met Leu Met Tyr Gly Tyr Trp
            100                 105                 110

Gly Gln Gly Thr Gln Val Thr Val Ser Ser
            115                 120
```

<210> SEQ ID NO 154
<211> LENGTH: 124
<212> TYPE: PRT
<213> ORGANISM: Artificial Sequence
<220> FEATURE:
<223> OTHER INFORMATION: Synthetic Construct

<400> SEQUENCE: 154

```
Gln Val Arg Leu Glu Gln Ser Gly Gly Gly Leu Val Gln Ala Gly Gly
1               5                   10                  15

Ser Leu Arg Leu Ala Cys Ala Ala Ser Gly Arg Thr Ala Arg Ser Tyr
```

```
                20                  25                  30

Asn Ile Gly Trp Phe Arg Gln Ala Pro Gly Lys Glu Arg Glu Phe Val
            35                  40                  45

Ala Ala Ile Ile Ser Ser Pro Arg Gly Thr Tyr Tyr Ser Asp Ser Val
50                  55                  60

Arg Gly Arg Phe Thr Ile Ser Gly Asn Ser Ala Glu Asn Thr Val Phe
65                  70                  75                  80

Leu Gln Met Asn Asn Leu Lys Pro Glu Asp Thr Ala Val Tyr His Cys
                85                  90                  95

Ala Ala Thr Thr Ser Ser Thr Tyr Tyr Ser Asp Lys Thr Tyr Tyr Ala
            100                 105                 110

Tyr Trp Gly Gln Gly Thr Gln Val Thr Val Ser Ser
            115                 120

<210> SEQ ID NO 155
<211> LENGTH: 117
<212> TYPE: PRT
<213> ORGANISM: Artificial Sequence
<220> FEATURE:
<223> OTHER INFORMATION: Synthetic Construct

<400> SEQUENCE: 155

Gln Val Arg Leu Val Glu Ser Gly Gly Gly Leu Val Gln Pro Gly Gly
1               5                   10                  15

Ser Leu Arg Leu Ala Cys Ala Ala Ser Gly Arg Ile Leu Ala Asp Thr
            20                  25                  30

Pro Met Ala Trp Tyr Arg Gln Ala Pro Gly Lys Gln Arg Glu Leu Val
            35                  40                  45

Ala Ala Ile Thr Ser Gly Gly Thr Thr Asn Tyr Ala Gly Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asn Ala Glu Gly Ser Gly Ser Arg Tyr Trp Gly Gln Gly Thr Gln
            100                 105                 110

Val Thr Val Ser Ser
        115

<210> SEQ ID NO 156
<211> LENGTH: 114
<212> TYPE: PRT
<213> ORGANISM: Artificial Sequence
<220> FEATURE:
<223> OTHER INFORMATION: Synthetic Construct

<400> SEQUENCE: 156

Gln Val Gln Leu Val Glu Ser Gly Gly Gly Leu Val Gln Pro Gly Gly
1               5                   10                  15

Ser Leu Arg Leu Ala Cys Ala Ala Ser Gly Arg Ile Leu Ala Asp Thr
            20                  25                  30

Pro Met Ala Trp Tyr Arg Gln Ala Pro Gly Lys Gln Arg Glu Leu Val
            35                  40                  45

Ala Ala Ile Thr Ser Gly Gly Thr Thr Asn Tyr Ala Gly Ser Val Lys
50                  55                  60

Gly Arg Phe Thr Ile Ser Arg Asp Asn Ala Lys Asn Thr Val Tyr Leu
65                  70                  75                  80
```

Gln Met Asn Ser Leu Lys Pro Glu Asp Thr Ala Val Tyr Tyr Cys Lys
            85                  90                  95

Val Met Tyr His Ala Gly Ser Trp Gly Gln Gly Thr Val Thr Val
            100                 105                 110

Ser Ser

<210> SEQ ID NO 157
<211> LENGTH: 25
<212> TYPE: PRT
<213> ORGANISM: Artificial Sequence
<220> FEATURE:
<223> OTHER INFORMATION: Synthetic Construct

<400> SEQUENCE: 157

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 158
<211> LENGTH: 17
<212> TYPE: PRT
<213> ORGANISM: Artificial Sequence
<220> FEATURE:
<223> OTHER INFORMATION: Synthetic Construct

<400> SEQUENCE: 158

Met His Trp Phe Arg Gln Ala Pro Gly Lys Gly Leu Glu Phe Val Ser
1               5                   10                  15

Ala

<210> SEQ ID NO 159
<211> LENGTH: 38
<212> TYPE: PRT
<213> ORGANISM: Artificial Sequence
<220> FEATURE:
<223> OTHER INFORMATION: Synthetic Construct

<400> SEQUENCE: 159

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 160
<211> LENGTH: 11
<212> TYPE: PRT
<213> ORGANISM: Artificial Sequence
<220> FEATURE:
<223> OTHER INFORMATION: Synthetic Construct

<400> SEQUENCE: 160

Trp Gly Gln Gly Thr Gln Val Thr Val Ser Ser
1               5                   10

<210> SEQ ID NO 161
<211> LENGTH: 25
<212> TYPE: PRT
<213> ORGANISM: Artificial Sequence
<220> FEATURE:
<223> OTHER INFORMATION: Synthetic Construct -continued

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 162
<211> LENGTH: 17
<212> TYPE: PRT
<213> ORGANISM: Artificial Sequence
<220> FEATURE:
<223> OTHER INFORMATION: Synthetic Construct

<400> SEQUENCE: 162

Met Ser Trp Phe Arg Gln Ala Pro Gly Lys Gly Leu Glu Leu Val Ala
1               5                   10                  15

Asn

<210> SEQ ID NO 163
<211> LENGTH: 39
<212> TYPE: PRT
<213> ORGANISM: Artificial Sequence
<220> FEATURE:
<223> OTHER INFORMATION: Synthetic Construct

<400> SEQUENCE: 163

Tyr Tyr Val Asp Ser Val Lys Gly Arg Phe Thr Ile Ser Arg Asp Asn
1               5                   10                  15

Ala Lys Asn Ser Leu Leu Tyr Leu Gln Met Asn Ser Leu Arg Ala Glu
            20                  25                  30

Asp Thr Ala Val Tyr Tyr Cys
        35

<210> SEQ ID NO 164
<211> LENGTH: 25
<212> TYPE: PRT
<213> ORGANISM: Artificial Sequence
<220> FEATURE:
<223> OTHER INFORMATION: Synthetic Construct

<400> SEQUENCE: 164

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 165
<211> LENGTH: 17
<212> TYPE: PRT
<213> ORGANISM: Artificial Sequence
<220> FEATURE:
<223> OTHER INFORMATION: Synthetic Construct

<400> SEQUENCE: 165

Met His Trp Phe Arg Gln Ala Pro Gly Lys Gly Leu Glu Leu Val Ser
1               5                   10                  15

Ala

<210> SEQ ID NO 166
<211> LENGTH: 38
<212> TYPE: PRT
<213> ORGANISM: Artificial Sequence
<220> FEATURE:

<223> OTHER INFORMATION: Synthetic Construct

<400> SEQUENCE: 166

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 167
<211> LENGTH: 25
<212> TYPE: PRT
<213> ORGANISM: Artificial Sequence
<220> FEATURE:
<223> OTHER INFORMATION: Synthetic Construct

<400> SEQUENCE: 167

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 168
<211> LENGTH: 17
<212> TYPE: PRT
<213> ORGANISM: Artificial Sequence
<220> FEATURE:
<223> OTHER INFORMATION: Synthetic Construct

<400> SEQUENCE: 168

Met His Trp Phe Arg Gln Ala Pro Gly Lys Gly Leu Glu Phe Val Ser
1               5                   10                  15

Ala

<210> SEQ ID NO 169
<211> LENGTH: 38
<212> TYPE: PRT
<213> ORGANISM: Artificial Sequence
<220> FEATURE:
<223> OTHER INFORMATION: Synthetic Construct

<400> SEQUENCE: 169

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 170
<211> LENGTH: 25
<212> TYPE: PRT
<213> ORGANISM: Artificial Sequence
<220> FEATURE:
<223> OTHER INFORMATION: Synthetic Construct

<400> SEQUENCE: 170

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 171
<211> LENGTH: 17
<212> TYPE: PRT
<213> ORGANISM: Artificial Sequence
<220> FEATURE:
<223> OTHER INFORMATION: Synthetic Construct

<400> SEQUENCE: 171

Met His Trp Phe Arg Gln Ala Pro Gly Lys Gly Leu Glu Phe Val Ser
1               5                   10                  15

Ala

<210> SEQ ID NO 172
<211> LENGTH: 38
<212> TYPE: PRT
<213> ORGANISM: Artificial Sequence
<220> FEATURE:
<223> OTHER INFORMATION: Synthetic Construct

<400> SEQUENCE: 172

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 173
<211> LENGTH: 25
<212> TYPE: PRT
<213> ORGANISM: Artificial Sequence
<220> FEATURE:
<223> OTHER INFORMATION: Synthetic Construct

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 174
<211> LENGTH: 17
<212> TYPE: PRT
<213> ORGANISM: Artificial Sequence
<220> FEATURE:
<223> OTHER INFORMATION: Synthetic Construct

<400> SEQUENCE: 174

Met Ser Trp Phe Arg Gln Ala Pro Gly Lys Gly Leu Glu Ala Val Ser
1               5                   10                  15

Ala

<210> SEQ ID NO 175
<211> LENGTH: 38
<212> TYPE: PRT
<213> ORGANISM: Artificial Sequence
<220> FEATURE:
<223> OTHER INFORMATION: Synthetic Construct

<400> SEQUENCE: 175

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp

Thr Ala Val Tyr Tyr Cys
        35

<210> SEQ ID NO 176
<211> LENGTH: 25
<212> TYPE: PRT
<213> ORGANISM: Artificial Sequence
<220> FEATURE:
<223> OTHER INFORMATION: Synthetic Construct

<400> SEQUENCE: 176

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 177
<211> LENGTH: 17
<212> TYPE: PRT
<213> ORGANISM: Artificial Sequence
<220> FEATURE:
<223> OTHER INFORMATION: Synthetic Construct

<400> SEQUENCE: 177

Met His Trp Phe Arg Gln Ala Pro Gly Lys Gly Leu Glu Phe Val Ser
1               5                   10                  15

Ala

<210> SEQ ID NO 178
<211> LENGTH: 38
<212> TYPE: PRT
<213> ORGANISM: Artificial Sequence
<220> FEATURE:
<223> OTHER INFORMATION: Synthetic Construct

<400> SEQUENCE: 178

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 179
<211> LENGTH: 25
<212> TYPE: PRT
<213> ORGANISM: Artificial Sequence
<220> FEATURE:
<223> OTHER INFORMATION: Synthetic Construct

<400> SEQUENCE: 179

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 180
<211> LENGTH: 17
<212> TYPE: PRT
<213> ORGANISM: Artificial Sequence
<220> FEATURE:
<223> OTHER INFORMATION: Synthetic Construct -continued

```
<400> SEQUENCE: 180

Met His Trp Phe Arg Gln Ala Pro Gly Lys Gly Leu Glu Phe Val Ser
1               5                   10                  15

Ala

<210> SEQ ID NO 181
<211> LENGTH: 38
<212> TYPE: PRT
<213> ORGANISM: Artificial Sequence
<220> FEATURE:
<223> OTHER INFORMATION: Synthetic Construct

<400> SEQUENCE: 181

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 182
<211> LENGTH: 25
<212> TYPE: PRT
<213> ORGANISM: Artificial Sequence
<220> FEATURE:
<223> OTHER INFORMATION: Synthetic Construct

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 183
<211> LENGTH: 17
<212> TYPE: PRT
<213> ORGANISM: Artificial Sequence
<220> FEATURE:
<223> OTHER INFORMATION: Synthetic Construct

<400> SEQUENCE: 183

Met Ser Trp Phe Arg Gln Ala Pro Gly Lys Gly Leu Glu Leu Val Ser
1               5                   10                  15

Ala

<210> SEQ ID NO 184
<211> LENGTH: 38
<212> TYPE: PRT
<213> ORGANISM: Artificial Sequence
<220> FEATURE:
<223> OTHER INFORMATION: Synthetic Construct

<400> SEQUENCE: 184

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 185
<211> LENGTH: 25
```

```
<212> TYPE: PRT
<213> ORGANISM: Artificial Sequence
<220> FEATURE:
<223> OTHER INFORMATION: Synthetic Construct

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 186
<211> LENGTH: 17
<212> TYPE: PRT
<213> ORGANISM: Artificial Sequence
<220> FEATURE:
<223> OTHER INFORMATION: Synthetic Construct

<400> SEQUENCE: 186

Met Ser Trp Phe Arg Gln Ala Pro Gly Lys Gly Leu Glu Gln Val Ser
1               5                   10                  15

Ala

<210> SEQ ID NO 187
<211> LENGTH: 38
<212> TYPE: PRT
<213> ORGANISM: Artificial Sequence
<220> FEATURE:
<223> OTHER INFORMATION: Synthetic Construct

<400> SEQUENCE: 187

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 188
<211> LENGTH: 25
<212> TYPE: PRT
<213> ORGANISM: Artificial Sequence
<220> FEATURE:
<223> OTHER INFORMATION: Synthetic Construct

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 189
<211> LENGTH: 17
<212> TYPE: PRT
<213> ORGANISM: Artificial Sequence
<220> FEATURE:
<223> OTHER INFORMATION: Synthetic Construct

<400> SEQUENCE: 189

Met Ser Trp Phe Arg Gln Ala Pro Gly Lys Gly Leu Glu Phe Val Ser
1               5                   10                  15

Ala
```

-continued

```
<210> SEQ ID NO 190
<211> LENGTH: 38
<212> TYPE: PRT
<213> ORGANISM: Artificial Sequence
<220> FEATURE:
<223> OTHER INFORMATION: Synthetic Construct

<400> SEQUENCE: 190

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 191
<211> LENGTH: 25
<212> TYPE: PRT
<213> ORGANISM: Artificial Sequence
<220> FEATURE:
<223> OTHER INFORMATION: Synthetic Construct

<400> SEQUENCE: 191

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 192
<211> LENGTH: 17
<212> TYPE: PRT
<213> ORGANISM: Artificial Sequence
<220> FEATURE:
<223> OTHER INFORMATION: Synthetic Construct

<400> SEQUENCE: 192

Met His Trp Phe Arg Gln Ala Pro Gly Lys Gly Leu Glu Phe Val Ser
1               5                   10                  15

Ala

<210> SEQ ID NO 193
<211> LENGTH: 38
<212> TYPE: PRT
<213> ORGANISM: Artificial Sequence
<220> FEATURE:
<223> OTHER INFORMATION: Synthetic Construct

<400> SEQUENCE: 193

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 194
<211> LENGTH: 25
<212> TYPE: PRT
<213> ORGANISM: Artificial Sequence
<220> FEATURE:
<223> OTHER INFORMATION: Synthetic Construct

<400> SEQUENCE: 194

Gln Val Gln Leu Val Glu Ser Gly Gly Gly Leu Val Gln Pro Gly Gly
```

```
1               5                   10                  15

Ser Leu Arg Leu Ser Cys Ser Ala Ser
            20                  25
```

<210> SEQ ID NO 195
<211> LENGTH: 17
<212> TYPE: PRT
<213> ORGANISM: Artificial Sequence
<220> FEATURE:
<223> OTHER INFORMATION: Synthetic Construct

<400> SEQUENCE: 195

```
Met His Trp Phe Arg Gln Ala Pro Gly Lys Gly Leu Glu Phe Val Ser
1               5                   10                  15

Ala
```

<210> SEQ ID NO 196
<211> LENGTH: 38
<212> TYPE: PRT
<213> ORGANISM: Artificial Sequence
<220> FEATURE:
<223> OTHER INFORMATION: Synthetic Construct

<400> SEQUENCE: 196

```
Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35
```

<210> SEQ ID NO 197
<211> LENGTH: 25
<212> TYPE: PRT
<213> ORGANISM: Artificial Sequence
<220> FEATURE:
<223> OTHER INFORMATION: Synthetic Construct

<400> SEQUENCE: 197

```
Gln Val Gln Leu Val Glu Ser Gly Gly Gly Leu Val Gln Pro Gly Gly
1               5                   10                  15

Ser Leu Arg Leu Ser Cys Ser Ala Ser
            20                  25
```

<210> SEQ ID NO 198
<211> LENGTH: 17
<212> TYPE: PRT
<213> ORGANISM: Artificial Sequence
<220> FEATURE:
<223> OTHER INFORMATION: Synthetic Construct

<400> SEQUENCE: 198

```
Met His Trp Phe Arg Gln Ala Pro Gly Lys Gly Leu Glu Phe Val Ser
1               5                   10                  15

Ala
```

<210> SEQ ID NO 199
<211> LENGTH: 38
<212> TYPE: PRT
<213> ORGANISM: Artificial Sequence
<220> FEATURE:
<223> OTHER INFORMATION: Synthetic Construct

<400> SEQUENCE: 199

```
Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 200
<211> LENGTH: 25
<212> TYPE: PRT
<213> ORGANISM: Artificial Sequence
<220> FEATURE:
<223> OTHER INFORMATION: Synthetic Construct

<400> SEQUENCE: 200

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 201
<211> LENGTH: 17
<212> TYPE: PRT
<213> ORGANISM: Artificial Sequence
<220> FEATURE:
<223> OTHER INFORMATION: Synthetic Construct

<400> SEQUENCE: 201

Met His Trp Phe Arg Gln Ala Pro Gly Lys Gly Leu Glu Tyr Val Ser
1               5                   10                  15

Ala

<210> SEQ ID NO 202
<211> LENGTH: 38
<212> TYPE: PRT
<213> ORGANISM: Artificial Sequence
<220> FEATURE:
<223> OTHER INFORMATION: Synthetic Construct

<400> SEQUENCE: 202

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 203
<211> LENGTH: 25
<212> TYPE: PRT
<213> ORGANISM: Artificial Sequence
<220> FEATURE:
<223> OTHER INFORMATION: Synthetic Construct

<400> SEQUENCE: 203

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 204
<211> LENGTH: 17
```

```
<212> TYPE: PRT
<213> ORGANISM: Artificial Sequence
<220> FEATURE:
<223> OTHER INFORMATION: Synthetic Construct

<400> SEQUENCE: 204

Met His Trp Phe Arg Gln Ala Pro Gly Lys Gly Leu Glu Phe Val Ser
1               5                   10                  15

Ala

<210> SEQ ID NO 205
<211> LENGTH: 38
<212> TYPE: PRT
<213> ORGANISM: Artificial Sequence
<220> FEATURE:
<223> OTHER INFORMATION: Synthetic Construct

<400> SEQUENCE: 205

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 206
<211> LENGTH: 25
<212> TYPE: PRT
<213> ORGANISM: Artificial Sequence
<220> FEATURE:
<223> OTHER INFORMATION: Synthetic Construct

<400> SEQUENCE: 206

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 207
<211> LENGTH: 17
<212> TYPE: PRT
<213> ORGANISM: Artificial Sequence
<220> FEATURE:
<223> OTHER INFORMATION: Synthetic Construct

<400> SEQUENCE: 207

Met His Trp Phe Arg Gln Ala Pro Gly Lys Gly Leu Glu Phe Val Ser
1               5                   10                  15

Ala

<210> SEQ ID NO 208
<211> LENGTH: 38
<212> TYPE: PRT
<213> ORGANISM: Artificial Sequence
<220> FEATURE:
<223> OTHER INFORMATION: Synthetic Construct

<400> SEQUENCE: 208

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
```

```
              35

<210> SEQ ID NO 209
<211> LENGTH: 25
<212> TYPE: PRT
<213> ORGANISM: Artificial Sequence
<220> FEATURE:
<223> OTHER INFORMATION: Synthetic Construct

<400> SEQUENCE: 209

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 210
<211> LENGTH: 17
<212> TYPE: PRT
<213> ORGANISM: Artificial Sequence
<220> FEATURE:
<223> OTHER INFORMATION: Synthetic Construct

<400> SEQUENCE: 210

Met Ser Trp Phe Arg Gln Ala Pro Gly Lys Gly Leu Glu Leu Val Ser
1               5                   10                  15

Val

<210> SEQ ID NO 211
<211> LENGTH: 39
<212> TYPE: PRT
<213> ORGANISM: Artificial Sequence
<220> FEATURE:
<223> OTHER INFORMATION: Synthetic Construct

<400> SEQUENCE: 211

Tyr Tyr Ala Asp Ser Val Lys Gly Arg Phe Thr Ile Ser Arg Asp Asn
1               5                   10                  15

Ser Lys Asn Thr Leu Leu Tyr Leu Gln Met Asn Ser Leu Arg Ala Glu
            20                  25                  30

Asp Thr Ala Val Tyr Tyr Cys
        35

<210> SEQ ID NO 212
<211> LENGTH: 25
<212> TYPE: PRT
<213> ORGANISM: Artificial Sequence
<220> FEATURE:
<223> OTHER INFORMATION: Synthetic Construct

<400> SEQUENCE: 212

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 213
<211> LENGTH: 17
<212> TYPE: PRT
<213> ORGANISM: Artificial Sequence
<220> FEATURE:
<223> OTHER INFORMATION: Synthetic Construct

<400> SEQUENCE: 213

Met His Trp Phe Arg Gln Ala Pro Gly Lys Gly Leu Glu Phe Val Ser
```

```
1               5                   10                  15
Ala

<210> SEQ ID NO 214
<211> LENGTH: 38
<212> TYPE: PRT
<213> ORGANISM: Artificial Sequence
<220> FEATURE:
<223> OTHER INFORMATION: Synthetic Construct

<400> SEQUENCE: 214

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 215
<211> LENGTH: 25
<212> TYPE: PRT
<213> ORGANISM: Artificial Sequence
<220> FEATURE:
<223> OTHER INFORMATION: Synthetic Construct

<400> SEQUENCE: 215

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 216
<211> LENGTH: 17
<212> TYPE: PRT
<213> ORGANISM: Artificial Sequence
<220> FEATURE:
<223> OTHER INFORMATION: Synthetic Construct

<400> SEQUENCE: 216

Met His Trp Phe Arg Gln Ala Pro Gly Lys Gly Leu Glu Tyr Val Ser
1               5                   10                  15

Ala

<210> SEQ ID NO 217
<211> LENGTH: 40
<212> TYPE: PRT
<213> ORGANISM: Artificial Sequence
<220> FEATURE:
<223> OTHER INFORMATION: Synthetic Construct

<400> SEQUENCE: 217

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Ala Arg
        35                  40

<210> SEQ ID NO 218
<211> LENGTH: 25
<212> TYPE: PRT
<213> ORGANISM: Artificial Sequence
<220> FEATURE:
```

<223> OTHER INFORMATION: Synthetic Construct

<400> SEQUENCE: 218

Gln Val Gln Leu Val Glu Ser Gly Gly Gly Leu Val Gln Pro Gly Gly
1               5                   10                  15
Ser Leu Arg Leu Ser Cys Ser Ala Ser
            20                  25

<210> SEQ ID NO 219
<211> LENGTH: 17
<212> TYPE: PRT
<213> ORGANISM: Artificial Sequence
<220> FEATURE:
<223> OTHER INFORMATION: Synthetic Construct

<400> SEQUENCE: 219

Met His Trp Phe Arg Gln Ala Pro Gly Lys Gly Leu Glu Leu Val Ser
1               5                   10                  15
Ala

<210> SEQ ID NO 220
<211> LENGTH: 38
<212> TYPE: PRT
<213> ORGANISM: Artificial Sequence
<220> FEATURE:
<223> OTHER INFORMATION: Synthetic Construct

<400> SEQUENCE: 220

Tyr Tyr Ala Asp Ser Val Lys Gly Arg Phe Thr Ile Ser Arg Asp Asn
1               5                   10                  15
Ser Lys Asn Thr Leu Tyr Leu Gln Met Asn Ser Leu Arg Ala Glu Asp
            20                  25                  30
Thr Ala Val Tyr Tyr Cys
        35

<210> SEQ ID NO 221
<211> LENGTH: 25
<212> TYPE: PRT
<213> ORGANISM: Artificial Sequence
<220> FEATURE:
<223> OTHER INFORMATION: Synthetic Construct

<400> SEQUENCE: 221

Gln Val Gln Leu Val Glu Ser Gly Gly Gly Leu Val Gln Pro Gly Gly
1               5                   10                  15
Ser Leu Arg Leu Ser Cys Ser Ala Ser
            20                  25

<210> SEQ ID NO 222
<211> LENGTH: 17
<212> TYPE: PRT
<213> ORGANISM: Artificial Sequence
<220> FEATURE:
<223> OTHER INFORMATION: Synthetic Construct

<400> SEQUENCE: 222

Met His Trp Phe Arg Gln Ala Pro Gly Lys Gly Leu Glu Phe Val Ser
1               5                   10                  15
Ala

<210> SEQ ID NO 223
<211> LENGTH: 40
<212> TYPE: PRT

```
<213> ORGANISM: Artificial Sequence
<220> FEATURE:
<223> OTHER INFORMATION: Synthetic Construct

<400> SEQUENCE: 223

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Ala Arg
        35                  40

<210> SEQ ID NO 224
<211> LENGTH: 25
<212> TYPE: PRT
<213> ORGANISM: Artificial Sequence
<220> FEATURE:
<223> OTHER INFORMATION: Synthetic Construct

<400> SEQUENCE: 224

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 225
<211> LENGTH: 17
<212> TYPE: PRT
<213> ORGANISM: Artificial Sequence
<220> FEATURE:
<223> OTHER INFORMATION: Synthetic Construct

<400> SEQUENCE: 225

Met His Trp Phe Arg Gln Ala Pro Gly Lys Gly Leu Glu Phe Val Ser
1               5                   10                  15

Ala

<210> SEQ ID NO 226
<211> LENGTH: 38
<212> TYPE: PRT
<213> ORGANISM: Artificial Sequence
<220> FEATURE:
<223> OTHER INFORMATION: Synthetic Construct

<400> SEQUENCE: 226

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 227
<211> LENGTH: 25
<212> TYPE: PRT
<213> ORGANISM: Artificial Sequence
<220> FEATURE:
<223> OTHER INFORMATION: Synthetic Construct

<400> SEQUENCE: 227

Gln Val Gln Leu Val Glu Ser Gly Gly Gly Val Val Gln Pro Gly Gly
1               5                   10                  15

Ser Leu Arg Leu Ser Cys Ala Ala Ser
```

<210> SEQ ID NO 228
<211> LENGTH: 17
<212> TYPE: PRT
<213> ORGANISM: Artificial Sequence
<220> FEATURE:
<223> OTHER INFORMATION: Synthetic Construct

<400> SEQUENCE: 228

Met His Trp Phe Arg Gln Ala Pro Gly Lys Gly Leu Glu Phe Val Ala
1               5                   10                  15

Phe

<210> SEQ ID NO 229
<211> LENGTH: 38
<212> TYPE: PRT
<213> ORGANISM: Artificial Sequence
<220> FEATURE:
<223> OTHER INFORMATION: Synthetic Construct

<400> SEQUENCE: 229

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 230
<211> LENGTH: 25
<212> TYPE: PRT
<213> ORGANISM: Artificial Sequence
<220> FEATURE:
<223> OTHER INFORMATION: Synthetic Construct

<400> SEQUENCE: 230

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 231
<211> LENGTH: 17
<212> TYPE: PRT
<213> ORGANISM: Artificial Sequence
<220> FEATURE:
<223> OTHER INFORMATION: Synthetic Construct

<400> SEQUENCE: 231

Met His Trp Phe Arg Gln Ala Pro Gly Lys Gly Leu Glu Phe Val Ser
1               5                   10                  15

Ala

<210> SEQ ID NO 232
<211> LENGTH: 38
<212> TYPE: PRT
<213> ORGANISM: Artificial Sequence
<220> FEATURE:
<223> OTHER INFORMATION: Synthetic Construct

<400> SEQUENCE: 232

Tyr Tyr Ala Asp Ser Val Lys Gly Arg Phe Thr Ile Ser Arg Asp Asn
1               5                   10                  15

```
Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 233
<211> LENGTH: 25
<212> TYPE: PRT
<213> ORGANISM: Artificial Sequence
<220> FEATURE:
<223> OTHER INFORMATION: Synthetic Construct

<400> SEQUENCE: 233

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 234
<211> LENGTH: 17
<212> TYPE: PRT
<213> ORGANISM: Artificial Sequence
<220> FEATURE:
<223> OTHER INFORMATION: Synthetic Construct

<400> SEQUENCE: 234

Met His Trp Phe Arg Gln Ala Pro Gly Lys Gly Leu Glu Phe Val Ser
1               5                   10                  15

Ala

<210> SEQ ID NO 235
<211> LENGTH: 38
<212> TYPE: PRT
<213> ORGANISM: Artificial Sequence
<220> FEATURE:
<223> OTHER INFORMATION: Synthetic Construct

<400> SEQUENCE: 235

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 236
<211> LENGTH: 25
<212> TYPE: PRT
<213> ORGANISM: Artificial Sequence
<220> FEATURE:
<223> OTHER INFORMATION: Synthetic Construct

<400> SEQUENCE: 236

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 237
<211> LENGTH: 17
<212> TYPE: PRT
<213> ORGANISM: Artificial Sequence
<220> FEATURE:
```

<223> OTHER INFORMATION: Synthetic Construct

<400> SEQUENCE: 237

Met Ser Trp Phe Arg Gln Ala Pro Gly Lys Gly Leu Glu Leu Val Ser
1               5                   10                  15

Val

<210> SEQ ID NO 238
<211> LENGTH: 39
<212> TYPE: PRT
<213> ORGANISM: Artificial Sequence
<220> FEATURE:
<223> OTHER INFORMATION: Synthetic Construct

<400> SEQUENCE: 238

Tyr Tyr Ala Asp Ser Val Lys Gly Arg Phe Thr Ile Ser Arg Asp Asn
1               5                   10                  15

Ser Lys Asn Thr Leu Leu Tyr Leu Gln Met Asn Ser Leu Arg Ala Glu
            20                  25                  30

Asp Thr Ala Val Tyr Tyr Cys
        35

<210> SEQ ID NO 239
<211> LENGTH: 25
<212> TYPE: PRT
<213> ORGANISM: Artificial Sequence
<220> FEATURE:
<223> OTHER INFORMATION: Synthetic Construct

<400> SEQUENCE: 239

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 240
<211> LENGTH: 17
<212> TYPE: PRT
<213> ORGANISM: Artificial Sequence
<220> FEATURE:
<223> OTHER INFORMATION: Synthetic Construct

<400> SEQUENCE: 240

Met His Trp Phe Arg Gln Ala Pro Gly Lys Gly Leu Glu Phe Val Ser
1               5                   10                  15

Ala

<210> SEQ ID NO 241
<211> LENGTH: 38
<212> TYPE: PRT
<213> ORGANISM: Artificial Sequence
<220> FEATURE:
<223> OTHER INFORMATION: Synthetic Construct

<400> SEQUENCE: 241

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

```
<210> SEQ ID NO 242
<211> LENGTH: 25
<212> TYPE: PRT
<213> ORGANISM: Artificial Sequence
<220> FEATURE:
<223> OTHER INFORMATION: Synthetic Construct

<400> SEQUENCE: 242

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 243
<211> LENGTH: 17
<212> TYPE: PRT
<213> ORGANISM: Artificial Sequence
<220> FEATURE:
<223> OTHER INFORMATION: Synthetic Construct

<400> SEQUENCE: 243

Met His Trp Phe Arg Gln Ala Pro Gly Lys Gly Leu Glu Ile Val Ser
1               5                   10                  15

Ala

<210> SEQ ID NO 244
<211> LENGTH: 38
<212> TYPE: PRT
<213> ORGANISM: Artificial Sequence
<220> FEATURE:
<223> OTHER INFORMATION: Synthetic Construct

<400> SEQUENCE: 244

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 245
<211> LENGTH: 25
<212> TYPE: PRT
<213> ORGANISM: Artificial Sequence
<220> FEATURE:
<223> OTHER INFORMATION: Synthetic Construct

<400> SEQUENCE: 245

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 246
<211> LENGTH: 17
<212> TYPE: PRT
<213> ORGANISM: Artificial Sequence
<220> FEATURE:
<223> OTHER INFORMATION: Synthetic Construct

<400> SEQUENCE: 246

Met His Trp Phe Arg Gln Ala Pro Gly Lys Gly Leu Glu Phe Val Ser
1               5                   10                  15

Ala
```

```
<210> SEQ ID NO 247
<211> LENGTH: 38
<212> TYPE: PRT
<213> ORGANISM: Artificial Sequence
<220> FEATURE:
<223> OTHER INFORMATION: Synthetic Construct

<400> SEQUENCE: 247

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 248
<211> LENGTH: 25
<212> TYPE: PRT
<213> ORGANISM: Artificial Sequence
<220> FEATURE:
<223> OTHER INFORMATION: Synthetic Construct

<400> SEQUENCE: 248

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 249
<211> LENGTH: 17
<212> TYPE: PRT
<213> ORGANISM: Artificial Sequence
<220> FEATURE:
<223> OTHER INFORMATION: Synthetic Construct

<400> SEQUENCE: 249

Met His Trp Phe Arg Gln Ala Pro Gly Lys Gly Leu Val Phe Val Ser
1               5                   10                  15

Arg

<210> SEQ ID NO 250
<211> LENGTH: 39
<212> TYPE: PRT
<213> ORGANISM: Artificial Sequence
<220> FEATURE:
<223> OTHER INFORMATION: Synthetic Construct

<400> SEQUENCE: 250

Ser Tyr Ala Asp Ser Val Lys Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Val Tyr Tyr Cys Ala
        35

<210> SEQ ID NO 251
<211> LENGTH: 25
<212> TYPE: PRT
<213> ORGANISM: Artificial Sequence
<220> FEATURE:
<223> OTHER INFORMATION: Synthetic Construct

<400> SEQUENCE: 251
```

```
Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 252
<211> LENGTH: 17
<212> TYPE: PRT
<213> ORGANISM: Artificial Sequence
<220> FEATURE:
<223> OTHER INFORMATION: Synthetic Construct

<400> SEQUENCE: 252

Met His Trp Phe Arg Gln Ala Pro Gly Lys Gly Leu Glu Phe Val Ser
1               5                   10                  15

Ala

<210> SEQ ID NO 253
<211> LENGTH: 40
<212> TYPE: PRT
<213> ORGANISM: Artificial Sequence
<220> FEATURE:
<223> OTHER INFORMATION: Synthetic Construct

<400> SEQUENCE: 253

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Ala Arg
        35                  40

<210> SEQ ID NO 254
<211> LENGTH: 25
<212> TYPE: PRT
<213> ORGANISM: Artificial Sequence
<220> FEATURE:
<223> OTHER INFORMATION: Synthetic Construct

<400> SEQUENCE: 254

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 255
<211> LENGTH: 17
<212> TYPE: PRT
<213> ORGANISM: Artificial Sequence
<220> FEATURE:
<223> OTHER INFORMATION: Synthetic Construct

<400> SEQUENCE: 255

Met His Trp Phe Arg Gln Ala Pro Gly Lys Gly Leu Glu Leu Val Ser
1               5                   10                  15

Ala

<210> SEQ ID NO 256
<211> LENGTH: 38
<212> TYPE: PRT
<213> ORGANISM: Artificial Sequence
<220> FEATURE:
<223> OTHER INFORMATION: Synthetic Construct
```

<400> SEQUENCE: 256

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
            35

<210> SEQ ID NO 257
<211> LENGTH: 25
<212> TYPE: PRT
<213> ORGANISM: Artificial Sequence
<220> FEATURE:
<223> OTHER INFORMATION: Synthetic Construct

<400> SEQUENCE: 257

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 258
<211> LENGTH: 17
<212> TYPE: PRT
<213> ORGANISM: Artificial Sequence
<220> FEATURE:
<223> OTHER INFORMATION: Synthetic Construct

<400> SEQUENCE: 258

Met His Trp Phe Arg Gln Ala Pro Gly Lys Gly Leu Glu Leu Val Ser
1               5                   10                  15

Ala

<210> SEQ ID NO 259
<211> LENGTH: 38
<212> TYPE: PRT
<213> ORGANISM: Artificial Sequence
<220> FEATURE:
<223> OTHER INFORMATION: Synthetic Construct

<400> SEQUENCE: 259

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
            35

<210> SEQ ID NO 260
<211> LENGTH: 609
<212> TYPE: PRT
<213> ORGANISM: Homo sapiens

<400> SEQUENCE: 260

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

-continued

```
Ile Ala Phe Ala Gln Tyr Leu Gln Gln Cys Pro Phe Glu Asp His Val
 50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
    435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
```

```
                465                 470                 475                 480
Leu Asn Gln Leu Cys Val Leu His Glu Lys Thr Pro Val Ser Asp Arg
                    485                 490                 495
Val Thr Lys Cys Cys Thr Glu Ser Leu Val Asn Arg Arg Pro Cys Phe
                    500                 505                 510
Ser Ala Leu Glu Val Asp Glu Thr Tyr Val Pro Lys Glu Phe Asn Ala
                    515                 520                 525
Glu Thr Phe Thr Phe His Ala Asp Ile Cys Thr Leu Ser Glu Lys Glu
                    530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                    565                 570                 575
Ala Phe Val Glu Lys Cys Cys Lys Ala Asp Asp Lys Glu Thr Cys Phe
                    580                 585                 590
Ala Glu Glu Gly Lys Lys Leu Val Ala Ala Ser Gln Ala Ala Leu Gly
                    595                 600                 605
Leu

<210> SEQ ID NO 261
<211> LENGTH: 417
<212> TYPE: PRT
<213> ORGANISM: Homo sapiens

<400> SEQUENCE: 261

Met Lys Trp Val Thr Phe Ile Ser Leu Leu Phe Leu Phe Ser Ser Ala
1               5                   10                  15
Tyr Ser Arg Gly Val Phe Arg Arg Asp Ala His Lys Ser Glu Val Ala
                20                  25                  30
His Arg Phe Lys Asp Leu Gly Glu Glu Asn Phe Lys Ala Trp Ala Val
            35                  40                  45
Ala Arg Leu Ser Gln Arg Phe Pro Lys Ala Glu Phe Ala Glu Val Ser
        50                  55                  60
Lys Leu Val Thr Asp Leu Thr Lys Val His Thr Glu Cys Cys His Gly
65                  70                  75                  80
Asp Leu Leu Glu Cys Ala Asp Asp Arg Ala Asp Leu Ala Lys Tyr Ile
                85                  90                  95
Cys Glu Asn Gln Asp Ser Ile Ser Ser Lys Leu Lys Glu Cys Cys Glu
                100                 105                 110
Lys Pro Leu Leu Glu Lys Ser His Cys Ile Ala Glu Val Glu Asn Asp
            115                 120                 125
Glu Met Pro Ala Asp Leu Pro Ser Leu Ala Ala Asp Phe Val Glu Ser
        130                 135                 140
Lys Asp Val Cys Lys Asn Tyr Ala Glu Ala Lys Asp Val Phe Leu Gly
145                 150                 155                 160
Met Phe Leu Tyr Glu Tyr Ala Arg Arg His Pro Asp Tyr Ser Val Val
                165                 170                 175
Leu Leu Leu Arg Leu Ala Lys Thr Tyr Glu Thr Thr Leu Glu Lys Cys
                180                 185                 190
Cys Ala Ala Ala Asp Pro His Glu Cys Tyr Ala Lys Val Phe Asp Glu
            195                 200                 205
Phe Lys Pro Leu Val Glu Glu Pro Gln Asn Leu Ile Lys Gln Asn Cys
        210                 215                 220
Glu Leu Phe Glu Gln Leu Gly Glu Tyr Lys Phe Gln Asn Ala Leu Leu
```

```
              225                 230                 235                 240
Val Arg Tyr Thr Lys Lys Val Pro Gln Val Ser Thr Pro Thr Leu Val
                245                 250                 255
Glu Val Ser Arg Asn Leu Gly Lys Val Gly Ser Lys Cys Cys Lys His
                260                 265                 270
Pro Glu Ala Lys Arg Met Pro Cys Ala Glu Asp Tyr Leu Ser Val Val
                275                 280                 285
Leu Asn Gln Leu Cys Val Leu His Glu Lys Thr Pro Val Ser Asp Arg
            290                 295                 300
Val Thr Lys Cys Cys Thr Glu Ser Leu Val Asn Arg Arg Pro Cys Phe
305                 310                 315                 320
Ser Ala Leu Glu Val Asp Glu Thr Tyr Val Pro Lys Glu Phe Asn Ala
                325                 330                 335
Glu Thr Phe Thr Phe His Ala Asp Ile Cys Thr Leu Ser Glu Lys Glu
                340                 345                 350
Arg Gln Ile Lys Lys Gln Thr Ala Leu Val Glu Leu Val Lys His Lys
                355                 360                 365
Pro Lys Ala Thr Lys Glu Gln Leu Lys Ala Val Met Asp Asp Phe Ala
            370                 375                 380
Ala Phe Val Glu Lys Cys Cys Lys Ala Asp Asp Lys Glu Thr Cys Phe
385                 390                 395                 400
Ala Glu Glu Gly Lys Lys Leu Val Ala Ala Ser Gln Ala Ala Leu Gly
                405                 410                 415
Leu

<210> SEQ ID NO 262
<211> LENGTH: 396
<212> TYPE: PRT
<213> ORGANISM: Homo sapiens

<400> SEQUENCE: 262

Met Lys Trp Val Thr Phe Ile Ser Leu Leu Phe Leu Phe Ser Ser Ala
1               5                   10                  15
Tyr Ser Arg Gly Val Phe Arg Arg Asp Ala His Lys Ser Glu Val Ala
                20                  25                  30
His Arg Phe Lys Asp Leu Gly Glu Glu Asn Phe Lys Ala Leu Val Leu
            35                  40                  45
Ile Ala Phe Ala Gln Tyr Leu Gln Gln Cys Pro Phe Glu Asp His Val
        50                  55                  60
Lys Leu Val Asn Glu Val Thr Glu Phe Ala Lys Thr Cys Val Ala Asp
65                  70                  75                  80
Glu Ser Ala Glu Asn Cys Asp Lys Ser Leu His Thr Leu Phe Gly Asp
                85                  90                  95
Lys Leu Cys Thr Val Ala Thr Leu Arg Glu Thr Tyr Gly Glu Met Ala
                100                 105                 110
Asp Cys Cys Ala Lys Gln Glu Pro Glu Arg Asn Glu Cys Phe Leu Gln
            115                 120                 125
His Lys Asp Asp Asn Pro Asn Leu Pro Arg Leu Val Arg Pro Glu Val
        130                 135                 140
Asp Val Met Cys Thr Ala Phe His Asp Asn Glu Glu Thr Phe Leu Lys
145                 150                 155                 160
Lys Tyr Leu Tyr Glu Thr Thr Leu Glu Lys Cys Cys Ala Ala Ala Asp
                165                 170                 175
Pro His Glu Cys Tyr Ala Lys Val Phe Asp Glu Phe Lys Pro Leu Val
```

```
                180                 185                 190
Glu Glu Pro Gln Asn Leu Ile Lys Gln Asn Cys Glu Leu Phe Glu Gln
            195                 200                 205

Leu Gly Glu Tyr Lys Phe Gln Asn Ala Leu Leu Val Arg Tyr Thr Lys
        210                 215                 220

Lys Val Pro Gln Val Ser Thr Pro Thr Leu Val Glu Val Ser Arg Asn
225                 230                 235                 240

Leu Gly Lys Val Gly Ser Lys Cys Cys Lys His Pro Glu Ala Lys Arg
                245                 250                 255

Met Pro Cys Ala Glu Asp Tyr Leu Ser Val Val Leu Asn Gln Leu Cys
            260                 265                 270

Val Leu His Glu Lys Thr Pro Val Ser Asp Arg Val Thr Lys Cys Cys
        275                 280                 285

Thr Glu Ser Leu Val Asn Arg Arg Pro Cys Phe Ser Ala Leu Glu Val
    290                 295                 300

Asp Glu Thr Tyr Val Pro Lys Glu Phe Asn Ala Glu Thr Phe Thr Phe
305                 310                 315                 320

His Ala Asp Ile Cys Thr Leu Ser Glu Lys Glu Arg Gln Ile Lys Lys
                325                 330                 335

Gln Thr Ala Leu Val Glu Leu Val Lys His Lys Pro Lys Ala Thr Lys
            340                 345                 350

Glu Gln Leu Lys Ala Val Met Asp Asp Phe Ala Ala Phe Val Glu Lys
        355                 360                 365

Cys Cys Lys Ala Asp Asp Lys Glu Thr Cys Phe Ala Glu Glu Gly Lys
    370                 375                 380

Lys Leu Val Ala Ala Ser Gln Ala Ala Leu Gly Leu
385                 390                 395

<210> SEQ ID NO 263
<211> LENGTH: 630
<212> TYPE: PRT
<213> ORGANISM: Homo sapiens

<400> SEQUENCE: 263

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160
```

```
Arg Leu Leu Pro Ala Leu Ala Cys Trp Gly Val Arg Gly Ser Leu
                165                 170                 175

Leu Ser Glu Ala Asp Val Arg Ala Leu Gly Leu Ala Cys Asp Leu
            180                 185                 190

Pro Gly Arg Phe Val Ala Glu Ser Ala Glu Val Leu Leu Pro Arg Leu
                195                 200                 205

Val Ser Cys Pro Gly Pro Leu Asp Gln Asp Gln Gln Glu Ala Ala Arg
    210                 215                 220

Ala Ala Leu Gln Gly Gly Pro Pro Tyr Gly Pro Pro Ser Thr Trp
225             230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
            275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
            355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
                420                 425                 430

Leu Asp Lys Asp Thr Leu Asp Thr Leu Thr Ala Phe Tyr Pro Gly Tyr
            435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
    515                 520                 525

Ala Thr Phe Met Lys Leu Arg Thr Asp Ala Val Leu Pro Leu Thr Val
530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
```

580                 585                 590
Gly Tyr Leu Val Leu Asp Leu Ser Met Gln Glu Ala Leu Ser Gly Thr
                595                 600                 605

Pro Cys Leu Leu Gly Pro Gly Pro Val Leu Thr Val Leu Ala Leu Leu
        610                 615                 620

Leu Ala Ser Thr Leu Ala
625                 630

<210> SEQ ID NO 264
<211> LENGTH: 622
<212> TYPE: PRT
<213> ORGANISM: Homo sapiens

<400> SEQUENCE: 264

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
        50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
                100                 105                 110

Glu Asp Leu Asp Ala Leu Pro Leu Asp Leu Leu Leu Phe Leu Asn Pro
            115                 120                 125

Asp Ala Phe Ser Gly Pro Gln Ala Cys Thr Arg Phe Phe Ser Arg Ile
        130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
                180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
        210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
            275                 280                 285

Leu Arg Pro Arg Phe Arg Glu Val Glu Lys Thr Ala Cys Pro Ser
        290                 295                 300

Gly Lys Lys Ala Arg Glu Ile Asp Glu Ser Leu Ile Phe Tyr Lys Lys
305                 310                 315                 320

-continued

```
Trp Glu Leu Glu Ala Cys Val Asp Ala Ala Leu Leu Ala Thr Gln Met
            325                 330                 335

Asp Arg Val Asn Ala Ile Pro Phe Thr Tyr Glu Gln Leu Asp Val Leu
        340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
            405                 410                 415

Arg Phe Val Lys Gly Arg Gly Gln Leu Asp Lys Asp Thr Leu Asp Thr
        420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
            485                 490                 495

Gln Ser Phe Leu Gly Gly Ala Pro Thr Glu Asp Leu Lys Ala Leu Ser
        500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
            565                 570                 575

Gly Leu Gln Gly Gly Ile Pro Asn Gly Tyr Leu Val Leu Asp Leu Ser
        580                 585                 590

Met Gln Glu Ala Leu Ser Gly Thr Pro Cys Leu Leu Gly Pro Gly Pro
        595                 600                 605

Val Leu Thr Val Leu Ala Leu Leu Ala Ser Thr Leu Ala
    610                 615                 620
```

<210> SEQ ID NO 265
<211> LENGTH: 656
<212> TYPE: PRT
<213> ORGANISM: Homo sapiens

<400> SEQUENCE: 265

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80
```

```
Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495
```

```
Gln Ser Phe Leu Gly Gly Ala Pro Thr Glu Asp Leu Lys Ala Leu Ser
                500                 505                 510

Gln Gln Asn Val Ser Met Asp Leu Ala Thr Phe Met Lys Leu Arg Thr
            515                 520                 525

Asp Ala Val Leu Pro Leu Thr Val Ala Glu Val Gln Lys Leu Leu Gly
        530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Val Gln Gly Gly Arg Gly Gly Gln Ala Arg Ala Gly Gly Arg Ala Gly
        595                 600                 605

Gly Val Glu Val Gly Ala Leu Ser His Pro Ser Leu Cys Arg Gly Pro
    610                 615                 620

Leu Gly Asp Ala Leu Pro Pro Arg Thr Trp Thr Cys Ser His Arg Pro
625                 630                 635                 640

Gly Thr Ala Pro Ser Leu His Pro Gly Leu Arg Ala Pro Leu Pro Cys
                645                 650                 655

<210> SEQ ID NO 266
<211> LENGTH: 621
<212> TYPE: PRT
<213> ORGANISM: Homo sapiens

<400> SEQUENCE: 266

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Ala Ala Pro Leu Asp
            35                  40                  45

Gly Val Leu Ala Asn Pro Pro Asn Ile Ser Ser Leu Ser Pro Arg Gln
        50                  55                  60

Leu Leu Gly Phe Pro Cys Ala Glu Val Ser Gly Leu Ser Thr Glu Arg
65                  70                  75                  80

Val Arg Glu Leu Ala Val Ala Leu Ala Gln Lys Asn Val Lys Leu Ser
                85                  90                  95

Thr Glu Gln Leu Arg Cys Leu Ala His Arg Leu Ser Glu Pro Pro Glu
            100                 105                 110

Asp Leu Asp Ala Leu Pro Leu Asp Leu Leu Leu Phe Leu Asn Pro Asp
        115                 120                 125

Ala Phe Ser Gly Pro Gln Ala Cys Thr Arg Phe Phe Ser Arg Ile Thr
    130                 135                 140

Lys Ala Asn Val Asp Leu Leu Pro Arg Gly Ala Pro Glu Arg Gln Arg
145                 150                 155                 160

Leu Leu Pro Ala Ala Leu Ala Cys Trp Gly Val Arg Gly Ser Leu Leu
                165                 170                 175

Ser Glu Ala Asp Val Arg Ala Leu Gly Gly Leu Ala Cys Asp Leu Pro
            180                 185                 190

Gly Arg Phe Val Ala Glu Ser Ala Glu Val Leu Leu Pro Arg Leu Val
        195                 200                 205

Ser Cys Pro Gly Pro Leu Asp Gln Asp Gln Gln Glu Ala Ala Arg Ala
    210                 215                 220
```

```
Ala Leu Gln Gly Gly Gly Pro Pro Tyr Gly Pro Pro Ser Thr Trp Ser
225                 230                 235                 240

Val Ser Thr Met Asp Ala Leu Arg Gly Leu Leu Pro Val Leu Gly Gln
            245                 250                 255

Pro Ile Ile Arg Ser Ile Pro Gln Gly Ile Val Ala Ala Trp Arg Gln
                260                 265                 270

Arg Ser Ser Arg Asp Pro Ser Trp Arg Gln Pro Glu Arg Thr Ile Leu
            275                 280                 285

Arg Pro Arg Phe Arg Glu Val Glu Lys Thr Ala Cys Pro Ser Gly
        290                 295                 300

Lys Lys Ala Arg Glu Ile Asp Glu Ser Leu Ile Phe Tyr Lys Lys Trp
305                 310                 315                 320

Glu Leu Glu Ala Cys Val Asp Ala Ala Leu Leu Ala Thr Gln Met Asp
                325                 330                 335

Arg Val Asn Ala Ile Pro Phe Thr Tyr Glu Gln Leu Asp Val Leu Lys
            340                 345                 350

His Lys Leu Asp Glu Leu Tyr Pro Gln Gly Tyr Pro Glu Ser Val Ile
            355                 360                 365

Gln His Leu Gly Tyr Leu Phe Leu Lys Met Ser Pro Glu Asp Ile Arg
370                 375                 380

Lys Trp Asn Val Thr Ser Leu Glu Thr Leu Lys Ala Leu Leu Glu Val
385                 390                 395                 400

Asn Lys Gly His Glu Met Ser Pro Gln Val Ala Thr Leu Ile Asp Arg
                405                 410                 415

Phe Val Lys Gly Arg Gly Gln Leu Asp Lys Asp Thr Leu Asp Thr Leu
            420                 425                 430

Thr Ala Phe Tyr Pro Gly Tyr Leu Cys Ser Leu Ser Pro Glu Glu Leu
            435                 440                 445

Ser Ser Val Pro Pro Ser Ser Ile Trp Ala Val Arg Pro Gln Asp Leu
450                 455                 460

Asp Thr Cys Asp Pro Arg Gln Leu Asp Val Leu Tyr Pro Lys Ala Arg
465                 470                 475                 480

Leu Ala Phe Gln Asn Met Asn Gly Ser Glu Tyr Phe Val Lys Ile Gln
                485                 490                 495

Ser Phe Leu Gly Gly Ala Pro Thr Glu Asp Leu Lys Ala Leu Ser Gln
            500                 505                 510

Gln Asn Val Ser Met Asp Leu Ala Thr Phe Met Lys Leu Arg Thr Asp
        515                 520                 525

Ala Val Leu Pro Leu Thr Val Ala Glu Val Gln Lys Leu Leu Gly Pro
530                 535                 540

His Val Glu Gly Leu Lys Ala Glu Glu Arg His Arg Pro Val Arg Asp
545                 550                 555                 560

Trp Ile Leu Arg Gln Arg Gln Asp Asp Leu Asp Thr Leu Gly Leu Gly
            565                 570                 575

Leu Gln Gly Gly Ile Pro Asn Gly Tyr Leu Val Leu Asp Leu Ser Met
            580                 585                 590

Gln Glu Ala Leu Ser Gly Thr Pro Cys Leu Leu Gly Pro Gly Pro Val
            595                 600                 605

Leu Thr Val Leu Ala Leu Leu Leu Ala Ser Thr Leu Ala
610                 615                 620

<210> SEQ ID NO 267
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 267

Lys Gly Pro Gln Gly Ile Ala Gly Gln
1               5

<210> SEQ ID NO 268
<211> LENGTH: 9
<212> TYPE: PRT
<213> ORGANISM: Artificial Sequence
<220> FEATURE:
<223> OTHER INFORMATION: Synthetic Construct

<400> SEQUENCE: 268

Phe Gly Pro Gln Gly Leu Ala Gly Gln
1               5

<210> SEQ ID NO 269
<211> LENGTH: 9
<212> TYPE: PRT
<213> ORGANISM: Artificial Sequence
<220> FEATURE:
<223> OTHER INFORMATION: Synthetic Construct

<400> SEQUENCE: 269

Arg Gly Pro Gln Gly Ile Phe Gly Gln
1               5

<210> SEQ ID NO 270
<211> LENGTH: 9
<212> TYPE: PRT
<213> ORGANISM: Artificial Sequence
<220> FEATURE:
<223> OTHER INFORMATION: Synthetic Construct

<400> SEQUENCE: 270

Ile Gly Pro Gln Gly Ile Trp Gly Gln
1               5

<210> SEQ ID NO 271
<211> LENGTH: 9
<212> TYPE: PRT
<213> ORGANISM: Artificial Sequence
<220> FEATURE:
<223> OTHER INFORMATION: Synthetic Construct

<400> SEQUENCE: 271

Met Gly Pro Gln Gly Ile Leu Gly Gln
1               5

<210> SEQ ID NO 272
<211> LENGTH: 9
<212> TYPE: PRT
<213> ORGANISM: Artificial Sequence
<220> FEATURE:
<223> OTHER INFORMATION: Synthetic Construct

<400> SEQUENCE: 272

Lys Gly Pro Gln Ser Ile Ala Gly Gln
1               5

<210> SEQ ID NO 273
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 273

Phe Gly Pro Gln Ser Leu Ala Gly Gln
1               5

<210> SEQ ID NO 274
<211> LENGTH: 9
<212> TYPE: PRT
<213> ORGANISM: Artificial Sequence
<220> FEATURE:
<223> OTHER INFORMATION: Synthetic Construct

<400> SEQUENCE: 274

Arg Gly Pro Gln Ser Ile Phe Gly Gln
1               5

<210> SEQ ID NO 275
<211> LENGTH: 9
<212> TYPE: PRT
<213> ORGANISM: Artificial Sequence
<220> FEATURE:
<223> OTHER INFORMATION: Synthetic Construct

<400> SEQUENCE: 275

Ile Gly Pro Gln Ser Ile Trp Gly Gln
1               5

<210> SEQ ID NO 276
<211> LENGTH: 9
<212> TYPE: PRT
<213> ORGANISM: Artificial Sequence
<220> FEATURE:
<223> OTHER INFORMATION: Synthetic Construct

<400> SEQUENCE: 276

Met Gly Pro Gln Ser Ile Leu Gly Gln
1               5

<210> SEQ ID NO 277
<211> LENGTH: 9
<212> TYPE: PRT
<213> ORGANISM: Artificial Sequence
<220> FEATURE:
<223> OTHER INFORMATION: Synthetic Construct

<400> SEQUENCE: 277

Lys Gly Pro Gln Thr Ile Ala Gly Gln
1               5

<210> SEQ ID NO 278
<211> LENGTH: 9
<212> TYPE: PRT
<213> ORGANISM: Artificial Sequence
<220> FEATURE:
<223> OTHER INFORMATION: Synthetic Construct

<400> SEQUENCE: 278

Phe Gly Pro Gln Thr Leu Ala Gly Gln
1               5

<210> SEQ ID NO 279
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 279

Arg Gly Pro Gln Thr Ile Phe Gly Gln
1               5

<210> SEQ ID NO 280
<211> LENGTH: 9
<212> TYPE: PRT
<213> ORGANISM: Artificial Sequence
<220> FEATURE:
<223> OTHER INFORMATION: Synthetic Construct

<400> SEQUENCE: 280

Ile Gly Pro Gln Thr Ile Trp Gly Gln
1               5

<210> SEQ ID NO 281
<211> LENGTH: 9
<212> TYPE: PRT
<213> ORGANISM: Artificial Sequence
<220> FEATURE:
<223> OTHER INFORMATION: Synthetic Construct

<400> SEQUENCE: 281

Phe Arg Pro Arg Ser Ile Thr Gly Gln
1               5

<210> SEQ ID NO 282
<211> LENGTH: 9
<212> TYPE: PRT
<213> ORGANISM: Artificial Sequence
<220> FEATURE:
<223> OTHER INFORMATION: Synthetic Construct

<400> SEQUENCE: 282

Met Gly Pro Gln Thr Ile Leu Gly Gln
1               5

<210> SEQ ID NO 283
<211> LENGTH: 311
<212> TYPE: PRT
<213> ORGANISM: Artificial Sequence
<220> FEATURE:
<223> OTHER INFORMATION: Synthetic Construct

<400> SEQUENCE: 283

Glu Val Glu Lys Thr Ala Cys Pro Ser Gly Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Glu Val Asn Lys Gly His Glu Met
            100                 105                 110

Ser Pro Gln Ala Pro Arg Arg Pro Leu Pro Gln Val Ala Thr Leu Ile
```

```
            115                 120                 125
Asp Arg Phe Val Lys Gly Arg Gly Gln Leu Asp Lys Asp Thr Leu Asp
    130                 135                 140

Thr Leu Thr Ala Phe Tyr Pro Gly Tyr Leu Cys Ser Leu Ser Pro Glu
145                 150                 155                 160

Glu Leu Ser Ser Val Pro Pro Ser Ser Ile Trp Ala Val Arg Pro Gln
                165                 170                 175

Asp Leu Asp Thr Cys Asp Pro Arg Gln Leu Asp Val Leu Tyr Pro Lys
            180                 185                 190

Ala Arg Leu Ala Phe Gln Asn Met Asn Gly Ser Glu Tyr Phe Val Lys
        195                 200                 205

Ile Gln Ser Phe Leu Gly Gly Ala Pro Thr Glu Asp Leu Lys Ala Leu
    210                 215                 220

Ser Gln Gln Asn Val Ser Met Asp Leu Ala Thr Phe Met Lys Leu Arg
225                 230                 235                 240

Thr Asp Ala Val Leu Pro Leu Thr Val Ala Glu Val Gln Lys Leu Leu
                245                 250                 255

Gly Pro His Val Glu Gly Leu Lys Ala Glu Glu Arg His Arg Pro Val
            260                 265                 270

Arg Asp Trp Ile Leu Arg Gln Arg Gln Asp Asp Leu Asp Thr Leu Gly
        275                 280                 285

Leu Gly Leu Gln Gly Gly Ile Pro Asn Gly Tyr Leu Val Leu Asp Leu
    290                 295                 300

Ser Met Gln Glu Ala Leu Ser
305                 310

<210> SEQ ID NO 284
<211> LENGTH: 50
<212> TYPE: PRT
<213> ORGANISM: Artificial Sequence
<220> FEATURE:
<223> OTHER INFORMATION: Synthetic Construct

<400> SEQUENCE: 284

Val Gln Lys Leu Leu Gly Pro His Val Glu Gly Leu Lys Ala Glu Glu
1               5                   10                  15

Arg His Arg Pro Val Arg Asp Trp Ile Leu Arg Gln Arg Gln Asp Asp
            20                  25                  30

Leu Asp Thr Leu Gly Leu Gly Leu Gln Gly Gly Ile Pro Asn Gly Tyr
        35                  40                  45

Leu Val
    50

<210> SEQ ID NO 285
<211> LENGTH: 118
<212> TYPE: PRT
<213> ORGANISM: Artificial Sequence
<220> FEATURE:
<223> OTHER INFORMATION: Synthetic Construct

<400> SEQUENCE: 285

Gln Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Pro Val Asn
            20                  25                  30

Ala Tyr Gly Trp Tyr Arg Gln Ala Pro Gly Lys Gln Arg Asp Leu Val
        35                  40                  45
```

```
Ala Ile Ile Ser Ala Gly Gly Thr Thr Asn Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Tyr
                 85                  90                  95

Leu Gln Arg Arg Ile Gly Met Leu Arg Asp Tyr Trp Gly Gln Gly Thr
                100                 105                 110

Gln Val Thr Val Ser Ser
            115
```

<210> SEQ ID NO 286
<211> LENGTH: 118
<212> TYPE: PRT
<213> ORGANISM: Artificial Sequence
<220> FEATURE:
<223> OTHER INFORMATION: Synthetic Construct

<400> SEQUENCE: 286

```
Gln Val Gln Leu Val Glu Ser Gly Gly Gly Leu Val Gln Ala Gly Gly
 1               5                  10                  15

Ser Leu Arg Leu Ser Cys Ala Ala Ser Gly Ile Thr Phe Pro Val Asn
                 20                  25                  30

Ala Tyr Gly Trp Tyr Arg Gln Ala Pro Gly Lys Gly Leu Glu Leu Val
             35                  40                  45

Ala Ile Ile Ser Ala Gly Gly Thr Thr Asn Tyr Ala Asp Ser Val Lys
 50                  55                  60

Gly Arg Phe Ala Ile Ser Lys Asp Asn Val Asn Asn Thr Val Tyr Leu
 65                  70                  75                  80

Gln Met Asn Ser Leu Thr Ser Glu Asp Thr Gly Val Tyr Tyr Cys Tyr
                 85                  90                  95

Leu Gln Arg Arg Ile Gly Met Leu Arg Asp Tyr Trp Gly Gln Gly Thr
                100                 105                 110

Gln Val Thr Val Ser Ser
            115
```

<210> SEQ ID NO 287
<211> LENGTH: 118
<212> TYPE: PRT
<213> ORGANISM: Artificial Sequence
<220> FEATURE:
<223> OTHER INFORMATION: Synthetic Construct

<400> SEQUENCE: 287

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Ile Thr Phe Pro Val Asn
                 20                  25                  30

Ala Tyr Gly Trp Tyr Arg Gln Ala Pro Gly Lys Gly Leu Glu Leu Val
             35                  40                  45

Ala Ile Ile Ser Ala Gly Gly Thr Thr Asn Tyr Ala Asp Ser Val Lys
 50                  55                  60

Gly Arg Phe Ala Ile Ser Lys Asp Asn Val Asn Asn Thr Val Tyr Leu
 65                  70                  75                  80

Gln Met Asn Ser Leu Thr Ser Glu Asp Thr Gly Val Tyr Tyr Cys Tyr
                 85                  90                  95

Leu Gln Arg Arg Ile Gly Met Leu Arg Asp Tyr Trp Gly Gln Gly Thr
                100                 105                 110
```

Gln Val Thr Val Ser Ser
        115

<210> SEQ ID NO 288
<211> LENGTH: 119
<212> TYPE: PRT
<213> ORGANISM: Artificial Sequence
<220> FEATURE:
<223> OTHER INFORMATION: Synthetic Construct

<400> SEQUENCE: 288

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ser Ser Ile Arg
            20                  25                  30

His Met Arg Trp Tyr Arg Gln Ala Pro Gly Lys Gln Arg Glu Leu Val
        35                  40                  45

Ala Thr Val Ser Asn Asp Gly Ser Ala Tyr Tyr Ala Gly Ser Val Lys
    50                  55                  60

Gly Arg Phe Thr Ile Ser Arg Asp Asn Ser Lys Asn Thr Leu Leu Tyr
65                  70                  75                  80

Leu Gln Met Asn Ser Leu Arg Ala Glu Asp Thr Ala Val Tyr Ile Cys
                85                  90                  95

Asn Ala Asp Thr Trp Gly Trp Pro Gly Ala Asp Tyr Trp Gly Gln Gly
            100                 105                 110

Thr Gln Val Thr Val Ser Ser
        115

<210> SEQ ID NO 289
<211> LENGTH: 119
<212> TYPE: PRT
<213> ORGANISM: Artificial Sequence
<220> FEATURE:
<223> OTHER INFORMATION: Synthetic Construct

<400> SEQUENCE: 289

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ser Ile Arg
            20                  25                  30

His Met Arg Trp Tyr Arg Gln Ala Pro Gly Lys Gly Leu Glu Leu Val
        35                  40                  45

Ala Thr Val Ser Asn Asp Gly Ser Ala Tyr Tyr Leu Gly Ser Val Lys
    50                  55                  60

Gly Arg Phe Thr Ile Ser Arg Thr Asn Ala Lys Asn Thr Leu Leu Tyr
65                  70                  75                  80

Leu Gln Met Asn Ser Leu Lys Pro Glu Asp Ser Ala Leu Tyr Ile Cys
                85                  90                  95

Asn Ala Asp Thr Trp Gly Trp Pro Gly Ala Asp Tyr Trp Gly Gln Gly
            100                 105                 110

Thr Gln Val Thr Val Ser Ser
        115

<210> SEQ ID NO 290
<211> LENGTH: 119
<212> TYPE: PRT
<213> ORGANISM: Artificial Sequence
<220> FEATURE:
<223> OTHER INFORMATION: Synthetic Construct

<400> SEQUENCE: 290

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ser Ser Ile Arg
            20                  25                  30

His Met Arg Trp Tyr Arg Gln Ala Pro Gly Lys Gly Leu Glu Leu Val
        35                  40                  45

Ala Thr Val Ser Asn Asp Ser Ala Tyr Tyr Leu Gly Ser Val Lys
    50                  55                  60

Gly Arg Phe Thr Ile Ser Arg Thr Asn Ala Lys Asn Thr Leu Leu Tyr
65                  70                  75                  80

Leu Gln Met Asn Ser Leu Lys Pro Glu Asp Ser Ala Leu Tyr Ile Cys
                85                  90                  95

Asn Ala Asp Thr Trp Gly Trp Pro Gly Ala Asp Tyr Trp Gly Gln Gly
            100                 105                 110

Thr Gln Val Thr Val Ser Ser
        115

<210> SEQ ID NO 291
<211> LENGTH: 112
<212> TYPE: PRT
<213> ORGANISM: Artificial Sequence
<220> FEATURE:
<223> OTHER INFORMATION: Synthetic Construct

<400> SEQUENCE: 291

Gln Val Gln Leu Val Glu Ser Gly Gly Gly Leu Val Gln Pro Gly Gly
1               5                   10                  15

Ser Leu Arg Leu Ser Cys Val Val Ser Gly Arg Thr Leu Glu Ser Tyr
            20                  25                  30

Val Met Ala Trp Phe Arg Gln Ala Pro Gly Lys Glu Arg Glu Ala Val
        35                  40                  45

Ala Ser Ile Asn Trp Ser Ser Gly Arg Leu Ile Tyr Ala Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110

<210> SEQ ID NO 292
<211> LENGTH: 112
<212> TYPE: PRT
<213> ORGANISM: Artificial Sequence
<220> FEATURE:
<223> OTHER INFORMATION: Synthetic Construct

<400> SEQUENCE: 292

Gln Val Gln Leu Val Glu Ser Gly Gly Gly Leu Val Gln Pro Gly Gly
1               5                   10                  15

Ser Leu Arg Leu Ser Cys Val Val Ser Gly Arg Thr Leu Glu Ser Tyr
            20                  25                  30

Val Met Ala Trp Phe Arg Gln Ala Pro Gly Lys Gly Leu Glu Ala Val
        35                  40                  45

Ala Ser Ile Asn Trp Ser Ser Gly Arg Leu Ile Tyr Ala Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110

<210> SEQ ID NO 293
<211> LENGTH: 112
<212> TYPE: PRT
<213> ORGANISM: Artificial Sequence
<220> FEATURE:
<223> OTHER INFORMATION: Synthetic Construct

<400> SEQUENCE: 293

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Leu Glu Ser Tyr
            20                  25                  30

Val Met Ala Trp Phe Arg Gln Ala Pro Gly Lys Gly Leu Glu Ala Val
        35                  40                  45

Ala Ser Ile Asn Trp Ser Ser Gly Arg Leu Ile Tyr Ala Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110

<210> SEQ ID NO 294
<211> LENGTH: 112
<212> TYPE: PRT
<213> ORGANISM: Artificial Sequence
<220> FEATURE:
<223> OTHER INFORMATION: Synthetic Construct

<400> SEQUENCE: 294

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Leu Glu Ser Tyr
            20                  25                  30

Val Met Ala Trp Phe Arg Gln Ala Pro Gly Lys Gly Leu Glu Ala Val
        35                  40                  45

Ala Ser Ile Asn Trp Ser Ser Gly Arg Leu Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110

<210> SEQ ID NO 295
<211> LENGTH: 112
<212> TYPE: PRT
<213> ORGANISM: Artificial Sequence
<220> FEATURE:
<223> OTHER INFORMATION: Synthetic Construct

<400> SEQUENCE: 295

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Leu Glu Ser Tyr
            20                  25                  30

Val Met Ala Trp Phe Arg Gln Ala Pro Gly Lys Glu Arg Glu Ala Val
        35                  40                  45

Ala Ser Ile Asn Trp Ser Ser Gly Arg Leu Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110
```

<210> SEQ ID NO 296
<211> LENGTH: 127
<212> TYPE: PRT
<213> ORGANISM: Artificial Sequence
<220> FEATURE:
<223> OTHER INFORMATION: Synthetic Construct

<400> SEQUENCE: 296

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Phe Asn Asn Asn
            20                  25                  30

Ala Met Ala Trp Phe Arg Gln Thr Pro Gly Lys Glu Arg Glu Phe Val
        35                  40                  45

Ala Ala Ile Thr Trp Val Gly Ser Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Gln Tyr Pro Phe Ser Ile Ile Gly Tyr Asn Ser Lys Asp
            100                 105                 110

Ala Trp Asn Tyr Trp Gly Gln Gly Thr Arg Val Thr Val Ser Ser
        115                 120                 125
```

<210> SEQ ID NO 297
<211> LENGTH: 127
<212> TYPE: PRT
<213> ORGANISM: Artificial Sequence
<220> FEATURE:
<223> OTHER INFORMATION: Synthetic Construct

<400> SEQUENCE: 297

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Phe Asn Asn Asn
            20                  25                  30

Ala Met Ala Trp Phe Arg Gln Thr Pro Gly Lys Gly Leu Glu Phe Val
        35                  40                  45

Ala Ala Ile Thr Trp Val Gly Ser Gly Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Arg Gln Tyr Pro Phe Ser Ile Ile Gly Tyr Asn Ser Lys Asp
            100                 105                 110

Ala Trp Asn Tyr Trp Gly Gln Gly Thr Arg Val Thr Val Ser Ser
        115                 120                 125
```

<210> SEQ ID NO 298
<211> LENGTH: 127
<212> TYPE: PRT
<213> ORGANISM: Artificial Sequence
<220> FEATURE:
<223> OTHER INFORMATION: Synthetic Construct

<400> SEQUENCE: 298

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Arg Ser Phe Asn Asn Asn
                 20                  25                  30

Ala Met Ser Trp Phe Arg Gln Ala Pro Gly Lys Gly Leu Glu Phe Val
             35                  40                  45

Ser Ala Ile Thr Trp Val Gly Ser Gly Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Arg Gln Tyr Pro Phe Ser Ile Ile Gly Tyr Asn Ser Lys Asp
            100                 105                 110

Ala Trp Asn Tyr Trp Gly Gln Gly Thr Arg Val Thr Val Ser Ser
        115                 120                 125
```

<210> SEQ ID NO 299
<211> LENGTH: 115
<212> TYPE: PRT
<213> ORGANISM: Artificial Sequence
<220> FEATURE:
<223> OTHER INFORMATION: Synthetic Construct

<400> SEQUENCE: 299

```
Gln Val Gln Leu Val Glu Ser Gly Gly Gly Leu Val Gln Pro Gly Gly
 1               5                  10                  15

Ser Leu Arg Leu Ser Cys Ala Ala Ser Thr Ser Ile Phe Ser Ile Gly
                 20                  25                  30

Thr Met Arg Trp Tyr Arg Gln Ala Pro Gly Lys Gln Arg Glu Tyr Ile
             35                  40                  45

Ala Gly Met Thr Ser Asp Gly Thr Thr Tyr Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Asn
                 85                  90                  95

Thr Val Ala His Phe Gln Asn Tyr Trp Gly Gln Gly Thr Gln Val Thr
            100                 105                 110

Val Ser Ser
```

115

<210> SEQ ID NO 300
<211> LENGTH: 115
<212> TYPE: PRT
<213> ORGANISM: Artificial Sequence
<220> FEATURE:
<223> OTHER INFORMATION: Synthetic Construct

<400> SEQUENCE: 300

```
Gln Val Gln Leu Val Glu Ser Gly Gly Gly Leu Val Gln Pro Gly Gly
1               5                   10                  15

Ser Leu Arg Leu Ser Cys Ala Ala Ser Thr Ser Ile Phe Ser Ile Gly
            20                  25                  30

Thr Met Arg Trp Tyr Arg Gln Ala Pro Gly Lys Gly Leu Glu Tyr Ile
        35                  40                  45

Ala Gly Met Thr Ser Asp Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Thr Val Ala His Phe Gln Asn Tyr Trp Gly Gln Gly Thr Gln Val Thr
            100                 105                 110

Val Ser Ser
        115
```

<210> SEQ ID NO 301
<211> LENGTH: 115
<212> TYPE: PRT
<213> ORGANISM: Artificial Sequence
<220> FEATURE:
<223> OTHER INFORMATION: Synthetic Construct

<400> SEQUENCE: 301

```
Gln Val Gln Leu Val Glu Ser Gly Gly Gly Leu Val Gln Pro Gly Gly
1               5                   10                  15

Ser Leu Arg Leu Ser Cys Ala Ala Ser Thr Ser Ile Phe Ser Ile Gly
            20                  25                  30

Thr Met His Trp Tyr Arg Gln Ala Pro Gly Lys Gly Leu Glu Tyr Val
        35                  40                  45

Ala Gly Met Thr Ser Asp Gly Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Thr Val Ala His Phe Gln Asn Tyr Trp Gly Gln Gly Thr Gln Val Thr
            100                 105                 110

Val Ser Ser
        115
```

<210> SEQ ID NO 302
<211> LENGTH: 345
<212> TYPE: PRT
<213> ORGANISM: Artificial Sequence
<220> FEATURE:
<223> OTHER INFORMATION: Synthetic Construct

<400> SEQUENCE: 302

Gln Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Pro Val Asn
            20                  25                  30

Ala Tyr Gly Trp Tyr Arg Gln Ala Pro Gly Lys Gln Arg Asp Leu Val
        35                  40                  45

Ala Ile Ile Ser Ala Gly Gly Thr Thr Asn Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Leu Gln Arg Arg Ile Gly Met Leu Arg Asp Tyr Trp Gly Gln Gly Thr
            100                 105                 110

Gln Val Thr Val Ser Ser Asp Lys Thr His Thr Cys Pro Pro Cys Pro
        115                 120                 125

Ala Pro Glu Leu Leu Gly Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 303
<211> LENGTH: 339
<212> TYPE: PRT
<213> ORGANISM: Artificial Sequence
<220> FEATURE:
<223> OTHER INFORMATION: Synthetic Construct

<400> SEQUENCE: 303

Gln Val Gln Leu Val Glu Ser Gly Gly Gly Leu Val Gln Pro Gly Gly
1               5                   10                  15

```
Ser Leu Arg Leu Ser Cys Ala Ala Ser Gly Arg Thr Leu Glu Ser Tyr
            20                  25                  30

Val Met Ala Trp Phe Arg Gln Ala Pro Gly Lys Glu Arg Glu Ala Val
        35                  40                  45

Ala Ser Ile Asn Trp Ser Ser Gly Arg Leu Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110

Asp Lys Thr His Thr Cys Pro Pro Cys Pro Ala Pro Glu Leu Leu Gly
            115                 120                 125

Gly Pro Ser Val Phe Leu Phe Pro Pro Lys Pro Lys Asp Thr Leu Met
130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
    210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Glu Glu Met Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
    290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys

<210> SEQ ID NO 304
<211> LENGTH: 346
<212> TYPE: PRT
<213> ORGANISM: Artificial Sequence
<220> FEATURE:
<223> OTHER INFORMATION: Synthetic Construct

<400> SEQUENCE: 304

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ser Ile Arg
            20                  25                  30
```

His Met Arg Trp Tyr Arg Gln Ala Pro Gly Lys Gln Arg Glu Leu Val
            35                  40                  45

Ala Thr Val Ser Asn Asp Gly Ser Ala Tyr Tyr Ala Gly Ser Val Lys
 50                  55                  60

Gly Arg Phe Thr Ile Ser Arg Asp Asn Ser Lys Asn Thr Leu Leu Tyr
 65                  70                  75                  80

Leu Gln Met Asn Ser Leu Arg Ala Glu Asp Thr Ala Val Tyr Ile Cys
                 85                  90                  95

Asn Ala Asp Thr Trp Gly Trp Pro Gly Ala Asp Tyr Trp Gly Gln Gly
            100                 105                 110

Thr Gln Val Thr Val Ser Ser Asp Lys Thr His Thr Cys Pro Pro Cys
        115                 120                 125

Pro Ala Pro Glu Leu Leu Gly Gly Pro Ser Val Phe Leu Phe Pro Pro
130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 305
<211> LENGTH: 354
<212> TYPE: PRT
<213> ORGANISM: Artificial Sequence
<220> FEATURE:
<223> OTHER INFORMATION: Synthetic Construct

<400> SEQUENCE: 305

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Phe Asn Asn Asn
            20                  25                  30

Ala Met Ala Trp Phe Arg Gln Thr Pro Gly Lys Glu Arg Glu Phe Val
        35                  40                  45

Ala Ala Ile Thr Trp Val Gly Ser Gly Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Arg Gln Tyr Pro Phe Ser Ile Ile Gly Tyr Asn Ser Lys Asp
            100                 105                 110

Ala Trp Asn Tyr Trp Gly Gln Gly Thr Arg Val Thr Val Ser Ser Asp
            115                 120                 125

Lys Thr His Thr Cys Pro Pro Cys Pro Ala Pro Glu Leu Leu Gly Gly
130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
            195                 200                 205

Val Val Ser Val Leu Thr Val Leu His Gln Asp Trp Leu Asn Gly Lys
210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
            275                 280                 285

Glu Ser Asn Gly Gln Pro Glu Asn Asn Tyr Lys Thr Thr Pro Pro Val
290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys

<210> SEQ ID NO 306
<211> LENGTH: 342
<212> TYPE: PRT
<213> ORGANISM: Artificial Sequence
<220> FEATURE:
<223> OTHER INFORMATION: Synthetic Construct

<400> SEQUENCE: 306

Gln Val Gln Leu Val Glu Ser Gly Gly Gly Leu Val Gln Pro Gly Gly
 1               5                  10                  15

Ser Leu Arg Leu Ser Cys Ala Ala Ser Thr Ser Ile Phe Ser Ile Gly
             20                  25                  30

Thr Met Arg Trp Tyr Arg Gln Ala Pro Gly Lys Gln Arg Glu Tyr Ile
         35                  40                  45

Ala Gly Met Thr Ser Asp Gly Thr Thr Tyr Tyr Ala Asp Ser Val Lys

```
                50              55              60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Asn
                 85                  90                  95

Thr Val Ala His Phe Gln Asn Tyr Trp Gly Gln Gly Thr Gln Val Thr
            100                 105                 110

Val Ser Ser Asp Lys Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 307
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(3)
<223> OTHER INFORMATION: Can be present in repeats of up to 6
<220> FEATURE:
<221> NAME/KEY: VARIANT
<222> LOCATION: (1)..(3)
<223> OTHER INFORMATION: Can be present in repeats of up to 5

<400> SEQUENCE: 307

Gly Ser Gly Gly Ser Gly
1               5

<210> SEQ ID NO 308
```

```
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 6

<400> SEQUENCE: 308

Gly Gly Gly Ser
1

<210> SEQ ID NO 309
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of up to 6

<400> SEQUENCE: 309

Gly Gly Gly Gly Ser
1               5

<210> SEQ ID NO 310
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(6)
<223> OTHER INFORMATION: Can be present in repeats of up to 6

<400> SEQUENCE: 310

Ala Glu Ala Ala Ala Lys Ala
1               5

<210> SEQ ID NO 311
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of up to 6

<400> SEQUENCE: 311

Pro Ala Pro Ala Pro
1               5

<210> SEQ ID NO 312
<211> LENGTH: 8
<212> TYPE: PRT
<213> ORGANISM: Artificial Sequence
<220> FEATURE:
<223> OTHER INFORMATION: Synthetic Construct

<400> SEQUENCE: 312

Ile Lys Arg Thr Val Ala Ala Pro
1               5
```

```
<210> SEQ ID NO 313
<211> LENGTH: 5
<212> TYPE: PRT
<213> ORGANISM: Artificial Sequence
<220> FEATURE:
<223> OTHER INFORMATION: Synthetic Construct

<400> SEQUENCE: 313

Arg Ala Lys Pro Ser
1               5

<210> SEQ ID NO 314
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 4

<400> SEQUENCE: 314

Gly Ser Gly Ser
1

<210> SEQ ID NO 315
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 4

<400> SEQUENCE: 315

Gly Gly Ser Gly
1

<210> SEQ ID NO 316
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 3

<400> SEQUENCE: 316

Pro Ala Pro Ala
1

<210> SEQ ID NO 317
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 3

<400> SEQUENCE: 317

Pro Gln Pro Gln
```

-continued

```
<210> SEQ ID NO 318
<211> LENGTH: 8
<212> TYPE: PRT
<213> ORGANISM: Artificial Sequence
<220> FEATURE:
<223> OTHER INFORMATION: Synthetic Construct

<400> SEQUENCE: 318

Ile Lys Arg Ala Asp Ala Ala Pro
1               5

<210> SEQ ID NO 319
<211> LENGTH: 6
<212> TYPE: PRT
<213> ORGANISM: Artificial Sequence
<220> FEATURE:
<223> OTHER INFORMATION: Synthetic Construct

<400> SEQUENCE: 319

Ala Ser Thr Lys Gly Pro
1               5

<210> SEQ ID NO 320
<211> LENGTH: 12
<212> TYPE: PRT
<213> ORGANISM: Artificial Sequence
<220> FEATURE:
<223> OTHER INFORMATION: Synthetic Construct

<400> SEQUENCE: 320

Gly Thr Asn Glu Val Cys Lys Cys Pro Lys Cys Pro
1               5                  10

<210> SEQ ID NO 321
<211> LENGTH: 35
<212> TYPE: PRT
<213> ORGANISM: Artificial Sequence
<220> FEATURE:
<223> OTHER INFORMATION: Synthetic Construct

<400> SEQUENCE: 321

Glu Pro Lys Ile Pro Gln Pro Gln Pro Lys Pro Gln Pro Gln Pro Gln
1               5                  10                  15

Pro Gln Pro Lys Pro Gln Pro Lys Pro Glu Pro Glu Cys Thr Cys Pro
                20                  25                  30

Lys Cys Pro
        35

<210> SEQ ID NO 322
<211> LENGTH: 28
<212> TYPE: PRT
<213> ORGANISM: Artificial Sequence
<220> FEATURE:
<223> OTHER INFORMATION: Synthetic Construct

<400> SEQUENCE: 322

Arg Arg Lys Arg Ala Pro Val Lys Gln Thr Leu Asn Phe Asp Leu Leu
1               5                  10                  15

Lys Leu Ala Gly Asp Val Glu Ser Asn Pro Gly Pro
                20                  25

<210> SEQ ID NO 323
<211> LENGTH: 5
```

```
<212> TYPE: PRT
<213> ORGANISM: Artificial Sequence
<220> FEATURE:
<223> OTHER INFORMATION: Synthetic Construct

<400> SEQUENCE: 323

Ser Gly Arg Ser Ala
1               5

<210> SEQ ID NO 324
<211> LENGTH: 6
<212> TYPE: PRT
<213> ORGANISM: Artificial Sequence
<220> FEATURE:
<223> OTHER INFORMATION: Synthetic Construct

<400> SEQUENCE: 324

Pro Val Gly Leu Ile Gly
1               5

<210> SEQ ID NO 325
<211> LENGTH: 389
<212> TYPE: PRT
<213> ORGANISM: Artificial Sequence
<220> FEATURE:
<223> OTHER INFORMATION: Synthetic Construct

<400> SEQUENCE: 325
```

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Gly Ser Gly Ser Gly Ser Gly Gly Ser
    130                 135                 140

Gly Gln Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr His Tyr Ala Asp Ser Val
        195                 200                 205

Lys Gly Arg Phe Thr Val Ser Arg Asp Asn Ala Glu Asn Thr Leu Val
    210                 215                 220

Leu Gln Met Asn Ser Leu Lys Pro Glu Asp Thr Ala Val Tyr Tyr Cys
225                 230                 235                 240

Tyr Ala Gln Ser Thr Trp Tyr Pro Pro Ser Trp Gly Gln Gly Thr Gln

```
                245                 250                 255
Val Thr Val Ser Ser Gly Gly Ser Gly Gly Ser Gly Gly
            260                 265                 270

Ser Gly Gly Gly Ser Gln Val Gln Leu Val Glu Ser Gly Gly Gly Leu
            275                 280                 285

Val Gln Pro Gly Gly Ser Leu Arg Leu Ser Cys Ala Ala Ser Gly Arg
        290                 295                 300

Thr Leu Glu Ser Tyr Val Met Ala Trp Phe Arg Gln Ala Pro Gly Lys
305                 310                 315                 320

Glu Arg Glu Ala Val Ala Ser Ile Asn Trp Ser Ser Gly Arg Leu Ile
                325                 330                 335

Tyr Ala Asp Ser Val Lys Gly Arg Phe Thr Ile Ser Arg Asp Asn Ser
                340                 345                 350

Lys Asn Thr Leu Tyr Leu Gln Met Asn Ser Leu Arg Ala Glu Asp Thr
            355                 360                 365

Ala Val Tyr Tyr Cys Ala Ala Gly Arg Tyr Trp Gly Gln Gly Thr Gln
        370                 375                 380

Val Thr Val Ser Ser
385

<210> SEQ ID NO 326
<211> LENGTH: 480
<212> TYPE: PRT
<213> ORGANISM: Artificial Sequence
<220> FEATURE:
<223> OTHER INFORMATION: Synthetic Construct

<400> SEQUENCE: 326

Gln Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Pro Val Asn
            20                  25                  30

Ala Tyr Gly Trp Tyr Arg Gln Ala Pro Gly Lys Gln Arg Asp Leu Val
        35                  40                  45

Ala Ile Ile Ser Ala Gly Gly Thr Thr Asn Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Leu Gln Arg Arg Ile Gly Met Leu Arg Asp Tyr Trp Gly Gln Gly Thr
            100                 105                 110

Gln Val Thr Val Ser Ser Gly Gly Gly Ser Gly Gly Gly Ser Gly Gly
        115                 120                 125

Gly Ser Gly Gly Gly Ser Gln Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Ser Thr Trp Ser Ile Asn Thr Leu Ala Trp Tyr Arg Gln Ala Pro Gly
                165                 170                 175

Lys Gln Arg Asp Leu Val Ala Arg Ile Ser Ser Gly Gly Ser Thr His
            180                 185                 190

Tyr Ala Asp Ser Val Lys Gly Arg Phe Thr Val Ser Arg Asp Asn Ala
        195                 200                 205

Glu Asn Thr Leu Val Leu Gln Met Asn Ser Leu Lys Pro Glu Asp Thr
```

```
            210                 215                 220
Ala Val Tyr Tyr Cys Tyr Ala Gln Ser Thr Trp Tyr Pro Ser Trp
225                 230                 235                 240

Gly Gln Gly Thr Gln Val Thr Val Ser Ser Gly Gly Gly Ser Gly
                245                 250                 255

Gly Gly Gly Ser Gly Gly Gly Ser Gly Gly Gly Gly Ser Ile Thr
            260                 265                 270

Cys Pro Pro Met Ser Val Glu His Ala Asp Ile Trp Val Lys Ser
                275                 280                 285

Tyr Ser Leu Tyr Ser Arg Glu Arg Tyr Ile Cys Asn Ser Gly Phe Lys
            290                 295                 300

Arg Lys Ala Gly Thr Ser Ser Leu Thr Glu Cys Val Leu Asn Lys Ala
305                 310                 315                 320

Thr Asn Val Ala His Trp Thr Thr Pro Ser Leu Lys Cys Ile Arg Asp
                325                 330                 335

Pro Ala Leu Val His Gln Arg Pro Ala Pro Pro Gly Ser Gly Gly
                340                 345                 350

Gly Gly Ser Gly Gly Gly Ser Gly Gly Gly Gly Ser Leu Gln Asn Trp
            355                 360                 365

Val Asn Val Ile Ser Asp Leu Lys Lys Ile Glu Asp Leu Ile Gln Ser
            370                 375                 380

Met His Ile Asp Ala Thr Leu Tyr Thr Glu Ser Asp Val His Pro Ser
385                 390                 395                 400

Cys Lys Val Thr Ala Met Lys Cys Phe Leu Leu Glu Leu Gln Val Ile
                405                 410                 415

Ser Leu Glu Ser Gly Asp Ala Ser Ile His Asp Thr Val Glu Asn Leu
                420                 425                 430

Ile Ile Leu Ala Asn Asn Ser Leu Ser Ser Asn Gly Asn Val Thr Glu
            435                 440                 445

Ser Gly Cys Lys Glu Cys Glu Glu Leu Glu Glu Lys Asn Ile Lys Glu
            450                 455                 460

Phe Leu Gln Ser Phe Val His Ile Val Gln Met Phe Ile Asn Thr Ser
465                 470                 475                 480

<210> SEQ ID NO 327
<211> LENGTH: 484
<212> TYPE: PRT
<213> ORGANISM: Artificial Sequence
<220> FEATURE:
<223> OTHER INFORMATION: Synthetic Construct

<400> SEQUENCE: 327

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
```

```
            100                 105                 110
Ser Leu Leu Gln Lys Met Ile His Gln His Leu Ser Ser Arg Thr His
        115                 120                 125

Gly Ser Glu Asp Ser Gly Ser Gly Gly Ser Gly Gly Ser
130                 135                 140

Gly Gln Val Gln Leu Val Glu Ser Gly Gly Gly Leu Val Glu Ala Gly
145                 150                 155                 160

Asp Ser Leu Arg Leu Ser Cys Val Val Ser Gly Arg Thr Leu Glu Ser
                165                 170                 175

Tyr Val Met Ala Trp Phe Arg Gln Ala Pro Gly Lys Glu Arg Glu Ala
            180                 185                 190

Val Ala Ser Ile Asn Trp Ser Ser Gly Arg Leu Ile Tyr Ala Asp Phe
        195                 200                 205

Val Lys Gly Arg Phe Thr Ile Ser Arg Asp Tyr Glu Lys Asn Thr Ile
    210                 215                 220

Tyr Leu Ser Met Asn Asn Leu Lys Pro Glu Asp Thr Ala Val Tyr Tyr
225                 230                 235                 240

Cys Ala Ala Gly Arg Tyr Trp Gly Gln Gly Thr Gln Val Thr Val Ser
                245                 250                 255

Ser Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Cys Arg Glu Glu Met Thr Lys Asn Gln Val
385                 390                 395                 400

Ser Leu Trp Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys

<210> SEQ ID NO 328
<211> LENGTH: 345
<212> TYPE: PRT
<213> ORGANISM: Artificial Sequence
<220> FEATURE:
```

<223> OTHER INFORMATION: Synthetic Construct

<400> SEQUENCE: 328

| | | | | | | | | | | | | | | | |
|---|---|---|---|---|---|---|---|---|---|---|---|---|---|---|---|
| Gln | Val | Gln | Leu | Val | Glu | Ser | Gly | Gly | Gly | Leu | Val | Gln | Ala | Gly | Gly |
| 1 | | | | 5 | | | | | 10 | | | | | 15 | |
| Ser | Leu | Arg | Leu | Ser | Cys | Ala | Ala | Ser | Gly | Ile | Thr | Phe | Pro | Val | Asn |
| | | | 20 | | | | | 25 | | | | | 30 | | |
| Ala | Tyr | Gly | Trp | Tyr | Arg | Gln | Ala | Pro | Gly | Lys | Gln | Arg | Asp | Leu | Val |
| | | 35 | | | | | 40 | | | | | 45 | | | |
| Ala | Ile | Ile | Ser | Ala | Gly | Gly | Thr | Thr | Asn | Tyr | Ala | Asp | Ser | Val | Lys |
| | 50 | | | | | 55 | | | | | 60 | | | | |
| Gly | Arg | Phe | Thr | Ile | Ser | Arg | Asp | Asn | Ser | Lys | Asn | Thr | Leu | Tyr | Leu |
| 65 | | | | | 70 | | | | | 75 | | | | | 80 |
| Gln | Met | Asn | Ser | Leu | Arg | Ala | Glu | Asp | Thr | Ala | Val | Tyr | Tyr | Cys | Tyr |
| | | | | 85 | | | | | 90 | | | | | 95 | |
| Leu | Gln | Arg | Arg | Ile | Gly | Met | Leu | Arg | Asp | Tyr | Trp | Gly | Gln | Gly | Thr |
| | | | 100 | | | | | 105 | | | | | 110 | | |
| Gln | Val | Thr | Val | Ser | Ser | Asp | Lys | Thr | His | Thr | Cys | Pro | Pro | Cys | Pro |
| | | | 115 | | | | | 120 | | | | | 125 | | |
| Ala | Pro | Glu | Leu | Leu | Gly | Gly | Pro | Ser | Val | Phe | Leu | Phe | Pro | Pro | Lys |
| | | 130 | | | | | 135 | | | | | 140 | | | |
| Pro | Lys | Asp | Thr | Leu | Met | Ile | Ser | Arg | Thr | Pro | Glu | Val | Thr | Cys | Val |
| 145 | | | | | 150 | | | | | 155 | | | | | 160 |
| Val | Val | Asp | Val | Ser | His | Glu | Asp | Pro | Glu | Val | Lys | Phe | Asn | Trp | Tyr |
| | | | | 165 | | | | | 170 | | | | | 175 | |
| Val | Asp | Gly | Val | Glu | Val | His | Asn | Ala | Lys | Thr | Lys | Pro | Arg | Glu | Glu |
| | | | 180 | | | | | 185 | | | | | 190 | | |
| Gln | Tyr | Asn | Ser | Thr | Tyr | Arg | Val | Val | Ser | Val | Leu | Thr | Val | Leu | His |
| | | | 195 | | | | | 200 | | | | | 205 | | |
| Gln | Asp | Trp | Leu | Asn | Gly | Lys | Glu | Tyr | Lys | Cys | Lys | Val | Ser | Asn | Lys |
| | | 210 | | | | | 215 | | | | | 220 | | | |
| Ala | Leu | Pro | Ala | Pro | Ile | Glu | Lys | Thr | Ile | Ser | Lys | Ala | Lys | Gly | Gln |
| 225 | | | | | 230 | | | | | 235 | | | | | 240 |
| Pro | Arg | Glu | Pro | Gln | Val | Cys | Thr | Leu | Pro | Pro | Ser | Arg | Glu | Glu | Met |
| | | | | 245 | | | | | 250 | | | | | 255 | |
| Thr | Lys | Asn | Gln | Val | Ser | Leu | Ser | Cys | Ala | Val | Lys | Gly | Phe | Tyr | Pro |
| | | | 260 | | | | | 265 | | | | | 270 | | |
| Ser | Asp | Ile | Ala | Val | Glu | Trp | Glu | Ser | Asn | Gly | Gln | Pro | Glu | Asn | Asn |
| | | 275 | | | | | 280 | | | | | 285 | | | |
| Tyr | Lys | Thr | Thr | Pro | Pro | Val | Leu | Asp | Ser | Asp | Gly | Ser | Phe | Phe | Leu |
| | 290 | | | | | 295 | | | | | 300 | | | | |
| Val | Ser | Lys | Leu | Thr | Val | Asp | Lys | Ser | Arg | Trp | Gln | Gln | Gly | Asn | Val |
| 305 | | | | | 310 | | | | | 315 | | | | | 320 |
| Phe | Ser | Cys | Ser | Val | Met | His | Glu | Ala | Leu | His | Asn | His | Tyr | Thr | Gln |
| | | | | 325 | | | | | 330 | | | | | 335 | |
| Lys | Ser | Leu | Ser | Leu | Ser | Pro | Gly | Lys | | | | | | | |
| | | | 340 | | | | | 345 | | | | | | | |

<210> SEQ ID NO 329
<211> LENGTH: 630
<212> TYPE: PRT
<213> ORGANISM: Artificial Sequence
<220> FEATURE:
<223> OTHER INFORMATION: Synthetic Construct

<400> SEQUENCE: 329

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Gly Ser Gly Gly Ser Gly Gly Ser
            130                 135                 140

Gly Gln Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr His Tyr Ala Asp Ser Val
                195                 200                 205

Lys Gly Arg Phe Thr Val Ser Arg Asp Asn Ala Glu Asn Thr Leu Val
            210                 215                 220

Leu Gln Met Asn Ser Leu Lys Pro Glu Asp Thr Ala Val Tyr Tyr Cys
225                 230                 235                 240

Tyr Ala Gln Ser Thr Trp Tyr Pro Pro Ser Trp Gly Gln Gly Thr Gln
                245                 250                 255

Val Thr Val Ser Ser Gly Gly Gly Ser Gly Gly Gly Ser Gly Gly Gly
            260                 265                 270

Ser Gly Gly Gly Ser Gly Gly Gly Ser Gly Arg Ser Ala Gly Gly
            275                 280                 285

Gly Gly Ser Gln Val Gln Leu Val Glu Ser Gly Gly Gly Leu Val Gln
        290                 295                 300

Pro Gly Gly Ser Leu Arg Leu Ser Cys Ala Ala Ser Gly Arg Thr Leu
305                 310                 315                 320

Glu Ser Tyr Val Met Ala Trp Phe Arg Gln Ala Pro Gly Lys Glu Arg
                325                 330                 335

Glu Ala Val Ala Ser Ile Asn Trp Ser Ser Gly Arg Leu Ile Tyr Ala
            340                 345                 350

Asp Ser Val Lys Gly Arg Phe Thr Ile Ser Arg Asp Asn Ser Lys Asn
            355                 360                 365

Thr Leu Tyr Leu Gln Met Asn Ser Leu Arg Ala Glu Asp Thr Ala Val
        370                 375                 380

Tyr Tyr Cys Ala Ala Gly Arg Tyr Trp Gly Gln Gly Thr Gln Val Thr
385                 390                 395                 400

Val Ser Ser Asp Lys Thr His Thr Cys Pro Pro Cys Pro Ala Pro Glu
            405                 410                 415
```

```
Leu Leu Gly Gly Pro Ser Val Phe Leu Phe Pro Pro Lys Pro Lys Asp
            420                 425                 430

Thr Leu Met Ile Ser Arg Thr Pro Glu Val Thr Cys Val Val Val Asp
        435                 440                 445

Val Ser His Glu Asp Pro Glu Val Lys Phe Asn Trp Tyr Val Asp Gly
    450                 455                 460

Val Glu Val His Asn Ala Lys Thr Lys Pro Arg Glu Glu Gln Tyr Asn
465                 470                 475                 480

Ser Thr Tyr Arg Val Val Ser Val Leu Thr Val Leu His Gln Asp Trp
                485                 490                 495

Leu Asn Gly Lys Glu Tyr Lys Cys Lys Val Ser Asn Lys Ala Leu Pro
            500                 505                 510

Ala Pro Ile Glu Lys Thr Ile Ser Lys Ala Lys Gly Gln Pro Arg Glu
        515                 520                 525

Pro Gln Val Tyr Thr Leu Pro Pro Cys Arg Glu Met Thr Lys Asn
    530                 535                 540

Gln Val Ser Leu Trp Cys Leu Val Lys Gly Phe Tyr Pro Ser Asp Ile
545                 550                 555                 560

Ala Val Glu Trp Glu Ser Asn Gly Gln Pro Glu Asn Asn Tyr Lys Thr
                565                 570                 575

Thr Pro Pro Val Leu Asp Ser Asp Gly Ser Phe Phe Leu Tyr Ser Lys
            580                 585                 590

Leu Thr Val Asp Lys Ser Arg Trp Gln Gln Gly Asn Val Phe Ser Cys
        595                 600                 605

Ser Val Met His Glu Ala Leu His Asn His Tyr Thr Gln Lys Ser Leu
    610                 615                 620

Ser Leu Ser Pro Gly Lys
625                 630

<210> SEQ ID NO 330
<211> LENGTH: 339
<212> TYPE: PRT
<213> ORGANISM: Artificial Sequence
<220> FEATURE:
<223> OTHER INFORMATION: Synthetic Construct

<400> SEQUENCE: 330

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Leu Glu Ser Tyr
            20                  25                  30

Val Met Ala Trp Phe Arg Gln Ala Pro Gly Lys Glu Arg Glu Ala Val
        35                  40                  45

Ala Ser Ile Asn Trp Ser Ser Gly Arg Leu Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110

Asp Lys Thr His Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Met
    130                 135                 140
```

```
Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
    210                 215                 220

Glu Lys Thr Ile Ser Lys Ala Lys Gly Gln Pro Arg Glu Pro Gln Val
225                 230                 235                 240

Cys Thr Leu Pro Pro Ser Arg Glu Glu Met Thr Lys Asn Gln Val Ser
                245                 250                 255

Leu Ser Cys Ala Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Val Ser Lys Leu Thr Val
    290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys

<210> SEQ ID NO 331
<211> LENGTH: 546
<212> TYPE: PRT
<213> ORGANISM: Artificial Sequence
<220> FEATURE:
<223> OTHER INFORMATION: Synthetic Construct

<400> SEQUENCE: 331

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Gly Ser Gly Gly Ser Gly Gly Ser Gly Gly Ser
    130                 135                 140

Gly Leu Ala Glu Ala Lys Val Leu Ala Asn Arg Glu Leu Asp Lys Tyr
145                 150                 155                 160

Gly Val Ser Asp Tyr Ala Lys Asn Leu Ile Asn Asn Ala Lys Thr Val
```

-continued

```
                165                 170                 175
Glu Gly Val Lys Ala Leu Ile Asp Glu Ile Leu Ala Ala Leu Pro Gly
            180                 185                 190
Gly Gly Gly Ser Pro Val Gly Leu Ile Gly Gly Gly Gly Ser Gln
        195                 200                 205
Val Gln Leu Val Glu Ser Gly Gly Leu Val Gln Pro Gly Gly Ser
    210                 215                 220
Leu Arg Leu Ser Cys Ala Ala Ser Gly Arg Thr Leu Glu Ser Tyr Val
225                 230                 235                 240
Met Ala Trp Phe Arg Gln Ala Pro Gly Lys Glu Arg Glu Ala Val Ala
                245                 250                 255
Ser Ile Asn Trp Ser Ser Gly Arg Leu Ile Tyr Ala Asp Ser Val Lys
            260                 265                 270
Gly Arg Phe Thr Ile Ser Arg Asp Asn Ser Lys Asn Thr Leu Tyr Leu
        275                 280                 285
Gln Met Asn Ser Leu Arg Ala Glu Asp Thr Ala Val Tyr Tyr Cys Ala
    290                 295                 300
Ala Gly Arg Tyr Trp Gly Gln Gly Thr Gln Val Thr Val Ser Ser Asp
305                 310                 315                 320
Lys Thr His Thr Cys Pro Pro Cys Pro Ala Pro Glu Leu Leu Gly Gly
                325                 330                 335
Pro Ser Val Phe Leu Phe Pro Pro Lys Pro Lys Asp Thr Leu Met Ile
            340                 345                 350
Ser Arg Thr Pro Glu Val Thr Cys Val Val Val Asp Val Ser His Glu
        355                 360                 365
Asp Pro Glu Val Lys Phe Asn Trp Tyr Val Asp Gly Val Glu Val His
    370                 375                 380
Asn Ala Lys Thr Lys Pro Arg Glu Glu Gln Tyr Asn Ser Thr Tyr Arg
385                 390                 395                 400
Val Val Ser Val Leu Thr Val Leu His Gln Asp Trp Leu Asn Gly Lys
                405                 410                 415
Glu Tyr Lys Cys Lys Val Ser Asn Lys Ala Leu Pro Ala Pro Ile Glu
            420                 425                 430
Lys Thr Ile Ser Lys Ala Lys Gly Gln Pro Arg Glu Pro Gln Val Tyr
        435                 440                 445
Thr Leu Pro Pro Cys Arg Glu Glu Met Thr Lys Asn Gln Val Ser Leu
    450                 455                 460
Trp Cys Leu Val Lys Gly Phe Tyr Pro Ser Asp Ile Ala Val Glu Trp
465                 470                 475                 480
Glu Ser Asn Gly Gln Pro Glu Asn Asn Tyr Lys Thr Thr Pro Pro Val
                485                 490                 495
Leu Asp Ser Asp Gly Ser Phe Phe Leu Tyr Ser Lys Leu Thr Val Asp
            500                 505                 510
Lys Ser Arg Trp Gln Gln Gly Asn Val Phe Ser Cys Ser Val Met His
        515                 520                 525
Glu Ala Leu His Asn His Tyr Thr Gln Lys Ser Leu Ser Leu Ser Pro
    530                 535                 540
Gly Lys
545

<210> SEQ ID NO 332
<211> LENGTH: 116
<212> TYPE: PRT
<213> ORGANISM: Artificial Sequence
```

<220> FEATURE:
<223> OTHER INFORMATION: Synthetic Construct

<400> SEQUENCE: 332

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr His Tyr Ala Asp Ser Val Lys
    50                  55                  60

Gly Arg Phe Thr Val Ser Arg Asp Asn Ala Glu Asn Thr Leu Val Leu
65                  70                  75                  80

Gln Met Asn Ser Leu Lys Pro Glu Asp Thr Ala Val Tyr Tyr Cys Tyr
                85                  90                  95

Ala Gln Ser Thr Trp Tyr Pro Pro Ser Trp Gly Gln Gly Thr Gln Val
            100                 105                 110

Thr Val Ser Ser
        115

<210> SEQ ID NO 333
<211> LENGTH: 116
<212> TYPE: PRT
<213> ORGANISM: Artificial Sequence
<220> FEATURE:
<223> OTHER INFORMATION: Synthetic Construct

<400> SEQUENCE: 333

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Gln Ser Thr Trp Tyr Pro Pro Ser Trp Gly Gln Gly Thr Leu Val
            100                 105                 110

Thr Val Ser Ser
        115

<210> SEQ ID NO 334
<211> LENGTH: 8
<212> TYPE: PRT
<213> ORGANISM: Artificial Sequence
<220> FEATURE:
<223> OTHER INFORMATION: Synthetic Construct

<400> SEQUENCE: 334

Gly Ser Thr Trp Ser Ile Asn Thr
1               5

<210> SEQ ID NO 335
<211> LENGTH: 7

```
<212> TYPE: PRT
<213> ORGANISM: Artificial Sequence
<220> FEATURE:
<223> OTHER INFORMATION: Synthetic Construct

<400> SEQUENCE: 335

Ile Ser Ser Gly Gly Ser Thr
1               5

<210> SEQ ID NO 336
<211> LENGTH: 10
<212> TYPE: PRT
<213> ORGANISM: Artificial Sequence
<220> FEATURE:
<223> OTHER INFORMATION: Synthetic Construct

<400> SEQUENCE: 336

Tyr Ala Gln Ser Thr Trp Tyr Pro Pro Ser
1               5                   10

<210> SEQ ID NO 337
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: Can be present in repeat of at least 1

<400> SEQUENCE: 337

Gly Ser Gly Ser
1

<210> SEQ ID NO 338
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeat of at least 1

<400> SEQUENCE: 338

Gly Ser Gly Gly Ser
1               5

<210> SEQ ID NO 339
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeat of at least 1

<400> SEQUENCE: 339

Gly Gly Gly Gly Ser
1               5

<210> SEQ ID NO 340
<211> LENGTH: 4
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeat of at least 1

<400> SEQUENCE: 340

Gly Gly Gly Ser
1

<210> SEQ ID NO 341
<211> LENGTH: 21
<212> TYPE: PRT
<213> ORGANISM: Artificial Sequence
<220> FEATURE:
<223> OTHER INFORMATION: Synthetic Construct

<400> SEQUENCE: 341

Ser Arg Gly Gly Gly Gly Ser Gly Gly Gly Gly Ser Gly Gly Gly Gly
1               5                   10                  15

Ser Leu Glu Met Ala
            20

<210> SEQ ID NO 342
<211> LENGTH: 7
<212> TYPE: PRT
<213> ORGANISM: Artificial Sequence
<220> FEATURE:
<223> OTHER INFORMATION: Synthetic Construct

<400> SEQUENCE: 342

Thr Ser Gly Gly Gly Gly Ser
1               5

<210> SEQ ID NO 343
<211> LENGTH: 18
<212> TYPE: PRT
<213> ORGANISM: Artificial Sequence
<220> FEATURE:
<223> OTHER INFORMATION: Synthetic Construct

<400> SEQUENCE: 343

Gly Glu Gly Thr Ser Thr Gly Ser Gly Gly Ser Gly Gly Ser Gly Gly
1               5                   10                  15

Ala Asp

<210> SEQ ID NO 344
<211> LENGTH: 22
<212> TYPE: PRT
<213> ORGANISM: Artificial Sequence
<220> FEATURE:
<223> OTHER INFORMATION: Synthetic Construct

<400> SEQUENCE: 344

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 345
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 345

Cys Pro Pro Cys Pro
1               5
```

ANTI-MESOTHELIN CONSTRUCTS AND USES THEREOF

CROSS-REFERENCE TO RELATED APPLICATIONS

This application is a National Stage of International Application No. PCT/US2019/037557, filed Jun. 17, 2019; which claims the benefit of U.S. Provisional Application No. 62/686,481, filed Jun. 18, 2028, and U.S. Provisional Application No. 62/809,496, filed Feb. 22, 2019; the disclosure of each of which is hereby incorporated by reference in its entirety.

FIELD OF THE APPLICATION

The present application relates to anti-mesothelin constructs (such as anti-mesothelin antibodies, cytokine fusion proteins that comprise the anti-mesothelin constructs) and methods of using the constructs (e.g., methods of treating a disease). The present application also relates to combination therapies for treating a disease (such as cancer).

REFERENCE TO A SEQUENCE LISTING

The present specification is being filed with a Sequence Listing in Computer Readable Form (CRF), which is entitled 216A001US01_SEQ_LIST_ST25.txt of 218,283 bytes in size and created Jul. 19, 2021; the content of which is incorporated herein by reference in its entirety.

BACKGROUND OF THE APPLICATION

Mesothelin is a glycoprotein present on the surface of cells of the mesothelial lining of the peritoneal, pleural and pericardial body cavities. It was originally purified from the human pancreatic cancer cell line HPC-Y5 and was shown to have megakaryocyte potentiating ability and hence named megakaryocyte potentiating factor (MPF) (Yamaguchi et al. (1994) J. Biol. Chem. 269:805-808). The mesothelin cDNA was cloned from a library prepared from the HPC-Y5 cell line (Kojima et al. (1995) J. Biol. Chem. 270:21984-21990). The cDNA also was cloned using the monoclonal antibody K1, which recognizes mesotheliomas (Chang and Pastan (1996) Proc. NatL. Acad. Sci. USA 93:136-40). Structurally, mesothelin is expressed on the cell surface as a 60 kDa precursor polypeptide, which is 20 proteolytically processed into a 31 kDa shed component (corresponding to MPF) and a 40 kDa membrane bound component (Hassan et al. (2004) Clin. Cancer. Res. 10:3937-3942). In addition to being expressed on normal mesothelial cells, mesothelin is overexpressed in several types of human tumors, including all mesotheliomas, ovarian and pancreatic cancers, and some stomach, lung and endometrial cancers. For example, mesothelin is expressed on approximately 70% of all ovarian cancers, approximately 82% of papillary, serous adenocarcinomas, approximately 83% of all pancreatic adenocarcinomas and approximately 86% of all ductal pancreatic adenocarcinomas.

Mesothelin specifically interacts with CA125 (also known as MUC 16), a mucin-like glycoprotein present on the surface of tumor cells that previously had been identified as an ovarian cancer antigen. Further, binding of CA1 25 to membrane-bound mesothelin mediates heterotypic cell adhesion and CA125 and mesothelin are co-expressed in advanced grade ovarian adenocarcinoma (Rump, A. et al. (2004) J. Bio. Chem. 279:9190-9198). Expression of mesothelin in the lining of the peritoneum correlates with the preferred site of metastasis formation of ovarian cancer and inesothelin-CA125 binding is thought to facilitate peritoneal metastasis of ovarian tumors (Gubbels, J. A et. al. (2006) Mol, Cancer 5:50).

In view of the foregoing, additional agents for modulating the activity of mesothelin are of interest.

BRIEF SUMMARY OF THE APPLICATION

The present application provides isolated anti-mesothelin (anti-MSLN) constructs comprising an antibody moiety comprising an anti-MSLN heavy chain variable region (VH) comprising: a) a heavy chain complementarity determining region (HC-CDR)1 comprising an amino acid sequence selected from the group consisting of SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, and SEQ ID NO: 120; b) an HC-CDR2 comprising an amino acid sequence selected from the group consisting of SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103, SEQ ID NO: 106, SEQ ID NO: 109, SEQ ID NO: 112, SEQ ID NO: 115, SEQ ID NO: 118, and SEQ ID NO: 121; and c) an HC-CDR3 comprising an amino acid sequence selected from the group consisting of SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, and SEQ ID NO: 122.

The present application also provides isolated anti-mesothelin (anti-MSLN) constructs comprising an antibody moiety comprising an anti-MSLN heavy chain variable region (VH) comprising: 1) an HC-CDR1 comprising an amino acid sequence of SEQ ID NO: 12, an HC-CDR2 comprising an amino acid sequence of SEQ ID NO: 13, and an HC-CDR3 comprising an amino acid sequence of SEQ ID NO: 14, or a variant thereof comprising up to about 5 (such as 4, 3, 2, 1) amino acid substitutions; 2) an HC-CDR1 comprising an amino acid sequence of SEQ ID NO: 15, an HC-CDR2 comprising an amino acid sequence of SEQ ID NO: 16, and an HC-CDR3 comprising an amino acid sequence of SEQ ID NO: 17, or a variant thereof comprising up to about 5 (such as 4, 3, 2, 1) amino acid substitutions; 3) an HC-CDR1 comprising an amino acid sequence of SEQ ID NO: 18, an HC-CDR2 comprising an amino acid sequence of SEQ ID NO: 19, and an HC-CDR3 comprising an amino acid sequence of SEQ ID NO: 20, or a variant thereof comprising up to about 5 (such as 4, 3, 2, 1) amino acid substitutions; 4) an HC-CDR1 comprising an amino acid sequence of SEQ ID NO: 21, an HC-CDR2 comprising an amino acid sequence of SEQ ID NO: 22, and an HC-CDR3 comprising an amino acid sequence of SEQ ID NO: 23, or a variant thereof comprising up to about 5 (such as 4, 3, 2, 1) amino acid substitutions; 5) an HC-CDR1 comprising an amino acid sequence of SEQ ID NO: 24, an HC-CDR2 comprising an amino acid sequence of SEQ ID NO: 25, and an HC-CDR3 comprising an amino acid sequence of SEQ ID NO: 26, or a variant thereof comprising up to about 5 (such as 4, 3, 2, 1) amino acid substitutions; 6) an HC-CDR1 comprising an amino acid sequence of SEQ ID NO:27, an HC-CDR2 comprising an amino acid sequence of SEQ ID NO: 28, and an HC-CDR3 comprising an amino acid sequence of SEQ ID NO: 29, or a variant thereof comprising up to about 5 (such as 4, 3, 2, 1) amino acid substitutions; 7) an HC-CDR1 comprising an amino acid sequence of SEQ ID NO: 30, an HC-CDR2 comprising an amino acid sequence of SEQ ID NO: 31, and an HC-CDR3 comprising an amino acid sequence of SEQ ID NO: 32, or a variant thereof comprising up to about 5 (such as 4, 3, 2, 1) amino acid substitutions; 8) an HC-CDR1 comprising an amino acid sequence of SEQ ID NO: 33, an HC-CDR2 comprising an amino acid sequence of SEQ ID NO: 34, and an HC-CDR3 comprising an amino acid sequence of SEQ ID NO: 35, or a variant thereof comprising up to about 5 (such as 4, 3, 2, 1) amino acid substitutions; 9) an HC-CDR1 comprising an amino acid sequence of SEQ ID NO: 36, an HC-CDR2 comprising an amino acid sequence of SEQ ID NO: 37, and an HC-CDR3 comprising an amino acid sequence of SEQ ID NO: 38, or a variant thereof comprising up to about 5 (such as 4, 3, 2, 1) amino acid substitutions; 10) an HC-CDR1 comprising an amino acid sequence of SEQ ID NO: 39, an HC-CDR2 comprising an amino acid sequence of SEQ ID NO: 40, and an HC-CDR3 comprising an amino acid sequence of SEQ ID NO: 41, or a variant thereof comprising up to about 5 (such as 4, 3, 2, 1) amino acid substitutions; 11) an HC-CDR1 comprising an amino acid sequence of SEQ ID NO: 42, an HC-CDR2 comprising an amino acid sequence of SEQ ID NO: 43, and an HC-CDR3 comprising an amino acid sequence of SEQ ID NO: 44, or a variant thereof comprising up to about 5 (such as 4, 3, 2, 1) amino acid substitutions; 12) an HC-CDR1 comprising an amino acid sequence of SEQ ID NO:45, an HC-CDR2 comprising an amino acid sequence of SEQ ID NO: 46, and an HC-CDR3 comprising an amino acid sequence of SEQ ID NO: 47, or a variant thereof comprising up to about 5 (such as 4, 3, 2, 1) amino acid substitutions; 13) an HC-CDR1 comprising an amino acid sequence of SEQ ID NO: 48, an HC-CDR2 comprising an amino acid sequence of SEQ ID NO: 49, and an HC-CDR3 comprising an amino acid sequence of SEQ ID NO: 50, or a variant thereof comprising up to about 5 (such as 4, 3, 2, 1) amino acid substitutions; 14) an HC-CDR1 comprising an amino acid sequence of SEQ ID NO: 51, an HC-CDR2 comprising an amino acid sequence of SEQ ID NO: 52, and an HC-CDR3 comprising an amino acid sequence of SEQ ID NO: 53, or a variant thereof comprising up to about 5 (such as 4, 3, 2, 1) amino acid substitutions; 15) an HC-CDR1 comprising an amino acid sequence of SEQ ID NO: 54, an HC-CDR2 comprising an amino acid sequence of SEQ ID NO: 55, and an HC-CDR3 comprising an amino acid sequence of SEQ ID NO: 56, or a variant thereof comprising up to about 5 (such as 4, 3, 2, 1) amino acid substitutions; 16) an HC-CDR1 comprising an amino acid sequence of SEQ ID NO: 57, an HC-CDR2 comprising an amino acid sequence of SEQ ID NO: 58, and an HC-CDR3 comprising an amino acid sequence of SEQ ID NO: 59, or a variant thereof comprising up to about 5 (such as 4, 3, 2, 1) amino acid substitutions; 17) an HC-CDR1 comprising an amino acid sequence of SEQ ID NO: 60, an HC-CDR2 comprising an amino acid sequence of SEQ ID NO: 61, and an HC-CDR3 comprising an amino acid sequence of SEQ ID NO: 62, or a variant thereof comprising up to about 5 (such as 4, 3, 2, 1) amino acid substitutions; 18) an HC-CDR1 comprising an amino acid sequence of SEQ ID NO: 63, an HC-CDR2 comprising an amino acid sequence of SEQ ID NO: 64, and an HC-CDR3 comprising an amino acid sequence of SEQ ID NO: 65, or a variant thereof comprising up to about 5 (such as 4, 3, 2, 1) amino acid substitutions; 19) an HC-CDR1 comprising an amino acid sequence of SEQ ID NO: 75, an HC-CDR2 comprising an amino acid sequence of SEQ ID NO: 76, and an HC-CDR3 comprising an amino acid sequence of SEQ ID NO: 77, or a variant thereof comprising up to about 5 (such as 4, 3, 2, 1) amino acid substitutions; 20) an HC-CDR1 comprising an amino acid sequence of SEQ ID NO: 78, an HC-CDR2 comprising an amino acid sequence of SEQ ID NO: 79, and an HC-CDR3 comprising an amino acid sequence of SEQ ID NO: 80, or a variant thereof comprising up to about 5 (such as 4, 3, 2, 1) amino acid substitutions; 21) an HC-CDR1 comprising an amino acid sequence of SEQ ID NO: 81; an HC-CDR2 comprising an amino acid sequence of SEQ ID NO: 82, and an HC-CDR3 comprising an amino acid sequence of SEQ ID NO: 83, or a variant thereof comprising up to about 5 (such as 4, 3, 2, 1) amino acid substitutions; 22) an HC-CDR1 comprising an amino acid sequence of SEQ ID NO:84, an HC-CDR2 comprising an amino acid sequence of SEQ ID NO: 85, and an HC-CDR3 comprising an amino acid sequence of SEQ ID NO: 86, or a variant thereof comprising up to about 5 (such as 4, 3, 2, 1) amino acid substitutions; 23) an HC-CDR1 comprising an amino acid sequence of SEQ ID NO: 87, an HC-CDR2 comprising an amino acid sequence of SEQ ID NO: 88, and an HC-CDR3 comprising an amino acid sequence of SEQ ID NO: 89, or a variant thereof comprising up to about 5 (such as 4, 3, 2, 1) amino acid substitutions; 24) an HC-CDR1 comprising an amino acid sequence of SEQ ID NO: 90, an HC-CDR2 comprising an amino acid sequence of SEQ ID NO: 91, and an HC-CDR3 comprising an amino acid sequence of SEQ ID NO: 92, or a variant thereof comprising up to about 5 (such as 4, 3, 2, 1) amino acid substitutions; 25) an HC-CDR1 comprising an amino acid sequence of SEQ ID NO: 93, an HC-CDR2 comprising an amino acid sequence of SEQ ID NO: 94, and an HC-CDR3 comprising an amino acid sequence of SEQ ID NO: 95, or a variant thereof comprising up to about 5 (such as 4, 3, 2, 1) amino acid substitutions; 26) an HC-CDR1 comprising an amino acid sequence of SEQ ID NO: 96, an HC-CDR2 comprising an amino acid sequence of SEQ ID NO: 97, and an HC-CDR3 comprising an amino acid sequence of SEQ ID NO: 98, or a variant thereof comprising up to about 5 (such as 4, 3, 2, 1) amino acid substitutions; 27) an HC-CDR1 comprising an amino acid sequence of SEQ ID NO: 99, an HC-CDR2 comprising an amino acid sequence of SEQ ID NO: 100, and an HC-CDR3 comprising an amino acid sequence of SEQ ID NO: 101, or a variant thereof comprising up to about 5 (such as 4, 3, 2, 1) amino acid substitutions; 28) an HC-CDR1 comprising an amino acid sequence of SEQ ID NO: 102, an HC-CDR2 comprising an amino acid sequence of SEQ ID NO: 103, and an HC-CDR3 comprising an amino acid sequence of SEQ ID NO: 104, or a variant thereof comprising up to about 5 (such as 4, 3, 2, 1) amino acid substitutions; 29) an HC-CDR1 comprising an amino acid sequence of SEQ ID NO: 105, an HC-CDR2 comprising an amino acid sequence of SEQ ID NO: 106, and an HC-CDR3 comprising an amino acid sequence of SEQ ID NO: 107, or a variant thereof comprising up to about 5 (such as 4, 3, 2, 1) amino acid substitutions; 30) an HC-CDR1 comprising an amino acid sequence of SEQ ID NO: 108, an HC-CDR2 comprising an amino acid sequence of SEQ ID NO: 109, and an HC-CDR3 comprising an amino acid sequence of SEQ ID NO: 110, or a variant thereof comprising up to about 5 (such as 4, 3, 2, 1) amino acid substitutions; 31) an HC-CDR1 comprising an amino acid sequence of SEQ ID NO 111, an HC-CDR2 comprising an amino acid sequence of SEQ ID NO: 112, and an HC-CDR3 comprising an amino acid sequence of SEQ ID NO: 113, or a variant thereof comprising up to about 5 (such as 4, 3, 2, 1) amino acid substitutions; 32) an HC-CDR1 comprising an amino acid sequence of SEQ ID NO: 114, an HC-CDR2 comprising an amino acid sequence of SEQ ID NO: 115, and an HC-CDR3 comprising an amino acid sequence of SEQ ID NO: 116, or a variant thereof comprising up to about 5 (such as 4, 3, 2, 1) amino acid substitutions; 33) an HC-CDR1 comprising an amino acid sequence of SEQ ID NO: 117, an HC-CDR2 comprising an amino acid sequence of SEQ ID NO: 118, and an HC-CDR3 comprising an amino acid sequence of SEQ ID NO: 119, or a variant thereof comprising up to about 5 (such as 4, 3, 2, 1) amino acid substitutions; or 34) an HC-CDR1 comprising an amino acid sequence of SEQ ID NO: 120, an HC-CDR2 comprising an amino acid sequence of SEQ ID NO: 121, and an HC-CDR3 comprising an amino acid sequence of SEQ ID NO: 122, or a variant thereof comprising up to about 5 (such as 4, 3, 2, 1) amino acid substitutions.

In some embodiments according to any one of the constructs described above, the HC-CDR1, HC-CDR2, and HC-CDR3 comprises the amino acid sequence of a CDR1, a CDR2, and a CDR3, respectively, of any of anti-MSLN-1, anti-MSLN-2, anti-MSLN-3, anti-MSLN-4, anti-MSLN-5, anti-MSLN-6, anti-MSLN-7, anti-MSLN-8, anti-MSLN-9, anti-MSLN-10, anti-MSLN-11, anti-MSLN-12, anti-MSLN-13, anti-MSLN-14, anti-MSLN-15, anti-MSLN-16, anti-MSLN-17, anti-MSLN-18, anti-MSLN-19, anti-MSLN-20, anti-MSLN-21, anti-MSLN-22, anti-MSLN-23, anti-MSLN-24, anti-MSLN-25, anti-MSLN-26, anti-MSLN-27, anti-MSLN-28, anti-MSLN-29, anti-MSLN-30, anti-MSLN-31, anti-MSLN-32, anti-MSLN-33, and anti-MSLN-34 as set forth in Table 10.

The present application provides isolated anti-mesothelin (anti-MSLN) constructs comprising an antibody moiety comprising an anti-MSLN heavy chain variable region (VH) comprising: a HC-CDR1, a HC-CDR2, and a HC-CDR3, respectively comprising the amino acid sequences of a CDR1, a CDR2, and a CDR3 within a VH chain region having the sequence set forth in any of SEQ ID NOS: 123-156 and 285-301.

In some embodiments according to any one of the constructs described above, the antibody moiety is a single-domain (sdAb) moiety. In some embodiments, the sdAb moiety that binds to the albumin is camelid, chimeric, human, partially humanized, or fully humanized.

In some embodiments according to any one of the constructs described above, the antibody moiety comprises the amino acid sequence of any one of SEQ ID Nos: 123-156 and 285-301, or a variant thereof having at least about 80% sequence identity to any one of SEQ ID NOs: 123-156 and 285-301.

In some embodiments according to any one of the constructs described above, the antibody moiety comprises a VHH domain comprising the amino acid sequence of any one of SEQ ID NOs: 123-156 and 285-301, or a variant thereof comprising up to about 3 (such as 3, 2, 1) amino acid substitutions in the VHH domain.

In some embodiments according to any one of the constructs described above, the antibody moiety has reduced fucosylation.

In some embodiments according to any one of the constructs described above, the construct is a fusion protein further comprising a half-life extending domain. In some embodiments, the half-life extending domain comprises an Fc domain or an albumin-binding domain.

In some embodiments according to any one of the constructs described above, the construct is a fusion protein further comprising a cytokine. In some embodiments, the cytokine is IL-21 or IL-15. In some embodiments, the half-life extending domain comprises an Fc domain or an albumin-binding domain. In some embodiments, the construct comprises a linker between the anti-MSLN antibody moiety and the cytokine. In some embodiments, the linker comprises an amino acid sequence of GSG or any one of SEQ ID NOS: 66-74, 267-282 and 307-324. In some embodiments, the linker is non-cleavable. In some embodiments, the linker is cleavable.

In some embodiments according to any one of the constructs described above, the construct is a fusion protein further comprising a) a half-life extending domain; and b) a cytokine. In some embodiments, the cytokine is IL-21 or IL-15. In some embodiments, the construct comprises a linker between the anti-MSLN antibody moiety and the cytokine. In some embodiments, the linker comprises an amino acid sequence of GSG or any one of SEQ ID NOS: 66-74, 267-282 and 307-324. In some embodiments, the linker is non-cleavable. In some embodiments, the linker is cleavable.

In some embodiments, the half-life extending domain is fused to N-terminus of the anti-MSLN antibody moiety. In some embodiments, the half-life extending domain is fused to C-terminus of the anti-MSLN antibody moiety. In some embodiments, the cytokine is fused to N-terminus of the anti-MSLN antibody moiety or the half-life extending domain. In some embodiments, the cytokine is fused to C-terminus of the anti-MSLN antibody moiety or the half-life extending domain.

The present application also provides polynucleotides encoding any of the anti-MSLN constructs described above.

The present application also provides nucleic acid constructs comprising any of the polynucleotides described herein, optionally further comprising a promoter in operative connection with the polynucleotide.

The present application also provides vectors comprising any of the nucleic acid constructs described above.

The present application also provides host cells comprising any of the polynucleotides, the nucleic acid constructs, or the vectors described above.

The present application also provides a culture medium comprising any of the anti-MSLN construct or host cells described herein.

The present application also provides kits comprising: a) any of the anti-MSLN constructs, the polynucleotides, the nucleic acid constructs, the vectors, the host cells, or the culture medium described above; and b) an instruction.

The present application also provides pharmaceutical compositions comprising any of the anti-MSLN constructs described above and a pharmaceutically acceptable carrier.

The present application also provides methods of treating a disease or condition into an individual, comprising administering any of the anti-MSLN constructs described above into the individual.

The present application also provides method of treating a disease or condition into an individual, comprising administering an anti-MSLN construct comprising an anti-MSLN antibody moiety that specifically binds to mesothelin, wherein the anti-MSLN antibody moiety has reduced fucosylation.

In some embodiments according to any one of the methods described above, the disease or condition is a cancer. In some embodiments, the cancer is mesothelin positive cancer. In some embodiments, the cancer is a solid cancer. In some embodiments, the cancer is selected from the group consisting of gastric cancer, lung cancer, ovarian cancer, esophageal cancer, pancreatic cancer, cervical cancer, mesothelioma, and breast cancer. In some embodiments, the cancer is gastric cancer or lung cancer.

In some embodiments according to any one of the methods described above, the method further comprises administering a second agent into the individual. In some embodiments, the second agent comprises a cytokine. In some embodiments, the cytokine is IL-21 or IL-15. In some embodiments, the IL-21 or IL-15 is in the form of a fusion protein comprising a half-life extending domain. In some embodiments, the IL-21 comprises an IL-21 variant lacking 1-11 amino acids at the C-terminus of SEQ ID NO: 1.

The present application also provides methods of treating a mesothelin positive cancer in an individual, comprising administering to the individual a) an anti-mesothelin agent; b) an anti-Her2 agent; and c) IL-21. In some embodiments, the IL-21 or IL-15 is in the form of a fusion protein comprising a half-life extending domain. In some embodiments, the IL-21 comprises an IL-21 variant lacking 1-11 amino acids at the C-terminus of SEQ ID NO: 1. In some embodiments, the anti-Her2 agent is Herceptin. In some embodiments, the anti-mesothelin agent comprises an anti-mesothelin antibody moiety comprising an anti-MSLN heavy chain variable region (VH) comprising: a HC-CDR1, a HC-CDR2, and a HC-CDR3, respectively comprising the amino acid sequences of a CDR1, a CDR2, and a CDR3 within a VH chain region having the sequence set forth in any of SEQ ID NOS: 123-156 and 285-301.

In some embodiments according to any one of the methods described above, the individual is a human.

DETAILED DESCRIPTION OF THE APPLICATION

Figure 1:
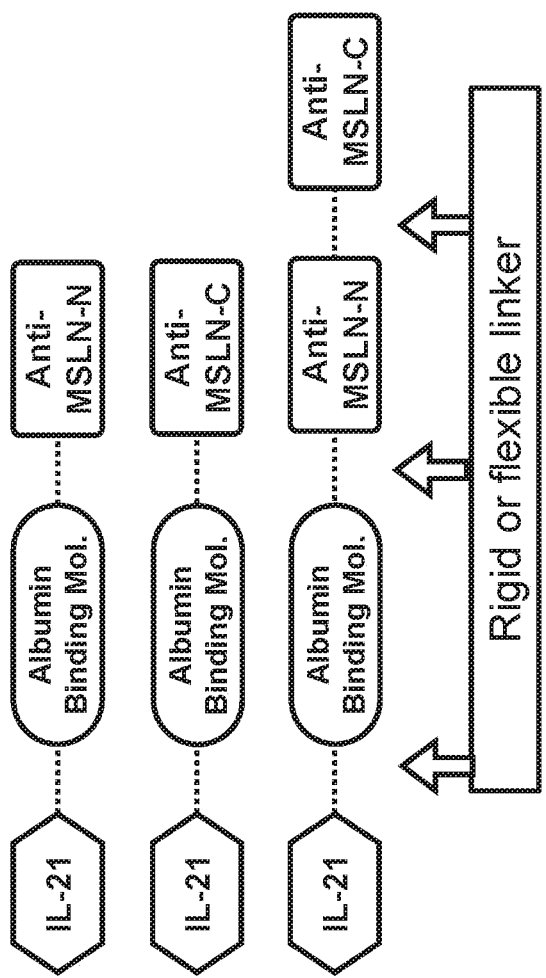
FIG. 1 depicts exemplary IL-21 fusion proteins provided herein.

The present disclosure provides novel fusion proteins comprising IL-21 or a variant thereof. The fusion proteins provided herein comprise IL-21 or a variant thereof, an albumin binding molecule, and a binding molecule that binds to an antigen (e.g., a cancer antigen), wherein the IL-21 or variant thereof is connected to the albumin binding molecule via a first linker, and wherein the albumin binding molecule is connected to the binding molecule via a second linker. FIG. 1 illustrates exemplary fusion proteins provided herein.

The fusion proteins disclosed herein provide many advantages. For example, in some embodiments, the binding molecule that binds to a cancer antigen (e.g., a solid tumor cancer antigen such as MSLN) in the present fusion protein enables the local delivery of IL-21 to cancer proximity, leading to lower off-target toxicity and increase efficacy.

Certain advantages are offered by the present fusion protein due to its tertiary structure and overall configuration design. For example, in some embodiments, by placing the IL-21, with an MMP sensitive linker, after a binding molecule targeting a cancer antigen and ABD (or anti-HSA), the interaction of IL-21 with IL-21R is temporarily blocked since its N-terminus (close to C-terminus in tertiary structure) is required for their interaction. When it binds to a cancer antigen, IL-21 is released from the fusion protein since cancer cells are known to secret various MMP's, which will cleave the linker between IL-21 and ABD or anti-albumin antibody. An MMP sensitive linker ensures that cancers, which typically have higher MMP activities, have higher exposure to active IL-21. Thus, unnecessary toxicity and side effects of IL-21 can be avoided. In addition, in such embodiments, by preventing the interaction between IL-21 and IL-21Rα on peripheral immune cells, the efficiency of cancer delivery of IL-21 fusion protein can be increased.

In certain embodiments, the presence of albumin binding molecule in the fusion protein provided herein may increase the circulation half life, resulting in higher drug exposure to cancer over a longer period of time as compared with a fusion protein without the albumin binding molecule.

In certain embodiments, an sdAb with relatively small molecular weight is used in the fusion protein provided herein, which may help increase cancer penetration of the fusion protein, making it better suited to treat certain cancers, e.g., a solid tumor cancer.

The present application provides anti-mesothelin constructs comprising an anti-MSLN antibody moiety comprising single domain antibody that specifically bind to anti-mesothelin. In some embodiments, the anti-mesothelin constructs (such as single domain anti-MSLN antibody) exhibit advantageous effects (such as killing tumor cells, such as treating tumor in an individual). In some embodiments, the anti-MSLN construct is a single domain anti-MSLN antibody. In some embodiments, the anti-MSLN construct is a fusion protein that comprises the anti-MSLN antibody moiety and a second domain. In some embodiments, the second domain is a half-life extending domain. In some embodiments, the second domain is a cytokine. In some embodiments, the anti-MSLN constructs comprise a fusion protein comprising a) an anti-MSLN antibody moiety as described herein, b) a second domain (such as a half-life extending domain), and c) a third domain (such as a cytokine).

The present application further provides methods of treating a disease or condition (such as a cancer) by administering an anti-mesothelin construct such as any of those described herein into an individual. In some embodiments, the methods further comprise administering a second agent such as a cytokine.

The present application further provides the methods of treating a disease (such as a cancer, such as a mesothelin positive cancer, such as a gastric cancer) comprising administering a) an anti-mesothelin construct such as any of the anti-MSLN constructs as described herein, b) a cytokine (such as IL-21); c) an anti-Her2 agent. In some embodiments, combination therapy as described in the above methods exhibit synergy.

Furthermore, the present disclosure provides novel antibodies targeting a cancer antigen (e.g., MSLN), when being part of the fusion protein provided herein, allowing efficient IL-21 delivery to cancer.

In certain embodiments, advantages are offered by having multiple antibodies targeting one or more cancer antigens in the IL-21 fusion protein provided herein. For example, in some embodiments, having two sdAbs each targeting different domains of a cancer antigen (e.g., MSLN) increases the avidity of cancer cell binding.

The above mentioned and other properties make the fusion proteins provided herein advantageous candidates for cancer therapy.

Definitions

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual (3d ed. 2001); Current Protocols in Molecular Biology (Ausubel et al. eds., 2003); Therapeutic Monoclonal Antibodies: From Bench to Clinic (An ed. 2009); Monoclonal Antibodies: Methods and Protocols (Albitar ed. 2010); and Antibody Engineering Vols 1 and 2 (Kontermann and Dübel eds., 2d ed. 2010).

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "binding molecule" refers to a protein comprising a portion (e.g., one or more binding regions such as CDRs) that binds to a target or an antigen and, optionally, a scaffold or framework portion (e.g., one or more scaffold or framework regions) that allows the binding portion to adopt a conformation that promotes binding of the binding protein to a polypeptide, fragment, or epitope. In the context of the present disclosure, a binding molecule is said to specifically bind or selectively bind to an antigen, for example, when the dissociation constant ($K_D$) is $\leq 10^{-6}$ M. In some embodiments, the binding molecule may specifically bind to an antigen with a $K_D$ of from about $10^{-6}$ M to about $10^{-12}$ M. In certain embodiments, the binding molecule may specifically bind to an antigen with high affinity when the $K_D$ is $\leq 10^{-7}$ M or $K_D$ is $\leq 10^{-8}$ M. In one embodiment, the binding molecule may specifically bind to a purified human antigen with a $K_D$ of from $1 \times 10^{-8}$ M to $10 \times 10^{-8}$ M as measured by OCTET®. In one embodiment, the binding molecule may specifically bind to a purified human antigen with a $K_D$ of from $1 \times 10^{-9}$ M to $10 \times 10^{-9}$ M as measured by OCTET®. In yet another embodiment, the binding molecule specifically binds to a human antigen expressed on cells with a $K_D$ of from $0.1 \times 10^{-9}$ M to $10 \times 10^{-9}$ M. In certain embodiments, the binding molecule specifically binds to a human antigen expressed on cells with a $K_D$ of about $0.1 \times 10^{-9}$ M, about $0.5 \times 10^{-9}$ M, about $1 \times 10^{-9}$ M, about $5 \times 10^{-9}$ M, about $10 \times 10^{-9}$ M, or any range or interval thereof. The term "binding molecule" includes antibodies and molecules derived from antibodies. The term "binding molecule" as used herein includes antibody fragments (e.g., single domain antibodies) that have relatively lower affinity to an antigen as compared with the parental intact antibodies.

The term "antibody," "immunoglobulin," or "Ig" is used interchangeably herein, and is used in the broadest sense and specifically covers, for example, monoclonal antibodies (including agonist, antagonist, neutralizing antibodies, full length or intact monoclonal antibodies), antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments thereof, as described below. An antibody can be human, humanized, chimeric and/or affinity matured, as well as an antibody from other species, for example, mouse and rabbit, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., Antibody Engineering (Borrebaeck ed., 2d ed. 1995); and Kuby, Immunology (3d ed. 1997). In specific embodiments, the specific molecular antigen can be bound by an antibody provided herein, including a polypeptide or an epitope. Antibodies also include, but are not limited to, synthetic antibodies, recombinantly produced antibodies, camelized antibodies or their humanized variants, intrabodies, anti-idiotypic (anti-Id) antibodies, and functional fragments (e.g., antigen-binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments) include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to an antigen (e.g., one or more CDRs of an antibody). Such antibody fragments can be found in, for example, Harlow and Lane, Antibodies: A Laboratory Manual (1989); Mol. Biology and Biotechnology: A Comprehensive Desk Reference (Myers ed., 1995); Huston et al., 1993, Cell Biophysics 22:189-224; Plückthun and Skerra, 1989, Meth. Enzymol. 178:497-515; and Day, Advanced Immunochemistry (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. Antibodies may be agonistic antibodies or antagonistic antibodies.

An "antigen" is a structure to which an antibody can selectively bind. A target antigen may be a polypeptide, carbohydrate, nucleic acid, lipid, hapten, or other naturally occurring or synthetic compound. In some embodiments, the target antigen is a polypeptide. In certain embodiments, an antigen is associated with a cell, for example, is present on or in a cell, for example, a cancer cell (e.g., a solid tumor cancer cell).

An "intact" antibody is one comprising an antigen-binding site as well as a CL and at least heavy chain constant regions, CH1, CH2 and CH3. The constant regions may include human constant regions or amino acid sequence variants thereof. In certain embodiments, an intact antibody has one or more effector functions.

The terms "antigen-binding fragment," "antigen-binding domain," "antigen-binding region," and similar terms refer to that portion of a binding molecule, which comprises the amino acid residues that interact with an antigen and confer on the binding agent its specificity and affinity for the antigen (e.g., the CDRs). "Antigen-binding fragment" as used herein include "antibody fragment," which comprise a portion of an intact antibody, such as the antigen-binding or variable region of the intact antibody. Examples of antibody fragments include, without limitation, Fab, Fab', F(ab')$_2$, and Fv fragments; diabodies and di-diabodies (see, e.g., Holliger et al., 1993, Proc. Natl. Acad. Sci. 90:6444-48; Lu et al., 2005, J. Biol. Chem. 280:19665-72; Hudson et al., 2003, Nat. Med. 9:129-34; WO 93/11161; and U.S. Pat. Nos. 5,837,242 and 6,492,123); single-chain antibody molecules (see, e.g., U.S. Pat. Nos. 4,946,778; 5,260,203; 5,482,858; and 5,476,786); dual variable domain antibodies (see, e.g., U.S. Pat. No. 7,612,181); single variable domain antibodies (sdAbs) (see, e.g., Woolven et al., 1999, Immunogenetics 50: 98-101; and Streltsov et al., 2004, Proc Natl Acad Sci USA. 101:12444-49); and multispecific antibodies formed from antibody fragments.

"Single domain antibody" or "sdAb" as used herein refer to antibody whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. According to one aspect of the invention, a single domain antibody as used herein is a single domain antibody known as heavy chain antibody devoid of light chains. Such single domain antibodies are disclosed in WO 9404678 for example. For clarity reasons, in certain instances, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, dromedary, alpaca and guanaco. Other species besides Camelidae may produce heavy chain antibodies naturally devoid of light chain; such VHHs are within the scope of the invention. In some embodiments, the single domain antibody provided herein has a structure of FR1-CDR1-FR2-CDR2-FR3-CDR3-FR4.

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as an antigen, is the affinity of the antibody or functional fragment for that epitope. The ratio of dissociation rate ($k_{off}$) to association rate ($k_{on}$) of a binding molecule (e.g., an antibody) to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent antigen, come in contact with antibodies containing multiple binding sites, the interaction of antibody with antigen at one site will increase the probability of a reaction at a second site. The strength of such multiple interactions between a multivalent antibody and antigen is called the avidity.

In connection with the binding molecules described herein terms such as "bind to," "that specifically bind to," and analogous terms are also used interchangeably herein and refer to binding molecules of antigen binding domains that specifically bind to an antigen, such as a polypeptide. A binding molecule or antigen binding domain that binds to or specifically binds to an antigen may be cross-reactive with related antigens. In certain embodiments, a binding molecule or antigen binding domain that binds to or specifically binds to an antigen does not cross-react with other antigens. A binding molecule or antigen binding domain that binds to or specifically binds to an antigen can be identified, for example, by immunoassays, Octet®, Biacore®, or other techniques known to those of skill in the art. In some embodiments, a binding molecule or antigen binding domain binds to or specifically binds to an antigen when it binds to an antigen with higher affinity than to any cross-reactive antigen as determined using experimental techniques, such as radioimmunoassays (RIA) and enzyme linked immunosorbent assays (ELISAs). Typically a specific or selective reaction will be at least twice background signal or noise and may be more than 10 times background. See, e.g., Fundamental Immunology 332-36 (Paul ed., 2d ed. 1989) for a discussion regarding binding specificity. In certain embodiments, the extent of binding of a binding molecule or antigen binding domain to a "non-target" protein is less than about 10% of the binding of the binding molecule or antigen binding domain to its particular target antigen, for example, as determined by fluorescence activated cell sorting (FACS) analysis or RIA. With regard terms such as "specific binding," "specifically binds to," or "is specific for" means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. A binding molecule or antigen binding domain that binds to an antigen includes one that is capable of binding the antigen with sufficient affinity such that the binding molecule is useful, for example, as a diagnostic fd fragment agent in targeting the antigen. In certain embodiments, a binding molecule or antigen binding domain that binds to an antigen has a dissociation constant ($K_D$) of less than or equal to 1000 nM, 800 nM, 500 nM, 250 nM, 100 nM, 50 nM, 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, a binding molecule or antigen binding domain binds to an epitope of an antigen that is conserved among the antigen from different species (e.g., between human and cyno species).

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a RIA, for example, performed with the Fab version of an antibody of interest and its antigen (Chen et al., 1999, J. Mol Biol 293:865-81). The $K_D$ or $K_D$ value may also be measured by using biolayer interferometry (BLI) or surface plasmon resonance (SPR) assays by Octet®, using, for example, an Octet®Red96 system, or by Biacore®, using, for example, a Biacore®TM-2000 or a Biacore®TM-3000. An "on-rate" or "rate of association" or "association rate" or "kon" may also be determined with the same biolayer interferometry (BLI) or surface plasmon resonance (SPR) techniques described above using, for example, the Octet®Red96, the Biacore®TM-2000, or the Biacore®TM-3000 system.

In certain embodiments, the binding molecules or antigen binding domains can comprise "chimeric" sequences in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55).

In certain embodiments, the binding molecules or antigen binding domains can comprise portions of "humanized" forms of nonhuman (e.g., murine) antibodies that are chimeric antibodies that include human immunoglobulins (e.g., recipient antibody) in which the native CDR residues are replaced by residues from the corresponding CDR of a nonhuman species (e.g., donor antibody) such as mouse, rat, rabbit, or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., 1986, Nature 321:522-25; Riechmann et al., 1988, Nature 332:323-29; Presta, 1992, Curr. Op. Struct. Biol. 2:593-96; Carter et al., 1992, Proc. Natl. Acad. Sci. USA 89:4285-89; U.S. Pat. Nos. 6,800,738; 6,719,971; 6,639,055; 6,407,213; and 6,054,297.

In certain embodiments, the binding molecules or antigen binding domains can comprise portions of a "fully human antibody" or "human antibody," wherein the terms are used interchangeably herein and refer to an antibody that comprises a human variable region and, for example, a human constant region. In specific embodiments, the terms refer to an antibody that comprises a variable region and constant region of human origin. "Fully human" antibodies, in certain embodiments, can also encompass antibodies which bind polypeptides and are encoded by nucleic acid sequences which are naturally occurring somatic variants of human germline immunoglobulin nucleic acid sequence. The term "fully human antibody" includes antibodies having variable and constant regions corresponding to human germline immunoglobulin sequences as described by Kabat et al. (See Kabat et al. (1991) Sequences of Proteins of Immunological Interest, Fifth Edition, U.S. Department of Health and Human Services, NIH Publication No. 91-3242). A "human antibody" is one that possesses an amino acid sequence which corresponds to that of an antibody produced by a human and/or has been made using any of the techniques for making human antibodies. This definition of a human antibody specifically excludes a humanized antibody comprising non-human antigen-binding residues. Human antibodies can be produced using various techniques known in the art, including phage-display libraries (Hoogenboom and Winter, 1991, J. Mol. Biol. 227:381; Marks et al., 1991, J. Mol. Biol. 222:581) and yeast display libraries (Chao et al., 2006, Nature Protocols 1: 755-68). Also available for the preparation of human monoclonal antibodies are methods described in Cole et al., Monoclonal Antibodies and Cancer Therapy 77 (1985); Boerner et al., 1991, J. Immunol. 147(1):86-95; and van Dijk and van de Winkel, 2001, Curr. Opin. Pharmacol. 5: 368-74. Human antibodies can be prepared by administering the antigen to a transgenic animal that has been modified to produce such antibodies in response to antigenic challenge, but whose endogenous loci have been disabled, e.g., mice (see, e.g., Jakobovits, 1995, Curr. Opin. Biotechnol. 6(5):561-66; Bruggemann and Taussing, 1997, Curr. Opin. Biotechnol. 8(4):455-58; and U.S. Pat. Nos. 6,075,181 and 6,150,584 regarding XENO-MOUSE™ technology). See also, for example, Li et al., 2006, Proc. Natl. Acad. Sci. USA 103:3557-62 regarding human antibodies generated via a human B-cell hybridoma technology.

In certain embodiments, the binding molecules or antigen binding domains can comprise portions of a "recombinant human antibody," wherein the phrase includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see e.g., Taylor, L. D. et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In certain embodiments, the binding molecules or antigen binding domains can comprise a portion of a "monoclonal antibody," wherein the term as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell. The term "monoclonal" is not limited to any particular method for making the antibody. For example, the monoclonal antibodies useful in the present disclosure may be prepared by the hybridoma methodology first described by Kohler et al., 1975, Nature 256:495, or may be made using recombinant DNA methods in bacterial or eukaryotic animal or plant cells (see, e.g., U.S. Pat. No. 4,816,567). The "monoclonal antibodies" may also be isolated from phage antibody libraries using the techniques described in Clackson et al., 1991, Nature 352:624-28 and Marks et al., 1991, J. Mol. Biol. 222:581-97, for example. Other methods for the preparation of clonal cell lines and of monoclonal antibodies expressed thereby are well known in the art. See, e.g., Short Protocols in Molecular Biology (Ausubel et al. eds., 5th ed. 2002).

A typical 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the $\alpha$ and $\gamma$ chains and four CH domains for $\mu$ and $\epsilon$ isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, Basic and Clinical Immunology 71 (Stites et al. eds., 8th ed. 1994); and Immunobiology (Janeway et al. eds., 5$^{th}$ ed. 2001).

The term "Fab" or "Fab region" refers to an antibody region that binds to antigens. A conventional IgG usually comprises two Fab regions, each residing on one of the two arms of the Y-shaped IgG structure. Each Fab region is typically composed of one variable region and one constant region of each of the heavy and the light chain. More specifically, the variable region and the constant region of the heavy chain in a Fab region are VH and CH1 regions, and the variable region and the constant region of the light chain in a Fab region are VL and CL regions. The VH, CH1, VL, and CL in a Fab region can be arranged in various ways to confer an antigen binding capability according to the present disclosure. For example, VH and CH1 regions can be on one polypeptide, and VL and CL regions can be on a separate polypeptide, similarly to a Fab region of a conventional IgG. Alternatively, VH, CH1, VL and CL regions can all be on the same polypeptide and oriented in different orders as described in more detail the sections below.

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a 13 sheet configuration, connected by three hypervariable regions, which form loops connecting, and in some cases form part of, the 13 sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering according to Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHon.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and ε contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains.

As used herein, the terms "hypervariable region," "HVR," "Complementarity Determining Region," and "CDR" are used interchangeably. A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences.

CDR regions are well known to those skilled in the art and have been defined by well-known numbering systems. For example, the Kabat Complementarity Determining Regions (CDRs) are based on sequence variability and are the most commonly used (see, e.g., Kabat et al., supra). Chothia refers instead to the location of the structural loops (see, e.g., Chothia and Lesk, 1987, J. Mol. Biol. 196:901-17). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., Antibody Engineering Vol. 2 (Kontermann and Dübel eds., 2d ed. 2010)). The "contact" hypervariable regions are based on an analysis of the available complex crystal structures. Another universal numbering system that has been developed and widely adopted is ImMunoGeneTics (IMGT) Information System® (Lafranc et al., 2003, Dev. Comp. Immunol. 27(1):55-77). IMGT is an integrated information system specializing in immunoglobulins (IG), T-cell receptors (TCR), and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Plückthun, 2001, J. Mol. Biol. 309: 657-70. Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra). The residues from each of these hypervariable regions or CDRs are noted below.

50-56 (L2), and 89-97 or 89-96 (L3) in the VL, and 26-35 or 26-35A (H1), 50-65 or 49-65 (H2), and 93-102, 94-102, or 95-102 (H3) in the VH.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a

TABLE 1

|  | Kabat | AbM | Chothia | Contact | IMGT |
|---|---|---|---|---|---|
| CDR L1 | L24--L34 | L24--L34 | L24--L34 | L30--L36 | L27--L38 |
| CDR L2 | L50--L56 | L50--L56 | L50--L56 | L46--L55 | L56--L65 |
| CDR L3 | L89--L97 | L89--L97 | L89--L97 | L89--L96 | L105-L117 |
| CDR H1 | H31--H35B (Kabat Numbering) | H26--H35B | H26--H32 ... 34 | H30--H35B | H27--H38 |
| CDR H1 | H31--H35 (Chothia Numbering) | H26--H35 | H26--H32 | H30--H35 |  |
| CDR H2 | H50--H65 | H50--H58 | H52--H56 | H47--H58 | H56--H65 |
| CDR H3 | H95--H102 | H95--H102 | H95--H102 | H93--H101 | H105--H117 |

The boundaries of a given CDR may vary depending on the scheme used for identification. Thus, unless otherwise specified, the terms "CDR" and "complementary determining region" of a given antibody or region thereof, such as a variable region, as well as individual CDRs (e.g., "CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the Kabat, Chothia, or Contact method. In other cases, the particular amino acid sequence of a CDR is given.

Hypervariable regions may comprise "extended hypervariable regions" as follows: 24-36 or 24-34 (L1), 46-56 or mixture of antibodies with and without the K447 residue. A "functional Fc region" possesses an "effector function" of a native sequence Fc region. Exemplary "effector functions" include C1q binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays known to those skilled in the art. A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith.

As used herein, an "epitope" is a term in the art and refers to a localized region of an antigen to which a binding molecule (e.g., an antibody) can specifically bind. An epitope can be a linear epitope or a conformational, non-linear, or discontinuous epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, a binding molecule binds to a group of amino acids regardless of whether they are folded in a natural three dimensional protein structure. In other embodiments, a binding molecule requires amino acid residues making up the epitope to exhibit a particular conformation (e.g., bend, twist, turn or fold) in order to recognize and bind the epitope.

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5):1792-1797, 2004; Edgar, R. C., *BMC Bioinformatics* 5(1):113, 2004).

As used herein, the term "cytokine" is understood to mean any protein or peptide, analog or functional fragment thereof, which is capable of stimulating or inducing a cytocidal immune response against a preselected cell-type, for example, a cancer cell or a virally-infected cell, in a mammal. Accordingly, it is contemplated that a variety of cytokines can be incorporated into this application. Useful cytokines include, for example, tumor necrosis factors (TNFs), interleukins (ILs), lymphokines (Ls), colony stimulating factors (CSFs), interferons (IFNs) including species variants, truncated analogs thereof which are capable of stimulating or inducing such cytocidal immune responses. Useful tumor necrosis factors include, for example, TNFα. Useful lymphokines include, for example, LT. Useful colony stimulating factors include, for example, GM-CSF and M-CSF. Useful interleukins include, for example, IL-2, IL-4, IL-5, IL-7, IL-12, IL-15, IL-18, IL-21, IL22, and IL-33. Useful interferons, include, for example, IFN-α, IFN-α and IFN-γ. The term "cytokine" is also understood to encompass any variant of a wildtype cytokine (such as IL-21, IL-7, IL-15, etc.) that comprises modification and maintains at least a significant portion (such as at least about 50%) of any of its desired function.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies or other members of the immunoglobulin superfamily, in certain embodiments, a "polypeptide" can occur as a single chain or as two or more associated chains.

The term "vector" refers to a substance that is used to carry or include a nucleic acid sequence, including for example, a nucleic acid sequence encoding a binding molecule (e.g., an antibody) as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product and it is further understood that expression levels can be optimized to obtain sufficient expression using methods well known in the art.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

An "isolated" antibody (or construct) is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator; or (3) to homogeneity by SDS-PAGE under non-reducing or reducing conditions using Coomassie Blue or, preferably, silver stain. Isolated antibody (or construct) includes the antibody in situ within recombinant cells since at least one component of the antibody's natural environment will not be present. Ordinarily, however, an isolated polypeptide, antibody, or construct will be prepared by at least one purification step.

An "isolated nucleic acid" is a nucleic acid, for example, an RNA, DNA, or a mixed nucleic acid, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces a binding molecule of the present disclosure may include a parent hybridoma cell, as well as bacterial and eukaryotic host cells into which nucleic acids encoding the antibodies have been introduced. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

The term "pharmaceutically acceptable" as used herein means being approved by a regulatory agency of the Federal or a state government, or listed in United States Pharmacopeia, European Pharmacopeia, or other generally recognized Pharmacopeia for use in animals, and more particularly in humans.

"Excipient" means a pharmaceutically-acceptable material, composition, or vehicle, such as a liquid or solid filler, diluent, solvent, or encapsulating material. Excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. The term "excipient" can also refer to a diluent, adjuvant (e.g., Freunds' adjuvant (complete or incomplete) or vehicle.

In some embodiments, excipients are pharmaceutically acceptable excipients. Examples of pharmaceutically acceptable excipients include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™. Other examples of pharmaceutically acceptable excipients are described in Remington and Gennaro, Remington's Pharmaceutical Sciences (18th ed. 1990).

In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, FL, 2009. In some embodiments, pharmaceutically acceptable excipients are nontoxic to the cell or mammal being exposed thereto at the dosages and concentrations employed. In some embodiments, a pharmaceutically acceptable excipient is an aqueous pH buffered solution.

In some embodiments, excipients are sterile liquids, such as water and oils, including those of petroleum, animal, vegetable, or synthetic origin, such as peanut oil, soybean oil, mineral oil, sesame oil, and the like. Water is an exemplary excipient when a composition (e.g., a pharmaceutical composition) is administered intravenously. Saline solutions and aqueous dextrose and glycerol solutions can also be employed as liquid excipients, particularly for injectable solutions. An excipient can also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like. Oral compositions, including formulations, can include standard excipients such as pharmaceutical grades of mannitol, lactose, starch, magnesium stearate, sodium saccharine, cellulose, magnesium carbonate, etc.

Compositions, including pharmaceutical compounds, may contain a binding molecule (e.g., an antibody), for example, in isolated or purified form, together with a suitable amount of excipients.

The term "effective amount" or "therapeutically effective amount" as used herein refers to the amount of binding molecule (e.g., an antibody) or pharmaceutical composition provided herein which is sufficient to result in the desired outcome.

The terms "subject" and "patient" may be used interchangeably. As used herein, in certain embodiments, a subject is a mammal, such as a non-primate (e.g., cow, pig, horse, cat, dog, rat, etc.) or a primate (e.g., monkey and human). In specific embodiments, the subject is a human. In one embodiment, the subject is a mammal, e.g., a human, diagnosed with a condition or disorder. In another embodiment, the subject is a mammal, e.g., a human, at risk of developing a condition or disorder.

"Administer" or "administration" refers to the act of injecting or otherwise physically delivering a substance as it exists outside the body into a patient, such as by mucosal, intradermal, intravenous, intramuscular delivery, and/or any other method of physical delivery described herein or known in the art.

As used herein, the terms "treat," "treatment" and "treating" refer to the reduction or amelioration of the progression, severity, and/or duration of a disease or condition resulting from the administration of one or more therapies. Treating may be determined by assessing whether there has been a decrease, alleviation and/or mitigation of one or more symptoms associated with the underlying disorder such that an improvement is observed with the patient, despite that the patient may still be afflicted with the underlying disorder. The term "treating" includes both managing and ameliorating the disease. The terms "manage," "managing," and "management" refer to the beneficial effects that a subject derives from a therapy which does not necessarily result in a cure of the disease.

The terms "prevent," "preventing," and "prevention" refer to reducing the likelihood of the onset (or recurrence) of a disease, disorder, condition, or associated symptom(s) (e.g., a cancer).

The term "cancer" or "cancer cell" is used herein to denote a tissue or cell found in a neoplasm which possesses characteristics which differentiate it from normal tissue or tissue cells. Among such characteristics include but are not limited to: degree of anaplasia, irregularity in shape, indistinctness of cell outline, nuclear size, changes in structure of nucleus or cytoplasm, other phenotypic changes, presence of cellular proteins indicative of a cancerous or pre-cancerous state, increased number of mitoses, and ability to metastasize. Words pertaining to "cancer" include carcinoma, sarcoma, tumor, epithelioma, leukemia, lymphoma, polyp, and scirrus, transformation, neoplasm, and the like.

The terms "about" and "approximately" mean within 20%, within 15%, within 10%, within 9%, within 8%, within 7%, within 6%, within 5%, within 4%, within 3%, within 2%, within 1%, or less of a given value or range.

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "between" as used in a phrase as such "between A and B" or "between A-B" refers to a range including both A and B.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

IL-21 Fusion Proteins
IL-21 and Variants Thereof

The IL-21 protein in the IL-21 fusion protein provided herein can be a human wild-type IL-21 protein having the amino acid sequence of SEQ ID NO: 1 (see below).

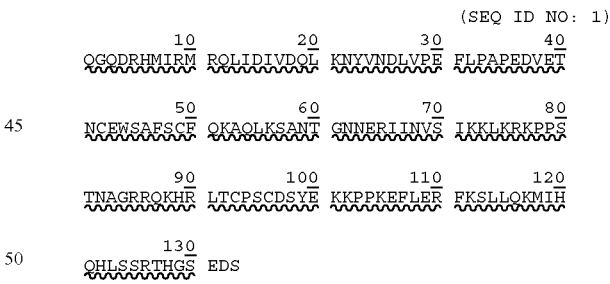

In some embodiments, an IL-21 variant can be in the IL-21 fusion protein provided herein. Variations may be a substitution, deletion, or insertion of one or more codons encoding the IL-21 polypeptide that results in a change in the amino acid sequence as compared with the human wide-type IL-21 protein Amino acid substitutions can be the result of replacing one amino acid with another amino acid having similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 10 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the full-length or mature native sequence.

Amino acid sequence insertions include amino- and/or carboxyl-terminal fusions ranging in length from one residue or multiple residues, as well as intrasequence insertions of single or multiple amino acid residues.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity (e.g., binding to IL-21 receptor or IL-21R) to identify mutants that retain activity. Following mutagenesis, the encoded protein can be expressed and the activity of the protein can be determined.

Conservative (e.g., within an amino acid group with similar properties and/or side chains) substitutions may be made, so as to maintain or not significantly change the properties of the IL-21 protein Amino acids may be grouped according to similarities in the properties of their side chains (see, e.g., Lehninger, Biochemistry 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His (H).

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Accordingly, in one embodiment, an IL-21 variant provided herein comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the IL-21 having SEQ ID NO: 1 described herein.

The variations can be made using methods known in the art such as oligonucleotide-mediated (site-directed) mutagenesis, alanine scanning, and PCR mutagenesis. Site-directed mutagenesis (see, e.g., Carter, 1986, Biochem J. 237:1-7; and Zoller et al., 1982, Nucl. Acids Res. 10:6487-500), cassette mutagenesis (see, e.g., Wells et al., 1985, Gene 34:315-23), or other known techniques can be performed on the cloned DNA to produce a polypeptide.

In some embodiments, the IL-21 variant lacks one or more amino acids between S124 and S133 at the C-terminus. In some embodiments, the IL-21 variant lacks any one amino acid between S124 and S133 at the C-terminus. In some embodiments, the IL-21 variant lacks any two amino acids between S124 and S133 at the C-terminus. In some embodiments, the IL-21 variant lacks any three amino acids between S124 and S133 at the C-terminus. In some embodiments, the IL-21 variant lacks any four amino acids between S124 and S133 at the C-terminus. In some embodiments, the IL-21 variant lacks any five amino acids between S124 and S133 at the C-terminus. In some embodiments, the IL-21 variant lacks any six amino acids between S124 and S133 at the C-terminus. In some embodiments, the IL-21 variant lacks any seven amino acids between S124 and S133 at the C-terminus. In some embodiments, the IL-21 variant lacks any eight amino acids between S124 and S133 at the C-terminus. In some embodiments, the IL-21 variant lacks any nine amino acids between S124 and S133 at the C-terminus. In some embodiments, the IL-21 variant lacks any ten amino acids between S124 and S133 at the C-terminus.

In some embodiments, the IL-21 variant lacks the 11 amino acids at the C-terminus of SEQ ID NO: 1. In some embodiments, the IL-21 variant lacks the 10 amino acids at the C-terminus of SEQ ID NO: 1. In some embodiments, the IL-21 variant lacks the 9 amino acids at the C-terminus of SEQ ID NO: 1. In some embodiments, the IL-21 variant lacks the 8 amino acids at the C-terminus of SEQ ID NO: 1. In some embodiments, the IL-21 variant lacks the 7 amino acids at the C-terminus of SEQ ID NO: 1. In some embodiments, the IL-21 variant lacks the 6 amino acids at the C-terminus of SEQ ID NO: 1. In some embodiments, the IL-21 variant lacks the 5 amino acids at the C-terminus of SEQ ID NO: 1. In some embodiments, the IL-21 variant lacks the 4 amino acids at the C-terminus of SEQ ID NO: 1. In some embodiments, the IL-21 variant lacks the 3 amino acids at the C-terminus of SEQ ID NO: 1. In some embodiments, the IL-21 variant lacks the 2 amino acids at the C-terminus of SEQ ID NO: 1. In some embodiments, the IL-21 variant lacks the 1 amino acid at the C-terminus of SEQ ID NO: 1.

In a specific embodiment, the IL-21 variant provided herein has an amino acid sequence of SEQ ID NO: 2, which lacks the 10 amino acids at the C-terminus and represents a sequence of Q1 to L123 of SEQ ID NO: 1.

Albumin Binding Molecules

Albumin (e.g., human serum albumin or HSA) has been used to increase the serum half life of biological drugs. See Dennis et al., *The Journal of Biological Chemistry*, 2002, 277 (38): 35035-35043; Adams et al., *MABS*, 2016, 8(7): 1336-1346. For example, human serum albumin (HSA) has been utilized. HSA is the most abundant protein in blood, and is widely distributed in tissues and has a non-acute function. It has a half like of 19 days. Therefore, in some embodiments, albumin (e.g., HSA) can be used herein to increase half life of the fusion protein provided herein among other advantages. Albumin can be used in a few ways. One exemplary approach is to directly include an albumin domain (e.g., HSA) in the fusion protein provided herein, either genetically or chemically. Another exemplary approach is to use an albumin binding domain (ABD) or anti-albumin antibody.

In some embodiments, the fusion protein provided herein comprise an albumin binding molecule. In some embodiments, the albumin binding molecule provided herein is an albumin binding domain (ABD). In some embodiments, the ABD can bind to human serum albumin (HSA). In other embodiments, ABD can bind to mouse serum albumin (MSA).

In some embodiments, the ABD binds to HSA with a $K_D$ of between 1-1000 nM. In some embodiments, the ABD binds to HSA with a $K_D$ of between 1-900 nM. In some embodiments, the ABD binds to HSA with a $K_D$ of between 1-800 nM. In some embodiments, the ABD binds to HSA with a $K_D$ of between 1-700 nM. In some embodiments, the ABD binds to HSA with a $K_D$ of between 1-600 nM. In some embodiments, the ABD binds to HSA with a $K_D$ of between 1-500 nM. In some embodiments, the ABD binds to HSA with a $K_D$ of between 1-400 nM. In some embodiments, the ABD binds to HSA with a $K_D$ of between 1-300 nM. In some embodiments, the ABD binds to HSA with a $K_D$ of between 1-200 nM. In some embodiments, the ABD binds to HSA with a $K_D$ of between 1-100 nM. In some embodiments, the ABD binds to HSA with a $K_D$ of between 1-50 nM. In some embodiments, the ABD binds to HSA with a $K_D$ of between 1-25 nM. In some embodiments, the ABD binds to HSA with a $K_D$ of between 0.1-1 nM. In other embodiments, the ABD binds to HSA with a $K_D$ of between 10-800 nM. In some embodiments, the ABD binds to HSA with a $K_D$ of between 20-500 nM. In other embodiments, the ABD binds to HSA with a $K_D$ of between 50-300 nM. In other embodiments, the ABD binds to HSA with a $K_D$ of between 100-200 nM.

In some specific embodiments, the ABD has an amino acid sequence of

```
                                           (SEQ ID NO: 3)
LAEAKVLANRELDKYGVSDYYKNLINNAKTVEGVKALIDEILAALP,
``` which has a $K_D$ to HSA of about 1.2 nM.

In some embodiments, an ABD having relatively lower affinity to HSA than the ABD of SEQ ID NO: 3 is preferred. Accordingly, variants of SEQ ID NO: 3 that have lower affinity to HSA are included in the present disclosure.

Variations may be a substitution, deletion, or insertion of one or more codons encoding the ABD polypeptide of SEQ ID NO: 3 that results in a change in the amino acid sequence. Amino acid substitutions can be the result of replacing one amino acid with another amino acid having similar or different structural and/or chemical properties. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 15 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule of SEQ ID NO: 3. The variation allowed may be determined by systematically making insertions, deletions, or substitutions of amino acids in the sequence and testing the resulting variants for activity and in some embodiments, variants having a lower affinity to HSA are selected. Certain such kind of variants are exemplified in Table 7 in Example 1 below.

In some specific embodiments, the ABD has an amino acid sequence of SEQ ID NO: 4. In other specific embodiments, the ABD has an amino acid sequence of SEQ ID NO: 5. In other specific embodiments, the ABD has an amino acid sequence of SEQ ID NO: 6. In yet other specific embodiments, the ABD has an amino acid sequence of SEQ ID NO: 7. In yet other specific embodiments, the ABD has an amino acid sequence of SEQ ID NO: 8. In yet other specific embodiments, the ABD has an amino acid sequence of SEQ ID NO: 9. In yet other specific embodiments, the ABD has an amino acid sequence of SEQ ID NO: 10. In yet other specific embodiments, the ABD has an amino acid sequence of SEQ ID NO: 11.

According to the present invention, the albumin binding molecule can also be anti-albumin antibody or antigen binding fragment thereof. In some embodiments, the anti-albumin antibody or antigen binding fragment thereof is an anti-HSA antibody or antigen binding fragment thereof.

A few isoforms of HSA are listed in Table 2 below (see UniProtKB—P02768 (ALBU_HUMAN))

TABLE 2

```
Isoform 1   MKWVTFISLL FLFSSAYSRG VFRRDAHKSE VAHRFKDLGE ENFKALVLIA
            FAQYLQQCPF EDHVKLVNEV TEFAKTCVAD ESAENCDKSL HTLFGDKLCT
            VATLRETYGE MADCCAKQEP ERNECFLQHK DDNPNLPRLV RPEVDVMCTA
            FHDNEETFLK KYLYEIARRH PYFYAPELLF FAKRYKAAFT ECCQAADKAA
            CLLPKLDELR DEGKASSAKQ RLKCASLQKF GERAFKAWAV ARLSQRFPKA
            EFAEVSKLVT DLTKVHTECC HGDLLECADD RADLAKYICE NQDSISSKLK
            ECCEKPLLEK SHCIAEVEND EMPADLPSLA ADFVESKDVC KNYAEAKDVF
            LGMFLYEYAR RHPDYSVVLL LRLAKTYETT LEKCCAAADP HECYAKVFDE
            FKPLVEEPQN LIKQNCELFE QLGEYKFQNA LLVRYTKKVP QVSTPTLVEV
            SRNLGKVGSK CCKHPEAKRM PCAEDYLSVV LNQLCVLHEK TPVSDRVTKC
            CTESLVNRRP CFSALEVDET YVPKEFNAET FTFHADICTL SEKERQIKKQ
            TALVELVKHK PKATKEQLKA VMDDFAAFVE KCCKADDKET CFAEEGKKLV
            AASQAALGL (SEQ ID NO: 260)

Isoform 2   MKWVTFISLL FLFSSAYSRG VFRRDAHKSE VAHRFKDLGE ENFKAWAVAR
            LSQRFPKAEF AEVSKLVTDL TKVHTECCHG DLLECADDRA DLAKYICENQ
            DSISSKLKEC CEKPLLEKSH CIAEVENDEM PADLPSLAAD FVESKDVCKN
            YAEAKDVFLG MFLYEYARRH PDYSVVLLLR LAKTYETTLE KCCAAADPHE
            CYAKVFDEFK PLVEEPQNLI KQNCELFEQL GEYKFQNALL VRYTKKVPQV
            STPTLVEVSR NLGKVGSKCC KHPEAKRMPC AEDYLSVVLN QLCVLHEKTP
            VSDRVTKCCT ESLVNRRPCF SALEVDETYV PKEFNAETFT FHADICTLSE
            KERQIKKQTA LVELVKHKPK ATKEQLKAVM DDFAAFVEKC CKADDKETCF
            AEEGKKLVAA SQAALGL (SEQ ID NO: 261)
```

TABLE 2-continued

```
Isoform 3   MKWVTFISLL  FLFSSAYSRG  VFRRDAHKSE  VAHRFKDLGE  ENFKALVLIA
            FAQYLQQCPF  EDHVKLVNEV  TEFAKTCVAD  ESAENCDKSL  HTLFGDKLCT
            VATLRETYGE  MADCCAKQEP  ERNECFLQHK  DDNPNLPRLV  RPEVDVMCTA
            FHDNEETFLK  KYLYETTLEK  CCAAADPHEC  YAKVFDEFKP  LVEEPQNLIK
            QNCELFEQLG  EYKFQNALLV  RYTKKVPQVS  TPTLVEVSRN  LGKVGSKCCK
            HPEAKRMPCA  EDYLSVVLNQ  LCVLHEKTPV  SDRVTKCCTE  SLVNRRPCFS
            ALEVDETYVP  KEFNAETFTF  HADICTLSEK  ERQIKKQTAL  VELVKHKPKA
            TKEQLKAVMD  DFAAFVEKCC  KADDKETCFA  EEGKKLVAAS  QAALGL (SEQ
            ID NO: 262)
```

The anti-HSA antibodies provided herein can bind to any of these isoforms or fragments thereof. In some embodiments, the anti-HSA antibody provided herein binds to SEQ ID NO: 260 or a fragment thereof. In some embodiments, the anti-HSA antibody provided herein binds to SEQ ID NO: 261 or a fragment thereof. In other embodiments, the anti-HSA antibody provided herein binds to SEQ ID NO: 262 or a fragment thereof.

The anti-HSA antibodies provided herein can be, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bis-pecific, etc.), camelized antibodies or their humanized versions, Fab fragments, F(ab') fragments, disulfide-linked Fvs (sdFv), anti-idiotypic (anti-Id) antibodies, and epitope-binding fragments of any of the above.

In particular, the anti-HSA antibodies provided herein include immunoglobulin molecules and immunologically active portions of immunoglobulin molecules, i.e., molecules that contain an antigen binding site that immunospecifically binds to HSA. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, the anti-HSA antibody provided herein is an IgG antibody, such as an IgG1 antibody.

Variants and derivatives of antibodies including antibody fragments that retain the ability to specifically bind to an epitope of HSA are also included in the present disclosure. Exemplary fragments include Fab fragments (an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')$_2$ (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, anti-HSA antibody provided herein comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in The Pharmacology of Monoclonal Antibodies, vol. 113, Rosenburg and Moore eds. Springer-Verlag, New York, pp. 269-315 (1994).

In certain circumstances there are advantages of using anti-HSA antibody fragments, rather than whole antibodies. The smaller size of the fragments allows for rapid clearance, and may lead to improved access to cells, tissues, or organs. For a review of certain antibody fragments, see Hudson et al., 2003, Nature Med. 9:129-34.

Various techniques have been developed for the production of antibody fragments. Traditionally, these fragments were derived via proteolytic digestion of intact antibodies (see, e.g., Morimoto et al., 1992, J. Biochem. Biophys. Methods 24:107-17; and Brennan et al., 1985, Science 229:81-83). However, these fragments can now be produced directly by recombinant host cells. Fab, Fv, and scFv antibody fragments can all be expressed in and secreted from E. coli or yeast cells, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., 1992, Bio/Technology 10:163-67). According to another approach, F(ab')$_2$ fragments can be isolated directly from recombinant host cell culture. Fab and F(ab')$_2$ fragment with increased in vivo half-life comprising salvage receptor binding epitope residues are described in, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894 and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv (See, e.g., Borrebaeck ed., supra). The antibody fragment may also be a "linear antibody," for example, as described in the references cited above. Such linear antibodies may be monospecific or multi-specific, such as bispecific. In a specific embodiment, the antibody fragment is a single domain antibody.

The anti-HSA antibodies provided herein may be from any animal origin including birds and mammals (e.g., human, murine, donkey, sheep, rabbit, goat, guinea pig, camel, horse, or chicken). In certain embodiments, the antibodies provided herein are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In certain embodiments, the anti-HSA antibodies are fully human antibodies, such as fully human antibodies that immunospecifically bind a cancer antigen. Such fully human antibodies would be advantageous over fully mouse (or other full or partial non-human species antibodies), humanized antibodies, or chimeric antibodies to minimize the development of unwanted or unneeded side effects, such as immune responses directed toward non-fully human antibodies when administered to the subject.

The anti-HSA antibodies provided herein may be monospecific, bispecific, trispecific or of greater multispecificity. Multispecific antibodies may be specific for different epitopes of a polypeptide or may be specific for both a polypeptide as well as for a heterologous epitope, such as a heterologous polypeptide or solid support material. In some embodiments, the antibodies provided herein are monospecific for a given epitope of a polypeptide and do not immunospecifically bind to other epitopes.

The anti-HSA antibodies provided herein may be monoclonal antibodies or derived from monoclonal antibodies. Monoclonal antibodies may be made using the hybridoma method first described by Kohler et al., 1975, Nature 256: 495-97, or may be made by recombinant DNA methods (see, e.g., U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice 59-103 (1986)).

The hybridoma cells thus prepared are seeded and grown in a suitable culture medium which, in certain embodiments, contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which prevent the growth of HGPRT-deficient cells.

Exemplary fusion partner myeloma cells are those that fuse efficiently, support stable high-level production of antibody by the selected antibody-producing cells, and are sensitive to a selective medium that selects against the unfused parental cells. Exemplary myeloma cell lines are murine myeloma lines, such as SP-2 and derivatives, for example, X63-Ag8-653 cells available from the American Type Culture Collection (Manassas, VA), and those derived from MOPC-21 and MPC-11 mouse tumors available from the Salk Institute Cell Distribution Center (San Diego, CA). Human myeloma and mouse-human heteromyeloma cell lines also have been described for the production of human monoclonal antibodies (Kozbor, 1984, Immunol. 133:3001-05; and Brodeur et al., Monoclonal Antibody Production Techniques and Applications 51-63 (1987)).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as RIA or ELISA. The binding affinity of the monoclonal antibody can, for example, be determined by the Scatchard analysis described in Munson et al., 1980, Anal. Biochem. 107:220-39.

Once hybridoma cells that produce anti-HSA antibodies of the desired specificity, affinity, and/or activity are identified, the clones may be subcloned by limiting dilution procedures and grown by standard methods (Goding, supra). Suitable culture media for this purpose include, for example, DMEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells can serve as a source of such DNA. Once isolated, the DNA may be placed into expression vectors, which are then transfected into host cells, such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., 1993, Curr. Opinion in Immunol. 5:256-62 and Plückthun, 1992, Immunol. Revs. 130:151-88.

In a further embodiment, monoclonal antibodies or antibody fragments can be isolated from antibody phage libraries generated using the techniques described in, for example, Antibody Phage Display: Methods and Protocols (O'Brien and Aitken eds., 2002). In phage display methods, functional antibody domains are displayed on the surface of phage particles which carry the polynucleotide sequences encoding them. Examples of phage display methods that can be used to make the antibodies described herein include those disclosed in Brinkman et al., 1995, J. Immunol. Methods 182:41-50; Ames et al., 1995, J. Immunol. Methods 184: 177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

In principle, synthetic antibody clones are selected by screening phage libraries containing phages that display various fragments of antibody variable region (Fv) fused to phage coat protein. Such phage libraries are screened against the desired antigen. Clones expressing Fv fragments capable of binding to the desired antigen are adsorbed to the antigen and thus separated from the non-binding clones in the library. The binding clones are then eluted from the antigen and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., 1994, Ann. Rev. Immunol. 12:433-55.

Repertoires of VH and VL genes can be separately cloned by PCR and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., 1993, EMBO J 12:725-34. Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, 1992, J. Mol. Biol. 227:381-88.

Screening of the libraries can be accomplished by various techniques known in the art. For example, HSA polypeptide or a fragment thereof can be used to coat the wells of adsorption plates, expressed on host cells affixed to adsorption plates or used in cell sorting, conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., 1990, Proteins 8:309-14 and WO 92/09690, and by use of a low coating density of antigen as described in Marks et al., 1992, Biotechnol. 10:779-83.

Antibodies can be obtained by designing a suitable antigen screening procedure to select for the phage clone of interest followed by construction of a full length antibody clone using VH and/or VL sequences (e.g., the Fv sequences), or various CDR sequences from VH and VL sequences, from the phage clone of interest and suitable constant region (e.g., Fc) sequences described in Kabat et al., supra.

Anti-HSA antibodies described herein can also, for example, include chimeric antibodies. A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415.

Anti-HSA antibodies or antigen-binding fragments produced using techniques such as those described herein can be isolated using standard, well known techniques. For example, antibodies or antigen-binding fragments can be suitably separated from, e.g., culture medium, ascites fluid, serum, cell lysate, synthesis reaction material or the like by conventional immunoglobulin purification procedures such as, for example, protein A-Sepharose, hydroxylapatite chromatography, gel electrophoresis, dialysis, or affinity chromatography. As used herein, an "isolated" or "purified" antibody is substantially free of cellular material or other proteins from the cell or tissue source from which the antibody is derived, or substantially free of chemical precursors or other chemicals when chemically synthesized.

In some more specific embodiments, the anti-albumin antibody or antigen binding fragment thereof is an sdAb that binds to HSA. In some embodiments, the sdAb is a $V_H H$ single domain antibody.

In some embodiments, the sdAb binds to HSA with a $K_D$ of between 1-1000 nM. In some embodiments, the sdAb binds to HSA with a $K_D$ of between 1-900 nM. In some embodiments, the sdAb binds to HSA with a $K_D$ of between 1-800 nM. In some embodiments, the sdAb binds to HSA with a $K_D$ of between 1-700 nM. In some embodiments, the sdAb binds to HSA with a $K_D$ of between 1-600 nM. In some embodiments, the sdAb binds to HSA with a $K_D$ of between 1-500 nM. In some embodiments, the sdAb binds to HSA with a $K_D$ of between 1-400 nM. In some embodiments, the sdAb binds to HSA with a $K_D$ of between 1-300 nM. In some embodiments, the sdAb binds to HSA with a $K_D$ of between 1-200 nM. In some embodiments, the sdAb binds to HSA with a $K_D$ of between 1-100 nM. In some embodiments, the sdAb binds to HSA with a $K_D$ of between 1-50 nM. In some embodiments, the sdAb binds to HSA with a $K_D$ of between 1-25 nM. In some embodiments, the sdAb binds to HSA with a $K_D$ of between 0.1-1 nM. In other embodiments, the sdAb binds to HSA with a $K_D$ of between 10-800 nM. In some embodiments, the sdAb binds to HSA with a $K_D$ of between 20-500 nM. In other embodiments, the sdAb binds to HSA with a $K_D$ of between 50-300 nM. In other embodiments, the sdAb binds to HSA with a $K_D$ of between 100-200 nM.

Cancer Antigen Binding Molecules

In some embodiments, the binding molecule that binds to an antigen in the fusion protein provided herein can bind to a caner antigen, and thereby facilitates with directing or delivering IL-21 or its variant to a cancer cell, e.g., a solid tumor cancer cell.

In some embodiments, the binding molecule is an antibody or antigen binding fragment thereof that binds to an antigen expressed on a cancer cell. In some embodiments, the cancer cell is a solid tumor cancer cell.

In some embodiments, the antibodies or antigen binding fragments thereof provided herein can immunospecifically bind to a polypeptide, a polypeptide fragment, or an epitope of an antigen expressed on a cancer cell. In one embodiment, the antibodies bind to a human cancer antigen. In some embodiments, the antibodies or antigen binding fragments thereof provided herein bind to the extracellular domain (ECD) of a cancer antigen. In certain embodiments, the antibodies bind to an epitope in the ECD of a cancer antigen. In some embodiments, the cancer antigen is expressed on a solid tumor cancer cell.

Antibodies that bind to a cancer antigen provided herein can be, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies or their humanized variants, Fab fragments, F(ab') fragments, disulfide-linked Fvs (sdFv), anti-idiotypic (anti-Id) antibodies, and epitope-binding fragments of any of the above.

In particular, antibodies provided herein include immunoglobulin molecules and immunologically active portions of immunoglobulin molecules, i.e., molecules that contain an antigen binding site that immunospecifically binds to a cancer antigen (e.g., a solid tumor cancer antigen). The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody, such as an IgG1 antibody.

Variants and derivatives of antibodies including antibody fragments that retain the ability to specifically bind to an epitope of a cancer antigen are also included in the present disclosure. Exemplary fragments include Fab fragments; Fab'; F(ab')2; a bispecific Fab; a single chain Fab chain comprising a variable region, also known as, a sFv; a disulfide-linked Fv, or dsFv; a camelized VH; a bispecific sFv; a diabody; and a triabody. Derivatives of antibodies also include one or more CDR sequences of an antibody combining site. The CDR sequences may be linked together on a scaffold when two or more CDR sequences are present. In certain embodiments, an antibody provided herein comprises a single-chain Fv ("scFv"). Various techniques have been developed for the production of antibody fragments as briefly described in the above section.

In some embodiments, single variable domain antibodies (sdAbs) that bind to a cancer antigen are preferred. Certain types of organisms, the camelids and cartilaginous fish, possess high affinity single V-like domains mounted on an Fc equivalent domain structure as part of their immune system. (Woolven et al., 1999, Immunogenetics 50: 98-101; and Streltsov et al., 2004, Proc Natl Acad Sci USA. 101: 12444-49). The V-like domains (called VhH in camelids and V-NAR in sharks) typically display long surface loops, which allow penetration of cavities of target antigens. They also stabilize isolated VH domains by masking hydrophobic surface patches.

These VhH and V-NAR domains have been used to engineer sdAbs. Human V domain variants have been designed using selection from phage libraries and other approaches that have resulted in stable, high binding VL- and VH-derived domains. In a specific embodiment, the antibody that binds to a cancer antigen is an sdAb. In one embodiment, the sdAb is a $V_HH$ single domain antibody.

The antibodies provided herein may be from any animal origin including birds and mammals (e.g., human, murine, donkey, sheep, rabbit, goat, guinea pig, camel, horse, or chicken). In certain embodiments, the antibodies provided herein are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In certain embodiments, the antibodies are fully human antibodies, such as fully human antibodies that immunospecifically bind a cancer antigen. Such fully human antibodies would be advantageous over fully mouse (or other full or partial non-human species antibodies), humanized antibodies, or chimeric antibodies to minimize the development of unwanted or unneeded side effects, such as immune responses directed toward non-fully human antibodies when administered to the subject.

The antibodies provided herein may be monospecific, bispecific, trispecific or of greater multispecificity. Multispecific antibodies may be specific for different epitopes of a polypeptide or may be specific for both a polypeptide as well as for a heterologous epitope, such as a heterologous polypeptide or solid support material. In some embodiments, the antibodies provided herein are monospecific for a given epitope of a polypeptide and do not immunospecifically bind to other epitopes.

The antibodies that bind to a cancer antigen provided herein may be monoclonal antibodies or derived from monoclonal antibodies. Monoclonal antibodies may be made using the hybridoma method first described by Kohler et al., 1975, Nature 256:495-97, or may be made by recombinant DNA methods (see, e.g., U.S. Pat. No. 4,816,567). Production of monoclonal antibodies is briefly described in the above section.

Antibodies described herein can also, for example, include chimeric antibodies. Antibodies or antigen-binding fragments produced using techniques such as those described herein can be isolated using standard, well known techniques.

In certain embodiments, the antigen binding molecule in the IL-21 fusion protein provided herein comprises multiple antibodies connected by linkers, each antibody (e.g., sdAb) binding to an antigen. In some embodiments, the antigen binding molecule comprises two antibodies or fragments thereof. In some embodiments, the antigen binding molecule comprises two sdAbs. In some embodiments, the antigen binding molecule comprises two sdAbs each binding to a different epitope of an antigen.

In some more specific embodiments, the antigen binding molecule comprises two sdAbs each binding to a different epitope of MSLN. For example, in some embodiments, one sdAbs targeting aa 296 to aa 359 (N-terminus) of MSLN and one sdAb targeting aa 538 to aa 622 (C-terminus) of MSLN are used in the IL-21 fusion protein provided herein. Certain advantages can be offered by having one or more antibodies targeting specific functional domain of cancer antigen in IL-21 fusion protein. Targeting N-terminus of MSLN with an sdAb disrupts the MSLN-MUC16 interaction and reduces the cancer cell metastasis. Targeting C-terminus of MSLN with an sdAb reduces the shedding of MSLN from cancer cell surface.

In some embodiments, the cancer antigen is mesothelin (MSLN). In some embodiments, the binding molecule is an sdAb that binds to MSLN, such as these described herein.

Anti-Mesothelin (Anti-MSLN) Construct

The present application provides anti-mesothelin constructs that specifically bind to mesothelin. The anti-mesothelin constructs an antibody moiety comprising an anti-MSLN heavy chain variable region (VH). In some embodiments, the anti-MSLN VH binds to an antigen comprising a sequence of SEQ ID NO: 283. In some embodiments, the anti-MSLN VH binds to an antigen comprising a sequence of SEQ ID NO: 284.

In some embodiments, the anti-mesothelin construct comprises an anti-MSLN antibody moiety comprising a single domain anti-mesothelin antibody as described herein.

In some embodiments, the anti-MSLN construct described herein comprises from N-terminal to C-terminal in an order of a) the anti-MSLN antibody moiety, b) a second domain. In some embodiments, the anti-MSLN construct described herein comprises from N-terminal to C-terminal in an order of a) a second domain, b) the anti-MSLN antibody moiety.

In some embodiments, the anti-MSLN construct described herein comprises from N-terminal to C-terminal in an order of a) the anti-MSLN antibody moiety, b) a second domain, c) a third domain. In some embodiments, the anti-MSLN construct described herein comprises from N-terminal to C-terminal in an order of a) a second domain, b) the anti-MSLN antibody moiety, c) a third domain. In some embodiments, the anti-MSLN construct described herein comprises from N-terminal to C-terminal in an order of a) a second domain, b) a third domain, c) the anti-MSLN antibody moiety.

In some embodiments, the second domain or the third domain is a half-life extending domain. In some embodiments, the second domain or the third domain is a cytokine.

In some embodiments, the construct is a fusion protein further comprising a half-life extending domain (such as an Fc domain or an albumin-binding domain). In some embodiments, the construct is a fusion protein further comprising a cytokine (such as IL-21, IL-15). In some embodiments, the construct is a fusion protein further comprising a) a half-life extending domain; and b) a cytokine. Exemplary fusion proteins are described herein.

In some embodiments, the half-life extending domain is fused to N- or C-terminus of the anti-MSLN antibody moiety. In some embodiments, the cytokine is fused to N-terminus of the anti-MSLN antibody moiety or the half-life extending domain. In some embodiments, the half-life extending domain is fused to N- or C-terminus of the cytokine.

In some embodiments, the construct comprises a linker between the anti-MSLN antibody moiety and a second domain or third domain (such as a cytokine). Exemplary linkers are described herein. In some embodiments, the linker comprises an amino acid sequence of any one of SEQ ID NOS: 66-74 and 267-282. In some embodiments, the linker is non-cleavable. In some embodiments, the linker is cleavable.

In some embodiments, the anti-MSLN construct comprises an amino acid sequence of any one of SEQ ID Nos: 123-156 and 285-331, or a variant thereof having at least about 80% (such as about 85%, 90%, 95%, 98%, or 99%) sequence identity to any one of SEQ ID NOs: 123-156 and 285-331.

Single Domain Antibody that Binds to Mesothelin (MSLN)

The present application provides single domain antibodies that specifically bind to mesothelin. In some embodiments, the sdAbs provided herein bind to human MSLN. A few isoforms of human MSLN are listed in Table 3 below (see UniProtKB—Q13421 (MSLN_HUMAN)). The isoform 2 of SEQ ID NO: 264 is the major human MSLN isoform.

TABLE 3

```
Isoform    MALPTARPLL  GSCGTPALGS  LLFLLFSLGW  VQPSRTLAGE  TGQEAAPLDG
1          VLANPPNISS  LSPRQLLGFP  CAEVSGLSTE  RVRELAVALA  QKNVKLSTEQ
           LRCLAHRLSE  PPEDLDALPL  DLLLFLNPDA  FSGPQACTRF  FSRITKANVD
           LLPRGAPERQ  RLLPAALACW  GVRGSLLSEA  DVRALGGLAC  DLPGRFVAES
           AEVLLPRLVS  CPGPLDQDQQ  EAARAALQGG  GPPYGPPSTW  SVSTMDALRG
           LLPVLGQPII  RSIPQGIVAA  WRQRSSRDPS  WRQPERTILR  PRFRREVEKT
           ACPSGKKARE  IDESLIFYKK  WELEACVDAA  LLATQMDRVN  AIPFTYEQLD
           VLKHKLDELY  PQGYPESVIQ  HLGYLFLKMS  PEDIRKWNVT  SLETLKALLE
           VNKGHEMSPQ  APRRPLPQVA  TLIDRFVKGR  GQLDKDTLDT  LTAFYPGYLC
           SLSPEELSSV  PPSSIWAVRP  QDLDTCDPRQ  LDVLYPKARL  AFQNMNGSEY
           FVKIQSFLGG  APTEDLKALS  QQNVSMDLAT  FMKLRTDAVL  PLTVAEVQKL
           LGPHVEGLKA  EERHRPVRDW  ILRQRQDDLD  TLGLGLQGGI  PNGYLVLDLS
           MQEALSGTPC  LLGPGPVLTV  LALLLASTLA  (SEQ ID NO: 263)

Isoform    MALPTARPLL  GSCGTPALGS  LLFLLFSLGW  VQPSRTLAGE  TGQEAAPLDG
2-major    VLANPPNISS  LSPRQLLGFP  CAEVSGLSTE  RVRELAVALA  QKNVKLSTEQ
form       LRCLAHRLSE  PPEDLDALPL  DLLLFLNPDA  FSGPQACTRF  FSRITKANVD
           LLPRGAPERQ  RLLPAALACW  GVRGSLLSEA  DVRALGGLAC  DLPGRFVAES
           AEVLLPRLVS  CPGPLDQDQQ  EAARAALQGG  GPPYGPPSTW  SVSTMDALRG
           LLPVLGQPII  RSIPQGIVAA  WRQRSSRDPS  WRQPERTILR  PRFRREVEKT
           ACPSGKKARE  IDESLIFYKK  WELEACVDAA  LLATQMDRVN  AIPFTYEQLD
           VLKHKLDELY  PQGYPESVIQ  HLGYLFLKMS  PEDIRKWNVT  SLETLKALLE
           VNKGHEMSPQ  VATLIDRFVK  GRGQLDKDTL  DTLTAFYPGY  LCSLSPEELS
           SVPPSSIWAV  RPQDLDTCDP  RQLDVLYPKA  RLAFQNMNGS  EYFVKIQSFL
           GGAPTEDLKA  LSQQNVSMDL  ATFMKLRTDA  VLPLTVAEVQ  KLLGPHVEGL
           KAEERHRPVR  DWILRQRQDD  LDTLGLGLQG  GIPNGYLVLD  LSMQEALSGT
           PCLLGPGPVL  TVLALLLAST  LA (SEQ ID  NO: 264)

Isoform    MALPTARPLL  GSCGTPALGS  LLFLLFSLGW  VQPSRTLAGE  TGQEAAPLDG
3          VLANPPNISS  LSPRQLLGFP  CAEVSGLSTE  RVRELAVALA  QKNVKLSTEQ
           LRCLAHRLSE  PPEDLDALPL  DLLLFLNPDA  FSGPQACTRF  FSRITKANVD
           LLPRGAPERQ  RLLPAALACW  GVRGSLLSEA  DVRALGGLAC  DLPGRFVAES
           AEVLLPRLVS  CPGPLDQDQQ  EAARAALQGG  GPPYGPPSTW  SVSTMDALRG
           LLPVLGQPII  RSIPQGIVAA  WRQRSSRDPS  WRQPERTILR  PRFRREVEKT
           ACPSGKKARE  IDESLIFYKK  WELEACVDAA  LLATQMDRVN  AIPFTYEQLD
           VLKHKLDELY  PQGYPESVIQ  HLGYLFLKMS  PEDIRKWNVT  SLETLKALLE
           VNKGHEMSPQ  VATLIDRFVK  GRGQLDKDTL  DTLTAFYPGY  LCSLSPEELS
           SVPPSSIWAV  RPQDLDTCDP  RQLDVLYPKA  RLAFQNMNGS  EYFVKIQSFL
           GGAPTEDLKA  LSQQNVSMDL  ATFMKLRTDA  VLPLTVAEVQ  KLLGPHVEGL
           KAEERHRPVR  DWILRQRQDD  LDTLGLGLQG  GIPNGYLVLD  LSVQGGRGGQ
           ARAGGRAGGV  EVGALSHPSL  CRGPLGDALP  PRTWTCSHRP  GTAPSLHPGL
           RAPLPC (SEQ  ID NO: 265)
```

TABLE 3-continued

```
Isoform   MALPTARPLL GSCGTPALGS LLFLLFSLGW VQPSRTLAGE TGQAAPLDGV
4         LANPPNISSL SPRQLLGFPC AEVSGLSTER VRELAVALAQ KNVKLSTEQL
          RCLAHRLSEP PEDLDALPLD LLLFLNPDAF SGPQACTRFF SRITKANVDL
          LPRGAPERQR LLPAALACWG VRGSLLSEAD VRALGGLACD LPGRFVAESA
          EVLLPRLVSC PGPLDQDQQE AARAALQGGG PPYGPPSTWS VSTMDALRGL
          LPVLGQPIIR SIPQGIVAAW RQRSSRDPSW RQPERTILRP RFRREVEKTA
          CPSGKKAREI DESLIFYKKW ELEACVDAAL LATQMDRVNA IPFTYEQLDV
          LKHKLDELYP QGYPESVIQH LGYLFLKMSP EDIRKWNVTS LETLKALLEV
          NKGHEMSPQV ATLIDRFVKG RGQLDKDTLD TLTAFYPGYL CSLSPEELSS
          VPPSSIWAVR PQDLDTCDPR QLDVLYPKAR LAFQNMNGSE YFVKIQSFLG
          GAPTEDLKAL SQQNVSMDLA TFMKLRTDAV LPLTVAEVQK LLGPHVEGLK
          AEERHRPVRD WILRQRQDDL DTLGLGLQGG IPNGYLVLDL SMQEALSGTP
          CLLGPGPVLT VLALLLASTL A (SEQ ID NO: 266)
```

The anti-MSLN antibodies (e.g., sdAbs) provided herein can bind to any of the isoforms listed in the table above or any fragments thereof. In some embodiments, the anti-MSLN antibody provided herein binds to SEQ ID NO: 263 or a fragment thereof. In some embodiments, the anti-MSLN antibody provided herein binds to SEQ ID NO: 264 or a fragment thereof. In other embodiments, the anti-MSLN antibody provided herein binds to SEQ ID NO: 265 or a fragment thereof. In yet other embodiments, the anti-MSLN antibody provided herein binds to SEQ ID NO: 266 or a fragment thereof. In some embodiments, the anti-MSLN antibody provided herein binds to SEQ ID NO: 283. In some embodiments, the anti-MSLN antibody provided herein binds to SEQ ID NO: 284.

Thus, in one aspect, provided herein is a single domain antibody (sdAb) that binds to mesothelin (MSLN) comprising the following structure: FR1-CDR1-FR2-CDR2-FR3-CDR3-FR4, wherein the CDR sequences are selected for those in Table 4 and Table 10 below.

More specifically, provided herein is a single domain antibody (sdAb) that binds to mesothelin (MSLN) comprising the following structure: FR1-CDR1-FR2-CDR2-FR3-CDR3-FR4, wherein: (i) CDR1 has an amino acid sequence selected from a group consisting of SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, and SEQ ID NO: 120; (ii) CDR2 has an amino acid sequence selected from a group consisting of SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103, SEQ ID NO: 106, SEQ ID NO: 109, SEQ ID NO: 112, SEQ ID NO: 115, SEQ ID NO: 118, and SEQ ID NO: 121; and/or (iii) CDR3 has an amino acid sequence selected from a group consisting of SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, and SEQ ID NO: 122.

In some embodiments, provided herein is a single domain antibody that binds to mesothelin (anti-MSLN sdAb) comprising a VH comprising CDR1, CDR2, and CDR3 of any one of antibodies anti-MSLN-1, anti-MSLN-2, anti-MSLN-3, anti-MSLN-4, anti-MSLN-5, anti-MSLN-6, anti-MSLN-7, anti-MSLN-8, anti-MSLN-9, anti-MSLN-10, anti-MSLN-11, anti-MSLN-12, anti-MSLN-13, anti-MSLN-14, anti-MSLN-15, anti-MSLN-16, anti-MSLN-17, anti-MSLN-18, anti-MSLN-19, anti-MSLN-20, anti-MSLN-21, anti-MSLN-22, anti-MSLN-23, anti-MSLN-24, anti-MSLN-25, anti-MSLN-26, anti-MSLN-27, anti-MSLN-28, anti-MSLN-29, anti-MSLN-30, anti-MSLN-31, anti-MSLN-32, anti-MSLN-33, and anti-MSLN-34 as set forth in Table 9

In some embodiments, CDR1 is of SEQ ID NO: 12, CDR2 is of SEQ ID NO: 13, and CDR3 is of SEQ ID NO: 14.

In some embodiments, CDR1 is of SEQ ID NO: 15, CDR2 is of SEQ ID NO: 16, and CDR3 is of SEQ ID NO: 17.

In some embodiments, CDR1 is of SEQ ID NO: 18, CDR2 is of SEQ ID NO: 19, and CDR3 is of SEQ ID NO: 20.

In some embodiments, CDR1 is of SEQ ID NO: 21, CDR2 is of SEQ ID NO: 22, and CDR3 is of SEQ ID NO: 23.

In some embodiments, CDR1 is of SEQ ID NO: 24, CDR2 is of SEQ ID NO: 25, and CDR3 is of SEQ ID NO: 26.

In some embodiments, CDR1 is of SEQ ID NO: 27, CDR2 is of SEQ ID NO: 28, and CDR3 is of SEQ ID NO: 29.

In some embodiments, CDR1 is of SEQ ID NO: 30, CDR2 is of SEQ ID NO: 31, and CDR3 is of SEQ ID NO: 32.

In some embodiments, CDR1 is of SEQ ID NO: 33, CDR2 is of SEQ ID NO: 34, and CDR3 is of SEQ ID NO: 35.

In some embodiments, CDR1 is of SEQ ID NO: 36, CDR2 is of SEQ ID NO: 37, and CDR3 is of SEQ ID NO: 38.

In other embodiments, CDR1 is of SEQ ID NO: 39, CDR2 is of SEQ ID NO: 40, and CDR3 is of SEQ ID NO: 41.

In other embodiments, CDR1 is of SEQ ID NO: 42, CDR2 is of SEQ ID NO: 43, and CDR3 is of SEQ ID NO: 44.

In other embodiments, CDR1 is of SEQ ID NO: 45, CDR2 is of SEQ ID NO: 46, and CDR3 is of SEQ ID NO: 47.

In other embodiments, CDR1 is of SEQ ID NO: 48, CDR2 is of SEQ ID NO: 49, and CDR3 is of SEQ ID NO: 50.

In other embodiments, CDR1 is of SEQ ID NO: 51, CDR2 is of SEQ ID NO: 52, and CDR3 is of SEQ ID NO: 53.

In other embodiments, CDR1 is of SEQ ID NO: 54, CDR2 is of SEQ ID NO: 55, and CDR3 is of SEQ ID NO: 56.

In other embodiments, CDR1 is of SEQ ID NO: 57, CDR2 is of SEQ ID NO: 58, and CDR3 is of SEQ ID NO: 59.

In yet other embodiments, CDR1 is of SEQ ID NO: 60, CDR2 is of SEQ ID NO: 61, and CDR3 is of SEQ ID NO: 62.

In yet other embodiments, CDR1 is of SEQ ID NO: 63, CDR2 is of SEQ ID NO: 64, and CDR3 is of SEQ ID NO: 65.

In yet other embodiments, CDR1 is of SEQ ID NO: 75, CDR2 is of SEQ ID NO: 76, and CDR3 is of SEQ ID NO: 77.

In yet other embodiments, CDR1 is of SEQ ID NO: 78, CDR2 is of SEQ ID NO: 79, and CDR3 is of SEQ ID NO: 80.

In yet other embodiments, CDR1 is of SEQ ID NO: 81, CDR2 is of SEQ ID NO: 82, and CDR3 is of SEQ ID NO: 83.

In yet other embodiments, CDR1 is of SEQ ID NO: 84, CDR2 is of SEQ ID NO: 85, and CDR3 is of SEQ ID NO: 86.

In yet other embodiments, CDR1 is of SEQ ID NO: 87, CDR2 is of SEQ ID NO: 88, and CDR3 is of SEQ ID NO: 89.

In yet other embodiments, CDR1 is of SEQ ID NO: 90, CDR2 is of SEQ ID NO: 91, and CDR3 is of SEQ ID NO: 92.

In yet other embodiments, CDR1 is of SEQ ID NO: 93, CDR2 is of SEQ ID NO: 94, and CDR3 is of SEQ ID NO: 95.

In yet other embodiments, CDR1 is of SEQ ID NO: 96, CDR2 is of SEQ ID NO: 97, and CDR3 is of SEQ ID NO: 98.

In yet other embodiments, CDR1 is of SEQ ID NO: 99, CDR2 is of SEQ ID NO: 100, and CDR3 is of SEQ ID NO: 101.

In yet other embodiments, CDR1 is of SEQ ID NO: 102, CDR2 is of SEQ ID NO: 103, and CDR3 is of SEQ ID NO: 104.

In yet other embodiments, CDR1 is of SEQ ID NO: 105, CDR2 is of SEQ ID NO: 106, and CDR3 is of SEQ ID NO: 107.

In yet other embodiments, CDR1 is of SEQ ID NO: 108, CDR2 is of SEQ ID NO: 109, and CDR3 is of SEQ ID NO: 110.

In yet other embodiments, CDR1 is of SEQ ID NO: 111, CDR2 is of SEQ ID NO: 112, and CDR3 is of SEQ ID NO: 113.

In yet other embodiments, CDR1 is of SEQ ID NO: 114, CDR2 is of SEQ ID NO: 115, and CDR3 is of SEQ ID NO: 116.

In yet other embodiments, CDR1 is of SEQ ID NO: 117, CDR2 is of SEQ ID NO: 118, and CDR3 is of SEQ ID NO: 119.

In yet other embodiments, CDR1 is of SEQ ID NO: 120, CDR2 is of SEQ ID NO: 121, and CDR3 is of SEQ ID NO: 122.

TABLE 4

| Regions | Sequences |
|---------|-----------|
| CDR1 | GGTASSYT (SEQ ID NO: 12) |
|  | GRTFSGS (SEQ ID NO: 15) |
|  | GSISSIRH (SEQ ID NO: 18) |
|  | GLTFSSRA (SEQ ID NO: 21) |
|  | GLTFTSHT (SEQ ID NO: 24) |
|  | GRTLESYV (SEQ ID NO: 27) |
|  | GRALSSYA (SEQ ID NO: 30) |
|  | GRAFSGYT (SEQ ID NO: 33) |
|  | GITFPVNA (SEQ ID NO: 36) |
|  | GFTFDNKQ (SEQ ID NO: 39) |
|  | GRTNSTVA (SEQ ID NO: 42) |
|  | GPTYTTET (SEQ ID NO: 45) |
|  | GRTFSPYT (SEQ ID NO: 48) |
|  | GRSFSTYR (SEQ ID NO: 51) |
|  | GRMFSSYA (SEQ ID NO: 54) |
|  | GRRVRTAA (SEQ ID NO: 57) |
|  | GRTISNYA (SEQ ID NO: 60) |
|  | GISDISS (SEQ ID NO: 63) |
|  | GHTFSVYA (SEQ ID NO: 75) |
|  | GRTASSYV (SEQ ID NO: 78) |
|  | GRTETTYN (SEQ ID NO: 81) |
|  | GRTFSHYA (SEQ ID NO: 84) |
|  | GRTWSTYP (SEQ ID NO: 87) |
|  | GRTDSTGI (SEQ ID NO: 90) |
|  | GRSFNTYA (SEQ ID NO: 93) |
|  | GRTISNYA (SEQ ID NO: 96) |
|  | GSLSSINT (SEQ ID NO: 99) |
|  | ERTYSRYA (SEQ ID NO: 102) |
|  | GRTFSSVS (SEQ ID NO: 105) |
|  | GRTFGSYT (SEQ ID NO: 108) |
|  | GGTFIRYA (SEQ ID NO: 111) |
|  | GRTARSYN (SEQ ID NO: 114) |
|  | GRILADTP (SEQ ID NO: 117) |
|  | GRILADTP (SEQ ID NO: 120) |
| CDR2 | ILWSGNTT (SEQ ID NO: 13) |
|  | FNWDGSS (SEQ ID NO: 16) |
|  | VSNDGSA (SEQ ID NO: 19) |
|  | IIHSGDYT (SEQ ID NO: 22) |
|  | ISWSGGNT (SEQ ID NO: 25) |
|  | INWSSGRL (SEQ ID NO: 28) |
|  | ITWNGGRT (SEQ ID NO: 31) |
|  | MTWSGDRT (SEQ ID NO: 34) |
|  | ISAGGTT (SEQ ID NO: 37) |
|  | ISISDGAT (SEQ ID NO: 40) |
|  | IVWSNGYS (SEQ ID NO: 43) |
|  | 1RWRGAHT (SEQ ID NO: 46) |
|  | ITWKSGST (SEQ ID NO: 49) |
|  | ITASGSWT (SEQ ID NO: 52) |
|  | ISYNGGAT (SEQ ID NO: 55) |
|  | ITWRGGER (SEQ ID NO: 58) |
|  | INWNGGGI (SEQ ID NO: 61) |
|  | IGSGGNT (SEQ ID NO: 64) |
|  | INWGDGLT (SEQ ID NO: 76) |
|  | VSRSGVST (SEQ ID NO: 79) |
|  | ISRGATIT (SEQ ID NO: 82) |
|  | ITESPDST (SEQ ID NO: 85) |
|  | 1RWTTGST (SEQ ID NO: 88) |
|  | 1RWSNNYA (SEQ ID NO: 91) |
|  | ITWSGAST (SEQ ID NO: 94) |
|  | VSWTGHGT (SEQ ID NO: 97) |
|  | ISSSGST (SEQ ID NO: 100) |
|  | ISWSGT (SEQ ID NO: 103) |
|  | ADWSGTT (SEQ ID NO: 106) |
|  | ISRSGGST (SEQ ID NO: 109) |
|  | ISQTGGST (SEQ ID NO: 112) |
|  | IISSPRGT (SEQ ID NO: 115) |
|  | ITSGGTT (SEQ ID NO: 118) |
|  | ITSGGTT (SEQ ID NO: 121) |

TABLE 4-continued

| Regions | Sequences |
|---|---|
| CDR3 | ARGGWGTTAEVSNYAY (SEQ ID NO: 14)<br>AGYYHTGGPLLRDNEYRY (SEQ ID NO: 17)<br>NADTWGWPGADY (SEQ ID NO: 20)<br>AADSVNKRGASSYYVRTTEYDY (SEQ ID NO: 23)<br>AADRSSFRSYGGSSRVKVEGEYNY (SEQ ID NO: 26)<br>AAGRY (SEQ ID NO: 29)<br>AADPRGDVYHRDKYNI (SEQ ID NO: 32)<br>ATKLGTYYNSHDLRRPDY (SEQ ID NO: 35)<br>YLQRRIGMLRDY (SEQ ID NO: 38)<br>ATNPTQIMIGTMRCDLESK (SEQ ID NO: 41)<br>ALDIRDSEITVQQKY (SEQ ID NO: 44)<br>AASRSFDYPRREDEYRY (SEQ ID NO: 47)<br>ASTSFAYGLTNSNKYNY (SEQ ID NO: 50)<br>AAAEILTAITTSSDYDY (SEQ ID NO: 53)<br>AARGGHWYSIHDPSNFRA (SEQ ID NO: 56)<br>AAGPWYTNHDTSQGYNY (SEQ ID NO: 59)<br>AAQRAGTWTY (SEQ ID NO: 62)<br>NAAQRIGAGPIVL (SEQ ID NO: 65)<br>AARQRREGWDY (SEQ ID NO: 77)<br>AADGKNFSNRWWSRDEYKY (SEQ ID NO: 80)<br>AASFTNLAVVARDYYY (SEQ ID NO: 83)<br>AAARSTLRWPFRGQGQYDYDY (SEQ ID NO: 86)<br>NAEVRAWYNRRKADY (SEQ ID NO: 89)<br>AAGTGWGFSISDYNY (SEQ ID NO: 92)<br>AASSQYGGAASAPTAYLY (SEQ ID NO: 95)<br>AADGKNFSNRWWSRDEYKY (SEQ ID NO: 98)<br>AAGKGSTWYNGAYK (SEQ ID NO: 101)<br>AYGYYSGAANYRDLASSTYRY (SEQ ID NO: 104)<br>AASDPRRSAYKY (SEQ ID NO: 107)<br>AASNTGGRASASYKY (SEQ ID NO: 110)<br>AVSTVQSKRMLMYGY (SEQ ID NO: 113)<br>AATTSSTYYSDKTYYAY (SEQ ID NO: 116)<br>AANAEGSGSRY (SEQ ID NO: 119)<br>KVMYHAGS (SEQ ID NO: 122) |

In some embodiments, provided herein is a single domain antibody that binds to mesothelin (anti-MSLN sdAb) comprising one or more CDR regions from any one of antibodies anti-MSLN-1, anti-MSLN-2, anti-MSLN-3, anti-MSLN-4, anti-MSLN-5, anti-MSLN-6, anti-MSLN-7, anti-MSLN-8, anti-MSLN-9, anti-MSLN-10, anti-MSLN-11, anti-MSLN-12, anti-MSLN-13, anti-MSLN-14, anti-MSLN-15, anti-MSLN-16, anti-MSLN-17, anti-MSLN-18, anti-MSLN-19, anti-MSLN-20, anti-MSLN-21, anti-MSLN-22, anti-MSLN-23, anti-MSLN-24, anti-MSLN-25, anti-MSLN-26, anti-MSLN-27, anti-MSLN-28, anti-MSLN-29, anti-MSLN-30, anti-MSLN-31, anti-MSLN-32, anti-MSLN-33, and anti-MSLN-34 as set forth in Table 9.

In some embodiments, the anti-MSLN sdAb provided herein has one or more CDR regions from anti-MSLN-1.

In some embodiments, the sdAb has a CDR1 having an amino acid sequence of the CDR1 as set forth in SEQ ID NO: 123. In some embodiments, the sdAb has a CDR2 having an amino acid sequence of the CDR2 as set forth in SEQ ID NO: 123. In other embodiments, the sdAb has a CDR3 having an amino acid sequence of the CDR3 as set forth in SEQ ID NO: 123. In some embodiments, the sdAb has a CDR1 and a CDR2 having amino acid sequences of the CDR1 and the CDR2 as set forth in SEQ ID NO: 123. In some embodiments, the sdAb has a CDR1 and a CDR3 having amino acid sequences of the CDR1 and the CDR3 as set forth in SEQ ID NO: 123. In some embodiments, the sdAb has a CDR2 and a CDR3 having amino acid sequences of the CDR2 and the CDR3 as set forth in SEQ ID NO: 123. In some embodiments, the sdAb has a CDR1, a CDR2, and a CDR3 having amino acid sequences of the CDR1, the CDR2, and the CDR3 as set forth in SEQ ID NO: 123. CDR sequences can be determined according to well-known numbering systems. As described above, CDR regions are well known to those skilled in the art and have been defined by well-known numbering systems. The residues from each of these hypervariable regions or CDRs are noted in Table 1 above. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 12. In some embodiments, the sdAb has a CDR2 of SEQ ID NO: 13. In other embodiments, the sdAb has a CDR3 of SEQ ID NO: 14. In some embodiments, the sdAb has a CDR1 of SEQ ID NO: 12 and a CDR2 of SEQ ID NO: 13. In some embodiments, the sdAb has a CDR1 of SEQ ID NO: 12 and a CDR3 of SEQ ID NO: 14. In some embodiments, the sdAb has a CDR2 of SEQ ID NO: 13 and a CDR3 of SEQ ID NO: 14. In a specific embodiment, the sdAb has a CDR1 of SEQ ID NO: 12, a CDR2 of SEQ ID NO: 13, and a CDR3 of SEQ ID NO: 14.

In some embodiments, the anti-MSLN sdAb provided herein has one or more CDR regions from anti-MSLN-2.

In some embodiments, the sdAb has a CDR1 having an amino acid sequence of the CDR1 as set forth in SEQ ID NO: 124. In some embodiments, the sdAb has a CDR2 having an amino acid sequence of the CDR2 as set forth in SEQ ID NO: 124. In other embodiments, the sdAb has a CDR3 having an amino acid sequence of the CDR3 as set forth in SEQ ID NO: 124. In some embodiments, the sdAb has a CDR1 and a CDR2 having amino acid sequences of the CDR1 and the CDR2 as set forth in SEQ ID NO: 124. In some embodiments, the sdAb has a CDR1 and a CDR3 having amino acid sequences of the CDR1 and the CDR3 as set forth in SEQ ID NO: 124. In some embodiments, the sdAb has a CDR2 and a CDR3 having amino acid sequences of the CDR2 and the CDR3 as set forth in SEQ ID NO: 124. In some embodiments, the sdAb has a CDR1, a CDR2, and a CDR3 having amino acid sequences of the CDR1, the CDR2, and the CDR3 as set forth in SEQ ID NO: 124. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 15. In some embodiments, the sdAb has a CDR2 of SEQ ID NO: 16. In other embodiments, the sdAb has a CDR3 of SEQ ID NO: 17. In some embodiments, the sdAb has a CDR1 of SEQ ID NO: 15 and a CDR2 of SEQ ID NO: 16. In some embodiments, the sdAb has a CDR1 of SEQ ID NO: 15 and a CDR3 of SEQ ID NO: 17. In some embodiments, the sdAb has a CDR2 of SEQ ID NO: 16 and a CDR3 of SEQ ID NO: 17. In a specific embodiment, the sdAb has a CDR1 of SEQ ID NO: 15, a CDR2 of SEQ ID NO: 16, and a CDR3 of SEQ ID NO: 17.

In some embodiments, the anti-MSLN sdAb provided herein has one or more CDR regions from anti-MSLN-3.

In some embodiments, the sdAb has a CDR1 having an amino acid sequence of the CDR1 as set forth in SEQ ID NO: 125. In some embodiments, the sdAb has a CDR2 having an amino acid sequence of the CDR2 as set forth in SEQ ID NO: 125. In other embodiments, the sdAb has a CDR3 having an amino acid sequence of the CDR3 as set forth in SEQ ID NO: 125. In some embodiments, the sdAb has a CDR1 and a CDR2 having amino acid sequences of the CDR1 and the CDR2 as set forth in SEQ ID NO: 125. In some embodiments, the sdAb has a CDR1 and a CDR3 having amino acid sequences of the CDR1 and the CDR3 as set forth in SEQ ID NO: 125. In some embodiments, the sdAb has a CDR2 and a CDR3 having amino acid sequences of the CDR2 and the CDR3 as set forth in SEQ ID NO: 125. In some embodiments, the sdAb has a CDR1, a CDR2, and a CDR3 having amino acid sequences of the CDR1, the CDR2, and the CDR3 as set forth in SEQ ID NO: 125. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 18. In some embodiments, the sdAb has a CDR2 of SEQ ID NO: 19. In other embodiments, the sdAb has a CDR3 of SEQ ID NO: 20. In some embodiments, the sdAb has a CDR1 of SEQ ID NO: 18 and a CDR2 of SEQ ID NO: 19. In some embodiments, the sdAb has a CDR1 of SEQ ID NO: 18 and a CDR3 of SEQ ID NO: 20. In some embodiments, the sdAb has a CDR2 of SEQ ID NO: 19 and a CDR3 of SEQ ID NO: 20. In a specific embodiment, the sdAb has a CDR1 of SEQ ID NO: 18, a CDR2 of SEQ ID NO: 19, and a CDR3 of SEQ ID NO: 20.

In some embodiments, the anti-MSLN sdAb provided herein has one or more CDR regions from anti-MSLN-4.

In some embodiments, the sdAb has a CDR1 having an amino acid sequence of the CDR1 as set forth in SEQ ID NO: 126. In some embodiments, the sdAb has a CDR2 having an amino acid sequence of the CDR2 as set forth in SEQ ID NO: 126. In other embodiments, the sdAb has a CDR3 having an amino acid sequence of the CDR3 as set forth in SEQ ID NO: 126. In some embodiments, the sdAb has a CDR1 and a CDR2 having amino acid sequences of the CDR1 and the CDR2 as set forth in SEQ ID NO: 126. In some embodiments, the sdAb has a CDR1 and a CDR3 having amino acid sequences of the CDR1 and the CDR3 as set forth in SEQ ID NO: 126. In some embodiments, the sdAb has a CDR2 and a CDR3 having amino acid sequences of the CDR2 and the CDR3 as set forth in SEQ ID NO: 126. In some embodiments, the sdAb has a CDR1, a CDR2, and a CDR3 having amino acid sequences of the CDR1, the CDR2, and the CDR3 as set forth in SEQ ID NO: 126. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 21. In some embodiments, the sdAb has a CDR2 of SEQ ID NO: 22. In other embodiments, the sdAb has a CDR3 of SEQ ID NO: 23. In some embodiments, the sdAb has a CDR1 of SEQ ID NO: 21 and a CDR2 of SEQ ID NO: 22. In some embodiments, the sdAb has a CDR1 of SEQ ID NO: 21 and a CDR3 of SEQ ID NO: 23. In some embodiments, the sdAb has a CDR2 of SEQ ID NO: 22 and a CDR3 of SEQ ID NO: 23. In a specific embodiment, the sdAb has a CDR1 of SEQ ID NO: 21, a CDR2 of SEQ ID NO: 22, and a CDR3 of SEQ ID NO: 23.

In some embodiments, the anti-MSLN sdAb provided herein has one or more CDR regions from anti-MSLN-5.

In some embodiments, the sdAb has a CDR1 having an amino acid sequence of the CDR1 as set forth in SEQ ID NO: 127. In some embodiments, the sdAb has a CDR2 having an amino acid sequence of the CDR2 as set forth in SEQ ID NO: 127. In other embodiments, the sdAb has a CDR3 having an amino acid sequence of the CDR3 as set forth in SEQ ID NO: 127. In some embodiments, the sdAb has a CDR1 and a CDR2 having amino acid sequences of the CDR1 and the CDR2 as set forth in SEQ ID NO: 127. In some embodiments, the sdAb has a CDR1 and a CDR3 having amino acid sequences of the CDR1 and the CDR3 as set forth in SEQ ID NO: 127. In some embodiments, the sdAb has a CDR2 and a CDR3 having amino acid sequences of the CDR2 and the CDR3 as set forth in SEQ ID NO: 127. In some embodiments, the sdAb has a CDR1, a CDR2, and a CDR3 having amino acid sequences of the CDR1, the CDR2, and the CDR3 as set forth in SEQ ID NO: 127. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 24. In some embodiments, the sdAb has a CDR2 of SEQ ID NO: 25. In other embodiments, the sdAb has a CDR3 of SEQ ID NO: 26. In some embodiments, the sdAb has a CDR1 of SEQ ID NO: 24 and a CDR2 of SEQ ID NO: 25. In some embodiments, the sdAb has a CDR1 of SEQ ID NO: 24 and a CDR3 of SEQ ID NO: 26. In some embodiments, the sdAb has a CDR2 of SEQ ID NO: 25 and a CDR3 of SEQ ID NO: 26. In a specific embodiment, the sdAb has a CDR1 of SEQ ID NO: 24, a CDR2 of SEQ ID NO: 25, and a CDR3 of SEQ ID NO: 26.

In some embodiments, the anti-MSLN sdAb provided herein has one or more CDR regions from anti-MSLN-6.

In some embodiments, the sdAb has a CDR1 having an amino acid sequence of the CDR1 as set forth in SEQ ID NO: 128. In some embodiments, the sdAb has a CDR2 having an amino acid sequence of the CDR2 as set forth in SEQ ID NO: 128. In other embodiments, the sdAb has a CDR3 having an amino acid sequence of the CDR3 as set forth in SEQ ID NO: 128. In some embodiments, the sdAb has a CDR1 and a CDR2 having amino acid sequences of the CDR1 and the CDR2 as set forth in SEQ ID NO: 128. In some embodiments, the sdAb has a CDR1 and a CDR3 having amino acid sequences of the CDR1 and the CDR3 as set forth in SEQ ID NO: 128. In some embodiments, the sdAb has a CDR2 and a CDR3 having amino acid sequences of the CDR2 and the CDR3 as set forth in SEQ ID NO: 128. In some embodiments, the sdAb has a CDR1, a CDR2, and a CDR3 having amino acid sequences of the CDR1, the CDR2, and the CDR3 as set forth in SEQ ID NO: 128. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 27. In some embodiments, the sdAb has a CDR2 of SEQ ID NO: 28. In other embodiments, the sdAb has a CDR3 of SEQ ID NO: 29. In some embodiments, the sdAb has a CDR1 of SEQ ID NO: 27 and a CDR2 of SEQ ID NO: 28. In some embodiments, the sdAb has a CDR1 of SEQ ID NO: 27 and a CDR3 of SEQ ID NO: 29. In some embodiments, the sdAb has a CDR2 of SEQ ID NO: 28 and a CDR3 of SEQ ID NO: 29. In a specific embodiment, the sdAb has a CDR1 of SEQ ID NO: 27, a CDR2 of SEQ ID NO: 28, and a CDR3 of SEQ ID NO: 29.

In some embodiments, the anti-MSLN sdAb provided herein has one or more CDR regions from anti-MSLN-7.

In some embodiments, the sdAb has a CDR1 having an amino acid sequence of the CDR1 as set forth in SEQ ID NO: 129. In some embodiments, the sdAb has a CDR2 having an amino acid sequence of the CDR2 as set forth in SEQ ID NO: 129. In other embodiments, the sdAb has a CDR3 having an amino acid sequence of the CDR3 as set forth in SEQ ID NO: 129. In some embodiments, the sdAb has a CDR1 and a CDR2 having amino acid sequences of the CDR1 and the CDR2 as set forth in SEQ ID NO: 129. In some embodiments, the sdAb has a CDR1 and a CDR3 having amino acid sequences of the CDR1 and the CDR3 as set forth in SEQ ID NO: 129. In some embodiments, the sdAb has a CDR2 and a CDR3 having amino acid sequences of the CDR2 and the CDR3 as set forth in SEQ ID NO: 129. In some embodiments, the sdAb has a CDR1, a CDR2, and a CDR3 having amino acid sequences of the CDR1, the CDR2, and the CDR3 as set forth in SEQ ID NO: 129. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 30. In some embodiments, the sdAb has a CDR2 of SEQ ID NO: 31. In other embodiments, the sdAb has a CDR3 of SEQ ID NO: 32. In some embodiments, the sdAb has a CDR1 of SEQ ID NO: 30 and a CDR2 of SEQ ID NO: 31. In some embodiments, the sdAb has a CDR1 of SEQ ID NO: 30 and a CDR3 of SEQ ID NO: 32. In some embodiments, the sdAb has a CDR2 of SEQ ID NO: 31 and a CDR3 of SEQ ID NO: 32. In a specific embodiment, the sdAb has a CDR1 of SEQ ID NO: 30, a CDR2 of SEQ ID NO: 31, and a CDR3 of SEQ ID NO: 32.

In some embodiments, the anti-MSLN sdAb provided herein has one or more CDR regions from anti-MSLN-8.

In some embodiments, the sdAb has a CDR1 having an amino acid sequence of the CDR1 as set forth in SEQ ID NO: 130. In some embodiments, the sdAb has a CDR2 having an amino acid sequence of the CDR2 as set forth in SEQ ID NO: 130. In other embodiments, the sdAb has a CDR3 having an amino acid sequence of the CDR3 as set forth in SEQ ID NO: 130. In some embodiments, the sdAb has a CDR1 and a CDR2 having amino acid sequences of the CDR1 and the CDR2 as set forth in SEQ ID NO: 130. In some embodiments, the sdAb has a CDR1 and a CDR3 having amino acid sequences of the CDR1 and the CDR3 as set forth in SEQ ID NO: 130. In some embodiments, the sdAb has a CDR2 and a CDR3 having amino acid sequences of the CDR2 and the CDR3 as set forth in SEQ ID NO: 130. In some embodiments, the sdAb has a CDR1, a CDR2, and a CDR3 having amino acid sequences of the CDR1, the CDR2, and the CDR3 as set forth in SEQ ID NO: 130. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 33. In some embodiments, the sdAb has a CDR2 of SEQ ID NO: 34. In other embodiments, the sdAb has a CDR3 of SEQ ID NO: 35. In some embodiments, the sdAb has a CDR1 of SEQ ID NO: 33 and a CDR2 of SEQ ID NO: 34. In some embodiments, the sdAb has a CDR1 of SEQ ID NO: 33 and a CDR3 of SEQ ID NO: 35. In some embodiments, the sdAb has a CDR2 of SEQ ID NO: 34 and a CDR3 of SEQ ID NO: 35. In a specific embodiment, the sdAb has a CDR1 of SEQ ID NO: 33, a CDR2 of SEQ ID NO: 34, and a CDR3 of SEQ ID NO: 35.

In some embodiments, the anti-MSLN sdAb provided herein has one or more CDR regions from anti-MSLN-9.

In some embodiments, the sdAb has a CDR1 having an amino acid sequence of the CDR1 as set forth in SEQ ID NO: 131. In some embodiments, the sdAb has a CDR2 having an amino acid sequence of the CDR2 as set forth in SEQ ID NO: 131. In other embodiments, the sdAb has a CDR3 having an amino acid sequence of the CDR3 as set forth in SEQ ID NO: 131. In some embodiments, the sdAb has a CDR1 and a CDR2 having amino acid sequences of the CDR1 and the CDR2 as set forth in SEQ ID NO: 131. In some embodiments, the sdAb has a CDR1 and a CDR3 having amino acid sequences of the CDR1 and the CDR3 as set forth in SEQ ID NO: 131. In some embodiments, the sdAb has a CDR2 and a CDR3 having amino acid sequences of the CDR2 and the CDR3 as set forth in SEQ ID NO: 131. In some embodiments, the sdAb has a CDR1, a CDR2, and a CDR3 having amino acid sequences of the CDR1, the CDR2, and the CDR3 as set forth in SEQ ID NO: 131. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 36. In some embodiments, the sdAb has a CDR2 of SEQ ID NO: 37. In other embodiments, the sdAb has a CDR3 of SEQ ID NO: 38. In some embodiments, the sdAb has a CDR1 of SEQ ID NO: 36 and a CDR2 of SEQ ID NO: 37. In some embodiments, the sdAb has a CDR1 of SEQ ID NO: 36 and a CDR3 of SEQ ID NO: 38. In some embodiments, the sdAb has a CDR2 of SEQ ID NO: 37 and a CDR3 of SEQ ID NO: 38. In a specific embodiment, the sdAb has a CDR1 of SEQ ID NO: 36, a CDR2 of SEQ ID NO: 37, and a CDR3 of SEQ ID NO: 38.

In some embodiments, the anti-MSLN sdAb provided herein has one or more CDR regions from anti-MSLN-10.

In some embodiments, the sdAb has a CDR1 having an amino acid sequence of the CDR1 as set forth in SEQ ID NO: 132. In some embodiments, the sdAb has a CDR2 having an amino acid sequence of the CDR2 as set forth in SEQ ID NO: 132. In other embodiments, the sdAb has a CDR3 having an amino acid sequence of the CDR3 as set forth in SEQ ID NO: 132. In some embodiments, the sdAb has a CDR1 and a CDR2 having amino acid sequences of the CDR1 and the CDR2 as set forth in SEQ ID NO: 132. In some embodiments, the sdAb has a CDR1 and a CDR3 having amino acid sequences of the CDR1 and the CDR3 as set forth in SEQ ID NO: 132. In some embodiments, the sdAb has a CDR2 and a CDR3 having amino acid sequences of the CDR2 and the CDR3 as set forth in SEQ ID NO: 132. In some embodiments, the sdAb has a CDR1, a CDR2, and a CDR3 having amino acid sequences of the CDR1, the CDR2, and the CDR3 as set forth in SEQ ID NO: 132. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 39. In some embodiments, the sdAb has a CDR2 of SEQ ID NO: 40. In other embodiments, the sdAb has a CDR3 of SEQ ID NO: 41. In some embodiments, the sdAb has a CDR1 of SEQ ID NO: 39 and a CDR2 of SEQ ID NO: 40. In some embodiments, the sdAb has a CDR1 of SEQ ID NO: 39 and a CDR3 of SEQ ID NO: 41. In some embodiments, the sdAb has a CDR2 of SEQ ID NO: 40 and a CDR3 of SEQ ID NO: 41. In a specific embodiment, the sdAb has a CDR1 of SEQ ID NO: 39, a CDR2 of SEQ ID NO: 40, and a CDR3 of SEQ ID NO: 41.

In some embodiments, the anti-MSLN sdAb provided herein has one or more CDR regions from anti-MSLN-11.

In some embodiments, the sdAb has a CDR1 having an amino acid sequence of the CDR1 as set forth in SEQ ID NO: 133. In some embodiments, the sdAb has a CDR2 having an amino acid sequence of the CDR2 as set forth in SEQ ID NO: 133. In other embodiments, the sdAb has a CDR3 having an amino acid sequence of the CDR3 as set forth in SEQ ID NO: 133. In some embodiments, the sdAb has a CDR1 and a CDR2 having amino acid sequences of the CDR1 and the CDR2 as set forth in SEQ ID NO: 133. In some embodiments, the sdAb has a CDR1 and a CDR3 having amino acid sequences of the CDR1 and the CDR3 as set forth in SEQ ID NO: 133. In some embodiments, the sdAb has a CDR2 and a CDR3 having amino acid sequences of the CDR2 and the CDR3 as set forth in SEQ ID NO: 133. In some embodiments, the sdAb has a CDR1, a CDR2, and a CDR3 having amino acid sequences of the CDR1, the CDR2, and the CDR3 as set forth in SEQ ID NO: 133. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 42. In some embodiments, the sdAb has a CDR2 of SEQ ID NO: 43. In other embodiments, the sdAb has a CDR3 of SEQ ID NO: 44. In some embodiments, the sdAb has a CDR1 of SEQ ID NO: 42 and a CDR2 of SEQ ID NO: 43. In some embodiments, the sdAb has a CDR1 of SEQ ID NO: 42 and a CDR3 of SEQ ID NO: 44. In some embodiments, the sdAb has a CDR2 of SEQ ID NO: 43 and a CDR3 of SEQ ID NO: 44. In a specific embodiment, the sdAb has a CDR1 of SEQ ID NO: 42, a CDR2 of SEQ ID NO: 43, and a CDR3 of SEQ ID NO: 44.

In some embodiments, the anti-MSLN sdAb provided herein has one or more CDR regions from anti-MSLN-12.

In some embodiments, the sdAb has a CDR1 having an amino acid sequence of the CDR1 as set forth in SEQ ID NO: 134. In some embodiments, the sdAb has a CDR2 having an amino acid sequence of the CDR2 as set forth in SEQ ID NO: 134. In other embodiments, the sdAb has a CDR3 having an amino acid sequence of the CDR3 as set forth in SEQ ID NO: 134. In some embodiments, the sdAb has a CDR1 and a CDR2 having amino acid sequences of the CDR1 and the CDR2 as set forth in SEQ ID NO: 134. In some embodiments, the sdAb has a CDR1 and a CDR3 having amino acid sequences of the CDR1 and the CDR3 as set forth in SEQ ID NO: 134. In some embodiments, the sdAb has a CDR2 and a CDR3 having amino acid sequences of the CDR2 and the CDR3 as set forth in SEQ ID NO: 134. In some embodiments, the sdAb has a CDR1, a CDR2, and a CDR3 having amino acid sequences of the CDR1, the CDR2, and the CDR3 as set forth in SEQ ID NO: 134. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 45. In some embodiments, the sdAb has a CDR2 of SEQ ID NO: 46. In other embodiments, the sdAb has a CDR3 of SEQ ID NO: 47. In some embodiments, the sdAb has a CDR1 of SEQ ID NO: 45 and a CDR2 of SEQ ID NO: 46. In some embodiments, the sdAb has a CDR1 of SEQ ID NO: 45 and a CDR3 of SEQ ID NO: 47. In some embodiments, the sdAb has a CDR2 of SEQ ID NO: 46 and a CDR3 of SEQ ID NO: 47. In a specific embodiment, the sdAb has a CDR1 of SEQ ID NO: 45, a CDR2 of SEQ ID NO: 46, and a CDR3 of SEQ ID NO: 47.

In some embodiments, the anti-MSLN sdAb provided herein has one or more CDR regions from anti-MSLN-13.

In some embodiments, the sdAb has a CDR1 having an amino acid sequence of the CDR1 as set forth in SEQ ID NO: 135. In some embodiments, the sdAb has a CDR2 having an amino acid sequence of the CDR2 as set forth in SEQ ID NO: 135. In other embodiments, the sdAb has a CDR3 having an amino acid sequence of the CDR3 as set forth in SEQ ID NO: 135. In some embodiments, the sdAb has a CDR1 and a CDR2 having amino acid sequences of the CDR1 and the CDR2 as set forth in SEQ ID NO: 135. In some embodiments, the sdAb has a CDR1 and a CDR3 having amino acid sequences of the CDR1 and the CDR3 as set forth in SEQ ID NO: 135. In some embodiments, the sdAb has a CDR2 and a CDR3 having amino acid sequences of the CDR2 and the CDR3 as set forth in SEQ ID NO: 135. In some embodiments, the sdAb has a CDR1, a CDR2, and a CDR3 having amino acid sequences of the CDR1, the CDR2, and the CDR3 as set forth in SEQ ID NO: 135. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 48. In some embodiments, the sdAb has a CDR2 of SEQ ID NO: 49. In other embodiments, the sdAb has a CDR3 of SEQ ID NO: 50. In some embodiments, the sdAb has a CDR1 of SEQ ID NO: 48 and a CDR2 of SEQ ID NO: 49. In some embodiments, the sdAb has a CDR1 of SEQ ID NO: 48 and a CDR3 of SEQ ID NO: 50. In some embodiments, the sdAb has a CDR2 of SEQ ID NO: 49 and a CDR3 of SEQ ID NO: 50. In a specific embodiment, the sdAb has a CDR1 of SEQ ID NO: 48, a CDR2 of SEQ ID NO: 49, and a CDR3 of SEQ ID NO: 50.

In some embodiments, the anti-MSLN sdAb provided herein has one or more CDR regions from anti-MSLN-14.

In some embodiments, the sdAb has a CDR1 having an amino acid sequence of the CDR1 as set forth in SEQ ID NO: 136. In some embodiments, the sdAb has a CDR2 having an amino acid sequence of the CDR2 as set forth in SEQ ID NO: 136. In other embodiments, the sdAb has a CDR3 having an amino acid sequence of the CDR3 as set forth in SEQ ID NO: 136. In some embodiments, the sdAb has a CDR1 and a CDR2 having amino acid sequences of the CDR1 and the CDR2 as set forth in SEQ ID NO: 136. In some embodiments, the sdAb has a CDR1 and a CDR3 having amino acid sequences of the CDR1 and the CDR3 as set forth in SEQ ID NO: 136. In some embodiments, the sdAb has a CDR2 and a CDR3 having amino acid sequences of the CDR2 and the CDR3 as set forth in SEQ ID NO: 136. In some embodiments, the sdAb has a CDR1, a CDR2, and a CDR3 having amino acid sequences of the CDR1, the CDR2, and the CDR3 as set forth in SEQ ID NO: 136. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 51. In some embodiments, the sdAb has a CDR2 of SEQ ID NO: 52. In other embodiments, the sdAb has a CDR3 of SEQ ID NO: 53. In some embodiments, the sdAb has a CDR1 of SEQ ID NO: 51 and a CDR2 of SEQ ID NO: 52. In some embodiments, the sdAb has a CDR1 of SEQ ID NO: 51 and a CDR3 of SEQ ID NO: 53. In some embodiments, the sdAb has a CDR2 of SEQ ID NO: 52 and a CDR3 of SEQ ID NO: 53. In a specific embodiment, the sdAb has a CDR1 of SEQ ID NO: 51, a CDR2 of SEQ ID NO: 52, and a CDR3 of SEQ ID NO: 53.

In some embodiments, the anti-MSLN sdAb provided herein has one or more CDR regions from anti-MSLN-15.

In some embodiments, the sdAb has a CDR1 having an amino acid sequence of the CDR1 as set forth in SEQ ID NO: 137. In some embodiments, the sdAb has a CDR2 having an amino acid sequence of the CDR2 as set forth in SEQ ID NO: 137. In other embodiments, the sdAb has a CDR3 having an amino acid sequence of the CDR3 as set forth in SEQ ID NO: 137. In some embodiments, the sdAb has a CDR1 and a CDR2 having amino acid sequences of the CDR1 and the CDR2 as set forth in SEQ ID NO: 137. In some embodiments, the sdAb has a CDR1 and a CDR3 having amino acid sequences of the CDR1 and the CDR3 as set forth in SEQ ID NO: 137. In some embodiments, the sdAb has a CDR2 and a CDR3 having amino acid sequences of the CDR2 and the CDR3 as set forth in SEQ ID NO: 137. In some embodiments, the sdAb has a CDR1, a CDR2, and a CDR3 having amino acid sequences of the CDR1, the CDR2, and the CDR3 as set forth in SEQ ID NO: 137. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 54. In some embodiments, the sdAb has a CDR2 of SEQ ID NO: 55. In other embodiments, the sdAb has a CDR3 of SEQ ID NO: 56. In some embodiments, the sdAb has a CDR1 of SEQ ID NO: 54 and a CDR2 of SEQ ID NO: 55. In some embodiments, the sdAb has a CDR1 of SEQ ID NO: 54 and a CDR3 of SEQ ID NO: 56. In some embodiments, the sdAb has a CDR2 of SEQ ID NO: 55 and a CDR3 of SEQ ID NO: 56. In a specific embodiment, the sdAb has a CDR1 of SEQ ID NO: 54, a CDR2 of SEQ ID NO: 55, and a CDR3 of SEQ ID NO: 56.

In some embodiments, the anti-MSLN sdAb provided herein has one or more CDR regions from anti-MSLN-16.

In some embodiments, the sdAb has a CDR1 having an amino acid sequence of the CDR1 as set forth in SEQ ID NO: 138. In some embodiments, the sdAb has a CDR2 having an amino acid sequence of the CDR2 as set forth in SEQ ID NO: 138. In other embodiments, the sdAb has a CDR3 having an amino acid sequence of the CDR3 as set forth in SEQ ID NO: 138. In some embodiments, the sdAb has a CDR1 and a CDR2 having amino acid sequences of the CDR1 and the CDR2 as set forth in SEQ ID NO: 138. In some embodiments, the sdAb has a CDR1 and a CDR3 having amino acid sequences of the CDR1 and the CDR3 as set forth in SEQ ID NO: 138. In some embodiments, the sdAb has a CDR2 and a CDR3 having amino acid sequences of the CDR2 and the CDR3 as set forth in SEQ ID NO: 138. In some embodiments, the sdAb has a CDR1, a CDR2, and a CDR3 having amino acid sequences of the CDR1, the CDR2, and the CDR3 as set forth in SEQ ID NO: 138. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 57. In some embodiments, the sdAb has a CDR2 of SEQ ID NO: 58. In other embodiments, the sdAb has a CDR3 of SEQ ID NO: 59. In some embodiments, the sdAb has a CDR1 of SEQ ID NO: 57 and a CDR2 of SEQ ID NO: 58. In some embodiments, the sdAb has a CDR1 of SEQ ID NO: 57 and a CDR3 of SEQ ID NO: 59. In some embodiments, the sdAb has a CDR2 of SEQ ID NO: 58 and a CDR3 of SEQ ID NO: 59. In a specific embodiment, the sdAb has a CDR1 of SEQ ID NO: 57, a CDR2 of SEQ ID NO: 58, and a CDR3 of SEQ ID NO: 59.

In some embodiments, the anti-MSLN sdAb provided herein has one or more CDR regions from anti-MSLN-17.

In some embodiments, the sdAb has a CDR1 having an amino acid sequence of the CDR1 as set forth in SEQ ID NO: 139. In some embodiments, the sdAb has a CDR2 having an amino acid sequence of the CDR2 as set forth in SEQ ID NO: 139. In other embodiments, the sdAb has a CDR3 having an amino acid sequence of the CDR3 as set forth in SEQ ID NO: 139. In some embodiments, the sdAb has a CDR1 and a CDR2 having amino acid sequences of the CDR1 and the CDR2 as set forth in SEQ ID NO: 139. In some embodiments, the sdAb has a CDR1 and a CDR3 having amino acid sequences of the CDR1 and the CDR3 as set forth in SEQ ID NO: 139. In some embodiments, the sdAb has a CDR2 and a CDR3 having amino acid sequences of the CDR2 and the CDR3 as set forth in SEQ ID NO: 139. In some embodiments, the sdAb has a CDR1, a CDR2, and a CDR3 having amino acid sequences of the CDR1, the CDR2, and the CDR3 as set forth in SEQ ID NO: 139. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 60. In some embodiments, the sdAb has a CDR2 of SEQ ID NO: 61. In other embodiments, the sdAb has a CDR3 of SEQ ID NO: 62. In some embodiments, the sdAb has a CDR1 of SEQ ID NO: 60 and a CDR2 of SEQ ID NO: 61. In some embodiments, the sdAb has a CDR1 of SEQ ID NO: 60 and a CDR3 of SEQ ID NO: 62. In some embodiments, the sdAb has a CDR2 of SEQ ID NO: 61 and a CDR3 of SEQ ID NO: 62. In a specific embodiment, the sdAb has a CDR1 of SEQ ID NO: 60, a CDR2 of SEQ ID NO: 61, and a CDR3 of SEQ ID NO: 62.

In some embodiments, the anti-MSLN sdAb provided herein has one or more CDR regions from anti-MSLN-18.

In some embodiments, the sdAb has a CDR1 having an amino acid sequence of the CDR1 as set forth in SEQ ID NO: 140. In some embodiments, the sdAb has a CDR2 having an amino acid sequence of the CDR2 as set forth in SEQ ID NO: 140. In other embodiments, the sdAb has a CDR3 having an amino acid sequence of the CDR3 as set forth in SEQ ID NO: 140. In some embodiments, the sdAb has a CDR1 and a CDR2 having amino acid sequences of the CDR1 and the CDR2 as set forth in SEQ ID NO: 140. In some embodiments, the sdAb has a CDR1 and a CDR3 having amino acid sequences of the CDR1 and the CDR3 as set forth in SEQ ID NO: 140. In some embodiments, the sdAb has a CDR2 and a CDR3 having amino acid sequences of the CDR2 and the CDR3 as set forth in SEQ ID NO: 140. In some embodiments, the sdAb has a CDR1, a CDR2, and a CDR3 having amino acid sequences of the CDR1, the CDR2, and the CDR3 as set forth in SEQ ID NO: 140. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 63. In some embodiments, the sdAb has a CDR2 of SEQ ID NO: 64. In other embodiments, the sdAb has a CDR3 of SEQ ID NO: 65. In some embodiments, the sdAb has a CDR1 of SEQ ID NO: 63 and a CDR2 of SEQ ID NO: 64. In some embodiments, the sdAb has a CDR1 of SEQ ID NO: 63 and a CDR3 of SEQ ID NO: 65. In some embodiments, the sdAb has a CDR2 of SEQ ID NO: 64 and a CDR3 of SEQ ID NO: 65. In a specific embodiment, the sdAb has a CDR1 of SEQ ID NO: 63, a CDR2 of SEQ ID NO: 64, and a CDR3 of SEQ ID NO: 65.

In some embodiments, the anti-MSLN sdAb provided herein has one or more CDR regions from anti-MSLN-19.

In some embodiments, the sdAb has a CDR1 having an amino acid sequence of the CDR1 as set forth in SEQ ID NO: 141. In some embodiments, the sdAb has a CDR2 having an amino acid sequence of the CDR2 as set forth in SEQ ID NO: 141. In other embodiments, the sdAb has a CDR3 having an amino acid sequence of the CDR3 as set forth in SEQ ID NO: 141. In some embodiments, the sdAb has a CDR1 and a CDR2 having amino acid sequences of the CDR1 and the CDR2 as set forth in SEQ ID NO: 141. In some embodiments, the sdAb has a CDR1 and a CDR3 having amino acid sequences of the CDR1 and the CDR3 as set forth in SEQ ID NO: 141. In some embodiments, the sdAb has a CDR2 and a CDR3 having amino acid sequences of the CDR2 and the CDR3 as set forth in SEQ ID NO: 141. In some embodiments, the sdAb has a CDR1, a CDR2, and a CDR3 having amino acid sequences of the CDR1, the CDR2, and the CDR3 as set forth in SEQ ID NO: 141. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 75. In some embodiments, the sdAb has a CDR2 of SEQ ID NO: 76. In other embodiments, the sdAb has a CDR3 of SEQ ID NO: 77. In some embodiments, the sdAb has a CDR1 of SEQ ID NO: 75 and a CDR2 of SEQ ID NO: 76. In some embodiments, the sdAb has a CDR1 of SEQ ID NO: 75 and a CDR3 of SEQ ID NO: 77. In some embodiments, the sdAb has a CDR2 of SEQ ID NO: 76 and a CDR3 of SEQ ID NO: 77. In a specific embodiment, the sdAb has a CDR1 of SEQ ID NO: 75, a CDR2 of SEQ ID NO: 76, and a CDR3 of SEQ ID NO: 77.

In some embodiments, the anti-MSLN sdAb provided herein has one or more CDR regions from anti-MSLN-20.

In some embodiments, the sdAb has a CDR1 having an amino acid sequence of the CDR1 as set forth in SEQ ID NO: 142. In some embodiments, the sdAb has a CDR2 having an amino acid sequence of the CDR2 as set forth in SEQ ID NO: 142. In other embodiments, the sdAb has a CDR3 having an amino acid sequence of the CDR3 as set forth in SEQ ID NO: 142. In some embodiments, the sdAb has a CDR1 and a CDR2 having amino acid sequences of the CDR1 and the CDR2 as set forth in SEQ ID NO: 142. In some embodiments, the sdAb has a CDR1 and a CDR3 having amino acid sequences of the CDR1 and the CDR3 as set forth in SEQ ID NO: 142. In some embodiments, the sdAb has a CDR2 and a CDR3 having amino acid sequences of the CDR2 and the CDR3 as set forth in SEQ ID NO: 142. In some embodiments, the sdAb has a CDR1, a CDR2, and a CDR3 having amino acid sequences of the CDR1, the CDR2, and the CDR3 as set forth in SEQ ID NO: 142. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 78. In some embodiments, the sdAb has a CDR2 of SEQ ID NO: 79. In other embodiments, the sdAb has a CDR3 of SEQ ID NO: 80. In some embodiments, the sdAb has a CDR1 of SEQ ID NO: 78 and a CDR2 of SEQ ID NO: 79. In some embodiments, the sdAb has a CDR1 of SEQ ID NO: 78 and a CDR3 of SEQ ID NO: 80. In some embodiments, the sdAb has a CDR2 of SEQ ID NO: 79 and a CDR3 of SEQ ID NO: 80. In a specific embodiment, the sdAb has a CDR1 of SEQ ID NO: 78, a CDR2 of SEQ ID NO: 79, and a CDR3 of SEQ ID NO: 80.

In some embodiments, the anti-MSLN sdAb provided herein has one or more CDR regions from anti-MSLN-21.

In some embodiments, the sdAb has a CDR1 having an amino acid sequence of the CDR1 as set forth in SEQ ID NO: 143. In some embodiments, the sdAb has a CDR2 having an amino acid sequence of the CDR2 as set forth in SEQ ID NO: 143. In other embodiments, the sdAb has a CDR3 having an amino acid sequence of the CDR3 as set forth in SEQ ID NO: 143. In some embodiments, the sdAb has a CDR1 and a CDR2 having amino acid sequences of the CDR1 and the CDR2 as set forth in SEQ ID NO: 143. In some embodiments, the sdAb has a CDR1 and a CDR3 having amino acid sequences of the CDR1 and the CDR3 as set forth in SEQ ID NO: 143. In some embodiments, the sdAb has a CDR2 and a CDR3 having amino acid sequences of the CDR2 and the CDR3 as set forth in SEQ ID NO: 143. In some embodiments, the sdAb has a CDR1, a CDR2, and a CDR3 having amino acid sequences of the CDR1, the CDR2, and the CDR3 as set forth in SEQ ID NO: 143. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 81. In some embodiments, the sdAb has a CDR2 of SEQ ID NO: 82. In other embodiments, the sdAb has a CDR3 of SEQ ID NO: 83. In some embodiments, the sdAb has a CDR1 of SEQ ID NO: 81 and a CDR2 of SEQ ID NO: 82. In some embodiments, the sdAb has a CDR1 of SEQ ID NO: 81 and a CDR3 of SEQ ID NO: 83. In some embodiments, the sdAb has a CDR2 of SEQ ID NO: 82 and a CDR3 of SEQ ID NO: 83. In a specific embodiment, the sdAb has a CDR1 of SEQ ID NO: 81, a CDR2 of SEQ ID NO: 82, and a CDR3 of SEQ ID NO: 83.

In some embodiments, the anti-MSLN sdAb provided herein has one or more CDR regions from anti-MSLN-22.

In some embodiments, the sdAb has a CDR1 having an amino acid sequence of the CDR1 as set forth in SEQ ID NO: 144. In some embodiments, the sdAb has a CDR2 having an amino acid sequence of the CDR2 as set forth in SEQ ID NO: 144. In other embodiments, the sdAb has a CDR3 having an amino acid sequence of the CDR3 as set forth in SEQ ID NO: 144. In some embodiments, the sdAb has a CDR1 and a CDR2 having amino acid sequences of the CDR1 and the CDR2 as set forth in SEQ ID NO: 144. In some embodiments, the sdAb has a CDR1 and a CDR3 having amino acid sequences of the CDR1 and the CDR3 as set forth in SEQ ID NO: 144. In some embodiments, the sdAb has a CDR2 and a CDR3 having amino acid sequences of the CDR2 and the CDR3 as set forth in SEQ ID NO: 144. In some embodiments, the sdAb has a CDR1, a CDR2, and a CDR3 having amino acid sequences of the CDR1, the CDR2, and the CDR3 as set forth in SEQ ID NO: 144. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 84. In some embodiments, the sdAb has a CDR2 of SEQ ID NO: 85. In other embodiments, the sdAb has a CDR3 of SEQ ID NO: 86. In some embodiments, the sdAb has a CDR1 of SEQ ID NO: 84 and a CDR2 of SEQ ID NO: 85. In some embodiments, the sdAb has a CDR1 of SEQ ID NO: 84 and a CDR3 of SEQ ID NO: 86. In some embodiments, the sdAb has a CDR2 of SEQ ID NO: 85 and a CDR3 of SEQ ID NO: 86. In a specific embodiment, the sdAb has a CDR1 of SEQ ID NO: 84, a CDR2 of SEQ ID NO: 85, and a CDR3 of SEQ ID NO: 86.

In some embodiments, the anti-MSLN sdAb provided herein has one or more CDR regions from anti-MSLN-23.

In some embodiments, the sdAb has a CDR1 having an amino acid sequence of the CDR1 as set forth in SEQ ID NO: 145. In some embodiments, the sdAb has a CDR2 having an amino acid sequence of the CDR2 as set forth in SEQ ID NO: 145. In other embodiments, the sdAb has a CDR3 having an amino acid sequence of the CDR3 as set forth in SEQ ID NO: 145. In some embodiments, the sdAb has a CDR1 and a CDR2 having amino acid sequences of the CDR1 and the CDR2 as set forth in SEQ ID NO: 145. In some embodiments, the sdAb has a CDR1 and a CDR3 having amino acid sequences of the CDR1 and the CDR3 as set forth in SEQ ID NO: 145. In some embodiments, the sdAb has a CDR2 and a CDR3 having amino acid sequences of the CDR2 and the CDR3 as set forth in SEQ ID NO: 145. In some embodiments, the sdAb has a CDR1, a CDR2, and a CDR3 having amino acid sequences of the CDR1, the CDR2, and the CDR3 as set forth in SEQ ID NO: 145. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 87. In some embodiments, the sdAb has a CDR2 of SEQ ID NO: 88. In other embodiments, the sdAb has a CDR3 of SEQ ID NO: 89. In some embodiments, the sdAb has a CDR1 of SEQ ID NO: 87 and a CDR2 of SEQ ID NO: 88. In some embodiments, the sdAb has a CDR1 of SEQ ID NO: 87 and a CDR3 of SEQ ID NO: 89. In some embodiments, the sdAb has a CDR2 of SEQ ID NO: 88 and a CDR3 of SEQ ID NO: 89. In a specific embodiment, the sdAb has a CDR1 of SEQ ID NO: 87, a CDR2 of SEQ ID NO: 88, and a CDR3 of SEQ ID NO: 89.

In some embodiments, the anti-MSLN sdAb provided herein has one or more CDR regions from anti-MSLN-24.

In some embodiments, the sdAb has a CDR1 having an amino acid sequence of the CDR1 as set forth in SEQ ID NO: 146. In some embodiments, the sdAb has a CDR2 having an amino acid sequence of the CDR2 as set forth in SEQ ID NO: 146. In other embodiments, the sdAb has a CDR3 having an amino acid sequence of the CDR3 as set forth in SEQ ID NO: 146. In some embodiments, the sdAb has a CDR1 and a CDR2 having amino acid sequences of the CDR1 and the CDR2 as set forth in SEQ ID NO: 146. In some embodiments, the sdAb has a CDR1 and a CDR3 having amino acid sequences of the CDR1 and the CDR3 as set forth in SEQ ID NO: 146. In some embodiments, the sdAb has a CDR2 and a CDR3 having amino acid sequences of the CDR2 and the CDR3 as set forth in SEQ ID NO: 146. In some embodiments, the sdAb has a CDR1, a CDR2, and a CDR3 having amino acid sequences of the CDR1, the CDR2, and the CDR3 as set forth in SEQ ID NO: 146. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 90. In some embodiments, the sdAb has a CDR2 of SEQ ID NO: 91. In other embodiments, the sdAb has a CDR3 of SEQ ID NO: 92. In some embodiments, the sdAb has a CDR1 of SEQ ID NO: 90 and a CDR2 of SEQ ID NO: 91. In some embodiments, the sdAb has a CDR1 of SEQ ID NO: 90 and a CDR3 of SEQ ID NO: 92. In some embodiments, the sdAb has a CDR2 of SEQ ID NO: 91 and a CDR3 of SEQ ID NO: 92. In a specific embodiment, the sdAb has a CDR1 of SEQ ID NO: 90, a CDR2 of SEQ ID NO: 91, and a CDR3 of SEQ ID NO: 92.

In some embodiments, the anti-MSLN sdAb provided herein has one or more CDR regions from anti-MSLN-25.

In some embodiments, the sdAb has a CDR1 having an amino acid sequence of the CDR1 as set forth in SEQ ID NO: 147. In some embodiments, the sdAb has a CDR2 having an amino acid sequence of the CDR2 as set forth in SEQ ID NO: 147. In other embodiments, the sdAb has a CDR3 having an amino acid sequence of the CDR3 as set forth in SEQ ID NO: 147. In some embodiments, the sdAb has a CDR1 and a CDR2 having amino acid sequences of the CDR1 and the CDR2 as set forth in SEQ ID NO: 147. In some embodiments, the sdAb has a CDR1 and a CDR3 having amino acid sequences of the CDR1 and the CDR3 as set forth in SEQ ID NO: 147. In some embodiments, the sdAb has a CDR2 and a CDR3 having amino acid sequences of the CDR2 and the CDR3 as set forth in SEQ ID NO: 147. In some embodiments, the sdAb has a CDR1, a CDR2, and a CDR3 having amino acid sequences of the CDR1, the CDR2, and the CDR3 as set forth in SEQ ID NO: 147. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 93. In some embodiments, the sdAb has a CDR2 of SEQ ID NO: 94. In other embodiments, the sdAb has a CDR3 of SEQ ID NO: 95. In some embodiments, the sdAb has a CDR1 of SEQ ID NO: 93 and a CDR2 of SEQ ID NO: 94. In some embodiments, the sdAb has a CDR1 of SEQ ID NO: 93 and a CDR3 of SEQ ID NO: 95. In some embodiments, the sdAb has a CDR2 of SEQ ID NO: 94 and a CDR3 of SEQ ID NO: 95. In a specific embodiment, the sdAb has a CDR1 of SEQ ID NO: 93, a CDR2 of SEQ ID NO: 94, and a CDR3 of SEQ ID NO: 95.

In some embodiments, the anti-MSLN sdAb provided herein has one or more CDR regions from anti-MSLN-26.

In some embodiments, the sdAb has a CDR1 having an amino acid sequence of the CDR1 as set forth in SEQ ID NO: 148. In some embodiments, the sdAb has a CDR2 having an amino acid sequence of the CDR2 as set forth in SEQ ID NO: 148. In other embodiments, the sdAb has a CDR3 having an amino acid sequence of the CDR3 as set forth in SEQ ID NO: 148. In some embodiments, the sdAb has a CDR1 and a CDR2 having amino acid sequences of the CDR1 and the CDR2 as set forth in SEQ ID NO: 148. In some embodiments, the sdAb has a CDR1 and a CDR3 having amino acid sequences of the CDR1 and the CDR3 as set forth in SEQ ID NO: 148. In some embodiments, the sdAb has a CDR2 and a CDR3 having amino acid sequences of the CDR2 and the CDR3 as set forth in SEQ ID NO: 148. In some embodiments, the sdAb has a CDR1, a CDR2, and a CDR3 having amino acid sequences of the CDR1, the CDR2, and the CDR3 as set forth in SEQ ID NO: 148. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 96. In some embodiments, the sdAb has a CDR2 of SEQ ID NO: 97. In other embodiments, the sdAb has a CDR3 of SEQ ID NO: 98. In some embodiments, the sdAb has a CDR1 of SEQ ID NO: 96 and a CDR2 of SEQ ID NO: 97. In some embodiments, the sdAb has a CDR1 of SEQ ID NO: 96 and a CDR3 of SEQ ID NO: 98. In some embodiments, the sdAb has a CDR2 of SEQ ID NO: 97 and a CDR3 of SEQ ID NO: 98. In a specific embodiment, the sdAb has a CDR1 of SEQ ID NO: 96, a CDR2 of SEQ ID NO: 97, and a CDR3 of SEQ ID NO: 98.

In some embodiments, the anti-MSLN sdAb provided herein has one or more CDR regions from anti-MSLN-27.

In some embodiments, the sdAb has a CDR1 having an amino acid sequence of the CDR1 as set forth in SEQ ID NO: 149. In some embodiments, the sdAb has a CDR2 having an amino acid sequence of the CDR2 as set forth in SEQ ID NO: 149. In other embodiments, the sdAb has a CDR3 having an amino acid sequence of the CDR3 as set forth in SEQ ID NO: 149. In some embodiments, the sdAb has a CDR1 and a CDR2 having amino acid sequences of the CDR1 and the CDR2 as set forth in SEQ ID NO: 149. In some embodiments, the sdAb has a CDR1 and a CDR3 having amino acid sequences of the CDR1 and the CDR3 as set forth in SEQ ID NO: 149. In some embodiments, the sdAb has a CDR2 and a CDR3 having amino acid sequences of the CDR2 and the CDR3 as set forth in SEQ ID NO: 149. In some embodiments, the sdAb has a CDR1, a CDR2, and a CDR3 having amino acid sequences of the CDR1, the CDR2, and the CDR3 as set forth in SEQ ID NO: 149. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 99. In some embodiments, the sdAb has a CDR2 of SEQ ID NO: 100. In other embodiments, the sdAb has a CDR3 of SEQ ID NO: 101. In some embodiments, the sdAb has a CDR1 of SEQ ID NO: 99 and a CDR2 of SEQ ID NO: 100. In some embodiments, the sdAb has a CDR1 of SEQ ID NO: 99 and a CDR3 of SEQ ID NO: 101. In some embodiments, the sdAb has a CDR2 of SEQ ID NO: 100 and a CDR3 of SEQ ID NO: 101. In a specific embodiment, the sdAb has a CDR1 of SEQ ID NO: 99, a CDR2 of SEQ ID NO: 100, and a CDR3 of SEQ ID NO: 101.

In some embodiments, the anti-MSLN sdAb provided herein has one or more CDR regions from anti-MSLN-28.

In some embodiments, the sdAb has a CDR1 having an amino acid sequence of the CDR1 as set forth in SEQ ID NO: 150. In some embodiments, the sdAb has a CDR2 having an amino acid sequence of the CDR2 as set forth in SEQ ID NO: 150. In other embodiments, the sdAb has a CDR3 having an amino acid sequence of the CDR3 as set forth in SEQ ID NO: 150. In some embodiments, the sdAb has a CDR1 and a CDR2 having amino acid sequences of the CDR1 and the CDR2 as set forth in SEQ ID NO: 150. In some embodiments, the sdAb has a CDR1 and a CDR3 having amino acid sequences of the CDR1 and the CDR3 as set forth in SEQ ID NO: 150. In some embodiments, the sdAb has a CDR2 and a CDR3 having amino acid sequences of the CDR2 and the CDR3 as set forth in SEQ ID NO: 150. In some embodiments, the sdAb has a CDR1, a CDR2, and a CDR3 having amino acid sequences of the CDR1, the CDR2, and the CDR3 as set forth in SEQ ID NO: 150. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 102. In some embodiments, the sdAb has a CDR2 of SEQ ID NO: 103. In other embodiments, the sdAb has a CDR3 of SEQ ID NO: 104. In some embodiments, the sdAb has a CDR1 of SEQ ID NO: 102 and a CDR2 of SEQ ID NO: 103. In some embodiments, the sdAb has a CDR1 of SEQ ID NO: 102 and a CDR3 of SEQ ID NO: 104. In some embodiments, the sdAb has a CDR2 of SEQ ID NO: 103 and a CDR3 of SEQ ID NO: 104. In a specific embodiment, the sdAb has a CDR1 of SEQ ID NO: 102, a CDR2 of SEQ ID NO: 103, and a CDR3 of SEQ ID NO: 104.

In some embodiments, the anti-MSLN sdAb provided herein has one or more CDR regions from anti-MSLN-29.

In some embodiments, the sdAb has a CDR1 having an amino acid sequence of the CDR1 as set forth in SEQ ID NO: 151. In some embodiments, the sdAb has a CDR2 having an amino acid sequence of the CDR2 as set forth in SEQ ID NO: 151. In other embodiments, the sdAb has a CDR3 having an amino acid sequence of the CDR3 as set forth in SEQ ID NO: 151. In some embodiments, the sdAb has a CDR1 and a CDR2 having amino acid sequences of the CDR1 and the CDR2 as set forth in SEQ ID NO: 151. In some embodiments, the sdAb has a CDR1 and a CDR3 having amino acid sequences of the CDR1 and the CDR3 as set forth in SEQ ID NO: 151. In some embodiments, the sdAb has a CDR2 and a CDR3 having amino acid sequences of the CDR2 and the CDR3 as set forth in SEQ ID NO: 151. In some embodiments, the sdAb has a CDR1, a CDR2, and a CDR3 having amino acid sequences of the CDR1, the CDR2, and the CDR3 as set forth in SEQ ID NO: 151. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 105. In some embodiments, the sdAb has a CDR2 of SEQ ID NO: 106. In other embodiments, the sdAb has a CDR3 of SEQ ID NO: 107. In some embodiments, the sdAb has a CDR1 of SEQ ID NO: 105 and a CDR2 of SEQ ID NO: 106. In some embodiments, the sdAb has a CDR1 of SEQ ID NO: 105 and a CDR3 of SEQ ID NO: 107. In some embodiments, the sdAb has a CDR2 of SEQ ID NO: 106 and a CDR3 of SEQ ID NO: 107. In a specific embodiment, the sdAb has a CDR1 of SEQ ID NO: 105, a CDR2 of SEQ ID NO: 106, and a CDR3 of SEQ ID NO: 107.

In some embodiments, the anti-MSLN sdAb provided herein has one or more CDR regions from anti-MSLN-30.

In some embodiments, the sdAb has a CDR1 having an amino acid sequence of the CDR1 as set forth in SEQ ID NO: 152. In some embodiments, the sdAb has a CDR2 having an amino acid sequence of the CDR2 as set forth in SEQ ID NO: 152. In other embodiments, the sdAb has a CDR3 having an amino acid sequence of the CDR3 as set forth in SEQ ID NO: 152. In some embodiments, the sdAb has a CDR1 and a CDR2 having amino acid sequences of the CDR1 and the CDR2 as set forth in SEQ ID NO: 152. In some embodiments, the sdAb has a CDR1 and a CDR3 having amino acid sequences of the CDR1 and the CDR3 as set forth in SEQ ID NO: 152. In some embodiments, the sdAb has a CDR2 and a CDR3 having amino acid sequences of the CDR2 and the CDR3 as set forth in SEQ ID NO: 152. In some embodiments, the sdAb has a CDR1, a CDR2, and a CDR3 having amino acid sequences of the CDR1, the CDR2, and the CDR3 as set forth in SEQ ID NO: 152. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 108. In some embodiments, the sdAb has a CDR2 of SEQ ID NO: 109. In other embodiments, the sdAb has a CDR3 of SEQ ID NO: 110. In some embodiments, the sdAb has a CDR1 of SEQ ID NO: 108 and a CDR2 of SEQ ID NO: 109. In some embodiments, the sdAb has a CDR1 of SEQ ID NO: 108 and a CDR3 of SEQ ID NO: 110. In some embodiments, the sdAb has a CDR2 of SEQ ID NO: 109 and a CDR3 of SEQ ID NO: 110. In a specific embodiment, the sdAb has a CDR1 of SEQ ID NO: 108, a CDR2 of SEQ ID NO: 109, and a CDR3 of SEQ ID NO: 110.

In some embodiments, the anti-MSLN sdAb provided herein has one or more CDR regions from anti-MSLN-31.

In some embodiments, the sdAb has a CDR1 having an amino acid sequence of the CDR1 as set forth in SEQ ID NO: 153. In some embodiments, the sdAb has a CDR2 having an amino acid sequence of the CDR2 as set forth in SEQ ID NO: 153. In other embodiments, the sdAb has a CDR3 having an amino acid sequence of the CDR3 as set forth in SEQ ID NO: 153. In some embodiments, the sdAb has a CDR1 and a CDR2 having amino acid sequences of the CDR1 and the CDR2 as set forth in SEQ ID NO: 153. In some embodiments, the sdAb has a CDR1 and a CDR3 having amino acid sequences of the CDR1 and the CDR3 as set forth in SEQ ID NO: 153. In some embodiments, the sdAb has a CDR2 and a CDR3 having amino acid sequences of the CDR2 and the CDR3 as set forth in SEQ ID NO: 153. In some embodiments, the sdAb has a CDR1, a CDR2, and a CDR3 having amino acid sequences of the CDR1, the CDR2, and the CDR3 as set forth in SEQ ID NO: 153. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 111. In some embodiments, the sdAb has a CDR2 of SEQ ID NO: 112. In other embodiments, the sdAb has a CDR3 of SEQ ID NO: 113. In some embodiments, the sdAb has a CDR1 of SEQ ID NO: 111 and a CDR2 of SEQ ID NO: 112. In some embodiments, the sdAb has a CDR1 of SEQ ID NO: 111 and a CDR3 of SEQ ID NO: 113. In some embodiments, the sdAb has a CDR2 of SEQ ID NO: 112 and a CDR3 of SEQ ID NO: 113. In a specific embodiment, the sdAb has a CDR1 of SEQ ID NO: 111, a CDR2 of SEQ ID NO: 112, and a CDR3 of SEQ ID NO: 113.

In some embodiments, the anti-MSLN sdAb provided herein has one or more CDR regions from anti-MSLN-32.

In some embodiments, the sdAb has a CDR1 having an amino acid sequence of the CDR1 as set forth in SEQ ID NO: 154. In some embodiments, the sdAb has a CDR2 having an amino acid sequence of the CDR2 as set forth in SEQ ID NO: 154. In other embodiments, the sdAb has a CDR3 having an amino acid sequence of the CDR3 as set forth in SEQ ID NO: 154. In some embodiments, the sdAb has a CDR1 and a CDR2 having amino acid sequences of the CDR1 and the CDR2 as set forth in SEQ ID NO: 154. In some embodiments, the sdAb has a CDR1 and a CDR3 having amino acid sequences of the CDR1 and the CDR3 as set forth in SEQ ID NO: 154. In some embodiments, the sdAb has a CDR2 and a CDR3 having amino acid sequences of the CDR2 and the CDR3 as set forth in SEQ ID NO: 154. In some embodiments, the sdAb has a CDR1, a CDR2, and a CDR3 having amino acid sequences of the CDR1, the CDR2, and the CDR3 as set forth in SEQ ID NO: 154. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 114. In some embodiments, the sdAb has a CDR2 of SEQ ID NO: 115. In other embodiments, the sdAb has a CDR3 of SEQ ID NO: 116. In some embodiments, the sdAb has a CDR1 of SEQ ID NO: 114 and a CDR2 of SEQ ID NO: 115. In some embodiments, the sdAb has a CDR1 of SEQ ID NO: 114 and a CDR3 of SEQ ID NO: 116. In some embodiments, the sdAb has a CDR2 of SEQ ID NO: 115 and a CDR3 of SEQ ID NO: 116. In a specific embodiment, the sdAb has a CDR1 of SEQ ID NO: 114, a CDR2 of SEQ ID NO: 115, and a CDR3 of SEQ ID NO: 116.

In some embodiments, the anti-MSLN sdAb provided herein has one or more CDR regions from anti-MSLN-33.

In some embodiments, the sdAb has a CDR1 having an amino acid sequence of the CDR1 as set forth in SEQ ID NO: 155. In some embodiments, the sdAb has a CDR2 having an amino acid sequence of the CDR2 as set forth in SEQ ID NO: 155. In other embodiments, the sdAb has a CDR3 having an amino acid sequence of the CDR3 as set forth in SEQ ID NO: 155. In some embodiments, the sdAb has a CDR1 and a CDR2 having amino acid sequences of the CDR1 and the CDR2 as set forth in SEQ ID NO: 155. In some embodiments, the sdAb has a CDR1 and a CDR3 having amino acid sequences of the CDR1 and the CDR3 as set forth in SEQ ID NO: 155. In some embodiments, the sdAb has a CDR2 and a CDR3 having amino acid sequences of the CDR2 and the CDR3 as set forth in SEQ ID NO: 155. In some embodiments, the sdAb has a CDR1, a CDR2, and a CDR3 having amino acid sequences of the CDR1, the CDR2, and the CDR3 as set forth in SEQ ID NO: 155. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 117. In some embodiments, the sdAb has a CDR2 of SEQ ID NO: 118. In other embodiments, the sdAb has a CDR3 of SEQ ID NO: 119. In some embodiments, the sdAb has a CDR1 of SEQ ID NO: 117 and a CDR2 of SEQ ID NO: 118. In some embodiments, the sdAb has a CDR1 of SEQ ID NO: 117 and a CDR3 of SEQ ID NO: 119. In some embodiments, the sdAb has a CDR2 of SEQ ID NO: 118 and a CDR3 of SEQ ID NO: 119. In a specific embodiment, the sdAb has a CDR1 of SEQ ID NO: 117, a CDR2 of SEQ ID NO: 118, and a CDR3 of SEQ ID NO: 119.

In some embodiments, the anti-MSLN sdAb provided herein has one or more CDR regions from anti-MSLN-34.

In some embodiments, the sdAb has a CDR1 having an amino acid sequence of the CDR1 as set forth in SEQ ID NO: 156. In some embodiments, the sdAb has a CDR2 having an amino acid sequence of the CDR2 as set forth in SEQ ID NO: 156. In other embodiments, the sdAb has a CDR3 having an amino acid sequence of the CDR3 as set forth in SEQ ID NO: 156. In some embodiments, the sdAb has a CDR1 and a CDR2 having amino acid sequences of the CDR1 and the CDR2 as set forth in SEQ ID NO: 156. In some embodiments, the sdAb has a CDR1 and a CDR3 having amino acid sequences of the CDR1 and the CDR3 as set forth in SEQ ID NO: 156. In some embodiments, the sdAb has a CDR2 and a CDR3 having amino acid sequences of the CDR2 and the CDR3 as set forth in SEQ ID NO: 156. In some embodiments, the sdAb has a CDR1, a CDR2, and a CDR3 having amino acid sequences of the CDR1, the CDR2, and the CDR3 as set forth in SEQ ID NO: 156. CDR sequences can be determined according to well-known numbering systems. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the CDRs are according to IMGT numbering.

In some embodiments, the sdAb has a CDR1 of SEQ ID NO: 120. In some embodiments, the sdAb has a CDR2 of SEQ ID NO: 121. In other embodiments, the sdAb has a CDR3 of SEQ ID NO: 122. In some embodiments, the sdAb has a CDR1 of SEQ ID NO: 120 and a CDR2 of SEQ ID NO: 121. In some embodiments, the sdAb has a CDR1 of SEQ ID NO: 120 and a CDR3 of SEQ ID NO: 122. In some embodiments, the sdAb has a CDR2 of SEQ ID NO: 121 and a CDR3 of SEQ ID NO: 122. In a specific embodiment, the sdAb has a CDR1 of SEQ ID NO: 120, a CDR2 of SEQ ID NO: 121, and a CDR3 of SEQ ID NO: 122.

In some embodiments of the various sdAbs that bind to MSLN provided herein, the sdAb further comprises one or more FR sequences of antibodies anti-MSLN-1, anti-MSLN-2, anti-MSLN-3, anti-MSLN-4, anti-MSLN-5, anti-MSLN-6, anti-MSLN-7, anti-MSLN-8, anti-MSLN-9, anti-MSLN-10, anti-MSLN-11, anti-MSLN-12, anti-MSLN-13, anti-MSLN-14, anti-MSLN-15, anti-MSLN-16, anti-MSLN-17, anti-MSLN-18, anti-MSLN-19, anti-MSLN-20, anti-MSLN-21, anti-MSLN-22, anti-MSLN-23, anti-MSLN-24, anti-MSLN-25, anti-MSLN-26, anti-MSLN-27, anti-MSLN-28, anti-MSLN-29, anti-MSLN-30, anti-MSLN-31, anti-MSLN-32, anti-MSLN-33, and anti-MSLN-34 as set forth in Table 9.

In some embodiments, the sdAb provided herein comprises a FR1 having an amino acid sequence of the FR1 as set forth in SEQ ID NO: 123. In some embodiments, the sdAb provided herein comprises a FR2 having an amino acid sequence of the FR2 as set forth in SEQ ID NO: 123. In some embodiments, the sdAb provided herein comprises a FR3 having an amino acid sequence of the FR3 as set forth in SEQ ID NO: 123. In some embodiments, the sdAb provided herein comprises a FR4 having an amino acid sequence of the FR4 as set forth in SEQ ID NO: 123. In some embodiments, the sdAb provided herein comprises a FR1 and a FR2 having amino acid sequences of the FR1 and the 1-R2 as set forth in SEQ ID NO: 123. In some embodiments, the sdAb provided herein comprises a FR1 and a FR3 having amino acid sequences of the FR1 and the FR3 as set forth in SEQ ID NO: 123. In some embodiments, the sdAb provided herein comprises a FR1 and a FR4 having amino acid sequences of the FR1 and the FR4 as set forth in SEQ ID NO: 123. In some embodiments, the sdAb provided herein comprises a 1-R2 and a 1-R3 having amino acid sequences of the FR2 and the FR3 as set forth in SEQ ID NO: 123. In some embodiments, the sdAb provided herein comprises a FR2 and a FR4 having amino acid sequences of the FR2 and the FR4 as set forth in SEQ ID NO: 123. In some embodiments, the sdAb provided herein comprises a FR3 and a FR4 having amino acid sequences of the FR3 and the FR4 as set forth in SEQ ID NO: 123. In some embodiments, the sdAb provided herein comprises a FR1, a FR2, and a FR3 having amino acid sequences of the FR1, the FR2, and the FR3 as set forth in SEQ ID NO: 123. In some embodiments, the sdAb provided herein comprises a FR1, a FR2, and a FR4 having amino acid sequences of the FR1, the FR2, and the FR4 as set forth in SEQ ID NO: 123. In some embodiments, the sdAb provided herein comprises a FR1, a FR3, and a FR4 having amino acid sequences of the FR1, the FR3, and the FR4 as set forth in SEQ ID NO: 123. In some embodiments, the sdAb provided herein comprises a FR2, a FR3, and a FR4 having amino acid sequences of the FR2, the FR3, and the FR4 as set forth in SEQ ID NO: 123. In a specific embodiment, the sdAb provided herein comprises a FR1, a FR2, a FR3, and a FR4 having amino acid sequences of the FR1, the FR2, the FR3, and the FR4 as set forth in SEQ ID NO: 123.

In some embodiments, the sdAb provided herein comprises a FR1 having an amino acid sequence of the FR1 as set forth in SEQ ID NO: 124. In some embodiments, the sdAb provided herein comprises a FR2 having an amino acid sequence of the FR2 as set forth in SEQ ID NO: 124. In some embodiments, the sdAb provided herein comprises a FR3 having an amino acid sequence of the FR3 as set forth in SEQ ID NO: 124. In some embodiments, the sdAb provided herein comprises a FR4 having an amino acid sequence of the FR4 as set forth in SEQ ID NO: 124. In some embodiments, the sdAb provided herein comprises a FR1 and a FR2 having amino acid sequences of the FR1 and the 1-R2 as set forth in SEQ ID NO: 124. In some embodiments, the sdAb provided herein comprises a FR1 and a FR3 having amino acid sequences of the FR1 and the FR3 as set forth in SEQ ID NO: 124. In some embodiments, the sdAb provided herein comprises a FR1 and a FR4 having amino acid sequences of the FR1 and the FR4 as set forth in SEQ ID NO: 124. In some embodiments, the sdAb provided herein comprises a FR2 and a 1-R3 having amino acid sequences of the FR2 and the FR3 as set forth in SEQ ID NO: 124. In some embodiments, the sdAb provided herein comprises a FR2 and a FR4 having amino acid sequences of the FR2 and the FR4 as set forth in SEQ ID NO: 124. In some embodiments, the sdAb provided herein comprises a FR3 and a FR4 having amino acid sequences of the FR3 and the FR4 as set forth in SEQ ID NO: 124. In some embodiments, the sdAb provided herein comprises a FR1, a FR2, and a FR3 having amino acid sequences of the FR1, the FR2, and the FR3 as set forth in SEQ ID NO: 124. In some embodiments, the sdAb provided herein comprises a FR1, a FR2, and a FR4 having amino acid sequences of the FR1, the FR2, and the FR4 as set forth in SEQ ID NO: 124. In some embodiments, the sdAb provided herein comprises a FR1, a FR3, and a FR4 having amino acid sequences of the FR1, the FR3, and the FR4 as set forth in SEQ ID NO: 124. In some embodiments, the sdAb provided herein comprises a FR2, a FR3, and a FR4 having amino acid sequences of the FR2, the FR3, and the FR4 as set forth in SEQ ID NO: 124. In a specific embodiment, the sdAb provided herein comprises a FR1, a FR2, a FR3, and a FR4 having amino acid sequences of the FR1, the FR2, the FR3, and the FR4 as set forth in SEQ ID NO: 124.

In some embodiments, the sdAb provided herein comprises a FR1 having an amino acid sequence of the FR1 as set forth in SEQ ID NO: 125. In some embodiments, the sdAb provided herein comprises a FR2 having an amino acid sequence of the FR2 as set forth in SEQ ID NO: 125. In some embodiments, the sdAb provided herein comprises a FR3 having an amino acid sequence of the FR3 as set forth in SEQ ID NO: 125. In some embodiments, the sdAb provided herein comprises a FR4 having an amino acid sequence of the FR4 as set forth in SEQ ID NO: 125. In some embodiments, the sdAb provided herein comprises a FR1 and a FR2 having amino acid sequences of the FR1 and the 1-R2 as set forth in SEQ ID NO: 125. In some embodiments, the sdAb provided herein comprises a FR1 and a FR3 having amino acid sequences of the FR1 and the FR3 as set forth in SEQ ID NO: 125. In some embodiments, the sdAb provided herein comprises a FR1 and a FR4 having amino acid sequences of the FR1 and the FR4 as set forth in SEQ ID NO: 125. In some embodiments, the sdAb provided herein comprises a FR2 and a 1-R3 having amino acid sequences of the FR2 and the FR3 as set forth in SEQ ID NO: 125. In some embodiments, the sdAb provided herein comprises a FR2 and a FR4 having amino acid sequences of the FR2 and the FR4 as set forth in SEQ ID NO: 125. In some embodiments, the sdAb provided herein comprises a FR3 and a FR4 having amino acid sequences of the FR3 and the FR4 as set forth in SEQ ID NO: 125. In some embodiments, the sdAb provided herein comprises a FR1, a FR2, and a FR3 having amino acid sequences of the FR1, the FR2, and the FR3 as set forth in SEQ ID NO: 125. In some embodiments, the sdAb provided herein comprises a FR1, a FR2, and a FR4 having amino acid sequences of the FR1, the FR2, and the FR4 as set forth in SEQ ID NO: 125. In some embodiments, the sdAb provided herein comprises a FR1, a FR3, and a FR4 having amino acid sequences of the FR1, the FR3, and the FR4 as set forth in SEQ ID NO: 125. In some embodiments, the sdAb provided herein comprises a FR2, a FR3, and a FR4 having amino acid sequences of the FR2, the FR3, and the FR4 as set forth in SEQ ID NO: 125. In a specific embodiment, the sdAb provided herein comprises a FR1, a FR2, a FR3, and a FR4 having amino acid sequences of the FR1, the FR2, the FR3, and the FR4 as set forth in SEQ ID NO: 125.

In some embodiments, the sdAb provided herein comprises a FR1 having an amino acid sequence of the FR1 as set forth in SEQ ID NO: 126. In some embodiments, the sdAb provided herein comprises a FR2 having an amino acid sequence of the FR2 as set forth in SEQ ID NO: 126. In some embodiments, the sdAb provided herein comprises a FR3 having an amino acid sequence of the FR3 as set forth in SEQ ID NO: 126. In some embodiments, the sdAb provided herein comprises a FR4 having an amino acid sequence of the FR4 as set forth in SEQ ID NO: 126. In some embodiments, the sdAb provided herein comprises a FR1 and a FR2 having amino acid sequences of the FR1 and the 1-R2 as set forth in SEQ ID NO: 126. In some embodiments, the sdAb provided herein comprises a FR1 and a FR3 having amino acid sequences of the FR1 and the FR3 as set forth in SEQ ID NO: 126. In some embodiments, the sdAb provided herein comprises a FR1 and a FR4 having amino acid sequences of the FR1 and the FR4 as set forth in SEQ ID NO: 126. In some embodiments, the sdAb provided herein comprises a 1-R2 and a 1-R3 having amino acid sequences of the FR2 and the FR3 as set forth in SEQ ID NO: 126. In some embodiments, the sdAb provided herein comprises a FR2 and a FR4 having amino acid sequences of the FR2 and the FR4 as set forth in SEQ ID NO: 126. In some embodiments, the sdAb provided herein comprises a FR3 and a FR4 having amino acid sequences of the FR3 and the FR4 as set forth in SEQ ID NO: 126. In some embodiments, the sdAb provided herein comprises a FR1, a FR2, and a FR3 having amino acid sequences of the FR1, the FR2, and the FR3 as set forth in SEQ ID NO: 126. In some embodiments, the sdAb provided herein comprises a FR1, a FR2, and a FR4 having amino acid sequences of the FR1, the FR2, and the FR4 as set forth in SEQ ID NO: 126. In some embodiments, the sdAb provided herein comprises a FR1, a FR3, and a FR4 having amino acid sequences of the FR1, the FR3, and the FR4 as set forth in SEQ ID NO: 126. In some embodiments, the sdAb provided herein comprises a FR2, a FR3, and a FR4 having amino acid sequences of the FR2, the FR3, and the FR4 as set forth in SEQ ID NO: 126. In a specific embodiment, the sdAb provided herein comprises a FR1, a FR2, a FR3, and a FR4 having amino acid sequences of the FR1, the FR2, the FR3, and the FR4 as set forth in SEQ ID NO: 126.

In some embodiments, the sdAb provided herein comprises a FR1 having an amino acid sequence of the FR1 as set forth in SEQ ID NO: 127. In some embodiments, the sdAb provided herein comprises a FR2 having an amino acid sequence of the FR2 as set forth in SEQ ID NO: 127. In some embodiments, the sdAb provided herein comprises a FR3 having an amino acid sequence of the FR3 as set forth in SEQ ID NO: 127. In some embodiments, the sdAb provided herein comprises a FR4 having an amino acid sequence of the FR4 as set forth in SEQ ID NO: 127. In some embodiments, the sdAb provided herein comprises a FR1 and a FR2 having amino acid sequences of the FR1 and the FR2 as set forth in SEQ ID NO: 127. In some embodiments, the sdAb provided herein comprises a FR1 and a FR3 having amino acid sequences of the FR1 and the FR3 as set forth in SEQ ID NO: 127. In some embodiments, the sdAb provided herein comprises a FR1 and a FR4 having amino acid sequences of the FR1 and the FR4 as set forth in SEQ ID NO: 127. In some embodiments, the sdAb provided herein comprises a 1-R2 and a 1-R3 having amino acid sequences of the FR2 and the FR3 as set forth in SEQ ID NO: 127. In some embodiments, the sdAb provided herein comprises a FR2 and a FR4 having amino acid sequences of the FR2 and the FR4 as set forth in SEQ ID NO: 127. In some embodiments, the sdAb provided herein comprises a FR3 and a FR4 having amino acid sequences of the FR3 and the FR4 as set forth in SEQ ID NO: 127. In some embodiments, the sdAb provided herein comprises a FR1, a FR2, and a FR3 having amino acid sequences of the FR1, the FR2, and the FR3 as set forth in SEQ ID NO: 127. In some embodiments, the sdAb provided herein comprises a FR1, a FR2, and a FR4 having amino acid sequences of the FR1, the FR2, and the FR4 as set forth in SEQ ID NO: 127. In some embodiments, the sdAb provided herein comprises a FR1, a FR3, and a FR4 having amino acid sequences of the FR1, the FR3, and the FR4 as set forth in SEQ ID NO: 127. In some embodiments, the sdAb provided herein comprises a FR2, a FR3, and a FR4 having amino acid sequences of the FR2, the FR3, and the FR4 as set forth in SEQ ID NO: 127. In a specific embodiment, the sdAb provided herein comprises a FR1, a FR2, a FR3, and a FR4 having amino acid sequences of the FR1, the FR2, the FR3, and the FR4 as set forth in SEQ ID NO: 127.

In some embodiments, the sdAb provided herein comprises a FR1 having an amino acid sequence of the FR1 as set forth in SEQ ID NO: 128. In some embodiments, the sdAb provided herein comprises a FR2 having an amino acid sequence of the FR2 as set forth in SEQ ID NO: 128. In some embodiments, the sdAb provided herein comprises a FR3 having an amino acid sequence of the FR3 as set forth in SEQ ID NO: 128. In some embodiments, the sdAb provided herein comprises a FR4 having an amino acid sequence of the FR4 as set forth in SEQ ID NO: 128. In some embodiments, the sdAb provided herein comprises a FR1 and a FR2 having amino acid sequences of the FR1 and the 1-R2 as set forth in SEQ ID NO: 128. In some embodiments, the sdAb provided herein comprises a FR1 and a FR3 having amino acid sequences of the FR1 and the FR3 as set forth in SEQ ID NO: 128. In some embodiments, the sdAb provided herein comprises a FR1 and a FR4 having amino acid sequences of the FR1 and the FR4 as set forth in SEQ ID NO: 128. In some embodiments, the sdAb provided herein comprises a 1-R2 and a 1-R3 having amino acid sequences of the FR2 and the FR3 as set forth in SEQ ID NO: 128. In some embodiments, the sdAb provided herein comprises a FR2 and a FR4 having amino acid sequences of the FR2 and the FR4 as set forth in SEQ ID NO: 128. In some embodiments, the sdAb provided herein comprises a FR3 and a FR4 having amino acid sequences of the FR3 and the FR4 as set forth in SEQ ID NO: 128. In some embodiments, the sdAb provided herein comprises a FR1, a FR2, and a FR3 having amino acid sequences of the FR1, the FR2, and the FR3 as set forth in SEQ ID NO: 128. In some embodiments, the sdAb provided herein comprises a FR1, a FR2, and a FR4 having amino acid sequences of the FR1, the FR2, and the FR4 as set forth in SEQ ID NO: 128. In some embodiments, the sdAb provided herein comprises a FR1, a FR3, and a FR4 having amino acid sequences of the FR1, the FR3, and the FR4 as set forth in SEQ ID NO: 128. In some embodiments, the sdAb provided herein comprises a FR2, a FR3, and a FR4 having amino acid sequences of the FR2, the FR3, and the FR4 as set forth in SEQ ID NO: 128. In a specific embodiment, the sdAb provided herein comprises a FR1, a FR2, a FR3, and a FR4 having amino acid sequences of the FR1, the FR2, the FR3, and the FR4 as set forth in SEQ ID NO: 128.

In some embodiments, the sdAb provided herein comprises a FR1 having an amino acid sequence of the FR1 as set forth in SEQ ID NO: 129. In some embodiments, the sdAb provided herein comprises a FR2 having an amino acid sequence of the FR2 as set forth in SEQ ID NO: 129. In some embodiments, the sdAb provided herein comprises a FR3 having an amino acid sequence of the FR3 as set forth in SEQ ID NO: 129. In some embodiments, the sdAb provided herein comprises a FR4 having an amino acid sequence of the FR4 as set forth in SEQ ID NO: 129. In some embodiments, the sdAb provided herein comprises a FR1 and a FR2 having amino acid sequences of the FR1 and the 1-R2 as set forth in SEQ ID NO: 129. In some embodiments, the sdAb provided herein comprises a FR1 and a FR3 having amino acid sequences of the FR1 and the FR3 as set forth in SEQ ID NO: 129. In some embodiments, the sdAb provided herein comprises a FR1 and a FR4 having amino acid sequences of the FR1 and the FR4 as set forth in SEQ ID NO: 129. In some embodiments, the sdAb provided herein comprises a 1-R2 and a 1-R3 having amino acid sequences of the FR2 and the FR3 as set forth in SEQ ID NO: 129. In some embodiments, the sdAb provided herein comprises a FR2 and a FR4 having amino acid sequences of the FR2 and the FR4 as set forth in SEQ ID NO: 129. In some embodiments, the sdAb provided herein comprises a FR3 and a FR4 having amino acid sequences of the FR3 and the FR4 as set forth in SEQ ID NO: 129. In some embodiments, the sdAb provided herein comprises a FR1, a FR2, and a FR3 having amino acid sequences of the FR1, the FR2, and the FR3 as set forth in SEQ ID NO: 129. In some embodiments, the sdAb provided herein comprises a FR1, a FR2, and a FR4 having amino acid sequences of the FR1, the FR2, and the FR4 as set forth in SEQ ID NO: 129. In some embodiments, the sdAb provided herein comprises a FR1, a FR3, and a FR4 having amino acid sequences of the FR1, the FR3, and the FR4 as set forth in SEQ ID NO: 129. In some embodiments, the sdAb provided herein comprises a FR2, a FR3, and a FR4 having amino acid sequences of the FR2, the FR3, and the FR4 as set forth in SEQ ID NO: 129. In a specific embodiment, the sdAb provided herein comprises a FR1, a FR2, a FR3, and a FR4 having amino acid sequences of the FR1, the FR2, the FR3, and the FR4 as set forth in SEQ ID NO: 129.

In some embodiments, the sdAb provided herein comprises a FR1 having an amino acid sequence of the FR1 as set forth in SEQ ID NO: 130. In some embodiments, the sdAb provided herein comprises a FR2 having an amino acid sequence of the FR2 as set forth in SEQ ID NO: 130. In some embodiments, the sdAb provided herein comprises a FR3 having an amino acid sequence of the FR3 as set forth in SEQ ID NO: 130. In some embodiments, the sdAb provided herein comprises a FR4 having an amino acid sequence of the FR4 as set forth in SEQ ID NO: 130. In some embodiments, the sdAb provided herein comprises a FR1 and a FR2 having amino acid sequences of the FR1 and the FR2 as set forth in SEQ ID NO: 130. In some embodiments, the sdAb provided herein comprises a FR1 and a FR3 having amino acid sequences of the FR1 and the FR3 as set forth in SEQ ID NO: 130. In some embodiments, the sdAb provided herein comprises a FR1 and a FR4 having amino acid sequences of the FR1 and the FR4 as set forth in SEQ ID NO: 130. In some embodiments, the sdAb provided herein comprises a 1-R2 and a 1-R3 having amino acid sequences of the FR2 and the FR3 as set forth in SEQ ID NO: 130. In some embodiments, the sdAb provided herein comprises a FR2 and a FR4 having amino acid sequences of the FR2 and the FR4 as set forth in SEQ ID NO: 130. In some embodiments, the sdAb provided herein comprises a FR3 and a FR4 having amino acid sequences of the FR3 and the FR4 as set forth in SEQ ID NO: 130. In some embodiments, the sdAb provided herein comprises a FR1, a FR2, and a FR3 having amino acid sequences of the FR1, the FR2, and the FR3 as set forth in SEQ ID NO: 130. In some embodiments, the sdAb provided herein comprises a FR1, a FR2, and a FR4 having amino acid sequences of the FR1, the FR2, and the FR4 as set forth in SEQ ID NO: 130. In some embodiments, the sdAb provided herein comprises a FR1, a FR3, and a FR4 having amino acid sequences of the FR1, the FR3, and the FR4 as set forth in SEQ ID NO: 130. In some embodiments, the sdAb provided herein comprises a FR2, a FR3, and a FR4 having amino acid sequences of the FR2, the FR3, and the FR4 as set forth in SEQ ID NO: 130. In a specific embodiment, the sdAb provided herein comprises a FR1, a FR2, a FR3, and a FR4 having amino acid sequences of the FR1, the FR2, the FR3, and the FR4 as set forth in SEQ ID NO: 130.

In some embodiments, the sdAb provided herein comprises a FR1 having an amino acid sequence of the FR1 as set forth in SEQ ID NO: 131. In some embodiments, the sdAb provided herein comprises a FR2 having an amino acid sequence of the FR2 as set forth in SEQ ID NO: 131. In some embodiments, the sdAb provided herein comprises a FR3 having an amino acid sequence of the FR3 as set forth in SEQ ID NO: 131. In some embodiments, the sdAb provided herein comprises a FR4 having an amino acid sequence of the FR4 as set forth in SEQ ID NO: 131. In some embodiments, the sdAb provided herein comprises a FR1 and a FR2 having amino acid sequences of the FR1 and the 1-R2 as set forth in SEQ ID NO: 131. In some embodiments, the sdAb provided herein comprises a FR1 and a FR3 having amino acid sequences of the FR1 and the FR3 as set forth in SEQ ID NO: 131. In some embodiments, the sdAb provided herein comprises a FR1 and a FR4 having amino acid sequences of the FR1 and the FR4 as set forth in SEQ ID NO: 131. In some embodiments, the sdAb provided herein comprises a 1-R2 and a 1-R3 having amino acid sequences of the FR2 and the FR3 as set forth in SEQ ID NO: 131. In some embodiments, the sdAb provided herein comprises a FR2 and a FR4 having amino acid sequences of the FR2 and the FR4 as set forth in SEQ ID NO: 131. In some embodiments, the sdAb provided herein comprises a FR3 and a FR4 having amino acid sequences of the FR3 and the FR4 as set forth in SEQ ID NO: 131. In some embodiments, the sdAb provided herein comprises a FR1, a FR2, and a FR3 having amino acid sequences of the FR1, the FR2, and the FR3 as set forth in SEQ ID NO: 131. In some embodiments, the sdAb provided herein comprises a FR1, a FR2, and a FR4 having amino acid sequences of the FR1, the FR2, and the FR4 as set forth in SEQ ID NO: 131. In some embodiments, the sdAb provided herein comprises a FR1, a FR3, and a FR4 having amino acid sequences of the FR1, the FR3, and the FR4 as set forth in SEQ ID NO: 131. In some embodiments, the sdAb provided herein comprises a FR2, a FR3, and a FR4 having amino acid sequences of the FR2, the FR3, and the FR4 as set forth in SEQ ID NO: 131. In a specific embodiment, the sdAb provided herein comprises a FR1, a FR2, a FR3, and a FR4 having amino acid sequences of the FR1, the FR2, the FR3, and the FR4 as set forth in SEQ ID NO: 131.

In some embodiments, the sdAb provided herein comprises a FR1 having an amino acid sequence of the FR1 as set forth in SEQ ID NO: 132. In some embodiments, the sdAb provided herein comprises a FR2 having an amino acid sequence of the FR2 as set forth in SEQ ID NO: 132. In some embodiments, the sdAb provided herein comprises a FR3 having an amino acid sequence of the FR3 as set forth in SEQ ID NO: 132. In some embodiments, the sdAb provided herein comprises a FR4 having an amino acid sequence of the FR4 as set forth in SEQ ID NO: 132. In some embodiments, the sdAb provided herein comprises a FR1 and a FR2 having amino acid sequences of the FR1 and the 1-R2 as set forth in SEQ ID NO: 132. In some embodiments, the sdAb provided herein comprises a FR1 and a FR3 having amino acid sequences of the FR1 and the FR3 as set forth in SEQ ID NO: 132. In some embodiments, the sdAb provided herein comprises a FR1 and a FR4 having amino acid sequences of the FR1 and the FR4 as set forth in SEQ ID NO: 132. In some embodiments, the sdAb provided herein comprises a FR2 and a 1-R3 having amino acid sequences of the FR2 and the FR3 as set forth in SEQ ID NO: 132. In some embodiments, the sdAb provided herein comprises a FR2 and a FR4 having amino acid sequences of the FR2 and the FR4 as set forth in SEQ ID NO: 132. In some embodiments, the sdAb provided herein comprises a FR3 and a FR4 having amino acid sequences of the FR3 and the FR4 as set forth in SEQ ID NO: 132. In some embodiments, the sdAb provided herein comprises a FR1, a FR2, and a FR3 having amino acid sequences of the FR1, the FR2, and the FR3 as set forth in SEQ ID NO: 132. In some embodiments, the sdAb provided herein comprises a FR1, a FR2, and a FR4 having amino acid sequences of the FR1, the FR2, and the FR4 as set forth in SEQ ID NO: 132. In some embodiments, the sdAb provided herein comprises a FR1, a FR3, and a FR4 having amino acid sequences of the FR1, the FR3, and the FR4 as set forth in SEQ ID NO: 132. In some embodiments, the sdAb provided herein comprises a FR2, a FR3, and a FR4 having amino acid sequences of the FR2, the FR3, and the FR4 as set forth in SEQ ID NO: 132. In a specific embodiment, the sdAb provided herein comprises a FR1, a FR2, a FR3, and a FR4 having amino acid sequences of the FR1, the FR2, the FR3, and the FR4 as set forth in SEQ ID NO: 132.

In some embodiments, the sdAb provided herein comprises a FR1 having an amino acid sequence of the FR1 as set forth in SEQ ID NO: 133. In some embodiments, the sdAb provided herein comprises a FR2 having an amino acid sequence of the FR2 as set forth in SEQ ID NO: 133. In some embodiments, the sdAb provided herein comprises a FR3 having an amino acid sequence of the FR3 as set forth in SEQ ID NO: 133. In some embodiments, the sdAb provided herein comprises a FR4 having an amino acid sequence of the FR4 as set forth in SEQ ID NO: 133. In some embodiments, the sdAb provided herein comprises a FR1 and a FR2 having amino acid sequences of the FR1 and the 1-R2 as set forth in SEQ ID NO: 133. In some embodiments, the sdAb provided herein comprises a FR1 and a FR3 having amino acid sequences of the FR1 and the FR3 as set forth in SEQ ID NO: 133. In some embodiments, the sdAb provided herein comprises a FR1 and a FR4 having amino acid sequences of the FR1 and the FR4 as set forth in SEQ ID NO: 133. In some embodiments, the sdAb provided herein comprises a FR2 and a 1-R3 having amino acid sequences of the FR2 and the FR3 as set forth in SEQ ID NO: 133. In some embodiments, the sdAb provided herein comprises a FR2 and a FR4 having amino acid sequences of the FR2 and the FR4 as set forth in SEQ ID NO: 133. In some embodiments, the sdAb provided herein comprises a FR3 and a FR4 having amino acid sequences of the FR3 and the FR4 as set forth in SEQ ID NO: 133. In some embodiments, the sdAb provided herein comprises a FR1, a FR2, and a FR3 having amino acid sequences of the FR1, the FR2, and the FR3 as set forth in SEQ ID NO: 133. In some embodiments, the sdAb provided herein comprises a FR1, a FR2, and a FR4 having amino acid sequences of the FR1, the FR2, and the FR4 as set forth in SEQ ID NO: 133. In some embodiments, the sdAb provided herein comprises a FR1, a FR3, and a FR4 having amino acid sequences of the FR1, the FR3, and the FR4 as set forth in SEQ ID NO: 133. In some embodiments, the sdAb provided herein comprises a FR2, a FR3, and a FR4 having amino acid sequences of the FR2, the FR3, and the FR4 as set forth in SEQ ID NO: 133. In a specific embodiment, the sdAb provided herein comprises a FR1, a FR2, a FR3, and a FR4 having amino acid sequences of the FR1, the FR2, the FR3, and the FR4 as set forth in SEQ ID NO: 133.

In some embodiments, the sdAb provided herein comprises a FR1 having an amino acid sequence of the FR1 as set forth in SEQ ID NO: 134. In some embodiments, the sdAb provided herein comprises a FR2 having an amino acid sequence of the FR2 as set forth in SEQ ID NO: 134. In some embodiments, the sdAb provided herein comprises a FR3 having an amino acid sequence of the FR3 as set forth in SEQ ID NO: 134. In some embodiments, the sdAb provided herein comprises a FR4 having an amino acid sequence of the FR4 as set forth in SEQ ID NO: 134. In some embodiments, the sdAb provided herein comprises a FR1 and a FR2 having amino acid sequences of the FR1 and the 1-R2 as set forth in SEQ ID NO: 134. In some embodiments, the sdAb provided herein comprises a FR1 and a FR3 having amino acid sequences of the FR1 and the FR3 as set forth in SEQ ID NO: 134. In some embodiments, the sdAb provided herein comprises a FR1 and a FR4 having amino acid sequences of the FR1 and the FR4 as set forth in SEQ ID NO: 134. In some embodiments, the sdAb provided herein comprises a 1-R2 and a 1-R3 having amino acid sequences of the FR2 and the FR3 as set forth in SEQ ID NO: 134. In some embodiments, the sdAb provided herein comprises a FR2 and a FR4 having amino acid sequences of the FR2 and the FR4 as set forth in SEQ ID NO: 134. In some embodiments, the sdAb provided herein comprises a FR3 and a FR4 having amino acid sequences of the FR3 and the FR4 as set forth in SEQ ID NO: 134. In some embodiments, the sdAb provided herein comprises a FR1, a FR2, and a FR3 having amino acid sequences of the FR1, the FR2, and the FR3 as set forth in SEQ ID NO: 134. In some embodiments, the sdAb provided herein comprises a FR1, a FR2, and a FR4 having amino acid sequences of the FR1, the FR2, and the FR4 as set forth in SEQ ID NO: 134. In some embodiments, the sdAb provided herein comprises a FR1, a FR3, and a FR4 having amino acid sequences of the FR1, the FR3, and the FR4 as set forth in SEQ ID NO: 134. In some embodiments, the sdAb provided herein comprises a FR2, a FR3, and a FR4 having amino acid sequences of the FR2, the FR3, and the FR4 as set forth in SEQ ID NO: 134. In a specific embodiment, the sdAb provided herein comprises a FR1, a FR2, a FR3, and a FR4 having amino acid sequences of the FR1, the FR2, the FR3, and the FR4 as set forth in SEQ ID NO: 134.

In some embodiments, the sdAb provided herein comprises a FR1 having an amino acid sequence of the FR1 as set forth in SEQ ID NO: 135. In some embodiments, the sdAb provided herein comprises a FR2 having an amino acid sequence of the FR2 as set forth in SEQ ID NO: 135. In some embodiments, the sdAb provided herein comprises a FR3 having an amino acid sequence of the FR3 as set forth in SEQ ID NO: 135. In some embodiments, the sdAb provided herein comprises a FR4 having an amino acid sequence of the FR4 as set forth in SEQ ID NO: 135. In some embodiments, the sdAb provided herein comprises a FR1 and a FR2 having amino acid sequences of the FR1 and the 1-R2 as set forth in SEQ ID NO: 135. In some embodiments, the sdAb provided herein comprises a FR1 and a FR3 having amino acid sequences of the FR1 and the FR3 as set forth in SEQ ID NO: 135. In some embodiments, the sdAb provided herein comprises a FR1 and a FR4 having amino acid sequences of the FR1 and the FR4 as set forth in SEQ ID NO: 135. In some embodiments, the sdAb provided herein comprises a FR2 and a 1-R3 having amino acid sequences of the FR2 and the FR3 as set forth in SEQ ID NO: 135. In some embodiments, the sdAb provided herein comprises a FR2 and a FR4 having amino acid sequences of the FR2 and the FR4 as set forth in SEQ ID NO: 135. In some embodiments, the sdAb provided herein comprises a FR3 and a FR4 having amino acid sequences of the FR3 and the FR4 as set forth in SEQ ID NO: 135. In some embodiments, the sdAb provided herein comprises a FR1, a FR2, and a FR3 having amino acid sequences of the FR1, the FR2, and the FR3 as set forth in SEQ ID NO: 135. In some embodiments, the sdAb provided herein comprises a FR1, a FR2, and a FR4 having amino acid sequences of the FR1, the FR2, and the FR4 as set forth in SEQ ID NO: 135. In some embodiments, the sdAb provided herein comprises a FR1, a FR3, and a FR4 having amino acid sequences of the FR1, the FR3, and the FR4 as set forth in SEQ ID NO: 135. In some embodiments, the sdAb provided herein comprises a FR2, a FR3, and a FR4 having amino acid sequences of the FR2, the FR3, and the FR4 as set forth in SEQ ID NO: 135. In a specific embodiment, the sdAb provided herein comprises a FR1, a FR2, a FR3, and a FR4 having amino acid sequences of the FR1, the FR2, the FR3, and the FR4 as set forth in SEQ ID NO: 135.

In some embodiments, the sdAb provided herein comprises a FR1 having an amino acid sequence of the FR1 as set forth in SEQ ID NO: 136. In some embodiments, the sdAb provided herein comprises a FR2 having an amino acid sequence of the FR2 as set forth in SEQ ID NO: 136. In some embodiments, the sdAb provided herein comprises a FR3 having an amino acid sequence of the FR3 as set forth in SEQ ID NO: 136. In some embodiments, the sdAb provided herein comprises a FR4 having an amino acid sequence of the FR4 as set forth in SEQ ID NO: 136. In some embodiments, the sdAb provided herein comprises a FR1 and a FR2 having amino acid sequences of the FR1 and the 1-R2 as set forth in SEQ ID NO: 136. In some embodiments, the sdAb provided herein comprises a FR1 and a FR3 having amino acid sequences of the FR1 and the FR3 as set forth in SEQ ID NO: 136. In some embodiments, the sdAb provided herein comprises a FR1 and a FR4 having amino acid sequences of the FR1 and the FR4 as set forth in SEQ ID NO: 136. In some embodiments, the sdAb provided herein comprises a FR2 and a 1-R3 having amino acid sequences of the FR2 and the FR3 as set forth in SEQ ID NO: 136. In some embodiments, the sdAb provided herein comprises a FR2 and a FR4 having amino acid sequences of the FR2 and the FR4 as set forth in SEQ ID NO: 136. In some embodiments, the sdAb provided herein comprises a FR3 and a FR4 having amino acid sequences of the FR3 and the FR4 as set forth in SEQ ID NO: 136. In some embodiments, the sdAb provided herein comprises a FR1, a FR2, and a FR3 having amino acid sequences of the FR1, the FR2, and the FR3 as set forth in SEQ ID NO: 136. In some embodiments, the sdAb provided herein comprises a FR1, a FR2, and a FR4 having amino acid sequences of the FR1, the FR2, and the FR4 as set forth in SEQ ID NO: 136. In some embodiments, the sdAb provided herein comprises a FR1, a FR3, and a FR4 having amino acid sequences of the FR1, the FR3, and the FR4 as set forth in SEQ ID NO: 136. In some embodiments, the sdAb provided herein comprises a FR2, a FR3, and a FR4 having amino acid sequences of the FR2, the FR3, and the FR4 as set forth in SEQ ID NO: 136. In a specific embodiment, the sdAb provided herein comprises a FR1, a FR2, a FR3, and a FR4 having amino acid sequences of the FR1, the FR2, the FR3, and the FR4 as set forth in SEQ ID NO: 136.

In some embodiments, the sdAb provided herein comprises a FR1 having an amino acid sequence of the FR1 as set forth in SEQ ID NO: 137. In some embodiments, the sdAb provided herein comprises a FR2 having an amino acid sequence of the FR2 as set forth in SEQ ID NO: 137. In some embodiments, the sdAb provided herein comprises a FR3 having an amino acid sequence of the FR3 as set forth in SEQ ID NO: 137. In some embodiments, the sdAb provided herein comprises a FR4 having an amino acid sequence of the FR4 as set forth in SEQ ID NO: 137. In some embodiments, the sdAb provided herein comprises a FR1 and a FR2 having amino acid sequences of the FR1 and the 1-R2 as set forth in SEQ ID NO: 137. In some embodiments, the sdAb provided herein comprises a FR1 and a FR3 having amino acid sequences of the FR1 and the FR3 as set forth in SEQ ID NO: 137. In some embodiments, the sdAb provided herein comprises a FR1 and a FR4 having amino acid sequences of the FR1 and the FR4 as set forth in SEQ ID NO: 137. In some embodiments, the sdAb provided herein comprises a 1-R2 and a 1-R3 having amino acid sequences of the FR2 and the FR3 as set forth in SEQ ID NO: 137. In some embodiments, the sdAb provided herein comprises a FR2 and a FR4 having amino acid sequences of the FR2 and the FR4 as set forth in SEQ ID NO: 137. In some embodiments, the sdAb provided herein comprises a FR3 and a FR4 having amino acid sequences of the FR3 and the FR4 as set forth in SEQ ID NO: 137. In some embodiments, the sdAb provided herein comprises a FR1, a FR2, and a FR3 having amino acid sequences of the FR1, the FR2, and the FR3 as set forth in SEQ ID NO: 137. In some embodiments, the sdAb provided herein comprises a FR1, a FR2, and a FR4 having amino acid sequences of the FR1, the FR2, and the FR4 as set forth in SEQ ID NO: 137. In some embodiments, the sdAb provided herein comprises a FR1, a FR3, and a FR4 having amino acid sequences of the FR1, the FR3, and the FR4 as set forth in SEQ ID NO: 137. In some embodiments, the sdAb provided herein comprises a FR2, a FR3, and a FR4 having amino acid sequences of the FR2, the FR3, and the FR4 as set forth in SEQ ID NO: 137. In a specific embodiment, the sdAb provided herein comprises a FR1, a FR2, a FR3, and a FR4 having amino acid sequences of the FR1, the FR2, the FR3, and the FR4 as set forth in SEQ ID NO: 137.

In some embodiments, the sdAb provided herein comprises a FR1 having an amino acid sequence of the FR1 as set forth in SEQ ID NO: 138. In some embodiments, the sdAb provided herein comprises a FR2 having an amino acid sequence of the FR2 as set forth in SEQ ID NO: 138. In some embodiments, the sdAb provided herein comprises a FR3 having an amino acid sequence of the FR3 as set forth in SEQ ID NO: 138. In some embodiments, the sdAb provided herein comprises a FR4 having an amino acid sequence of the FR4 as set forth in SEQ ID NO: 138. In some embodiments, the sdAb provided herein comprises a FR1 and a FR2 having amino acid sequences of the FR1 and the FR2 as set forth in SEQ ID NO: 138. In some embodiments, the sdAb provided herein comprises a FR1 and a FR3 having amino acid sequences of the FR1 and the FR3 as set forth in SEQ ID NO: 138. In some embodiments, the sdAb provided herein comprises a FR1 and a FR4 having amino acid sequences of the FR1 and the FR4 as set forth in SEQ ID NO: 138. In some embodiments, the sdAb provided herein comprises a 1-R2 and a 1-R3 having amino acid sequences of the FR2 and the FR3 as set forth in SEQ ID NO: 138. In some embodiments, the sdAb provided herein comprises a FR2 and a FR4 having amino acid sequences of the FR2 and the FR4 as set forth in SEQ ID NO: 138. In some embodiments, the sdAb provided herein comprises a FR3 and a FR4 having amino acid sequences of the FR3 and the FR4 as set forth in SEQ ID NO: 138. In some embodiments, the sdAb provided herein comprises a FR1, a FR2, and a FR3 having amino acid sequences of the FR1, the FR2, and the FR3 as set forth in SEQ ID NO: 138. In some embodiments, the sdAb provided herein comprises a FR1, a FR2, and a FR4 having amino acid sequences of the FR1, the FR2, and the FR4 as set forth in SEQ ID NO: 138. In some embodiments, the sdAb provided herein comprises a FR1, a FR3, and a FR4 having amino acid sequences of the FR1, the FR3, and the FR4 as set forth in SEQ ID NO: 138. In some embodiments, the sdAb provided herein comprises a FR2, a FR3, and a FR4 having amino acid sequences of the FR2, the FR3, and the FR4 as set forth in SEQ ID NO: 138. In a specific embodiment, the sdAb provided herein comprises a FR1, a FR2, a FR3, and a FR4 having amino acid sequences of the FR1, the FR2, the FR3, and the FR4 as set forth in SEQ ID NO: 138.

In some embodiments, the sdAb provided herein comprises a FR1 having an amino acid sequence of the FR1 as set forth in SEQ ID NO: 139. In some embodiments, the sdAb provided herein comprises a FR2 having an amino acid sequence of the FR2 as set forth in SEQ ID NO: 139. In some embodiments, the sdAb provided herein comprises a FR3 having an amino acid sequence of the FR3 as set forth in SEQ ID NO: 139. In some embodiments, the sdAb provided herein comprises a FR4 having an amino acid sequence of the FR4 as set forth in SEQ ID NO: 139. In some embodiments, the sdAb provided herein comprises a FR1 and a FR2 having amino acid sequences of the FR1 and the 1-R2 as set forth in SEQ ID NO: 139. In some embodiments, the sdAb provided herein comprises a FR1 and a FR3 having amino acid sequences of the FR1 and the FR3 as set forth in SEQ ID NO: 139. In some embodiments, the sdAb provided herein comprises a FR1 and a FR4 having amino acid sequences of the FR1 and the FR4 as set forth in SEQ ID NO: 139. In some embodiments, the sdAb provided herein comprises a 1-R2 and a 1-R3 having amino acid sequences of the FR2 and the FR3 as set forth in SEQ ID NO: 139. In some embodiments, the sdAb provided herein comprises a FR2 and a FR4 having amino acid sequences of the FR2 and the FR4 as set forth in SEQ ID NO: 139. In some embodiments, the sdAb provided herein comprises a FR3 and a FR4 having amino acid sequences of the FR3 and the FR4 as set forth in SEQ ID NO: 139. In some embodiments, the sdAb provided herein comprises a FR1, a FR2, and a FR3 having amino acid sequences of the FR1, the FR2, and the FR3 as set forth in SEQ ID NO: 139. In some embodiments, the sdAb provided herein comprises a FR1, a FR2, and a FR4 having amino acid sequences of the FR1, the FR2, and the FR4 as set forth in SEQ ID NO: 139. In some embodiments, the sdAb provided herein comprises a FR1, a FR3, and a FR4 having amino acid sequences of the FR1, the FR3, and the FR4 as set forth in SEQ ID NO: 139. In some embodiments, the sdAb provided herein comprises a FR2, a FR3, and a FR4 having amino acid sequences of the FR2, the FR3, and the FR4 as set forth in SEQ ID NO: 139. In a specific embodiment, the sdAb provided herein comprises a FR1, a FR2, a FR3, and a FR4 having amino acid sequences of the FR1, the FR2, the FR3, and the FR4 as set forth in SEQ ID NO: 139.

In some embodiments, the sdAb provided herein comprises a FR1 having an amino acid sequence of the FR1 as set forth in SEQ ID NO: 140. In some embodiments, the sdAb provided herein comprises a FR2 having an amino acid sequence of the FR2 as set forth in SEQ ID NO: 140. In some embodiments, the sdAb provided herein comprises a FR3 having an amino acid sequence of the FR3 as set forth in SEQ ID NO: 140. In some embodiments, the sdAb provided herein comprises a FR4 having an amino acid sequence of the FR4 as set forth in SEQ ID NO: 140. In some embodiments, the sdAb provided herein comprises a FR1 and a FR2 having amino acid sequences of the FR1 and the 1-R2 as set forth in SEQ ID NO: 140. In some embodiments, the sdAb provided herein comprises a FR1 and a FR3 having amino acid sequences of the FR1 and the FR3 as set forth in SEQ ID NO: 140. In some embodiments, the sdAb provided herein comprises a FR1 and a FR4 having amino acid sequences of the FR1 and the FR4 as set forth in SEQ ID NO: 140. In some embodiments, the sdAb provided herein comprises a 1-R2 and a 1-R3 having amino acid sequences of the FR2 and the FR3 as set forth in SEQ ID NO: 140. In some embodiments, the sdAb provided herein comprises a FR2 and a FR4 having amino acid sequences of the FR2 and the FR4 as set forth in SEQ ID NO: 140. In some embodiments, the sdAb provided herein comprises a FR3 and a FR4 having amino acid sequences of the FR3 and the FR4 as set forth in SEQ ID NO: 140. In some embodiments, the sdAb provided herein comprises a FR1, a FR2, and a FR3 having amino acid sequences of the FR1, the FR2, and the FR3 as set forth in SEQ ID NO: 140. In some embodiments, the sdAb provided herein comprises a FR1, a FR2, and a FR4 having amino acid sequences of the FR1, the FR2, and the FR4 as set forth in SEQ ID NO: 140. In some embodiments, the sdAb provided herein comprises a FR1, a FR3, and a FR4 having amino acid sequences of the FR1, the FR3, and the FR4 as set forth in SEQ ID NO: 140. In some embodiments, the sdAb provided herein comprises a FR2, a FR3, and a FR4 having amino acid sequences of the FR2, the FR3, and the FR4 as set forth in SEQ ID NO: 140. In a specific embodiment, the sdAb provided herein comprises a FR1, a FR2, a FR3, and a FR4 having amino acid sequences of the FR1, the FR2, the FR3, and the FR4 as set forth in SEQ ID NO: 140.

In some embodiments, the sdAb provided herein comprises a FR1 having an amino acid sequence of the FR1 as set forth in SEQ ID NO: 141. In some embodiments, the sdAb provided herein comprises a FR2 having an amino acid sequence of the FR2 as set forth in SEQ ID NO: 141. In some embodiments, the sdAb provided herein comprises a FR3 having an amino acid sequence of the FR3 as set forth in SEQ ID NO: 141. In some embodiments, the sdAb provided herein comprises a FR4 having an amino acid sequence of the FR4 as set forth in SEQ ID NO: 141. In some embodiments, the sdAb provided herein comprises a FR1 and a FR2 having amino acid sequences of the FR1 and the FR2 as set forth in SEQ ID NO: 141. In some embodiments, the sdAb provided herein comprises a FR1 and a FR3 having amino acid sequences of the FR1 and the FR3 as set forth in SEQ ID NO: 141. In some embodiments, the sdAb provided herein comprises a FR1 and a FR4 having amino acid sequences of the FR1 and the FR4 as set forth in SEQ ID NO: 141. In some embodiments, the sdAb provided herein comprises a FR2 and a FR3 having amino acid sequences of the FR2 and the FR3 as set forth in SEQ ID NO: 141. In some embodiments, the sdAb provided herein comprises a FR2 and a FR4 having amino acid sequences of the FR2 and the FR4 as set forth in SEQ ID NO: 141. In some embodiments, the sdAb provided herein comprises a FR3 and a FR4 having amino acid sequences of the FR3 and the FR4 as set forth in SEQ ID NO: 141. In some embodiments, the sdAb provided herein comprises a FR1, a FR2, and a FR3 having amino acid sequences of the FR1, the FR2, and the FR3 as set forth in SEQ ID NO: 141. In some embodiments, the sdAb provided herein comprises a FR1, a FR2, and a FR4 having amino acid sequences of the FR1, the FR2, and the FR4 as set forth in SEQ ID NO: 141. In some embodiments, the sdAb provided herein comprises a FR1, a FR3, and a FR4 having amino acid sequences of the FR1, the FR3, and the FR4 as set forth in SEQ ID NO: 141. In some embodiments, the sdAb provided herein comprises a FR2, a FR3, and a FR4 having amino acid sequences of the FR2, the FR3, and the FR4 as set forth in SEQ ID NO: 141. In a specific embodiment, the sdAb provided herein comprises a FR1, a FR2, a FR3, and a FR4 having amino acid sequences of the FR1, the FR2, the FR3, and the FR4 as set forth in SEQ ID NO: 141.

In some embodiments, the sdAb provided herein comprises a FR1 having an amino acid sequence of the FR1 as set forth in SEQ ID NO: 142. In some embodiments, the sdAb provided herein comprises a FR2 having an amino acid sequence of the FR2 as set forth in SEQ ID NO: 142. In some embodiments, the sdAb provided herein comprises a FR3 having an amino acid sequence of the FR3 as set forth in SEQ ID NO: 142. In some embodiments, the sdAb provided herein comprises a FR4 having an amino acid sequence of the FR4 as set forth in SEQ ID NO: 142. In some embodiments, the sdAb provided herein comprises a FR1 and a FR2 having amino acid sequences of the FR1 and the 1-R2 as set forth in SEQ ID NO: 142. In some embodiments, the sdAb provided herein comprises a FR1 and a FR3 having amino acid sequences of the FR1 and the FR3 as set forth in SEQ ID NO: 142. In some embodiments, the sdAb provided herein comprises a FR1 and a FR4 having amino acid sequences of the FR1 and the FR4 as set forth in SEQ ID NO: 142. In some embodiments, the sdAb provided herein comprises a 1-R2 and a 1-R3 having amino acid sequences of the FR2 and the FR3 as set forth in SEQ ID NO: 142. In some embodiments, the sdAb provided herein comprises a FR2 and a FR4 having amino acid sequences of the FR2 and the FR4 as set forth in SEQ ID NO: 142. In some embodiments, the sdAb provided herein comprises a FR3 and a FR4 having amino acid sequences of the FR3 and the FR4 as set forth in SEQ ID NO: 142. In some embodiments, the sdAb provided herein comprises a FR1, a FR2, and a FR3 having amino acid sequences of the FR1, the FR2, and the FR3 as set forth in SEQ ID NO: 142. In some embodiments, the sdAb provided herein comprises a FR1, a FR2, and a FR4 having amino acid sequences of the FR1, the FR2, and the FR4 as set forth in SEQ ID NO: 142. In some embodiments, the sdAb provided herein comprises a FR1, a FR3, and a FR4 having amino acid sequences of the FR1, the FR3, and the FR4 as set forth in SEQ ID NO: 142. In some embodiments, the sdAb provided herein comprises a FR2, a FR3, and a FR4 having amino acid sequences of the FR2, the FR3, and the FR4 as set forth in SEQ ID NO: 142. In a specific embodiment, the sdAb provided herein comprises a FR1, a FR2, a FR3, and a FR4 having amino acid sequences of the FR1, the FR2, the FR3, and the FR4 as set forth in SEQ ID NO: 142.

In some embodiments, the sdAb provided herein comprises a FR1 having an amino acid sequence of the FR1 as set forth in SEQ ID NO: 143. In some embodiments, the sdAb provided herein comprises a FR2 having an amino acid sequence of the FR2 as set forth in SEQ ID NO: 143. In some embodiments, the sdAb provided herein comprises a FR3 having an amino acid sequence of the FR3 as set forth in SEQ ID NO: 143. In some embodiments, the sdAb provided herein comprises a FR4 having an amino acid sequence of the FR4 as set forth in SEQ ID NO: 143. In some embodiments, the sdAb provided herein comprises a FR1 and a FR2 having amino acid sequences of the FR1 and the 1-R2 as set forth in SEQ ID NO: 143. In some embodiments, the sdAb provided herein comprises a FR1 and a FR3 having amino acid sequences of the FR1 and the FR3 as set forth in SEQ ID NO: 143. In some embodiments, the sdAb provided herein comprises a FR1 and a FR4 having amino acid sequences of the FR1 and the FR4 as set forth in SEQ ID NO: 143. In some embodiments, the sdAb provided herein comprises a FR2 and a 1-R3 having amino acid sequences of the FR2 and the FR3 as set forth in SEQ ID NO: 143. In some embodiments, the sdAb provided herein comprises a FR2 and a FR4 having amino acid sequences of the FR2 and the FR4 as set forth in SEQ ID NO: 143. In some embodiments, the sdAb provided herein comprises a FR3 and a FR4 having amino acid sequences of the FR3 and the FR4 as set forth in SEQ ID NO: 143. In some embodiments, the sdAb provided herein comprises a FR1, a FR2, and a FR3 having amino acid sequences of the FR1, the FR2, and the FR3 as set forth in SEQ ID NO: 143. In some embodiments, the sdAb provided herein comprises a FR1, a FR2, and a FR4 having amino acid sequences of the FR1, the FR2, and the FR4 as set forth in SEQ ID NO: 143. In some embodiments, the sdAb provided herein comprises a FR1, a FR3, and a FR4 having amino acid sequences of the FR1, the FR3, and the FR4 as set forth in SEQ ID NO: 143. In some embodiments, the sdAb provided herein comprises a FR2, a FR3, and a FR4 having amino acid sequences of the FR2, the FR3, and the FR4 as set forth in SEQ ID NO: 143. In a specific embodiment, the sdAb provided herein comprises a FR1, a FR2, a FR3, and a FR4 having amino acid sequences of the FR1, the FR2, the FR3, and the FR4 as set forth in SEQ ID NO: 143.

In some embodiments, the sdAb provided herein comprises a FR1 having an amino acid sequence of the FR1 as set forth in SEQ ID NO: 144. In some embodiments, the sdAb provided herein comprises a FR2 having an amino acid sequence of the FR2 as set forth in SEQ ID NO: 144. In some embodiments, the sdAb provided herein comprises a FR3 having an amino acid sequence of the FR3 as set forth in SEQ ID NO: 144. In some embodiments, the sdAb provided herein comprises a FR4 having an amino acid sequence of the FR4 as set forth in SEQ ID NO: 144. In some embodiments, the sdAb provided herein comprises a FR1 and a FR2 having amino acid sequences of the FR1 and the FR2 as set forth in SEQ ID NO: 144. In some embodiments, the sdAb provided herein comprises a FR1 and a FR3 having amino acid sequences of the FR1 and the FR3 as set forth in SEQ ID NO: 144. In some embodiments, the sdAb provided herein comprises a FR1 and a FR4 having amino acid sequences of the FR1 and the FR4 as set forth in SEQ ID NO: 144. In some embodiments, the sdAb provided herein comprises a FR2 and a FR3 having amino acid sequences of the FR2 and the FR3 as set forth in SEQ ID NO: 144. In some embodiments, the sdAb provided herein comprises a FR2 and a FR4 having amino acid sequences of the FR2 and the FR4 as set forth in SEQ ID NO: 144. In some embodiments, the sdAb provided herein comprises a FR3 and a FR4 having amino acid sequences of the FR3 and the FR4 as set forth in SEQ ID NO: 144. In some embodiments, the sdAb provided herein comprises a FR1, a FR2, and a FR3 having amino acid sequences of the FR1, the FR2, and the FR3 as set forth in SEQ ID NO: 144. In some embodiments, the sdAb provided herein comprises a FR1, a FR2, and a FR4 having amino acid sequences of the FR1, the FR2, and the FR4 as set forth in SEQ ID NO: 144. In some embodiments, the sdAb provided herein comprises a FR1, a FR3, and a FR4 having amino acid sequences of the FR1, the FR3, and the FR4 as set forth in SEQ ID NO: 144. In some embodiments, the sdAb provided herein comprises a FR2, a FR3, and a FR4 having amino acid sequences of the FR2, the FR3, and the FR4 as set forth in SEQ ID NO: 144. In a specific embodiment, the sdAb provided herein comprises a FR1, a FR2, a FR3, and a FR4 having amino acid sequences of the FR1, the FR2, the FR3, and the FR4 as set forth in SEQ ID NO: 144.

In some embodiments, the sdAb provided herein comprises a FR1 having an amino acid sequence of the FR1 as set forth in SEQ ID NO: 145. In some embodiments, the sdAb provided herein comprises a FR2 having an amino acid sequence of the FR2 as set forth in SEQ ID NO: 145. In some embodiments, the sdAb provided herein comprises a FR3 having an amino acid sequence of the FR3 as set forth in SEQ ID NO: 145. In some embodiments, the sdAb provided herein comprises a FR4 having an amino acid sequence of the FR4 as set forth in SEQ ID NO: 145. In some embodiments, the sdAb provided herein comprises a FR1 and a FR2 having amino acid sequences of the FR1 and the FR2 as set forth in SEQ ID NO: 145. In some embodiments, the sdAb provided herein comprises a FR1 and a FR3 having amino acid sequences of the FR1 and the FR3 as set forth in SEQ ID NO: 145. In some embodiments, the sdAb provided herein comprises a FR1 and a FR4 having amino acid sequences of the FR1 and the FR4 as set forth in SEQ ID NO: 145. In some embodiments, the sdAb provided herein comprises a FR2 and a FR3 having amino acid sequences of the FR2 and the FR3 as set forth in SEQ ID NO: 145. In some embodiments, the sdAb provided herein comprises a FR2 and a FR4 having amino acid sequences of the FR2 and the FR4 as set forth in SEQ ID NO: 145. In some embodiments, the sdAb provided herein comprises a FR3 and a FR4 having amino acid sequences of the FR3 and the FR4 as set forth in SEQ ID NO: 145. In some embodiments, the sdAb provided herein comprises a FR1, a FR2, and a FR3 having amino acid sequences of the FR1, the FR2, and the FR3 as set forth in SEQ ID NO: 145. In some embodiments, the sdAb provided herein comprises a FR1, a FR2, and a FR4 having amino acid sequences of the FR1, the FR2, and the FR4 as set forth in SEQ ID NO: 145. In some embodiments, the sdAb provided herein comprises a FR1, a FR3, and a FR4 having amino acid sequences of the FR1, the FR3, and the FR4 as set forth in SEQ ID NO: 145. In some embodiments, the sdAb provided herein comprises a FR2, a FR3, and a FR4 having amino acid sequences of the FR2, the FR3, and the FR4 as set forth in SEQ ID NO: 145. In a specific embodiment, the sdAb provided herein comprises a FR1, a FR2, a FR3, and a FR4 having amino acid sequences of the FR1, the FR2, the FR3, and the FR4 as set forth in SEQ ID NO: 145.

In some embodiments, the sdAb provided herein comprises a FR1 having an amino acid sequence of the FR1 as set forth in SEQ ID NO: 146. In some embodiments, the sdAb provided herein comprises a FR2 having an amino acid sequence of the FR2 as set forth in SEQ ID NO: 146. In some embodiments, the sdAb provided herein comprises a FR3 having an amino acid sequence of the FR3 as set forth in SEQ ID NO: 146. In some embodiments, the sdAb provided herein comprises a FR4 having an amino acid sequence of the FR4 as set forth in SEQ ID NO: 146. In some embodiments, the sdAb provided herein comprises a FR1 and a FR2 having amino acid sequences of the FR1 and the 1-R2 as set forth in SEQ ID NO: 146. In some embodiments, the sdAb provided herein comprises a FR1 and a FR3 having amino acid sequences of the FR1 and the FR3 as set forth in SEQ ID NO: 146. In some embodiments, the sdAb provided herein comprises a FR1 and a FR4 having amino acid sequences of the FR1 and the FR4 as set forth in SEQ ID NO: 146. In some embodiments, the sdAb provided herein comprises a FR2 and a 1-R3 having amino acid sequences of the FR2 and the FR3 as set forth in SEQ ID NO: 146. In some embodiments, the sdAb provided herein comprises a FR2 and a FR4 having amino acid sequences of the FR2 and the FR4 as set forth in SEQ ID NO: 146. In some embodiments, the sdAb provided herein comprises a FR3 and a FR4 having amino acid sequences of the FR3 and the FR4 as set forth in SEQ ID NO: 146. In some embodiments, the sdAb provided herein comprises a FR1, a FR2, and a FR3 having amino acid sequences of the FR1, the FR2, and the FR3 as set forth in SEQ ID NO: 146. In some embodiments, the sdAb provided herein comprises a FR1, a FR2, and a FR4 having amino acid sequences of the FR1, the FR2, and the FR4 as set forth in SEQ ID NO: 146. In some embodiments, the sdAb provided herein comprises a FR1, a FR3, and a FR4 having amino acid sequences of the FR1, the FR3, and the FR4 as set forth in SEQ ID NO: 146. In some embodiments, the sdAb provided herein comprises a FR2, a FR3, and a FR4 having amino acid sequences of the FR2, the FR3, and the FR4 as set forth in SEQ ID NO: 146. In a specific embodiment, the sdAb provided herein comprises a FR1, a FR2, a FR3, and a FR4 having amino acid sequences of the FR1, the FR2, the FR3, and the FR4 as set forth in SEQ ID NO: 146.

In some embodiments, the sdAb provided herein comprises a FR1 having an amino acid sequence of the FR1 as set forth in SEQ ID NO: 147. In some embodiments, the sdAb provided herein comprises a FR2 having an amino acid sequence of the FR2 as set forth in SEQ ID NO: 147. In some embodiments, the sdAb provided herein comprises a FR3 having an amino acid sequence of the FR3 as set forth in SEQ ID NO: 147. In some embodiments, the sdAb provided herein comprises a FR4 having an amino acid sequence of the FR4 as set forth in SEQ ID NO: 147. In some embodiments, the sdAb provided herein comprises a FR1 and a FR2 having amino acid sequences of the FR1 and the FR2 as set forth in SEQ ID NO: 147. In some embodiments, the sdAb provided herein comprises a FR1 and a FR3 having amino acid sequences of the FR1 and the FR3 as set forth in SEQ ID NO: 147. In some embodiments, the sdAb provided herein comprises a FR1 and a FR4 having amino acid sequences of the FR1 and the FR4 as set forth in SEQ ID NO: 147. In some embodiments, the sdAb provided herein comprises a FR2 and a FR3 having amino acid sequences of the FR2 and the FR3 as set forth in SEQ ID NO: 147. In some embodiments, the sdAb provided herein comprises a FR2 and a FR4 having amino acid sequences of the FR2 and the FR4 as set forth in SEQ ID NO: 147. In some embodiments, the sdAb provided herein comprises a FR3 and a FR4 having amino acid sequences of the FR3 and the FR4 as set forth in SEQ ID NO: 147. In some embodiments, the sdAb provided herein comprises a FR1, a FR2, and a FR3 having amino acid sequences of the FR1, the FR2, and the FR3 as set forth in SEQ ID NO: 147. In some embodiments, the sdAb provided herein comprises a FR1, a FR2, and a FR4 having amino acid sequences of the FR1, the FR2, and the FR4 as set forth in SEQ ID NO: 147. In some embodiments, the sdAb provided herein comprises a FR1, a FR3, and a FR4 having amino acid sequences of the FR1, the FR3, and the FR4 as set forth in SEQ ID NO: 147. In some embodiments, the sdAb provided herein comprises a FR2, a FR3, and a FR4 having amino acid sequences of the FR2, the FR3, and the FR4 as set forth in SEQ ID NO: 147. In a specific embodiment, the sdAb provided herein comprises a FR1, a FR2, a FR3, and a FR4 having amino acid sequences of the FR1, the FR2, the FR3, and the FR4 as set forth in SEQ ID NO: 147.

In some embodiments, the sdAb provided herein comprises a FR1 having an amino acid sequence of the FR1 as set forth in SEQ ID NO: 148. In some embodiments, the sdAb provided herein comprises a FR2 having an amino acid sequence of the FR2 as set forth in SEQ ID NO: 148. In some embodiments, the sdAb provided herein comprises a FR3 having an amino acid sequence of the FR3 as set forth in SEQ ID NO: 148. In some embodiments, the sdAb provided herein comprises a FR4 having an amino acid sequence of the FR4 as set forth in SEQ ID NO: 148. In some embodiments, the sdAb provided herein comprises a FR1 and a FR2 having amino acid sequences of the FR1 and the FR2 as set forth in SEQ ID NO: 148. In some embodiments, the sdAb provided herein comprises a FR1 and a FR3 having amino acid sequences of the FR1 and the FR3 as set forth in SEQ ID NO: 148. In some embodiments, the sdAb provided herein comprises a FR1 and a FR4 having amino acid sequences of the FR1 and the FR4 as set forth in SEQ ID NO: 148. In some embodiments, the sdAb provided herein comprises a FR2 and a FR3 having amino acid sequences of the FR2 and the FR3 as set forth in SEQ ID NO: 148. In some embodiments, the sdAb provided herein comprises a FR2 and a FR4 having amino acid sequences of the FR2 and the FR4 as set forth in SEQ ID NO: 148. In some embodiments, the sdAb provided herein comprises a FR3 and a FR4 having amino acid sequences of the FR3 and the FR4 as set forth in SEQ ID NO: 148. In some embodiments, the sdAb provided herein comprises a FR1, a FR2, and a FR3 having amino acid sequences of the FR1, the FR2, and the FR3 as set forth in SEQ ID NO: 148. In some embodiments, the sdAb provided herein comprises a FR1, a FR2, and a FR4 having amino acid sequences of the FR1, the FR2, and the FR4 as set forth in SEQ ID NO: 148. In some embodiments, the sdAb provided herein comprises a FR1, a FR3, and a FR4 having amino acid sequences of the FR1, the FR3, and the FR4 as set forth in SEQ ID NO: 148. In some embodiments, the sdAb provided herein comprises a FR2, a FR3, and a FR4 having amino acid sequences of the FR2, the FR3, and the FR4 as set forth in SEQ ID NO: 148. In a specific embodiment, the sdAb provided herein comprises a FR1, a FR2, a FR3, and a FR4 having amino acid sequences of the FR1, the FR2, the FR3, and the FR4 as set forth in SEQ ID NO: 148.

In some embodiments, the sdAb provided herein comprises a FR1 having an amino acid sequence of the FR1 as set forth in SEQ ID NO: 149. In some embodiments, the sdAb provided herein comprises a FR2 having an amino acid sequence of the FR2 as set forth in SEQ ID NO: 149. In some embodiments, the sdAb provided herein comprises a FR3 having an amino acid sequence of the FR3 as set forth in SEQ ID NO: 149. In some embodiments, the sdAb provided herein comprises a FR4 having an amino acid sequence of the FR4 as set forth in SEQ ID NO: 149. In some embodiments, the sdAb provided herein comprises a FR1 and a FR2 having amino acid sequences of the FR1 and the FR2 as set forth in SEQ ID NO: 149. In some embodiments, the sdAb provided herein comprises a FR1 and a FR3 having amino acid sequences of the FR1 and the FR3 as set forth in SEQ ID NO: 149. In some embodiments, the sdAb provided herein comprises a FR1 and a FR4 having amino acid sequences of the FR1 and the FR4 as set forth in SEQ ID NO: 149. In some embodiments, the sdAb provided herein comprises a 1-R2 and a 1-R3 having amino acid sequences of the FR2 and the FR3 as set forth in SEQ ID NO: 149. In some embodiments, the sdAb provided herein comprises a FR2 and a FR4 having amino acid sequences of the FR2 and the FR4 as set forth in SEQ ID NO: 149. In some embodiments, the sdAb provided herein comprises a FR3 and a FR4 having amino acid sequences of the FR3 and the FR4 as set forth in SEQ ID NO: 149. In some embodiments, the sdAb provided herein comprises a FR1, a FR2, and a FR3 having amino acid sequences of the FR1, the FR2, and the FR3 as set forth in SEQ ID NO: 149. In some embodiments, the sdAb provided herein comprises a FR1, a FR2, and a FR4 having amino acid sequences of the FR1, the FR2, and the FR4 as set forth in SEQ ID NO: 149. In some embodiments, the sdAb provided herein comprises a FR1, a FR3, and a FR4 having amino acid sequences of the FR1, the FR3, and the FR4 as set forth in SEQ ID NO: 149. In some embodiments, the sdAb provided herein comprises a FR2, a FR3, and a FR4 having amino acid sequences of the FR2, the FR3, and the FR4 as set forth in SEQ ID NO: 149. In a specific embodiment, the sdAb provided herein comprises a FR1, a FR2, a FR3, and a FR4 having amino acid sequences of the FR1, the FR2, the FR3, and the FR4 as set forth in SEQ ID NO: 149.

In some embodiments, the sdAb provided herein comprises a FR1 having an amino acid sequence of the FR1 as set forth in SEQ ID NO: 150. In some embodiments, the sdAb provided herein comprises a FR2 having an amino acid sequence of the FR2 as set forth in SEQ ID NO: 150. In some embodiments, the sdAb provided herein comprises a FR3 having an amino acid sequence of the FR3 as set forth in SEQ ID NO: 150. In some embodiments, the sdAb provided herein comprises a FR4 having an amino acid sequence of the FR4 as set forth in SEQ ID NO: 150. In some embodiments, the sdAb provided herein comprises a FR1 and a FR2 having amino acid sequences of the FR1 and the 1-R2 as set forth in SEQ ID NO: 150. In some embodiments, the sdAb provided herein comprises a FR1 and a FR3 having amino acid sequences of the FR1 and the FR3 as set forth in SEQ ID NO: 150. In some embodiments, the sdAb provided herein comprises a FR1 and a FR4 having amino acid sequences of the FR1 and the FR4 as set forth in SEQ ID NO: 150. In some embodiments, the sdAb provided herein comprises a FR2 and a FR3 having amino acid sequences of the FR2 and the FR3 as set forth in SEQ ID NO: 150. In some embodiments, the sdAb provided herein comprises a FR2 and a FR4 having amino acid sequences of the FR2 and the FR4 as set forth in SEQ ID NO: 150. In some embodiments, the sdAb provided herein comprises a FR3 and a FR4 having amino acid sequences of the FR3 and the FR4 as set forth in SEQ ID NO: 150. In some embodiments, the sdAb provided herein comprises a FR1, a FR2, and a FR3 having amino acid sequences of the FR1, the FR2, and the FR3 as set forth in SEQ ID NO: 150. In some embodiments, the sdAb provided herein comprises a FR1, a FR2, and a FR4 having amino acid sequences of the FR1, the FR2, and the FR4 as set forth in SEQ ID NO: 150. In some embodiments, the sdAb provided herein comprises a FR1, a FR3, and a FR4 having amino acid sequences of the FR1, the FR3, and the FR4 as set forth in SEQ ID NO: 150. In some embodiments, the sdAb provided herein comprises a FR2, a FR3, and a FR4 having amino acid sequences of the FR2, the FR3, and the FR4 as set forth in SEQ ID NO: 150. In a specific embodiment, the sdAb provided herein comprises a FR1, a FR2, a FR3, and a FR4 having amino acid sequences of the FR1, the FR2, the FR3, and the FR4 as set forth in SEQ ID NO: 150.

In some embodiments, the sdAb provided herein comprises a FR1 having an amino acid sequence of the FR1 as set forth in SEQ ID NO: 151. In some embodiments, the sdAb provided herein comprises a FR2 having an amino acid sequence of the FR2 as set forth in SEQ ID NO: 151. In some embodiments, the sdAb provided herein comprises a FR3 having an amino acid sequence of the FR3 as set forth in SEQ ID NO: 151. In some embodiments, the sdAb provided herein comprises a FR4 having an amino acid sequence of the FR4 as set forth in SEQ ID NO: 151. In some embodiments, the sdAb provided herein comprises a FR1 and a FR2 having amino acid sequences of the FR1 and the FR2 as set forth in SEQ ID NO: 151. In some embodiments, the sdAb provided herein comprises a FR1 and a FR3 having amino acid sequences of the FR1 and the FR3 as set forth in SEQ ID NO: 151. In some embodiments, the sdAb provided herein comprises a FR1 and a FR4 having amino acid sequences of the FR1 and the FR4 as set forth in SEQ ID NO: 151. In some embodiments, the sdAb provided herein comprises a FR2 and a FR3 having amino acid sequences of the FR2 and the FR3 as set forth in SEQ ID NO: 151. In some embodiments, the sdAb provided herein comprises a FR2 and a FR4 having amino acid sequences of the FR2 and the FR4 as set forth in SEQ ID NO: 151. In some embodiments, the sdAb provided herein comprises a FR3 and a FR4 having amino acid sequences of the FR3 and the FR4 as set forth in SEQ ID NO: 151. In some embodiments, the sdAb provided herein comprises a FR1, a FR2, and a FR3 having amino acid sequences of the FR1, the FR2, and the FR3 as set forth in SEQ ID NO: 151. In some embodiments, the sdAb provided herein comprises a FR1, a FR2, and a FR4 having amino acid sequences of the FR1, the FR2, and the FR4 as set forth in SEQ ID NO: 151. In some embodiments, the sdAb provided herein comprises a FR1, a FR3, and a FR4 having amino acid sequences of the FR1, the FR3, and the FR4 as set forth in SEQ ID NO: 151. In some embodiments, the sdAb provided herein comprises a FR2, a FR3, and a FR4 having amino acid sequences of the FR2, the FR3, and the FR4 as set forth in SEQ ID NO: 151. In a specific embodiment, the sdAb provided herein comprises a FR1, a FR2, a FR3, and a FR4 having amino acid sequences of the FR1, the FR2, the FR3, and the FR4 as set forth in SEQ ID NO: 151.

In some embodiments, the sdAb provided herein comprises a FR1 having an amino acid sequence of the FR1 as set forth in SEQ ID NO: 152. In some embodiments, the sdAb provided herein comprises a FR2 having an amino acid sequence of the FR2 as set forth in SEQ ID NO: 152. In some embodiments, the sdAb provided herein comprises a FR3 having an amino acid sequence of the FR3 as set forth in SEQ ID NO: 152. In some embodiments, the sdAb provided herein comprises a FR4 having an amino acid sequence of the FR4 as set forth in SEQ ID NO: 152. In some embodiments, the sdAb provided herein comprises a FR1 and a FR2 having amino acid sequences of the FR1 and the FR2 as set forth in SEQ ID NO: 152. In some embodiments, the sdAb provided herein comprises a FR1 and a FR3 having amino acid sequences of the FR1 and the FR3 as set forth in SEQ ID NO: 152. In some embodiments, the sdAb provided herein comprises a FR1 and a FR4 having amino acid sequences of the FR1 and the FR4 as set forth in SEQ ID NO: 152. In some embodiments, the sdAb provided herein comprises a FR2 and a FR3 having amino acid sequences of the FR2 and the FR3 as set forth in SEQ ID NO: 152. In some embodiments, the sdAb provided herein comprises a FR2 and a FR4 having amino acid sequences of the FR2 and the FR4 as set forth in SEQ ID NO: 152. In some embodiments, the sdAb provided herein comprises a FR3 and a FR4 having amino acid sequences of the FR3 and the FR4 as set forth in SEQ ID NO: 152. In some embodiments, the sdAb provided herein comprises a FR1, a FR2, and a FR3 having amino acid sequences of the FR1, the FR2, and the FR3 as set forth in SEQ ID NO: 152. In some embodiments, the sdAb provided herein comprises a FR1, a FR2, and a FR4 having amino acid sequences of the FR1, the FR2, and the FR4 as set forth in SEQ ID NO: 152. In some embodiments, the sdAb provided herein comprises a FR1, a FR3, and a FR4 having amino acid sequences of the FR1, the FR3, and the FR4 as set forth in SEQ ID NO: 152. In some embodiments, the sdAb provided herein comprises a FR2, a FR3, and a FR4 having amino acid sequences of the FR2, the FR3, and the FR4 as set forth in SEQ ID NO: 152. In a specific embodiment, the sdAb provided herein comprises a FR1, a FR2, a FR3, and a FR4 having amino acid sequences of the FR1, the FR2, the FR3, and the FR4 as set forth in SEQ ID NO: 152.

In some embodiments, the sdAb provided herein comprises a FR1 having an amino acid sequence of the FR1 as set forth in SEQ ID NO: 153. In some embodiments, the sdAb provided herein comprises a FR2 having an amino acid sequence of the FR2 as set forth in SEQ ID NO: 153. In some embodiments, the sdAb provided herein comprises a FR3 having an amino acid sequence of the FR3 as set forth in SEQ ID NO: 153. In some embodiments, the sdAb provided herein comprises a FR4 having an amino acid sequence of the FR4 as set forth in SEQ ID NO: 153. In some embodiments, the sdAb provided herein comprises a FR1 and a FR2 having amino acid sequences of the FR1 and the 1-R2 as set forth in SEQ ID NO: 153. In some embodiments, the sdAb provided herein comprises a FR1 and a FR3 having amino acid sequences of the FR1 and the FR3 as set forth in SEQ ID NO: 153. In some embodiments, the sdAb provided herein comprises a FR1 and a FR4 having amino acid sequences of the FR1 and the FR4 as set forth in SEQ ID NO: 153. In some embodiments, the sdAb provided herein comprises a 1-R2 and a 1-R3 having amino acid sequences of the FR2 and the FR3 as set forth in SEQ ID NO: 153. In some embodiments, the sdAb provided herein comprises a FR2 and a FR4 having amino acid sequences of the FR2 and the FR4 as set forth in SEQ ID NO: 153. In some embodiments, the sdAb provided herein comprises a FR3 and a FR4 having amino acid sequences of the FR3 and the FR4 as set forth in SEQ ID NO: 153. In some embodiments, the sdAb provided herein comprises a FR1, a FR2, and a FR3 having amino acid sequences of the FR1, the FR2, and the FR3 as set forth in SEQ ID NO: 153. In some embodiments, the sdAb provided herein comprises a FR1, a FR2, and a FR4 having amino acid sequences of the FR1, the FR2, and the FR4 as set forth in SEQ ID NO: 153. In some embodiments, the sdAb provided herein comprises a FR1, a FR3, and a FR4 having amino acid sequences of the FR1, the FR3, and the FR4 as set forth in SEQ ID NO: 153. In some embodiments, the sdAb provided herein comprises a FR2, a FR3, and a FR4 having amino acid sequences of the FR2, the FR3, and the FR4 as set forth in SEQ ID NO: 153. In a specific embodiment, the sdAb provided herein comprises a FR1, a FR2, a FR3, and a FR4 having amino acid sequences of the FR1, the FR2, the FR3, and the FR4 as set forth in SEQ ID NO: 153.

In some embodiments, the sdAb provided herein comprises a FR1 having an amino acid sequence of the FR1 as set forth in SEQ ID NO: 154. In some embodiments, the sdAb provided herein comprises a FR2 having an amino acid sequence of the FR2 as set forth in SEQ ID NO: 154. In some embodiments, the sdAb provided herein comprises a FR3 having an amino acid sequence of the FR3 as set forth in SEQ ID NO: 154. In some embodiments, the sdAb provided herein comprises a FR4 having an amino acid sequence of the FR4 as set forth in SEQ ID NO: 154. In some embodiments, the sdAb provided herein comprises a FR1 and a FR2 having amino acid sequences of the FR1 and the 1-R2 as set forth in SEQ ID NO: 154. In some embodiments, the sdAb provided herein comprises a FR1 and a FR3 having amino acid sequences of the FR1 and the FR3 as set forth in SEQ ID NO: 154. In some embodiments, the sdAb provided herein comprises a FR1 and a FR4 having amino acid sequences of the FR1 and the FR4 as set forth in SEQ ID NO: 154. In some embodiments, the sdAb provided herein comprises a FR2 and a 1-R3 having amino acid sequences of the FR2 and the FR3 as set forth in SEQ ID NO: 154. In some embodiments, the sdAb provided herein comprises a FR2 and a FR4 having amino acid sequences of the FR2 and the FR4 as set forth in SEQ ID NO: 154. In some embodiments, the sdAb provided herein comprises a FR3 and a FR4 having amino acid sequences of the FR3 and the FR4 as set forth in SEQ ID NO: 154. In some embodiments, the sdAb provided herein comprises a FR1, a FR2, and a FR3 having amino acid sequences of the FR1, the FR2, and the FR3 as set forth in SEQ ID NO: 154. In some embodiments, the sdAb provided herein comprises a FR1, a FR2, and a FR4 having amino acid sequences of the FR1, the FR2, and the FR4 as set forth in SEQ ID NO: 154. In some embodiments, the sdAb provided herein comprises a FR1, a FR3, and a FR4 having amino acid sequences of the FR1, the FR3, and the FR4 as set forth in SEQ ID NO: 154. In some embodiments, the sdAb provided herein comprises a FR2, a FR3, and a FR4 having amino acid sequences of the FR2, the FR3, and the FR4 as set forth in SEQ ID NO: 154. In a specific embodiment, the sdAb provided herein comprises a FR1, a FR2, a FR3, and a FR4 having amino acid sequences of the FR1, the FR2, the FR3, and the FR4 as set forth in SEQ ID NO: 154.

In some embodiments, the sdAb provided herein comprises a FR1 having an amino acid sequence of the FR1 as set forth in SEQ ID NO: 155. In some embodiments, the sdAb provided herein comprises a FR2 having an amino acid sequence of the FR2 as set forth in SEQ ID NO: 155. In some embodiments, the sdAb provided herein comprises a FR3 having an amino acid sequence of the FR3 as set forth in SEQ ID NO: 155. In some embodiments, the sdAb provided herein comprises a FR4 having an amino acid sequence of the FR4 as set forth in SEQ ID NO: 155. In some embodiments, the sdAb provided herein comprises a FR1 and a FR2 having amino acid sequences of the FR1 and the 1-R2 as set forth in SEQ ID NO: 155. In some embodiments, the sdAb provided herein comprises a FR1 and a FR3 having amino acid sequences of the FR1 and the FR3 as set forth in SEQ ID NO: 155. In some embodiments, the sdAb provided herein comprises a FR1 and a FR4 having amino acid sequences of the FR1 and the FR4 as set forth in SEQ ID NO: 155. In some embodiments, the sdAb provided herein comprises a FR2 and a 1-R3 having amino acid sequences of the FR2 and the FR3 as set forth in SEQ ID NO: 155. In some embodiments, the sdAb provided herein comprises a FR2 and a FR4 having amino acid sequences of the FR2 and the FR4 as set forth in SEQ ID NO: 155. In some embodiments, the sdAb provided herein comprises a FR3 and a FR4 having amino acid sequences of the FR3 and the FR4 as set forth in SEQ ID NO: 155. In some embodiments, the sdAb provided herein comprises a FR1, a FR2, and a FR3 having amino acid sequences of the FR1, the FR2, and the FR3 as set forth in SEQ ID NO: 155. In some embodiments, the sdAb provided herein comprises a FR1, a FR2, and a FR4 having amino acid sequences of the FR1, the FR2, and the FR4 as set forth in SEQ ID NO: 155. In some embodiments, the sdAb provided herein comprises a FR1, a FR3, and a FR4 having amino acid sequences of the FR1, the FR3, and the FR4 as set forth in SEQ ID NO: 155. In some embodiments, the sdAb provided herein comprises a FR2, a FR3, and a FR4 having amino acid sequences of the FR2, the FR3, and the FR4 as set forth in SEQ ID NO: 155. In a specific embodiment, the sdAb provided herein comprises a FR1, a FR2, a FR3, and a FR4 having amino acid sequences of the FR1, the FR2, the FR3, and the FR4 as set forth in SEQ ID NO: 155.

In some embodiments, the sdAb provided herein comprises a FR1 having an amino acid sequence of the FR1 as set forth in SEQ ID NO: 156. In some embodiments, the sdAb provided herein comprises a FR2 having an amino acid sequence of the FR2 as set forth in SEQ ID NO: 156. In some embodiments, the sdAb provided herein comprises a FR3 having an amino acid sequence of the FR3 as set forth in SEQ ID NO: 156. In some embodiments, the sdAb provided herein comprises a FR4 having an amino acid sequence of the FR4 as set forth in SEQ ID NO: 156. In some embodiments, the sdAb provided herein comprises a FR1 and a FR2 having amino acid sequences of the FR1 and the 1-R2 as set forth in SEQ ID NO: 156. In some embodiments, the sdAb provided herein comprises a FR1 and a FR3 having amino acid sequences of the FR1 and the FR3 as set forth in SEQ ID NO: 156. In some embodiments, the sdAb provided herein comprises a FR1 and a FR4 having amino acid sequences of the FR1 and the FR4 as set forth in SEQ ID NO: 156. In some embodiments, the sdAb provided herein comprises a 1-R2 and a 1-R3 having amino acid sequences of the FR2 and the FR3 as set forth in SEQ ID NO: 156. In some embodiments, the sdAb provided herein comprises a FR2 and a FR4 having amino acid sequences of the FR2 and the FR4 as set forth in SEQ ID NO: 156. In some embodiments, the sdAb provided herein comprises a FR3 and a FR4 having amino acid sequences of the FR3 and the FR4 as set forth in SEQ ID NO: 156. In some embodiments, the sdAb provided herein comprises a FR1, a FR2, and a FR3 having amino acid sequences of the FR1, the FR2, and the FR3 as set forth in SEQ ID NO: 156. In some embodiments, the sdAb provided herein comprises a FR1, a FR2, and a FR4 having amino acid sequences of the FR1, the FR2, and the FR4 as set forth in SEQ ID NO: 156. In some embodiments, the sdAb provided herein comprises a FR1, a FR3, and a FR4 having amino acid sequences of the FR1, the FR3, and the FR4 as set forth in SEQ ID NO: 156. In some embodiments, the sdAb provided herein comprises a FR2, a FR3, and a FR4 having amino acid sequences of the FR2, the FR3, and the FR4 as set forth in SEQ ID NO: 156. In a specific embodiment, the sdAb provided herein comprises a FR1, a FR2, a FR3, and a FR4 having amino acid sequences of the FR1, the FR2, the FR3, and the FR4 as set forth in SEQ ID NO: 156.

In some embodiments, the sdAb provided herein is a humanized sdAb comprising one or more humanized FR sequences in Table 11. More detailed description of the humanized sdAbs provided herein is provided below.

Framework regions described herein are determined based upon the boundaries of the CDR numbering system. In other words, if the CDRs are determined by, e.g., Kabat, IMGT, or Chothia, then the framework regions are the amino acid residues surrounding the CDRs in the variable region in the format, from the N-terminus to C-terminus: FR1-CDR1-FR2-CDR2-FR3-CDR3-FR4. For example, FR1 is defined as the amino acid residues N-terminal to the CDR1 amino acid residues as defined by, e.g., the Kabat numbering system, the IMGT numbering system, or the Chothia numbering system, FR2 is defined as the amino acid residues between CDR1 and CDR2 amino acid residues as defined by, e.g., the Kabat numbering system, the IMGT numbering system, or the Chothia numbering system, FR3 is defined as the amino acid residues between CDR2 and CDR3 amino acid residues as defined by, e.g., the Kabat numbering system, the IMGT numbering system, or the Chothia numbering system, and FR4 is defined as the amino acid residues C-terminal to the CDR3 amino acid residues as defined by, e.g., the Kabat numbering system, the IMGT numbering system, or the Chothia numbering system.

In certain more specific embodiments, the sdAb comprises the VH (or VHH) sequences as set forth in Table 9 in the Examples below.

In some embodiments, the sdAb comprises an amino acid sequence of SEQ ID NO: 123.

In some embodiments, the sdAb comprises an amino acid sequence of SEQ ID NO: 124.

In some embodiments, the sdAb comprises an amino acid sequence of SEQ ID NO: 125.

In some embodiments, the sdAb comprises an amino acid sequence of SEQ ID NO: 126.

In some embodiments, the sdAb comprises an amino acid sequence of SEQ ID NO: 127.

In some embodiments, the sdAb comprises an amino acid sequence of SEQ ID NO: 128.

In some embodiments, the sdAb comprises an amino acid sequence of SEQ ID NO: 129.

In some embodiments, the sdAb comprises an amino acid sequence of SEQ ID NO: 130.

In some embodiments, the sdAb comprises an amino acid sequence of SEQ ID NO: 131.

In some embodiments, the sdAb comprises an amino acid sequence of SEQ ID NO: 132.

In some embodiments, the sdAb comprises an amino acid sequence of SEQ ID NO: 133.

In some embodiments, the sdAb comprises an amino acid sequence of SEQ ID NO: 134.

In some embodiments, the sdAb comprises an amino acid sequence of SEQ ID NO: 135.

In some embodiments, the sdAb comprises an amino acid sequence of SEQ ID NO: 136.

In some embodiments, the sdAb comprises an amino acid sequence of SEQ ID NO: 137.

In some embodiments, the sdAb comprises an amino acid sequence of SEQ ID NO: 138.

In some embodiments, the sdAb comprises an amino acid sequence of SEQ ID NO: 139.

In some embodiments, the sdAb comprises an amino acid sequence of SEQ ID NO: 140.

In some embodiments, the sdAb comprises an amino acid sequence of SEQ ID NO: 150.

In some embodiments, the sdAb comprises an amino acid sequence of SEQ ID NO: 151.

In some embodiments, the sdAb comprises an amino acid sequence of SEQ ID NO: 152.

In some embodiments, the sdAb comprises an amino acid sequence of SEQ ID NO: 153.

In some embodiments, the sdAb comprises an amino acid sequence of SEQ ID NO: 154.

In some embodiments, the sdAb comprises an amino acid sequence of SEQ ID NO: 155.

In some embodiments, the sdAb comprises an amino acid sequence of SEQ ID NO: 156.

In some embodiments, the sdAb binds to MSLN with a $K_D$ of between 0.01-100 nM. In some embodiments, the sdAb binds to MSLN with a $K_D$ of between 0.1-100 nM. In some embodiments, the sdAb binds to MSLN with a $K_D$ of between 1-100 nM. In other embodiments, the sdAb binds to MSLN with a $K_D$ of between 1-90 nM. In other embodiments, the sdAb binds to MSLN with a $K_D$ of between 1-80 nM. In other embodiments, the sdAb binds to MSLN with a $K_D$ of between 1-70 nM. In some embodiments, the sdAb binds to MSLN with a $K_D$ of between 1-60 nM. In some embodiments, the sdAb binds to MSLN with a $K_D$ of between 1-50 nM. In some embodiments, the sdAb binds to MSLN with a $K_D$ of between 1-40 nM. In some embodiments, the sdAb binds to MSLN with a $K_D$ of between 1-30 nM. In some embodiments, the sdAb binds to MSLN with a $K_D$ of between 1-20 nM. In some embodiments, the sdAb binds to MSLN with a $K_D$ of between 1-10 nM. In some embodiments, the sdAb binds to MSLN with a $K_D$ of between 0.1-1 nM. In some embodiments, the sdAb binds to MSLN with a $K_D$ of between 0.01-1 nM. In some embodiments, the sdAb binds to MSLN with a $K_D$ of between 0.01-0.1 nM.

In some embodiments, the binding molecule that binds to a cancer antigen comprises two antibodies or antigen binding fragments thereof each binding to an antigen expressed on a cancer cell. In some embodiments, the cancer cell is a solid tumor cancer cell. In some embodiments, the two antibodies or antigen binding fragments thereof are two sdAbs. In some embodiments, the two sdAbs are VHH single domain antibodies. In some embodiments, the two sdAb each bind to two different epitopes of MSLN. In some embodiments, one epitope is on the N-terminus of MSLN and the other epitope is on the C-terminus of MSLN.

In some embodiments, each of the two sdAbs binds to MSLN with a $K_D$ of between 0.01-100 nM. In some embodiments, each of the two sdAbs binds to MSLN with a $K_D$ of between 0.1-100 nM. In some embodiments, each of the two sdAbs binds to MSLN with a $K_D$ of between 1-100 nM. In some embodiments, each of the two sdAbs binds to MSLN with a $K_D$ of between 1-90 nM. In some embodiments, each of the two sdAbs binds to MSLN with a $K_D$ of between 1-80 nM. In some embodiments, each of the two sdAbs binds to MSLN with a $K_D$ of between 1-70 nM. In some embodiments, each of the two sdAbs binds to MSLN with a $K_D$ of between 1-60 nM. In other embodiments, each of the two sdAbs binds to MSLN with a $K_D$ of between 1-50 nM. In other embodiments, each of the two sdAbs binds to MSLN with a $K_D$ of between 1-40 nM. In other embodiments, each of the two sdAbs binds to MSLN with a $K_D$ of between 1-30 nM. In other embodiments, each of the two sdAbs binds to MSLN with a $K_D$ of between 1-20 nM. In other embodiments, each of the two sdAbs binds to MSLN with a $K_D$ of between 1-10 nM. In other embodiments, each of the two sdAbs binds to MSLN with a $K_D$ of between 0.1-1 nM. In some embodiments, each of the two sdAbs binds to MSLN with a $K_D$ of between 0.01-0.1 nM.

In other embodiments, the two antibodies or antigen binding fragments thereof are connected by a third linker.

In yet another aspect, provided herein are antibodies that compete with one of the single domain antibodies binding to MSLN described above. Such antibodies may also bind to the same epitope as one of the above mentioned single domain antibodies, or an overlapping epitope. Antibodies and fragments that compete with or bind to the same epitope as the above-mentioned antibodies are expected to show similar functional properties. The exemplified antigen-binding proteins and fragments include those with the VH regions, and CDRs provided herein, including those in Tables 5 and 7.

In certain embodiments, an antibody described herein or an antigen-binding fragment thereof comprises amino acid sequences with certain percent identity relative to any one of antibodies anti-MSLN-1, anti-MSLN-2, anti-MSLN-3, anti-MSLN-4, anti-MSLN-5, anti-MSLN-6, anti-MSLN-7, anti-MSLN-8, anti-MSLN-9, anti-MSLN-10, anti-MSLN-11, anti-MSLN-12, anti-MSLN-13, anti-MSLN-14, anti-MSLN-15, anti-MSLN-16, anti-MSLN-17, anti-MSLN-18, anti-MSLN-19, anti-MSLN-20, anti-MSLN-21, anti-MSLN-22, anti-MSLN-23, anti-MSLN-24, anti-MSLN-25, anti-MSLN-26, anti-MSLN-27, anti-MSLN-28, anti-MSLN-29, anti-MSLN-30, anti-MSLN-31, anti-MSLN-32, anti-MSLN-33, and anti-MSLN-34 as set forth in Table 9.

The determination of percent identity between two sequences (e.g., amino acid sequences or nucleic acid sequences) can be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecule described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 123, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 124, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 125, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 126, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 127, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 128, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 129, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 130, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 131, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 132, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 133, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 134, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 135, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 136, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 137, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 138, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 139, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 140, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 141, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 142, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 143, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 144, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 145, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 146, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 147, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 148, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 149, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 150, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 151, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 152, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 153, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 154, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 155, wherein the antibody immunospecifically binds to MSLN. In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 156, wherein the antibody immunospecifically binds to MSLN.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 123, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-1.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 124, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-2.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 125, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-3.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 126, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-4.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 127, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-5.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 128, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-6.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 129, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-7.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 130, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-8.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 131, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-9.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 132, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-10.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 133, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-11.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 134, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-12.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 135, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-13.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 136, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-14.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 137, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-15.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 138, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-16.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 139, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-17.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 140, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-18.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 141, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-19.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 142, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-20.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 143, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-21.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 144, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-22.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 145, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-23.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 146, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-24.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 147, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-25.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 148, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-26.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 149, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-27.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 150, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-28.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 151, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-29.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 152, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-30.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 153, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-31.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 154, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-32.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 155, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-33.

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 156, wherein the antibody immunospecifically binds to MSLN. In specific embodiments, such an antibody comprises CDRs (e.g., VH CDRs 1-3) identical to the CDRs (e.g., VH CDRs 1-3) of antibody anti-MSLN-34.

Humanized Single Domain Antibodies

The single domain antibodies described herein can include humanized single domain antibodies.

Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padano, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

In some embodiments, antibodies provided herein can be humanized antibodies that bind MSLN, including human MSLN. For example, humanized antibodies of the present disclosure may comprise one or more CDRs as shown in Table 4 and Table 10. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., 1986, Nature 321:522-25; Riechmann et al., 1988, Nature 332: 323-27; and Verhoeyen et al., 1988, Science 239:1534-36), by substituting hypervariable region sequences for the corresponding sequences of a human antibody.

In some cases, the humanized antibodies are constructed by CDR grafting, in which the amino acid sequences of the CDRs of the parent non-human antibody are grafted onto a human antibody framework. For example, Padlan et al. determined that only about one third of the residues in the CDRs actually contact the antigen, and termed these the "specificity determining residues," or SDRs (Padlan et al., 1995, FASEB J. 9:133-39). In the technique of SDR grafting, only the SDR residues are grafted onto the human antibody framework (see, e.g., Kashmiri et al., 2005, Methods 36:25-34).

The choice of human variable domains to be used in making the humanized antibodies can be important to reduce antigenicity. For example, according to the so-called "best-fit" method, the sequence of the variable domain of a non-human antibody is screened against the entire library of known human variable-domain sequences. The human sequence that is closest to that of the non-human antibody may be selected as the human framework for the humanized antibody (Sims et al., 1993, J. Immunol. 151:2296-308; and Chothia et al., 1987, J. Mol. Biol. 196:901-17). Another method uses a particular framework derived from the consensus sequence of all human antibodies of a particular subgroup of light or heavy chains. The same framework may be used for several different humanized antibodies (Carter et al., 1992, Proc. Natl. Acad. Sci. USA 89:4285-89; and Presta et al., 1993, J. Immunol. 151:2623-32). In some cases, the framework is derived from the consensus sequences of the most abundant human subclasses, $V_L 6$ subgroup I ($V_L 6I$) and $V_H$ subgroup III ($V_H III$). In another method, human germline genes are used as the source of the framework regions.

In an alternative paradigm based on comparison of CDRs, called superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., 2002, J. Immunol. 169:1119-25).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, 2000, Protein Eng. 13:819-24), Modeller (Sali and Blundell, 1993, J. Mol. Biol. 234:779-815), and Swiss PDB Viewer (Guex and Peitsch, 1997, Electrophoresis 18:2714-23). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes, and the differences are scored as HSC. The target sequence is then humanized by maximizing its HSC rather than using a global identity measure to generate multiple diverse humanized variants (Lazar et al., 2007, Mol. Immunol. 44:1986-98).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome, and yeast display libraries as well as by bacterial colony screening (see, e.g., Hoogenboom, 2005, Nat. Biotechnol. 23:1105-16; Dufner et al., 2006, Trends Biotechnol. 24:523-29; Feldhaus et al., 2003, Nat. Biotechnol. 21:163-70; and Schlapschy et al., 2004, Protein Eng. Des. Sel. 17:847-60).

In the FR library approach, a collection of residue variants is introduced at specific positions in the FR followed by screening of the library to select the FR that best supports the grafted CDR. The residues to be substituted may include some or all of the "Vernier" residues identified as potentially contributing to CDR structure (see, e.g., Foote and Winter, 1992, J. Mol. Biol. 224:487-99), or from the more limited set of target residues identified by Baca et al. (1997, J. Biol. Chem. 272:10678-84).

In FR shuffling, whole FRs are combined with the non-human CDRs instead of creating combinatorial libraries of selected residue variants (see, e.g., Dall'Acqua et al., 2005, Methods 36:43-60). A one-step FR shuffling process may be used. Such a process has been shown to be efficient, as the resulting antibodies exhibited improved biochemical and physicochemical properties including enhanced expression, increased affinity, and thermal stability (see, e.g., Damschroder et al., 2007, Mol. Immunol. 44:3049-60).

The "humaneering" method is based on experimental identification of essential minimum specificity determinants (MSDs) and is based on sequential replacement of non-human fragments into libraries of human FRs and assessment of binding. This methodology typically results in epitope retention and identification of antibodies from multiple subclasses with distinct human V-segment CDRs.

The "human engineering" method involves altering a non-human antibody or antibody fragment by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human antibody as "low risk," "moderate risk," or "high risk" residues. The classification is performed using a global risk/reward calculation that evaluates the predicted benefits of making particular substitution (e.g., for immunogenicity in humans) against the risk that the substitution will affect the resulting antibody's folding. The particular human amino acid residue to be substituted at a given position (e.g., low or moderate risk) of a non-human antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., 1994, Protein Engineering 7:805-14; U.S. Pat. Nos. 5,766,886; 5,770,196; 5,821,123; and 5,869,619; and PCT Publication WO 93/11794.

A composite human antibody can be generated using, for example, Composite Human Antibody™ technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody.

A deimmunized antibody is an antibody in which T-cell epitopes have been removed. Methods for making deimmunized antibodies have been described. See, e.g., Jones et al., Methods Mol Biol. 2009; 525:405-23, xiv, and De Groot et al., Cell. Immunol. 244:148-153(2006)). Deimmunized antibodies comprise T-cell epitope-depleted variable regions and human constant regions. Briefly, variable regions of an antibody are cloned and T-cell epitopes are subsequently identified by testing overlapping peptides derived from the variable regions of the antibody in a T cell proliferation assay. T cell epitopes are identified via in silico methods to identify peptide binding to human MHC class II. Mutations are introduced in the variable regions to abrogate binding to human MHC class II. Mutated variable regions are then utilized to generate the deimmunized antibody.

In a specific embodiment, the single domain antibodies provided herein are humanized single domain antibodies generated according to the method described in Example 3 below. In some embodiments, the single domain antibody provided herein are humanized single domain antibodies comprising one or more FR sequences listed in Table 11 in Example 3 below.

In some embodiments, the sdAb has one or more FR sequences of the humanized anti-MSLN-1.

In some embodiments, the humanized sdAb has a FR1 of SEQ ID NO: 157. In some embodiments, the humanized sdAb has a FR2 of SEQ ID NO: 158. In some embodiments, the humanized sdAb has a FR3 of SEQ ID NO: 159. In other embodiments, the humanized sdAb has a FR4 of SEQ ID NO: 160. In some embodiments, the humanized sdAb has a FR1 of SEQ ID NO: 157 and a FR2 of SEQ ID NO: 158. In some embodiments, the humanized sdAb has a FR1 of SEQ ID NO: 157 and a FR3 of SEQ ID NO: 159. In some embodiments, the humanized sdAb has a FR1 of SEQ ID NO: 157 and a FR4 of SEQ ID NO: 160. In some embodiments, the humanized sdAb has a FR2 of SEQ ID NO: 158 and a FR3 of SEQ ID NO: 159. In some embodiments, the humanized sdAb has a FR2 of SEQ ID NO: 158 and a FR4 of SEQ ID NO: 160. In some embodiments, the humanized sdAb has a FR3 of SEQ ID NO: 159 and a FR4 of SEQ ID NO: 160. In some embodiments, the humanized sdAb has a FR1 of SEQ ID NO: 157, a FR2 of SEQ ID NO: 158 and a FR3 of SEQ ID NO: 159. In some embodiments, the humanized sdAb has a FR1 of SEQ ID NO: 157, a FR2 of SEQ ID NO: 158 and a FR4 of SEQ ID NO: 160. In some embodiments, the humanized sdAb has a FR1 of SEQ ID NO: 157, a FR3 of SEQ ID NO: 159 and a FR4 of SEQ ID NO: 160. In some embodiments, the humanized sdAb has a FR2 of SEQ ID NO: 158, a FR3 of SEQ ID NO: 159 and a FR4 of SEQ ID NO: 160. In a specific embodiment, the humanized sdAb has a FR1 of SEQ ID NO: 157, a FR2 of SEQ ID NO: 158, a FR3 of SEQ ID NO: 159, and a FR4 of SEQ ID NO: 160.

In a specific embodiment, the humanized sdAb has a CDR1 of SEQ ID NO: 12, a CDR2 of SEQ ID NO: 13, a CDR3 of SEQ ID NO: 14, a FR1 of SEQ ID NO: 157, a FR2 of SEQ ID NO: 158, a FR3 of SEQ ID NO: 159, and a FR4 of SEQ ID NO: 160.

In some embodiments, the sdAb has one or more FR sequences of the humanized anti-MSLN-2.

In some embodiments, the humanized sdAb has a FR1 of SEQ ID NO: 161. In some embodiments, the humanized sdAb has a FR2 of SEQ ID NO: 162. In some embodiments, the humanized sdAb has a FR3 of SEQ ID NO: 163. In other embodiments, the humanized sdAb has a FR4 of SEQ ID NO: 160. In some embodiments, the humanized sdAb has a FR1 of SEQ ID NO: 161 and a FR2 of SEQ ID NO: 162. In some embodiments, the humanized sdAb has a FR1 of SEQ ID NO: 161 and a FR3 of SEQ ID NO: 163. In some embodiments, the humanized sdAb has a FR1 of SEQ ID NO: 161 and a FR4 of SEQ ID NO: 160. In some embodiments, the humanized sdAb has a FR2 of SEQ ID NO: 162 and a FR3 of SEQ ID NO: 163. In some embodiments, the humanized sdAb has a FR2 of SEQ ID NO: 162 and a FR4 of SEQ ID NO: 160. In some embodiments, the humanized sdAb has a FR3 of SEQ ID NO: 163 and a FR4 of SEQ ID NO: 160. In some embodiments, the humanized sdAb has a FR1 of SEQ ID NO: 161, a FR2 of SEQ ID NO: 162 and a FR3 of SEQ ID NO: 163. In some embodiments, the humanized sdAb has a FR1 of SEQ ID NO: 161, a FR2 of SEQ ID NO: 162 and a FR4 of SEQ ID NO: 160. In some embodiments, the humanized sdAb has a FR1 of SEQ ID NO: 161, a FR3 of SEQ ID NO: 163 and a FR4 of SEQ ID NO: 160. In some embodiments, the humanized sdAb has a FR2 of SEQ ID NO: 162, a FR3 of SEQ ID NO: 163 and a FR4 of SEQ ID NO: 160. In a specific embodiment, the humanized sdAb has a FR1 of SEQ ID NO: 161, a FR2 of SEQ ID NO: 162, a FR3 of SEQ ID NO: 163, and a FR4 of SEQ ID NO: 160.

In a specific embodiment, the humanized sdAb has a CDR1 of SEQ ID NO: 15, a CDR2 of SEQ ID NO: 16, a CDR3 of SEQ ID NO: 17, a FR1 of SEQ ID NO: 161, a FR2 of SEQ ID NO: 162, a FR3 of SEQ ID NO: 163, and a FR4 of SEQ ID NO: 160.

In some embodiments, the sdAb has one or more FR sequences of the humanized anti-MSLN-3.

In some embodiments, the humanized sdAb has a FR1 of SEQ ID NO: 164. In some embodiments, the humanized sdAb has a FR2 of SEQ ID NO: 165. In some embodiments, the humanized sdAb has a FR3 of SEQ ID NO: 166. In other embodiments, the humanized sdAb has a FR4 of SEQ ID NO: 160. In some embodiments, the humanized sdAb has a FR1 of SEQ ID NO: 164 and a FR2 of SEQ ID NO: 165. In some embodiments, the humanized sdAb has a FR1 of SEQ ID NO: 164 and a FR3 of SEQ ID NO: 166. In some embodiments, the humanized sdAb has a FR1 of SEQ ID NO: 164 and a FR4 of SEQ ID NO: 160. In some embodiments, the humanized sdAb has a FR2 of SEQ ID NO: 165 and a FR3 of SEQ ID NO: 166. In some embodiments, the humanized sdAb has a FR2 of SEQ ID NO: 165 and a FR4 of SEQ ID NO: 160. In some embodiments, the humanized sdAb has a FR3 of SEQ ID NO: 166 and a FR4 of SEQ ID NO: 160. In some embodiments, the humanized sdAb has a FR1 of SEQ ID NO: 164, a FR2 of SEQ ID NO: 165 and a FR3 of SEQ ID NO: 166. In some embodiments, the humanized sdAb has a FR1 of SEQ ID NO: 164, a FR2 of SEQ ID NO: 165 and a FR4 of SEQ ID NO: 160. In some embodiments, the humanized sdAb has a FR1 of SEQ ID NO: 164, a FR3 of SEQ ID NO: 166 and a FR4 of SEQ ID NO: 160. In some embodiments, the humanized sdAb has a FR2 of SEQ ID NO: 165, a FR3 of SEQ ID NO: 166 and a FR4 of SEQ ID NO: 160. In a specific embodiment, the humanized sdAb has a FR1 of SEQ ID NO: 164, a FR2 of SEQ ID NO: 165, a FR3 of SEQ ID NO: 166, and a FR4 of SEQ ID NO: 160.

In a specific embodiment, the humanized sdAb has a CDR1 of SEQ ID NO: 18, a CDR2 of SEQ ID NO: 19, a CDR3 of SEQ ID NO: 20, a FR1 of SEQ ID NO: 164, a FR2 of SEQ ID NO: 165, a FR3 of SEQ ID NO: 166, and a FR4 of SEQ ID NO: 160.

In some embodiments, the sdAb has one or more FR sequences of the humanized anti-MSLN-4.

In some embodiments, the humanized sdAb has a FR1 of SEQ ID NO: 167. In some embodiments, the humanized sdAb has a FR2 of SEQ ID NO: 168. In some embodiments, the humanized sdAb has a FR3 of SEQ ID NO: 169. In other embodiments, the humanized sdAb has a FR4 of SEQ ID NO: 160. In some embodiments, the humanized sdAb has a FR1 of SEQ ID NO: 167 and a FR2 of SEQ ID NO: 168. In some embodiments, the humanized sdAb has a FR1 of SEQ ID NO: 167 and a FR3 of SEQ ID NO: 169. In some embodiments, the humanized sdAb has a FR1 of SEQ ID NO: 167 and a FR4 of SEQ ID NO: 160. In some embodiments, the humanized sdAb has a FR2 of SEQ ID NO: 168 and a FR3 of SEQ ID NO: 169. In some embodiments, the humanized sdAb has a FR2 of SEQ ID NO: 168 and a FR4 of SEQ ID NO: 160. In some embodiments, the humanized sdAb has a FR3 of SEQ ID NO: 169 and a FR4 of SEQ ID NO: 160. In some embodiments, the humanized sdAb has a FR1 of SEQ ID NO: 167, a FR2 of SEQ ID NO: 168 and a FR3 of SEQ ID NO: 169. In some embodiments, the humanized sdAb has a FR1 of SEQ ID NO: 167, a FR2 of SEQ ID NO: 168 and a FR4 of SEQ ID NO: 160. In some embodiments, the humanized sdAb has a FR1 of SEQ ID NO: 167, a FR3 of SEQ ID NO: 169 and a FR4 of SEQ ID NO: 160. In some embodiments, the humanized sdAb has a FR2 of SEQ ID NO: 168, a FR3 of SEQ ID NO: 169 and a FR4 of SEQ ID NO: 160. In a specific embodiment, the humanized sdAb has a FR1 of SEQ ID NO: 167, a FR2 of SEQ ID NO: 168, a FR3 of SEQ ID NO: 169, and a FR4 of SEQ ID NO: 160.

In a specific embodiment, the humanized sdAb has a CDR1 of SEQ ID NO: 21, a CDR2 of SEQ ID NO: 22, a CDR3 of SEQ ID NO: 23, a FR1 of SEQ ID NO: 167, a FR2 of SEQ ID NO: 168, a FR3 of SEQ ID NO: 169, and a FR4 of SEQ ID NO: 160.

In some embodiments, the sdAb has one or more FR sequences of the humanized anti-MSLN-5.

In some embodiments, the humanized sdAb has a FR1 of SEQ ID NO: 170. In some embodiments, the humanized sdAb has a FR2 of SEQ ID NO: 171. In some embodiments, the humanized sdAb has a FR3 of SEQ ID NO: 172. In other embodiments, the humanized sdAb has a FR4 of SEQ ID NO: 160. In some embodiments, the humanized sdAb has a FR1 of SEQ ID NO: 170 and a FR2 of SEQ ID NO: 171. In some embodiments, the humanized sdAb has a FR1 of SEQ ID NO: 170 and a FR3 of SEQ ID NO: 172. In some embodiments, the humanized sdAb has a FR1 of SEQ ID NO: 170 and a FR4 of SEQ ID NO: 160. In some embodiments, the humanized sdAb has a FR2 of SEQ ID NO: 171 and a FR3 of SEQ ID NO: 172. In some embodiments, the humanized sdAb has a FR2 of SEQ ID NO: 171 and a FR4 of SEQ ID NO: 160. In some embodiments, the humanized sdAb has a FR3 of SEQ ID NO: 172 and a FR4 of SEQ ID NO: 160. In some embodiments, the humanized sdAb has a FR1 of SEQ ID NO: 170, a FR2 of SEQ ID NO: 171 and a FR3 of SEQ ID NO: 172. In some embodiments, the humanized sdAb has a FR1 of SEQ ID NO: 170, a FR2 of SEQ ID NO: 171 and a FR4 of SEQ ID NO: 160. In some embodiments, the humanized sdAb has a FR1 of SEQ ID NO: 170, a FR3 of SEQ ID NO: 172 and a FR4 of SEQ ID NO: 160. In some embodiments, the humanized sdAb has a FR2 of SEQ ID NO: 171, a FR3 of SEQ ID NO: 172 and a FR4 of SEQ ID NO: 160. In a specific embodiment, the humanized sdAb has a FR1 of SEQ ID NO: 170, a FR2 of SEQ ID NO: 171, a FR3 of SEQ ID NO: 172, and a FR4 of SEQ ID NO: 160.

In a specific embodiment, the humanized sdAb has a CDR1 of SEQ ID NO: 24, a CDR2 of SEQ ID NO: 25, a CDR3 of SEQ ID NO: 26, a FR1 of SEQ ID NO: 170, a FR2 of SEQ ID NO: 171, a FR3 of SEQ ID NO: 172, and a FR4 of SEQ ID NO: 160.

In some embodiments, the sdAb has one or more FR sequences of the humanized anti-MSLN-6.

In some embodiments, the humanized sdAb has a FR1 of SEQ ID NO: 173. In some embodiments, the humanized sdAb has a FR2 of SEQ ID NO: 174. In some embodiments, the humanized sdAb has a FR3 of SEQ ID NO: 175. In other embodiments, the humanized sdAb has a FR4 of SEQ ID NO: 160. In some embodiments, the humanized sdAb has a FR1 of SEQ ID NO: 173 and a FR2 of SEQ ID NO: 174. In some embodiments, the humanized sdAb has a FR1 of SEQ ID NO: 173 and a FR3 of SEQ ID NO: 175. In some embodiments, the humanized sdAb has a FR1 of SEQ ID NO: 173 and a FR4 of SEQ ID NO: 160. In some embodiments, the humanized sdAb has a FR2 of SEQ ID NO: 174 and a FR3 of SEQ ID NO: 175. In some embodiments, the humanized sdAb has a FR2 of SEQ ID NO: 174 and a FR4 of SEQ ID NO: 160. In some embodiments, the humanized sdAb has a FR3 of SEQ ID NO: 175 and a FR4 of SEQ ID NO: 160. In some embodiments, the humanized sdAb has a FR1 of SEQ ID NO: 173, a FR2 of SEQ ID NO: 174 and a FR3 of SEQ ID NO: 175. In some embodiments, the humanized sdAb has a FR1 of SEQ ID NO: 173, a FR2 of SEQ ID NO: 174 and a FR4 of SEQ ID NO: 160. In some embodiments, the humanized sdAb has a FR1 of SEQ ID NO: 173, a FR3 of SEQ ID NO: 175 and a FR4 of SEQ ID NO: 160. In some embodiments, the humanized sdAb has a FR2 of SEQ ID NO: 174, a FR3 of SEQ ID NO: 175 and a FR4 of SEQ ID NO: 160. In a specific embodiment, the humanized sdAb has a FR1 of SEQ ID NO: 173, a FR2 of SEQ ID NO: 174, a FR3 of SEQ ID NO: 175, and a FR4 of SEQ ID NO: 160.

In a specific embodiment, the humanized sdAb has a CDR1 of SEQ ID NO: 27, a CDR2 of SEQ ID NO: 28, a CDR3 of SEQ ID NO: 29, a FR1 of SEQ ID NO: 173, a FR2 of SEQ ID NO: 174, a FR3 of SEQ ID NO: 175, and a FR4 of SEQ ID NO: 160.

In some embodiments, the sdAb has one or more FR sequences of the humanized anti-MSLN-7.

In some embodiments, the humanized sdAb has a FR1 of SEQ ID NO: 176. In some embodiments, the humanized sdAb has a FR2 of SEQ ID NO: 177. In some embodiments, the humanized sdAb has a FR3 of SEQ ID NO: 178. In other embodiments, the humanized sdAb has a FR4 of SEQ ID NO: 160. In some embodiments, the humanized sdAb has a FR1 of SEQ ID NO: 176 and a FR2 of SEQ ID NO: 177. In some embodiments, the humanized sdAb has a FR1 of SEQ ID NO: 176 and a FR3 of SEQ ID NO: 178. In some embodiments, the humanized sdAb has a FR1 of SEQ ID NO: 176 and a FR4 of SEQ ID NO: 160. In some embodiments, the humanized sdAb has a FR2 of SEQ ID NO: 177 and a FR3 of SEQ ID NO: 178. In some embodiments, the humanized sdAb has a FR2 of SEQ ID NO: 177 and a FR4 of SEQ ID NO: 160. In some embodiments, the humanized sdAb has a FR3 of SEQ ID NO: 178 and a FR4 of SEQ ID NO: 160. In some embodiments, the humanized sdAb has a FR1 of SEQ ID NO: 176, a FR2 of SEQ ID NO: 177 and a FR3 of SEQ ID NO: 178. In some embodiments, the humanized sdAb has a FR1 of SEQ ID NO: 176, a FR2 of SEQ ID NO: 177 and a FR4 of SEQ ID NO: 160. In some embodiments, the humanized sdAb has a FR1 of SEQ ID NO: 176, a FR3 of SEQ ID NO: 178 and a FR4 of SEQ ID NO: 160. In some embodiments, the humanized sdAb has a FR2 of SEQ ID NO: 177, a FR3 of SEQ ID NO: 178 and a FR4 of SEQ ID NO: 160. In a specific embodiment, the humanized sdAb has a FR1 of SEQ ID NO: 176, a FR2 of SEQ ID NO: 177, a FR3 of SEQ ID NO: 178, and a FR4 of SEQ ID NO: 160.

In a specific embodiment, the humanized sdAb has a CDR1 of SEQ ID NO: 30, a CDR2 of SEQ ID NO: 31, a CDR3 of SEQ ID NO: 32, a FR1 of SEQ ID NO: 176, a FR2 of SEQ ID NO: 177, a FR3 of SEQ ID NO: 178, and a FR4 of SEQ ID NO: 160.

In some embodiments, the sdAb has one or more FR sequences of the humanized anti-MSLN-8.

In some embodiments, the humanized sdAb has a FR1 of SEQ ID NO: 179. In some embodiments, the humanized sdAb has a FR2 of SEQ ID NO: 180. In some embodiments, the humanized sdAb has a FR3 of SEQ ID NO: 181. In other embodiments, the humanized sdAb has a FR4 of SEQ ID NO: 160. In some embodiments, the humanized sdAb has a FR1 of SEQ ID NO: 179 and a FR2 of SEQ ID NO: 180. In some embodiments, the humanized sdAb has a FR1 of SEQ ID NO: 179 and a FR3 of SEQ ID NO: 181. In some embodiments, the humanized sdAb has a FR1 of SEQ ID NO: 179 and a FR4 of SEQ ID NO: 160. In some embodiments, the humanized sdAb has a FR2 of SEQ ID NO: 180 and a FR3 of SEQ ID NO: 181. In some embodiments, the humanized sdAb has a FR2 of SEQ ID NO: 180 and a FR4 of SEQ ID NO: 160. In some embodiments, the humanized sdAb has a FR3 of SEQ ID NO: 181 and a FR4 of SEQ ID NO: 160. In some embodiments, the humanized sdAb has a FR1 of SEQ ID NO: 179, a FR2 of SEQ ID NO: 180 and a FR3 of SEQ ID NO: 181. In some embodiments, the humanized sdAb has a FR1 of SEQ ID NO: 179, a FR2 of SEQ ID NO: 180 and a FR4 of SEQ ID NO: 160. In some embodiments, the humanized sdAb has a FR1 of SEQ ID NO: 179, a FR3 of SEQ ID NO: 181 and a FR4 of SEQ ID NO: 160. In some embodiments, the humanized sdAb has a FR2 of SEQ ID NO: 180, a FR3 of SEQ ID NO: 181 and a FR4 of SEQ ID NO: 160. In a specific embodiment, the humanized sdAb has a FR1 of SEQ ID NO: 179, a FR2 of SEQ ID NO: 180, a FR3 of SEQ ID NO: 181, and a FR4 of SEQ ID NO: 160.

In a specific embodiment, the humanized sdAb has a CDR1 of SEQ ID NO: 33, a CDR2 of SEQ ID NO: 34, a CDR3 of SEQ ID NO: 35, a FR1 of SEQ ID NO: 179, a FR2 of SEQ ID NO: 180, a FR3 of SEQ ID NO: 181, and a FR4 of SEQ ID NO: 160.

In some embodiments, the sdAb has one or more FR sequences of the humanized anti-MSLN-9.

In some embodiments, the humanized sdAb has a FR1 of SEQ ID NO: 182. In some embodiments, the humanized sdAb has a FR2 of SEQ ID NO: 183. In some embodiments, the humanized sdAb has a FR3 of SEQ ID NO: 184. In other embodiments, the humanized sdAb has a FR4 of SEQ ID NO: 160. In some embodiments, the humanized sdAb has a FR1 of SEQ ID NO: 182 and a FR2 of SEQ ID NO: 183. In some embodiments, the humanized sdAb has a FR1 of SEQ ID NO: 182 and a FR3 of SEQ ID NO: 184. In some embodiments, the humanized sdAb has a FR1 of SEQ ID NO: 182 and a FR4 of SEQ ID NO: 160. In some embodiments, the humanized sdAb has a FR2 of SEQ ID NO: 183 and a FR3 of SEQ ID NO: 184. In some embodiments, the humanized sdAb has a FR2 of SEQ ID NO: 183 and a FR4 of SEQ ID NO: 160. In some embodiments, the humanized sdAb has a FR3 of SEQ ID NO: 184 and a FR4 of SEQ ID NO: 160. In some embodiments, the humanized sdAb has a FR1 of SEQ ID NO: 182, a FR2 of SEQ ID NO: 183 and a FR3 of SEQ ID NO: 184. In some embodiments, the humanized sdAb has a FR1 of SEQ ID NO: 182, a FR2 of SEQ ID NO: 183 and a FR4 of SEQ ID NO: 160. In some embodiments, the humanized sdAb has a FR1 of SEQ ID NO: 182, a FR3 of SEQ ID NO: 184 and a FR4 of SEQ ID NO: 160. In some embodiments, the humanized sdAb has a FR2 of SEQ ID NO: 183, a FR3 of SEQ ID NO: 184 and a FR4 of SEQ ID NO: 160. In a specific embodiment, the humanized sdAb has a FR1 of SEQ ID NO: 182, a FR2 of SEQ ID NO: 183, a FR3 of SEQ ID NO: 184, and a FR4 of SEQ ID NO: 160.

In a specific embodiment, the humanized sdAb has a CDR1 of SEQ ID NO: 36, a CDR2 of SEQ ID NO: 37, a CDR3 of SEQ ID NO: 38, a FR1 of SEQ ID NO: 182, a FR2 of SEQ ID NO: 183, a FR3 of SEQ ID NO: 184, and a FR4 of SEQ ID NO: 160.

In some embodiments, the sdAb has one or more FR sequences of the humanized anti-MSLN-10.

In some embodiments, the humanized sdAb has a FR1 of SEQ ID NO: 185. In some embodiments, the humanized sdAb has a FR2 of SEQ ID NO: 186. In some embodiments, the humanized sdAb has a FR3 of SEQ ID NO: 187. In other embodiments, the humanized sdAb has a FR4 of SEQ ID NO: 160. In some embodiments, the humanized sdAb has a FR1 of SEQ ID NO: 185 and a FR2 of SEQ ID NO: 186. In some embodiments, the humanized sdAb has a FR1 of SEQ ID NO: 185 and a FR3 of SEQ ID NO: 187. In some embodiments, the humanized sdAb has a FR1 of SEQ ID NO: 185 and a FR4 of SEQ ID NO: 160. In some embodiments, the humanized sdAb has a FR2 of SEQ ID NO: 186 and a FR3 of SEQ ID NO: 187. In some embodiments, the humanized sdAb has a FR2 of SEQ ID NO: 186 and a FR4 of SEQ ID NO: 160. In some embodiments, the humanized sdAb has a FR3 of SEQ ID NO: 187 and a FR4 of SEQ ID NO: 160. In some embodiments, the humanized sdAb has a FR1 of SEQ ID NO: 185, a FR2 of SEQ ID NO: 186 and a FR3 of SEQ ID NO: 187. In some embodiments, the humanized sdAb has a FR1 of SEQ ID NO: 185, a FR2 of SEQ ID NO: 186 and a FR4 of SEQ ID NO: 160. In some embodiments, the humanized sdAb has a FR1 of SEQ ID NO: 185, a FR3 of SEQ ID NO: 187 and a FR4 of SEQ ID NO: 160. In some embodiments, the humanized sdAb has a FR2 of SEQ ID NO: 186, a FR3 of SEQ ID NO: 187 and a FR4 of SEQ ID NO: 160. In a specific embodiment, the humanized sdAb has a FR1 of SEQ ID NO: 185, a FR2 of SEQ ID NO: 186, a FR3 of SEQ ID NO: 187, and a FR4 of SEQ ID NO: 160.

In a specific embodiment, the humanized sdAb has a CDR1 of SEQ ID NO: 39, a CDR2 of SEQ ID NO: 40, a CDR3 of SEQ ID NO: 41, a FR1 of SEQ ID NO: 185, a FR2 of SEQ ID NO: 186, a FR3 of SEQ ID NO: 187, and a FR4 of SEQ ID NO: 160.

In some embodiments, the sdAb has one or more FR sequences of the humanized anti-MSLN-11.

In some embodiments, the humanized sdAb has a FR1 of SEQ ID NO: 188. In some embodiments, the humanized sdAb has a FR2 of SEQ ID NO: 189. In some embodiments, the humanized sdAb has a FR3 of SEQ ID NO: 190. In other embodiments, the humanized sdAb has a FR4 of SEQ ID NO: 160. In some embodiments, the humanized sdAb has a FR1 of SEQ ID NO: 188 and a FR2 of SEQ ID NO: 189. In some embodiments, the humanized sdAb has a FR1 of SEQ ID NO: 188 and a FR3 of SEQ ID NO: 190. In some embodiments, the humanized sdAb has a FR1 of SEQ ID NO: 188 and a FR4 of SEQ ID NO: 160. In some embodiments, the humanized sdAb has a FR2 of SEQ ID NO: 189 and a FR3 of SEQ ID NO: 190. In some embodiments, the humanized sdAb has a FR2 of SEQ ID NO: 189 and a FR4 of SEQ ID NO: 160. In some embodiments, the humanized sdAb has a FR3 of SEQ ID NO: 190 and a FR4 of SEQ ID NO: 160. In some embodiments, the humanized sdAb has a FR1 of SEQ ID NO: 188, a FR2 of SEQ ID NO: 189 and a FR3 of SEQ ID NO: 190. In some embodiments, the humanized sdAb has a FR1 of SEQ ID NO: 188, a FR2 of SEQ ID NO: 189 and a FR4 of SEQ ID NO: 160. In some embodiments, the humanized sdAb has a FR1 of SEQ ID NO: 188, a FR3 of SEQ ID NO: 190 and a FR4 of SEQ ID NO: 160. In some embodiments, the humanized sdAb has a FR2 of SEQ ID NO: 189, a FR3 of SEQ ID NO: 190 and a FR4 of SEQ ID NO: 160. In a specific embodiment, the humanized sdAb has a FR1 of SEQ ID NO: 188, a FR2 of SEQ ID NO: 189, a FR3 of SEQ ID NO: 190, and a FR4 of SEQ ID NO: 160.

In a specific embodiment, the humanized sdAb has a CDR1 of SEQ ID NO: 42, a CDR2 of SEQ ID NO: 43, a CDR3 of SEQ ID NO: 44, a FR1 of SEQ ID NO: 188, a FR2 of SEQ ID NO: 189, a FR3 of SEQ ID NO: 190, and a FR4 of SEQ ID NO: 160.

In some embodiments, the sdAb has one or more FR sequences of the humanized anti-MSLN-12.

In some embodiments, the humanized sdAb has a FR1 of SEQ ID NO: 191. In some embodiments, the humanized sdAb has a FR2 of SEQ ID NO: 192. In some embodiments, the humanized sdAb has a FR3 of SEQ ID NO: 193. In other embodiments, the humanized sdAb has a FR4 of SEQ ID NO: 160. In some embodiments, the humanized sdAb has a FR1 of SEQ ID NO: 191 and a FR2 of SEQ ID NO: 192. In some embodiments, the humanized sdAb has a FR1 of SEQ ID NO: 191 and a FR3 of SEQ ID NO: 193. In some embodiments, the humanized sdAb has a FR1 of SEQ ID NO: 191 and a FR4 of SEQ ID NO: 160. In some embodiments, the humanized sdAb has a FR2 of SEQ ID NO: 192 and a FR3 of SEQ ID NO: 193. In some embodiments, the humanized sdAb has a FR2 of SEQ ID NO: 192 and a FR4 of SEQ ID NO: 160. In some embodiments, the humanized sdAb has a FR3 of SEQ ID NO: 193 and a FR4 of SEQ ID NO: 160. In some embodiments, the humanized sdAb has a FR1 of SEQ ID NO: 191, a FR2 of SEQ ID NO: 192 and a FR3 of SEQ ID NO: 193. In some embodiments, the humanized sdAb has a FR1 of SEQ ID NO: 191, a FR2 of SEQ ID NO: 192 and a FR4 of SEQ ID NO: 160. In some embodiments, the humanized sdAb has a FR1 of SEQ ID NO: 191, a FR3 of SEQ ID NO: 193 and a FR4 of SEQ ID NO: 160. In some embodiments, the humanized sdAb has a FR2 of SEQ ID NO: 192, a FR3 of SEQ ID NO: 193 and a FR4 of SEQ ID NO: 160. In a specific embodiment, the humanized sdAb has a FR1 of SEQ ID NO: 191, a FR2 of SEQ ID NO: 192, a FR3 of SEQ ID NO: 193, and a FR4 of SEQ ID NO: 160.

In a specific embodiment, the humanized sdAb has a CDR1 of SEQ ID NO: 45, a CDR2 of SEQ ID NO: 46, a CDR3 of SEQ ID NO: 47, a FR1 of SEQ ID NO: 191, a FR2 of SEQ ID NO: 192, a FR3 of SEQ ID NO: 193, and a FR4 of SEQ ID NO: 160.

In some embodiments, the sdAb has one or more FR sequences of the humanized anti-MSLN-13.

In some embodiments, the humanized sdAb has a FR1 of SEQ ID NO: 194. In some embodiments, the humanized sdAb has a FR2 of SEQ ID NO: 195. In some embodiments, the humanized sdAb has a FR3 of SEQ ID NO: 196. In other embodiments, the humanized sdAb has a FR4 of SEQ ID NO: 160. In some embodiments, the humanized sdAb has a FR1 of SEQ ID NO: 194 and a FR2 of SEQ ID NO: 195. In some embodiments, the humanized sdAb has a FR1 of SEQ ID NO: 194 and a FR3 of SEQ ID NO: 196. In some embodiments, the humanized sdAb has a FR1 of SEQ ID NO: 194 and a FR4 of SEQ ID NO: 160. In some embodiments, the humanized sdAb has a FR2 of SEQ ID NO: 195 and a FR3 of SEQ ID NO: 196. In some embodiments, the humanized sdAb has a FR2 of SEQ ID NO: 195 and a FR4 of SEQ ID NO: 160. In some embodiments, the humanized sdAb has a FR3 of SEQ ID NO: 196 and a FR4 of SEQ ID NO: 160. In some embodiments, the humanized sdAb has a FR1 of SEQ ID NO: 194, a FR2 of SEQ ID NO: 195 and a FR3 of SEQ ID NO: 196. In some embodiments, the humanized sdAb has a FR1 of SEQ ID NO: 194, a FR2 of SEQ ID NO: 195 and a FR4 of SEQ ID NO: 160. In some embodiments, the humanized sdAb has a FR1 of SEQ ID NO: 194, a FR3 of SEQ ID NO: 196 and a FR4 of SEQ ID NO: 160. In some embodiments, the humanized sdAb has a FR2 of SEQ ID NO: 195, a FR3 of SEQ ID NO: 196 and a FR4 of SEQ ID NO: 160. In a specific embodiment, the humanized sdAb has a FR1 of SEQ ID NO: 194, a FR2 of SEQ ID NO: 195, a FR3 of SEQ ID NO: 196, and a FR4 of SEQ ID NO: 160.

In a specific embodiment, the humanized sdAb has a CDR1 of SEQ ID NO: 48, a CDR2 of SEQ ID NO: 49, a CDR3 of SEQ ID NO: 50, a FR1 of SEQ ID NO: 194, a FR2 of SEQ ID NO: 195, a FR3 of SEQ ID NO: 196, and a FR4 of SEQ ID NO: 160.

In some embodiments, the sdAb has one or more FR sequences of the humanized anti-MSLN-14.

In some embodiments, the humanized sdAb has a FR1 of SEQ ID NO: 197. In some embodiments, the humanized sdAb has a FR2 of SEQ ID NO: 198. In some embodiments, the humanized sdAb has a FR3 of SEQ ID NO: 199. In other embodiments, the humanized sdAb has a FR4 of SEQ ID NO: 160. In some embodiments, the humanized sdAb has a FR1 of SEQ ID NO: 197 and a FR2 of SEQ ID NO: 198. In some embodiments, the humanized sdAb has a FR1 of SEQ ID NO: 197 and a FR3 of SEQ ID NO: 199. In some embodiments, the humanized sdAb has a FR1 of SEQ ID NO: 197 and a FR4 of SEQ ID NO: 160. In some embodiments, the humanized sdAb has a FR2 of SEQ ID NO: 198 and a FR3 of SEQ ID NO: 199. In some embodiments, the humanized sdAb has a FR2 of SEQ ID NO: 198 and a FR4 of SEQ ID NO: 160. In some embodiments, the humanized sdAb has a FR3 of SEQ ID NO: 199 and a FR4 of SEQ ID NO: 160. In some embodiments, the humanized sdAb has a FR1 of SEQ ID NO: 197, a FR2 of SEQ ID NO: 198 and a FR3 of SEQ ID NO: 199. In some embodiments, the humanized sdAb has a FR1 of SEQ ID NO: 197, a FR2 of SEQ ID NO: 198 and a FR4 of SEQ ID NO: 160. In some embodiments, the humanized sdAb has a FR1 of SEQ ID NO: 197, a FR3 of SEQ ID NO: 199 and a FR4 of SEQ ID NO: 160. In some embodiments, the humanized sdAb has a FR2 of SEQ ID NO: 198, a FR3 of SEQ ID NO: 199 and a FR4 of SEQ ID NO: 160. In a specific embodiment, the humanized sdAb has a FR1 of SEQ ID NO: 197, a FR2 of SEQ ID NO: 198, a FR3 of SEQ ID NO: 199, and a FR4 of SEQ ID NO: 160.

In a specific embodiment, the humanized sdAb has a CDR1 of SEQ ID NO: 51, a CDR2 of SEQ ID NO: 52, a CDR3 of SEQ ID NO: 53, a FR1 of SEQ ID NO: 197, a FR2 of SEQ ID NO: 198, a FR3 of SEQ ID NO: 199, and a FR4 of SEQ ID NO: 160.

In some embodiments, the sdAb has one or more FR sequences of the humanized anti-MSLN-15.

In some embodiments, the humanized sdAb has a FR1 of SEQ ID NO: 200. In some embodiments, the humanized sdAb has a FR2 of SEQ ID NO: 201. In some embodiments, the humanized sdAb has a FR3 of SEQ ID NO: 202. In other embodiments, the humanized sdAb has a FR4 of SEQ ID NO: 160. In some embodiments, the humanized sdAb has a FR1 of SEQ ID NO: 200 and a FR2 of SEQ ID NO: 201. In some embodiments, the humanized sdAb has a FR1 of SEQ ID NO: 200 and a FR3 of SEQ ID NO: 202. In some embodiments, the humanized sdAb has a FR1 of SEQ ID NO: 200 and a FR4 of SEQ ID NO: 160. In some embodiments, the humanized sdAb has a FR2 of SEQ ID NO: 201 and a FR3 of SEQ ID NO: 202. In some embodiments, the humanized sdAb has a FR2 of SEQ ID NO: 201 and a FR4 of SEQ ID NO: 160. In some embodiments, the humanized sdAb has a FR3 of SEQ ID NO: 202 and a FR4 of SEQ ID NO: 160. In some embodiments, the humanized sdAb has a FR1 of SEQ ID NO: 200, a FR2 of SEQ ID NO: 201 and a FR3 of SEQ ID NO: 202. In some embodiments, the humanized sdAb has a FR1 of SEQ ID NO: 200, a FR2 of SEQ ID NO: 201 and a FR4 of SEQ ID NO: 160. In some embodiments, the humanized sdAb has a FR1 of SEQ ID NO: 200, a FR3 of SEQ ID NO: 202 and a FR4 of SEQ ID NO: 160. In some embodiments, the humanized sdAb has a FR2 of SEQ ID NO: 201, a FR3 of SEQ ID NO: 202 and a FR4 of SEQ ID NO: 160. In a specific embodiment, the humanized sdAb has a FR1 of SEQ ID NO: 200, a FR2 of SEQ ID NO: 201, a FR3 of SEQ ID NO: 202, and a FR4 of SEQ ID NO: 160.

In a specific embodiment, the humanized sdAb has a CDR1 of SEQ ID NO: 54, a CDR2 of SEQ ID NO: 55, a CDR3 of SEQ ID NO: 56, a FR1 of SEQ ID NO: 200, a FR2 of SEQ ID NO: 201, a FR3 of SEQ ID NO: 202, and a FR4 of SEQ ID NO: 160.

In some embodiments, the sdAb has one or more FR sequences of the humanized anti-MSLN-16.

In some embodiments, the humanized sdAb has a FR1 of SEQ ID NO: 203. In some embodiments, the humanized sdAb has a FR2 of SEQ ID NO: 204. In some embodiments, the humanized sdAb has a FR3 of SEQ ID NO: 205. In other embodiments, the humanized sdAb has a FR4 of SEQ ID NO: 160. In some embodiments, the humanized sdAb has a FR1 of SEQ ID NO: 203 and a FR2 of SEQ ID NO: 204. In some embodiments, the humanized sdAb has a FR1 of SEQ ID NO: 203 and a FR3 of SEQ ID NO: 205. In some embodiments, the humanized sdAb has a FR1 of SEQ ID NO: 203 and a FR4 of SEQ ID NO: 160. In some embodiments, the humanized sdAb has a FR2 of SEQ ID NO: 204 and a FR3 of SEQ ID NO: 205. In some embodiments, the humanized sdAb has a FR2 of SEQ ID NO: 204 and a FR4 of SEQ ID NO: 160. In some embodiments, the humanized sdAb has a FR3 of SEQ ID NO: 205 and a FR4 of SEQ ID NO: 160. In some embodiments, the humanized sdAb has a FR1 of SEQ ID NO: 203, a FR2 of SEQ ID NO: 204 and a FR3 of SEQ ID NO: 205. In some embodiments, the humanized sdAb has a FR1 of SEQ ID NO: 203, a FR2 of SEQ ID NO: 204 and a FR4 of SEQ ID NO: 160. In some embodiments, the humanized sdAb has a FR1 of SEQ ID NO: 203, a FR3 of SEQ ID NO: 205 and a FR4 of SEQ ID NO: 160. In some embodiments, the humanized sdAb has a FR2 of SEQ ID NO: 204, a FR3 of SEQ ID NO: 205 and a FR4 of SEQ ID NO: 160. In a specific embodiment, the humanized sdAb has a FR1 of SEQ ID NO: 203, a FR2 of SEQ ID NO: 204, a FR3 of SEQ ID NO: 205, and a FR4 of SEQ ID NO: 160.

In a specific embodiment, the humanized sdAb has a CDR1 of SEQ ID NO: 57, a CDR2 of SEQ ID NO: 58, a CDR3 of SEQ ID NO: 59, a FR1 of SEQ ID NO: 203, a FR2 of SEQ ID NO: 204, a FR3 of SEQ ID NO: 205, and a FR4 of SEQ ID NO: 160.

In some embodiments, the sdAb has one or more FR sequences of the humanized anti-MSLN-17.

In some embodiments, the humanized sdAb has a FR1 of SEQ ID NO: 206. In some embodiments, the humanized sdAb has a FR2 of SEQ ID NO: 207. In some embodiments, the humanized sdAb has a FR3 of SEQ ID NO: 208. In other embodiments, the humanized sdAb has a FR4 of SEQ ID NO: 160. In some embodiments, the humanized sdAb has a FR1 of SEQ ID NO: 206 and a FR2 of SEQ ID NO: 207. In some embodiments, the humanized sdAb has a FR1 of SEQ ID NO: 206 and a FR3 of SEQ ID NO: 208. In some embodiments, the humanized sdAb has a FR1 of SEQ ID NO: 206 and a FR4 of SEQ ID NO: 160. In some embodiments, the humanized sdAb has a FR2 of SEQ ID NO: 207 and a FR3 of SEQ ID NO: 208. In some embodiments, the humanized sdAb has a FR2 of SEQ ID NO: 207 and a FR4 of SEQ ID NO: 160. In some embodiments, the humanized sdAb has a FR3 of SEQ ID NO: 208 and a FR4 of SEQ ID NO: 160. In some embodiments, the humanized sdAb has a FR1 of SEQ ID NO: 206, a FR2 of SEQ ID NO: 207 and a FR3 of SEQ ID NO: 208. In some embodiments, the humanized sdAb has a FR1 of SEQ ID NO: 206, a FR2 of SEQ ID NO: 207 and a FR4 of SEQ ID NO: 160. In some embodiments, the humanized sdAb has a FR1 of SEQ ID NO: 206, a FR3 of SEQ ID NO: 208 and a FR4 of SEQ ID NO: 160. In some embodiments, the humanized sdAb has a FR2 of SEQ ID NO: 207, a FR3 of SEQ ID NO: 208 and a FR4 of SEQ ID NO: 160. In a specific embodiment, the humanized sdAb has a FR1 of SEQ ID NO: 206, a FR2 of SEQ ID NO: 207, a FR3 of SEQ ID NO: 208, and a FR4 of SEQ ID NO: 160.

In a specific embodiment, the humanized sdAb has a CDR1 of SEQ ID NO: 60, a CDR2 of SEQ ID NO: 61, a CDR3 of SEQ ID NO: 62, a FR1 of SEQ ID NO: 206, a FR2 of SEQ ID NO: 207, a FR3 of SEQ ID NO: 208, and a FR4 of SEQ ID NO: 160.

In some embodiments, the sdAb has one or more FR sequences of the humanized anti-MSLN-18.

In some embodiments, the humanized sdAb has a FR1 of SEQ ID NO: 209. In some embodiments, the humanized sdAb has a FR2 of SEQ ID NO: 210. In some embodiments, the humanized sdAb has a FR3 of SEQ ID NO: 211. In other embodiments, the humanized sdAb has a FR4 of SEQ ID NO: 160. In some embodiments, the humanized sdAb has a FR1 of SEQ ID NO: 209 and a FR2 of SEQ ID NO: 210. In some embodiments, the humanized sdAb has a FR1 of SEQ ID NO: 209 and a FR3 of SEQ ID NO: 211. In some embodiments, the humanized sdAb has a FR1 of SEQ ID NO: 209 and a FR4 of SEQ ID NO: 160. In some embodiments, the humanized sdAb has a FR2 of SEQ ID NO: 210 and a FR3 of SEQ ID NO: 211. In some embodiments, the humanized sdAb has a FR2 of SEQ ID NO: 210 and a FR4 of SEQ ID NO: 160. In some embodiments, the humanized sdAb has a FR3 of SEQ ID NO: 211 and a FR4 of SEQ ID NO: 160. In some embodiments, the humanized sdAb has a FR1 of SEQ ID NO: 209, a FR2 of SEQ ID NO: 210 and a FR3 of SEQ ID NO: 211. In some embodiments, the humanized sdAb has a FR1 of SEQ ID NO: 209, a FR2 of SEQ ID NO: 210 and a FR4 of SEQ ID NO: 160. In some embodiments, the humanized sdAb has a FR1 of SEQ ID NO: 209, a FR3 of SEQ ID NO: 211 and a FR4 of SEQ ID NO: 160. In some embodiments, the humanized sdAb has a FR2 of SEQ ID NO: 210, a FR3 of SEQ ID NO: 211 and a FR4 of SEQ ID NO: 160. In a specific embodiment, the humanized sdAb has a FR1 of SEQ ID NO: 209, a FR2 of SEQ ID NO: 210, a FR3 of SEQ ID NO: 211, and a FR4 of SEQ ID NO: 160.

In a specific embodiment, the humanized sdAb has a CDR1 of SEQ ID NO: 63, a CDR2 of SEQ ID NO: 64, a CDR3 of SEQ ID NO: 65, a FR1 of SEQ ID NO: 209, a FR2 of SEQ ID NO: 210, a FR3 of SEQ ID NO: 211, and a FR4 of SEQ ID NO: 160.

In some embodiments, the sdAb has one or more FR sequences of the humanized anti-MSLN-19.

In some embodiments, the humanized sdAb has a FR1 of SEQ ID NO: 212. In some embodiments, the humanized sdAb has a FR2 of SEQ ID NO: 213. In some embodiments, the humanized sdAb has a FR3 of SEQ ID NO: 214. In other embodiments, the humanized sdAb has a FR4 of SEQ ID NO: 160. In some embodiments, the humanized sdAb has a FR1 of SEQ ID NO: 212 and a FR2 of SEQ ID NO: 213. In some embodiments, the humanized sdAb has a FR1 of SEQ ID NO: 212 and a FR3 of SEQ ID NO: 214. In some embodiments, the humanized sdAb has a FR1 of SEQ ID NO: 212 and a FR4 of SEQ ID NO: 160. In some embodiments, the humanized sdAb has a FR2 of SEQ ID NO: 213 and a FR3 of SEQ ID NO: 214. In some embodiments, the humanized sdAb has a FR2 of SEQ ID NO: 213 and a FR4 of SEQ ID NO: 160. In some embodiments, the humanized sdAb has a FR3 of SEQ ID NO: 214 and a FR4 of SEQ ID NO: 160. In some embodiments, the humanized sdAb has a FR1 of SEQ ID NO: 212, a FR2 of SEQ ID NO: 213 and a FR3 of SEQ ID NO: 214. In some embodiments, the humanized sdAb has a FR1 of SEQ ID NO: 212, a FR2 of SEQ ID NO: 213 and a FR4 of SEQ ID NO: 160. In some embodiments, the humanized sdAb has a FR1 of SEQ ID NO: 212, a FR3 of SEQ ID NO: 214 and a FR4 of SEQ ID NO: 160. In some embodiments, the humanized sdAb has a FR2 of SEQ ID NO: 213, a FR3 of SEQ ID NO: 214 and a FR4 of SEQ ID NO: 160. In a specific embodiment, the humanized sdAb has a FR1 of SEQ ID NO: 212, a FR2 of SEQ ID NO: 213, a FR3 of SEQ ID NO: 214, and a FR4 of SEQ ID NO: 160.

In a specific embodiment, the humanized sdAb has a CDR1 of SEQ ID NO: 75, a CDR2 of SEQ ID NO: 76, a CDR3 of SEQ ID NO: 77, a FR1 of SEQ ID NO: 212, a FR2 of SEQ ID NO: 213, a FR3 of SEQ ID NO: 214, and a FR4 of SEQ ID NO: 160.

In some embodiments, the sdAb has one or more FR sequences of the humanized anti-MSLN-20.

In some embodiments, the humanized sdAb has a FR1 of SEQ ID NO: 215. In some embodiments, the humanized sdAb has a FR2 of SEQ ID NO: 216. In some embodiments, the humanized sdAb has a FR3 of SEQ ID NO: 217. In other embodiments, the humanized sdAb has a FR4 of SEQ ID NO: 160. In some embodiments, the humanized sdAb has a FR1 of SEQ ID NO: 215 and a FR2 of SEQ ID NO: 216. In some embodiments, the humanized sdAb has a FR1 of SEQ ID NO: 215 and a FR3 of SEQ ID NO: 217. In some embodiments, the humanized sdAb has a FR1 of SEQ ID NO: 215 and a FR4 of SEQ ID NO: 160. In some embodiments, the humanized sdAb has a FR2 of SEQ ID NO: 216 and a FR3 of SEQ ID NO: 217. In some embodiments, the humanized sdAb has a FR2 of SEQ ID NO: 216 and a FR4 of SEQ ID NO: 160. In some embodiments, the humanized sdAb has a FR3 of SEQ ID NO: 217 and a FR4 of SEQ ID NO: 160. In some embodiments, the humanized sdAb has a FR1 of SEQ ID NO: 215, a FR2 of SEQ ID NO: 216 and a FR3 of SEQ ID NO: 217. In some embodiments, the humanized sdAb has a FR1 of SEQ ID NO: 215, a FR2 of SEQ ID NO: 216 and a FR4 of SEQ ID NO: 160. In some embodiments, the humanized sdAb has a FR1 of SEQ ID NO: 215, a FR3 of SEQ ID NO: 217 and a FR4 of SEQ ID NO: 160. In some embodiments, the humanized sdAb has a FR2 of SEQ ID NO: 216, a FR3 of SEQ ID NO: 217 and a FR4 of SEQ ID NO: 160. In a specific embodiment, the humanized sdAb has a FR1 of SEQ ID NO: 215, a FR2 of SEQ ID NO: 216, a FR3 of SEQ ID NO: 217, and a FR4 of SEQ ID NO: 160.

In a specific embodiment, the humanized sdAb has a CDR1 of SEQ ID NO: 78, a CDR2 of SEQ ID NO: 79, a CDR3 of SEQ ID NO: 80, a FR1 of SEQ ID NO: 215, a FR2 of SEQ ID NO: 216, a FR3 of SEQ ID NO: 217, and a FR4 of SEQ ID NO: 160.

In some embodiments, the sdAb has one or more FR sequences of the humanized anti-MSLN-21.

In some embodiments, the humanized sdAb has a FR1 of SEQ ID NO: 218. In some embodiments, the humanized sdAb has a FR2 of SEQ ID NO: 219. In some embodiments, the humanized sdAb has a FR3 of SEQ ID NO: 220. In other embodiments, the humanized sdAb has a FR4 of SEQ ID NO: 160. In some embodiments, the humanized sdAb has a FR1 of SEQ ID NO: 218 and a FR2 of SEQ ID NO: 219. In some embodiments, the humanized sdAb has a FR1 of SEQ ID NO: 218 and a FR3 of SEQ ID NO: 220. In some embodiments, the humanized sdAb has a FR1 of SEQ ID NO: 218 and a FR4 of SEQ ID NO: 160. In some embodiments, the humanized sdAb has a FR2 of SEQ ID NO: 219 and a FR3 of SEQ ID NO: 220. In some embodiments, the humanized sdAb has a FR2 of SEQ ID NO: 219 and a FR4 of SEQ ID NO: 160. In some embodiments, the humanized sdAb has a FR3 of SEQ ID NO: 220 and a FR4 of SEQ ID NO: 160. In some embodiments, the humanized sdAb has a FR1 of SEQ ID NO: 218, a FR2 of SEQ ID NO: 219 and a FR3 of SEQ ID NO: 220. In some embodiments, the humanized sdAb has a FR1 of SEQ ID NO: 218, a FR2 of SEQ ID NO: 219 and a FR4 of SEQ ID NO: 160. In some embodiments, the humanized sdAb has a FR1 of SEQ ID NO: 218, a FR3 of SEQ ID NO: 220 and a FR4 of SEQ ID NO: 160. In some embodiments, the humanized sdAb has a FR2 of SEQ ID NO: 219, a FR3 of SEQ ID NO: 220 and a FR4 of SEQ ID NO: 160. In a specific embodiment, the humanized sdAb has a FR1 of SEQ ID NO: 218, a FR2 of SEQ ID NO: 219, a FR3 of SEQ ID NO: 220, and a FR4 of SEQ ID NO: 160.

In a specific embodiment, the humanized sdAb has a CDR1 of SEQ ID NO: 81, a CDR2 of SEQ ID NO: 82, a CDR3 of SEQ ID NO: 83, a FR1 of SEQ ID NO: 218, a FR2 of SEQ ID NO: 219, a FR3 of SEQ ID NO: 220, and a FR4 of SEQ ID NO: 160.

In some embodiments, the sdAb has one or more FR sequences of the humanized anti-MSLN-22.

In some embodiments, the humanized sdAb has a FR1 of SEQ ID NO: 221. In some embodiments, the humanized sdAb has a FR2 of SEQ ID NO: 222. In some embodiments, the humanized sdAb has a FR3 of SEQ ID NO: 223. In other embodiments, the humanized sdAb has a FR4 of SEQ ID NO: 160. In some embodiments, the humanized sdAb has a FR1 of SEQ ID NO: 221 and a FR2 of SEQ ID NO: 222. In some embodiments, the humanized sdAb has a FR1 of SEQ ID NO: 221 and a FR3 of SEQ ID NO: 223. In some embodiments, the humanized sdAb has a FR1 of SEQ ID NO: 221 and a FR4 of SEQ ID NO: 160. In some embodiments, the humanized sdAb has a FR2 of SEQ ID NO: 222 and a FR3 of SEQ ID NO: 223. In some embodiments, the humanized sdAb has a FR2 of SEQ ID NO: 222 and a FR4 of SEQ ID NO: 160. In some embodiments, the humanized sdAb has a FR3 of SEQ ID NO: 223 and a FR4 of SEQ ID NO: 160. In some embodiments, the humanized sdAb has a FR1 of SEQ ID NO: 221, a FR2 of SEQ ID NO: 222 and a FR3 of SEQ ID NO: 223. In some embodiments, the humanized sdAb has a FR1 of SEQ ID NO: 221, a FR2 of SEQ ID NO: 222 and a FR4 of SEQ ID NO: 160. In some embodiments, the humanized sdAb has a FR1 of SEQ ID NO: 221, a FR3 of SEQ ID NO: 223 and a FR4 of SEQ ID NO: 160. In some embodiments, the humanized sdAb has a FR2 of SEQ ID NO: 222, a FR3 of SEQ ID NO: 223 and a FR4 of SEQ ID NO: 160. In a specific embodiment, the humanized sdAb has a FR1 of SEQ ID NO: 221, a FR2 of SEQ ID NO: 222, a FR3 of SEQ ID NO: 223, and a FR4 of SEQ ID NO: 160.

In a specific embodiment, the humanized sdAb has a CDR1 of SEQ ID NO: 84, a CDR2 of SEQ ID NO: 85, a CDR3 of SEQ ID NO: 86, a FR1 of SEQ ID NO: 221, a FR2 of SEQ ID NO: 222, a FR3 of SEQ ID NO: 223, and a FR4 of SEQ ID NO: 160.

In some embodiments, the sdAb has one or more FR sequences of the humanized anti-MSLN-23.

In some embodiments, the humanized sdAb has a FR1 of SEQ ID NO: 224. In some embodiments, the humanized sdAb has a FR2 of SEQ ID NO: 225. In some embodiments, the humanized sdAb has a FR3 of SEQ ID NO: 226. In other embodiments, the humanized sdAb has a FR4 of SEQ ID NO: 160. In some embodiments, the humanized sdAb has a FR1 of SEQ ID NO: 224 and a FR2 of SEQ ID NO: 225. In some embodiments, the humanized sdAb has a FR1 of SEQ ID NO: 224 and a FR3 of SEQ ID NO: 226. In some embodiments, the humanized sdAb has a FR1 of SEQ ID NO: 224 and a FR4 of SEQ ID NO: 160. In some embodiments, the humanized sdAb has a FR2 of SEQ ID NO: 225 and a FR3 of SEQ ID NO: 226. In some embodiments, the humanized sdAb has a FR2 of SEQ ID NO: 225 and a FR4 of SEQ ID NO: 160. In some embodiments, the humanized sdAb has a FR3 of SEQ ID NO: 226 and a FR4 of SEQ ID NO: 160. In some embodiments, the humanized sdAb has a FR1 of SEQ ID NO: 224, a FR2 of SEQ ID NO: 225 and a FR3 of SEQ ID NO: 226. In some embodiments, the humanized sdAb has a FR1 of SEQ ID NO: 224, a FR2 of SEQ ID NO: 225 and a FR4 of SEQ ID NO: 160. In some embodiments, the humanized sdAb has a FR1 of SEQ ID NO: 224, a FR3 of SEQ ID NO: 226 and a FR4 of SEQ ID NO: 160. In some embodiments, the humanized sdAb has a FR2 of SEQ ID NO: 225, a FR3 of SEQ ID NO: 226 and a FR4 of SEQ ID NO: 160. In a specific embodiment, the humanized sdAb has a FR1 of SEQ ID NO: 224, a FR2 of SEQ ID NO: 225, a FR3 of SEQ ID NO: 226, and a FR4 of SEQ ID NO: 160.

In a specific embodiment, the humanized sdAb has a CDR1 of SEQ ID NO: 87, a CDR2 of SEQ ID NO: 88, a CDR3 of SEQ ID NO: 89, a FR1 of SEQ ID NO: 224, a FR2 of SEQ ID NO: 225, a FR3 of SEQ ID NO: 226, and a FR4 of SEQ ID NO: 160.

In some embodiments, the sdAb has one or more FR sequences of the humanized anti-MSLN-24.

In some embodiments, the humanized sdAb has a FR1 of SEQ ID NO: 227. In some embodiments, the humanized sdAb has a FR2 of SEQ ID NO: 228. In some embodiments, the humanized sdAb has a FR3 of SEQ ID NO: 229. In other embodiments, the humanized sdAb has a FR4 of SEQ ID NO: 160. In some embodiments, the humanized sdAb has a FR1 of SEQ ID NO: 227 and a FR2 of SEQ ID NO: 228. In some embodiments, the humanized sdAb has a FR1 of SEQ ID NO: 227 and a FR3 of SEQ ID NO: 229. In some embodiments, the humanized sdAb has a FR1 of SEQ ID NO: 227 and a FR4 of SEQ ID NO: 160. In some embodiments, the humanized sdAb has a FR2 of SEQ ID NO: 228 and a FR3 of SEQ ID NO: 229. In some embodiments, the humanized sdAb has a FR2 of SEQ ID NO: 228 and a FR4 of SEQ ID NO: 160. In some embodiments, the humanized sdAb has a FR3 of SEQ ID NO: 229 and a FR4 of SEQ ID NO: 160. In some embodiments, the humanized sdAb has a FR1 of SEQ ID NO: 227, a FR2 of SEQ ID NO: 228 and a FR3 of SEQ ID NO: 229. In some embodiments, the humanized sdAb has a FR1 of SEQ ID NO: 227, a FR2 of SEQ ID NO: 228 and a FR4 of SEQ ID NO: 160. In some embodiments, the humanized sdAb has a FR1 of SEQ ID NO: 227, a FR3 of SEQ ID NO: 229 and a FR4 of SEQ ID NO: 160. In some embodiments, the humanized sdAb has a FR2 of SEQ ID NO: 228, a FR3 of SEQ ID NO: 229 and a FR4 of SEQ ID NO: 160. In a specific embodiment, the humanized sdAb has a FR1 of SEQ ID NO: 227, a FR2 of SEQ ID NO: 228, a FR3 of SEQ ID NO: 229, and a FR4 of SEQ ID NO: 160.

In a specific embodiment, the humanized sdAb has a CDR1 of SEQ ID NO: 90, a CDR2 of SEQ ID NO: 91, a CDR3 of SEQ ID NO: 92, a FR1 of SEQ ID NO: 227, a FR2 of SEQ ID NO: 228, a FR3 of SEQ ID NO: 229, and a FR4 of SEQ ID NO: 160.

In some embodiments, the sdAb has one or more FR sequences of the humanized anti-MSLN-25.

In some embodiments, the humanized sdAb has a FR1 of SEQ ID NO: 230. In some embodiments, the humanized sdAb has a FR2 of SEQ ID NO: 231. In some embodiments, the humanized sdAb has a FR3 of SEQ ID NO: 232. In other embodiments, the humanized sdAb has a FR4 of SEQ ID NO: 160. In some embodiments, the humanized sdAb has a FR1 of SEQ ID NO: 230 and a FR2 of SEQ ID NO: 231. In some embodiments, the humanized sdAb has a FR1 of SEQ ID NO: 230 and a FR3 of SEQ ID NO: 232. In some embodiments, the humanized sdAb has a FR1 of SEQ ID NO: 230 and a FR4 of SEQ ID NO: 160. In some embodiments, the humanized sdAb has a FR2 of SEQ ID NO: 231 and a FR3 of SEQ ID NO: 232. In some embodiments, the humanized sdAb has a FR2 of SEQ ID NO: 231 and a FR4 of SEQ ID NO: 160. In some embodiments, the humanized sdAb has a FR3 of SEQ ID NO: 232 and a FR4 of SEQ ID NO: 160. In some embodiments, the humanized sdAb has a FR1 of SEQ ID NO: 230, a FR2 of SEQ ID NO: 231 and a FR3 of SEQ ID NO: 232. In some embodiments, the humanized sdAb has a FR1 of SEQ ID NO: 230, a FR2 of SEQ ID NO: 231 and a FR4 of SEQ ID NO: 160. In some embodiments, the humanized sdAb has a FR1 of SEQ ID NO: 230, a FR3 of SEQ ID NO: 232 and a FR4 of SEQ ID NO: 160. In some embodiments, the humanized sdAb has a FR2 of SEQ ID NO: 231, a FR3 of SEQ ID NO: 232 and a FR4 of SEQ ID NO: 160. In a specific embodiment, the humanized sdAb has a FR1 of SEQ ID NO: 230, a FR2 of SEQ ID NO: 231, a FR3 of SEQ ID NO: 232, and a FR4 of SEQ ID NO: 160.

In a specific embodiment, the humanized sdAb has a CDR1 of SEQ ID NO: 93, a CDR2 of SEQ ID NO: 94, a CDR3 of SEQ ID NO: 95, a FR1 of SEQ ID NO: 230, a FR2 of SEQ ID NO: 231, a FR3 of SEQ ID NO: 232, and a FR4 of SEQ ID NO: 160.

In some embodiments, the sdAb has one or more FR sequences of the humanized anti-MSLN-26.

In some embodiments, the humanized sdAb has a FR1 of SEQ ID NO: 233. In some embodiments, the humanized sdAb has a FR2 of SEQ ID NO: 234. In some embodiments, the humanized sdAb has a FR3 of SEQ ID NO: 235. In other embodiments, the humanized sdAb has a FR4 of SEQ ID NO: 160. In some embodiments, the humanized sdAb has a FR1 of SEQ ID NO: 233 and a FR2 of SEQ ID NO: 234. In some embodiments, the humanized sdAb has a FR1 of SEQ ID NO: 233 and a FR3 of SEQ ID NO: 235. In some embodiments, the humanized sdAb has a FR1 of SEQ ID NO: 233 and a FR4 of SEQ ID NO: 160. In some embodiments, the humanized sdAb has a FR2 of SEQ ID NO: 234 and a FR3 of SEQ ID NO: 235. In some embodiments, the humanized sdAb has a FR2 of SEQ ID NO: 234 and a FR4 of SEQ ID NO: 160. In some embodiments, the humanized sdAb has a FR3 of SEQ ID NO: 235 and a FR4 of SEQ ID NO: 160. In some embodiments, the humanized sdAb has a FR1 of SEQ ID NO: 233, a FR2 of SEQ ID NO: 234 and a FR3 of SEQ ID NO: 235. In some embodiments, the humanized sdAb has a FR1 of SEQ ID NO: 233, a FR2 of SEQ ID NO: 234 and a FR4 of SEQ ID NO: 160. In some embodiments, the humanized sdAb has a FR1 of SEQ ID NO: 233, a FR3 of SEQ ID NO: 235 and a FR4 of SEQ ID NO: 160. In some embodiments, the humanized sdAb has a FR2 of SEQ ID NO: 234, a FR3 of SEQ ID NO: 235 and a FR4 of SEQ ID NO: 160. In a specific embodiment, the humanized sdAb has a FR1 of SEQ ID NO: 233, a FR2 of SEQ ID NO: 234, a FR3 of SEQ ID NO: 235, and a FR4 of SEQ ID NO: 160.

In a specific embodiment, the humanized sdAb has a CDR1 of SEQ ID NO: 96, a CDR2 of SEQ ID NO: 97, a CDR3 of SEQ ID NO: 98, a FR1 of SEQ ID NO: 233, a FR2 of SEQ ID NO: 234, a FR3 of SEQ ID NO: 235, and a FR4 of SEQ ID NO: 160.

In some embodiments, the sdAb has one or more FR sequences of the humanized anti-MSLN-27.

In some embodiments, the humanized sdAb has a FR1 of SEQ ID NO: 236. In some embodiments, the humanized sdAb has a FR2 of SEQ ID NO: 237. In some embodiments, the humanized sdAb has a FR3 of SEQ ID NO: 238. In other embodiments, the humanized sdAb has a FR4 of SEQ ID NO: 160. In some embodiments, the humanized sdAb has a FR1 of SEQ ID NO: 236 and a FR2 of SEQ ID NO: 237. In some embodiments, the humanized sdAb has a FR1 of SEQ ID NO: 236 and a FR3 of SEQ ID NO: 238. In some embodiments, the humanized sdAb has a FR1 of SEQ ID NO: 236 and a FR4 of SEQ ID NO: 160. In some embodiments, the humanized sdAb has a FR2 of SEQ ID NO: 237 and a FR3 of SEQ ID NO: 238. In some embodiments, the humanized sdAb has a FR2 of SEQ ID NO: 237 and a FR4 of SEQ ID NO: 160. In some embodiments, the humanized sdAb has a FR3 of SEQ ID NO: 238 and a FR4 of SEQ ID NO: 160. In some embodiments, the humanized sdAb has a FR1 of SEQ ID NO: 236, a FR2 of SEQ ID NO: 237 and a FR3 of SEQ ID NO: 238. In some embodiments, the humanized sdAb has a FR1 of SEQ ID NO: 236, a FR2 of SEQ ID NO: 237 and a FR4 of SEQ ID NO: 160. In some embodiments, the humanized sdAb has a FR1 of SEQ ID NO: 236, a FR3 of SEQ ID NO: 238 and a FR4 of SEQ ID NO: 160. In some embodiments, the humanized sdAb has a FR2 of SEQ ID NO: 237, a FR3 of SEQ ID NO: 238 and a FR4 of SEQ ID NO: 160. In a specific embodiment, the humanized sdAb has a FR1 of SEQ ID NO: 236, a FR2 of SEQ ID NO: 237, a FR3 of SEQ ID NO: 238, and a FR4 of SEQ ID NO: 160.

In a specific embodiment, the humanized sdAb has a CDR1 of SEQ ID NO: 99, a CDR2 of SEQ ID NO: 100, a CDR3 of SEQ ID NO: 101, a FR1 of SEQ ID NO: 236, a FR2 of SEQ ID NO: 237, a FR3 of SEQ ID NO: 238, and a FR4 of SEQ ID NO: 160.

In some embodiments, the sdAb has one or more FR sequences of the humanized anti-MSLN-28.

In some embodiments, the humanized sdAb has a FR1 of SEQ ID NO: 239. In some embodiments, the humanized sdAb has a FR2 of SEQ ID NO: 240. In some embodiments, the humanized sdAb has a FR3 of SEQ ID NO: 241. In other embodiments, the humanized sdAb has a FR4 of SEQ ID NO: 160. In some embodiments, the humanized sdAb has a FR1 of SEQ ID NO: 239 and a FR2 of SEQ ID NO: 240. In some embodiments, the humanized sdAb has a FR1 of SEQ ID NO: 239 and a FR3 of SEQ ID NO: 241. In some embodiments, the humanized sdAb has a FR1 of SEQ ID NO: 239 and a FR4 of SEQ ID NO: 160. In some embodiments, the humanized sdAb has a FR2 of SEQ ID NO: 240 and a FR3 of SEQ ID NO: 241. In some embodiments, the humanized sdAb has a FR2 of SEQ ID NO: 240 and a FR4 of SEQ ID NO: 160. In some embodiments, the humanized sdAb has a FR3 of SEQ ID NO: 241 and a FR4 of SEQ ID NO: 160. In some embodiments, the humanized sdAb has a FR1 of SEQ ID NO: 239, a FR2 of SEQ ID NO: 240 and a FR3 of SEQ ID NO: 241. In some embodiments, the humanized sdAb has a FR1 of SEQ ID NO: 239, a FR2 of SEQ ID NO: 240 and a FR4 of SEQ ID NO: 160. In some embodiments, the humanized sdAb has a FR1 of SEQ ID NO: 239, a FR3 of SEQ ID NO: 241 and a FR4 of SEQ ID NO: 160. In some embodiments, the humanized sdAb has a FR2 of SEQ ID NO: 240, a FR3 of SEQ ID NO: 241 and a FR4 of SEQ ID NO: 160. In a specific embodiment, the humanized sdAb has a FR1 of SEQ ID NO: 239, a FR2 of SEQ ID NO: 240, a FR3 of SEQ ID NO: 241, and a FR4 of SEQ ID NO: 160.

In a specific embodiment, the humanized sdAb has a CDR1 of SEQ ID NO: 102, a CDR2 of SEQ ID NO: 103, a CDR3 of SEQ ID NO: 104, a FR1 of SEQ ID NO: 239, a FR2 of SEQ ID NO: 240, a FR3 of SEQ ID NO: 241, and a FR4 of SEQ ID NO: 160.

In some embodiments, the sdAb has one or more FR sequences of the humanized anti-MSLN-29.

In some embodiments, the humanized sdAb has a FR1 of SEQ ID NO: 242. In some embodiments, the humanized sdAb has a FR2 of SEQ ID NO: 243. In some embodiments, the humanized sdAb has a FR3 of SEQ ID NO: 244. In other embodiments, the humanized sdAb has a FR4 of SEQ ID NO: 160. In some embodiments, the humanized sdAb has a FR1 of SEQ ID NO: 242 and a FR2 of SEQ ID NO: 243. In some embodiments, the humanized sdAb has a FR1 of SEQ ID NO: 242 and a FR3 of SEQ ID NO: 244. In some embodiments, the humanized sdAb has a FR1 of SEQ ID NO: 242 and a FR4 of SEQ ID NO: 160. In some embodiments, the humanized sdAb has a FR2 of SEQ ID NO: 243 and a FR3 of SEQ ID NO: 244. In some embodiments, the humanized sdAb has a FR2 of SEQ ID NO: 243 and a FR4 of SEQ ID NO: 160. In some embodiments, the humanized sdAb has a FR3 of SEQ ID NO: 244 and a FR4 of SEQ ID NO: 160. In some embodiments, the humanized sdAb has a FR1 of SEQ ID NO: 242, a FR2 of SEQ ID NO: 243 and a FR3 of SEQ ID NO: 244. In some embodiments, the humanized sdAb has a FR1 of SEQ ID NO: 242, a FR2 of SEQ ID NO: 243 and a FR4 of SEQ ID NO: 160. In some embodiments, the humanized sdAb has a FR1 of SEQ ID NO: 242, a FR3 of SEQ ID NO: 244 and a FR4 of SEQ ID NO: 160. In some embodiments, the humanized sdAb has a FR2 of SEQ ID NO: 243, a FR3 of SEQ ID NO: 244 and a FR4 of SEQ ID NO: 160. In a specific embodiment, the humanized sdAb has a FR1 of SEQ ID NO: 242, a FR2 of SEQ ID NO: 243, a FR3 of SEQ ID NO: 244, and a FR4 of SEQ ID NO: 160.

In a specific embodiment, the humanized sdAb has a CDR1 of SEQ ID NO: 105, a CDR2 of SEQ ID NO: 106, a CDR3 of SEQ ID NO: 107, a FR1 of SEQ ID NO: 242, a FR2 of SEQ ID NO: 243, a FR3 of SEQ ID NO: 244, and a FR4 of SEQ ID NO: 160.

In some embodiments, the sdAb has one or more FR sequences of the humanized anti-MSLN-30.

In some embodiments, the humanized sdAb has a FR1 of SEQ ID NO: 245. In some embodiments, the humanized sdAb has a FR2 of SEQ ID NO: 246. In some embodiments, the humanized sdAb has a FR3 of SEQ ID NO: 247. In other embodiments, the humanized sdAb has a FR4 of SEQ ID NO: 160. In some embodiments, the humanized sdAb has a FR1 of SEQ ID NO: 245 and a FR2 of SEQ ID NO: 246. In some embodiments, the humanized sdAb has a FR1 of SEQ ID NO: 245 and a FR3 of SEQ ID NO: 247. In some embodiments, the humanized sdAb has a FR1 of SEQ ID NO: 245 and a FR4 of SEQ ID NO: 160. In some embodiments, the humanized sdAb has a FR2 of SEQ ID NO: 246 and a FR3 of SEQ ID NO: 247. In some embodiments, the humanized sdAb has a FR2 of SEQ ID NO: 246 and a FR4 of SEQ ID NO: 160. In some embodiments, the humanized sdAb has a FR3 of SEQ ID NO: 247 and a FR4 of SEQ ID NO: 160. In some embodiments, the humanized sdAb has a FR1 of SEQ ID NO: 245, a FR2 of SEQ ID NO: 246 and a FR3 of SEQ ID NO: 247. In some embodiments, the humanized sdAb has a FR1 of SEQ ID NO: 245, a FR2 of SEQ ID NO: 246 and a FR4 of SEQ ID NO: 160. In some embodiments, the humanized sdAb has a FR1 of SEQ ID NO: 245, a FR3 of SEQ ID NO: 247 and a FR4 of SEQ ID NO: 160. In some embodiments, the humanized sdAb has a FR2 of SEQ ID NO: 246, a FR3 of SEQ ID NO: 247 and a FR4 of SEQ ID NO: 160. In a specific embodiment, the humanized sdAb has a FR1 of SEQ ID NO: 245, a FR2 of SEQ ID NO: 246, a FR3 of SEQ ID NO: 247, and a FR4 of SEQ ID NO: 160.

In a specific embodiment, the humanized sdAb has a CDR1 of SEQ ID NO: 108, a CDR2 of SEQ ID NO: 109, a CDR3 of SEQ ID NO: 110, a FR1 of SEQ ID NO: 245, a FR2 of SEQ ID NO: 246, a FR3 of SEQ ID NO: 247, and a FR4 of SEQ ID NO: 160.

In some embodiments, the sdAb has one or more FR sequences of the humanized anti-MSLN-31.

In some embodiments, the humanized sdAb has a FR1 of SEQ ID NO: 248. In some embodiments, the humanized sdAb has a FR2 of SEQ ID NO: 249. In some embodiments, the humanized sdAb has a FR3 of SEQ ID NO: 250. In other embodiments, the humanized sdAb has a FR4 of SEQ ID NO: 160. In some embodiments, the humanized sdAb has a FR1 of SEQ ID NO: 248 and a FR2 of SEQ ID NO: 249. In some embodiments, the humanized sdAb has a FR1 of SEQ ID NO: 248 and a FR3 of SEQ ID NO: 250. In some embodiments, the humanized sdAb has a FR1 of SEQ ID NO: 248 and a FR4 of SEQ ID NO: 160. In some embodiments, the humanized sdAb has a FR2 of SEQ ID NO: 249 and a FR3 of SEQ ID NO: 250. In some embodiments, the humanized sdAb has a FR2 of SEQ ID NO: 249 and a FR4 of SEQ ID NO: 160. In some embodiments, the humanized sdAb has a FR3 of SEQ ID NO: 250 and a FR4 of SEQ ID NO: 160. In some embodiments, the humanized sdAb has a FR1 of SEQ ID NO: 248, a FR2 of SEQ ID NO: 249 and a FR3 of SEQ ID NO: 250. In some embodiments, the humanized sdAb has a FR1 of SEQ ID NO: 248, a FR2 of SEQ ID NO: 249 and a FR4 of SEQ ID NO: 160. In some embodiments, the humanized sdAb has a FR1 of SEQ ID NO: 248, a FR3 of SEQ ID NO: 250 and a FR4 of SEQ ID NO: 160. In some embodiments, the humanized sdAb has a FR2 of SEQ ID NO: 249, a FR3 of SEQ ID NO: 250 and a FR4 of SEQ ID NO: 160. In a specific embodiment, the humanized sdAb has a FR1 of SEQ ID NO: 248, a FR2 of SEQ ID NO: 249, a FR3 of SEQ ID NO: 250, and a FR4 of SEQ ID NO: 160.

In a specific embodiment, the humanized sdAb has a CDR1 of SEQ ID NO: 111, a CDR2 of SEQ ID NO: 112, a CDR3 of SEQ ID NO: 113, a FR1 of SEQ ID NO: 248, a FR2 of SEQ ID NO: 249, a FR3 of SEQ ID NO: 250, and a FR4 of SEQ ID NO: 160.

In some embodiments, the sdAb has one or more FR sequences of the humanized anti-MSLN-32.

In some embodiments, the humanized sdAb has a FR1 of SEQ ID NO: 251. In some embodiments, the humanized sdAb has a FR2 of SEQ ID NO: 252. In some embodiments, the humanized sdAb has a FR3 of SEQ ID NO: 253. In other embodiments, the humanized sdAb has a FR4 of SEQ ID NO: 160. In some embodiments, the humanized sdAb has a FR1 of SEQ ID NO: 251 and a FR2 of SEQ ID NO: 252. In some embodiments, the humanized sdAb has a FR1 of SEQ ID NO: 251 and a FR3 of SEQ ID NO: 253. In some embodiments, the humanized sdAb has a FR1 of SEQ ID NO: 251 and a FR4 of SEQ ID NO: 160. In some embodiments, the humanized sdAb has a FR2 of SEQ ID NO: 252 and a FR3 of SEQ ID NO: 253. In some embodiments, the humanized sdAb has a FR2 of SEQ ID NO: 252 and a FR4 of SEQ ID NO: 160. In some embodiments, the humanized sdAb has a FR3 of SEQ ID NO: 253 and a FR4 of SEQ ID NO: 160. In some embodiments, the humanized sdAb has a FR1 of SEQ ID NO: 251, a FR2 of SEQ ID NO: 252 and a FR3 of SEQ ID NO: 253. In some embodiments, the humanized sdAb has a FR1 of SEQ ID NO: 251, a FR2 of SEQ ID NO: 252 and a FR4 of SEQ ID NO: 160. In some embodiments, the humanized sdAb has a FR1 of SEQ ID NO: 251, a FR3 of SEQ ID NO: 253 and a FR4 of SEQ ID NO: 160. In some embodiments, the humanized sdAb has a FR2 of SEQ ID NO: 252, a FR3 of SEQ ID NO: 253 and a FR4 of SEQ ID NO: 160. In a specific embodiment, the humanized sdAb has a FR1 of SEQ ID NO: 251, a FR2 of SEQ ID NO: 252, a FR3 of SEQ ID NO: 253, and a FR4 of SEQ ID NO: 160.

In a specific embodiment, the humanized sdAb has a CDR1 of SEQ ID NO: 114, a CDR2 of SEQ ID NO: 115, a CDR3 of SEQ ID NO: 116, a FR1 of SEQ ID NO: 251, a FR2 of SEQ ID NO: 252, a FR3 of SEQ ID NO: 253, and a FR4 of SEQ ID NO: 160.

In some embodiments, the sdAb has one or more FR sequences of the humanized anti-MSLN-33.

In some embodiments, the humanized sdAb has a FR1 of SEQ ID NO: 254. In some embodiments, the humanized sdAb has a FR2 of SEQ ID NO: 255. In some embodiments, the humanized sdAb has a FR3 of SEQ ID NO: 256. In other embodiments, the humanized sdAb has a FR4 of SEQ ID NO: 160. In some embodiments, the humanized sdAb has a FR1 of SEQ ID NO: 254 and a FR2 of SEQ ID NO: 255. In some embodiments, the humanized sdAb has a FR1 of SEQ ID NO: 254 and a FR3 of SEQ ID NO: 256. In some embodiments, the humanized sdAb has a FR1 of SEQ ID NO: 254 and a FR4 of SEQ ID NO: 160. In some embodiments, the humanized sdAb has a FR2 of SEQ ID NO: 255 and a FR3 of SEQ ID NO: 256. In some embodiments, the humanized sdAb has a FR2 of SEQ ID NO: 255 and a FR4 of SEQ ID NO: 160. In some embodiments, the humanized sdAb has a FR3 of SEQ ID NO: 256 and a FR4 of SEQ ID NO: 160. In some embodiments, the humanized sdAb has a FR1 of SEQ ID NO: 254, a FR2 of SEQ ID NO: 255 and a FR3 of SEQ ID NO: 256. In some embodiments, the humanized sdAb has a FR1 of SEQ ID NO: 254, a FR2 of SEQ ID NO: 255 and a FR4 of SEQ ID NO: 160. In some embodiments, the humanized sdAb has a FR1 of SEQ ID NO: 254, a FR3 of SEQ ID NO: 256 and a FR4 of SEQ ID NO: 160. In some embodiments, the humanized sdAb has a FR2 of SEQ ID NO: 255, a FR3 of SEQ ID NO: 256 and a FR4 of SEQ ID NO: 160. In a specific embodiment, the humanized sdAb has a FR1 of SEQ ID NO: 254, a FR2 of SEQ ID NO: 255, a FR3 of SEQ ID NO: 256, and a FR4 of SEQ ID NO: 160.

In a specific embodiment, the humanized sdAb has a CDR1 of SEQ ID NO: 117, a CDR2 of SEQ ID NO: 118, a CDR3 of SEQ ID NO: 119, a FR1 of SEQ ID NO: 254, a FR2 of SEQ ID NO: 255, a FR3 of SEQ ID NO: 256, and a FR4 of SEQ ID NO: 160.

In some embodiments, the sdAb has one or more FR sequences of the humanized anti-MSLN-34.

In some embodiments, the humanized sdAb has a FR1 of SEQ ID NO: 257. In some embodiments, the humanized sdAb has a FR2 of SEQ ID NO: 258. In some embodiments, the humanized sdAb has a FR3 of SEQ ID NO: 259. In other embodiments, the humanized sdAb has a FR4 of SEQ ID NO: 160. In some embodiments, the humanized sdAb has a FR1 of SEQ ID NO: 257 and a FR2 of SEQ ID NO: 258. In some embodiments, the humanized sdAb has a FR1 of SEQ ID NO: 257 and a FR3 of SEQ ID NO: 259. In some embodiments, the humanized sdAb has a FR1 of SEQ ID NO: 257 and a FR4 of SEQ ID NO: 160. In some embodiments, the humanized sdAb has a FR2 of SEQ ID NO: 258 and a FR3 of SEQ ID NO: 259. In some embodiments, the humanized sdAb has a FR2 of SEQ ID NO: 258 and a FR4 of SEQ ID NO: 160. In some embodiments, the humanized sdAb has a FR3 of SEQ ID NO: 259 and a FR4 of SEQ ID NO: 160. In some embodiments, the humanized sdAb has a FR1 of SEQ ID NO: 257, a FR2 of SEQ ID NO: 258 and a FR3 of SEQ ID NO: 259. In some embodiments, the humanized sdAb has a FR1 of SEQ ID NO: 257, a FR2 of SEQ ID NO: 258 and a FR4 of SEQ ID NO: 160. In some embodiments, the humanized sdAb has a FR1 of SEQ ID NO: 257, a FR3 of SEQ ID NO: 259 and a FR4 of SEQ ID NO: 160. In some embodiments, the humanized sdAb has a FR2 of SEQ ID NO: 258, a FR3 of SEQ ID NO: 259 and a FR4 of SEQ ID NO: 160. In a specific embodiment, the humanized sdAb has a FR1 of SEQ ID NO: 257, a FR2 of SEQ ID NO: 258, a FR3 of SEQ ID NO: 259, and a FR4 of SEQ ID NO: 160.

In a specific embodiment, the humanized sdAb has a CDR1 of SEQ ID NO: 120, a CDR2 of SEQ ID NO: 121, a CDR3 of SEQ ID NO: 122, a FR1 of SEQ ID NO: 257, a FR2 of SEQ ID NO: 258, a FR3 of SEQ ID NO: 259, and a FR4 of SEQ ID NO: 160.

In some embodiments, the humanized sdAb binds to MSLN with a $K_D$ of between 0.01-100 nM. In some embodiments, the humanized sdAb binds to MSLN with a $K_D$ of between 0.1-100 nM. In some embodiments, the humanized sdAb binds to MSLN with a $K_D$ of between 1-100 nM. In other embodiments, the humanized sdAb binds to MSLN with a $K_D$ of between 1-90 nM. In other embodiments, the humanized sdAb binds to MSLN with a $K_D$ of between 1-80 nM. In other embodiments, the humanized sdAb binds to MSLN with a $K_D$ of between 1-70 nM. In some embodiments, the humanized sdAb binds to MSLN with a $K_D$ of between 1-60 nM. In some embodiments, the humanized sdAb binds to MSLN with a $K_D$ of between 1-50 nM. In some embodiments, the humanized sdAb binds to MSLN with a $K_D$ of between 1-40 nM. In some embodiments, the humanized sdAb binds to MSLN with a $K_D$ of between 1-30 nM. In some embodiments, the humanized sdAb binds to MSLN with a $K_D$ of between 1-20 nM. In some embodiments, the humanized sdAb binds to MSLN with a $K_D$ of between 1-10 nM. In some embodiments, the humanized sdAb binds to MSLN with a $K_D$ of between 0.1-1 nM. In some embodiments, the humanized sdAb binds to MSLN with a $K_D$ of between 0.01-1 nM. In some embodiments, the humanized sdAb binds to MSLN with a $K_D$ of between 0.01-0.1 nM.

In some embodiments, the binding molecule that binds to a cancer antigen comprises multiple humanized sdAbs, for example, two sdAbs that bind to MSLN connected by a linker.

In some embodiments, each of the two humanized sdAbs binds to MSLN with a $K_D$ of between 0.01-100 nM. In some embodiments, each of the two humanized sdAbs binds to MSLN with a $K_D$ of between 0.1-100 nM. In some embodiments, each of the two humanized sdAbs binds to MSLN with a $K_D$ of between 1-100 nM. In some embodiments, each of the two humanized sdAbs binds to MSLN with a $K_D$ of between 1-90 nM. In some embodiments, each of the two humanized sdAbs binds to MSLN with a $K_D$ of between 1-80 nM. In some embodiments, each of the two humanized sdAbs binds to MSLN with a $K_D$ of between 1-70 nM. In some embodiments, each of the two humanized sdAbs binds to MSLN with a $K_D$ of between 1-60 nM. In other embodiments, each of the two humanized sdAbs binds to MSLN with a $K_D$ of between 1-50 nM. In other embodiments, each of the two humanized sdAbs binds to MSLN with a $K_D$ of between 1-40 nM. In other embodiments, each of the two humanized sdAbs binds to MSLN with a $K_D$ of between 1-30 nM. In other embodiments, each of the two humanized sdAbs binds to MSLN with a $K_D$ of between 1-20 nM. In other embodiments, each of the two humanized sdAbs binds to MSLN with a $K_D$ of between 1-10 nM. In other embodiments, each of the two humanized sdAbs binds to MSLN with a $K_D$ of between 0.1-1 nM. In some embodiments, each of the two humanized sdAbs binds to MSLN with a $K_D$ of between 0.01-0.1 nM.

Single Domain Antibody Variants

In some embodiments, amino acid sequence modification(s) of the single domain antibodies that bind to MSLN described herein are contemplated. For example, it may be desirable to optimize the binding affinity and/or other biological properties of the antibody, including but not limited to specificity, thermostability, expression level, effector functions, glycosylation, reduced immunogenicity, or solubility. Thus, in addition to the anti-MSLN antibodies described herein, it is contemplated that anti-MSLN antibody variants can be prepared. For example, anti-MSLN antibody variants can be prepared by introducing appropriate nucleotide changes into the encoding DNA, and/or by synthesis of the desired antibody or polypeptide. Those skilled in the art who appreciate that amino acid changes may alter post-translational processes of the anti-MSLN antibody, such as changing the number or position of glycosylation sites or altering the membrane anchoring characteristics.

In some embodiments, the single domain antibodies provided herein are chemically modified, for example, by the covalent attachment of any type of molecule to the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

Variations may be a substitution, deletion, or insertion of one or more codons encoding the single domain antibody or polypeptide that results in a change in the amino acid sequence as compared with the original antibody or polypeptide Amino acid substitutions can be the result of replacing one amino acid with another amino acid having similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 5 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the parental anti-MSLN antibodies.

Amino acid sequence insertions include amino- and/or carboxyl-terminal fusions ranging in length from one residue to polypeptides containing multiple residues, as well as intrasequence insertions of single or multiple amino acid residues. Examples of terminal insertions include an antibody with an N-terminal methionyl residue.

Antibodies generated by conservative amino acid substitutions are included in the present disclosure. In a conservative amino acid substitution, an amino acid residue is replaced with an amino acid residue having a side chain with a similar charge. As described above, families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined. conservative (e.g., within an amino acid group with similar properties and/or side chains) substitutions may be made, so as to maintain or not significantly change the properties.

Amino acids may be grouped according to similarities in the properties of their side chains (see, e.g., Lehninger, Biochemistry 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His(H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

For example, any cysteine residue not involved in maintaining the proper conformation of the anti-MSLN antibody also may be substituted, for example, with another amino acid, such as alanine or serine, to improve the oxidative stability of the molecule and to prevent aberrant crosslinking.

The variations can be made using methods known in the art such as oligonucleotide-mediated (site-directed) mutagenesis, alanine scanning, and PCR mutagenesis. Site-directed mutagenesis (see, e.g., Carter, 1986, Biochem J. 237:1-7; and Zoller et al., 1982, Nucl. Acids Res. 10:6487-500), cassette mutagenesis (see, e.g., Wells et al., 1985, Gene 34:315-23), or other known techniques can be performed on the cloned DNA to produce the anti-MSLN antibody variant DNA.

In Vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed on the surface of an organism (e.g., phage, bacteria, yeast, or mammalian cell) or in association (e.g., covalently or non-covalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Affinity matured antibodies can have nanomolar or even picomolar affinities for the target antigen.

Phage display is a widespread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning" Phage bound to antigen are recovered and used to infect bacteria to produce phage for further rounds of selection. For review, see, for example, Hoogenboom, 2002, Methods. Mol. Biol. 178:1-37; and Bradbury and Marks, 2004, J. Immunol. Methods 290:29-49.

In a yeast display system (see, e.g., Boder et al., 1997, Nat. Biotech. 15:553-57; and Chao et al., 2006, Nat. Protocols 1:755-68), the antibody may be fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the scFv. Expression has been shown to correlate with the stability of the displayed protein, and thus antibodies can be selected for improved stability as well as affinity (see, e.g., Shusta et al., 1999, J. Mol. Biol. 292:949-56). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently "titrated" while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., U.S. Pat. Publication 2003/0186374; and Blaise et al., 2004, Gene 342:211-18).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reverse transcribed back into cDNA, which can then undergo mutagenesis and be used in the next round of selection (see, e.g., Fukuda et al., 2006, Nucleic Acids Res. 34:e127). In mRNA display, a covalent bond between antibody and mRNA is established using puromycin as an adaptor molecule (Wilson et al., 2001, Proc. Natl. Acad. Sci. USA 98:3750-55).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerases, as no library must be transformed after any diversification step.

In some embodiments, mammalian display systems may be used.

Diversity may also be introduced into the CDRs of the antibody libraries in a targeted manner or via random introduction. The former approach includes sequentially targeting all the CDRs of an antibody via a high or low level of mutagenesis or targeting isolated hot spots of somatic hypermutations (see, e.g., Ho et al., 2005, J. Biol. Chem. 280:607-17) or residues suspected of affecting affinity on experimental basis or structural reasons. Diversity may also be introduced by replacement of regions that are naturally diverse via DNA shuffling or similar techniques (see, e.g., Lu et al., 2003, J. Biol. Chem. 278:43496-507; U.S. Pat. Nos. 5,565,332 and 6,989,250). Alternative techniques target hypervariable loops extending into framework-region residues (see, e.g., Bond et al., 2005, J. Mol. Biol. 348:699-709) employ loop deletions and insertions in CDRs or use hybridization-based diversification (see, e.g., U.S. Pat. Publication No. 2004/0005709). Additional methods of generating diversity in CDRs are disclosed, for example, in U.S. Pat. No. 7,985,840. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

Screening of the libraries can be accomplished by various techniques known in the art. For example, anti-MSLN antibodies can be immobilized onto solid supports, columns, pins, or cellulose/poly(vinylidene fluoride) membranes/other filters, expressed on host cells affixed to adsorption plates or used in cell sorting, or conjugated to biotin for capture with streptavidin-coated beads or used in any other method for panning display libraries.

For review of in vitro affinity maturation methods, see, e.g., Hoogenboom, 2005, Nature Biotechnology 23:1105-16; Quiroz and Sinclair, 2010, Revista Ingeneria Biomedia 4:39-51; and references therein.

Modifications of Anti-MSLN Single Domain Antibodies

Covalent modifications of anti-MSLN antibodies are included within the scope of the present disclosure. Covalent modifications include reacting targeted amino acid residues of an anti-MSLN antibody with an organic derivatizing agent that is capable of reacting with selected side chains or the N- or C-terminal residues of the anti-MSLN antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see, e.g., Creighton, Proteins: Structure and Molecular Properties 79-86 (1983)), acetylation of the N-terminal amine, and amidation of any C-terminal carboxyl group.

Other types of covalent modification of the anti-MSLN antibody included within the scope of this present disclosure include altering the native glycosylation pattern of the antibody or polypeptide (see, e.g., Beck et al., 2008, Curr. Pharm. Biotechnol. 9:482-501; and Walsh, 2010, Drug Discov. Today 15:773-80), and linking the antibody to one of a variety of nonproteinaceous polymers, e.g., polyethylene glycol (PEG), polypropylene glycol, or polyoxyalkylenes, in the manner set forth, for example, in U.S. Pat. Nos. 4,640,835; 4,496,689; 4,301,144; 4,670,417; 4,791,192; or 4,179,337.

An anti-MSLN antibody of the present disclosure may also be modified to form chimeric molecules comprising an anti-MSLN antibody fused to another, heterologous polypeptide or amino acid sequence, for example, an epitope tag (see, e.g., Terpe, 2003, Appl. Microbiol. Biotechnol. 60:523-33) or the Fc region of an IgG molecule (see, e.g., Aruffo, Antibody Fusion Proteins 221-42 (Chamow and Ashkenazi eds., 1999)).

Also provided herein are fusion proteins comprising an antibody provided herein that binds to an MSLN antigen and a heterologous polypeptide. In some embodiments, the heterologous polypeptide to which the antibody is fused is useful for targeting the antibody to cells having cell surface-expressed MSLN.

Also provided herein are panels of antibodies that bind to an MSLN antigen. In specific embodiments, the panels of antibodies have different association rates, different dissociation rates, different affinities for an MSLN antigen, and/or different specificities for an MSLN antigen. In some embodiments, the panels comprise or consist of about 10, about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96-well or 384-well plates, for assays such as ELISAs.

Preparation of Anti-MSLN Single Domain Antibodies

Anti-MSLN single domain antibodies provided herein may be produced by culturing cells transformed or transfected with a vector containing anti-anti-MSLN antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridomas cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression, and purification are further described in Plückthun et al., Antibody Engineering: Producing antibodies in *Escherichia coli*: From PCR to fermentation 203-52 (McCafferty et al. eds., 1996); Kwong and Rader, *E. coli Expression and Purification of Fab Antibody Fragments, in* Current Protocols in Protein Science (2009); Tachibana and Takekoshi, *Production of Antibody Fab Fragments in Escherischia coli, in* Antibody Expression and Production (Al-Rubeai ed., 2011); and Therapeutic Monoclonal Antibodies: From Bench to Clinic (An ed., 2009).

It is, of course, contemplated that alternative methods, which are well known in the art, may be employed to prepare anti-MSLN antibodies. For instance, the appropriate amino acid sequence, or portions thereof, may be produced by direct peptide synthesis using solid-phase techniques (see, e.g., Stewart et al., Solid-Phase Peptide Synthesis (1969); and Merrifield, 1963, J. Am. Chem. Soc. 85:2149-54). In vitro protein synthesis may be performed using manual techniques or by automation. Various portions of the anti-MSLN antibody may be chemically synthesized separately and combined using chemical or enzymatic methods to produce the desired anti-MSLN antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

Immunoconjugates

The present disclosure also provides conjugates comprising any one of the anti-MSLN antibodies of the present disclosure covalently bound by a synthetic linker to one or more non-antibody agents.

In some embodiments, antibodies provided herein are conjugated or recombinantly fused, e.g., to a diagnostic or detectable molecule. The conjugated or recombinantly fused antibodies can be useful, for example, for monitoring or prognosing the onset, development, progression, and/or severity of a MSLN-mediated disease.

Such diagnosis and detection can be accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin or avidin/biotin; fluorescent materials, such as, but not limited to, umbelliferone, fluorescein, fluorescein isothiocynate, rhodamine, dichlorotriazinylamine fluorescein, dansyl chloride, or phycoerythrin; luminescent materials, such as, but not limited to, luminol; bioluminescent materials, such as, but not limited to, luciferase, luciferin, or aequorin; chemiluminescent material, such as, but not limited to, an acridinium based compound or a HALOTAG; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga and 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, or 117Sn; positron emitting metals using various positron emission tomographies; and non-radioactive paramagnetic metal ions.

Also provided herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90, or about 100 amino acids) to generate fusion proteins, as well as uses thereof. In particular, provided herein are fusion proteins comprising an antigen-binding fragment of an antibody provided herein (e.g., CDR1, CDR2, and/or CDR3) and a heterologous protein, polypeptide, or peptide. In one embodiment, the heterologous protein, polypeptide, or peptide that the antibody is fused to is useful for targeting the antibody to a particular cell type, such as a cell that expresses MSLN. For example, an antibody that binds to a cell surface receptor expressed by a particular cell type may be fused or conjugated to a modified antibody provided herein.

Moreover, antibodies provided herein can be fused to marker or "tag" sequences, such as a peptide, to facilitate purification. In specific embodiments, the marker or tag amino acid sequence is a hexa-histidine peptide, such as the tag provided in a pQE vector (see, e.g., QIAGEN, Inc.), among others, many of which are commercially available. For example, as described in Gentz et al., 1989, Proc. Natl. Acad. Sci. USA 86:821-24, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767-78), and the "FLAG" tag.

Methods for fusing or conjugating moieties (including polypeptides) to antibodies are known (see, e.g., Arnon et al., Monoclonal Antibodies for Immunotargeting of Drugs in Cancer Therapy, in Monoclonal Antibodies and Cancer Therapy 243-56 (Reisfeld et al. eds., 1985); Hellstrom et al., Antibodies for Drug Delivery, in Controlled Drug Delivery 623-53 (Robinson et al. eds., 2d ed. 1987); Thorpe, Antibody Carriers of Cytotoxic Agents in Cancer Therapy: A Review, in Monoclonal Antibodies: Biological and Clinical Applications 475-506 (Pinchera et al. eds., 1985); Analysis, Results, and Future Prospective of the Therapeutic Use of Radiolabeled Antibody in Cancer Therapy, in Monoclonal Antibodies for Cancer Detection and Therapy 303-16 (Baldwin et al. eds., 1985); Thorpe et al., 1982, Immunol. Rev. 62:119-58; U.S. Pat. Nos. 5,336,603; 5,622,929; 5,359,046; 5,349,053;

5,447,851; 5,723,125; 5,783,181; 5,908,626; 5,844,095; and 5,112,946; EP 307,434; EP 367,166; EP 394,827; PCT publications WO 91/06570, WO 96/04388, WO 96/22024, WO 97/34631, and WO 99/04813; Ashkenazi et al., 1991, Proc. Natl. Acad. Sci. USA, 88: 10535-39; Traunecker et al., 1988, Nature, 331:84-86; Zheng et al., 1995, J. Immunol. 154:5590-600; and Vil et al., 1992, Proc. Natl. Acad. Sci. USA 89:11337-41).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of anti-MSLN antibodies as provided herein, including, for example, antibodies with higher affinities and lower dissociation rates (see, e.g., U.S. Pat. Nos. 5,605,793; 5,811,238; 5,830,721; 5,834,252; and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-13). Antibodies, or the encoded antibodies, may be altered by being subjected to random mutagenesis by error-prone PCR, random nucleotide insertion, or other methods prior to recombination. A polynucleotide encoding an antibody provided herein may be recombined with one or more components, motifs, sections, parts, domains, fragments, etc. of one or more heterologous molecules.

An antibody provided herein (e.g., sdAb) can also be conjugated to a second antibody to form an antibody heteroconjugate as described, for example, in U.S. Pat. No. 4,676,980.

Antibodies that bind to MSLN as provided herein may also be attached to solid supports, which are particularly useful for immunoassays or purification of the target antigen. Such solid supports include, but are not limited to, glass, cellulose, polyacrylamide, nylon, polystyrene, polyvinyl chloride, or polypropylene.

The linker may be a "cleavable linker" facilitating release of the conjugated agent in the cell, but non-cleavable linkers are also contemplated herein. Linkers for use in the conjugates of the present disclosure include, without limitation, acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers (see, e.g., Chari et al., 1992, Cancer Res. 52:127-31; and U.S. Pat. No. 5,208,020), thioether linkers, or hydrophilic linkers designed to evade multidrug transporter-mediated resistance (see, e.g., Kovtun et al., 2010, Cancer Res. 70:2528-37).

Conjugates of the antibody and agent may be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate). The present disclosure further contemplates that conjugates of antibodies and agents may be prepared using any suitable methods as disclosed in the art (see, e.g., Bioconjugate Techniques (Hermanson ed., 2d ed. 2008)).

Conventional conjugation strategies for antibodies and agents have been based on random conjugation chemistries involving the ε-amino group of Lys residues or the thiol group of Cys residues, which results in heterogenous conjugates. Recently developed techniques allow site-specific conjugation to antibodies, resulting in homogeneous loading and avoiding conjugate subpopulations with altered antigen-binding or pharmacokinetics. These include engineering of "thiomabs" comprising cysteine substitutions at positions on the heavy and light chains that provide reactive thiol groups and do not disrupt immunoglobulin folding and assembly or alter antigen binding (see, e.g., Junutula et al., 2008, J. Immunol. Meth. 332: 41-52; and Junutula et al., 2008, Nature Biotechnol. 26:925-32). In another method, selenocysteine is cotranslationally inserted into an antibody sequence by recoding the stop codon UGA from termination to selenocysteine insertion, allowing site specific covalent conjugation at the nucleophilic selenol group of selenocysteine in the presence of the other natural amino acids (see, e.g., Hofer et al., 2008, Proc. Natl. Acad. Sci. USA 105: 12451-56; and Hofer et al., 2009, Biochemistry 48(50): 12047-57).

Anti-Mesothelin Fc Fusion Proteins

The anti-MSLN constructs (such as isolated anti-MSLN constructs) in some embodiments are Fc fusion proteins (hereinafter referred to as "anti-MSLN-Fc fusion protein") comprising an anti-MSLN antibody moiety described herein fused to an Fc fragment (such as IgG1 Fc fragment). In some embodiments, the anti-MSLN antibody moiety is fused to an Fc fragment via a linker (such as peptide linker). In some embodiments, the anti-MSLN-Fc fusion protein comprises an antibody comprising an Fc fragment. In some embodiments, the anti-MSLN-Fc fusion protein is a full-length antibody. Any of the anti-MSLN antibody moieties described in the "anti-MSLN antibody moiety section" can be employed in the anti-MSLN Fc fusion protein.

Fc Fragment

The term "Fc region," "Fc domain" or "Fc" refers to a C-terminal non-antigen binding region of an immunoglobulin heavy chain that contains at least a portion of the constant region. The term includes native Fc regions and variant Fc regions. In some embodiments, a human IgG heavy chain Fc region extends from Cys226 to the carboxyl-terminus of the heavy chain. However, the C-terminal lysine (Lys447) of the Fc region may or may not be present, without affecting the structure or stability of the Fc region. Unless otherwise specified herein, numbering of amino acid residues in the IgG or Fc region is according to the EU numbering system for antibodies, also called the EU index, as described in Kabat et al., Sequences of Proteins of Immunological Interest, 5th Ed. Public Health Service, National Institutes of Health, Bethesda, MD, 1991.

In some embodiments, the Fc fragment comprises an immunoglobulin IgG heavy chain constant region comprising a hinge region (starting at Cys226), an IgG CH2 domain and CH3 domain. The term "hinge region" or "hinge sequence" as used herein refers to the amino acid sequence located between the linker and the CH2 domain. In some embodiments, the fusion protein comprises an Fc fragment comprising a hinge region. In some embodiments, the hinge region comprises the amino acid sequence CPPCP (SEQ ID NO: 345), a sequence found in the native IgG1 hinge region, to facilitate dimerization. In some embodiments, the Fc fragment of the fusion protein starts at the hinge region and extends to the C-terminus of the IgG heavy chain. In some embodiments, the fusion protein comprises an Fc fragment that does not comprise the hinge region.

In some embodiments, the fusion protein comprises an Fc fragment selected from the group consisting of Fc fragments from IgG, IgA, IgD, IgE, IgM, and combinations and hybrids thereof. In some embodiments, the Fc fragment is derived from a human IgG. In some embodiments, the Fc fragment comprises the Fc region of human IgG1, IgG2, IgG3, IgG4, or a combination or hybrid IgG. In some embodiments, the Fc fragment is an IgG1 Fc fragment. In some embodiments, the Fc fragment comprises the CH2 and CH3 domains of IgG1. In some embodiments, the Fc fragment is an IgG4 Fc fragment. In some embodiments, the Fc fragment comprises the CH2 and CH3 domains of IgG4. IgG4 Fc is known to exhibit less effector activity than IgG1 Fc, and thus may be desirable for some applications. In some embodiments, the Fc fragment is derived from of a mouse immunoglobulin.

In some embodiments, the IgG CH2 domain starts at Ala231. In some embodiments, the CH3 domain starts at Gly341. It is understood that the C-terminus Lys residue of human IgG can be optionally absent. It is also understood that conservative amino acid substitutions of the Fc region without affecting the desired structure and/or stability of Fc is contemplated within the scope of the invention.

Additionally, anti-MSLN-Fc fusion proteins comprising any of the Fc variants described below, or combinations thereof, are contemplated. In some embodiments, the Fc fragment comprises sequence that has been altered or otherwise changed so that it has enhanced antibody dependent cellular cytotoxicity (ADCC) or complement dependent cytotoxicity (CDC) effector function.

In some embodiments, each chain of the Fc fragment is fused to the same entity. In some embodiments, the anti-MSLN-Fc fusion protein comprises two identical anti-MSLN antibody moieties described herein (specifically recognizing mesothelin), each fused with one chain of the Fc fragment. In some embodiments, the two chains of the Fc fragment are identical. In some embodiments, the anti-MSLN-Fc fusion protein (including anti-MSLN-Fc fusion proteins comprising an antibody) comprising the Fc fragment is a homodimer.

In some embodiments, each chain of the Fc fragment is fused to a different entity. In some embodiments, the fusion protein comprises two different anti-MSLN antibody moieties, each fused to one chain of the Fc fragment. In some embodiments, the two anti-MSLN antibody moieties are different but both specifically recognize mesothelin. In some embodiments, the two anti-MSLN antibody moieties are different but both specifically recognize mesothelin. In some embodiments, the anti-MSLN-Fc fusion protein is monovalent, i.e., only one anti-MSLN antibody moiety is fused to one chain of the Fc fragment, and the second chain of the Fc fragment is not fused to an anti-MSLN antibody moiety. In some embodiments, the anti-MSLN-Fc fusion protein (including anti-MSLN-Fc fusion proteins comprising an antibody) comprising the Fc fragment is a heterodimer.

Heterodimerization of non-identical polypeptides in the anti-MSLN-Fc fusion protein can be facilitated by methods known in the art, including without limitation, heterodimerization by the knob-into-hole technology. The structure and assembly method of the knob-into-hole technology can be found in, e.g., U.S. Pat. Nos. 5,821,333, 7,642,228, US 2011/0287009 and PCT/US2012/059810, hereby incorporated by reference in their entireties. This technology was developed by introducing a "knob" (or a protuberance) by replacing a small amino acid residue with a large one in the CH3 domain of one Fc, and introducing a "hole" (or a cavity) in the CH3 domain of the other Fc by replacing one or more large amino acid residues with smaller ones. In some embodiments, one chain of the Fc fragment in the fusion protein comprises a knob, and the second chain of the Fc fragment comprises a hole.

The preferred residues for the formation of a knob generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the knob has a small side chain volume, such as alanine, asparagine, aspartic acid, glycine, serine, threonine or valine. Exemplary amino acid substitutions in the CH3 domain for forming the knob include without limitation the T366W, T366Y or F405W substitution.

The preferred residues for the formation of a hole are usually naturally occurring amino acid residues and are preferably selected from alanine (A), serine (S), threonine (T) and valine (V). In one embodiment, the original residue for the formation of the hole has a large side chain volume, such as tyrosine, arginine, phenylalanine or tryptophan. Exemplary amino acid substitutions in the CH3 domain for generating the hole include without limitation the T366S, L368A, F405A, Y407A, Y407T and Y407V substitutions. In certain embodiments, the knob comprises T366W substitution, and the hole comprises the T366S/L368A/Y 407V substitutions. It is understood that other modifications to the Fc region known in the art that facilitate heterodimerization are also contemplated and encompassed by the instant application.

Other anti-MSLN Fc fusion protein variants (such as variants of isolated anti-MSLN-Fc fusion protein, e.g., a full-length anti-MSLN antibody variant) comprising any of the variants described herein (e.g., Fc variants, effector function variants, glycosylation variants, cysteine engineered variants), or combinations thereof, are contemplated. See "anti-MSLN variants" section for all applicable variations for the anti-MSLN Fc fusion protein (e.g., full-length anti-MSLN antibody).

Reduced Fucosylation

In some embodiments, the anti-mesothelin constructs comprises a) an anti-mesothelin antibody moiety, and b) an Fc fragment fused to the anti-mesothelin antibody moiety, wherein the Fc fragment has a reduced fucosylation. In some embodiments, the Fc is fragment selected from the group consisting of Fc fragments from IgG, IgA, IgD, IgE, IgM, and combinations and hybrids thereof. In some embodiments, the Fc fragment is derived from a human IgG. In some embodiments, the Fc fragment comprises the Fc region of human IgG1, IgG2, IgG3, IgG4, or a combination or hybrid IgG. In some embodiments, the Fc fragment is an IgG1 Fc fragment. In some embodiments, the Fc fragment has at least 10%, 20%, 30%, 40%, 50%, 60%, 70%, 80%, or 90% less fucosylation than a corresponding wildtype Fc fragment.

In some embodiments, the anti-mesothelin construct comprises a) an anti-mesothelin antibody comprising i) an anti-mesothelin antibody moiety, ii) an Fc fragment fused to the anti-mesothelin antibody moiety, and b) a cytokine (such as a cytokine fusion protein comprising an IL-21 and a half-life extending domain (e.g., an antibody that binds to albumin)) fused to the anti-mesothelin antibody. In some embodiments, the cytokine is fused to the N-terminus of the anti-mesothelin antibody moiety. In some embodiments, the cytokine is fused to the anti-mesothelin antibody via a linker (such as a peptide linker). In some embodiments, the peptide linker is a stable linker, which is not cleavable by protease, such as by Matrix metalloproteinases (MMPs).

Multi-Specific Anti-Mesothelin Constructs

The anti-mesothelin constructs in some embodiments comprise a multi-specific (e.g., bispecific) anti-mesothelin molecule comprising an anti-mesothelin antibody moiety according to any one of the anti-mesothelin antibody moieties described herein, and a second binding moiety (such as a second antibody moiety) specifically recognizing a second antigen. In some embodiments, the multi-specific anti-mesothelin molecule comprises an anti-mesothelin antibody moiety and a second antibody moiety specifically recognizing a second antigen.

Multi-specific molecules are molecules that have binding specificities for at least two different antigens or epitopes (e.g., bispecific antibodies have binding specificities for two antigens or epitopes). Multi-specific molecules with more than two valences and/or specificities are also contemplated. For example, trispecific antibodies can be prepared (Tutt et al. *J. Immunol.* 147: 60 (1991)). It is to be appreciated that one of skill in the art could select appropriate features of individual multi-specific molecules described herein to combine with one another to form a multi-specific anti-mesothelin molecule of the application.

In some embodiments, the multi-specific anti-mesothelin construct is, for example, a diabody (Db), a single-chain diabody (scDb), a tandem scDb (Tandab), a linear dimeric scDb (LD-scDb), a circular dimeric scDb (CD-scDb), a di-diabody, a tandem scFv, a tandem di-scFv (e.g., a bispecific T cell engager), a tandem tri-scFv, a tri(a)body, a bispecific Fab2, a di-miniantibody, a tetrabody, an scFv-Fc-scFv fusion, a dual-affinity retargeting (DART) antibody, a dual variable domain (DVD) antibody, an IgG-scFab, an scFab-ds-scFv, an Fv2-Fc, an IgG-scFv fusion, a dock and lock (DNL) antibody, a knob-into-hole (KiH) antibody (bispecific IgG prepared by the KiH technology), a DuoBody (bispecific IgG prepared by the Duobody technology), a heteromultimeric antibody, or a heteroconjugate antibody. In some embodiments, the multi-specific anti-mesothelin molecule is a tandem scFv (e.g., a tandem di-scFv, such as a bispecific T cell engager).

Second Antigen

In some embodiments, the anti-MSLN construct comprises a multi-specific (e.g., bispecific) anti-MSLN molecule comprising an anti-MSLN antibody moiety and a second antibody moiety (e.g. scFv) specifically recognizing a second antigen. In some embodiments, the second antigen is also mesothelin but comprises a different epitope compared to that recognized by the anti-MSLN antibody moiety. In some embodiments, the second antigen is not mesothelin. In some embodiments, the second antigen is a tumor antigen. In some embodiments, the second antigen is CD3 (e.g., human CD3)

In some embodiments, the multi-specific (e.g., bispecific) anti-MSLN constructs described herein can be engineered to facilitate killing (e.g., cytotoxic lysis or phagocytosis) of tumor cells by directing (or recruiting) an effector cell (such as a cytotoxic T cell) to a tumor site. In some embodiments, tumor cytotoxicity can be tested using an LDH Cytotoxicity Assay. In some embodiments, the multi-specific (e.g., bispecific) anti-MSLN molecule can effectively direct an effector cell (e.g., T cell, NK cell, CAR-T cell, caTCR-T cell) to a target cell in an immunosuppressive environment, such as an immunosuppressive tumor environment.

Exemplary effector cells include without limitation a T cell, a B cell, a natural killer (NK) cell, a dendritic cell (DC), a macrophage, a monocyte, a neutrophil, a natural killer T (NKT) cell, an antibody-dependent cytotoxic cell, a chimeric antigen receptor (CAR) effector cell (e.g., CAR-T), a chimeric antibody-T cell receptor (TCR) construct (caTCR) effector cell (see caTCR section below), or the like. In some embodiments, the effector cell is a T cell (e.g., a cytotoxic T cell, a helper T cell, or an NKT cell). In some embodiments, the effector cell is a cytotoxic T cell. In some embodiments, the effector cell is allogenic. In some embodiments, the effector cell is autologous.

Inducible Expression

In some embodiments, the expression of the multi-specific (e.g., bispecific) anti-MSLN molecule (e.g., anti-MSLN×CD3 tandem di-scFv T cell engager) is inducible. In some embodiments, an effector cell (e.g., T cell, CAR-T cell, caTCR T cell) comprises a nucleic acid sequence encoding the multi-specific (e.g., bispecific) anti-MSLN molecule (e.g., anti-MSLN×CD3 bispecific T cell engager) operably linked to an inducible promoter, including any inducible promoter described herein (e.g., see "Nucleic Acids" section). In some embodiments, the expression of the multi-specific (e.g., bispecific) anti-MSLN molecule (e.g., anti-MSLN×CD3 tandem di-scFv T cell engager) in the effector cell (e.g., T cell, CAR-T cell, caTCR T cell) is inducible upon signaling through a signaling receptor on the effector cell (e.g., TCR, CAR, caTCR). In some such embodiments, a CAR-T cell comprises a nucleic acid sequence encoding the multi-specific (e.g., bispecific) anti-MSLN molecule (e.g., anti-MSLN×CD3 tandem di-scFv T cell engager) operably linked to a promoter or regulatory element responsive to signaling through the CAR. In some such embodiments, a caTCR-T cell comprises a nucleic acid sequence encoding the multi-specific (e.g., bispecific) anti-MSLN molecule (e.g., anti-MSLN×CD3 tandem di-scFv T cell engager) operably linked to a promoter or regulatory element responsive to signaling through the caTCR. In some embodiments, the nucleic acid sequence encoding the multi-specific (e.g., bispecific) anti-MSLN molecule (e.g., anti-MSLN×CD3 tandem di-scFv T cell engager) is operably linked to a nuclear-factor of the activated T-cell (NFAT)-derived promoter. In some embodiments, the NFAT-derived promoter is an NFAT-derived minimal promoter (see for example Durand, D. et. al., *Molec. Cell. Biol.* 8, 1715-1724 (1988); Clipstone, N A, Crabtree, G R. *Nature.* 1992 357 (6380): 695-7; Chmielewski, M., et al. *Cancer research* 71.17 (2011): 5697-5706; and Zhang, L., et al. *Molecular therapy* 19.4 (2011): 751-759). The NFAT family of transcription factors are important regulators of T cell activation. In some embodiments, the nucleic acid sequence encoding the multi-specific (e.g., bispecific) anti-MSLN molecule (e.g., anti-MSLN×CD3 tandem di-scFv T cell engager) is operably linked to an IL-2 promoter.

Chimeric Antigen Receptor (CAR) and CAR Effector Cells

The anti-MSLN construct in some embodiments is a CAR comprising an anti-MSLN antibody moiety (also referred to herein as an "anti-MSLN CAR"). Any one of the anti-MSLN antibody moieties described herein can be employed in the anti-MSLN CAR. Also provided is a CAR effector cell (e.g., T cell) comprising a CAR comprising an anti-MSLN antibody moiety (also referred to herein as an "anti-MSLN CAR effector cell", e.g., "anti-MSLN CAR T cell"). In some embodiments, the anti-MSLN CAR comprises an anti-MSLN antibody moiety specifically recognizing a cell surface-bound MSLN.

The anti-MSLN CAR comprises a) an extracellular domain comprising an anti-MSLN antibody moiety that specifically binds to MSLN, and b) an intracellular signaling domain. A transmembrane domain may be present between the extracellular domain and the intracellular domain.

Between the extracellular domain and the transmembrane domain of the anti-MSLN CAR, or between the intracellular domain and the transmembrane domain of the anti-MSLN CAR, there may be a spacer domain. The spacer domain can be any oligo- or polypeptide that functions to link the transmembrane domain to the extracellular domain or the intracellular domain in the polypeptide chain. A spacer domain may comprise up to about 300 amino acids, including for example about 10 to about 100, or about 25 to about 50 amino acids.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the α, β, δ, or γ chain of the T-cell receptor, CD28, CD3ε, CD3ζ, CD45, CD4, CD5, CD8, CD9, CD16, CD22, CD33, CD37, CD64, CD80, CD86, CD134, CD137, or CD154. In some embodiments, the transmembrane domain may be synthetic, in which case it may comprise predominantly hydrophobic residues such as leucine and valine. In some embodiments, a triplet of phenylalanine, tryptophan and valine may be found at each end of a synthetic transmembrane domain. In some embodiments, a short oligo- or polypeptide linker, having a length of, for example, between about 2 and about 10 (such as about any of 2, 3, 4, 5, 6, 7, 8, 9, or 10) amino acids in length may form the linkage between the transmembrane domain and the intracellular signaling domain of the anti-MSLN CAR. In some embodiments, the linker is a glycine-serine doublet.

In some embodiments, the transmembrane domain that is naturally associated with one of the sequences in the intracellular domain of the anti-MSLN CAR is used (e.g., if an anti-MSLN CAR intracellular domain comprises a CD28 co-stimulatory sequence, the transmembrane domain of the anti-MSLN CAR is derived from the CD28 transmembrane domain). In some embodiments, the transmembrane domain can be selected or modified by amino acid substitution to avoid binding of such domains to the transmembrane domains of the same or different surface membrane proteins to minimize interactions with other members of the receptor complex.

The intracellular signaling domain of the anti-MSLN CAR is responsible for activation of at least one of the normal effector functions of the immune cell in which the anti-MSLN CAR has been placed in. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term "intracellular signaling sequence" is thus meant to include any truncated portion of the intracellular signaling domain sufficient to transduce the effector function signal.

Examples of intracellular signaling domains for use in the anti-MSLN CAR of the invention include the cytoplasmic sequences of the TCR and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of intracellular signaling sequence: those that initiate antigen-dependent primary activation through the TCR (primary signaling sequences) and those that act in an antigen-independent manner to provide a secondary or co-stimulatory signal (co-stimulatory signaling sequences).

Primary signaling sequences regulate primary activation of the TCR complex either in a stimulatory way, or in an inhibitory way. Primary signaling sequences that act in a stimulatory manner may contain signaling motifs which are known as immunoreceptor tyrosine-based activation motifs or ITAMs. The anti-MSLN CAR constructs in some embodiments comprise one or more ITAMs.

Examples of ITAM containing primary signaling sequences that are of particular use in the invention include those derived from TCRζ, FcRγ, FcRβ, CD3γ, CD3δ, CD3ε, CD5, CD22, CD79a, CD79b, and CD66d.

In some embodiments, the anti-MSLN CAR comprises a primary signaling sequence derived from CD3ζ. For example, the intracellular signaling domain of the CAR can comprise the CD3ζ intracellular signaling sequence by itself or combined with any other desired intracellular signaling sequence(s) useful in the context of the anti-MSLN CAR of the invention. For example, the intracellular domain of the anti-MSLN CAR can comprise a CD3ζ intracellular signaling sequence and a costimulatory signaling sequence. The costimulatory signaling sequence can be a portion of the intracellular domain of a costimulatory molecule including, for example, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like.

In some embodiments, the intracellular signaling domain of the anti-MSLN CAR comprises the intracellular signaling sequence of CD3ζ and the intracellular signaling sequence of CD28. In some embodiments, the intracellular signaling domain of the anti-MSLN CAR comprises the intracellular signaling sequence of CD3ζ and the intracellular signaling sequence of 4-1BB. In some embodiments, the intracellular signaling domain of the anti-MSLN CAR comprises the intracellular signaling sequence of CD3ζ and the intracellular signaling sequences of CD28 and 4-1BB.

In some embodiments, there is provided an anti-MSLN CAR comprising a) an extracellular domain comprising an anti-MSLN antibody moiety that specifically binds to MSLN, comprising an anti-MSLN heavy chain variable region (VH) comprising: a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NOS: 123-156 and 285-301; b) a transmembrane domain, and c) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence. In some embodiments, the antibody moiety comprises the amino acid sequence of any one of SEQ ID Nos: 123-156 and 285-301, or a variant thereof having at least about 80% (such as about 85%, 90%, 95%, 98%, or 99%) sequence identity to any one of SEQ ID NOs: 123-156 and 285-301.

Also provided is a method of producing an effector cell expressing an anti-MSLN CAR, the method comprising introducing a vector comprising a nucleic acid encoding the anti-MSLN CAR into the effector cell. In some embodiments, introducing the vector into the effector cell comprises transducing the effector cell with the vector. In some embodiments, introducing the vector into the effector cell comprises transfecting the effector cell with the vector. Transduction or transfection of the vector into the effector cell can be carried about using any method known in the art.

In some embodiments, there is provided an anti-MSLN CAR effector cell (such as lymphocytes, e.g., T cells) comprising a nucleic acid sequence encoding a multi-specific (e.g., bispecific) anti-MSLN molecule (e.g., anti-MSLN×CD3 bispecific T cell engager) described herein operably linked to an inducible promoter. In some embodiments, the expression of the multi-specific (e.g., bispecific) anti-MSLN construct in the anti-MSLN CAR effector cell is inducible upon signaling through the anti-MSLN CAR. In some embodiments, the nucleic acid sequence encoding the multi-specific (e.g., bispecific) anti-MSLN construct is operably linked to an NFAT-derived promoter. In some embodiments, the NFAT-derived promoter is an NFAT-derived minimal promoter. In some embodiments, the nucleic acid sequence encoding the multi-specific (e.g., bispecific) anti-MSLN molecule (is operably linked to an IL-2 promoter.

Linkers

In some embodiments, the fusion proteins or anti-mesothelin constructs comprises a linker between two domains (such as between an anti-mesothelin antibody moiety and a second domain such as a cytokine, an Fc domain etc.). The linker can be any of the linkers described below as either as "a first linker" or "a second linker."

In some embodiments, the fusion proteins comprising IL-21 comprises a first linker between IL-21 or variant thereof and the albumin binding molecule and a second linker between the albumin binding molecule and the binding molecule that binds to an antigen. In some embodiments, the first linker and/or the second linker can be independently a rigid linker or a flexible linker.

In some embodiments, the linker (e.g., the first linker, the second linker) is a non-peptide linker. In some embodiments, the linker (e.g., the first linker, the second linker) is a peptide linker.

Non-Peptide Linkers

Any one or all of the linkers described herein can be accomplished by any chemical reaction that will bind the two molecules so long as the components or fragments retain their respective activities, e.g. binding to target mesothelin, binding to FcR, or ADCC/CDC. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents are useful in coupling protein molecules, such as an Fc fragment to the anti-mesothelin antibody moiety of the present invention. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents (see Killen and Lindstrom, Jour. Immun 133:1335-2549 (1984); Jansen et al., Immunological Reviews 62:185-216 (1982); and Vitetta et al., Science 238:1098 (1987)).

Linkers that can be applied in the present application are described in the literature (see, for example, Ramakrishnan, S. et al., Cancer Res. 44:201-208 (1984) describing use of MBS (M-maleimidobenzoyl-N-hydroxysuccinimide ester)). In some embodiments, non-peptide linkers used herein include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to anti-mesothelin constructs with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form fusion protein with increased stability. Disulfide linkages, are in general, less stable than other linkages because the disulfide linkage is cleaved in vitro, resulting in less fusion protein available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Peptide Linker

Any one or all of the linkers described herein can be peptide linkers. The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker comprises the amino acid sequence of CPPCP (SEQ ID NO: 345), a sequence found in the native IgG1 hinge region.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids (aa) long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 aa to about 10 aa, about 1 aa to about 20 aa, about 1 aa to about 30 aa, about 5 aa to about 15 aa, about 10 aa to about 25 aa, about 5 aa to about 30 aa, about 10 aa to about 30 aa, about 30 aa to about 50 aa, about 50 aa to about 100 aa, or about 1 aa to about 100 aa.

An essential technical feature of such peptide linker is that said peptide linker does not comprise any polymerization activity. The characteristics of a peptide linker, which comprise the absence of the promotion of secondary structures, are known in the art and described, e.g., in Dall'Acqua et al. (Biochem. (1998) 37, 9266-9273), Cheadle et al. (Mol Immunol (1992) 29, 21-30) and Raag and Whitlow (FASEB (1995) 9(1), 73-80). A particularly preferred amino acid in context of the "peptide linker" is Gly. Furthermore, peptide linkers that also do not promote any secondary structures are preferred. The linkage of the molecules to each other can be provided by, e.g., genetic engineering. Methods for preparing fused and operatively linked antibody constructs and expressing them in mammalian cells or bacteria are well-known in the art (e.g. WO 99/54440, Ausubel, Current Protocols in Molecular Biology, Green Publishing Associates and Wiley Interscience, N. Y. 1989 and 1994 or Sambrook et al., Molecular Cloning: A Laboratory Manual, Cold Spring Harbor Laboratory Press, Cold Spring Harbor, N. Y., 2001).

In some embodiments, the peptide linker is a stable linker, which is not cleavable by protease, such as by Matrix metalloproteinases (MMPs).

In some embodiments, the peptide linker tends not to adopt a rigid three-dimensional structure, but rather provide flexibility to a polypeptide (e.g., first and/or second components), such as providing flexibility between the anti-mesothelin antibody moiety and the Fc fragment. In some embodiments, the peptide linker is a flexible linker. Exemplary flexible linkers include glycine polymers $(G)_n$, glycine-serine polymers (including, for example, GS, $GS(GS)_n$ (SEQ ID NO: 337), $(GSGGS)_n$ (SEQ ID NO: 338), $(GGGGS)_n$ (SEQ ID NO: 339), and $(GGGS)_n$ (SEQ ID NO: 340), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11 173-142 (1992)). The ordinarily skilled artisan will recognize that design of an anti-mesothelin construct can include linkers that are all or partially flexible, such that the linker can include a flexible linker portion as well as one or more portions that confer less flexible structure to provide a desired fusion protein structure.

In some embodiments, two domains in any of the anti-MSLN constructs described herein (such as the anti-MSLN antibody moiety and the half-life extending domain or cytokine) are linked together by a linker of sufficient length to enable the anti-MSLN construct to fold in such a way as to permit binding to target MSLN and other desired antigens. In some embodiments, the linker comprises the amino acid sequence of SRGGGGSGGGGSGGGGSLEMA (SEQ ID NO: 341). In some embodiments, the linker is or comprises a $(GGGGS)_n$ sequence (SEQ ID NO: 339), wherein n is equal to 1, 2, 3, 4, 5, 6, 7, 8, 9, 10 or more. In some embodiments, the linker comprises the amino acid sequence of TSGGGS (SEQ ID NO: 342). In some embodiments, the linker comprises the amino acid sequence of GEGTSTGSGGSGGSGGAD (SEQ ID NO: 343).

Natural linkers adopt various conformations in secondary structure, such as helical, β-strand, coil/bend and turns, to exert their functions. Linkers in an α-helix structure might serve as rigid spacers to effectively separate protein domains, thus reducing their unfavorable interactions. Non-helical linkers with Pro-rich sequence could increase the linker rigidity and function in reducing inter-domain interference. In some embodiments, two domains in the anti-MSLN construct (such as the anti-MSLN antibody moiety and the half-life extending domain or cytokine) is linked together by an α-helical linker with an amino acid sequence of $A(EAAAK)_4A$ (SEQ ID NO: 344).

In certain embodiments, the first linker is a Matrix metalloproteinase (MMP) sensitive linker. In certain embodiments, the second linker is a MMP sensitive linker. In certain embodiments, both the first and the second linker are MMP sensitive linkers.

In certain embodiments, the MMP sensitive linker is a linker cleavable by a MMP (e.g., MMP-7, MMP-9, or MMP-13). MMP, mostly abundant in the tumor extracellular matrix (ECM), tumor cells, and tumor vasculatures, are closely correlated with tumor progression and metastasis. In some embodiments, the first linker is sensitive to MMP-7. In some embodiments, the first linker is sensitive to MMP-9. In some embodiments, the first linker is sensitive to MMP-13. In some embodiments, the second linker is sensitive to MMP-7. In some embodiments, the second linker is sensitive to MMP-9. In some embodiments, the second linker is sensitive to MMP-13.

In some embodiments, the MMP cleavable linker consists of or comprises a portion having a structure of: P5-P4-Pro-P2-P1-P1'-P2'-P3'-P4'.

In some embodiments, P5 can be any amino acids other than Pro and preferably an amino acid with small aliphatic side chain.

In some embodiments, P4 can be any amino acid other than Pro and preferably Gly.

In some embodiments, P2 can be selected from a group consisting of Gln, Ala, Ser, Arg, and Lys.

In some embodiments, P1 can be selected from a group consisting of Ser, Thr, and Gly.

In some embodiments, P1' can be Leu or Ile, or any hydrophobic amino acids such as Phe, Ala, Val, or Met.

In some embodiments, P2' can be an amino acid with hydrophobic side chain.

In some embodiments, P3' can be an amino acid with small aliphatic side chain and preferably Gly.

In some embodiments, P4' can be an amino acid with hydrophobic side chain and preferably Gln.

In some embodiments, P5 is any amino acids other than Pro and preferably an amino acid with small aliphatic side chain; P4 is any amino acid other than Pro and preferably Gly; P2 is selected from a group consisting of Gln, Ala, Ser, Arg, and Lys; P1 is selected from a group consisting of Ser, Thr, and Gly; P1' is Leu or Ile, or any hydrophobic amino acids such as Phe, Ala, Val, or Met; P2' is an amino acid with hydrophobic side chain; P3' is an amino acid with small aliphatic side chain and preferably Gly; and P4' is an amino acid with hydrophobic side chain and preferably Gln.

In some embodiments, the first linker and/or the second linker comprises a sequence selected from Table 5 below.

TABLE 5

Lys-Gly-Pro-Gln-Gly-Ile-Ala-Gly-Gln
(SEQ ID NO: 267)

Phe-Gly-Pro-Gln-Gly-Leu-Ala-Gly-Gln
(SEQ ID NO: 268)

Arg-Gly-Pro-Gln-Gly-Ile-Phe-Gly-Gln
(SEQ ID NO: 269)

Ile-Gly-Pro-Gln-Gly-Ile-Trp-Gly-Gln
(SEQ ID NO: 270)

Met-Gly-Pro-Gln-Gly-Ile-Leu-Gly-Gln
(SEQ ID NO: 271)

Lys-Gly-Pro-Gln-Ser-Ile-Ala-Gly-Gln
(SEQ ID NO: 272)

Phe-Gly-Pro-Gln-Ser-Leu-Ala-Gly-Gln
(SEQ ID NO: 273)

TABLE 5-continued

```
Arg-Gly-Pro-Gln-Ser-Ile-Phe-Gly-Gln
(SEQ ID NO: 274)

Ile-Gly-Pro-Gln-Ser-Ile-Trp-Gly-Gln
(SEQ ID NO: 275)

Met-Gly-Pro-Gln-Ser-Ile-Leu-Gly-Gln
(SEQ ID NO: 276)

Lys-Gly-Pro-Gln-Thr-Ile-Ala-Gly-Gln
(SEQ ID NO: 277)

Phe-Gly-Pro-Gln-Thr-Leu-Ala-Gly-Gln
(SEQ ID NO: 278)

Arg-Gly-Pro-Gln-Thr-Ile-Phe-Gly-Gln
(SEQ ID NO: 279)

Ile-Gly-Pro-Gln-Thr-Ile-Trp-Gly-Gln
(SEQ ID NO: 280)

Phe-Arg-Pro-Arg-Ser-Ile-Thr-Gly-Gln
(SEQ ID NO: 281)

Met-Gly-Pro-Gln-Thr-Ile-Leu-Gly-Gln
(SEQ ID NO: 282)
```

In some embodiments, the first linker comprises a sequence of SEQ ID NO: 267. In other embodiments, the first linker comprises a sequence of SEQ ID NO: 268. In other embodiments, the first linker comprises a sequence of SEQ ID NO: 269. In yet other embodiments, the first linker comprises a sequence of SEQ ID NO: 270. In yet other embodiments, the first linker comprises a sequence of SEQ ID NO: 270. In yet other embodiments, the first linker comprises a sequence of SEQ ID NO: 271. In yet other embodiments, the first linker comprises a sequence of SEQ ID NO: 272. In yet other embodiments, the first linker comprises a sequence of SEQ ID NO: 273. In yet other embodiments, the first linker comprises a sequence of SEQ ID NO: 274. In yet other embodiments, the first linker comprises a sequence of SEQ ID NO: 275. In yet other embodiments, the first linker comprises a sequence of SEQ ID NO: 276. In yet other embodiments, the first linker comprises a sequence of SEQ ID NO: 277. In yet other embodiments, the first linker comprises a sequence of SEQ ID NO: 278. In yet other embodiments, the first linker comprises a sequence of SEQ ID NO: 279. In yet other embodiments, the first linker comprises a sequence of SEQ ID NO: 280. In yet other embodiments, the first linker comprises a sequence of SEQ ID NO: 281. In yet other embodiments, the first linker comprises a sequence of SEQ ID NO: 282.

In some embodiments, the second linker comprises a sequence of SEQ ID NO: 267. In other embodiments, the second linker comprises a sequence of SEQ ID NO: 268. In other embodiments, the second linker comprises a sequence of SEQ ID NO: 269. In yet other embodiments, the second linker comprises a sequence of SEQ ID NO: 270. In yet other embodiments, the second linker comprises a sequence of SEQ ID NO: 270. In yet other embodiments, the second linker comprises a sequence of SEQ ID NO: 271. In yet other embodiments, the second linker comprises a sequence of SEQ ID NO: 272. In yet other embodiments, the second linker comprises a sequence of SEQ ID NO: 273. In yet other embodiments, the second linker comprises a sequence of SEQ ID NO: 274. In yet other embodiments, the second linker comprises a sequence of SEQ ID NO: 275. In yet other embodiments, the second linker comprises a sequence of SEQ ID NO: 276. In yet other embodiments, the second linker comprises a sequence of SEQ ID NO: 277. In yet other embodiments, the second linker comprises a sequence of SEQ ID NO: 278. In yet other embodiments, the second linker comprises a sequence of SEQ ID NO: 279. In yet other embodiments, the second linker comprises a sequence of SEQ ID NO: 280. In yet other embodiments, the second linker comprises a sequence of SEQ ID NO: 281. In yet other embodiments, the second linker comprises a sequence of SEQ ID NO: 282.

In some embodiments, the first linker and the second linker are each independently selected from a group consisting of SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73 and SEQ ID NO: 74 as set forth in Table 8 in Examples below.

In some embodiments, the first linker is of SEQ ID NO: 66. In some embodiments, the first linker is of SEQ ID NO: 67. In some embodiments, the first linker is of SEQ ID NO: 68. In some embodiments, the first linker is of SEQ ID NO: 69. In other embodiments, the first linker is of SEQ ID NO: 70. In other embodiments, the first linker is of SEQ ID NO: 71. In other embodiments, the first linker is of SEQ ID NO: 72. In yet other embodiments, the first linker is of SEQ ID NO: 73. In yet other embodiments, the first linker is of SEQ ID NO: 74.

In some embodiments, the second linker is of SEQ ID NO: 66. In some embodiments, the second linker is of SEQ ID NO: 67. In some embodiments, the second linker is of SEQ ID NO: 68. In some embodiments, the second linker is of SEQ ID NO: 69. In other embodiments, the second linker is of SEQ ID NO: 70. In other embodiments, the second linker is of SEQ ID NO: 71. In other embodiments, the second linker is of SEQ ID NO: 72. In yet other embodiments, the second linker is of SEQ ID NO: 73. In yet other embodiments, the second linker is of SEQ ID NO: 74.

In certain IL-21 fusion proteins provided herein, the binding molecule that binds to an antigen comprises two or more antibodies or antigen binding fragments thereof. In some embodiments, the binding molecule that binds to an antigen comprises two antibodies or antigen binding fragments thereof. In some embodiments, the two antibodies or antigen binding fragments are connected with a third linker. For example, as described in the Examples below, the anti-MSLN functional module (the binding molecule that binds to MSLN) of IL-21-αHSA-anti-MSLN comprises two single domain antibodies (sdAbs) targeting different domains of mesothelin, and the two sdAbs are connected by a third linker.

In some embodiments, the third linker is a MMP sensitive linker.

In some embodiments, the third linker is selected from a group consisting of SEQ ID NO: 66, SEQ ID NO: 67, SEQ ID NO: 68, SEQ ID NO: 69, and SEQ ID NO: 70 as set forth in Table 8 below. In some embodiments, the third linker is of SEQ ID NO: 66. In some embodiments, the third linker is of SEQ ID NO: 67. In some embodiments, the third linker is of SEQ ID NO: 68. In other embodiments, the third linker is of SEQ ID NO: 69. In other embodiments, the third linker is of SEQ ID NO: 70.

In some embodiments, the first linker is connected to the C-terminus of the IL-21 or a variant thereof at S123 to S132. In other embodiments, the first linker is connected to the IL-21 or a variant thereof at an amino acid within amino acids 123 to 132 of the IL-21 or a variant thereof. In other embodiments, the first linker is connected to the IL-21 or a variant thereof at the last 10 amino acids of the C-terminus of the IL-21 or a variant thereof.

In one embodiment, the first linker is connected to amino acid 123 of the IL-21 or a variant thereof. In one embodiment, the first linker is connected to amino acid 124 of the IL-21 or a variant thereof. In one embodiment, the first linker is connected to amino acid 125 of the IL-21 or a variant thereof. In one embodiment, the first linker is connected to amino acid 126 of the IL-21 or a variant thereof. In one embodiment, the first linker is connected to amino acid 127 of the IL-21 or a variant thereof. In one embodiment, the first linker is connected to amino acid 128 of the IL-21 or a variant thereof. In one embodiment, the first linker is connected to amino acid 129 of the IL-21 or a variant thereof. In one embodiment, the first linker is connected to amino acid 130 of the IL-21 or a variant thereof. In one embodiment, the first linker is connected to amino acid 131 of the IL-21 or a variant thereof. In one embodiment, the first linker is connected to amino acid 132 of the IL-21 or a variant thereof.

In other embodiments, the first linker is connected to L123 of the IL-21 or a variant thereof.

In some embodiments, the first linker is connected to the N-terminus of the IL-21 or a variant thereof at Q1 to D4. In some embodiments, the first linker is connected to amino acid 1 of the IL-21 or a variant thereof. In some embodiments, the first linker is connected to amino acid 2 of the IL-21 or a variant thereof. In some embodiments, the first linker is connected to amino acid 3 of the IL-21 or a variant thereof. In some embodiments, the first linker is connected to amino acid 4 of the IL-21 or a variant thereof.

In some embodiments, the second linker is connected to the C-terminus of the albumin binding molecule. In other embodiments, the second linker is connected to the N-terminus of the albumin binding molecule.

In some embodiments, the second linker is connected to the N-terminus of the binding molecule that binds to an antigen. In some embodiments, the second linker is connected to the C-terminus of the binding molecule that binds to an antigen.

Polynucleotides

In certain embodiments, the disclosure encompasses polynucleotides that encode the fusion proteins described herein. The term "polynucleotides that encode a polypeptide" encompasses a polynucleotide that includes only coding sequences for the polypeptide as well as a polynucleotide which includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, a polynucleotide comprises the coding sequence for a polypeptide fused in the same reading frame to a polynucleotide which aids, for example, in expression and secretion of a polypeptide from a host cell (e.g., a leader sequence which functions as a secretory sequence for controlling transport of a polypeptide). The polypeptide can have the leader sequence cleaved by the host cell to form a "mature" form of the polypeptide.

In certain embodiments, a polynucleotide comprises the coding sequence for a polypeptide fused in the same reading frame to a marker or tag sequence. For example, in some embodiments, a marker sequence is a hexa-histidine tag supplied by a vector that allows efficient purification of the polypeptide fused to the marker in the case of a bacterial host. In some embodiments, a marker is used in conjunction with other affinity tags.

The present disclosure further relates to variants of the polynucleotides described herein, wherein the variant encodes, for example, fragments, analogs, and/or derivatives of a polypeptide. In certain embodiments, the present disclosure provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a binding molecule described herein.

As used herein, the phrase "a polynucleotide having a nucleotide sequence at least, for example, 95% "identical" to a reference nucleotide sequence" is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In certain embodiments, a polynucleotide is isolated. In certain embodiments, a polynucleotide is substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises one or more expression vectors comprising polynucleotide molecules. In some embodiments, a host cell comprises a polynucleotide molecule. In some embodiments, a host cell comprises one or more polynucleotide molecules. Construction of the vectors provided herein is exemplified in the Examples below.

Methods of Making the Anti-Mesothelin Constructs or Fusion Proteins

In yet another aspect, provided herein are methods for making the various anti-mesothelin constructs or fusion proteins provided herein.

Recombinant expression of an anti-MSLN construct or fusion protein provided herein may require construction of an expression vector containing a polynucleotide that encodes the anti-MSLN construct or the fusion protein or a fragment thereof. Once a polynucleotide encoding an anti-MSLN construct or a fusion protein provided herein or a fragment thereof has been obtained, the vector for the production of the binding molecule may be produced by recombinant DNA technology using techniques well-known in the art. Thus, methods for preparing a protein by expressing a polynucleotide containing an encoding nucleotide sequence are described herein. Methods which are well known to those skilled in the art can be used to construct expression vectors containing coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an anti-MSLN construct or a fusion protein provided herein, or a fragment thereof, or a CDR, operably linked to a promoter.

The expression vector can be transferred to a host cell by conventional techniques and the transfected cells are then cultured by conventional techniques to produce an anti-MSLN construct or a fusion protein provided herein. Thus, also provided herein are host cells containing a polynucleotide encoding an anti-MSLN construct or a fusion protein provided herein or fragments thereof operably linked to a heterologous promoter.

A variety of host-expression vector systems may be utilized to express the anti-MSLN construct or fusion protein provided herein (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express a fusion protein provided herein in situ. These include but are not limited to microorganisms such as bacteria (e.g., *E. coli* and *B. subtilis*) transformed with recombinant bacteriophage DNA, plasmid DNA or cosmid DNA expression vectors containing coding sequences; yeast (e.g., *Saccharomyces Pichia*) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV, tobacco mosaic virus, TMV) or transformed with recombinant plasmid expression vectors (e.g., Ti plasmid) containing coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or, eukaryotic cells, especially for the expression of whole recombinant antibody molecule, can be used for the expression of a recombinant anti-MSLN construct or fusion protein. For example, mammalian cells such as Chinese hamster ovary cells (CHO), in conjunction with a vector such as the major intermediate early gene promoter element from human cytomegalovirus is an effective expression system for antibodies or variants thereof (Foecking et al., 1986, Gene 45:101; and Cockett et al., 1990, Bio/Technology 8:2). In some embodiments, anti-MSLN constructs or fusion proteins provided herein are produced in CHO cells. In a specific embodiment, the expression of nucleotide sequences encoding the anti-MSLN constructs or fusion proteins provided herein is regulated by a constitutive promoter, inducible promoter or tissue specific promoter.

In bacterial systems, a number of expression vectors may be advantageously selected depending upon the use intended for the anti-MSLN construct or fusion protein being expressed. For example, when a large quantity of such anti-MSLN construct or a fusion protein is to be produced, for the generation of pharmaceutical compositions of an anti-MSLN construct or a fusion protein, vectors which direct the expression of high levels of anti-MSLN construct or fusion protein products that are readily purified may be desirable. Such vectors include, but are not limited to, the *E. coli* expression vector pUR278 (Ruther et al., 1983, EMBO 12:1791), in which the coding sequence may be ligated individually into the vector in frame with the lac Z coding region so that an anti-MSLN construct or a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as anti-MSLN constructs or fusion proteins with glutathione 5-transferase (GST). In general, such anti-MSLN constructs or fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region El or E3) will result in a recombinant virus that is viable and capable of expressing the anti-MSLN construct or fusion protein in infected hosts (e.g., see Logan & Shenk, 1984, Proc. Natl. Acad. Sci. USA 8 1:355-359). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NSO (a murine myeloma cell line that does not endogenously produce any immunoglobulin chains), CRL7O3O and HsS78Bst cells.

For long-term, high-yield production of recombinant proteins, stable expression can be utilized. For example, cell lines which stably express the anti-MSLN constructs or fusion proteins may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the anti-MSLN construct or fusion protein. Such engineered cell lines may be particularly useful in screening and evaluation of compositions that interact directly or indirectly with the binding molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds.), Current Protocols in Human Genetics, John Wiley & Sons, N Y (1994); Colberre-Garapin et al., 1981, J. Mol. Biol. 150:1, which are incorporated by reference herein in their entireties.

The expression level of an anti-MSLN construct or a fusion protein can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing an anti-MSLN construct or a fusion protein is amplifiable, increase in the level of inhibitor present in culture of host cell will increase the number of copies of the marker gene. Since the amplified region is associated with the anti-MSLN construct or fusion protein gene, production of the anti-MSLN construct or fusion protein will also increase (Crouse et al., 1983, Mol. Cell. Biol. 3:257).

The host cell may be co-transfected with multiple expression vectors provided herein. The vectors may contain identical selectable markers which enable equal expression of respective encoding polypeptides. Alternatively, a single vector may be used which encodes, and is capable of expressing multiple polypeptides. The coding sequences may comprise cDNA or genomic DNA.

Once an anti-MSLN construct or a fusion protein provided herein has been produced by recombinant expression, it may be purified by any method known in the art for purification of a polypeptide (e.g., an immunoglobulin molecule), for example, by chromatography (e.g., ion exchange, affinity, particularly by affinity for the specific antigen after Protein A, sizing column chromatography, and Kappa select affinity chromatography), centrifugation, differential solubility, or by any other standard technique for the purification of proteins. Further, the anti-MSLN construct or fusion protein molecules provided herein can be fused to heterologous polypeptide sequences described herein or otherwise known in the art to facilitate purification.

Examples below exemplifies a method of making an anti-MSLN construct or a fusion protein provided herein.

Pharmaceutical Compositions

In one aspect, the present disclosure further provides pharmaceutical compositions comprising at least one anti-MSLN construct or fusion protein of the present disclosure. In some embodiments, a pharmaceutical composition comprises therapeutically effective amount of an anti-MSLN construct or a fusion protein provided herein and a pharmaceutically acceptable excipient.

Pharmaceutical compositions comprising an anti-MSLN construct or a fusion protein are prepared for storage by mixing the anti-MSLN construct or fusion protein having the desired degree of purity with optional physiologically acceptable excipients (see, e.g., Remington, Remington's Pharmaceutical Sciences (18th ed. 1980)) in the form of aqueous solutions or lyophilized or other dried forms.

The anti-MSLN construct or fusion protein of the present disclosure may be formulated in any suitable form for delivery to a target cell/tissue, e.g., as microcapsules or macroemulsions (Remington, supra; Park et al., 2005, Molecules 10:146-61; Malik et al., 2007, Curr. Drug. Deliv. 4:141-51), as sustained release formulations (Putney and Burke, 1998, Nature Biotechnol. 16:153-57), or in liposomes (Maclean et al., 1997, Int. J. Oncol. 11:325-32; Kontermann, 2006, Curr. Opin. Mol. Ther. 8:39-45).

An anti-MSLN construct or a fusion protein provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles, and nanocapsules) or in macroemulsions. Such techniques are disclosed, for example, in Remington, supra.

Various compositions and delivery systems are known and can be used with an anti-MSLN construct or a fusion protein as described herein, including, but not limited to, encapsulation in liposomes, microparticles, microcapsules, recombinant cells capable of expressing the anti-MSLN construct or fusion protein, receptor-mediated endocytosis (see, e.g., Wu and Wu, 1987, J. Biol. Chem. 262:4429-32), construction of a nucleic acid as part of a retroviral or other vector, etc. In another embodiment, a composition can be provided as a controlled release or sustained release system. In one embodiment, a pump may be used to achieve controlled or sustained release (see, e.g., Langer, supra; Sefton, 1987, Crit. Ref. Biomed. Eng. 14:201-40; Buchwald et al., 1980, Surgery 88:507-16; and Saudek et al., 1989, N. Engl. J. Med. 321:569-74). In another embodiment, polymeric materials can be used to achieve controlled or sustained release of a prophylactic or therapeutic agent (e.g., a fusion protein as described herein) or a composition provided herein (see, e.g., Medical Applications of Controlled Release (Langer and Wise eds., 1974); Controlled Drug Bioavailability, Drug Product Design and Performance (Smolen and Ball eds., 1984); Ranger and Peppas, 1983, J. Macromol. Sci. Rev. Macromol. Chem. 23:61-126; Levy et al., 1985, Science 228:190-92; During et al., 1989, Ann. Neurol. 25:351-56; Howard et al., 1989, J. Neurosurg. 71:105-12; U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable.

In yet another embodiment, a controlled or sustained release system can be placed in proximity of a particular target tissue, for example, the nasal passages or lungs, thus requiring only a fraction of the systemic dose (see, e.g., Goodson, Medical Applications of Controlled Release Vol. 2, 115-38 (1984)). Controlled release systems are discussed, for example, by Langer, 1990, Science 249:1527-33. Any technique known to one of skill in the art can be used to produce sustained release formulations comprising one or more anti-MSLN constructs or fusion proteins as described herein (see, e.g., U.S. Pat. No. 4,526,938, PCT publication Nos. WO 91/05548 and WO 96/20698, Ning et al., 1996, Radiotherapy & Oncology 39:179-89; Song et al., 1995, PDA J. of Pharma. Sci. & Tech. 50:372-97; Cleek et al., 1997, Pro. Int'l. Symp. Control. Rel. Bioact. Mater. 24:853-54; and Lam et al., 1997, Proc. Int'l. Symp. Control Rel. Bioact. Mater. 24:759-60).

Methods of Use

In a specific embodiment, provided herein are compositions for use in the prevention and/or treatment of a disease or condition comprising anti-MSLN construct or a fusion protein provided herein. In one embodiment, provided herein are compositions for use in the prevention of a disease or condition, wherein the composition comprises an anti-MSLN construct or a fusion protein provided herein. In one embodiment, provided herein are compositions for use in the treatment of a disease or condition, wherein the composition comprises an anti-MSLN construct or a fusion protein provided herein. In some embodiments, the disease or condition is a cancer. In some embodiments, the cancer is a solid tumor cancer. In certain embodiments, the subject is a subject in need thereof. In some embodiments, the subject has the disease or condition. In other embodiments, the subject is at risk of having the disease or condition. In some embodiments, the administration results in the prevention, management, treatment or amelioration of the disease or condition.

In one embodiment, provided herein are compositions for use in the prevention and/or treatment of a symptom of a disease or condition, wherein the composition comprises an anti-MSLN construct or a fusion protein provided herein. In one embodiment, provided herein are compositions for use in the prevention of a symptom of a disease or condition, wherein the composition comprises an anti-MSLN construct or a fusion protein provided herein. In one embodiment, provided herein are compositions for use in the treatment of a symptom of a disease or condition, wherein the composition comprises an anti-MSLN construct or a fusion protein provided herein. In one embodiment, the disease is cancer. In certain embodiments, the subject is a subject in need thereof. In some embodiments, the subject has the disease or condition. In other embodiments, the subject is at risk of having the disease or condition. In some embodiments, the administration results in the prevention or treatment of the symptom of the disease or condition.

In another embodiment, provided herein are methods of preventing and/or treating a disease or condition in a subject, comprising administering an effective amount of an anti-mesothelin construct or a fusion protein provided herein. In one embodiment, provided herein are methods of preventing a disease or condition in a subject, comprising administering an effective amount of an anti-mesothelin construct or a fusion protein provided herein. In one embodiment, provided herein are methods of treating a disease or condition in a subject, comprising administering an effective amount of an anti-mesothelin construct or a fusion protein provided herein. In one embodiment, the disease or condition is cancer. In certain embodiments, the subject is a subject in need thereof. In some embodiments, the subject has the disease or condition. In other embodiments, the subject is at risk of having the disease or condition. In some embodiments, the administration results in the prevention or treatment of the disease or condition.

In another embodiment, provided herein are methods of preventing and/or treating a symptom of a disease or condition in a subject, comprising administering an effective amount of an anti-mesothelin construct or a fusion protein provided herein. In one embodiment, provided herein are methods of preventing a symptom of a disease or condition in a subject, comprising administering an effective amount of an anti-mesothelin construct or a fusion protein provided herein. In one embodiment, provided herein are methods of treating a symptom of a disease or condition in a subject, comprising administering an effective amount of an antimesothelin construct or a fusion protein provided herein. In one embodiment, the disease or condition is cancer. In certain embodiments, the subject is a subject in need thereof. In some embodiments, the subject has the disease or condition. In other embodiments, the subject is at risk of having the disease or condition. In some embodiments, the administration results in the prevention or treatment of the symptom of the disease or condition.

Also provided herein are methods of preventing and/or treating a disease or condition by administrating to a subject of an effective amount of an anti-mesothelin construct or a fusion protein provided herein, or pharmaceutical composition comprising an anti-MSLN construct or a fusion protein provided herein. In one aspect, the fusion protein is substantially purified (i.e., substantially free from substances that limit its effect or produce undesired side-effects). The subject administered a therapy can be a mammal such as non-primate (e.g., cows, pigs, horses, cats, dogs, rats etc.) or a primate (e.g., a monkey, such as a cynomolgus monkey, or a human). In a one embodiment, the subject is a human. In another embodiment, the subject is a human with a disease or condition, e.g., cancer including solid tumor cancer.

Also provided herein are methods of preventing and/or treating a disease or condition by administrating to a subject of an effective amount of an anti-mesothelin construct comprising an anti-MSLN antibody moiety that specifically binds to mesothelin, wherein the anti-MSLN antibody moiety has reduced fucosylation.

Disease or Condition

The methods described herein can be used to treat a disease or condition. In some embodiments, the disease or condition is a cancer. In some embodiments, the cancer is mesothelin positive cancer. In some embodiments, the cancer is a solid cancer. In some embodiments, the cancer is selected from the group consisting of gastric cancer, lung cancer (such as non-small cell lung cancer), ovarian cancer (such as epithelial ovarian cancer), esophageal cancer, pancreatic cancer, cervical cancer, mesothelioma (such as malignant mesothelioma, malignant epithelial pleural mesothelioma, advanced recurrent epithelioid mesothelioma), stomach cancer, endometrial cancer, ductal pancreatic adenocarcinomas, and breast cancer.

Combination Therapy

In some embodiments, the method described herein further comprises administering a second agent. In some embodiments, the second agent comprises a cytokine. In some embodiments, the cytokine is IL-21 or IL-15. In some embodiments, the IL-21 or IL-15 is in the form of a fusion protein comprising a half-life extending domain. In some embodiments, the half-life extending domain is an Fc domain or an albumin binding domain. In some embodiments, the anti-mesothelin construct and the cytokine are administered simultaneously.

In some embodiments, there is provided a method of treating a gastric cancer in an individual, comprising administering to the individual a) an anti-mesothelin agent; b) an anti-Her2 agent; and c) IL-21. In some embodiments, the IL-21 is in the form of a fusion protein comprising a half-life extending domain. In some embodiments, the anti-Her2 agent is Herceptin. In some embodiments, the anti-mesothelin agent comprises an anti-mesothelin construct as described herein. In some embodiments, the anti-mesothelin agent comprises an anti-mesothelin antibody moiety comprising an anti-MSLN heavy chain variable region (VH) comprising: a HC-CDR1, a HC-CDR2, and a HC-CDR3, respectively comprising the amino acid sequences of a CDR1, a CDR2, and a CDR3 within a $V_H$ chain region having the sequence set forth in any of SEQ ID NOS: 123-156 and 285-301. In some embodiments, the anti-mesothelin construct, the anti-Her2 agent and IL-21 are administered simultaneously.

Dosing Regimen

The anti-mesothelin constructs and/or second agents may be administered to the individual using any suitable dosage and routes of administration. In some embodiments, the anti-mesothelin construct and/or the second agent is administered parenterally into the individual. The route of administration is in accordance with known and accepted methods, such as by single or multiple bolus or infusion over a period of time in a suitable manner, e.g., injection or infusion by subcutaneous, intravenous, intraperitoneal, intramuscular, intra-arterial, intralesional, intraarticular, intratumoral, or oral routes.

In some embodiments, the anti-mesothelin construct and the second agent are administered simultaneously, concurrently or sequentially into the individual.

The determination of the appropriate dosage or route of administration is well within the skill of an ordinary artisan. Animal experiments provide reliable guidance for the determination of effective doses for human diagnostic applications. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

In some embodiments, the anti-MSLN construct is administered at a frequency of about once a week to about twice a week. In some embodiments, the anti-MSLN construct is administered at a frequency of at least about once a week. In some embodiments, the anti-MSLN construct is administered at a frequency of no more than about twice a week. In some embodiments, the anti-MSLN construct is administered for at least about one, two, three, four or five weeks for each treatment cycle.

In some embodiments, the amount of anti-MSLN construct for each administration into a human being is an amount equivalent to a dosage of about 5 mg/kg for mice. In some embodiments, the amount of anti-MSLN construct for each administration into a human being is an amount equivalent to a dosage of about 100 µg for mice. See Nair, A. B., & Jacob, S. (2016). A simple practice guide for dose conversion between animals and human. Journal of basic and clinical pharmacy, 7(2), 27.

In some embodiments, the second agent comprises a cytokine (such as a cytokine fusion protein, such as an IL-21-anti-HSA fusion protein). In some embodiments, the cytokine is administered at a frequency of about twice a week. In some embodiments, the cytokine is administered for at least about one, two, or two and a half weeks for each treatment cycle. In some embodiments, the amount of the cytokine for each administration into a human being is an amount equivalent to a dosage of about 5 µg to about 25 µg for mice.

In some embodiments, the second agent comprises an anti-Her2 agent (such as Herceptin). In some embodiments, the anti-Her2 agent is administered at a frequency of about twice a week. In some embodiments, the cytokine is administered for at least about one, two, or two and a half weeks for each treatment cycle. In some embodiments, the amount of the cytokine for each administration into a human being is an amount equivalent to a dosage of about 20 µg for mice.

Various delivery systems are known and can be used to administer a prophylactic or therapeutic agent (e.g., a fusion protein provided herein), including, but not limited to, encapsulation in liposomes, microparticles, microcapsules, recombinant cells capable of expressing the fusion protein, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent (e.g., a fusion protein provided herein), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., a fusion protein provided herein), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

In a specific embodiment, it may be desirable to administer a prophylactic or therapeutic agent, or a pharmaceutical composition provided herein locally to the area in need of treatment. This may be achieved by, for example, and not by way of limitation, local infusion, by topical administration (e.g., by intranasal spray), by injection, or by means of an implant, said implant being of a porous, non-porous, or gelatinous material, including membranes, such as sialastic membranes, or fibers. In some embodiments, when administering a fusion protein provided herein, care must be taken to use materials to which the fusion protein does not absorb.

In another embodiment, a prophylactic or therapeutic agent, or a composition provided herein can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In another embodiment, a prophylactic or therapeutic agent, or a composition provided herein can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an antibody provided herein) or a composition provided herein (see e.g., Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In an embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the nasal passages or lungs, thus requiring only a fraction of the systemic dose (see, e.g., Goodson, in Medical Applications of Controlled Release, supra, vol. 2, pp. 115-138 (1984)). Controlled release systems are discussed in the review by Langer (1990, Science 249:1527-1533). Any technique known to one of skill in the art can be used to produce sustained release formulations comprising one or more fusion protein provided herein. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

In a specific embodiment, where the composition provided herein is a nucleic acid encoding a prophylactic or therapeutic agent (e.g., a fusion protein provided herein), the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

In a specific embodiment, a composition provided herein comprises one, two or more fusion proteins provided herein. In another embodiment, a composition provided herein comprises one, two or more fusion proteins provided herein and a prophylactic or therapeutic agent other than a fusion protein provided herein. In one embodiment, the agents are known to be useful for or have been or are currently used for the prevention, management, treatment and/or amelioration of a disease or condition. In addition to prophylactic or therapeutic agents, the compositions provided herein may also comprise an excipient.

The compositions provided herein include bulk drug compositions useful in the manufacture of pharmaceutical compositions (e.g., compositions that are suitable for administration to a subject or patient) that can be used in the preparation of unit dosage forms. In an embodiment, a composition provided herein is a pharmaceutical composition. Such compositions comprise a prophylactically or therapeutically effective amount of one or more prophylactic or therapeutic agents (e.g., a fusion protein provided herein or other prophylactic or therapeutic agent), and a pharmaceutically acceptable excipient. The pharmaceutical compositions can be formulated to be suitable for the route of administration to a subject.

In a specific embodiment, the term "excipient" can also refer to a diluent, adjuvant (e.g., Freunds' adjuvant (complete or incomplete) or vehicle. Pharmaceutical excipients can be sterile liquids, such as water and oils, including those of petroleum, animal, vegetable or synthetic origin, such as peanut oil, soybean oil, mineral oil, sesame oil and the like. Water is an exemplary excipient when the pharmaceutical composition is administered intravenously. Saline solutions and aqueous dextrose and glycerol solutions can also be employed as liquid excipients, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in Remington's Pharmaceutical Sciences (1990) Mack Publishing Co., Easton, PA. Such compositions will contain a prophylactically or therapeutically effective amount of the fusion protein provided herein, such as in purified form, together with a suitable amount of excipient so as to provide the form for proper administration to the patient. The formulation should suit the mode of administration.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Such compositions, however, may be administered by a route other than intravenous.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

A fusion protein provided herein can be packaged in a hermetically sealed container such as an ampoule or sachette indicating the quantity of antibody. In one embodiment, the fusion protein is supplied as a dry sterilized lyophilized powder or water free concentrate in a hermetically sealed container and can be reconstituted, e.g., with water or saline to the appropriate concentration for administration to a subject. The lyophilized fusion protein can be stored at between 2 and 8° C. in its original container and the fusion protein can be administered within 12 hours, such as within 6 hours, within 5 hours, within 3 hours, or within 1 hour after being reconstituted. In an alternative embodiment, a fusion protein provided herein is supplied in liquid form in a hermetically sealed container indicating the quantity and concentration of the antibody.

The compositions provided herein can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a prophylactic or therapeutic agent (e.g., a fusion protein provided herein), or a composition provided herein that will be effective in the prevention and/or treatment of a disease or condition can be determined by standard clinical techniques. In addition, in vitro assays may optionally be employed to help identify optimal dosage ranges. The precise dose to be employed in the formulation will also depend on the route of administration, and the seriousness of a disease or condition, and should be decided according to the judgment of the practitioner and each patient's circumstances.

Effective doses may be extrapolated from dose-response curves derived from in vitro or animal model test systems.

In certain embodiments, the route of administration for a dose of a fusion protein provided herein to a patient is intranasal, intramuscular, intravenous, or a combination thereof, but other routes described herein are also acceptable. Each dose may or may not be administered by an identical route of administration. In some embodiments, a fusion protein provided herein may be administered via multiple routes of administration simultaneously or subsequently to other doses of the same or a different fusion protein provided herein.

In certain embodiments, the fusion proteins provided herein are administered prophylactically or therapeutically to a subject. The fusion proteins provided herein can be prophylactically or therapeutically administered to a subject so as to prevent, lessen or ameliorate a disease or symptom thereof.

For the sake of conciseness, certain abbreviations are used herein. One example is the single letter abbreviation to represent amino acid residues. The amino acids and their corresponding three letter and single letter abbreviations are as follows:

| | | |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |

| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

Articles of Manufacture and Kits

In some embodiments of the invention, there is provided an article of manufacture containing materials useful for the treatment of a disease or condition (such as a cancer, such as a mesothelin-positive cancer) in an individual, for administering an anti-MSLN construct into the individual. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is an anti-MSLN construct described herein. The label or package insert indicates that the composition is used for treating the particular condition. The label or package insert will further comprise instructions for administering the anti-MSLN construct to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a disease or condition (such as a cancer, such as a mesothelin-positive cancer).

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a disease or condition (such as a cancer, such as a mesothelin-positive cancer) described herein, for administering an anti-MSLN construct into an individual, optionally in combination with the articles of manufacture. Kits of the invention include one or more containers comprising an anti-MSLN construct composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-MSLN construct. In some embodiments, the kit comprises a) a composition comprising an anti-MSLN construct, and b) an effective amount of at least one other agent as described herein. In some embodiments, the kit comprises a) a composition comprising an anti-MSLN construct, and b) instructions for administering the anti-MSLN construct composition to an individual for treatment. In some embodiments, the kit comprises a) a composition comprising an anti-MSLN construct, b) an effective amount of at least one other agent as described herein, and c) instructions for administering the anti-MSLN construct composition and the other agent(s) to an individual for treatment. The anti-MSLN construct and the other agent (s) can be present in separate containers or in a single container. For example, the kit may comprise one distinct composition or two or more compositions wherein one composition comprises an anti-MSLN construct and another composition comprises another agent.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-MSLN construct compositions generally include information as to dosage, dosing schedule, and route of administration for the intended treatment. The containers may be unit doses, bulk packages (e.g., multi-dose packages) or subunit doses. For example, kits may be provided that contain sufficient dosages of an anti-MSLN construct as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-MSLN construct and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this application. The invention will now be described in greater detail by reference to the following non-limiting examples. The following examples further illustrate the invention but, of course, should not be construed as in any way limiting its scope.

EXEMPLARY EMBODIMENTS

1. A fusion protein comprising: (a) Interleukin 21 (IL-21) or a variant thereof; (b) an albumin binding molecule;

and (c) a binding molecule that binds to an antigen, wherein the IL-21 or variant thereof is connected to the albumin binding molecule via a first linker, and wherein the albumin binding molecule is connected to the binding molecule via a second linker.

2. The fusion protein of claim 1, wherein the IL-21 or variant thereof comprises an amino acid sequence of SEQ ID NO: 1.

3. The fusion protein of claim 1, wherein the IL-21 or variant thereof comprises one or more deletions within SEQ ID NO: 1.

4. The fusion protein of claim 1, wherein the IL-21 or variant thereof comprises an amino acid sequence of SEQ ID NO: 2.

5. The fusion protein of claim 1, wherein the IL-21 or variant thereof comprises an amino acid sequence with more than 80% identity to SEQ ID NO: 1.

6. The fusion protein of claim 1, wherein the IL-21 or variant thereof comprises an amino acid sequence with more than 90% identity to SEQ ID NO: 1.

7. The fusion protein of claim 1, wherein the IL-21 or variant thereof comprises an amino acid sequence with more than 95% identity to SEQ ID NO: 1.

8. The fusion protein of any one of claims 1 to 7, wherein the albumin binding molecule is an albumin binding domain (ABD).

9. The fusion protein of claim 8, wherein the ABD binds to human serum albumin (HSA).

10. The fusion protein of claim 8, wherein the ABD binds to mouse serum albumin (MSA).

11. The fusion protein of claim 8, wherein the ABD binds to HSA with a $K_D$ of between 1-1000 nM.

12. The fusion protein of claim 8, wherein the ABD binds to HSA with a $K_D$ of between 10-500 nM.

13. The fusion protein of claim 8, wherein the ABD binds to HSA with a $K_D$ of between 20-200 nM.

14. The fusion protein of claim 8, wherein the ABD binds to HSA with a $K_D$ of between 50-100 nM.

15. The fusion protein of claim 8, wherein the ABD comprises an amino acid sequence of SEQ ID NO: 3.

16. The fusion protein of claim 8, wherein the ABD comprises an amino acid sequence of SEQ ID NO: 4.

17. The fusion protein of claim 8, wherein the ABD comprises an amino acid sequence of SEQ ID NO: 5.

18. The fusion protein of claim 8, wherein the ABD comprises an amino acid sequence of SEQ ID NO: 6.

19. The fusion protein of claim 8, wherein the ABD comprises an amino acid sequence of SEQ ID NO: 7.

20. The fusion protein of claim 8, wherein the ABD comprises an amino acid sequence of SEQ ID NO: 8.

21. The fusion protein of claim 8, wherein the ABD comprises an amino acid sequence of SEQ ID NO: 9.

22. The fusion protein of claim 8, wherein the ABD comprises an amino acid sequence of SEQ ID NO: 10.

23. The fusion protein of claim 8, wherein the ABD comprises an amino acid sequence of SEQ ID NO: 11.

24. The fusion protein of any one of claims 1 to 7, wherein the albumin binding molecule is an anti-albumin antibody or antigen binding fragment thereof.

25. The fusion protein of claim 24, wherein the anti-albumin antibody or antigen binding fragment thereof is an sdAb that binds to HSA.

26. The fusion protein of claim 25, wherein the sdAb is a VHH single domain antibody.

27. The fusion protein of claim 25 or claim 26, wherein the sdAb binds to HSA with a $K_D$ of between 1-1000 nM.

28. The fusion protein of claim 25 or claim 26, wherein the sdAb binds to HSA with a $K_D$ of between 10-500 nM.

29. The fusion protein of claim 25 or claim 26, wherein the sdAb binds to HSA with a $K_D$ of between 20-200 nM.

30. The fusion protein of claim 25 or claim 26, wherein the sdAb binds to HSA with a $K_D$ of between 50-100 nM.

31. The fusion protein of claim 1, wherein the binding molecule is an antibody or an antigen binding fragment thereof that binds to an antigen expressed on a cancer cell, wherein the cancer cell is optionally a solid tumor cancer cell.

32. The fusion protein of claim 31, wherein the binding molecule is a sdAb.

33. The fusion protein of claim 32, wherein the sdAb is a VHH single domain antibody.

34. The fusion protein of claim 33, wherein the sdAb binds to mesothelin (MSLN).

35. The fusion protein of claim 34, wherein the sdAb comprises a heavy chain variable region (VH) comprising (i) complementarity determining region 1 (CDR1) having an amino acid sequence selected from a group consisting of SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, and SEQ ID NO: 120; (ii) complementarity determining region 2 (CDR2) having an amino acid sequence selected from a group consisting of SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103, SEQ ID NO: 106, SEQ ID NO: 109, SEQ ID NO: 112, SEQ ID NO: 115, SEQ ID NO: 118, and SEQ ID NO: 121; and (iii) complementarity determining region 3 (CDR3) having an amino acid sequence selected from a group consisting of SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, and SEQ ID NO: 122.

36. The fusion protein of claim 34, wherein the sdAb comprises a VH comprising CDR1 of SEQ ID NO: 12, CDR2 of SEQ ID NO: 13, and CDR3 of SEQ ID NO: 14.

37. The fusion protein of claim 34, wherein the sdAb comprises a VH comprising CDR1 of SEQ ID NO: 15, CDR2 of SEQ ID NO: 16, and CDR3 of SEQ ID NO: 17.

38. The fusion protein of claim 34, wherein the sdAb comprises a VH comprising CDR1 of SEQ ID NO: 18, CDR2 of SEQ ID NO: 19, and CDR3 of SEQ ID NO: 20.

39. The fusion protein of claim 34, wherein the sdAb comprises a VH comprising CDR1 of SEQ ID NO: 21, CDR2 of SEQ ID NO: 22, and CDR3 of SEQ ID NO: 23.

40. The fusion protein of claim 34, wherein the sdAb comprises a VH comprising CDR1 of SEQ ID NO: 24, CDR2 of SEQ ID NO: 25, and CDR3 of SEQ ID NO: 26.

41. The fusion protein of claim 34, wherein the sdAb comprises a VH comprising CDR1 of SEQ ID NO: 27, CDR2 of SEQ ID NO: 28, and CDR3 of SEQ ID NO: 29.

42. The fusion protein of claim 34, wherein the sdAb comprises a VH comprising CDR1 of SEQ ID NO: 30, CDR2 of SEQ ID NO: 31, and CDR3 of SEQ ID NO: 32.

43. The fusion protein of claim 34, wherein the sdAb comprises a VH comprising CDR1 of SEQ ID NO: 33, CDR2 of SEQ ID NO: 34, and CDR3 of SEQ ID NO: 35.

44. The fusion protein of claim 34, wherein the sdAb comprises a VH comprising CDR1 of SEQ ID NO: 36, CDR2 of SEQ ID NO: 37, and CDR3 of SEQ ID NO: 38.

45. The fusion protein of claim 34, wherein the sdAb comprises a VH comprising CDR1 of SEQ ID NO: 39, CDR2 of SEQ ID NO: 40, and CDR3 of SEQ ID NO: 41.

46. The fusion protein of claim 34, wherein the sdAb comprises a VH comprising CDR1 of SEQ ID NO: 42, CDR2 of SEQ ID NO: 43, and CDR3 of SEQ ID NO: 44.

47. The fusion protein of claim 34, wherein the sdAb comprises a VH comprising CDR1 of SEQ ID NO: 45, CDR2 of SEQ ID NO: 46, and CDR3 of SEQ ID NO: 47.

48. The fusion protein of claim 34, wherein the sdAb comprises a VH comprising CDR1 of SEQ ID NO: 48, CDR2 of SEQ ID NO: 49, and CDR3 of SEQ ID NO: 50.

49. The fusion protein of claim 34, wherein the sdAb comprises a VH comprising CDR1 of SEQ ID NO: 51, CDR2 of SEQ ID NO: 52, and CDR3 of SEQ ID NO: 53.

50. The fusion protein of claim 34, wherein the sdAb comprises a VH comprising CDR1 of SEQ ID NO: 54, CDR2 of SEQ ID NO: 55, and CDR3 of SEQ ID NO: 56.

51. The fusion protein of claim 34, wherein the sdAb comprises a VH comprising CDR1 of SEQ ID NO: 57, CDR2 of SEQ ID NO: 58, and CDR3 of SEQ ID NO: 59.

52. The fusion protein of claim 34, wherein the sdAb comprises a VH comprising CDR1 of SEQ ID NO: 60, CDR2 of SEQ ID NO: 61, and CDR3 of SEQ ID NO: 62.

53. The fusion protein of claim 34, wherein the sdAb comprises a VH comprising CDR1 of SEQ ID NO: 63, CDR2 of SEQ ID NO: 64, and CDR3 of SEQ ID NO: 65.

54. The fusion protein of claim 34, wherein the sdAb comprises a VH comprising CDR1 of SEQ ID NO: 75, CDR2 of SEQ ID NO: 76, and CDR3 of SEQ ID NO: 77.

55. The fusion protein of claim 34, wherein the sdAb comprises a VH comprising CDR1 of SEQ ID NO: 78, CDR2 of SEQ ID NO: 79, and CDR3 of SEQ ID NO: 80.

56. The fusion protein of claim 34, wherein the sdAb comprises a VH comprising CDR1 of SEQ ID NO: 81, CDR2 of SEQ ID NO: 82, and CDR3 of SEQ ID NO: 83.

57. The fusion protein of claim 34, wherein the sdAb comprises a VH comprising CDR1 of SEQ ID NO: 84, CDR2 of SEQ ID NO: 85, and CDR3 of SEQ ID NO: 86.

58. The fusion protein of claim 34, wherein the sdAb comprises a VH comprising CDR1 of SEQ ID NO: 87, CDR2 of SEQ ID NO: 88, and CDR3 of SEQ ID NO: 89.

59. The fusion protein of claim 34, wherein the sdAb comprises a VH comprising CDR1 of SEQ ID NO: 90, CDR2 of SEQ ID NO: 91, and CDR3 of SEQ ID NO: 92.

60. The fusion protein of claim 34, wherein the sdAb comprises a VH comprising CDR1 of SEQ ID NO: 93, CDR2 of SEQ ID NO: 94, and CDR3 of SEQ ID NO: 95.

61. The fusion protein of claim 34, wherein the sdAb comprises a VH comprising CDR1 of SEQ ID NO: 96, CDR2 of SEQ ID NO: 97, and CDR3 of SEQ ID NO: 98.

62. The fusion protein of claim 34, wherein the sdAb comprises a VH comprising CDR1 of SEQ ID NO: 99, CDR2 of SEQ ID NO: 100, and CDR3 of SEQ ID NO: 101.

63. The fusion protein of claim 34, wherein the sdAb comprises a VH comprising CDR1 of SEQ ID NO: 102, CDR2 of SEQ ID NO: 103, and CDR3 of SEQ ID NO: 104.

64. The fusion protein of claim 34, wherein the sdAb comprises a VH comprising CDR1 of SEQ ID NO: 105, CDR2 of SEQ ID NO: 106, and CDR3 of SEQ ID NO: 107.

65. The fusion protein of claim 34, wherein the sdAb comprises a VH comprising CDR1 of SEQ ID NO: 108, CDR2 of SEQ ID NO: 109, and CDR3 of SEQ ID NO: 110.

66. The fusion protein of claim 34, wherein the sdAb comprises a VH comprising CDR1 of SEQ ID NO: 111, CDR2 of SEQ ID NO: 112, and CDR3 of SEQ ID NO: 113.

67. The fusion protein of claim 34, wherein the sdAb comprises a VH comprising CDR1 of SEQ ID NO: 114, CDR2 of SEQ ID NO: 115, and CDR3 of SEQ ID NO: 116.

68. The fusion protein of claim 34, wherein the sdAb comprises a VH comprising CDR1 of SEQ ID NO: 117, CDR2 of SEQ ID NO: 118, and CDR3 of SEQ ID NO: 119.

69. The fusion protein of claim 34, wherein the sdAb comprises a VH comprising CDR1 of SEQ ID NO: 120, CDR2 of SEQ ID NO: 121, and CDR3 of SEQ ID NO: 122.

70. The fusion protein of any one of claims 34 to 69, wherein the sdAb further comprises one or more FR sequences of antibodies anti-MSLN-1, anti-MSLN-2, anti-MSLN-3, anti-MSLN-4, anti-MSLN-5, anti-MSLN-6, anti-MSLN-7, anti-MSLN-8, anti-MSLN-9, anti-MSLN-10, anti-MSLN-11, anti-MSLN-12, anti-MSLN-13, anti-MSLN-14, anti-MSLN-15, anti-MSLN-16, anti-MSLN-17, anti-MSLN-18, anti-MSLN-19, anti-MSLN-20, anti-MSLN-21, anti-MSLN-22, anti-MSLN-23, anti-MSLN-24, anti-MSLN-25, anti-MSLN-26, anti-MSLN-27, anti-MSLN-28, anti-MSLN-29, anti-MSLN-30, anti-MSLN-31, anti-MSLN-32, anti-MSLN-33, or anti-MSLN-34 as set forth in Table 9.

71. The fusion protein of claim 34, wherein the sdAb comprises an amino acid sequence of SEQ ID NO: 123.

72. The fusion protein of claim 34, wherein the sdAb comprises an amino acid sequence of SEQ ID NO: 124.

73. The fusion protein of claim 34, wherein the sdAb comprises an amino acid sequence of SEQ ID NO: 125.

74. The fusion protein of claim 34, wherein the sdAb comprises an amino acid sequence of SEQ ID NO: 126.

75. The fusion protein of claim 34, wherein the sdAb comprises an amino acid sequence of SEQ ID NO: 127.

76. The fusion protein of claim 34, wherein the sdAb comprises an amino acid sequence of SEQ ID NO: 128.

77. The fusion protein of claim 34, wherein the sdAb comprises an amino acid sequence of SEQ ID NO: 129.

78. The fusion protein of claim 34, wherein the sdAb comprises an amino acid sequence of SEQ ID NO: 130.

79. The fusion protein of claim 34, wherein the sdAb comprises an amino acid sequence of SEQ ID NO: 131.

80. The fusion protein of claim 34, wherein the sdAb comprises an amino acid sequence of SEQ ID NO: 132.

81. The fusion protein of claim 34, wherein the sdAb comprises an amino acid sequence of SEQ ID NO: 133.

82. The fusion protein of claim 34, wherein the sdAb comprises an amino acid sequence of SEQ ID NO: 134.

83. The fusion protein of claim 34, wherein the sdAb comprises an amino acid sequence of SEQ ID NO: 135.

84. The fusion protein of claim 34, wherein the sdAb comprises an amino acid sequence of SEQ ID NO: 136.

85. The fusion protein of claim 34, wherein the sdAb comprises an amino acid sequence of SEQ ID NO: 137.

86. The fusion protein of claim 34, wherein the sdAb comprises an amino acid sequence of SEQ ID NO: 138.

87. The fusion protein of claim 34, wherein the sdAb comprises an amino acid sequence of SEQ ID NO: 139.

88. The fusion protein of claim 34, wherein the sdAb comprises an amino acid sequence of SEQ ID NO: 140.

89. The fusion protein of claim 34, wherein the sdAb comprises an amino acid sequence of SEQ ID NO: 141.

90. The fusion protein of claim 34, wherein the sdAb comprises an amino acid sequence of SEQ ID NO: 142.

91. The fusion protein of claim 34, wherein the sdAb comprises an amino acid sequence of SEQ ID NO: 143.

92. The fusion protein of claim 34, wherein the sdAb comprises an amino acid sequence of SEQ ID NO: 144.

93. The fusion protein of claim 34, wherein the sdAb comprises an amino acid sequence of SEQ ID NO: 145.

94. The fusion protein of claim 34, wherein the sdAb comprises an amino acid sequence of SEQ ID NO: 146.

95. The fusion protein of claim 34, wherein the sdAb comprises an amino acid sequence of SEQ ID NO: 147.

96. The fusion protein of claim 34, wherein the sdAb comprises an amino acid sequence of SEQ ID NO: 148.

97. The fusion protein of claim 34, wherein the sdAb comprises an amino acid sequence of SEQ ID NO: 149.

98. The fusion protein of claim 34, wherein the sdAb comprises an amino acid sequence of SEQ ID NO: 150.

99. The fusion protein of claim 34, wherein the sdAb comprises an amino acid sequence of SEQ ID NO: 151.

100. The fusion protein of claim 34, wherein the sdAb comprises an amino acid sequence of SEQ ID NO: 152.

101. The fusion protein of claim 34, wherein the sdAb comprises an amino acid sequence of SEQ ID NO: 153.

102. The fusion protein of claim 34, wherein the sdAb comprises an amino acid sequence of SEQ ID NO: 154.

103. The fusion protein of claim 34, wherein the sdAb comprises an amino acid sequence of SEQ ID NO: 155.

104. The fusion protein of claim 34, wherein the sdAb comprises an amino acid sequence of SEQ ID NO: 156.

105. The fusion protein of any one of claims 34 to 69, wherein the sdAb further comprises one or more humanized FR sequences as set forth in Table 11.

106. The fusion protein of claim 105, wherein the sdAb binds to MSLN with a $K_D$ of between 1-100 nM.

107. The fusion protein of claim 105, wherein the sdAb binds to MSLN with a $K_D$ of between 1-80 nM.

108. The fusion protein of claim 105, wherein the sdAb binds to MSLN with a $K_D$ of between 1-70 nM.

109. The fusion protein of claim 105, wherein the sdAb binds to MSLN with a $K_D$ of between 1-60 nM.

110. The fusion protein of claim 105, wherein the sdAb binds to MSLN with a $K_D$ of between 1-50 nM.

111. The fusion protein of claim 1, wherein the binding molecule comprises two antibodies or antigen binding fragments thereof each binding to an antigen expressed on a cancer cell, wherein the cancer cell is optionally a solid tumor cancer cell, and wherein the two antibodies or antigen binding fragments thereof are connected by a third linker.

112. The fusion protein of claim 111, wherein the two antibodies or antigen binding fragments thereof are two sdAbs.

113. The fusion protein of claim 112, wherein the two sdAbs are VHH single domain antibodies.

114. The fusion protein of claim 112, wherein the two sdAb bind to two different epitopes of MSLN.

115. The fusion protein of claim 114, wherein one epitope is on the N-terminus of MSLN and the other epitope is on the C-terminus of MSLN.

116. The fusion protein of any one of claims 112-115, wherein each sdAb binds to MSLN with a $K_D$ of between 0.1-100 nM.

117. The fusion protein of any one of claims 112-115, wherein each sdAb binds to MSLN with a $K_D$ of between 1-100 nM.

118. The fusion protein of any one of claims 112-115, wherein each sdAb binds to MSLN with a $K_D$ of between 1-80 nM.

119. The fusion protein of any one of claims 112-115, wherein each sdAb binds to MSLN with a $K_D$ of between 1-70 nM.

120. The fusion protein of any one of claims 112-115, wherein each sdAb binds to MSLN with a $K_D$ of between 1-60 nM.
121. The fusion protein of any one of claims 112-115, wherein each sdAb binds to MSLN with a $K_D$ of between 1-50 nM.
122. The fusion protein of any one of claims 1 to 121, wherein the first linker and the second linker are each independently selected from a group consisting of SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73 and SEQ ID NO: 74.
123. The fusion protein of claim 121, wherein the third linker is selected from a group consisting of SEQ ID NO: 66, SEQ ID NO: 67, SEQ ID NO: 68, SEQ ID NO: 69, and SEQ ID NO: 70.
124. The fusion protein of claim 1, wherein the first linker is connected to the C-terminus of the IL-21 or a variant thereof.
125. The fusion protein of claim 1, wherein the first linker is connected to the IL-21 or a variant thereof at an amino acid within amino acids 123 to 132 of the IL-21 or a variant thereof.
126. The fusion protein of claim 1, wherein the first linker is connected to the IL-21 or a variant thereof at one of the last 10 amino acids of the C-terminus of the IL-21 or a variant thereof.
127. The fusion protein of claim 1 or 4, wherein the first linker is connected to L123 of the IL-21 or a variant thereof.
128. The fusion protein of claim 1, wherein the first linker is connected to the N-terminus of the IL-21 or a variant thereof at Q1 to D4.
129. A pharmaceutical composition comprising the fusion protein of any one of claims 1 to 128 and a pharmaceutically acceptable excipient.
130. A method of treating a cancer comprising administering a therapeutically effective amount of the fusion protein of any one of claims 1 to 128 to a subject.
131. The method of claim 130, wherein the cancer is a solid tumor cancer.
132. The method of claim 131, wherein the subject is a human subject.
133. A polynucleotide comprising nucleotide sequences encoding the fusion protein of any one of claims 1 to 128.
134. A vector comprising the polynucleotide of claim 133.
135. A cell comprising the polynucleotide of claim 133.
136. A cell comprising the vector of claim 134.
137. A method of making a fusion protein comprising culturing the cell of claim 135 or 136 to express the fusion protein.
138. A single domain antibody that binds to mesothelin (MSLN) comprising the following structure: FR1-CDR1-FR2-CDR2-FR3-CDR3-FR4, wherein (i) CDR1 comprises an amino acid sequence selected from a group consisting of SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 75, SEQ ID NO: 78, SEQ ID NO: 81, SEQ ID NO: 84, SEQ ID NO: 87, SEQ ID NO: 90, SEQ ID NO: 93, SEQ ID NO: 96, SEQ ID NO: 99, SEQ ID NO: 102, SEQ ID NO: 105, SEQ ID NO: 108, SEQ ID NO: 111, SEQ ID NO: 114, SEQ ID NO: 117, and SEQ ID NO: 120; (ii) CDR2 comprises an amino acid sequence selected from a group consisting of SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 76, SEQ ID NO: 79, SEQ ID NO: 82, SEQ ID NO: 85, SEQ ID NO: 88, SEQ ID NO: 91, SEQ ID NO: 94, SEQ ID NO: 97, SEQ ID NO: 100, SEQ ID NO: 103, SEQ ID NO: 106, SEQ ID NO: 109, SEQ ID NO: 112, SEQ ID NO: 115, SEQ ID NO: 118, and SEQ ID NO: 121; and (iii) CDR3 comprises an amino acid sequence selected from a group consisting of SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, and SEQ ID NO: 122.
139. The single domain antibody of claim 138, wherein CDR1 is of SEQ ID NO: 12, CDR2 is of SEQ ID NO: 13, and CDR3 is of SEQ ID NO: 14.
140. The single domain antibody of claim 138, wherein CDR1 is of SEQ ID NO: 15, CDR2 is of SEQ ID NO: 16, and CDR3 is of SEQ ID NO: 17.
141. The single domain antibody of claim 138, wherein CDR1 is of SEQ ID NO: 18, CDR2 is of SEQ ID NO: 19, and CDR3 is of SEQ ID NO: 20.
142. The single domain antibody of claim 138, wherein CDR1 is of SEQ ID NO: 21, CDR2 is of SEQ ID NO: 22, and CDR3 is of SEQ ID NO: 23.
143. The single domain antibody of claim 138, wherein CDR1 is of SEQ ID NO: 24, CDR2 is of SEQ ID NO: 25, and CDR3 is of SEQ ID NO: 26.
144. The single domain antibody of claim 138, wherein CDR1 is of SEQ ID NO: 27, CDR2 is of SEQ ID NO: 28, and CDR3 is of SEQ ID NO: 29.
145. The single domain antibody of claim 138, wherein CDR1 is of SEQ ID NO: 30, CDR2 is of SEQ ID NO: 31, and CDR3 is of SEQ ID NO: 32.
146. The single domain antibody of claim 138, wherein CDR1 is of SEQ ID NO: 33, CDR2 is of SEQ ID NO: 34, and CDR3 is of SEQ ID NO: 35.
147. The single domain antibody of claim 138, wherein CDR1 is of SEQ ID NO: 36, CDR2 is of SEQ ID NO: 37, and CDR3 is of SEQ ID NO: 38.
148. The single domain antibody of claim 138, wherein CDR1 is of SEQ ID NO: 39, CDR2 is of SEQ ID NO: 40, and CDR3 is of SEQ ID NO: 41.
149. The single domain antibody of claim 138, wherein CDR1 is of SEQ ID NO: 42, CDR2 is of SEQ ID NO: 43, and CDR3 is of SEQ ID NO: 44.
150. The single domain antibody of claim 138, wherein CDR1 is of SEQ ID NO: 45, CDR2 is of SEQ ID NO: 46, and CDR3 is of SEQ ID NO: 47.
151. The single domain antibody of claim 138, wherein CDR1 is of SEQ ID NO: 48, CDR2 is of SEQ ID NO: 49, and CDR3 is of SEQ ID NO: 50.

152. The single domain antibody of claim 138, wherein CDR1 is of SEQ ID NO: 51, CDR2 is of SEQ ID NO: 52, and CDR3 is of SEQ ID NO: 53.

153. The single domain antibody of claim 138, wherein CDR1 is of SEQ ID NO: 54, CDR2 is of SEQ ID NO: 55, and CDR3 is of SEQ ID NO: 56.

154. The single domain antibody of claim 138, wherein CDR1 is of SEQ ID NO: 57, CDR2 is of SEQ ID NO: 58, and CDR3 is of SEQ ID NO: 59.

155. The single domain antibody of claim 138, wherein CDR1 is of SEQ ID NO: 60, CDR2 is of SEQ ID NO: 61, and CDR3 is of SEQ ID NO: 62.

156. The single domain antibody of claim 138, wherein CDR1 is of SEQ ID NO: 63, CDR2 is of SEQ ID NO: 64, and CDR3 is of SEQ ID NO: 65.

157. The single domain antibody of claim 138, wherein CDR1 is of SEQ ID NO: 75, CDR2 is of SEQ ID NO: 76, and CDR3 is of SEQ ID NO: 77.

158. The single domain antibody of claim 138, wherein CDR1 is of SEQ ID NO: 78, CDR2 is of SEQ ID NO: 79, and CDR3 is of SEQ ID NO: 80.

159. The single domain antibody of claim 138, wherein CDR1 is of SEQ ID NO: 81, CDR2 is of SEQ ID NO: 82, and CDR3 is of SEQ ID NO: 83.

160. The single domain antibody of claim 138, wherein CDR1 is of SEQ ID NO: 84, CDR2 is of SEQ ID NO: 85, and CDR3 is of SEQ ID NO: 86.

161. The single domain antibody of claim 138, wherein CDR1 is of SEQ ID NO: 87, CDR2 is of SEQ ID NO: 88, and CDR3 is of SEQ ID NO: 89.

162. The single domain antibody of claim 138, wherein CDR1 is of SEQ ID NO: 90, CDR2 is of SEQ ID NO: 91, and CDR3 is of SEQ ID NO: 92.

163. The single domain antibody of claim 138, wherein CDR1 is of SEQ ID NO: 93, CDR2 is of SEQ ID NO: 94, and CDR3 is of SEQ ID NO: 95.

164. The single domain antibody of claim 138, wherein CDR1 is of SEQ ID NO: 96, CDR2 is of SEQ ID NO: 97, and CDR3 is of SEQ ID NO: 98.

165. The single domain antibody of claim 138, wherein CDR1 is of SEQ ID NO: 99, CDR2 is of SEQ ID NO: 100, and CDR3 is of SEQ ID NO: 101.

166. The single domain antibody of claim 138, wherein CDR1 is of SEQ ID NO: 102, CDR2 is of SEQ ID NO: 103, and CDR3 is of SEQ ID NO: 104.

167. The single domain antibody of claim 138, wherein CDR1 is of SEQ ID NO: 105, CDR2 is of SEQ ID NO: 106, and CDR3 is of SEQ ID NO: 107.

168. The single domain antibody of claim 138, wherein CDR1 is of SEQ ID NO: 108, CDR2 is of SEQ ID NO: 109, and CDR3 is of SEQ ID NO: 110.

169. The single domain antibody of claim 138, wherein CDR1 is of SEQ ID NO: 111, CDR2 is of SEQ ID NO: 112, and CDR3 is of SEQ ID NO: 113.

170. The single domain antibody of claim 138, wherein CDR1 is of SEQ ID NO: 114, CDR2 is of SEQ ID NO: 115, and CDR3 is of SEQ ID NO: 116.

171. The single domain antibody of claim 138, wherein CDR1 is of SEQ ID NO: 117, CDR2 is of SEQ ID NO: 118, and CDR3 is of SEQ ID NO: 119.

172. The single domain antibody of claim 138, wherein CDR1 is of SEQ ID NO: 120, CDR2 is of SEQ ID NO: 121, and CDR3 is of SEQ ID NO: 122.

173. The single domain antibody of any one of claims 138 to 172, wherein the sdAb further comprises one or more FR sequences of antibodies anti-MSLN-1, anti-MSLN-2, anti-MSLN-3, anti-MSLN-4, anti-MSLN-5, anti-MSLN-6, anti-MSLN-7, anti-MSLN-8, anti-MSLN-9, anti-MSLN-10, anti-MSLN-11, anti-MSLN-12, anti-MSLN-13, anti-MSLN-14, anti-MSLN-15, anti-MSLN-16, anti-MSLN-17, anti-MSLN-18, anti-MSLN-19, anti-MSLN-20, anti-MSLN-21, anti-MSLN-22, anti-MSLN-23, anti-MSLN-24, anti-MSLN-25, anti-MSLN-26, anti-MSLN-27, anti-MSLN-28, anti-MSLN-29, anti-MSLN-30, anti-MSLN-31, anti-MSLN-32, anti-MSLN-33, or anti-MSLN-34 as set forth in Table 9.

174. The single domain antibody of claim 138, wherein the sdAb comprises an amino acid sequence of SEQ ID NO: 123.

175. The single domain antibody of claim 138, wherein the sdAb comprises an amino acid sequence of SEQ ID NO: 124.

176. The single domain antibody of claim 138, wherein the sdAb comprises an amino acid sequence of SEQ ID NO: 125.

177. The single domain antibody of claim 138, wherein the sdAb comprises an amino acid sequence of SEQ ID NO: 126.

178. The single domain antibody of claim 138, wherein the sdAb comprises an amino acid sequence of SEQ ID NO: 127.

179. The single domain antibody of claim 138, wherein the sdAb comprises an amino acid sequence of SEQ ID NO: 128.

180. The single domain antibody of claim 138, wherein the sdAb comprises an amino acid sequence of SEQ ID NO: 129.

181. The single domain antibody of claim 138, wherein the sdAb comprises an amino acid sequence of SEQ ID NO: 130.

182. The single domain antibody of claim 138, wherein the sdAb comprises an amino acid sequence of SEQ ID NO: 131.

183. The single domain antibody of claim 138, wherein the sdAb comprises an amino acid sequence of SEQ ID NO: 132.

184. The single domain antibody of claim 138, wherein the sdAb comprises an amino acid sequence of SEQ ID NO: 133.

185. The single domain antibody of claim 138, wherein the sdAb comprises an amino acid sequence of SEQ ID NO: 134.

186. The single domain antibody of claim 138, wherein the sdAb comprises an amino acid sequence of SEQ ID NO: 135.

187. The single domain antibody of claim 138, wherein the sdAb comprises an amino acid sequence of SEQ ID NO: 136.

188. The single domain antibody of claim 138, wherein the sdAb comprises an amino acid sequence of SEQ ID NO: 137.

189. The single domain antibody of claim 138, wherein the sdAb comprises an amino acid sequence of SEQ ID NO: 138.

190. The single domain antibody of claim 138, wherein the sdAb comprises an amino acid sequence of SEQ ID NO: 139.

191. The single domain antibody of claim 138, wherein the sdAb comprises an amino acid sequence of SEQ ID NO: 140.

192. The single domain antibody of claim 138, wherein the sdAb comprises an amino acid sequence of SEQ ID NO: 141.

193. The single domain antibody of claim 138, wherein the sdAb comprises an amino acid sequence of SEQ ID NO: 142.
194. The single domain antibody of claim 138, wherein the sdAb comprises an amino acid sequence of SEQ ID NO: 143.
195. The single domain antibody of claim 138, wherein the sdAb comprises an amino acid sequence of SEQ ID NO: 144.
196. The single domain antibody of claim 138, wherein the sdAb comprises an amino acid sequence of SEQ ID NO: 145.
197. The single domain antibody of claim 138, wherein the sdAb comprises an amino acid sequence of SEQ ID NO: 146.
198. The single domain antibody of claim 138, wherein the sdAb comprises an amino acid sequence of SEQ ID NO: 147.
199. The single domain antibody of claim 138, wherein the sdAb comprises an amino acid sequence of SEQ ID NO: 148.
200. The single domain antibody of claim 138, wherein the sdAb comprises an amino acid sequence of SEQ ID NO: 149.
201. The single domain antibody of claim 138, wherein the sdAb comprises an amino acid sequence of SEQ ID NO: 150.
202. The single domain antibody of claim 138, wherein the sdAb comprises an amino acid sequence of SEQ ID NO: 151.
203. The single domain antibody of claim 138, wherein the sdAb comprises an amino acid sequence of SEQ ID NO: 152.
204. The single domain antibody of claim 138, wherein the sdAb comprises an amino acid sequence of SEQ ID NO: 153.
205. The single domain antibody of claim 138, wherein the sdAb comprises an amino acid sequence of SEQ ID NO: 154.
206. The single domain antibody of claim 138, wherein the sdAb comprises an amino acid sequence of SEQ ID NO: 155.
207. The single domain antibody of claim 138, wherein the sdAb comprises an amino acid sequence of SEQ ID NO: 156.
208. The single domain antibody of any one of claims 138 to 172, wherein the sdAb further comprises one or more humanized FR sequences as set forth in Table 11.

EXAMPLES

The following is a description of various methods and materials used in the studies, and are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present invention. Efforts have been made to ensure accuracy with respect to numbers used (e.g., amounts, percentages, etc.), but some experimental errors and deviations should be accounted for.

Example 1: Exemplary IL-21 Fusion Proteins

This example illustrates certain exemplary IL-21 fusion proteins provided herein. It is to be understood that the exemplary IL-21 fusion proteins described in this example are not intended to represent the full scope of the present invention.

The IL-21-(HSA binding molecule)-(anti-MSLN) is used herein to present certain exemplary IL-fusion proteins, which comprise 1) an IL-21 or a variant thereof, e.g., a truncated IL-21; 2) a peptide (e.g., an ABD or a sdAb) that binds to human serum albumin (HSA); 3) one or more antibody or antigen binding fragment thereof targeting tumor antigen mesothelin (MSLN), 4) a first linker (L1) composed of 4-20 amino acids which connects C-terminus of IL-21 and N-terminus of αHSA; and 5) a second linker (L2) composed of 4-20 amino acids which connects C-terminus of αHSA and N-terminus of anti-MSLN.

The IL-21 can have an amino acid sequence of SEQ ID NO: 1 (see Table 6 below). Alternatively, the IL-21 can be a truncated human IL-21 having an amino acid sequence of SEQ ID NO: 2 (see Table 6 below).

TABLE 6

| SEQ ID NO | Sequence | Name |
|---|---|---|
| 1 | QGQDRHMIRMRQLIDIVDQLKNYVNDLVPEFLPAPEDV ETNCEWSAFSCFQKAQLKSANTGNNERIINVSIKKLKRK PPSTNAGRRQKHRLTCPSCDSYEKKPPKEFLERFKSLLQ KMIHQHLSSRTHGSEDS | Human IL-21, Full Length |
| 2 | QGQDRHMIRMRQLIDIVDQLKNYVNDLVPEFLPAPEDV ETNCEWSAFSCFQKAQLKSANTGNNERIINVSIKKLKRK PPSTNAGRRQKHRLTCPSCDSYEKKPPKEFLERFKSLLQ KMIHQHL | Human IL-21, Truncated |

Table 7 below lists a few options for an HSA binding peptide (SEQ ID NO: 3 to SEQ ID NO: 11).

TABLE 7

| SEQ ID NO | Sequence | Name |
|---|---|---|
| 3 | LAEAKVLANRELDKYGVSDYYKNLINNAKTVEG VKALIDEILAALP | G148-ABD-wt |
| 4 | LAEAKVLANRELDKYGVSDFAKRLINKAKTVEG VEALKDEILAALP | LI-ABD-1 |

TABLE 7-continued

| SEQ ID NO | Sequence | Name |
|---|---|---|
| 5 | LAEAKVLANRELDKYGVSDFAKRAINKAKTVEG VEALKDEILAALP | LI-ABD-2 |
| 6 | LAEAKVLANRELDKYGVSDFAKRAINKAKTVEG AEALKDEILAALP | LI-ABD-3 |
| 7 | LAEAKVLANRELDKYGVSDFYKRLINKAKTVEG VEALKLHILAALP | ABD-035 |
| 8 | LAEAKVLANRELDKYGVSDYAKNLINNAKTVEG VKALIDEILAALP | ABD$_{Y21A}$ |
| 9 | LAEAKVLANRELDKYGVADAYANLINNAKTVE GVKALIDEILAALP | ABD$_{S18Y20K22A}$ |
| 10 | LKEAKEKAIEELKKAGITSDYYFDLINKAKTVEG VNALKDEILKA | ABDcon |
| 11 | TIDEWLLKEAKEKAIEELKKAGITSDYYFDLINK AKTVEGVNALKDEILKA | ABDcon12 |

In these exemplary fusion proteins, the anti-MSLN portion of the fusion proteins can be selected from any of the 34 anti-MSLN sdAbs and humanized versions thereof described in Example 2.

The L1 and L2 linkers each can be independently selected from the linkers listed in Table 8 below, as well as cleavable linker listed in Table 5.

TABLE 8

| SEQ ID NO | Sequence | Name |
|---|---|---|
| 66 | (GSGS)n (n = 1-4) | GSGS Linker, |
| 67 | (GGSG)n (n = 1-4) | GGSG Linker |
| 68 | (GGGGS)n (n = 1-3) | GGGGS Linker |
| 69 | (PAPA)n (n = 1-3) | PAPA Linker |
| 70 | (PQPQ)n (n = 1-3) | PQPQ Linker |
| 71 | IKRADAAP | VL-CL Native Linker |
| 72 | AEAAAKEAAAKA | Helix-forming Linker |
| 73 | GTNEVCKCPKCP | Dromedary IgG3 hinge |
| 74 | EPKIPQPQPKPQPQPQPKPQPKPEPECTCPKCP | Dromedary IgG2a hinge |
|  | GSG | GSG linker |
| 307 | (GSG)n | GSG linker, n = 2-6 |
| 308 | (G3S)n | G3S linker, n = 1-6 |
| 309 | (G4S)n | G4S linker, n = 1-6 |
| 310 | A(EAAAK)nA | EAAAK linker, n = 1-6 |
| 311 | (PAPAP)n | PAPAP linker, n = 1-6 |
| 312 | IKRTVAAP | VLVH. Linker |
| 313 | RAKPS | SIRPα linker |
| 314 | (GSGS)n (n = 1-4) | GSGS Linker, |
| 315 | (GGSG)n (n = 1-4) | GGSG Linker |
| 316 | (PAPA)n (n = 1-3) | PAPA Linker |
| 317 | (PQPQ)n (n = 1-3) | PQPQ Linker |
| 318 | IKRADAAP | VL-CL Native Linker |
| 319 | ASTKGP | VH-CH1 linker |
| 320 | GTNEVCKCPKCP | Dromedary IgG3 hinge |
| 321 | EPKIPQPQPKPQPQPQPKPQPKPEPECTCPKCP | Dromedary IgG2a hinge |

TABLE 8-continued

| SEQ ID NO | Sequence | Name |
|---|---|---|
| 322 | RRKRAPVKQTLNFDLLKLAGDVESNPGP | F2A (cleavable) |
| 323 | SGRSA | UPA linker (cleavable) |
| 324 | PVGLIG | MMP linker (cleavable) |
| 267 | Lys-Gly-Pro-Gln-Gly-Ile-Ala-Gly-Gln | Cleavable linker |
| 268 | Phe-Gly-Pro-Gln-Gly-Leu-Ala-Gly-Gln | Cleavable linker |
| 269 | Arg-Gly-Pro-Gln-Gly-Ile-Phe-Gly-Gln | Cleavable linker |
| 270 | Ile-Gly-Pro-Gln-Gly-Ile-Trp-Gly-Gln | Cleavable linker |
| 271 | Met-Gly-Pro-Gln-Gly-Ile-Leu-Gly-Gln | Cleavable linker |
| 272 | Lys-Gly-Pro-Gln-Ser-Ile-Ala-Gly-Gln | Cleavable linker |
| 273 | Phe-Gly-Pro-Gln-Ser-Leu-Ala-Gly-Gln | Cleavable linker |
| 274 | Arg-Gly-Pro-Gln-Ser-Ile-Phe-Gly-Gln | Cleavable linker |
| 275 | Ile-Gly-Pro-Gln-Ser-Ile-Trp-Gly-Gln | Cleavable linker |
| 276 | Met-Gly-Pro-Gln-Ser-Ile-Leu-Gly-Gln | Cleavable linker |
| 277 | Lys-Gly-Pro-Gln-Thr-Ile-Ala-Gly-Gln | Cleavable linker |
| 278 | Phe-Gly-Pro-Gln-Thr-Leu-Ala-Gly-Gln | Cleavable linker |
| 279 | Arg-Gly-Pro-Gln-Thr-Ile-Phe-Gly-Gln | Cleavable linker |
| 280 | Ile-Gly-Pro-Gln-Thr-Ile-Trp-Gly-Gln | Cleavable linker |
| 281 | Phe-Arg-Pro-Arg-Ser-Ile-Thr-Gly-Gln | Cleavable linker |
| 282 | Met-Gly-Pro-Gln-Thr-Ile-Leu-Gly-Gln | Cleavable linker |

In certain exemplary IL-21 fusion proteins, the anti-MSLN functional module comprises two single domain antibodies (sdAbs) targeting different domains of mesothelin, and the two sdAbs are connected by a third linker composed of 4-20 amino acids (L3). The L3 linker can be selected from SEQ ID NOs: 66 to 70 in Table 8 above.

The design of the exemplary IL-21 fusion proteins of the present example contemplates all possible combinations of various components of the IL-21 fusion proteins described above.

Example 2: Generation of Anti-MSLN Single Domain Antibodies

Two different antigen peptides were used to immunize llama to produce anti-MSLN single domain antibodies (VHH antibodies). The first antigen peptide (MSLN antigen 1) represents the cell membrane anchored MSLN. The second antigen peptide (MSLN antigen 2) represents the C-terminus of cell membrane anchored MSLN. The sequences of these two peptides are as follows:

MSLN antigen 1 (MSLN cleaved form)
(SEQ ID NO: 283)
EVEKTACPSGKKAREIDESLIFYKKWELEACVDAALLATQMDRVNAIPF

TYEQLDVLKHKLDELYPQGYPESVIQHLGYLFLKMSPEDIRKWNVTSLE

TLKALLEVNKGHEMSPQAPRRPLPQVATLIDRFVKGRGQLDKDTLDTLT

AFYPGYLCSLSPEELSSVPPSSIWAVRPQDLDTCDPRQLDVLYPKARLA

FQNMNGSEYFVKIQSFLGGAPTEDLKALSQQNVSMDLATFMKLRTDAVL

PLTVAEVQKLLGPHVEGLKAEERHRPVRDWILRQRQDDLDTLGLGLQGG

IPNGYLVLDLSMQEALS;

MSLN antigen 2 (MSLN C-terminus)
(SEQ ID NO: 284)
VQKLLGPHVEGLKAEERHRPVRDWILRQRQDDLDTLGLGLQGGIPNGYLV.

After immunization, peripheral mononuclear cells (PBMC) were isolated for RNA extraction. VHH antibody phage display libraries were constructed with mRNA/cDNA that encodes the antibody genes. The constructed phage display libraries were screened through multiple rounds of affinity binding with antigen. Positive clones were identified through ELISA. Antibody genes of the positive clones were sequenced and cloned into UCOE vector (EMD Millipore) for CHO cell expression.

Table 9 below lists the 34 exemplary novel anti-MSLN single domain (VHH) antibodies (i.e., anti-MSLN-1 to anti-MSLN-34) generated according to the method described above. The CDR sequences of these 34 exemplary novel VHH antibodies are listed in Table 10 below. Among the 34 antibodies, 31 antibodies (anti-MSLN-1 to anti-MSLN-31) were generated using the first MSLN antigen (MSLN antigen 1), and 3 antibodies (anti-MSLN-32 to anti-MSLN-34) were generated using the second MSLN antigen (MSLN antigen 2).

TABLE 9

| | sdAb name | VHH Sequences (SEQ ID NO) |
|---|---|---|
| Anti-MSLN-1 | R2-B02(D2) or R2D2 | QVQLVESGGGLVQAGGSLRLSCVASGGTASSYTMAWFRQ APGKERDFVASILWSGNTTAYANFVKGRFTISRDNAKNM MYLQMNSLKPEDTAVYYCARARGGWGTTAEVSNYAYW GQGTQVTVSS (SEQ ID NO: 123) |
| Anti-MSLN-2 | R2-B04(B6) | QVQLVESGGGLVQAGGSLRLSCAASGRTFSGSMGWFRQA PGEERKLVSTFNWDGSSYYADSVKGRFTISKDNAKNTMY LQMNSLKPEDTAVYYCAAAGYYHTGGPLLRDNEYRYWG QGTQVTVSS (SEQ ID NO: 124) |
| Anti-MSLN-3 | R3-B08(D5) or R3D5 | QVQLVESGGGLVQAGGSLRLSCAASGSISSIRHMRWYRQ APGKQRELVATVSNDGSAYYLGSVKGRFTISRTNAKNTLL YLQMNSLKPEDSALYICNADTWGWPGADYWGQGTQVTV SS (SEQ ID NO: 125) |
| Anti-MSLN-4 | R2-D03(F4) | QVQLVESGGGLVQAGGSLTLSCSVSGLTFSSRAMGWFRQ ASGKEREFVAAIIHSGDYTYYADSVKGRFTVSRDNAKNTV YLQMNSLKLGDTAVYYCAADSVNKRGASSYYVRTTEYD YWGQGTQVTVSS (SEQ ID NO: 126) |
| Anti-MSLN-5 | R2-E03(H4) | QVQLVESGGGLVQAGGSLTLSCAASGLTFTSHTMGWFRQ APGKEREFVATISWSGGNTYYADSVKGRFTISRDNAKNTV YPQMNSLKPEDAAVYYCAADRSSFRSYGGSSRVKVEGEY NYWGQGTRVTVSS (SEQ ID NO: 127) |
| Anti-MSLN-6 | R3-E08(C7) or R3C7 | QVQLVESGGGLVEAGDSLRLSCVVSGRTLESYVMAWFRQ APGKEREAVASINWSSGRLIYADFVKGRFTISRDYEKNTIY LSMNNLKPEDTAVYYCAAGRYWGQGTQVTVSS (SEQ ID NO: 128) |
| Anti-MSLN-7 | R2-G01(A2) | QVQLVESGGGLVQAGGSLRLSCTASGRALSSYAVGWFRQ APGKEREFVAAITWNGGRTYYADSEKGRSIISMDVAKSTV YLQMNSLKLEDTAVYYCAADPRGDVYHRDKYNIWGQGT QVTVSS (SEQ ID NO: 129) |
| Anti-MSLN-8 | R2-G05(A10) | QVQLVESGGGLVQAGGSLRLSCAASGRAFSGYTMAWFR QAPGKEREFVAGMTWSGDRTYYSDSVKDRFAISRDNVKN MGYLQMNSLKPEDTAVYYCATKLGTYYNSHDLRRPDYW GQGTQVTVSS (SEQ ID NO: 130) |
| Anti-MSLN-9 | R2-G06(G12) or R2G12 | QVQLVESGGGLVQAGGSLRLSCAASGITFPVNAYGWYRQ APGKQRDLVAIISAGGTTNYADSVKGRFAISKDNVNNTVY LQMNSLTSEDTGVYYCYLQRRIGMLRDYWGQGTQVTVSS (SEQ ID NO: 131) |
| Anti-MSLN-10 | R3-E09(E11) | QRQVAESGGGSVQPGGSLRLSCAASGFTFDNKQVAWFRE VPGKEREQISCISISDGATRYTDSVKGRFAVSRDYATNTVV LQMNNLRPEDTAIYYCATNPTQIMIGTMRCDLESKWYGT WGPGTQVTVSG (SEQ ID NO: 132) |
| Anti-MSLN-11 | R3-A09(E10) | QVQLVESGGGLVRAGDSLRLSCAASGRTNSTVAMGWFR QTPGKEREFVAVIVWSNGYSHYADSVKDRFSISRNKARNT VYLQLNSLKPEDTAVYYCALDIRDSEITVQQKYWGMGTQ VTVSS (SEQ ID NO: 133) |
| Anti-MSLN-12 | R2-C03(A4) | QVQLIESGGGLVQPGDSLRLSCAASGPTYTTETMGWFRQA PGKEREFVSSIRWRGAHTNYGDFVKGRFTISKDSAKQTVY LQMNSLKPEDTAVYFCAASRSFDYPRREDEYRYWGQGTQ VTVSS (SEQ ID NO: 134) |
| Anti-MSLN-13 | R2-D01(F1) | QVQLVESGGGLVQAGGSLRLSCAATGRTFSPYTMGWFRQ APGKEREFVTRITWKSGSTYYADSVKGRFTISRDNAKNTV TLQMDSLKPEDTAVYFCASTSFAYGLTNSNKYNYWGQGT QVTVSG (SEQ ID NO: 135) |
| Anti-MSLN-14 | R2-D02(G2) | QVQLVESGGGLVQAGGSLRLSCAASGRSFSTYRMGWFRQ APGKAREFVATITASGSWTYYSDSVKGRSTISRDNAKNTV YLQMNSLKPGDTAVYYCAAAEILTAITTSSDYDYWGQGT QVTVSS (SEQ ID NO: 136) |

TABLE 9-continued

| sdAb name | | VHH Sequences (SEQ ID NO) |
|---|---|---|
| Anti-MSLN-15 | R4-(E04) | QVQLSERGGGLVQAGDSLRLSCAASGRMFSSYAVGWFRQ APGKEREYVAAISYNGGATYYLNSVEGRFTISRDNAKNM VYLQMNSLKPEDTAIYTCAARGGHWYSIHDPSNFRAWGQ GTQVTVSS (SEQ ID NO: 137) |
| Anti-MSLN-16 | R4-(D10) | QVQLIESGGGLVQAGGSLRLSCVASGRRVRTAAMAWFRR VPGKEREFVSSITWRGGERNYADAVKDRFTISKDNAKNTV YLQMNSLKPEDTASYYCAAGPWYTNHDTSQGYNYWGQ GTQVTVSS (SEQ ID NO: 138) |
| Anti-MSLN-17 | R4-(P2D2) | QVQLAESGGGLVQAGGSLRLSCSASGRTISNYAMGWFRQ APGKEREFVASINWNGGGITYTSSVKGRFTISRDNAKSTV YLQMNSLKPEDAAVYYCAAQRAGTWTYWGQGTQVTVS S (SEQ ID NO: 139) |
| Anti-MSLN-18 | R4-(P2F4) | QVQLVESGGGLVQPGGSLTLSCAASGISDISSMGWYRQAP GEQRELVAIIGSGGNTKYSDSLKGRFTISIDNAKNTVYLRM NSLKPEDTSVYYCNAAQRIGAGPIVLYWGQGTQVTVSS (SEQ ID NO: 140) |
| Anti-MSLN-19 | R3-G07(B5) | QVQLVESGGGLVQAGGSLRLSCAASGHTFSVYAIGWFRQ APGKEREFVSSINWGDGLTYYTDSVKGRFIISKDNAKNTD YLQMNSLKPEDTAVYYCAARQRREGWDYWGQGTQVTV SS (SEQ ID NO: 141) |
| Anti-MSLN-20 | R2-B12-5 | QVQLVESGGGLVQAGGSLRLSCAASGRTASSYVIAWFRQA PGKAREYVASVSRSGVSTYYADSVKGRFTISRDKPKNTVF LQMNSLKLEDTAVYYCAADGKNFSNRWWSRDEYKYWG QGTQVTVSG (SEQ ID NO: 142) |
| Anti-MSLN-21 | R2-B12-7 | QVQLVESGGGLVQTGGSLRLSCVVSGRTETTYNIGWFRQ APGKERELVTAISRGATITYYADSVKGRFTISRDNAKNAV YLQMNSLKPEDTAVYYCAASFTNLAVVARDYYYWGQGT QVTVSS (SEQ ID NO: 143) |
| Anti-MSLN-22 | R2-F2-6 | QAQLVESGGGLVQAGGSLRLSCVVSGRTFSHYAMGWFR QPPGKEREFVAAITESPDSTIYADSVKGRFTISRDGAVNTV YLKMNNLKPEDTAVYYCAAARSTLRWPFRGQGQYDYDY WGQGTQVTVSG (SEQ ID NO: 144) |
| Anti-MSLN-23 | R2-G3-8 | QVHLVESGGGLVQAGGSLMLSCAASGRTWSTYPMGWFR QAPGKEREFVAAIRWTTGSTYYQDSVKGRFTISRDNAKNT VYLQMNSLKPEDTAVYYCNAEVRAWYNRRKADYWGQG TQVTVSS (SEQ ID NO: 145) |
| Anti-MSLN-24 | R2-H10-6 | QVHLVEAGGGLVQAGGSLRVSCAISGRTDSTGILGWFRRA PGKEREFVALIRWSNNYAWYEDSAKGRFTISRDNAKNTV YLQMNSLKPEDTAVYYCAAGTGWGFSISDYNYWGQGTQ VTVSG (SEQ ID NO: 146) |
| Anti-MSLN-25 | R3-H8-8 | QVQLVESGGGLVQAGNSLRLSCAATGRSFNTYAMAWFR QAPGKEREFVASITWSGASTPYSDSVKGRFTISRDNAKSTV YLQMNSLKREDTAVYYCAASSQYGGAASAPTAYLYWGQ GTQVTVSG (SEQ ID NO: 147) |
| Anti-MSLN-26 | R4-G5-6 | QVQLAESGGGLVQAGGSLRLSCSASGRTISNYAMGWFRQ APGQEREFVAAVSWTGHGTFHATAVKGRFTISRDNAENT VFLQMNSLKLEDTAVYYCAADGKNFSNRWWSRDEYKY WGQGTQVTVSS (SEQ ID NO: 148) |
| Anti-MSLN-27 | R2-H12-6 | QVQLVESGGGLVQPGGSLRLSCAASGSLSSINTMAWYRQ APGKQRELVAVISSSGSTNYADSVKGRFTISRDNAKTTVY LQLNRLKPEDTAAYYCAAGKGSTWYNGAYKYWGQGTQ VTVSS (SEQ ID NO: 149) |
| Anti-MSLN-28 | R3-E12-2 | QVQLVESGGGLVQAGGSLRLSCAASERTYSRYAMAWFR QAPGKEREFVAAISWSGTAYRDSVKGRFTISGDNAKNTVY LQMNSLNVEDTAVYYCAYGYYSGAANYRDLASSTYRYW GQGTQVTVSS (SEQ ID NO: 150) |
| Anti-MSLN-29 | R2-H12-1 | QVQLVESGGGLVQPGGSLRLSCEASGRTFSSVSMGWFRQ APGKERVIVAAADWSGTTYYTGSLKGRFTISRDNAKNMV YLQMNSLKPEDTAVYYCAASDPRRSAYKYWGQGTQVTV SS (SEQ ID NO: 151) |

TABLE 9-continued

| sdAb name | | VHH Sequences (SEQ ID NO) |
|---|---|---|
| Anti-MSLN-30 | R2-H12-4 | QVQLVESGGGLVQAGGSLRLSCAASGRTFGSYTMGWFRQ APGQEREFVASISRSGGSTYYTDSVKGRFTISRDNAKNTVY LQMNSLKPEDTAVYYCAASNTGGRASASYKYWGQGTQV TVSS (SEQ ID NO: 152) |
| Anti-MSLN-31 | R4-A7-2 | QVQLVESGGGLVQAGGSLRLSCAASGGTFIRYAMAWFRQ APGKERVFVASISQTGGSTDYSDSVKERFTISRDNAKNTM YLQMNSLKPEDTAVYYCAVSTVQSKRMLMYGYWGQGT QVTVSS (SEQ ID NO: 153) |
| Anti-MSLN-32 | p-P3A12 | QVRLEQSGGGLVQAGGSLRLACAASGRTARSYNIGWFRQ APGKEREFVAAIISSPRGTYYSDSVRGRFTISGNSAENTVFL QMNNLKPEDTAVYHCAATTSSTYYSDKTYYAYWGQGTQ VTVSS (SEQ ID NO: 154) |
| Anti-MSLN-33 | p-P3D4 | QVRLVESGGGLVQPGGSLRLACAASGRILADTPMAWYRQ APGKQRELVAAITSGGTTNYAGSVKGRFTISRDNAKNTVY LQMNSLKPEDTAVYYCAANAEGSGSRYWGQGTQVTVSS (SEQ ID NO: 155) |
| Anti-MSLN-34 | p-P3B4 | QVQLVESGGGLVQPGGSLRLACAASGRILADTPMAWYRQ APGKQRELVAAITSGGTTNYAGSVKGRFTISRDNAKNTVY LQMNSLKPEDTAVYYCKVMYHAGSWGQGTQVTVSS (SEQ ID NO: 156) |

TABLE 10

| Sequence | sdAb Name |
|---|---|
| [CDR1]GGTASSYT (SEQ ID NO: 12)<br>[CDR2]ILWSGNTT (SEQ ID NO: 13)<br>[CDR3]ARGGWGTTAEVSNYAY (SEQ ID NO: 14) | Anti-MSLN-1 |
| [CDR1]GRTFSGS (SEQ ID NO: 15)<br>[CDR2]FNWDGSS (SEQ ID NO: 16)<br>[CDR3]AGYYHTGGPLLRDNEYRY (SEQ ID NO: 17) | Anti-MSLN-2 |
| [CDR1]GSISSIRH (SEQ ID NO: 18)<br>[CDR2]VSNDGSA (SEQ ID NO: 19)<br>[CDR3]NADTWGWPGADY (SEQ ID NO: 20) | Anti-MSLN-3 |
| [CDR1]GLTFSSRA (SEQ ID NO: 21)<br>[CDR2]IIHSGDYT (SEQ ID NO: 22)<br>[CDR3]AADSVNKRGASSYYVRTTEYDY (SEQ ID NO: 23) | Anti-MSLN-4 |
| [CDR1]GLTFTSHT (SEQ ID NO: 24)<br>[CDR2]ISWSGGNT (SEQ ID NO: 25)<br>[CDR3]AADRSSFRSYGGSSRVKVEGEYNY (SEQ ID NO: 26) | Anti-MSLN-5 |
| [CDR1]GRTLESYV (SEQ ID NO: 27)<br>[CDR2]INWSSGRL (SEQ ID NO: 28)<br>[CDR3]AAGRY (SEQ ID NO: 29) | Anti-MSLN-6 |
| [CDR1]GRALSSYA (SEQ ID NO: 30)<br>[CDR2]ITWNGGRT (SEQ ID NO: 31)<br>[CDR3]AADPRGDVYHRDKYNI (SEQ ID NO: 32) | Anti-MSLN-7 |
| [CDR1]GRAFSGYT (SEQ ID NO: 33)<br>[CDR2]MTWSGDRT (SEQ ID NO: 34)<br>[CDR3]ATKLGTYYNSHDLRRPDY (SEQ ID NO: 35) | Anti-MSLN-8 |
| [CDR1]GITFPVNA (SEQ ID NO: 36)<br>[CDR2]ISAGGTT (SEQ ID NO: 37)<br>[CDR3]YLQRRIGMLRDY (SEQ ID NO: 38) | Anti-MSLN-9 |
| [CDR1]GFTFDNKQ (SEQ ID NO: 39)<br>[CDR2]ISISDGAT (SEQ ID NO: 40)<br>[CDR3]ATNPTQIMIGTMRCDLESK (SEQ ID NO: 41) | Anti-MSLN-10 |
| [CDR1]GRTNSTVA (SEQ ID NO: 42)<br>[CDR2]IVWSNGYS (SEQ ID NO: 43)<br>[CDR3]ALDIRDSEITVQQKY (SEQ ID NO: 44) | Anti-MSLN-11 |

TABLE 10-continued

| Sequence | sdAb Name |
|---|---|
| [CDR1]GPTYTTET (SEQ ID NO: 45)<br>[CDR2]IRWRGAHT (SEQ ID NO: 46)<br>[CDR3]AASRSFDYPRREDEYRY (SEQ ID NO: 47) | Anti-MSLN-12 |
| [CDR1]GRTFSPYT (SEQ ID NO: 48)<br>[CDR2]ITWKSGST (SEQ ID NO: 49)<br>[CDR3]ASTSFAYGLTNSNKYNY (SEQ ID NO: 50) | Anti-MSLN-13 |
| [CDR1]GRSFSTYR (SEQ ID NO: 51)<br>[CDR2]ITASGSWT (SEQ ID NO: 52)<br>[CDR3]AAAEILTAITTSSDYDY (SEQ ID NO: 53) | Anti-MSLN-14 |
| [CDR1]GRMFSSYA (SEQ ID NO: 54)<br>[CDR2]ISYNGGAT (SEQ ID NO: 55)<br>[CDR3]AARGGHWYSIHDPSNFRA (SEQ ID NO: 56) | Anti-MSLN-15 |
| [CDR1]GRRVRTAA (SEQ ID NO: 57)<br>[CDR2]ITWRGGER (SEQ ID NO: 58)<br>[CDR3]AAGPWYTNHDTSQGYNY (SEQ ID NO: 59) | Anti-MSLN-16 |
| [CDR1]GRTISNYA (SEQ ID NO: 60)<br>[CDR2]INWNGGGI (SEQ ID NO: 61)<br>[CDR3]AAQRAGTWTY (SEQ ID NO: 62) | Anti-MSLN-17 |
| [CDR1]GISDISS (SEQ ID NO: 63)<br>[CDR2]IGSGGNT (SEQ ID NO: 64)<br>[CDR3]NAAQRIGAGPIVL (SEQ ID NO: 65) | Anti-MSLN-18 |
| [CDR1]GHTFSVYA (SEQ ID NO: 75)<br>[CDR2]INWGDGLT (SEQ ID NO: 76)<br>[CDR3]AARQRREGWDY (SEQ ID NO: 77) | Anti-MSLN-19 |
| [CDR1]GRTASSYV (SEQ ID NO: 78)<br>[CDR2]VSRSGVST (SEQ ID NO: 79)<br>[CDR3]AADGKNFSNRWWSRDEYKY (SEQ ID NO: 80) | Anti-MSLN-20 |
| [CDR1]GRTETTYN (SEQ ID NO: 81)<br>[CDR2]ISRGATIT (SEQ ID NO: 82)<br>[CDR3]AASFTNLAVVARDYYY (SEQ ID NO: 83) | Anti-MSLN-21 |
| [CDR1]GRTFSHYA (SEQ ID NO: 84)<br>[CDR2]ITESPDST (SEQ ID NO: 85)<br>[CDR3]AAARSTLRWPFRGQGQYDYDY (SEQ ID NO: 86) | Anti-MSLN-22 |
| [CDR1]GRTWSTYP (SEQ ID NO: 87)<br>[CDR2]IRWTTGST (SEQ ID NO: 88)<br>[CDR3]NAEVRAWYNRRKADY (SEQ ID NO: 89) | Anti-MSLN-23 |
| [CDR1]GRTDSTGI (SEQ ID NO: 90)<br>[CDR2]IRWSNNYA (SEQ ID NO: 91)<br>[CDR3]AAGTGWGFSISDYNY (SEQ ID NO: 92) | Anti-MSLN-24 |
| [CDR1]GRSFNTYA (SEQ ID NO: 93)<br>[CDR2]ITWSGAST (SEQ ID NO: 94)<br>[CDR3]AASSQYGGAASAPTAYLY (SEQ ID NO: 95) | Anti-MSLN-25 |
| [CDR1]GRTISNYA (SEQ ID NO: 96)<br>[CDR2]VSWTGHGT (SEQ ID NO: 97)<br>[CDR3]AADGKNFSNRWWSRDEYKY (SEQ ID NO: 98) | Anti-MSLN-26 |
| [CDR1]GSLSSINT (SEQ ID NO: 99)<br>[CDR2]ISSSGST (SEQ ID NO: 100)<br>[CDR3]AAGKGSTWYNGAYK (SEQ ID NO: 101) | Anti-MSLN-27 |
| [CDR1]ERTYSRYA (SEQ ID NO: 102)<br>[CDR2]ISWSGT (SEQ ID NO: 103)<br>[CDR3]AYGYYSGAANYRDLASSTYRY (SEQ ID NO: 104) | Anti-MSLN-28 |
| [CDR1]GRTFSSVS (SEQ ID NO: 105)<br>[CDR2]ADWSGTT (SEQ ID NO: 106)<br>[CDR3]AASDPRRSAYKY (SEQ ID NO: 107) | Anti-MSLN-29 |
| [CDR1]GRTFGSYT (SEQ ID NO: 108)<br>[CDR2]ISRSGGST (SEQ ID NO: 109)<br>[CDR3]AASNTGGRASASYKY (SEQ ID NO: 110) | Anti-MSLN-30 |

TABLE 10-continued

| Sequence | sdAb Name |
|---|---|
| [CDR1]GGTFIRYA (SEQ ID NO: 111)<br>[CDR2]ISQTGGST (SEQ ID NO: 112)<br>[CDR3]AVSTVQSKRMLMYGY (SEQ ID NO: 113) | Anti-MSLN-31 |
| [CDR1]GRTARSYN (SEQ ID NO: 114)<br>[CDR2]IISSPRGT (SEQ ID NO: 115)<br>[CDR3]AATTSSTYYSDKTYYAY (SEQ ID NO: 116) | Anti-MSLN-32 |
| [CDR1]GRILADTP (SEQ ID NO: 117)<br>[CDR2]ITSGGTT (SEQ ID NO: 118)<br>[CDR3]AANAEGSGSRY (SEQ ID NO: 119) | Anti-MSLN-33 |
| [CDR1]GRILADTP (SEQ ID NO: 120)<br>[CDR2]ITSGGTT (SEQ ID NO: 121)<br>[CDR3]KVMYHAGS (SEQ ID NO: 122) | Anti-MSLN-34 |

Any of the above described sdAbs can be used in the IL-21 fusion protein provided herein.

Example 3: Generation of Humanized Anti-MSLN Single Domain Antibodies

Each llama sequences of the above 34 sdAbs was blasted against IMGT data base to identify the best matched human IGHV3 germ lines. When multiple germ lines have similar homology, the similarity of amino acid at position 52 of FR 2 (in IGMT numbering system) is used to determine which germ line is adopted as the humanization scaffold. The FR1 and FR3 from the chosen germ line are then adopted as "humanized" 1R1 and FR3. For FR2, most of human sequence except position 42 and 52, where the respective llama sequences were retained.

Table 11 below shows the exemplary human FR region sequences for each of the 34 antibodies.

TABLE 11

| sdAb Name (humanized) | Matched Human Germ Line | Human FR1 | Human FR2 | Human FR3 | Human FR4 |
|---|---|---|---|---|---|
| Anti-MSLN-1 | IGHV3-64*04 | QVQLVESGGGLVQPGGSLRLSCSAS (SEQ ID NO: 157) | MHWFRQAPGKGLEFVSA (SEQ ID NO: 158) | YYADSVKGRFTISRDNSKNTLYLQMNSLRAEDTAVYYC (SEQ ID NO: 159) | WGQGTQVTVSS (SEQ ID NO: 160) |
| Anti-MSLN-2 | IGHV3-7*01 | EVQLVESGGGLVQPGGSLRLSCAAS (SEQ ID NO: 161) | MSWFRQAPGKGLELVAN (SEQ ID NO: 162) | YYVDSVKGRFTISRDNAKNSLLYLQMNSLRAEDTAVYYC (SEQ ID NO: 163) | WGQGTQVTVSS (SEQ ID NO: 160) |
| Anti-MSLN-3 | IGHV3-64*04 | QVQLVESGGGLVQPGGSLRLSCSAS (SEQ ID NO: 164) | MHWFRQAPGKGLELVSA (SEQ ID NO: 165) | YYADSVKGRFTISRDNSKNTLYLQMNSLRAEDTAVYYC (SEQ ID NO: 166) | WGQGTQVTVSS (SEQ ID NO: 160) |
| Anti-MSLN-4 | IGHV3-64*04 | QVQLVESGGGLVQPGGSLRLSCSAS (SEQ ID NO: 167) | MHWFRQAPGKGLEFVSA (SEQ ID NO: 168) | YYADSVKGRFTISRDNSKNTLYLQMNSLRAEDTAVYYC (SEQ ID NO: 169) | WGQGTQVTVSS (SEQ ID NO: 160) |
| Anti-MSLN-5 | IGHV3-64*04 | QVQLVESGGGLVQPGGSLRLSCSAS (SEQ ID NO: 170) | MHWFRQAPGKGLEFVSA (SEQ ID NO: 171) | YYADSVKGRFTISRDNSKNTLYLQMNSLRAEDTAVYYC (SEQ ID NO: 172) | WGQGTQVTVSS (SEQ ID NO: 160) |
| Anti-MSLN-6 | IGHV3-23*01 | EVQLVESGGGLVQPGGSLRLSCAAS (SEQ ID NO: 173) | MSWFRQAPGKGLEAVSA (SEQ ID NO: 174) | YYADSVKGRFTISRDNSKNTLYLQMNSLRAEDTAVYYC (SEQ ID NO: 175) | WGQGTQVTVSS (SEQ ID NO: 160) |
| Anti-MSLN-7 | IGHV3-64*04 | QVQLVESGGGLVQPGGSLRLSCSAS (SEQ ID NO: 176) | MHWFRQAPGKGLEFVSA (SEQ ID NO: 177) | YYADSVKGRFTISRDNSKNTLYLQMNSLRAEDTAVYYC (SEQ ID NO: 178) | WGQGTQVTVSS (SEQ ID NO: 160) |

TABLE 11-continued

| sdAb Name (humanized) | Matched Human Germ Line | Human FR1 | Human FR2 | Human FR3 | Human FR4 |
|---|---|---|---|---|---|
| Anti-MSLN-8 | IGHV3-64*04 | QVQLVESGGGLVQPGGSLRLSCSAS (SEQ ID NO: 179) | MHWFRQAPGKGLEFVSA (SEQ ID NO: 180) | YYADSVKGRFTISRDNSKNTLYLQMNSLRAEDTAVYYC (SEQ ID NO: 181) | WGQGTQVTVSS (SEQ ID NO: 160) |
| Anti-MSLN-9 | IGHV3-23*04 | EVQLVESGGGLVQPGGSLRLSCAAS (SEQ ID NO: 182) | MSWFRQAPGKGLELVSA (SEQ ID NO: 183) | YYADSVKGRFTISRDNSKNTLYLQMNSLRAEDTAVYYC (SEQ ID NO: 184) | WGQGTQVTVSS (SEQ ID NO: 160) |
| Anti-MSLN-10 | IGHV3-23*04 | EVQLVESGGGLVQPGGSLRLSCAAS (SEQ ID NO: 185) | MSWFRQAPGKGLEQVSA (SEQ ID NO: 186) | YYADSVKGRFTISRDNSKNTLYLQMNSLRAEDTAVYYC (SEQ ID NO: 187) | WGQGTQVTVSS (SEQ ID NO: 160) |
| Anti-MSLN-11 | IGHV3-23*04 | EVQLVESGGGLVQPGGSLRLSCAAS (SEQ ID NO: 188) | MSWFRQAPGKGLEFVSA (SEQ ID NO: 189) | YYADSVKGRFTISRDNSKNTLYLQMNSLRAEDTAVYYC (SEQ ID NO: 190) | WGQGTQVTVSS (SEQ ID NO: 160) |
| Anti-MSLN-12 | IGHV3-64*04 | QVQLVESGGGLVQPGGSLRLSCSAS (SEQ ID NO: 191) | MHWFRQAPGKGLEFVSA (SEQ ID NO: 192) | YYADSVKGRFTISRDNSKNTLYLQMNSLRAEDTAVYYC (SEQ ID NO: 193) | WGQGTQVTVSS (SEQ ID NO: 160) |
| Anti-MSLN-13 | IGHV3-64*04 | QVQLVESGGGLVQPGGSLRLSCSAS (SEQ ID NO: 194) | MHWFRQAPGKGLEFVSA (SEQ ID NO: 195) | YYADSVKGRFTISRDNSKNTLYLQMNSLRAEDTAVYYC (SEQ ID NO: 196) | WGQGTQVTVSS (SEQ ID NO: 160) |
| Anti-MSLN-14 | IGHV3-64*04 | QVQLVESGGGLVQPGGSLRLSCSAS (SEQ ID NO: 197) | MHWFRQAPGKGLEFVSA (SEQ ID NO: 198) | YYADSVKGRFTISRDNSKNTLYLQMNSLRAEDTAVYYC (SEQ ID NO: 199) | WGQGTQVTVSS (SEQ ID NO: 160) |
| Anti-MSLN-15 | IGHV3-64*04 | QVQLVESGGGLVQPGGSLRLSCSAS (SEQ ID NO: 200) | MHWFRQAPGKGLEYVSA (SEQ ID NO: 201) | YYADSVKGRFTISRDNSKNTLYLQMNSLRAEDTAVYYC (SEQ ID NO: 202) | WGQGTQVTVSS (SEQ ID NO: 160) |
| Anti-MSLN-16 | IGHV3-64*04 | QVQLVESGGGLVQPGGSLRLSCSAS (SEQ ID NO: 203) | MHWFRQAPGKGLEFVSA (SEQ ID NO: 204) | YYADSVKGRFTISRDNSKNTLYLQMNSLRAEDTAVYYC (SEQ ID NO: 205) | WGQGTQVTVSS (SEQ ID NO: 160) |
| Anti-MSLN-17 | IGHV3-64*04 | QVQLVESGGGLVQPGGSLRLSCSAS (SEQ ID NO: 206) | MHWFRQAPGKGLEFVSA (SEQ ID NO: 207) | YYADSVKGRFTISRDNSKNTLYLQMNSLRAEDTAVYYC (SEQ ID NO: 208) | WGQGTQVTVSS (SEQ ID NO: 160) |
| Anti-MSLN-18 | IGHV3-66*01 | EVQLVESGGGLVQPGGSLRLSCAAS (SEQ ID NO: 209) | MSWFRQAPGKGLELVSV (SEQ ID NO: 210) | YYADSVKGRFTISRDNSKNTLLYLQMNSLRAEDTAVYYC (SEQ ID NO: 211) | WGQGTQVTVSS (SEQ ID NO: 160) |
| Anti-MSLN-19 | IGHV3-64*04 | QVQLVESGGGLVQPGGSLRLSCSAS (SEQ ID NO: 212) | MHWFRQAPGKGLEFVSA (SEQ ID NO: 213) | YYADSVKGRFTISRDNSKNTLYLQMNSLRAEDTAVYYC (SEQ ID NO: 214) | WGQGTQVTVSS (SEQ ID NO: 160) |

TABLE 11-continued

| sdAb Name (humanized) | Matched Human Germ Line | Human FR1 | Human FR2 | Human FR3 | Human FR4 |
|---|---|---|---|---|---|
| Anti-MSLN-20 | IGHV3-64*04 | QVQLVESGGGLVQPGGSLRLSCSAS (SEQ ID NO: 215) | MHWFRQAPGKGLEYVSA (SEQ ID NO: 216) | YYADSVKGRFTISRDNSKNTLYLQMNSLRAEDTAVYYCAR (SEQ ID NO: 217) | WGQGTQVTVSS (SEQ ID NO: 160) |
| Anti-MSLN-21 | IGHV3-64*04 | QVQLVESGGGLVQPGGSLRLSCSAS (SEQ ID NO: 218) | MHWFRQAPGKGLELVSA (SEQ ID NO: 219) | YYADSVKGRFTISRDNSKNTLYLQMNSLRAEDTAVYYC (SEQ ID NO: 220) | WGQGTQVTVSS (SEQ ID NO: 160) |
| Anti-MSLN-22 | IGHV3-64*04 | QVQLVESGGGLVQPGGSLRLSCSAS (SEQ ID NO: 221) | MHWFRQAPGKGLEFVSA (SEQ ID NO: 222) | YYADSVKGRFTISRDNSKNTLYLQMNSLRAEDTAVYYCAR (SEQ ID NO: 223) | WGQGTQVTVSS (SEQ ID NO: 160) |
| Anti-MSLN-23 | IGHV3-64*04 | QVQLVESGGGLVQPGGSLRLSCSAS (SEQ ID NO: 224) | MHWFRQAPGKGLEFVSA (SEQ ID NO: 225) | YYADSVKGRFTISRDNSKNTLYLQMNSLRAEDTAVYYC (SEQ ID NO: 226) | WGQGTQVTVSS (SEQ ID NO: 160) |
| Anti-MSLN-24 | IGVH3-30*02 | QVQLVESGGGVVQPGGSLRLSCAAS (SEQ ID NO: 227) | MHWFRQAPGKGLEFVAF (SEQ ID NO: 228) | YYADSVKGRFTISRDNSKNTLYLQMNSLRAEDTAVYYC (SEQ ID NO: 229) | WGQGTQVTVSS (SEQ ID NO: 160) |
| Anti-MSLN-25 | IGHV3-64*04 | QVQLVESGGGLVQPGGSLRLSCSAS (SEQ ID NO: 230) | MHWFRQAPGKGLEFVSA (SEQ ID NO: 231) | YYADSVKGRFTISRDNSKNTLYLQMNSLRAEDTAVYYC (SEQ ID NO: 232) | WGQGTQVTVSS (SEQ ID NO: 160) |
| Anti-MSLN-26 | IGHV3-64*04 | QVQLVESGGGLVQPGGSLRLSCSAS (SEQ ID NO: 233) | MHWFRQAPGKGLEFVSA (SEQ ID NO: 234) | YYADSVKGRFTISRDNSKNTLYLQMNSLRAEDTAVYYC (SEQ ID NO: 235) | WGQGTQVTVSS (SEQ ID NO: 160) |
| Anti-MSLN-27 | IGVH3-66*01 | EVQLVESGGGLVQPGGSLRLSCAAS (SEQ ID NO: 236) | MSWFRQAPGKGLELVSV (SEQ ID NO: 237) | YYADSVKGRFTISRDNSKNTLLYLQMNSLRAEDTAVYYC (SEQ ID NO: 238) | WGQGTQVTVSS (SEQ ID NO: 160) |
| Anti-MSLN-28 | IGHV3-64*04 | QVQLVESGGGLVQPGGSLRLSCSAS (SEQ ID NO: 239) | MHWFRQAPGKGLEFVSA (SEQ ID NO: 240) | YYADSVKGRFTISRDNSKNTLYLQMNSLRAEDTAVYYC (SEQ ID NO: 241) | WGQGTQVTVSS (SEQ ID NO: 160) |
| Anti-MSLN-29 | IGHV3-64*04 | QVQLVESGGGLVQPGGSLRLSCSAS (SEQ ID NO: 242) | MHWFRQAPGKGLEIVSA (SEQ ID NO: 243) | YYADSVKGRFTISRDNSKNTLYLQMNSLRAEDTAVYYC (SEQ ID NO: 244) | WGQGTQVTVSS (SEQ ID NO: 160) |
| Anti-MSLN-30 | IGHV3-64*04 | QVQLVESGGGLVQPGGSLRLSCSAS (SEQ ID NO: 245) | MHWFRQAPGKGLEFVSA (SEQ ID NO: 246) | YYADSVKGRFTISRDNSKNTLYLQMNSLRAEDTAVYYC (SEQ ID NO: 247) | WGQGTQVTVSS (SEQ ID NO: 160) |
| Anti-MSLN-31 | IGVH3-74*01 | EVQLVESGGGLVQPGGSLRLSCAAS (SEQ ID NO: 248) | MHWFRQAPGKGLVFVSR (SEQ ID NO: 249) | SYADSVKGRFTISRDNAKNTLYLQMNSLRAEDTAVYYCA (SEQ ID NO: 250) | WGQGTQVTVSS (SEQ ID NO: 160) |

TABLE 11-continued

| sdAb Name (human-ized) | Matched Human Germ Line | Human FR1 | Human FR2 | Human FR3 | Human FR4 |
|---|---|---|---|---|---|
| Anti-MSLN-32 | IGHV3-64*04 | QVQLVESG GGLVQPGG SLRLSCSAS (SEQ ID NO: 251) | MHWFRQAPGK GLEFVSA (SEQ ID NO: 252) | YYADSVKGRFTI SRDNSKNTLYLQ MNSLRAEDTAV YYCAR (SEQ ID NO: 253) | WGQGTQVT VSS (SEQ ID NO: 160) |
| Anti-MSLN-33 | IGHV3-64*04 | QVQLVESG GGLVQPGG SLRLSCSAS (SEQ ID NO: 254) | MHWFRQAPGK GLELVSA (SEQ ID NO: 255) | YYADSVKGRFTI SRDNSKNTLYLQ MNSLRAEDTAV YYC (SEQ ID NO: 256) | WGQGTQVT VSS (SEQ ID NO: 160) |
| Anti-MSLN-34 | IGHV3-64*04 | QVQLVESG GGLVQPGG SLRLSCSAS (SEQ ID NO: 257) | MHWFRQAPGK GLELVSA (SEQ ID NO: 258) | YYADSVKGRFTI SRDNSKNTLYLQ MNSLRAEDTAV YYC (SEQ ID NO: 259) | WGQGTQVT VSS (SEQ ID NO: 160) |

Any of these humanized anti-MSLN sdAbs can be used in any of the anti-mesothelin constructs (such as any of the IL-21 fusion proteins) provided herein. Table 12 lists sequences of exemplary anti-MSLN constructs.

TABLE 12

| Exemplary anti-MSLN construct | | Sequences (SEQ ID NO) |
|---|---|---|
| Anti-MSLN-35 | R2G12 v1.1 | QVQLVESGGGLVQPGGSLRLSCAASGITFPVNAYGWYRQ APGKQRDLVAIISAGGTTNYADSVKGRFTISRDNSKNTLY LQMNSLRAEDTAVYYCYLQRRIGMLRDYWGQGTQVTVS S (SEQ ID NO: 285) |
| Anti-MSLN-36 | R2G12 v1.2 | QVQLVESGGGLVQAGGSLRLSCAASGITFPVNAYGWYRQ APGKGLELVAIISAGGTTNYADSVKGRFAISKDNVNNTVY LQMNSLTSEDTGVYYCYLQRRIGMLRDYWGQGTQVTVSS (SEQ ID NO: 286) |
| Anti-MSLN-37 | R2G12 v1.3 | QVQLVESGGGLVQPGGSLRLSCAASGITFPVNAYGWYRQ APGKGLELVAIISAGGTTNYADSVKGRFAISKDNVNNTVY LQMNSLTSEDTGVYYCYLQRRIGMLRDYWGQGTQVTVSS (SEQ ID NO: 287) |
| Anti-MSLN-38 | R3D5 v1.1 | QVQLVESGGGLVQPGGSLRLSCAASGSISSIRHMRWYRQA PGKQRELVATVSNDGSAYYAGSVKGRFTISRDNSKNTLLY LQMNSLRAEDTAVYICNADTWGWPGADYWGQGTQVTV SS (SEQ ID NO: 288) |
| Anti-MSLN-39 | R3D5 v1.2 | QVQLVESGGGLVQAGGSLRLSCAASGSISSIRHMRWYRQ APGKGLELVATVSNDGSAYYLGSVKGRFTISRTNAKNTLL YLQMNSLKPEDSALYICNADTWGWPGADYWGQGTQVTV SS (SEQ ID NO: 289) |
| Anti-MSLN-40 | R3D5 v1.3 | QVQLVESGGGLVQPGGSLRLSCAASGSISSIRHMRWYRQA PGKGLELVATVSNDGSAYYLGSVKGRFTISRTNAKNTLLY LQMNSLKPEDSALYICNADTWGWPGADYWGQGTQVTVS S (SEQ ID NO: 290) |
| Anti-MSLN-41 | R3C7 v1.1 | QVQLVESGGGLVQPGGSLRLSCVVSGRTLESYVMAWFRQ APGKEREAVASINWSSGRLIYADFVKGRFTISRDNSKNTLY LQMNSLRPEDTAVYYCAAGRYWGQGTQVTVSS (SEQ ID NO: 291) |
| Anti-MSLN-42 | R3C7 v1.2 | QVQLVESGGGLVQPGGSLRLSCVVSGRTLESYVMAWFRQ APGKGLEAVASINWSSGRLIYADFVKGRFTISRDNSKNTL YLQMNSLRPEDTAVYYCAAGRYWGQGTQVTVSS (SEQ ID NO: 292) |
| Anti-MSLN-43 | R3C7 v1.3 | QVQLVESGGGLVQPGGSLRLSCAASGRTLESYVMAWFRQ APGKGLEAVASINWSSGRLIYADFVKGRFTISRDNSKNTL YLQMNSLRPEDTAVYYCAAGRYWGQGTQVTVSS (SEQ ID NO: 293) |

TABLE 12-continued

| Exemplary anti-MSLN construct | | Sequences (SEQ ID NO) |
|---|---|---|
| Anti-MSLN-44 | R3C7 v1.4 | QVQLVESGGGLVQPGGSLRLSCAASGRTLESYVMAWFRQ APGKGLEAVASINWSSGRLIYADSVKGRFTISRDNSKNTL YLQMNSLRAEDTAVYYCAAGRYWGQGTQVTVSS (SEQ ID NO: 294) |
| Anti-MSLN-45 | R3C7 v1.5 | QVQLVESGGGLVQPGGSLRLSCAASGRTLESYVMAWFRQ APGKEREAVASINWSSGRLIYADSVKGRFTISRDNSKNTLY LQMNSLRAEDTAVYYCAAGRYWGQGTQVTVSS (SEQ ID NO: 295) |
| Anti-MSLN-46 | R2P2C1 v1.1 | QVQLVESGGGLVQPGGSLRLSCAASGRSFNNNAMAWFRQ TPGKEREFVAAITWVGSGTYYADSVKGRFTISRDNSKNTL YLQMNSLRAEDTAVYYCAARQYPFSIIGYNSKDAWNYW GQGTRVTVSS (SEQ ID NO: 296) |
| Anti-MSLN-47 | R2P2C1 v1.2 | QVQLVESGGGLVQPGGSLRLSCAASGRSFNNNAMAWFRQ TPGKGLEFVAAITWVGSGTYYADSVKGRFTISRDNSKNTL YLQMNSLRAEDTAVYYCAARQYPFSIIGYNSKDAWNYW GQGTRVTVSS (SEQ ID NO: 297) |
| Anti-MSLN-48 | R2P2C1 v1.3 | QVQLVESGGGLVQPGGSLRLSCAASGRSFNNNAMSWFRQ APGKGLEFVSAITWVGSGTYYADSVKGRFTISRDNSKNTL YLQMNSLRAEDTAVYYCAARQYPFSIIGYNSKDAWNYW GQGTRVTVSS (SEQ ID NO: 298) |
| Anti-MSLN-49 | R2P4G9 v1.1 | QVQLVESGGGLVQPGGSLRLSCAASTSIFSIGTMRWYRQA PGKQREYIAGMTSDGTTYYADSVKGRFTISRDNSKNTLYL QMNSLRAEDTAVYYCNTVAHFQNYWGQGTQVTVSS (SEQ ID NO: 299) |
| Anti-MSLN-50 | R2P4G9 v1.2 | QVQLVESGGGLVQPGGSLRLSCAASTSIFSIGTMRWYRQA PGKGLEYIAGMTSDGTTYYADSVKGRFTISRDNSKNTLYL QMNSLRAEDTAVYYCNTVAHFQNYWGQGTQVTVSS (SEQ ID NO: 300) |
| Anti-MSLN-51 | R2P4G9 v1.3 | QVQLVESGGGLVQPGGSLRLSCAASTSIFSIGTMHWYRQA PGKGLEYVAGMTSDGTTYYADSVKGRFTISRDNSKNTLY LQMNSLRAEDTAVYYCNTVAHFQNYWGQGTQVTVSS (SEQ ID NO: 301) |
| Anti-MSLN-52 | R2G12-IgG1 P197 | QVQLVESGGGLVQPGGSLRLSCAASGITFPVNAYGWYRQ APGKQRDLVAIISAGGTTNYADSVKGRFTISRDNSKNTLY LQMNSLRAEDTAVYYCYLQRRIGMLRDYWGQGTQVTVS SDKTHTCPPCPAPELLGGPSVFLFPPKPKDTLMISRTPEVTC VVVDVSHEDPEVKFNWYVDGVEVHNAKTKPREEQYNST YRVVSVLTVLHQDWLNGKEYKCKVSNKALPAPIEKTISK AKGQPREPQVYTLPPSREEMTKNQVSLTCLVKGFYPSDIA VEWESNGQPENNYKTTPPVLDSDGSFFLYSKLTVDKSRW QQGNVFSCSVMHEALHNHYTQKSLSLSPGK (SEQ ID NO: 302) |
| Anti-MSLN-53 | R3C7-IgG1 P303 | QVQLVESGGGLVQPGGSLRLSCAASGRTLESYVMAWFRQ APGKEREAVASINWSSGRLIYADSVKGRFTISRDNSKNTL YLQMNSLRAEDTAVYYCAAGRYWGQGTQVTVSSDKTHTC PPCPAPELLGGPSVFLFPPKPKDTLMISRTPEVTCVVVDVS HEDPEVKFNWYVDGVEVHNAKTKPREEQYNSTYRVVSV LTVLHQDWLNGKEYKCKVSNKALPAPIEKTISKAKGQPRE PQVYTLPPSREEMTKNQVSLTCLVKGFYPSDIAVEWESNG QPENNYKTTPPVLDSDGSFFLYSKLTVDKSRWQQGNVFSC SVMHEALHNHYTQKSLSLSPGK (SEQ ID NO: 303) |
| Anti-MSLN-54 | R3D5 IgG1 P200 | QVQLVESGGGLVQPGGSLRLSCAASGSISSIRHMRWYRQA PGKQRELVATVSNDGSAYYAGSVKGRFTISRDNSKNTLLY LQMNSLRAEDTAVYICNADTWGWPGADYWGQGTQVTV SSDKTHTCPPCPAPELLGGPSVFLFPPKPKDTLMISRTPEVT CVVVDVSHEDPEVKFNWYVDGVEVHNAKTKPREEQYNS TYRVVSVLTVLHQDWLNGKEYKCKVSNKALPAPIEKTISK AKGQPREPQVYTLPPSREEMTKNQVSLTCLVKGFYPSDIA VEWESNGQPENNYKTTPPVLDSDGSFFLYSKLTVDKSRW QQGNVFSCSVMHEALHNHYTQKSLSLSPGK (SEQ ID NO: 304) |
| Anti-MSLN-55 | R2P2C1-IgG1 P215 | QVQLVESGGGLVQPGGSLRLSCAASGRSFNNNAMAWFRQ TPGKEREFVAAITWVGSGTYYADSVKGRFTISRDNSKNTL YLQMNSLRAEDTAVYYCAARQYPFSIIGYNSKDAWNYW GQGTRVTVSSDKTHTCPPCPAPELLGGPSVFLFPPKPKDTL MISRTPEVTCVVVDVSHEDPEVKFNWYVDGVEVHNAKTK |

TABLE 12-continued

| Exemplary anti-MSLN construct | Sequences (SEQ ID NO) |
|---|---|
| | PREEQYNSTYRVVSVLTVLHQDWLNGKEYKCKVSNKALP<br>APIEKTISKAKGQPREPQVYTLPPSREEMTKNQVSLTCLVK<br>GFYPSDIAVEWESNGQPENNYKTTPPVLDSDGSFFLYSKLT<br>VDKSRWQQGNVFSCSVMHEALHNHYTQKSLSLSPGK<br>(SEQ ID NO: 305) |
| Anti-MSLN-56 | R2P4G9-IgG1<br>P218 | QVQLVESGGGLVQPGGSLRLSCAASTSIFSIGTMRWYRQA<br>PGKQREYIAGMTSDGTTYYADSVKGRFTISRDNSKNTLYL<br>QMNSLRAEDTAVYYCNTVAHFQNYWGQGTQVTVSSDKT<br>HTCPPCPAPELLGGPSVFLFPPKPKDTLMISRTPEVTCVVV<br>DVSHEDPEVKFNWYVDGVEVHNAKTKPREEQYNSTYRV<br>VSVLTVLHQDWLNGKEYKCKVSNKALPAPIEKTISKAKG<br>QPREPQVYTLPPSREEMTKNQVSLTCLVKGFYPSDIAVEW<br>ESNGQPENNYKTTPPVLDSDGSFFLYSKLTVDKSRWQQG<br>NVFSCSVMHEALHNHYTQKSLSLSPGK (SEQ ID NO: 306) |
| Anti-MSLN-57 | IL-21-anti-albumin-anti-MSLN<br>P375 | QGQDRHMIRMRQLIDIVDQLKNYVNDLVPEFLPAPEDVET<br>NCEWSAFSCFQKAQLKSANTGNNERIINVSIKKLKRKPPST<br>NAGRRQKHRLTCPSCDSYEKKPPKEFLERFKSLLQKMIHQ<br>HLSSRTHGSEDSGSGGSGGSGGSGQVQLVESGGGLVQPG<br>GSLRLSCAASGSTWSINTLAWYRQAPGKQRDLVARISSGG<br>STHYADSVKGRFTVSRDNAENTLVLQMNSLKPEDTAVYY<br>CYAQSTWYPPSWGQGTQVTVSSGGGSGGGSGGGSGGGS<br>QVQLVESGGGLVQPGGSLRLSCAASGRTLESYVMAWFRQ<br>APGKEREAVASINWSSGRLIYADSVKGRFTISRDNSKNTLY<br>LQMNSLRAEDTAVYYCAAGRYWGQGTQVTVSS (SEQ ID<br>NO: 325) |
| Anti-MSLN-58 | anti-MSLN-anti-albumin-IL-15Ra-IL-15<br>P669 | QVQLVESGGGLVQPGGSLRLSCAASGITFPVNAYGWYRQ<br>APGKQRDLVAIISAGGTTNYADSVKGRFTISRDNSKNTLY<br>LQMNSLRAEDTAVYYCYLQRRIGMLRDYWGQGTQVTVS<br>SGGGGSGGGSGGGGSGGGSQVQLVESGGGLVQPGGSLRLSC<br>AASGSTWSINTLAWYRQAPGKQRDLVARISSGGSTHYAD<br>SVKGRFTVSRDNAENTLVLQMNSLKPEDTAVYYCYAQST<br>WYPPSWGQGTQVTVSSGGGGSGGGGSGGGGSGGGGSITC<br>PPPMSVEHADIWVKSYSLYSRERYICNSGFKRKAGTSSLTE<br>CVLNKATNVAHWTTPSLKCIRDPALVHQRPAPPGGSGGG<br>GSGGGSGGGGSLQNWVNVISDLKKIEDLIQSMHIDATLYT<br>ESDVHPSCKVTAMKCFLLELQVISLESGDASIHDTVENLIIL<br>ANNSLSSNGNVTESGCKECEELEEKNIKEFLQSFVHIVQMF<br>INTS (SEQ ID NO: 326) |
| Anti-MSLN-59 | hIL-21-R3C7-IgG1 (KIH)<br>P286 | QGQDRHMIRMRQLIDIVDQLKNYVNDLVPEFLPAPEDVET<br>NCEWSAFSCFQKAQLKSANTGNNERIINVSIKKLKRKPPST<br>NAGRRQKHRLTCPSCDSYEKKPPKEFLERFKSLLQKMIHQ<br>HLSSRTHGSEDSGSGGSGGSGGSGQVQLVESGGGLVEAG<br>DSLRLSCVVSGRTLESYVMAWFRQAPGKEREAVASINWS<br>SGRLIYADFVKGRFTISRDYEKNTIYLSMNNLKPEDTAVY<br>YCAAGRYWGQGTQVTVSSDKTHTCPPCPAPELLGGPSVF<br>LFPPKPKDTLMISRTPEVTCVVVDVSHEDPEVKFNWYVDG<br>VEVHNAKTKPREEQYNSTYRVVSVLTVLHQDWLNGKEY<br>KCKVSNKALPAPIEKTISKAKGQPREPQVYTLPPCREEMTK<br>NQVSLWCLVKGFYPSDIAVEWESNGQPENNYKTTPPVLD<br>SDGSFFLYSKLTVDKSRWQQGNVFSCSVMHEALHNHYTQ<br>KSLSLSPGK (SEQ ID NO: 327) |
| Anti-MSLN-60 | R2G12-IgG1 (KIH)<br>P288 | QVQLVESGGGLVQAGGSLRLSCAASGITFPVNAYGWYRQ<br>APGKQRDLVAIISAGGTTNYADSVKGRFTISRDNSKNTLY<br>LQMNSLRAEDTAVYYCYLQRRIGMLRDYWGQGTQVTVS<br>SDKTHTCPPCPAPELLGGPSVFLFPPKPKDTLMISRTPEVTC<br>VVVDVSHEDPEVKFNWYVDGVEVHNAKTKPREEQYNST<br>YRVVSVLTVLHQDWLNGKEYKCKVSNKALPAPIEKTISK<br>AKGQPREPQVCTLPPSREEMTKNQVSLSCAVKGFYPSDIA<br>VEWESNGQPENNYKTTPPVLDSDGSFFLVSKLTVDKSRW<br>QQGNVFSCSVMHEALHNHYTQKSLSLSPGK (SEQ ID NO: 328) |
| Anti-MSLN-61 | hIL-21-anti-HSA-R3C7-IgG1 (KIH)<br>P431 | QGQDRHMIRMRQLIDIVDQLKNYVNDLVPEFLPAPEDVET<br>NCEWSAFSCFQKAQLKSANTGNNERIINVSIKKLKRKPPST<br>NAGRRQKHRLTCPSCDSYEKKPPKEFLERFKSLLQKMIHQ<br>HLSSRTHGSEDSGSGGSGGSGGSGQVQLVESGGGLVQPG<br>GSLRLSCAASGSTWSINTLAWYRQAPGKQRDLVARISSGG<br>STHYADSVKGRFTVSRDNAENTLVLQMNSLKPEDTAVYY<br>CYAQSTWYPPSWGQGTQVTVSSGGGSGGGSGGGSGGGS<br>GGGGSGRSAGGGGSQVQLVESGGGLVQPGGSLRLSCAAS<br>GRTLESYVMAWFRQAPGKEREAVASINWSSGRLIYADSV<br>KGRFTISRDNSKNTLYLQMNSLRAEDTAVYYCAAGRYWG |

TABLE 12-continued

| Exemplary anti-MSLN construct | | Sequences (SEQ ID NO) |
|---|---|---|
| | | QGTQVTVSSDKTHTCPPCPAPELLGGPSVFLFPPKPKDTLM<br>ISRTPEVTCVVVDVSHEDPEVKFNWYVDGVEVHNAKTKP<br>REEQYNSTYRVVSVLTVLHQDWLNGKEYKCKVSNKALP<br>APIEKTISKAKGQPREPQVYTLPPCREEMTKNQVSLWCLV<br>KGFYPSDIAVEWESNGQPENNYKTTPPVLDSDGSFFLYSK<br>LTVDKSRWQQGNVFSCSVMHEALHNHYTQKSLSLSPGK<br>(SEQ ID NO: 329) |
| Anti_<br>MSLN-62 | R3C7-IgG1<br>(KIH)<br>P435 | QVQLVESGGGLVQPGGSLRLSCAASGRTLESYVMAWFRQ<br>APGKEREAVASINWSSGRLIYADSVKGRFTISRDNSKNTLY<br>LQMNSLRAEDTAVYYCAAGRYWGQGTQVTVSSDKTHTC<br>PPCPAPELLGGPSVFLFPPKPKDTLMISRTPEVTCVVVDVS<br>HEDPEVKFNWYVDGVEVHNAKTKPREEQYNSTYRVVSV<br>LTVLHQDWLNGKEYKCKVSNKALPAPIEKTISKAKGQPRE<br>PQVCTLPPSREEMTKNQVSLSCAVKGFYPSDIAVEWESNG<br>QPENNYKTTPPVLDSDGSFFLVSKLTVDKSRWQQGNVFSC<br>SVMHEALHNHYTQKSLSLSPGK (SEQ ID NO: 330) |
| Anti_<br>MSLN-63 | hIL-21-ABD-<br>R3C7-IgG1<br>(KIH)<br>P545 | QGQDRHMIRMRQLIDIVDQLKNYVNDLVPEFLPAPEDVET<br>NCEWSAFSCFQKAQLKSANTGNNERIINVSIKKLKRKPPST<br>NAGRRQKHRLTCPSCDSYEKKPPKEFLERFKSLLQKMIHQ<br>HLSSRTHGSEDSGSGGSGGSGGSGLAEAKVLANRELDKY<br>GVSDYAKNLINNAKTVEGVKALIDEILAALPGGGGSPVGL<br>IGGGGGSQVQLVESGGGLVQPGGSLRLSCAASGRTLESYV<br>MAWFRQAPGKEREAVASINWSSGRLIYADSVKGRFTISRD<br>NSKNTLYLQMNSLRAEDTAVYYCAAGRYWGQGTQVTVS<br>SDKTHTCPPCPAPELLGGPSVFLFPPKPKDTLMISRTPEVTC<br>VVVDVSHEDPEVKFNWYVDGVEVHNAKTKPREEQYNST<br>YRVVSVLTVLHQDWLNGKEYKCKVSNKALPAPIEKTISK<br>AKGQPREPQVYTLPPCREEMTKNQVSLWCLVKGFYPSDIA<br>VEWESNGQPENNYKTTPPVLDSDGSFPLYSKLTVDKSRW<br>QQGNVFSCSVMHEALHNHYTQKSLSLSPGK (SEQ ID NO: 331) |

Example 4: Molecular Cloning of the IL-21 Fusion Protein

Oligonucleotide Synthesis

An exemplary oligonucleotide synthesis procedure is described below. cDNA sequences encoding human IL-21 full length (SEQ ID NO: 1), human IL-21 truncated (SEQ ID NO: 2), G148-ABD-wt (SEQ ID NO: 3), low immunogenicity G148-ABD variants (SEQ ID NO: 4-11), humanized sdAb targeting HSA, and humanized sdAb targeting MSLN (e.g., those listed in Table 12) were obtained by gene synthesis using GeneArt Gene Synthesis (ThermoFisher Scientific) or gBlocks Gene Fragments (Integrated DNA Technologies) with NgoMIV restriction enzyme site and Kozak sequence added to 5' and SalI restriction enzyme site added to 3'. The codon usage of these genes was optimized for expression in Chinese hamster ovary (CHO) cells. Synthesized oligonucleotides were inserted into UCOE expression vector CET1019-AS-Puro (CS221284, Millipore Sigma) by NgoMIV/SalI digest-ligation method.

Construction of IL-21 Fusion Protein Expression Vector

Figure 2:
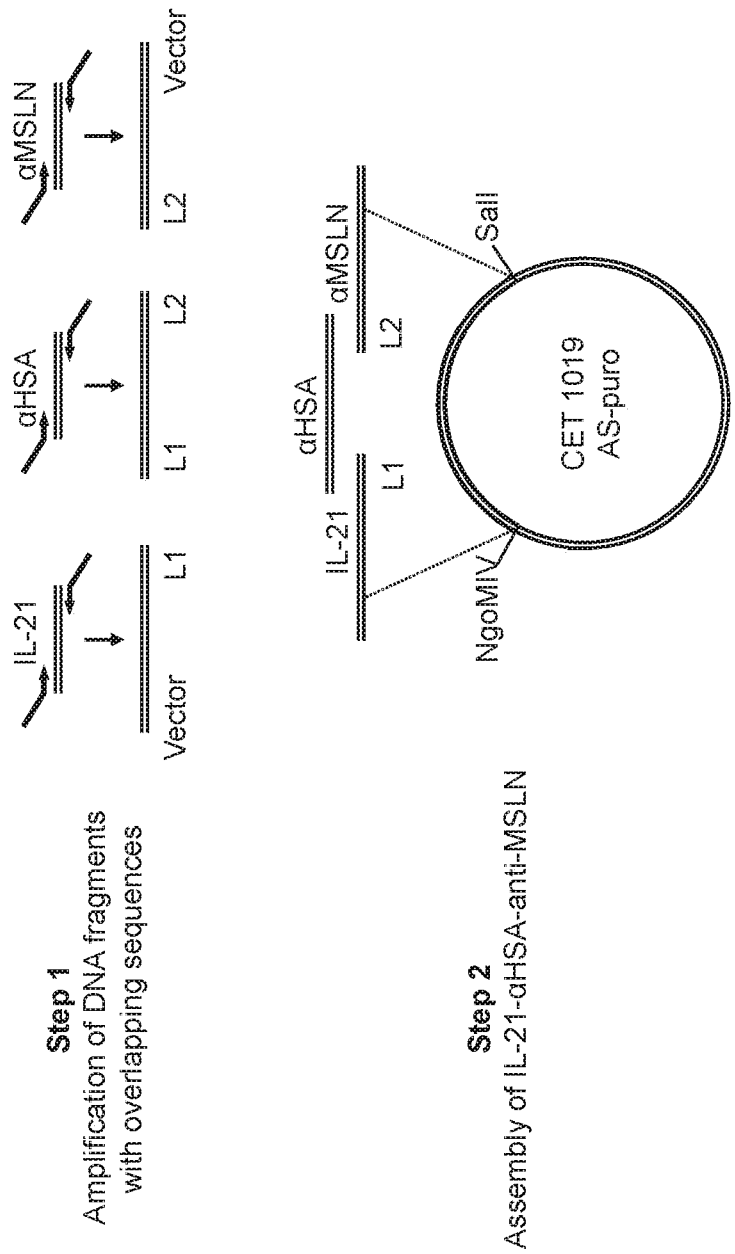
FIG. 2 depicts assembly of an exemplary IL-21 fusion protein expression vector wherein the albumin binding molecule is an anti-HSA antibody.

Construction of IL-21 fusion protein expression vector is exemplified herein. C-terminus of IL-21 was fused to N-terminus of albumin binding domain or albumin binding sdAb (αHSA) via a peptide linker (L1), and the C-terminus of albumin binding domain or albumin binding sdAb was fused with mesothelin binding sdAb (anti-MSLN) via a second peptide linker (L2). The DNA sequences encoding these polypeptides can be seamlessly assembled together by Gibson Assembly (Synthetic Genomics) or similar in vitro recombination method. To produce DNA fragments with overlapping sequence to its neighboring fragments for Gibson Assembly reaction, 20-40 base pair (bp) overlapping sequences encoding L1 or L2 linker peptide or CET1019-AS-Puro vector sequence were introduced at the 5' ends of the primers (see FIG. 2, Step 1). After amplification, the PCR products were purified and harvested by gel extraction using PureLink Gel Extraction Kit (ThermoFisher Scientific). The purified DNA fragments of desired gene-linker-vector combination were mixed and assembled together by Gibson Assembly Master Mix (New England BioLabs) or NEBuilder HiFi DNA Assembly Master Mix (New England BioLabs) according to the manufacturer's protocol (see FIG. 2, Step 2).

Figure 3:
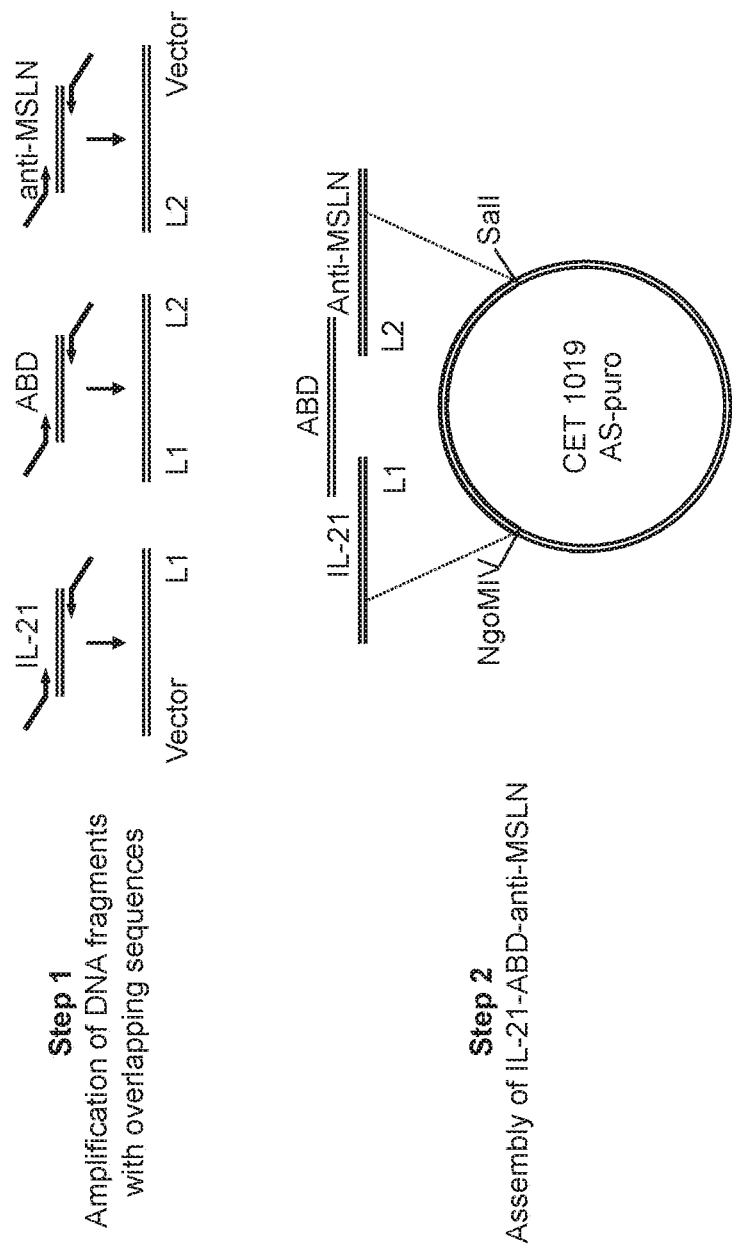
FIG. 3 depicts assembly of an exemplary IL-21 fusion protein expression vector wherein the albumin binding molecule is an ABD that binds to HSA.

Similarly, FIG. 3 illustrates the construction of an exemplary IL-21 fusion protein provided herein when the albumin binding molecule is an ABD.

A 6His tag can be optionally fused to the C-terminus of anti-MSLN sdAb. In such cases, the DNA sequence encoding 6His was used as overlapping sequence for designing the reverse primer for amplification of anti-MSLN and the forward primer for amplification of CET1019 AS-puro vector backbone.

After assembly reaction, 2 μl of the assembly product was used for transformation of NEB 5-alpha Competent E. coli cells (New England BioLabs) according to the manufacturer's protocol. Colonies from Amp selection plates were picked for subsequent mini-prep using PureLink Quick Plasmid Miniprep Kit (ThermoFisher Scientific) and DNA sequencing verification (ELIM Biopharmaceuticals).

Example 5: Expression and Purification of the IL-21 Fusion Protein

DNA sequences encoding the IL-21 fusion protein is transiently expressed in ExpiCHO cells. Briefly, on Day −1, CHO cells are seeded at 3-4×10e6 cells/ml in 25 ml of transient transfection medium (BalanCD® Transfectory™

CHO, Irvine Scientific, #91147), plus 4 mM glutamine in a 125 ml non-baffled flask. On Day 0, 22.5 ug plasmid DNA is mixed with 112.5 ug PEI in 1.5 ml transient transfection medium and is incubated at RT for 7 minutes. The mixture is then slowly added to the cells. The cells are fed once on Day 1 with 1) 0.5 mM Valproic acid (50 ul to 25 ml), 2) 10% post-TF supplement (Irvine Scientific #91148), 3) 1.5 ml Glucose stock (200 g/L), and 4) 5% IS Feed with 50 g/L TC Yeastolyte. CHO cells are harvested on Day 8 for purification over affinity column.

Example 6: In Vitro NK Cell Proliferation Assay

Human NK cells are isolated using a negative selection kit—Kit II (all beads are from Miltenyi Biotech, Bergisch Gladbach, Germany). Purification is performed manually or with an AutoMACS (Miltenyi). The purity of the cells is always controlled by fluorescence-activated cell sorting (FACS) and is more than 90%. The isolated NK cells are treated with the fusion proteins provided herein including those described above in Example 1. The proliferation of NK cells is monitored with CD69 signal using FACS analysis.

Example 7: In Vitro Cytotoxicity Assay

Human lung carcinoma cell A549 is mixed with freshly isolated human PBMC and incubated with 0, 5, 10, and 50 ng/mL of purified IL-21 fusion protein. In the case an MMP cleavable linker is used, a parallel set of experiment is set up with MMP9 added to activate IL-21. The mixed culture is incubated for up to 72 hour and MTS method is used to determine the percentage of the lyzed target cells in the study.

Example 8: In Vivo Efficacy Study

Neu mice are implanted with A549 cancer cells on Day 0. After tumors grow to approximate 50-100 mm$^3$, mice are randomized and treated with the IL-fusion protein provided herein and a control (e.g., an isotype control antibody in PBS) every other day. IL-21 fusion proteins provided herein are expected to show better efficacy at the same dose or achieve a similar efficacy at much lower dose when compared with IL-21 combination study (the study of combination treatment with IL-21 and a second agent).

Tumor sizes and body weights are measured at baseline before dosing. Tumor sizes and body weights are measured 3 times per week for two weeks post treatment. Terminal blood samples are collected for PK/PD analysis.

Example 9: Binding of Anti-MSLN Antibodies to Human or Monkey Mesothelin (MSLN)

Figure 4A:
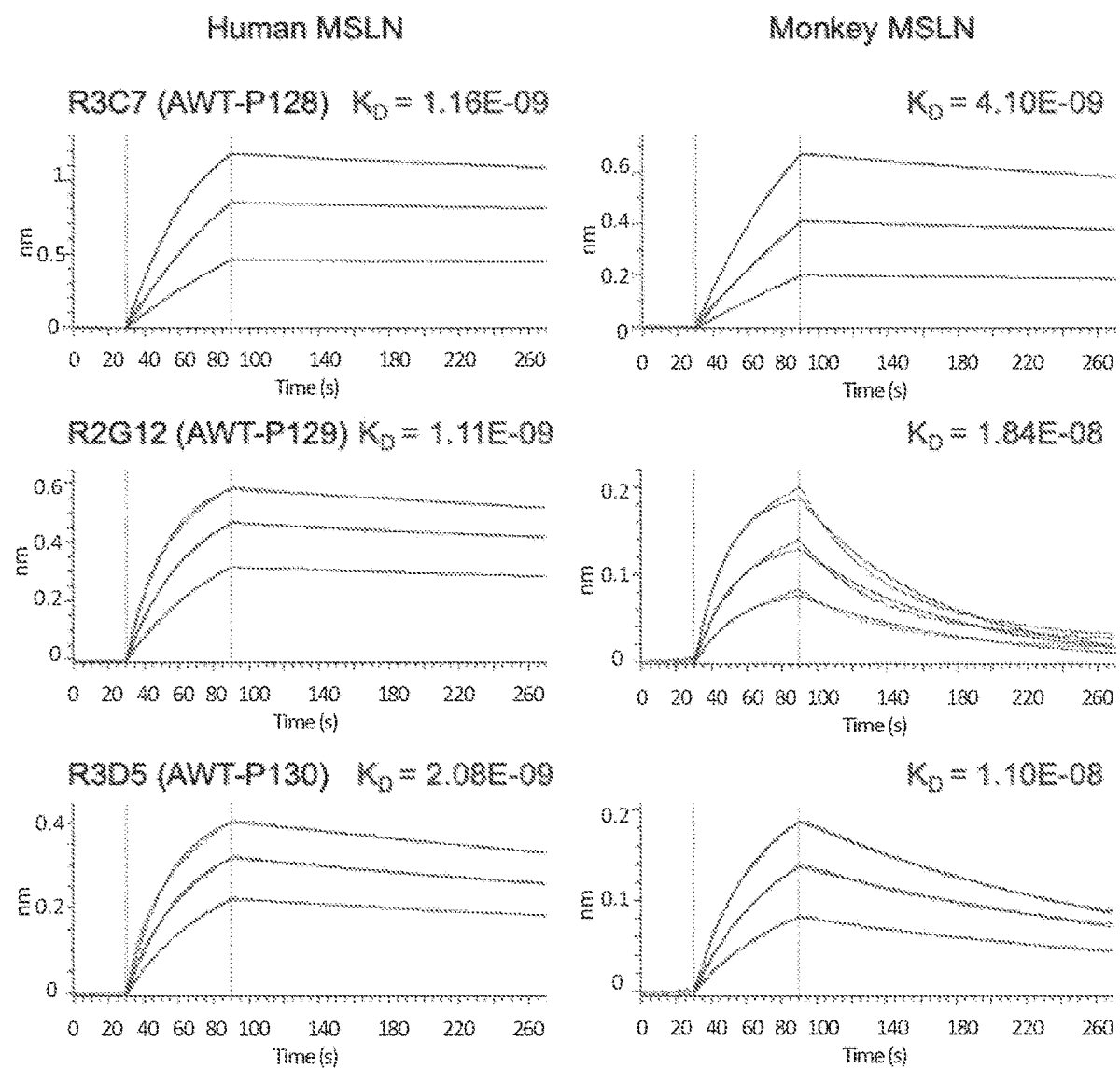
FIGS. 4A-4B depicts binding of anti-MSLN antibodies to human or monkey mesothelin (MSLN).
Figure 4B:
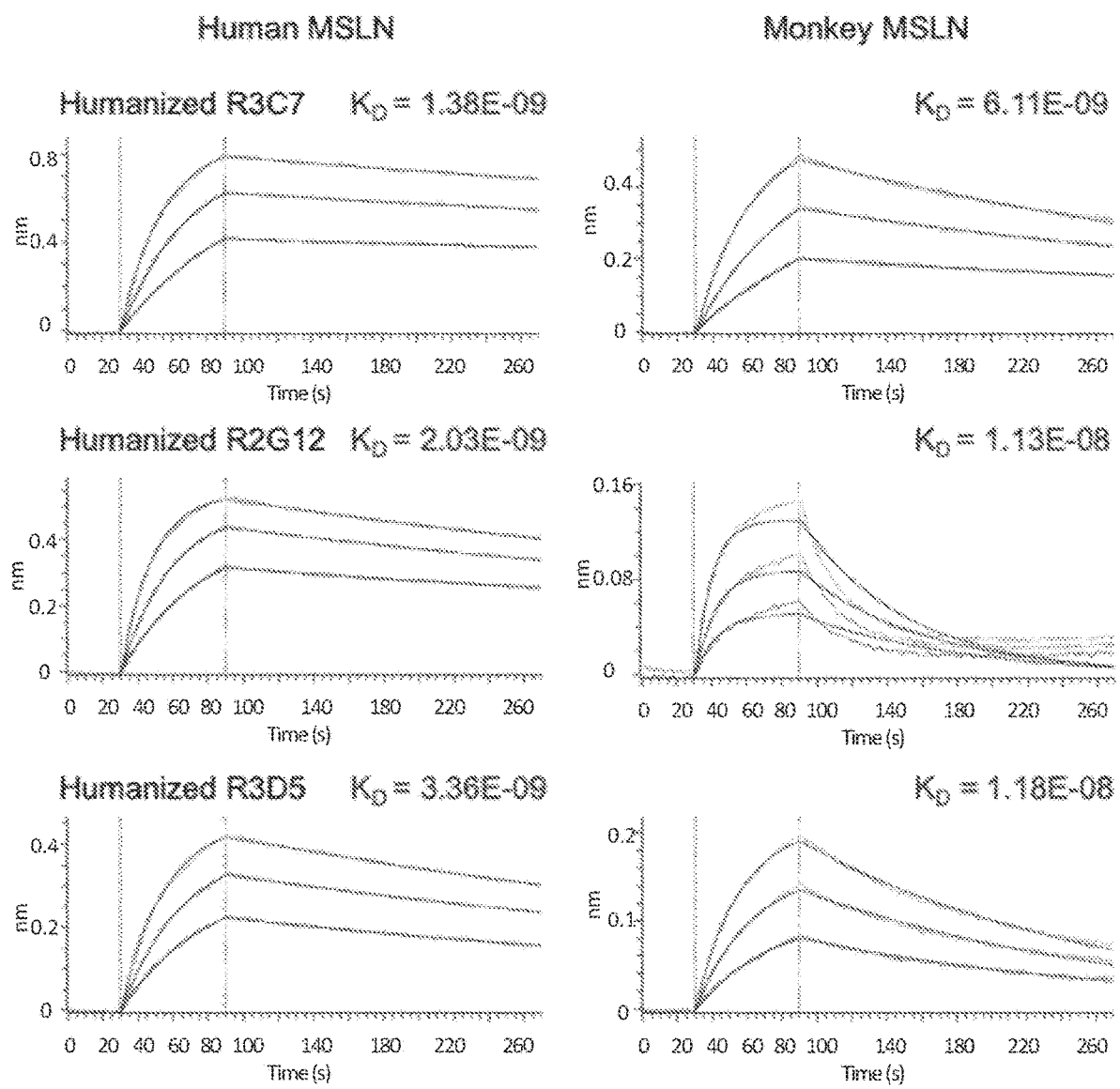

An Octet RED96 (ForteBio) was used to characterize the interaction. Briefly, Anti-MSLN-hgG1 Fc fusion proteins were loaded onto protein A biosensor and dip into human or monkey MSLN at 100 nM, 50 nM or 25 nM concentration. Primary experimental data was analyzed with global fitting to determine the $K_D$. Compared to the original llama antibodies (FIG. 4A), the humanized anti-MSLN antibodies (i.e., humanized R3C7, humanized R2G12, and humanized R3D5) retained the binding affinity to both human and monkey MSLN (FIG. 4B).

Example 10: Binding of Anti-MSLN Antibodies to Cell Surface

Four cancer cell lines, NCI-H226, OVCAR3, NCI-N87 and AsPC-1, known to express mesothelin were incubated with anti-MSLN antibodies R2G12, R3C7 or control antibody MORAb-009 for 20 minutes at 4 C. After washing, cells were incubated with Alexa Fluor 488 conjugated secondary antibody (anti-human IgG, Life Technologies) for 20 minutes at 4 C. Cells were washed and then fluorescence intensity of the cells was quantified by flow cytometry. Fluorescence intensity values were plotted for different concentrations of antibody as shown in FIG. 5. Anti-mesothelin antibodies all bind to cell surface mesothelin with similar potencies.

Example 11: Cytotoxicity of Anti-Mesothelin Antibodies

Part A.
NCI-H226 cancer cell lines were maintained in RPMI-1640 containing 10% fetal bovine serum and penicillin/streptomycin. On day 0, 5,000 NCI-H226 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% $CO_2$, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (MORAb-009— Reference anti-mesothelin antibody; R2G12, R3C7, R3D5, anti-mesothelin antibodies as shown in Example 2.)

Figure 5A:
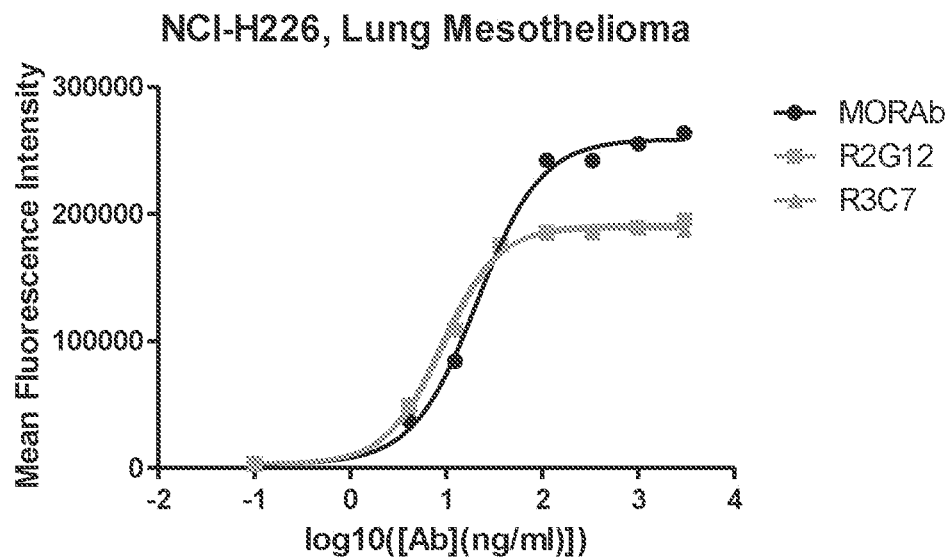
FIG. 5A-5D depict the dose-dependent binding of anti-MSLN antibody-IgG1 Fc fusion proteins to the cell surface of cancer cell lines NCI-H226, OVCAR3, NCI-N87 and AsPC-1.
Figure 5B:
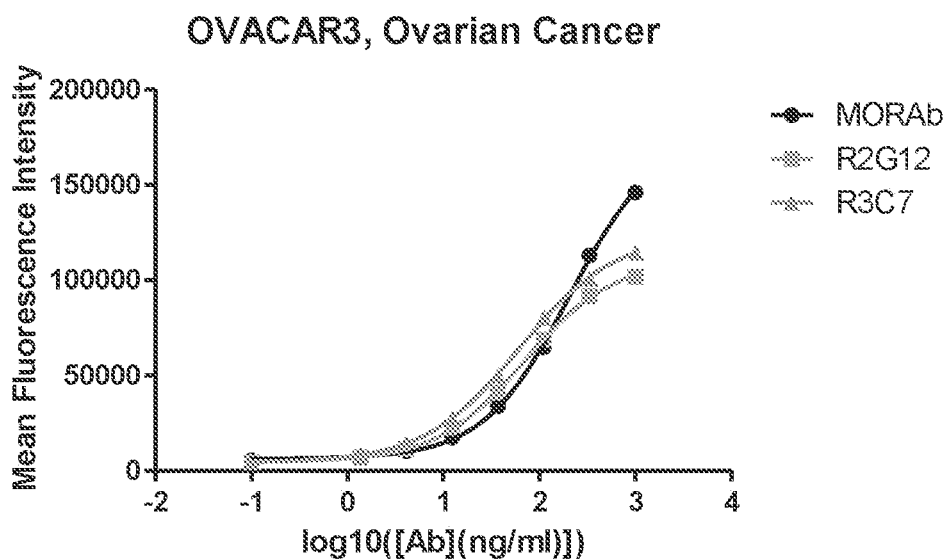
Figure 5C:
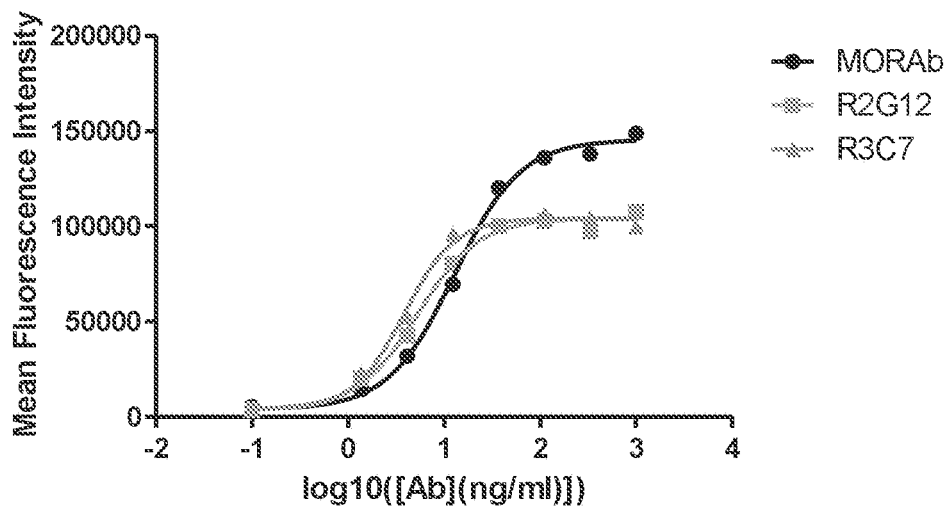
Figure 5D:
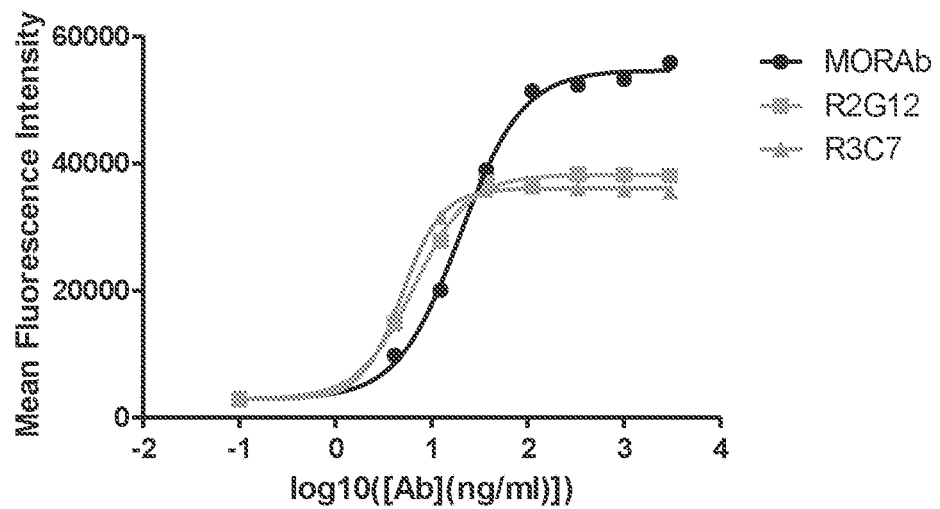
Figure 6A:
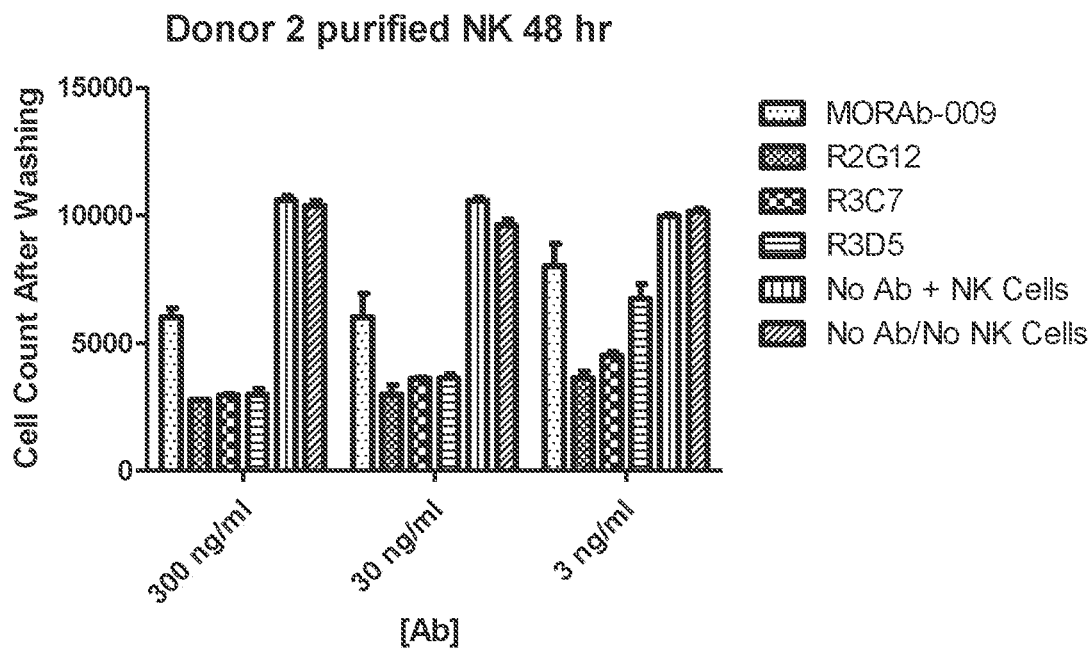
FIG. 6A depicts remaining tumor cell numbers after treatments of NK cells alone or in combination with anti-mesothelin antibody MORAb-009, R2G12, R3C7, or R3D5.
Figure 6B:
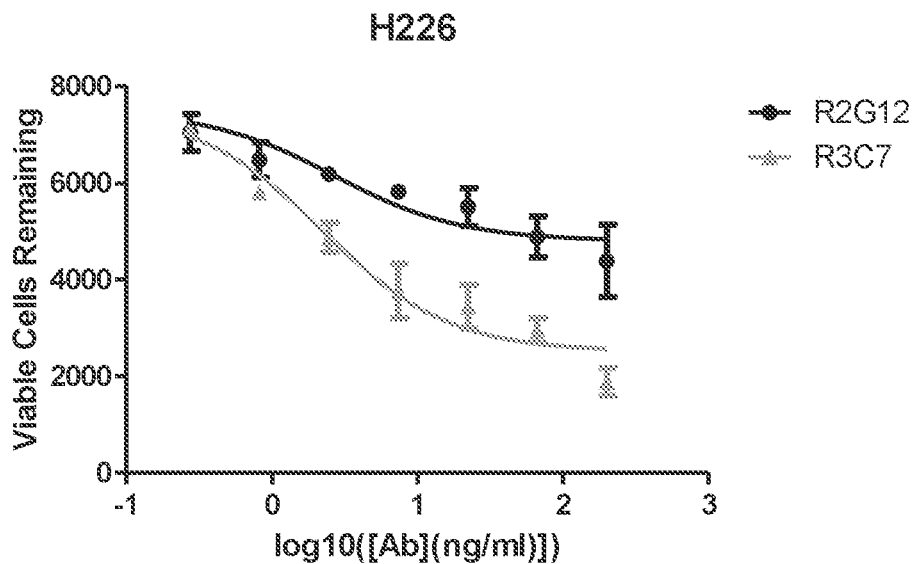
FIG. 6B (NCI-H226), 6C (OVCAR3), 6D (NCI-N87) and 6E (AsPC-1) depict the NK cell-mediated antibody dependent cell cytotoxicity dose-response curve of anti-MSLN antibodies R2G12 and R3C7 against four human cancer cell lines.
Figure 6C:
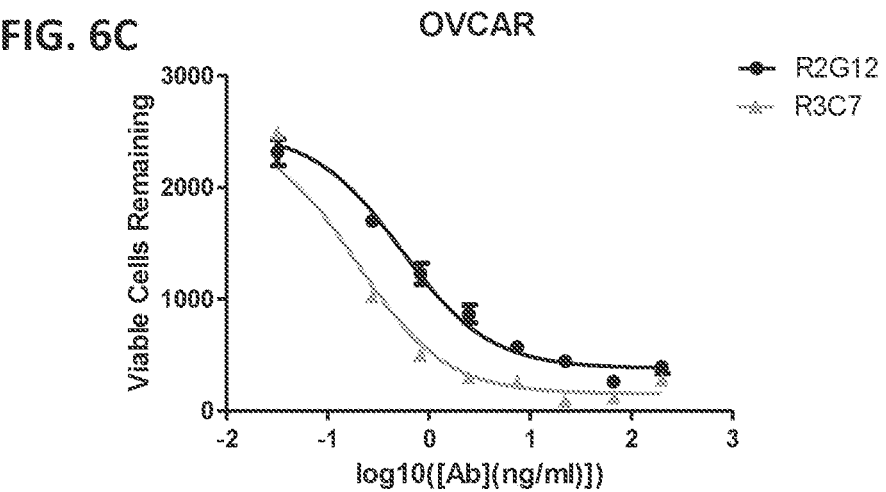
Figure 6D:
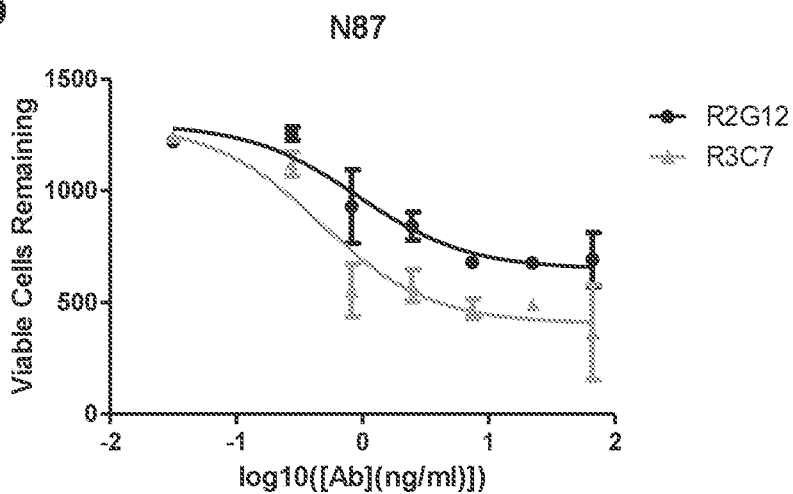
Figure 6E:
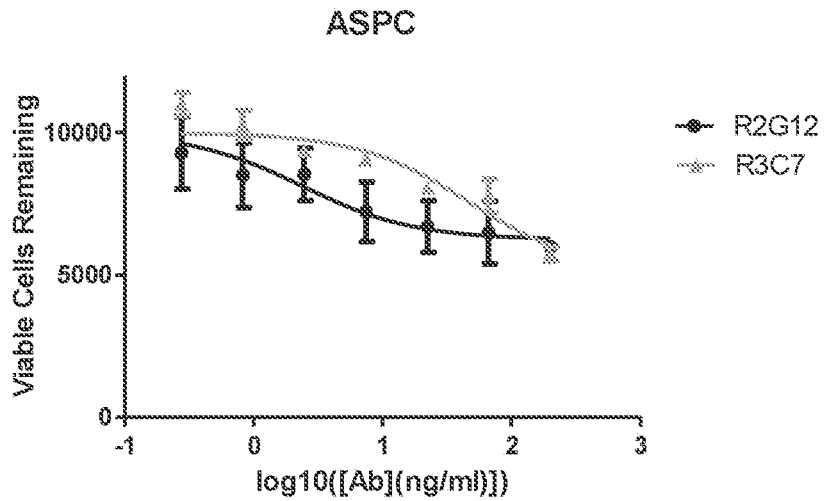

As shown in FIG. 5A, R2G12, R3C7 and R3D5 resulted in better antibody dependent cellular cytotoxicity as compared to control antibody MORAb-009. Moreover, R3C7 and R2G12 showed better ADCC compared to R3D5 at the 3 ng/ml dose.

Part B.
NCI-H226, OVCAR3, NCI-N87 and AsPC-1 cells were maintained in RPMI-1640 containing 10% fetal bovine serum and penicillin/streptomycin. On day 0, 10,000 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing.

As shown in FIGS. 6B-6E, R2G12 and R3C7 elicited antibody dependent cell cytotoxicity against all four cancer cell lines.

NCI-N87 cancer cell lines were maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% $CO_2$, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (MORAb-009—reference anti-mesothelin antibody; P303 (i.e., R3C7), anti-mesothelin antibodies as discussed in Example 2; P303F (i.e., R3C7F), R303 with reduced fucose)

Figure 7:
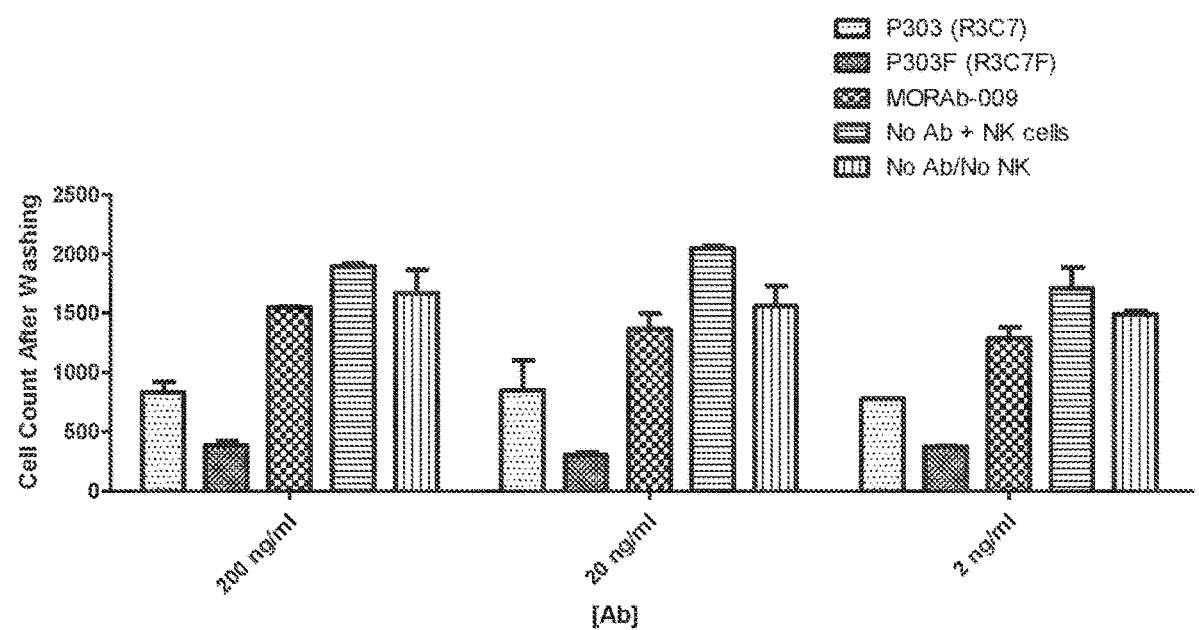
FIG. 7 depicts remaining tumor cell numbers after treatments of NK cells alone or in combination with anti-mesothelin antibody P303, P303F, or MORAb-009.

As shown in FIG. 7, P303 and P303F resulted in better ADCC activity compared to reference antibody MORAb-009. Moreover, P303F with reduced fucose resulted in better ADCC compared to P303.

Part D.

NCI-N87 and NCI-H226 human cancer cell lines were maintained in RPMI-1640 containing 10% fetal bovine serum and penicillin/streptomycin. CT26/MSLN mouse cancer cell line stably transfected to express human mesothelin protein was maintained in RPMI-1640 containing 10% fetal bovine serum and penicillin/streptomycin. On day 0, 10,000 NCI-N87, 5,000 NCI-H226 and 5,000 CT26/MSLN cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P303 (i.e., R3C7) and P197 (i.e., R2G12)—anti-mesothelin antibodies as discussed in Example 2; P303F (i.e., R3C7F) and P197F (i.e., R2G12F)—R303 and P197 with reduced fucose, respectively).

Figure 8A:
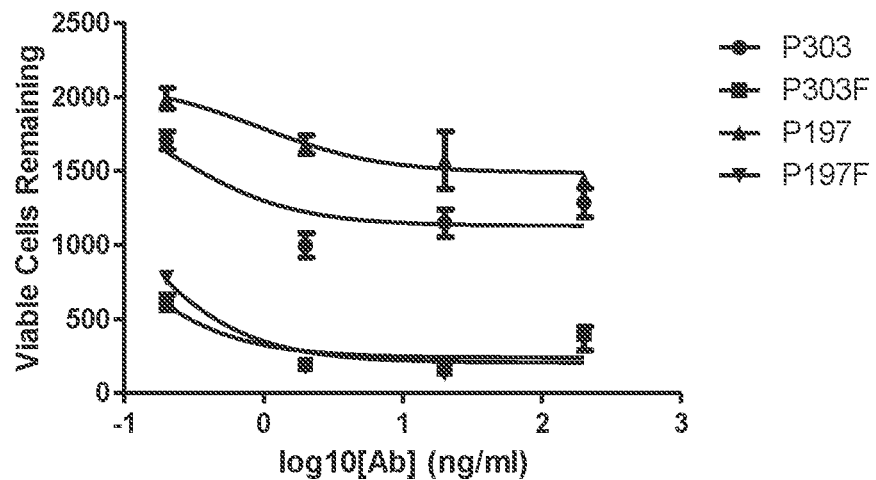
FIGS. 8A-8C depicts remaining cell numbers of N87 cells (FIG. 8A), H226 cells (FIG. 8B), and CT26/MSLN cells (FIG. 8C) after 48 hours of treatments of NK cells in combination with anti-mesothelin antibody P303, P303F, P197 and P197F.
Figure 8B:
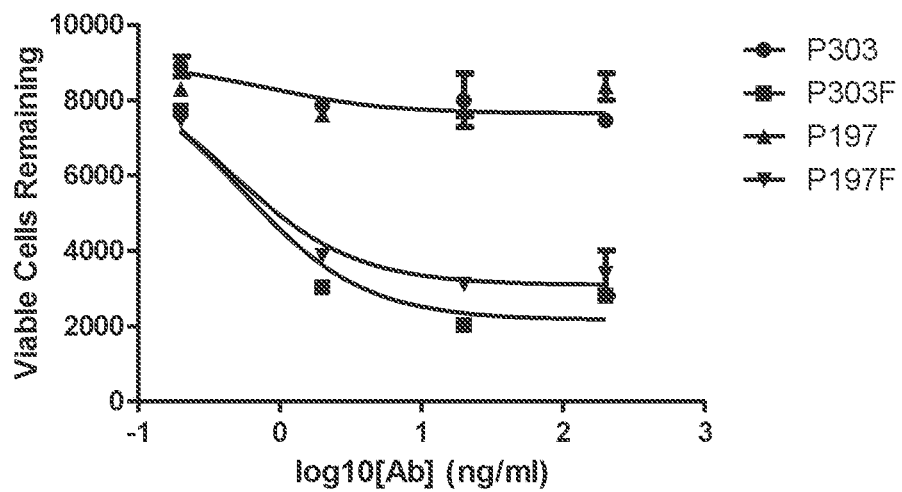
Figure 8C:
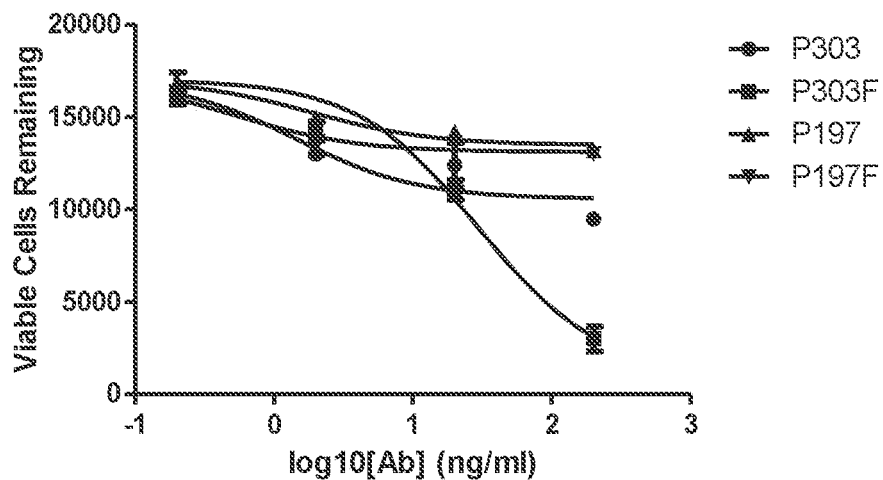

As shown in FIGS. 8A-8C, reducing antibody fucose content by inhibiting fucosylation during antibody production enhanced anti-mesothelin antibody ADCC activity for antibodies R3C7 and R2G12. Specifically, P303F (R3C7F) exhibited the best ADCC activity when using the CT26/MSLN cell line.

Example 12: Anti-Mesothelin Antibodies for Treating Tumor

Part A.

NCI-N87 cells were cultured and maintained in RPMI media supplemented with 10% FBS+glutamax+Pen/Strep. Cells were trypsinized, washed with media, and counted. Cells were then washed with PBS, and $3\times10^6$ cells (in 100 ul PBS) were injected subcutaneously into anesthetized SCID mice (Taconic) using an 18-gauge needle. Stock study drug (MORAb-009, P303F, P303, P197F and P197) were diluted to the appropriate concentration in PBS on the day of dosing, and animals were dosed intraperitoneally (IP) with 5 mg/kg of each study drug in 100 ul PBS twice per week for a total of five doses. Tumor measurements (length (L) and width (W)) were collected twice per week using digital calipers, and the tumor volume was calculated (L×W×W)/2.

Figure 9A:
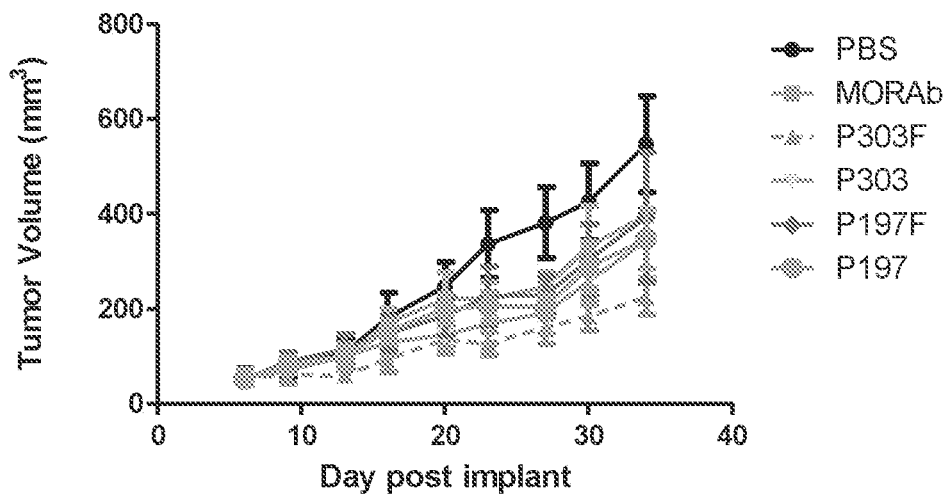
FIG. 9A depicts change of tumor volume in animal model of SCID mice with N87 tumor after treatment with anti-mesothelin antibody MORAb, P303F, P303, P197F or P197.

As shown in FIG. 9A, all anti-mesothelin antibodies reduced tumor growth in SCID mouse model relative to the PBS control group. P303F (R3C7F) treatment resulted in better tumor growth inhibition than MORAb-009, P197, P197F and P303.

Part B.

NCI-N87 cells were cultured and maintained in RPMI media supplemented with 10% FBS+glutamax+Pen/Strep. Cells were trypsinized, washed with media, and counted. Cells were then washed with PBS, and $3\times10^6$ cells (in 100 ul PBS) were injected subcutaneously into anesthetized NSG mice (Jackson) using a 23-gauge needle. After 6 days, $10\times10^6$ human PBMCs were injected into the tail vein in 100 ul PBS per mouse. Stock study drug P197 was diluted to the appropriate concentration in PBS on the day of dosing, and animals were dosed with 5 mg/kg (100 ul) study drug IP twice per week for a total of 5 doses. Tumor measurements (length (L) and width (W)) were collected twice per week using digital calipers, and the tumor volume was calculated (L×W×W)/2.

Figure 9B:
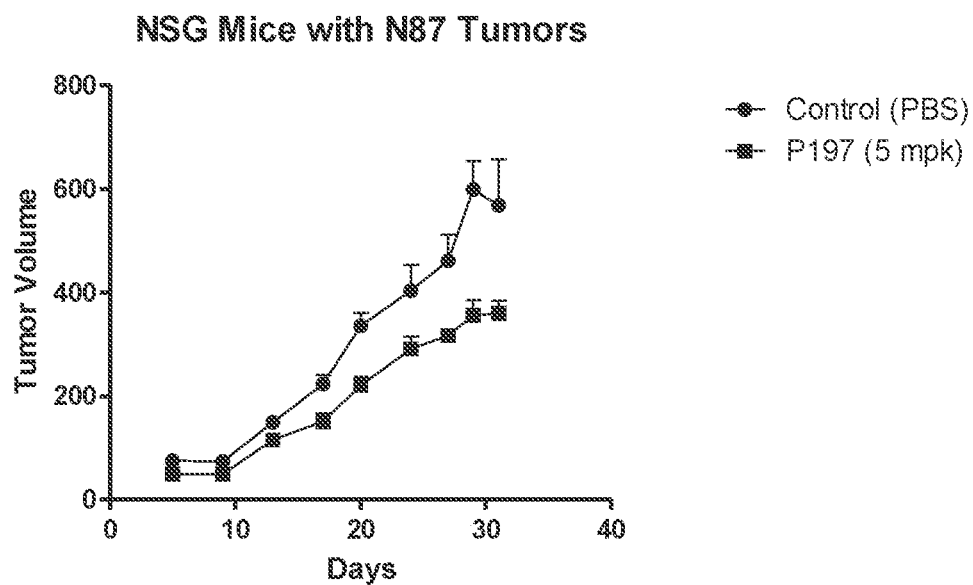
FIG. 9B depicts change of tumor volume in animal model of NSG mice with N87 tumor after treatment with anti-mesothelin antibody P197.

As shown in FIG. 9B, anti-mesothelin antibody P197 (R2G12) reduces tumor growth in NSG mice with a humanized immune system.

Part C.

CT26 mouse cells transfected with human mesothelin (CT26/MSLN) were cultured and maintained in RPMI media supplemented with 10% FBS+glutamax+Pen/Strep. Cells were trypsinized, washed with media, and counted. Cells were then washed with PBS, and $1\times10^6$ cells (in 100 ul PBS) were injected subcutaneously into anesthetized BALB/c mice using a 23-gauge needle. Stock study drug was diluted to the appropriate concentration in PBS on the day of dosing, and animals were dosed with 5 mg/kg (100 ul) study drug IP twice per week for a total of 5 doses. Tumor measurements (length (L) and width (W)) were collected twice per week using digital calipers, and the tumor volume was calculated (L×W×W)/2.

Figure 9C:
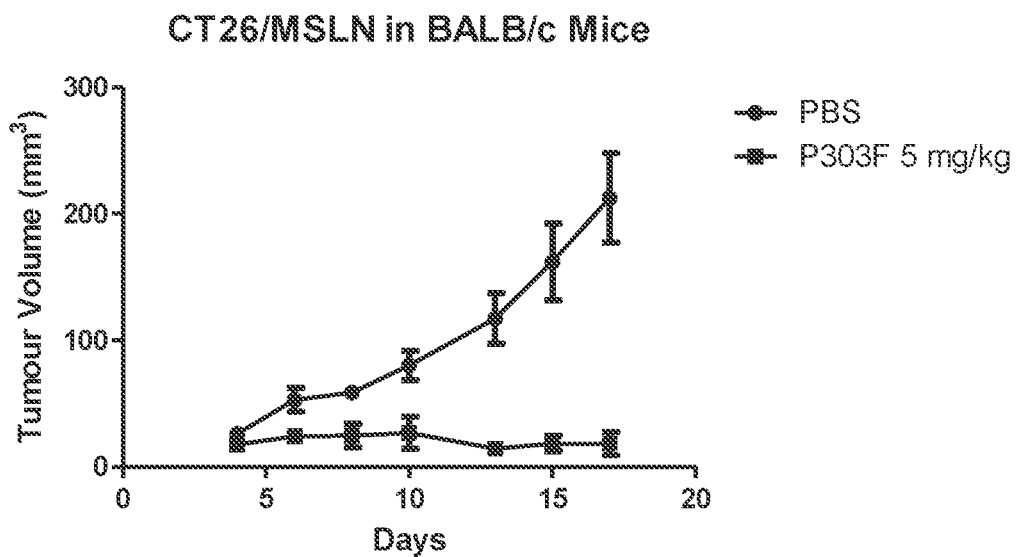
FIG. 9C depicts change of tumor volume in animal model of BALB/c mice with CT26/MSLN tumor after treatment with anti-mesothelin antibody P303F.

As shown in FIG. 9C, anti-mesothelin antibody with reduced fucosylation P303F (R3C7F) reduces tumor growth relative to the PBS control in a syngeneic CT26 mouse model.

Example 13. Anti-HSA Antibodies

Albumin is the most abundant protein in human serum and it has a half-live of three weeks. The long half-life of serum albumin is largely attributed to the protection from neonatal Fc receptor (FcRn). Serum albumin can be up taken by somatic cells through a process named fluid phase pinocytosis. Pinocytotic vesicles subsequently fuse with endosomal compartment, where the pH is in a range of 4.5-6.5. If the protein in the vesicle is released from their receptors, they would be further sorted for lysosomal degradation. The binding between serum albumin and FcRn only occurs at acidic pH (<6.5), allowing FcRn to rescue albumin from endosome and recycle them back to serum (Grevys et al., 2018). Therefore, as an albumin dependent half-life extending moiety, anti-HSA antibodies need to retain their binding affinity at both neutral and acidic pH.

An exemplary anti-HSA antibody (P367) interacts with both human and monkey serum albumin at pH 7.4 and pH 5.5. The binding was measured using Octet RED96 (ForteBio) and the $K_D$ was determined by global fitting using Octet Data Analysis HT software. P367-hgG1 Fc fusion protein was loaded onto protein A biosensor and dip into human or monkey serum albumin at pH 7.4 (left graph) or pH 5.5 (right graph). Table 13 shows the calculated $K_D$ of P367 at both pH 5.5 and pH 7.4. P367 show an increase in binding affinity to human serum albumin at pH 5.5.

TABLE 13

| Antibody | Binding Condition | KD (M) Human SA | KD (M) Cyno SA |
| --- | --- | --- | --- |
| AWT-P367 | pH 7.4 | $29.6 \times 10^{-9}$ | $18.9 \times 10^{-9}$ |
|  | pH 5.5 | $9.6 \times 10^{-9}$ | $20.5 \times 10^{-9}$ |

Figures 10A, 10B:
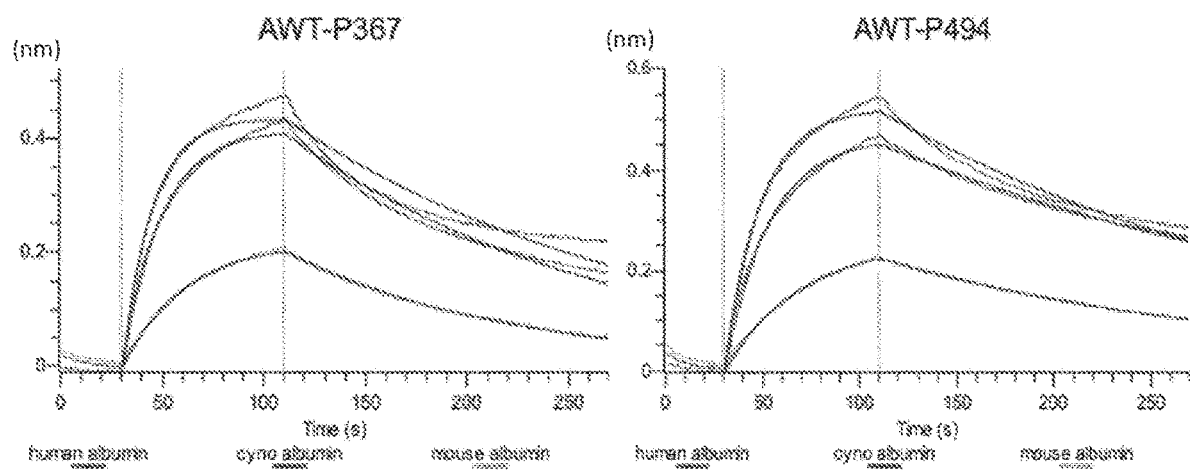
FIG. 10A depicts the binding of anti-HSA antibody AWT-P367 (i.e., P367) and its humanized anti-AWT-P494 (i.e., P494) with human, monkey or mouse albumin
FIG. 10B depicts $K_D$ of the binding of AWT-P367 or AWT-494 with human, monkey or mouse albumin.

An Octet RED96 (ForteBio) was used to characterize the interaction between anti-HSA antibody AWT-P367 or its humanized version AWT-P494 to human, monkey or mouse albumin. Briefly, AWT-P367 or AWT-P494 were loaded onto AHC biosensor and dip into human, monkey or mouse serum albumin at 200 nM concentration. Primary experimental data was analyzed with global fitting to determine the $K_D$. As shown in FIGS. 10A-10B, the binding affinity of humanized anti-HSA antibody AWT-P494 is similar to its original clone AWT-P367.

Sequences of exemplary anti-albumin antibodies are listed in Table 14 below.

TABLE 14

| SEQ ID NO. | Description | Sequence CDR sequences (IGMT definitions) are highlighted |
|---|---|---|
| 332 | P367 | QVQLVESGGGLVQPGGSLRLSCAASGSTWSINTLAWYRQAPG KQRDLVARISSGGSTHYADSVKGRFTVSRDNAENTLVLQMNS LKPEDTAVYYCYAQSTWYPPSWGQGTQVTVSS |
| 333 | P494 (humanized P367) | EVQLVESGGGLVQPGGSLRLSCAASGSTWSINTLAWYRQAPG KQRDLVARISSGGSTYYADSVKGRFTISRDNSKNTLYLQMNS LRAEDTAVYYCYAQSTWYPPSWGQGTLVTVSS |
| 334 | P367/P494 CDR1 | GSTWSINT |
| 335 | P367/P494 CDR2 | ISSGGST |
| 336 | P367/P494 CDR3 | YAQSTWYPPS |

Example 14: Anti-Mesothelin Antibody, Cytokine, or Cytokine Fusion Protein for Inhibiting Cancer Cells NCI-N87 cancer cell line was maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P303—R3C7 anti-MSLN antibody, P303F-R3C7 anti-mesothelin antibody with reduced fucosylation, P394—human IL-21-anti-HSA, P390—mouse IL-21-anti-HSA, P431/435—human IL-21-anti-HSA-IgG1-R3C7, P479-anti-HSA-Human-IL-15 RA Sushi/IL-15, P480—anti-HSA-Human-IL-15 RA Sushi/IL-15, rhIL-21—recombinant human IL-21, rhIL-15—recombinant human IL-15)

Figure 11:
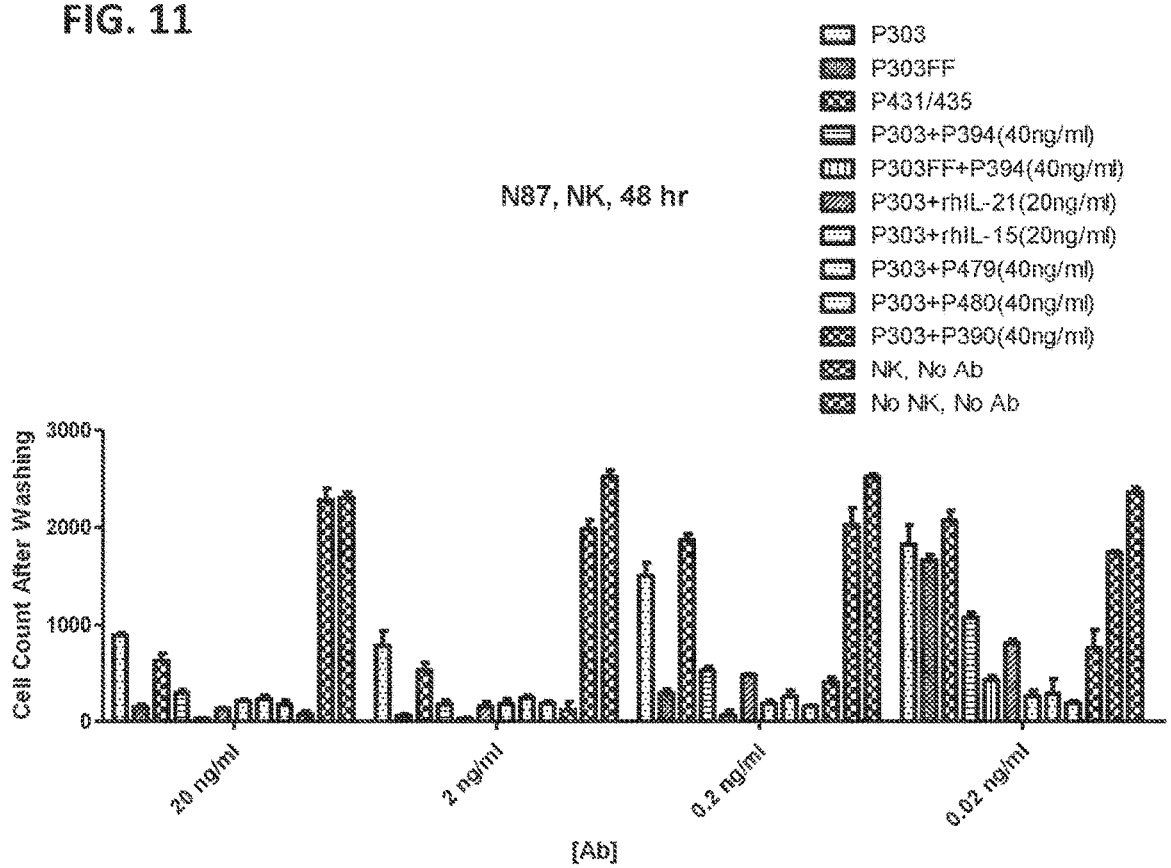
FIG. 11 depicts remaining cell numbers of N87 cells after treatment of NK cells alone or in combination with study drug as shown in the figure.

As shown in FIG. 11, rhIL-21, mIL-21 (P390) and hIL-21 (P394) anti-HSA fusion proteins enhanced NK cell ADCC activity to a similar extent when combined with anti-MSLN antibody P303(R3C7) compared to P303 alone. Moreover, rhIL-15 and hIL-15/IL-15RA anti-HSA fusion proteins (P479 and P480) enhanced NK cell ADCC activity to a similar extent when combined with anti-MSLN antibody P303(R3C7) compared to P303 alone. Cytokine-anti-HSA fusion proteins maintained full ADCC activity compared to the equivalent recombinant cytokines.

Example 15: Anti-Mesothelin Antibody Alone or in Combination with Herceptin for Inhibiting Cancer Cells NCI-N87 cancer cell line was maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P303F-anti-mesothelin antibody with reduced fucosylation, P380—human IL-33-anti-HSA, P394—human IL-21-anti-HSA)

Figure 12:
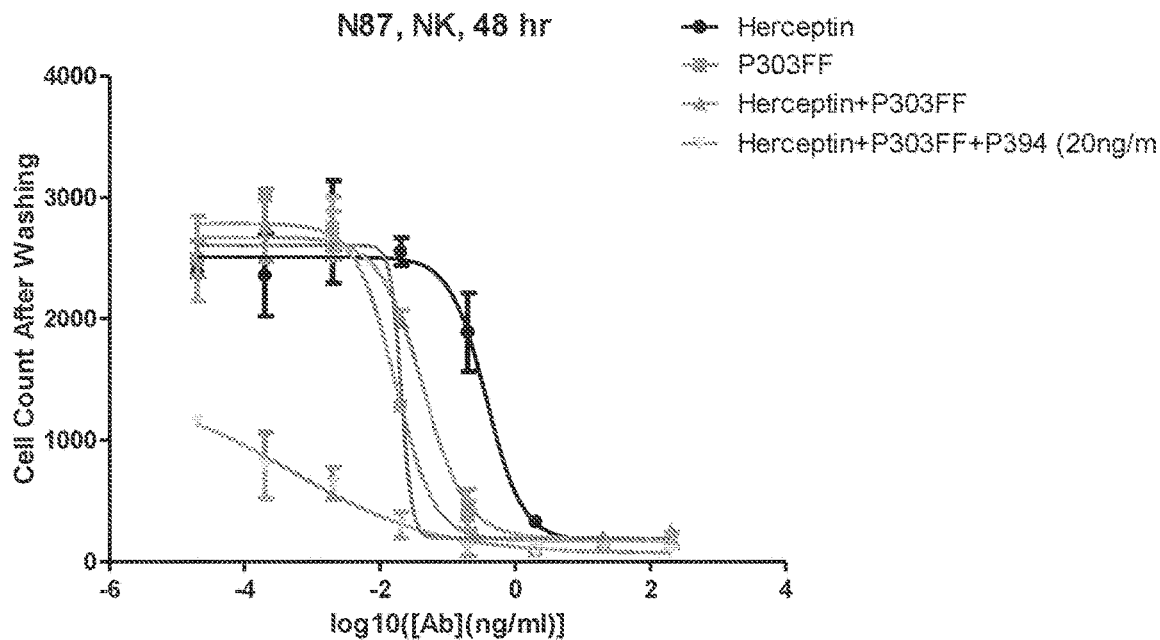
FIG. 12 depicts remaining cell numbers of N87 cells after treatment of NK cells alone or in combination with a) Herceptin alone, b) P303F alone, c) Herceptin and P303F, or d) Herceptin, P303F, and IL-21-anti-HSA fusion protein P394.

As shown in FIG. 12, P303F (R3C7 anti-mesothelin antibody) was more potent than Herceptin in NK cell ADCC and the combination of P303F and Herceptin was similar to P303F alone. Addition of P394 (human IL-21-anti-HSA) to P303F and Herceptin resulted in significantly improved ADCC function and improved potency.

Example 16: Anti-Mesothelin Antibody Alone or in Combination with Cytokine Fusion Proteins for Inhibiting Cancer Cells NCI-N87 cancer cell line was maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 24 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P303F-anti-mesothelin IgG1 antibody R3C7 with reduced fucosylation, P480—anti-HSA- Human-IL-15 RA Sushi/IL-15, rhIL-21—recombinant human IL-21, rhIL-15—recombinant human IL-15)

Figure 13:
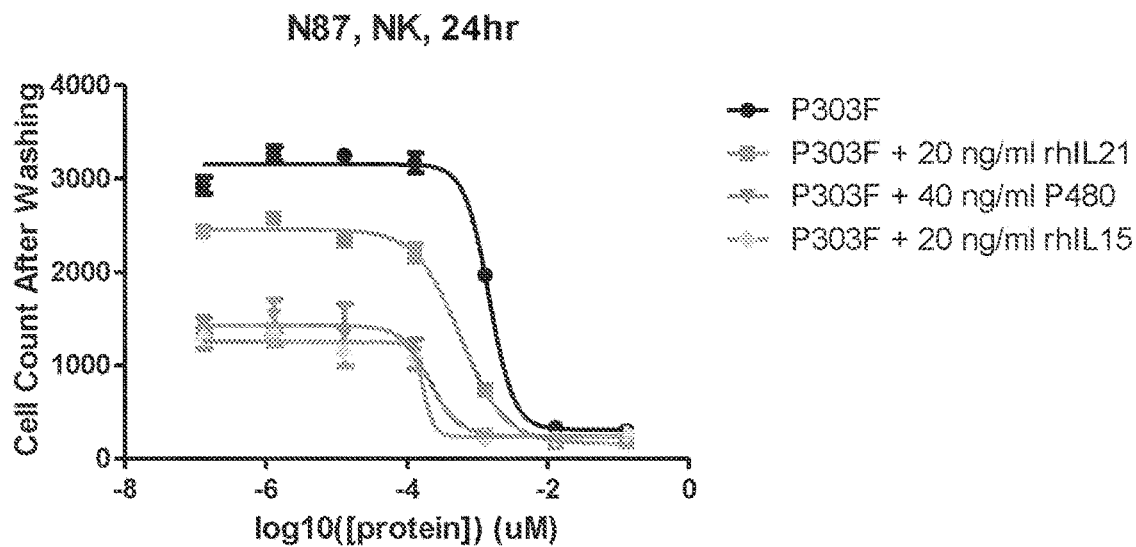
FIG. 13 depicts remaining cell numbers of N87 cells after treatment of NK cells in combination with a) P303F, b) P303F and recombinant human IL-21 (i.e., rhIL-21), c) P303F and P480, or d) P303F and recombination human IL-15 (i.e., rhIL-15).

As shown in FIG. 13, rhIL-15 and IL-15-anti-HSA (P480) enhanced NK cell ADCC activity when combined with anti-MSLN antibody P303F better than P303F and P303F with rhIL-21. P480 (IL-15/IL-15R sushi-anti-HSA) enhanced NK mediated ADCC with similar potency and magnitude compared to rhIL-15 suggesting full IL-15 activity was retained in the antibody fusion protein.

Example 17: Cytokine Fusion Proteins for Inhibiting Cancer Cells

NCI-N87 cancer cell line was maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 24 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P303F-anti-mesothelin IgG1 antibody R3C7 with reduced fucosylation, P431/P435—human IL-21-anti-HSA-IgG1-R3C7, P545/P435—human IL-21-anti-HSA-Cleavable linker-IgG1-R3CF7, rhIL-21—recombinant human IL-21)

Figure 14:
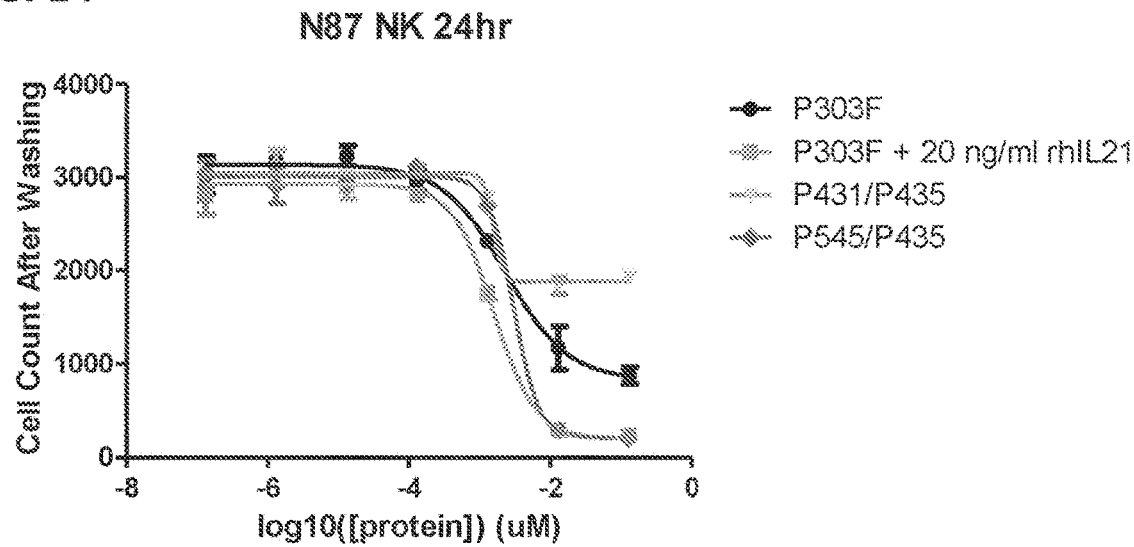
FIG. 14 depicts remaining cell numbers of N87 cells after treatment of NK cells in combination with a) P303F, b) P303F and recombinant human IL-21 (i.e., rhIL-21), c) P431/P435, or d) P545/P435.

As shown in FIG. 14, IL-21-anti-HSA-IgG1-R3C7F fusion proteins have similar NK cell ADCC activities compared with P303F plus rhIL-21, except for P431/P435 (human IL-21-anti-HSA-IgG1-R3C7) which does not have reduced fucosylation Example 18: IL-15-Anti-HSA Fusion Protein for Inhibiting Cancer Cells NCI-N87 cancer cell line was maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P303—anti-mesothelin antibody R3C7, P480—anti-HSA-Human-IL-15 RA Sushi/IL-15, P597—anti-HSA-Human-IL-15 RA Sushi-peptide linker-IL-15, rhIL-15—recombinant human IL-15)

Figure 15:
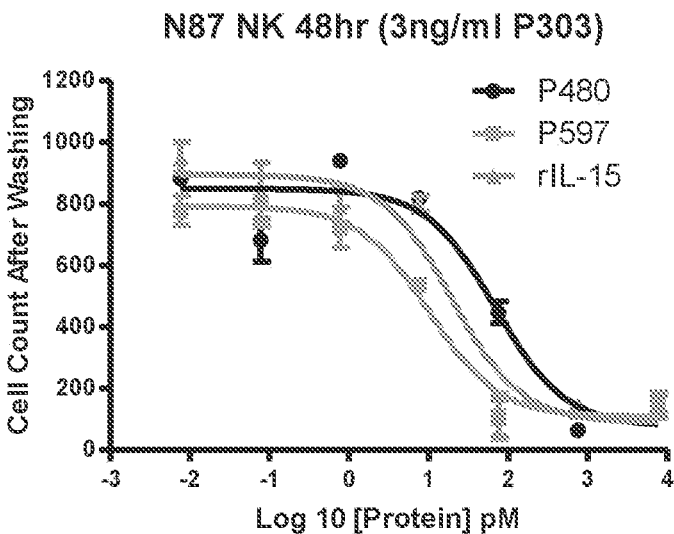
FIG. 15 depicts remaining cell numbers of N87 cells after treatment of NK cells in combination with a) P480, b) P597, or c) rIL-15 (upper panel) and IC50 of three drugs (lower panel).

As shown in FIG. 15, anti-HSA fusion protein P597, with a peptide linker between IL-15R sushi and IL-15, improved ADCC activity compared to P480, an anti-HSA fusion protein without a linker between IL-15R sushi and IL-15. The ADCC potency of P597 was similar to rhIL-15, suggesting full IL-15 activity was retained in the fusion protein.

Example 19: IL-21 Fusion Proteins for Inhibiting Cancer Cells

NCI-N87 and H226 cancer cell lines were maintained in RPMI-1640 containing 10% fetal bovine serum and penicillin/streptomycin. On day 0, 10,000 NCI-N87 cells/well, 5000 H226 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P129—anti-mesothelin antibody R2G12, P126—human IL-21-R2G12-IgG1 fusion, P107—human IL-21-IgG1 fusion, P325—human IL-21-R2D2 fusion, P286/288—human IL-21-R3C7-IgG1-R2G12 fusion.)

Figure 16:
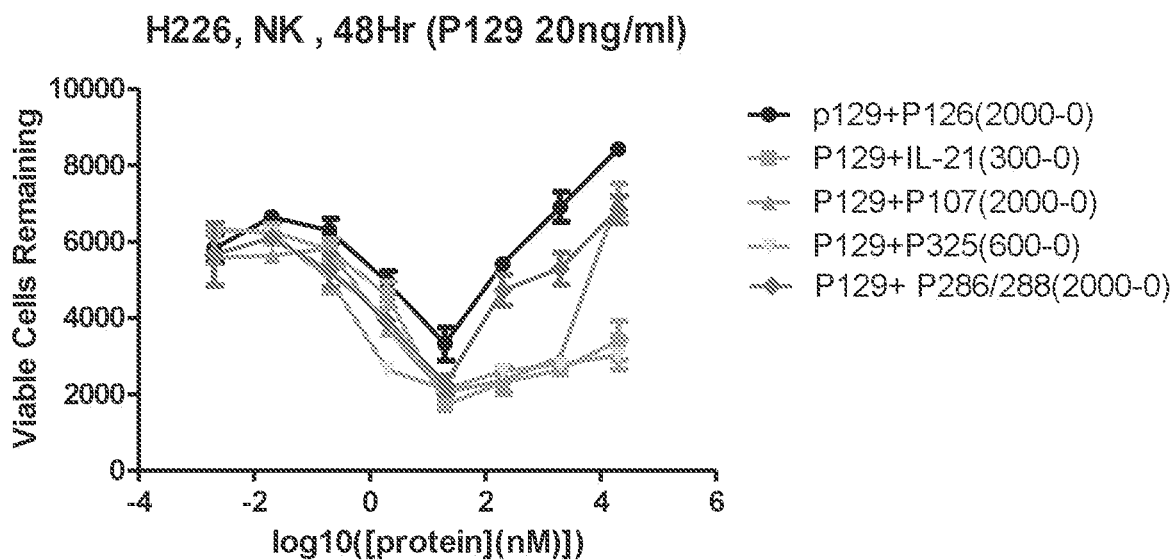
FIG. 16 depicts remaining cell numbers of H226 cells after treatment of NK cells in combination with a) anti-mesothelin antibody P129 (i.e., R2G12) and P126, (i.e., human IL-21-R2G12-IgG1 fusion), b) P129 and IL-21, c) P129 and P107 (human IL-21-IgG1 fusion), d) P129 and P325 (human IL-21-R2D2 fusion), or e) P129 and P286/288 (human IL-21-R3C7-IgG1-R2G12).

As shown in FIG. 16, lower concentrations of IL-21-Fc fusion proteins (P107, P126, P288/286) enhanced NK cell ADCC activity when combined with anti-MSLN antibody P129 (i.e., R2G12). However, at higher concentrations (>100 nM), IL-21-Fc fusion proteins (P107, P126, P288/286) inhibited NK cell ADCC activity when combined with anti-MSLN antibody P129 (R2G12). This inhibition was not observed for IL-21 or IL-21 fusion protein without the Fc domain (P325).

Example 20: IL-21-Anti-HSA Fusion Proteins in Combination with Anti-Mesothelin Antibodies for Inhibiting Cancer Cells NCI-N87 cancer cells were maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P197—anti-mesothelin antibody R2G12, P390—mouse IL-21-anti-HSA, P394—human IL-21-anti-HSA)

Figure 17:
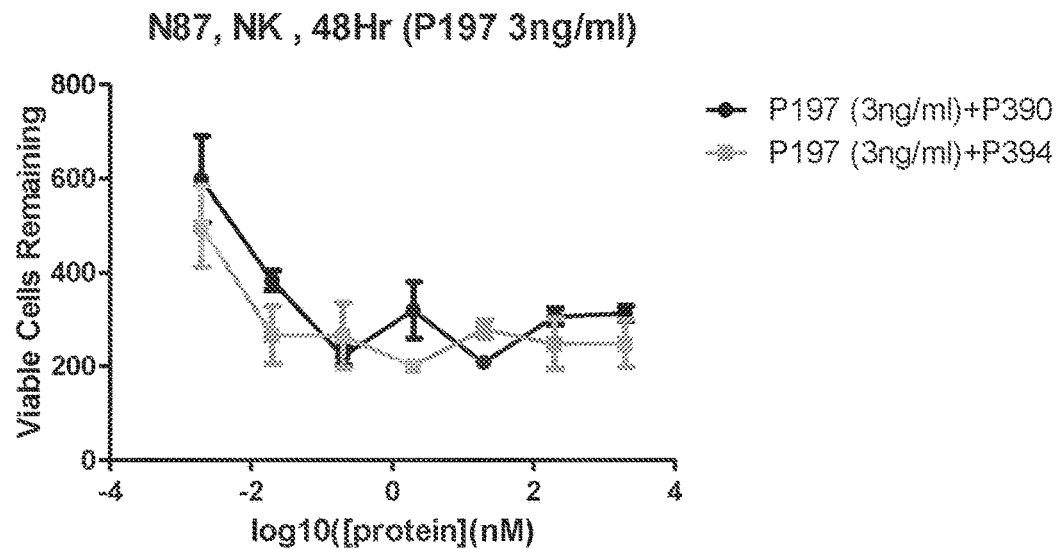
FIG. 17 depicts remaining cell numbers of N87 cells after treatment of NK cells in combination with a) P197 and P390; or b) P197 and P394.

As shown in FIG. 17, both mouse and human IL-21-anti-HSA fusion proteins (P390 and P394) enhance NK cell ADCC activity potently when combined with anti-MSLN antibody P197 (R2G12).

Example 21: Anti-Mesothelin Antibodies and/or IL-21-Anti-HSA Fusion Protein in Treating Cancer NCI-N87 cells were cultured and maintained in RPMI media supplemented with 10% FBS+glutamax+Pen/Strep. Cells were trypsinized, washed with media, and counted. Cells were then washed with PBS, and $3 \times 10^6$ cells (in 100 ul PBS) were injected subcutaneously into anesthetized NSG mice (Jackson) using a 23-gauge needle. After 6 days, $10 \times 10^6$ human PBMCs were injected into the tail vein in 100 ul PBS per mouse. Stock study drug was diluted to the appropriate concentration in PBS on the day of dosing, and animals were dosed IP with 100 ug P303F (anti-mesothelin antibody), 25 ug P394 (human IL-21-anti-HSA) or a combination of 100 ug P303F with either 25 ug or 5 ug P394 twice per week for a total of 5 doses. Tumor measurements (length (L) and width (W)) were collected twice per week using digital calipers, and the tumor volume was calculated (L×W×W)/2.

Figure 18:
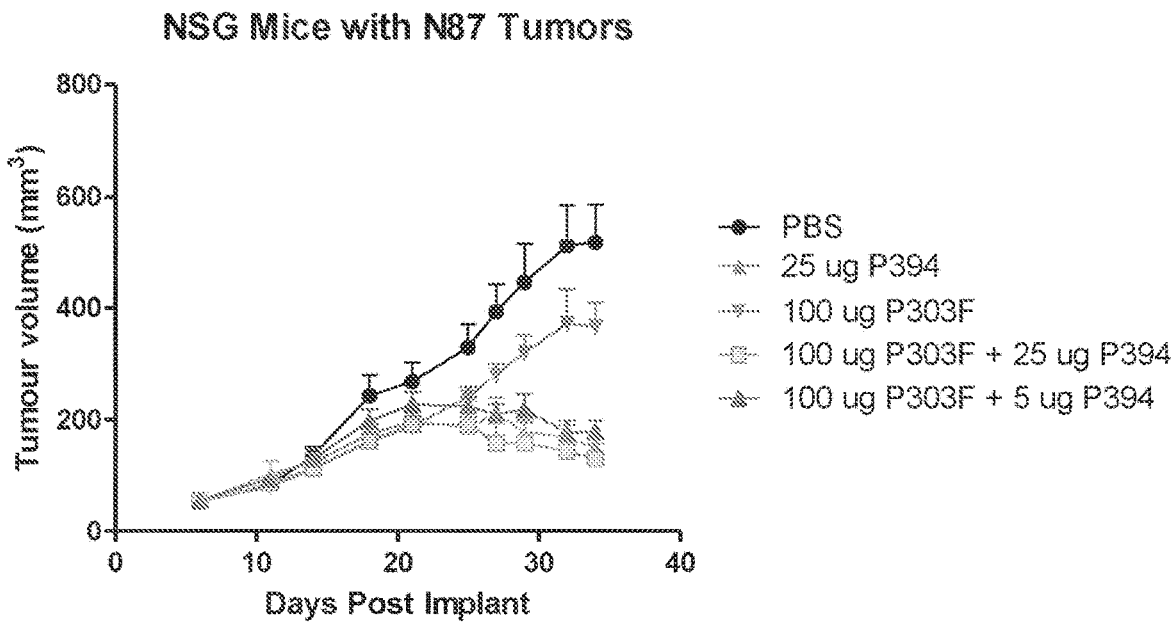
FIG. 18 depicts change of tumor volume in animal model of NSG mice with N87 tumors after treatment with a) 25 μg of P394, b) 100 μg of P303F, c) 100 μg of P303F and 25 μg of P394, or d) 100 μg of P303F and 5 μg of P394.

As shown in FIG. 18, P303F reduces tumor growth relative to the control. All mice receiving P394 alone or in combination with P303F had significantly reduced tumor growth relative to PBS control or P303F alone.

Example 22: Anti-Mesothelin Antibodies and/or IL-21-Anti-HSA Fusion Proteins in Treating Cancer NCI-N87 cells were cultured and maintained in RPMI media supplemented with 10% FBS+glutamax+Pen/Strep. Cells were trypsinized, washed with media, and counted. Cells were then washed with PBS, and $3 \times 10^6$ cells (in 100 ul PBS) were injected subcutaneously into anesthetized SCID mice (Taconic) using an 18-gauge needle. Stock study drug was diluted to the appropriate concentration in PBS on the day of dosing, and animals were dosed IP with 100 ug P303F (anti-mesothelin antibody) or P303F in combination with 25 ug P390 (mouse IL-21-anti-HSA), 5 ug P390, or 2.5 ug recombinant mouse IL-21 (equivalent molarity to the 5 ug P390 dose) in 100 ul PBS twice per week for a total of 5 doses. Tumor measurements (length (L) and width (W)) were collected twice per week using digital calipers, and the tumor volume was calculated (L×W×W)/2.

Figure 19:
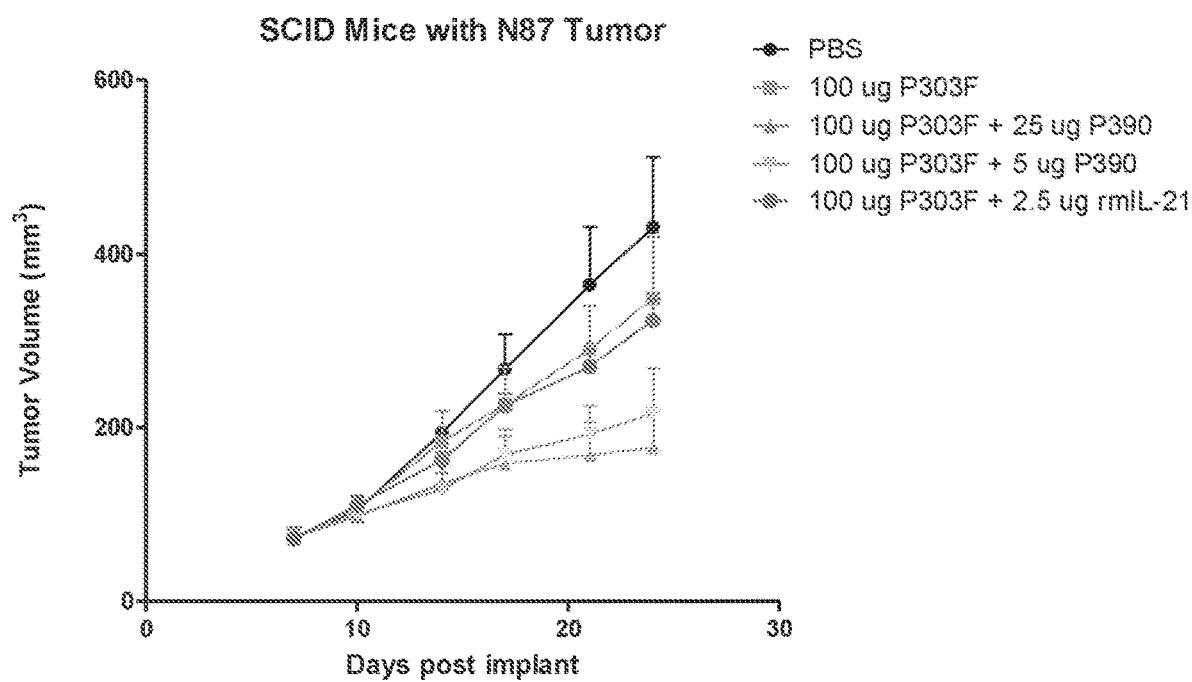
FIG. 19 depicts change of tumor volume in animal model of SCID mice with N87 tumors after treatment with 100 μg of P303F alone or in combination with a) 25 μg of P390 b) 5 μg of P390, or c) 2.5 μg of rmIL-21.

As shown in FIG. 19, the combination of P303F and 25 ug or 5 ug P390 resulted in significantly reduced tumor growth compared to PBS control, P303F monotherapy and P303F combined with rmIL-21. P303F with 2.5 ug rmIL-21 showed similar tumor growth as P303F suggesting that recombinant IL-21 is not efficacious at this dose. The combination of P303F with 5 ug P390 shows significantly reduced tumor growth compared to P303F with 2.5 ug rmIL-21, highlighting the improved efficacy of half-life extended IL-21 compared to the recombinant cytokine.

The invention claimed is:

1. An isolated anti-mesothelin (anti-MSLN) construct comprising a single-domain antibody (sdAb) moiety that comprises an anti-MSLN heavy chain variable region (VH) comprising:
an HC-CDR1 comprising an amino acid sequence of SEQ ID NO: 27, an HC-CDR2 comprising an amino acid sequence of SEQ ID NO: 28, and an HC-CDR3 comprising an amino acid sequence of SEQ ID NO: 29.

2. The anti-MSLN construct of claim 1, wherein the sdAb moiety comprises the amino acid sequence of any one of SEQ ID NOS: 128 and 291 to 295.

3. The anti-MSLN construct of claim 1, wherein the construct is a fusion protein further comprising a half-life extending domain.

4. The anti-MSLN construct of claim 3, wherein the half-life extending domain comprises an Fc domain.

5. The anti-MSLN construct of claim 4, wherein the Fc domain comprises a human IgG1, IgG2, IgG3 or IgG4.

6. The anti-MSLN construct of claim 4, wherein the fusion protein comprises the amino acid sequence of SEQ ID NO: 303.

7. The anti-MSLN construct of claim 4, wherein the half-life extending domain is fused to the N-terminus of the sdAb moiety.

8. The anti-MSLN construct of claim 4, wherein the half-life extending domain is fused to the C-terminus of the sdAb moiety.

9. The anti-MSLN construct of claim 4, wherein the construct comprises a first linker between the sdAb moiety and the half-life extending domain.

10. The anti-MSLN construct of claim 1, wherein the anti-MSLN construct is a fusion protein further comprising a cytokine.

11. The anti-MSLN construct of claim 10, wherein the cytokine is an IL-21, IL-15, IL-15 bound to IL-15Rα, or IL-33.

12. The anti-MSLN construct of claim 1, wherein the construct comprises the amino acid sequence of any one of SEQ ID NOS: 128, 291 to 295, 303, 325, 327, and 329 to 331.

13. A polynucleotide encoding the anti-MSLN construct of claim 1.

14. A kit comprising:
a) the anti-MSLN construct of claim 1, and
b) an instruction.

15. A pharmaceutical composition comprising the anti-MSLN construct of claim 1 and a pharmaceutically acceptable carrier.

16. A method of treating a mesothelin positive cancer in an individual, comprising administering into the individual in need thereof a therapeutically effective amount of the anti-MSLN construct of claim 1.

17. The method of claim 16, wherein the cancer is a solid cancer.

* * * * *